US012018011B2

(12) United States Patent
Zhu et al.

(10) Patent No.: US 12,018,011 B2
(45) Date of Patent: Jun. 25, 2024

(54) MACROCYCLIC COMPOUNDS AND COMPOSITIONS, AND METHODS OF PREPARING AND USING THE SAME

(71) Applicant: Kura Oncology, Inc., San Diego, CA (US)

(72) Inventors: Xuefeng Zhu, San Diego, CA (US); Pingda Ren, San Diego, CA (US); Zhu Bai, Shanghai (CN); Wanting Xiong, Shanghai (CN); Dan Xu, Shanghai (CN); Yahu Arthur Liu, San Diego, CA (US)

(73) Assignee: Kura Oncology, Inc., San Diego, CA (US)

( * ) Notice: Subject to any disclaimer, the term of this patent is extended or adjusted under 35 U.S.C. 154(b) by 0 days.

(21) Appl. No.: 18/329,479

(22) Filed: Jun. 5, 2023

(65) Prior Publication Data
US 2023/0322711 A1    Oct. 12, 2023

Related U.S. Application Data

(63) Continuation of application No. PCT/US2022/080565, filed on Nov. 29, 2022.

(60) Provisional application No. 63/385,117, filed on Nov. 28, 2022, provisional application No. 63/285,412, filed on Dec. 2, 2021.

(30) Foreign Application Priority Data

Nov. 30, 2021 (CN) .......................... 202111442658.4
Nov. 23, 2022 (CN) .......................... 202211471486.8

(51) Int. Cl.
*A61P 35/00* (2006.01)
*C07D 401/10* (2006.01)
*C07D 491/044* (2006.01)

(52) U.S. Cl.
CPC ............ *C07D 401/10* (2013.01); *A61P 35/00* (2018.01); *C07D 491/044* (2013.01)

(58) Field of Classification Search
CPC ................ C07D 401/10; C07D 401/04; C07D 491/044; C07D 491/08; C07D 491/01; C07D 491/18; A61P 35/00
See application file for complete search history.

(56) References Cited

FOREIGN PATENT DOCUMENTS

WO    WO 1997/021701 A1    6/1997

OTHER PUBLICATIONS

Chemical Abstract Service, STN Database, Registry No. 1639044-71-5 [online][Entered STN: Dec. 18, 2014] (Year: 2014).*
Chemical Abstract Service, STN Database, Registry No. 190441-46-4 [online][Entered STN: Dec. 18, 2014] (Year: 1997).*
Dinsmore et al., 2001, "Conformational Restriction of Flexible Ligands Guided by the Transferred NOE Experiment: Potent Macrocyclic Inhibitors of Farnesyltransferase," Journal of the American Chemical Society 123(9):2107-2108.
Driggers et al., 2008, "The exploration of macrocycles for drug discovery—an underexploited structural class," Nature Reviews Drug Discovery 7(7):608-624.
International Search Report and Written Opinion mailed Feb. 16, 2023 for PCT/US2022/080565 filed Nov. 29, 2022.
Kraus et al., 2010, "Second Generation Analogues of the Cancer Drug Clinical Candidate Tipifarnib for Anti-Chagas Disease Drug Discovery," Journal of Medicinal Chemistry 53(10):3887-3898.

* cited by examiner

*Primary Examiner* — Amanda L. Aguirre
(74) *Attorney, Agent, or Firm* — Jones Day

(57) ABSTRACT

The present invention relates to macrocyclic compounds of any one of Formula (I), or a pharmaceutically acceptable form thereof, pharmaceutical compositions comprising the same, methods of preparing the same, and methods of treating cancer dependent on a farnesylated protein, using the same.

222 Claims, No Drawings

MACROCYCLIC COMPOUNDS AND COMPOSITIONS, AND METHODS OF PREPARING AND USING THE SAME

1. CROSS REFERENCE

This application is a continuation of International Patent Application No. PCT/US2022/080565, filed Nov. 29, 2022, which claims the benefit of priority from Chinese Application No. 202111442658.4, filed Nov. 30, 2021, U.S. Provisional Application No. 63/285,412, filed Dec. 2, 2021, Chinese Application No. 202211471486.8, filed Nov. 23, 2022, and U.S. Provisional Application No. 63/385,117, filed Nov. 28, 2022. Each of the foregoing related applications, in its entirety, is incorporated herein by reference.

2. FIELD

The present invention relates to macrocyclic compounds, and pharmaceutical compositions comprising the same, that are useful in the treatment of cancer dependent on a farnesylated protein. The present invention also relates to methods of preparing such macrocyclic compounds, and pharmaceutical compositions comprising the same. This invention also relates to the use of such macrocyclic compounds, and pharmaceutical compositions comprising the same, in methods of inhibition of farnesyltransferase and methods of treating cancer dependent on a farnesylated protein.

3. BACKGROUND

Activated Ras oncogenes are frequently identified in cancerous tumors and transformed Ras protein is involved in the proliferation of cancer cells. Ras protein, the protein product of the ras oncogene, is a small GTPase that is important in signal transduction, cell growth, and cell proliferation. Shields, J. M., et al., Trends Cell Biol. 2000, 10, 147-154. Ras protein must associate (or bind) with the inner surface of the plasma membrane to transduce extracellular signals, which can lead to the proliferation of cancer cells.

To bind to the plasma membrane of the cell and transduce extracellular signals, the Ras protein must undergo several post-translational modifications, including farnesylation of the cysteine in the CAAX box at the C-terminal end (where C represents cysteine, A represents an aliphatic amino acid, and X represents any amino acid). Rowinsky, E. K., et al., J. Clin. Oncol. 1999, 17, 3631-3652. The enzyme farnesyltransferase (FTase) recognizes the CAAX motif and farnesylates the Ras protein (transferring a 15-carbon farnesyl isoprenoid from farnesyl diphosphate to the cysteine residue). Once farnesylated, the Ras protein can bind to the cell membrane. Inhibition of farnesyltransferase, thereby blocking Ras protein cell membrane binding, represents a path to reducing cell proliferation of cancer cells and may offer potential clinical benefit to cancer patients.

4. SUMMARY

In one aspect, provided herein is a compound of Formula (I):

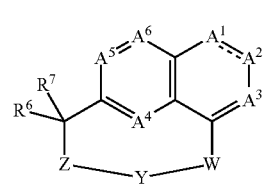

Formula (I)

or a pharmaceutically acceptable form thereof, wherein:
the dashed line indicates a single bond or double bond between $A^1$ and $A^2$;
$A^1$ is independently N, $NR^{1a}$, $CR^{1b}$, or —C(=O)—;
$A^2$ is independently N, $NR^{2a}$, $CR^{2b}$, or —C(=O)—;
$A^3$ is independently $CR^3$ or N;
$A^4$ is $CR^8$ or N;
$A^5$ and $A^6$ are each independently $CR^8$ or N, or $A^5$ and $A^6$ taken together are O, $NR^9$, or S;
W is a $C_{6-12}$ aryl or a 5-12 membered heteroaryl, each of which is optionally substituted with 1-4 $R^4$ substituents;
Y is a bond or a linker having a length of up to 6 atoms;
Z is a $C_{6-12}$ aryl or a 5-12 membered heteroaryl, each of which is optionally substituted with 1-4 $R^5$ substituents;
$R^{1a}$ and $R^{2a}$ are each independently $R^9$, —$OR^9$, —C(O)$R^9$, —C(O)$R^9$, —C(O)$NR^{10}R^{11}$, —S(O)$_pR^9$, or —S(O)$_2NR^{10}R^{11}$;
$R^{1b}$, $R^{2b}$, $R^3$, $R^5$ and $R^8$, at each occurrence, are each independently $R^9$, —$OR^9$, halo, CN, $NO_2$, —C(O)$R^9$, —C(O)$R^9$, —OC(O)$R^9$, —OC(O)$R^9$, —C(O)$NR^{10}R^{11}$, —$NR^{10}R^{11}$, —$NR^{10}C(O)R^9$, —$NR^{10}C(O)R^9$, —$NR^{10}C(O)NR^{10}R^{11}$, —$NR^{10}S(O)_2R^9$, —S(O)$_pR^9$, —S(O)$_2NR^{10}R^{11}$ or —$NR^{10}S(O)_2NR^{10}R^{11}$;
$R^4$, at each occurrence, is independently hydrogen, halo, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, —$NR^{14}R^{15}$, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, $C_{6-12}$ aryl, or 5-12 membered heteroaryl of the $R^4$ is optionally independently substituted with one, two, three, four, five, or six substituents selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);
$R^6$ is CN, $R^9$, —$OR^9$, —C(O)$R^9$, —C(O)$OR^9$, —OC(O)$R^9$, —OC(O)$OR^9$, —C(O)$NR^{10}R^{11}$, —$NR^{10}R^{11}$, —$NR^{10}R^9$, —$NR^{10}C(O)R^9$, —$NR^{10}C(O)OR^9$, —$NR^{10}C(O)NR^{10}R^{11}$, —$NR^{10}S(O)_2R^9$, —$NR^{10}C(NR^{10})NROR^{11}$, —S(O)$_pR^9$, —S(O)$_2NR^{10}R^{11}$, or —$NR^{10}S(O)_2NR^{10}R^{11}$;
$R^7$ is a 5-12 membered heteroaryl, optionally substituted with 1-4 substituents independently selected from halo, CN, $NO_2$, $R^9$, —$OR^9$, —C(O)$R^9$, —C(O)$OR^9$, —OC(O)$R^9$, —OC(O)$OR^9$, —C(O)$NROR^{11}$, —$NR^{10}R^{11}$, —$NR^{10}C(O)R^9$, —$NR^{10}C(O)OR^9$, —$NR^{10}C(O)NR^{10}R^{11}$, —$NR^{10}S(O)_2R^9$, —S(O)$_pR^9$, —S(O)$_2NR^{10}R^{11}$ and —$NR^{10}S(O)_2NR^{10}R^{11}$;

R$^9$, at each occurrence, is independently hydrogen, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{6-12}$ aryl, or 5-12 membered heteroaryl, wherein each C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{6-12}$ aryl, or 5-12 membered heteroaryl of the R$^9$ is optionally independently substituted with one, two, three, four, five, or six substituents selected from halo, hydroxy, CN, NO$_2$, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_3$-6 cycloalkyl, 3-6 membered heterocycloalkyl, C$_{1-6}$ alkoxy, C$_{1-6}$ haloalkoxy, (O), —C(O)R$^{12}$, —C(O)OR$^{12}$, —OC(O)R$^{12}$, —OC(O)OR$^{12}$, —C(O)NR$^{10}$R$^{11}$, —NR$^{10}$R$^{11}$, —NR$^{10}$C(O)R$^{12}$, —NR$^{10}$C(O)OR$^{12}$, —NR$^{10}$C(O)NROR$^{11}$, —NR$^{10}$S(O)$_2$R$^{12}$, —S(O)$_p$R$^{12}$, —S(O)$_2$NR$^{10}$R$^{11}$, and —NR$^{10}$S(O)$_2$NR$^{10}$R$^{11}$;

R$^{10}$ and R$^{11}$, at each occurrence, are each independently hydrogen, hydroxy, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{6-12}$ aryl, or 5-12 membered heteroaryl, or together with the N to which each is attached are combined to form a 3-6 membered heterocycloalkyl, wherein each C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{6-12}$ aryl, or 5-12 membered heteroaryl of the R$^{10}$ and the R$^{11}$ is optionally independently substituted with one, two, three, four, five, or six substituents selected from halo, hydroxy, CN, NO$_2$, C$_{1-6}$ alkyl, C$_{2-6}$ alkenyl, C$_{2-6}$ alkynyl, C$_{1-6}$ haloalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, (O), —C(O)R$^{13}$, —C(O)OR$^{13}$, —OC(O)R$^{13}$, —OC(O)OR$^{13}$, —C(O)NR$^{14}$R$^{15}$, —NR$^{14}$R$^{15}$, —NR$^{14}$C(O)R$^{13}$, —NR$^{14}$C(O)OR$^{13}$, —NR$^{14}$C(O)NR$^{14}$R$^{15}$, —NR$^{14}$S(O)$_2$R$^{13}$, —S(O)$_p$R$^{13}$, —S(O)$_2$NR$^{14}$R$^{15}$, and —NR$^{14}$S(O)$_2$NR$^{14}$R$^{15}$;

R$^{12}$, at each occurrence, is independently hydrogen, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{6-12}$ aryl, or 5-12 membered heteroaryl, wherein each C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{6-12}$ aryl, or 5-12 membered heteroaryl of the R$^{12}$ is optionally independently substituted with one, two, three, four, five, or six substituents selected from halo, hydroxy, CN, NO$_2$, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_3$-6 cycloalkyl, 3-6 membered heterocycloalkyl, C$_{1-6}$ alkoxy, C$_{1-6}$ haloalkoxy, (O), —C(O)R$^{13}$, —C(O)OR$^{13}$, —OC(O)R$^{13}$, —OC(O)OR$^{13}$, —C(O)NR$^{10}$R$^{11}$, —NR$^{10}$R$^{11}$, —NR$^{10}$C(O)R$^{13}$, —NR$^{10}$C(O)OR$^{13}$, —NR$^{10}$C(O)NR$^{10}$R$^{11}$, —NR$^{10}$S(O)$_2$R$^{13}$, —S(O)$_p$R$^{13}$, —S(O)$_2$NR$^{10}$R$^{11}$, and —NR$^{10}$S(O)$_2$NR$^{10}$R$^{11}$;

R$^{13}$, at each occurrence, is independently hydrogen, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ heteroalkyl, C$_{3-6}$ cycloalkyl, or 3-6 membered heterocycloalkyl;

R$^{14}$ and R$^{15}$, at each occurrence, are each independently hydrogen, hydroxy, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ heteroalkyl, C$_{3-6}$ cycloalkyl, 3-6 membered heterocycloalkyl, or C$_{1-6}$ alkoxy, or together with the N to which each is attached are combined to form a 3-6 membered heterocycloalkyl; and each p is independently an integer of 0, 1 or 2.

In certain embodiments, the compound of Formula (I) is a compound of Formula (II):

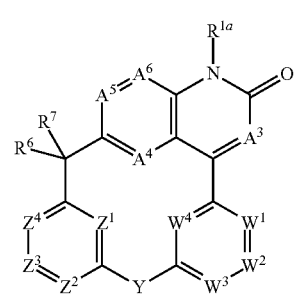

Formula (II)

wherein:
W$^1$, W$^2$, W$^3$, and W$^4$ are each independently N or CR$^4$, or W$^1$ and W$^2$ taken together are O, NR$^{4A}$, or S, or W$^2$ and W$^3$ taken together is O, NR$^{4A}$, or S;

Z$^1$, Z$^2$, Z$^3$, and Z$^4$ are each independently N or CR$^5$, or Z$^2$ and Z$^3$ taken together is O, NR$^{5A}$ or S, or Z$^3$ and Z$^4$ taken together is O, NR$^{5A}$, or S; and R$^{4A}$ and R$^{5A}$ are independently hydrogen, C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{6-12}$ aryl, or 5-12 membered heteroaryl, wherein each C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{6-12}$ aryl, or 5-12 membered heteroaryl of the R$^{4A}$ and the R$^{5A}$ is optionally independently substituted with one, two, three, four, five, or six substituents independently selected from halo, hydroxy, C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, and (O);

or a pharmaceutically acceptable form thereof.

In certain embodiments, the compound of Formula (I) is a compound of Formula (III):

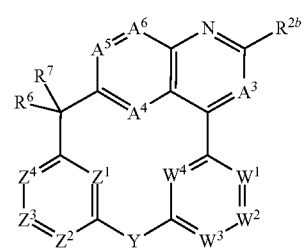

Formula (III)

wherein:
W$^1$, W$^2$, W$^3$, and W$^4$ are each independently N or CR$^4$, or W$^1$ and W$^2$ taken together is O, NR$^{4A}$ or S, or W$^2$ and W$^3$ taken together is O, NR$^{4A}$, or S;

Z$^1$, Z$^2$, Z$^3$, and Z$^4$ are each independently N or CR$^5$, or Z$^2$ and Z$^3$ taken together is O, NR$^{5A}$ or S, or Z$^3$ and Z$^4$ taken together is O, NR$^{5A}$, or S; and R$^{4A}$ and R$^{5A}$ are independently hydrogen, C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{4A}$ and the $R^{5A}$ is optionally independently substituted with one, two, three, four, five, or six substituents selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);

or a pharmaceutically acceptable form thereof.

In certain embodiments, the compound of Formula (I) is a compound of Formula (IV):

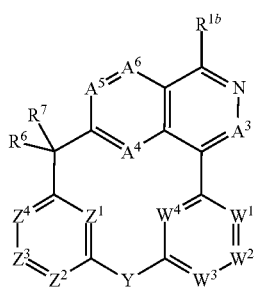

Formula (IV)

wherein:
$W^1$, $W^2$, $W^3$, and $W^4$ are each independently N or $CR^4$, or $W^1$ and $W^2$ taken together is O, $NR^{4A}$ or S, or $W^2$ and $W^3$ taken together is O, $NR^{4A}$, or S;
$Z^1$, $Z^2$, $Z^3$, and $Z^4$ are each independently N or $CR^5$, or $Z^2$ and $Z^3$ taken together is O, $NR^{5A}$ or S, or $Z^3$ and $Z^4$ taken together is O, $NR^{5A}$, or S; and
$R^{4A}$ and $R^{5A}$ are independently hydrogen, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{4A}$ and the $R^{5A}$ is optionally independently substituted with one, two, three, four, five, or six substituents selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);

or a pharmaceutically acceptable form thereof.

In certain embodiments, the compound of Formula (I) is a compound of Formula (V):

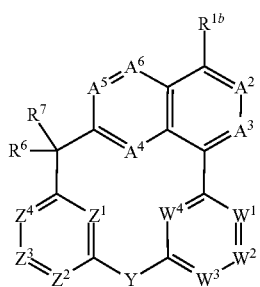

Formula (V)

wherein:
$W^1$, $W^2$, $W^3$, and $W^4$ are each independently N or $CR^4$, or $W^1$ and $W^2$ taken together are O, $NR^{4A}$, or S, or $W^2$ and $W^3$ taken together are O, $NR^{4A}$, or S;
$Z^1$, $Z^2$, $Z^3$, and $Z^4$ are each independently N or $CR^5$, or $Z^2$ and $Z^3$ taken together are O, $NR^{5A}$ or S, or $Z^3$ and $Z^4$ taken together are O, $NR^{5A}$, or S; and
$R^{4A}$ and $R^{5A}$ are independently hydrogen, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{4A}$ and the $R^{5A}$ is optionally independently substituted with 1-6 substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O); or a pharmaceutically acceptable form thereof.

In certain embodiments, the compound of Formula (I) is a compound of Formula (VI):

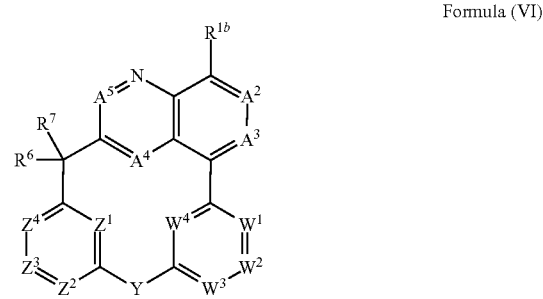

Formula (VI)

wherein:
$W^1$, $W^2$, $W^3$, and $W^4$ are each independently N or $CR^4$, or $W^1$ and $W^2$ taken together are O, $NR^{4A}$, or S, or $W^2$ and $W^3$ taken together are O, $NR^{4A}$, or S;
$Z^1$, $Z^2$, $Z^3$, and $Z^4$ are each independently N or $CR^5$, or $Z^2$ and $Z^3$ taken together are 0, $NR^{5A}$ or S, or $Z^3$ and $Z^4$ taken together are 0, $NR^{5A}$, or S; and
$R^{4A}$ and $R^{5A}$ are independently hydrogen, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{4A}$ and the $R^{5A}$ is optionally independently substituted with 1-6 substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O); or a pharmaceutically acceptable form thereof.

In certain embodiments, provided herein is a compound of Formula (I), (II), (III), or (IV), or of Formula (V) or (VI), wherein Y is a bond. In certain embodiments, Y is a linker having a length of up to 5 atoms, up to 4 atoms, up to 3 atoms, or up to 2 atoms. In certain embodiments, Y is in the direction of Z-Y-W (wherein Z refers to Z or the Z-containing ring and W refers to W or the W-containing ring as applicable in Formula (I), (II), (III), or (IV), or of Formula (V) or (VI), and subformulae thereof). In certain embodiments, Y is a $C_{1-6}$ alkylene, wherein one or more —$CH_2$— is optionally independently replaced by —O—, —C(O)—, —N(R$^{10}$)—, —N(R$^{10}$)C(O)—, —C(O)N(R$^{10}$)—, —N(R$^{10}$)C(O)N(R$^{11}$)—, —S(O)$_p$—, —N(R$^{10}$)S(O)$_2$—, —S(O)$_2$N(R$^{10}$)—, or —N(R$^{10}$)S(O)$_2$N(R$^{11}$)—. In certain embodiments, Y is —(CR$^{16}$R$^{17}$)$_q$—, —(CR$^{16}$R$^{17}$)$_m$O(CR$^{16}$R$^{17}$)$_n$—, —(CR$^{16}$R$^{17}$)$_m$C(O)(CR$^{16}$R$^{17}$)$_n$—, —(CR$^{16}$R$^{17}$)$_m$N(R$^{10}$)(CR$^{16}$R$^{17}$)$_n$—, —(CR$^{16}$R$^{17}$)$_m$N(R$^{10}$)C(O)(CR$^{16}$R$^{17}$)$_n$—, —(CR$^{16}$R$^{17}$)$_m$C(O)N(R$^{10}$)(CR$^{16}$R$^{17}$)$_n$—, —(CR$^{16}$R$^{17}$)$_m$N(R$^{10}$)C(O)N(R$^{11}$)(CR$^{16}$R$^{17}$)$_n$—, —(CR$^{16}$R$^{17}$)$_m$S(O)$_p$(CR$^{16}$R$^{17}$)$_n$—, —(CR$^{16}$R$^{17}$)$_m$N(R$^{10}$)S(O)$_2$(CR$^{16}$R$^{17}$)$_n$—, —(CR$^{16}$R$^{17}$)$_m$S(O)$_2$N(R$^{10}$)(CR$^{16}$R$^{17}$)$_n$—, or —(CR$^{16}$R$^{17}$)$_m$N(R$^{10}$)S(O)$_2$N(R$^{11}$)(CR$^{16}$R$^{17}$)$_n$—;

wherein:
  R$^{16}$ and R$^{17}$, at each occurrence, are each independently hydrogen, halo, hydroxy, CN, NO$_2$, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, C$_{1-6}$ hydroxyalkoxy, C$_{1-6}$ heteroalkoxy, or 3-6 membered heterocycloalkoxy, or together with the C to which each is attached are combined to form a C(O), C$_{3-6}$ cycloalkyl, or 3-6 membered heterocycloalkyl;
  each m is independently an integer of 0, 1, 2, or 3;
  each n is independently an integer of 0, 1, 2, or 3;
  wherein the sum of m and n is 0, 1, 2, 3, 4, 5, or 6;
  each p is independently an integer of 0, 1, or 2; and each q is independently an integer of 0, 1, 2, 3, 4, 5, or 6.

In certain embodiments, provided herein is a compound of Formula (I), (II), (III), or (IV), or of Formula (V) or (VI), wherein R$^7$ is an imidazolyl, a triazolyl, a tetrazolyl, an oxazolyl, a thiazolyl, an oxadiazolyl, a thiadiazolyl, a pyridyl, or a pyrimidinyl, each optionally substituted with 1-4 substituents independently selected from halo, CN, NO$_2$, R$^9$, —OR$^9$, —C(O)R$^9$, —C(O)OR$^9$, —OC(O)R$^9$, —OC(O)OR$^9$, —C(O)NR$^{10}$R$^{11}$, —NR$^{10}$R$^{11}$, —NR$^{10}$C(O)R$^9$, —NR$^{10}$C(O)OR$^9$, —NR$^{10}$C(O)NR$^{10}$R$^{11}$, —NR$^{10}$S(O)$_2$R$^9$, —S(O)$_p$R$^9$, —S(O)$_2$NR$^{10}$R$^{11}$, or —NR$^{10}$S(O)$_2$NR$^{10}$R$^{11}$.

In certain embodiments, provided herein is a compound of Formula (I), (II), (III), or (IV), or of Formula (V) or (VI), wherein R$^6$ is CN, R$^9$, —OR$^9$, —OC(O)R$^9$, —OC(O)OR$^9$, —NR$^{10}$R$^{11}$, —NR$^{10}$R$^9$, —NR$^{10}$C(O)R$^9$ or —NR$^{10}$C(NR$^{10}$)NR$^{10}$R$^{11}$.

In certain embodiments, provided herein is a compound of Formula (I), (II), (III), or (IV), or of Formula (V) or (VI), wherein R$^6$ is CN, R$^9$, —OR$^9$, —OC(O)R$^9$, —OC(O)OR$^9$, —NR$^{10}$R$^{11}$, —NR$^{10}$R$^9$, or —NR$^{10}$C(O)R$^9$.

In certain embodiments, provided herein is a compound of Formula (I), (II), (III), or (IV), or of Formula (V) or (VI), wherein R$^{10}$ and R$^{11}$ together form a divalent group, such as —(CH$_2$)$_x$—, wherein x=2-5, —CH$_2$CH$_2$OCH$_2$CH$_2$—, or —CH$_2$CH$_2$NR$^{18}$CH$_2$CH$_2$—, wherein R$^{18}$ is independently hydrogen, C$_{1-6}$ alkyl, C$_{1-6}$ haloalkyl, C$_{1-6}$ hydroxyalkyl, C$_{1-6}$ heteroalkyl, 3-6 membered heterocycloalkyl, or 5-12 membered heteroaryl.

In certain embodiments, provided herein is a compound of Formula (I), (II), (III), or (IV), or of Formula (V) or (VI), wherein R$^6$ is hydrogen, —CH$_3$, hydroxy, —OCH$_3$, —OCD$_3$, —NH$_2$, —NHCH$_3$, or —NH(OCH$_3$). In some embodiments, R$^6$ is —NH(CH$_2$CH$_2$)Cl, —NH(CH$_2$CH$_2$)F, or N-linked morpholino.

In certain embodiments, provided herein is a compound of Formula (I), (II), (III), or (IV), or of Formula (V) or (VI), wherein the compound has a MW of no more than 1,000 g/mol. In certain embodiments, the compound has a MW of no more than 900 g/mol, no more than 800 g/mol, no more than 700 g/mol, no more than 600 g/mol, or no more than 500 g/mol. In certain embodiments, the compound has a MW of no more than 600 g/mol. In certain embodiments, the compound has a MW of no more than 500 g/mol.

In certain embodiments, provided herein is a compound of Formula (I), (II), (III), or (IV), or of Formula (V) or (VI), wherein the compound is a racemate or a mixture of diastereomers, or a mixture of stereoisomers.

In certain embodiments, the compound of Formula (I) is a compound of Formula (Ia) or the compound of Formula (I) is a compound of Formula (Ib):

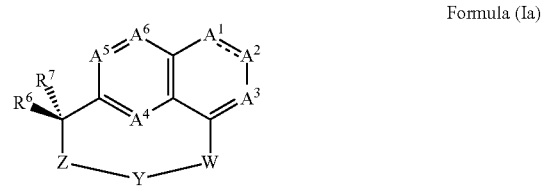

Formula (Ia)

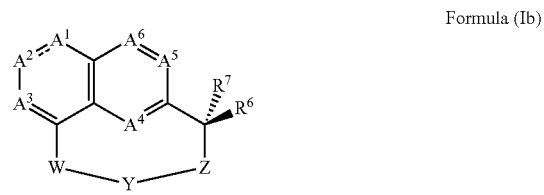

Formula (Ib)

or a pharmaceutically acceptable form thereof.

In certain embodiments, the compound of Formula (II) is a compound of Formula (IIa) or the compound of Formula (II) is a compound of Formula (IIb):

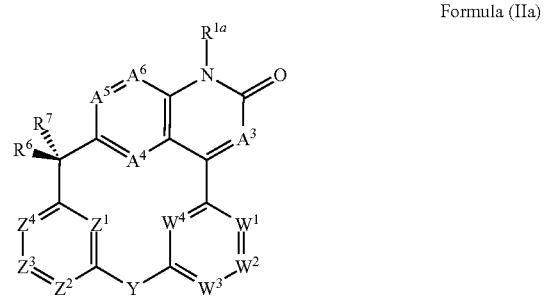

Formula (IIa)

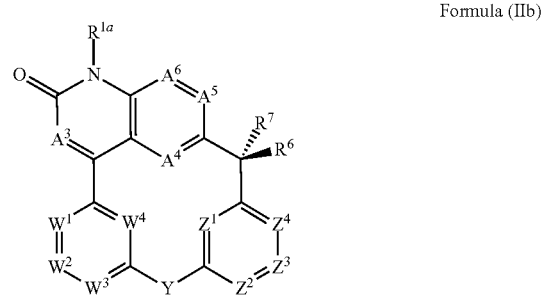

Formula (IIb)

or a pharmaceutically acceptable form thereof.

In certain embodiments, the compound of Formula (II) is a compound of Formula (II-1):

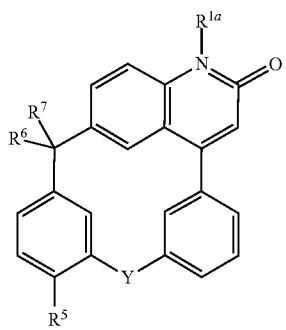

Formula (II-1)

or a pharmaceutically acceptable form thereof.

In certain embodiments, the compound of Formula (II-1) is a compound of Formula (IIa-1) or the compound of Formula (II-1) is a compound of Formula (IIb-1):

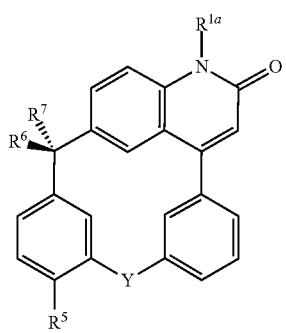

Formula (IIa-1)

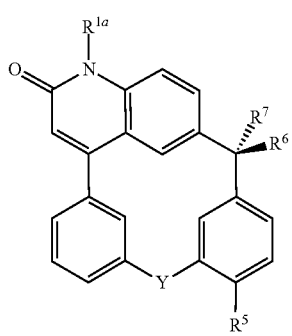

Formula (IIb-1)

or a pharmaceutically acceptable form thereof.

In certain embodiments, the compound of Formula (II) is a compound of Formula (II-2):

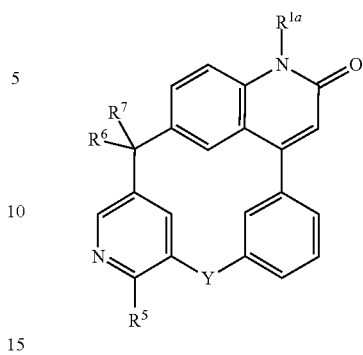

Formula (II-2)

or a pharmaceutically acceptable form thereof.

In certain embodiments, the compound of Formula (II-2) is a compound of Formula (IIa-2) or the compound of Formula (II-2) is a compound of Formula (IIb-2):

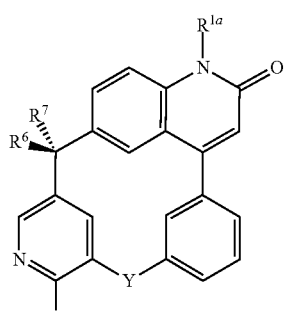

Formula (IIa-2)

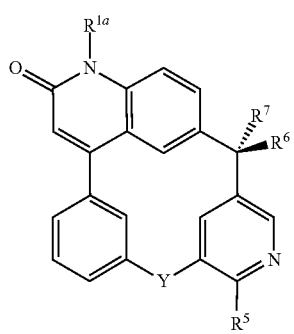

Formula (IIb-2)

or a pharmaceutically acceptable form thereof.

In certain embodiments, the compound of Formula (III) is a compound of Formula (IIIa) or the compound of Formula (III) is a compound of Formula (IIIb):

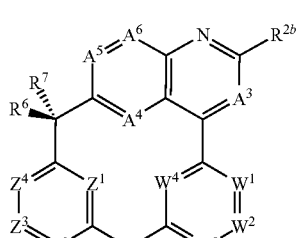

Formula (IIIa)

Formula (IIIb)

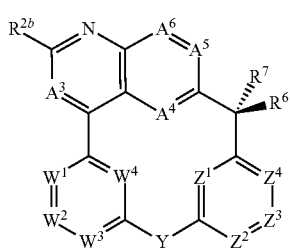

or a pharmaceutically acceptable form thereof.

In certain embodiments, the compound of Formula (III) is a compound of Formula (III-1):

Formula (III-1)

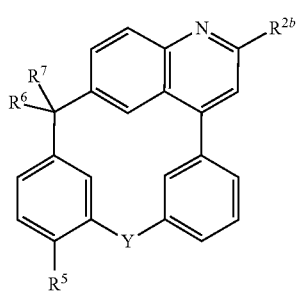

or a pharmaceutically acceptable form thereof.

In certain embodiments, the compound of Formula (III-1) is a compound of Formula (IIIa-1) or the compound of Formula (III-1) is a compound of Formula (IIIb-1):

Formula (IIIa-1)

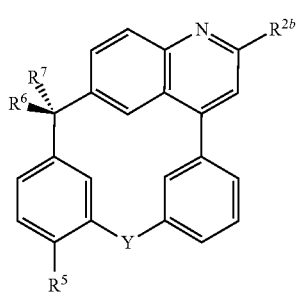

Formula (IIIb-1)

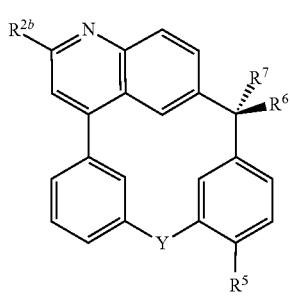

or a pharmaceutically acceptable form thereof.

In certain embodiments, the compound of Formula (III) is a compound of Formula (III-2):

Formula (III-2)

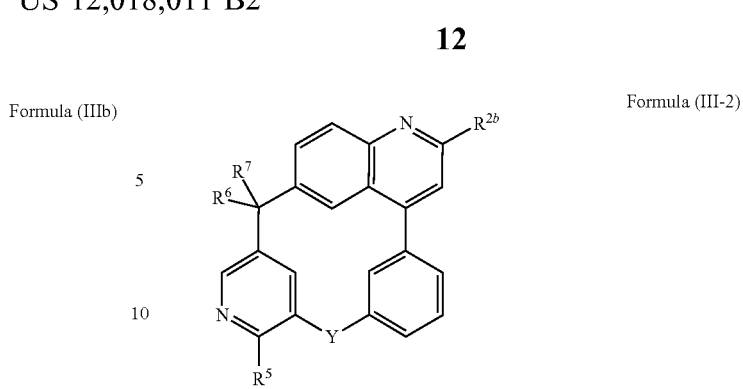

or a pharmaceutically acceptable form thereof.

In certain embodiments, the compound of Formula (III-2) is a compound of Formula (IIIa-2) or the compound of Formula (III-2) is a compound of Formula (IIIb-2):

Formula (IIIa-2)

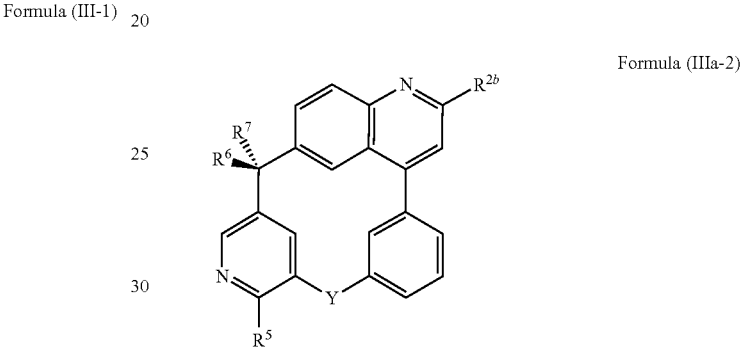

Formula (IIIb-2)

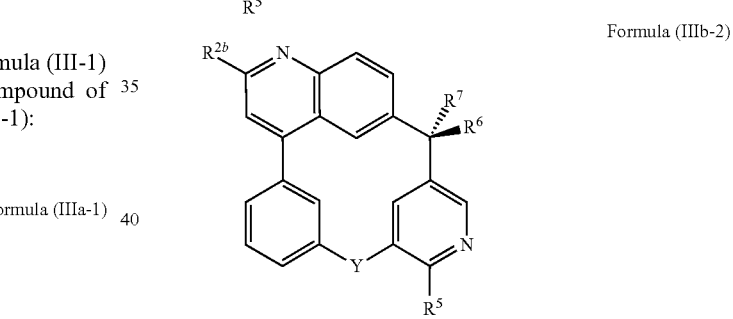

or a pharmaceutically acceptable form thereof.

In certain embodiments, the compound of Formula (III) is a compound of Formula (III-3):

Formula (III-3)

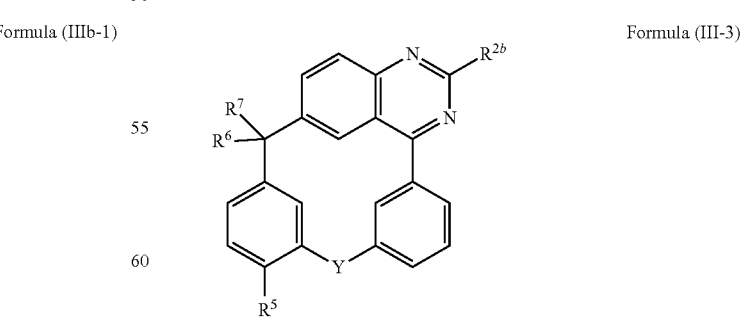

or a pharmaceutically acceptable form thereof.

In some embodiments, the compound of Formula (III-3) is a compound of Formula (IIIa-3) or Formula (IIIb-3):

Formula (IIIa-3)

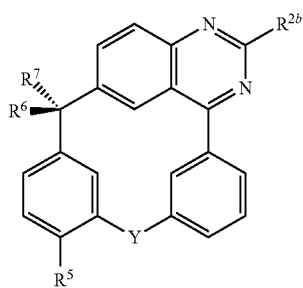

Formula (IIIb-3)

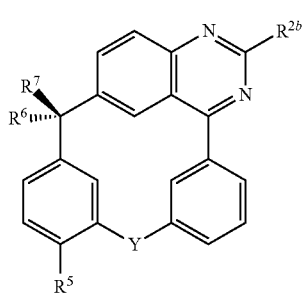

or a pharmaceutically acceptable form thereof.

In certain embodiments, the compound of Formula (IV) is a compound of Formula (IVa) or the compound of Formula (IV) is a compound of Formula (IVb):

Formula (IVa)

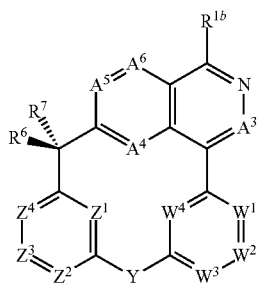

Formula (IVb)

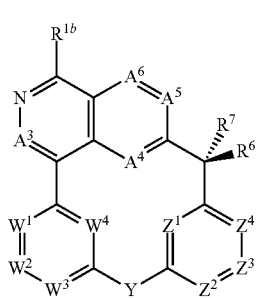

or a pharmaceutically acceptable form thereof.

In certain embodiments, the compound of Formula (IV) is a compound of Formula (IV-1):

Formula (IV-1)

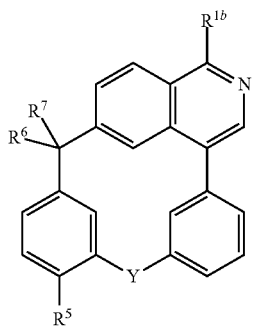

or a pharmaceutically acceptable form thereof.

In certain embodiments, the compound of Formula (IV-1) is a compound of Formula (IVa-1) or the compound of Formula (IV-1) is a compound of Formula (IVb-1):

Formula (IVa-1)

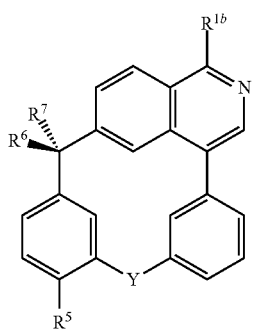

Formula (IVb-1)

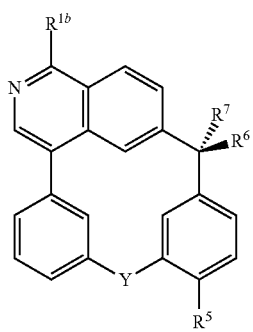

or a pharmaceutically acceptable form thereof.

In certain embodiments, the compound of Formula (IV) is a compound of Formula (IV-2):

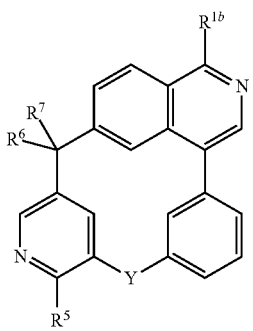

Formula (IV-2)

or a pharmaceutically acceptable form thereof.

In certain embodiments, the compound of Formula (IV-2) is a compound of Formula (IVa-2) or the compound of Formula (IV-2) is a compound of Formula (IVb-2):

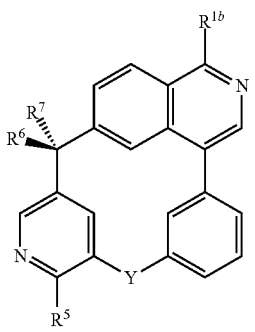

Formula (IVa-2)

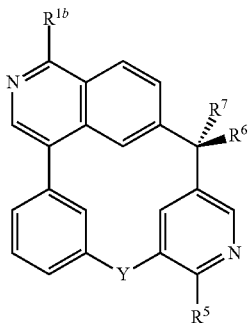

Formula (IVb-2)

or a pharmaceutically acceptable form thereof.

In some embodiments, the compound of Formula (V) is a compound of Formula (Va) or Formula (Vb):

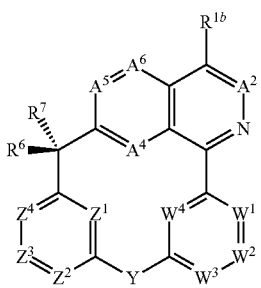

Formula (Va)

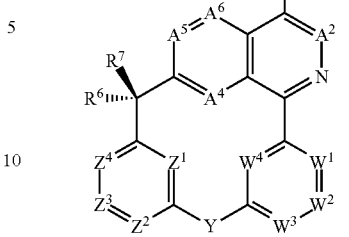

Formula (Vb)

or a pharmaceutically acceptable form thereof.

In some embodiments, the compound of Formula (V) is a compound of Formula (V-1):

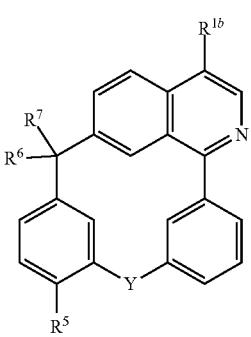

Formula (V-1)

or a pharmaceutically acceptable form thereof.

In some embodiments, the compound of Formula (V-1) is a compound of Formula (Va-1) or Formula (Vb-1):

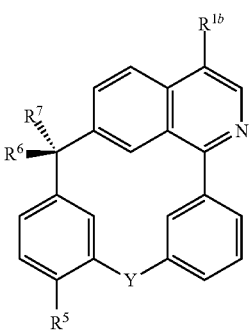

Formula (Va-1)

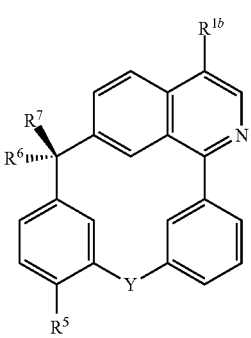

Formula (Vb-1)

or a pharmaceutically acceptable form thereof.

In some embodiments, the compound of Formula (VI) is a compound of Formula (VIa) or Formula (VIb):

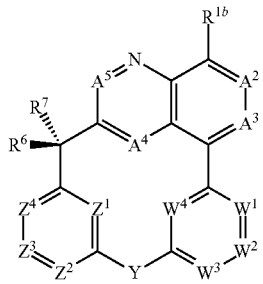

Formula (VIa)

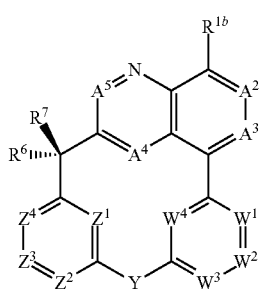

Formula (VIb)

or a pharmaceutically acceptable form thereof.

In some embodiments, the compound of Formula (VI) is a compound of Formula (VI-1):

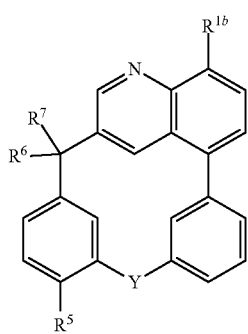

Formula (VI-1)

or a pharmaceutically acceptable form thereof.

In some embodiments, the compound of Formula (VI-1) is a compound of Formula (VIa-1) or Formula (VIb-1):

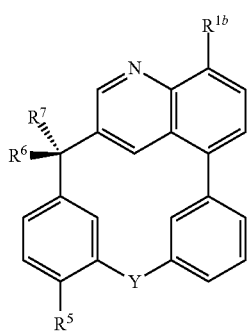

Formula (VIa-1)

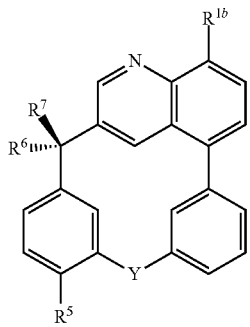

Formula (VIb-1)

or a pharmaceutically acceptable form thereof.

In certain embodiments, the compound of Formula (I), (II), (II-1), (II-2), (III), (III-1), (III-2), (IV), (IV-1), or (IV-2), for example, the compound of Formula (Ia), (Ib), (IIa), (IIa-1), (IIa-2), (IIb), (IIb-1), (IIb-2), (IIIa), (IIIa-1), (IIIa-2), (IIIb), (IIIb-1), (IIIb-2), (IVa), (IVa-1), (IVa-2), (IVb), (IVb-1), or (IVb-2), or the compound of Formula (III-3), (IIIa-3), (IIIb-3), (V), (Va), (Vb), (V-1), (Va-1), (Vb-1), (VI), (VIa), (VIb), (VI-1), (VIa-1), or (VIb-1), or a pharmaceutically acceptable form thereof, as disclosed herein, is a single enantiomer or a single diastereomer. In certain embodiments, a compound disclosed herein is a single enantiomer. In certain embodiments, a compound disclosed herein is an (R)-enantiomer. In certain embodiments, a compound disclosed herein has an enantiomeric excess of greater than 10% f the (R)-enantiomer, such as an enantiomeric excess of 15% or more, 20% or more, 25% or more, 30% or more, 35% or more, 40% or more, 45% or more, 50% or more, 55% or more, 60% r more, 65% or more, 70% or more, 75% or more, 80% or more, 85% or more, 90% or more, 95% or more, 98% or more, 99% or more, of the (R)-enantiomer. In certain embodiments, a compound disclosed herein is an (S)-enantiomer. In certain embodiments, a compound disclosed herein has an enantiomeric excess of greater than 10% f the (S)-enantiomer, such as an enantiomeric excess of 15% or more, 20% or more, 25% or more, 30% or more, 35% or more, 40% or more, 45% or more, 50% or more, 55% or more, 60% or more, 65% or more, 70% r more, 75% or more, 80% or more, 85% or more, 90% or more, 95% or more, 98% or more, 99% or more, of the (S)-enantiomer.

In certain embodiments, provided herein is a pharmaceutical composition comprising a compound of Formula (I), (II), (II-1), (II-2), (III), (III-1), (III-2), (IV), (IV-1), or (IV-2), for example, the compound of Formula (Ia), (Ib), (IIa), (IIa-1), (IIa-2), (IIb), (IIb-1), (IIb-2), (IIIa), (IIIa-1), (IIIa-2), (IIIb), (IIIb-1), (IIIb-2), (IVa), (IVa-1), (IVa-2), (IVb), (IVb-1), or (IVb-2), or pharmaceutically acceptable form thereof, or the compound of Formula (III-3), (IIIa-3), (IIIb-3), (V), (Va), (Vb), (V-1), (Va-1), (Vb-1), (VI), (VIa), (VIb), (VI-1), (VIa-1), or (VIb-1), or a pharmaceutically acceptable form thereof, and a pharmaceutically acceptable carrier, excipient or diluent.

In certain embodiments, the compound of Formula (I), (II), (II-1), (II-2), (III), (III-1), (III-2), (IV), (IV-1), or (IV-2), for example, the compound of Formula (Ia), (Ib), (IIa), (IIa-1), (IIa-2), (IIb), (IIb-1), (IIb-2), (IIIa), (IIIa-1), (IIIa-2), (IIIb), (IIIb-1), (IIIb-2), (IVa), (IVa-1), (IVa-2), (IVb), (IVb-1), or (IVb-2), or a pharmaceutically acceptable form thereof, or the compound of Formula (III-3), (IIIa-3), (IIIb-3), (V), (Va), (Vb), (V-1), (Va-1), (Vb-1), (VI), (VIa), (VIb), (VI-1), (VIa-1), or (VIb-1), or a pharmaceutically acceptable form thereof, as disclosed herein, is a farnesyltransferase inhibitor. In certain embodiments, the compound, or pharmaceutically acceptable form thereof, as disclosed herein, is a selective farnesyltransferase inhibitor, relative to inhibition of geranylgeranyl transferase type-1, such as geranylgeranyl transferase type-1.

In certain embodiments, the compound of Formula (I), (II), (II-1), (II-2), (III), (III-1), (III-2), (IV), (IV-1), or (IV-2), for example, the compound of Formula (Ia), (Ib), (IIa), (IIa-1), (IIa-2), (IIb), (IIb-1), (IIb-2), (IIIa), (IIIa-1), (IIIa-2), (IIIb), (IIIb-1), (IIIb-2), (IVa), (IVa-1), (IVa-2), (IVb), (IVb-1), or (IVb-2), or a pharmaceutically acceptable form thereof, or the compound of Formula (III-3), (IIIa-3), (IIIb-3), (V), (Va), (Vb), (V-1), (Va-1), (Vb-1), (VI), (VIa), (VIb), (VI-1), (VIa-1), or (VIb-1), or a pharmaceutically acceptable form thereof, as disclosed herein, is metabolically stable, for example, metabolically stable to liver metabolism in a subject, such as metabolically stable to liver metabolism in a human.

In certain embodiments, provided herein is a method of inhibiting a farnesyltransferase, comprising contacting the farnesyltransferase with an effective amount of a compound of Formula (I), (II), (II-1), (II-2), (III), (III-1), (III-2), (IV), (IV-1), or (IV-2), for example, the compound of Formula (Ia), (Ib), (IIa), (IIa-1), (IIa-2), (IIb), (IIb-1), (IIb-2), (IIIa), (IIIa-1), (IIIa-2), (IIIb), (IIIb-1), (IIIb-2), (IVa), (IVa-1), (IVa-2), (IVb), (IVb-1), or (IVb-2), or pharmaceutically acceptable form thereof, or the compound of Formula (III-3), (IIIa-3), (IIIb-3), (V), (Va), (Vb), (V-1), (Va-1), (Vb-1), (VI), (VIa), (VIb), (VI-1), (VIa-1), or (VIb-1), or a pharmaceutically acceptable form thereof. In certain embodiments, provided herein is a method of inhibiting a farnesyltransferase, comprising contacting the farnesyltransferase with an effective amount of a pharmaceutical composition comprising a compound of Formula (I), (II), (II-1), (II-2), (III), (III-1), (III-2), (IV), (IV-1), or (IV-2), for example, the compound of Formula (Ia), (Ib), (IIa), (IIa-1), (IIa-2), (IIb), (IIb-1), (IIb-2), (IIIa), (IIIa-1), (IIIa-2), (IIIb), (IIIb-1), (IIIb-2), (IVa), (IVa-1), (IVa-2), (IVb), (IVb-1), or (IVb-2), or pharmaceutically acceptable form thereof, or the compound of Formula (III-3), (IIIa-3), (IIIb-3), (V), (Va), (Vb), (V-1), (Va-1), (Vb-1), (VI), (VIa), (VIb), (VI-1), (VIa-1), or (VIb-1), or a pharmaceutically acceptable form thereof, and a pharmaceutically acceptable carrier, excipient or diluent. In certain embodiments, the method of inhibiting a farnesyltransferase inhibits farnesylation of H-Ras protein. In certain embodiments, the H-Ras protein has a mutation. In certain embodiments, the method of inhibiting a farnesyltransferase inhibits farnesylation farnesylation of N-Ras protein. In certain embodiments, the N-Ras protein has a mutation.

In certain embodiments, provided herein is a method of treating cancer dependent on a farnesylated protein in a subject, comprising administering a therapeutically effective amount of a compound of Formula (I), (II), (II-1), (II-2), (III), (III-1), (III-2), (IV), (IV-1), or (IV-2), for example, the compound of Formula (Ia), (Ib), (IIa), (IIa-1), (IIa-2), (IIb), (IIb-1), (IIb-2), (IIIa), (IIIa-1), (IIIa-2), (IIIb), (IIIb-1), (IIIb-2), (IVa), (IVa-1), (IVa-2), (IVb), (IVb-1), or (IVb-2), or pharmaceutically acceptable form thereof, or the compound of Formula (III-3), (IIIa-3), (IIIb-3), (V), (Va), (Vb), (V-1), (Va-1), (Vb-1), (VI), (VIa), (VIb), (VI-1), (VIa-1), or (VIb-1), or a pharmaceutically acceptable form thereof, to the subject having cancer dependent on a farnesylated protein. In certain embodiments, provided herein is a method of treating cancer dependent on a farnesylated protein in a subject, comprising administering a therapeutically effective amount of a pharmaceutical composition comprising a compound of Formula (I), (II), (II-1), (II-2), (III), (III-1), (III-2), (IV), (IV-1), or (IV-2), for example, the compound of Formula (Ia), (Ib), (IIa), (IIa-1), (IIa-2), (IIb), (IIb-1), (IIb-2), (IIIa), (IIIa-1), (IIIa-2), (IIIb), (IIIb-1), (IIIb-2), (IVa), (IVa-1), (IVa-2), (IVb), (IVb-1), or (IVb-2), or pharmaceutically acceptable form thereof, or the compound of Formula (III-3), (IIIa-3), (IIIb-3), (V), (Va), (Vb), (V-1), (Va-1), (Vb-1), (VI), (VIa), (VIb), (VI-1), (VIa-1), or (VIb-1), or a pharmaceutically acceptable form thereof, and a pharmaceutically acceptable carrier, excipient or diluent to the subject having cancer dependent on a farnesylated protein. In certain embodiments, the cancer dependent on a farnesylated protein is a solid tumor. In certain embodiments, the cancer dependent on a farnesylated protein is a cancer dependent on farnesylated H-Ras protein. In certain embodiments, the cancer dependent on a farnesylated protein has an H-Ras protein mutation. In certain embodiments, the cancer dependent on a farnesylated protein is head and neck cancer. In certain embodiments, the cancer dependent on a farnesylated protein is a squamous cell carcinoma (SCC). In certain embodiments, the head and neck cancer is head and neck squamous cell carcinoma (HNSCC). In certain embodiments, provided herein is a method of treating cancer dependent on a farnesylated protein in a subject, wherein the subject is a human.

In certain embodiments, provided herein is a method of treating cancer dependent on a farnesylated protein in a subject, comprising administering a therapeutically effective amount of a compound of Formula (I), (II), (II-1), (II-2), (III), (III-1), (III-2), (IV), (IV-1), or (IV-2), for example, the compound of Formula (Ia), (Ib), (IIa), (IIa-1), (IIa-2), (IIb), (IIb-1), (IIb-2), (IIIa), (IIIa-1), (IIIa-2), (IIIb), (IIIb-1), (IIIb-2), (IVa), (IVa-1), (IVa-2), (IVb), (IVb-1), or (IVb-2), or pharmaceutically acceptable form thereof, or the compound of Formula (III-3), (IIIa-3), (IIIb-3), (V), (Va), (Vb), (V-1), (Va-1), (Vb-1), (VI), (VIa), (VIb), (VI-1), (VIa-1), or (VIb-1), or a pharmaceutically acceptable form thereof, to the subject having cancer dependent on a farnesylated protein. In certain embodiments, provided herein is a method of treating cancer dependent on a farnesylated protein in a subject, comprising administering a therapeutically effective amount of a pharmaceutical composition comprising a compound of Formula (I), (II), (II-1), (II-2), (III), (III-1), (III-2), (IV), (IV-1), or (IV-2), for example, the compound of Formula (Ia), (Ib), (IIa), (IIa-1), (IIa-2), (IIb), (IIb-1), (IIb-2), (IIIa), (IIIa-1), (IIIa-2), (IIIb), (IIIb-1), (IIIb-2), (IVa), (IVa-1), (IVa-2), (IVb), (IVb-1), or (IVb-2), or pharmaceutically acceptable form thereof, or the compound of Formula (III-3), (IIIa-3), (IIIb-3), (V), (Va), (Vb), (V-1), (Va-1), (Vb-1), (VI), (VIa), (VIb), (VI-1), (VIa-1), or (VIb-1), or a pharmaceutically acceptable form thereof, and a pharmaceutically acceptable carrier, excipient or diluent to the subject having cancer dependent on a farnesylated protein. In certain embodiments, the cancer dependent on a farnesylated protein is a solid tumor. In certain embodiments, the cancer dependent on a farnesylated protein is a cancer dependent on farnesylated N-Ras protein. In certain embodiments, the cancer dependent on a farnesylated protein has an N-Ras protein mutation. In certain embodiments, the cancer dependent on a farnesylated protein is melanoma, acute myeloid leukemia (AML), thyroid carcinoma, lung adenocarcinoma, rectal carcinoma, endometrial carcinoma, or colorectal carcinoma. In certain embodiments, provided herein is a method of treating cancer dependent on a farnesylated protein in a subject, wherein the subject is a human.

5. DETAILED DESCRIPTION

In one embodiment, provided herein are compounds having a structure of any one of Formula (I), (II), (III), or (IV), or a pharmaceutically acceptable form thereof. In one embodiment, provided herein are compounds having a structure of Formula (V) or (VI), or a pharmaceutically acceptable form thereof. In one embodiment, provided herein are compounds having a structure of any one of Formula (Ia), (Ib), (IIa), (IIb), (IIIa), (IIIb), (IVa), or (IVb), or a pharmaceutically acceptable form thereof. In one embodiment, provided herein are compounds having a structure of any one of Formula (Va), (Vb), (VIa), or (VIb), or a pharmaceutically acceptable form thereof. In one embodiment, provided herein are compounds having a structure of any one of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or a pharmaceutically acceptable form thereof. In one embodiment, provided herein are compounds having a structure of any one of Formula (III-3), (IIIa-3), (IIIb-3), (V-1), (Va-1), (Vb-1), (VI-1), (VIa-1), or (VIb-1), or a pharmaceutically acceptable form thereof.

In one embodiment, provided herein is a pharmaceutical composition comprising a compound having a structure of any one of Formula (I), (II), (III), or (IV), or a pharmaceutically acceptable form thereof, and a pharmaceutically acceptable carrier, diluent or excipient. In one embodiment, provided herein is a pharmaceutical composition comprising a compound having a structure of Formula (V) or (VI), or a pharmaceutically acceptable form thereof, and a pharmaceutically acceptable carrier, diluent or excipient. In one embodiment, provided herein is a pharmaceutical composition comprising a compound having a structure of any one of Formula (Ia), (Ib), (IIa), (IIb), (IIIa), (IIIb), (IVa), or (IVb), or a pharmaceutically acceptable form thereof, or of Formula (Va), (Vb), (VIa), or (VIb), or a pharmaceutically acceptable form thereof, and a pharmaceutically acceptable carrier, diluent or excipient. In one embodiment, provided herein is a pharmaceutical composition comprising a compound having a structure of any one of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or a pharmaceutically acceptable form thereof, or of Formula (III-3), (IIIa-3), (IIIb-3), (V-1), (Va-1), (Vb-1), (VI-1), (VIa-1), or (VIb-1), or a pharmaceutically acceptable form thereof, and a pharmaceutically acceptable carrier, diluent or excipient.

In another embodiment, provided are methods of treating cancer dependent on a farnesylated protein, which comprises administering to a subject a therapeutically effective amount of a compound having a structure of any one of Formula (I), (II), (III), or (IV), or a pharmaceutically acceptable form thereof, or administering a pharmaceutical composition comprising the same. In another embodiment, provided are methods of treating cancer dependent on a farnesylated protein, which comprises administering to a subject a therapeutically effective amount of a compound having a structure of Formula (V) or (VI), or a pharmaceutically acceptable form thereof, or administering a pharmaceutical composition comprising the same. In another embodiment, provided are methods of treating cancer dependent on a farnesylated protein, which comprises administering to a subject a therapeutically effective amount of a compound having a structure of any one of Formula (Ia), (Ib), (IIa), (IIb), (IIIa), (IIIb), (IVa), or (IVb), or a pharmaceutically acceptable form thereof, or of Formula (Va), (Vb), (VIa), or (VIb), or a pharmaceutically acceptable form thereof, or administering a pharmaceutical composition comprising the same. In another embodiment, provided are methods of treating cancer, which comprises administering to a subject a therapeutically effective amount of a compound having a structure of any one of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or a pharmaceutically acceptable form thereof, or of Formula (III-3), (IIIa-3), (IIIb-3), (V-1), (Va-1), (Vb-1), (VI-1), (VIa-1), or (VIb-1), or a pharmaceutically acceptable form thereof or administering a pharmaceutical composition comprising the same. Examples of the cancers dependent on a farnesylated protein treated according to the methods of treating provided herein, are described herein.

While specific embodiments have been discussed, the specification is illustrative only and not restrictive. Many variations of this disclosure will become apparent to those skilled in the art upon review of this specification.

Unless defined otherwise, all technical and scientific terms used herein have the same meaning as is commonly understood by one skilled in the art to which this specification pertains.

As used herein, the articles "a," "an," and "the" refer to one or to more than one of the grammatical object of the article. By way of example, a sample refers to one sample or two or more samples.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% f a given value or range.

As used herein, the term "administer," "administering," or "administration" refers to the act of delivering, or causing to be delivered, a compound or a pharmaceutical composition to the body of a subject by a method described herein or otherwise known in the art. Administering a compound or a pharmaceutical composition includes prescribing a compound or a pharmaceutical composition to be delivered into the body of a patient. Exemplary forms of administration include oral dosage forms, such as tablets, capsules, syrups, suspensions; injectable dosage forms, such as intravenous (IV), intramuscular (IM), or intraperitoneal (IP); transdermal dosage forms, including creams, jellies, powders, or patches; buccal dosage forms; inhalation powders, sprays, suspensions, and rectal suppositories.

The term "effective amount" or "therapeutically effective amount" or "dose" or "dosage" refers to that amount of a compound or pharmaceutical composition described herein that is sufficient to effect the intended application including, but not limited to, disease treatment, as illustrated below. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The specific dose will vary depending on, for example, the particular compound chosen, the dosing regimen to be followed, whether it is administered in combination with other agents, timing of administration, the tissue to which it is administered, and the physical delivery system in which it is carried. In certain embodiments, the therapeutically effective amount is sufficient to provide a therapeutic benefit in the treatment or management of the disease or disorder or to delay or minimize one or more symptoms associated with the disease or disorder. The term also refers to the amount of a compound that sufficiently elicits the biological or medical response of a biological molecule (e.g., a protein, enzyme, RNA, or DNA), cell, tissue, system, animal, or human, which is being sought by a researcher, veterinarian, medical doctor, or clinician.

"Enantiomers" are a pair of stereoisomers that are non-superimposable mirror images of each other. A mixture of a pair of enantiomers in any proportion can be known as a "racemic" mixture. The term "(±)" or "(rac)" is used to designate a racemic mixture where appropriate. "Diastereoisomers" are stereoisomers that have at least two asymmetric atoms, but which are not mirror-images of each other. The absolute stereochemistry can be specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

The "enantiomeric excess" or "% enantiomeric excess" of composition, for example a composition comprising a mixture of enantiomers of a compound, can be calculated using the equation shown below. In the example shown below, a mixture containing 90% f one enantiomer, e.g., an S enantiomer, and 10% f the other enantiomer, e.g., an R enantiomer, is said to have an enantiomeric excess of 80%.

$$ee=(90-10)/100=80\%.$$

In some embodiments, a compound described herein is a mixture of enantiomers of the compound and contains an enantiomeric excess of at least about 1%, about 5%, about 10%, about 20%, about 30%, about 40%, about 50%, about 60%, about 70%, about 75%, about 80%, about 85%, about 90%, about 95%, about 97%, about 98%, or about 99% f the S enantiomer. In other words, in some embodiments, a compound described herein is a mixture of enantiomers of the compound and contains an enantiomeric excess of the S enantiomer over the R enantiomer. In other embodiments, a compound described herein is a mixture of enantiomers of the compound and contains an enantiomeric excess of at least about 1%, about 5%, about 10%, about 20%, about 30%, about 40%, about 50%, about 60%, about 70%, about 75%, about 80%, about 85%, about 90%, about 95%, about 97%, about 98%, or about 99% f the R enantiomer. In other words, in some embodiments, a compound described herein is a mixture of enantiomers of the compound and contains an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the amount of one enantiomer is greater than the amount of that one enantiomer in a control mixture of the racemic composition (e.g., greater than 1:1 by weight). For example, an enantiomerically enriched preparation of the S enantiomer, means a preparation of the compound having greater than about 50% by weight of the S enantiomer relative to the total weight of the preparation (e.g., total weight of S and R isomers), such as at least about 55% by weight, at least about 60% by weight, at least about 65% by weight, at least about 70% by weight, at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to the total weight of the preparation, such as at least about 90% by weight, and further such as at least about 95% by weight. In certain embodiments, the compound provided herein is made up of at least about 90% by weight of one enantiomer. In other embodiments, the compound is made up of at least about 95%, about 98%, or about 99% by weight of one enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, in some embodiments, the compound mixture has an (S)-enantiomeric excess of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, or greater than about 99%. In some embodiments, the compound mixture has an (S)-enantiomeric excess of about 55%, about 60%, about 65%, about 70%, about 75%, about 80%, about 85%, about 90%, about 95%, about 96%, about 97%, about 98%, about 99%, or about 99.5%, or more. In some embodiments, the compound mixture has an (S)-enantiomeric excess of about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

In other embodiments, the compound mixture has an (R)-enantiomeric excess of greater than about 10%, greater than about 20%, greater than about 30%, greater than about 40%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, or greater than about 99%. In some embodiments, the compound mixture has an (R)-enantiomeric excess of about 55%, about 60%, about 65%, about 70%, about 75%, about 80%, about 85%, about 90%, about 95%, about 96%, about 97%, about 98%, about 99%, or about 99.5%, or more. In some embodiments, the compound mixture has an (R)-enantiomeric excess of about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%.

In other embodiments, the compound mixture contains identical chemical entities except for their stereochemical orientations, namely (S)- or (R)-isomers. For example, if a compound disclosed herein has —CH(R)— unit, and R is not hydrogen, then the —CH(R)— is in an (S)- or (R)-stereochemical orientation for each of the identical chemical entities (i.e., (S)- or (R)-stereoisomers). In some embodiments, the mixture of identical chemical entities (i.e., mixture of stereoisomers) is a racemic mixture of (S)- and (R)-isomers. In another embodiment, the mixture of the identical chemical entities (i.e., mixture of stereoisomers) contains predominately (S)-isomer or predominately (R)-isomer. For example, in some embodiments, the (S)-isomer in the mixture of identical chemical entities (i.e., mixture of stereoisomers) is present at about 55%, about 60%, about 65%, about 70%, about 75%, about 80%, about 85%, about 90%, about 95%, about 96%, about 97%, about 98%, about 99%, or about 99.5% by weight, or more, relative to the total weight of the mixture of (S)- and (R)-isomers. In some embodiments, the (S)-isomer in the mixture of identical chemical entities (i.e., mixture of stereoisomers) is present at an (S)-enantiomeric excess of about 10% to about 99.5%, about 20% to about 99.5%, about 30% to about 99.5%, about 40% to about 99.5%, about 50% to about 99.5%, about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%. In other embodiments, the (R)-isomer in the mixture of identical chemical entities (i.e., mixture of stereoisomers) is present at about 55%, about 60%, about 65%, about 70%, about 75%, about 80%, about 85%, about 90%, about 95%, about 96%, about 97%, about 98%, about 99%, or about 99.5% by weight, or more, relative to the total weight of the mixture of (S)- and (R)-isomers. In some embodiments, the (R)-isomers in the mixture of identical chemical entities (i.e., mixture of stereoisomers) is present at an (R)-enantiomeric excess of about 10% to about 99.5%, about 20% to about 99.5%, about 30% to about 99.5%, about 40% to about 99.5%, about 50% to about 99.5%, about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%. Enantiomers can be isolated from racemic mixtures by any method known to those skilled in the art, including chiral high pressure liquid chromatography (HPLC) and supercritical fluid chromatography (SFC), the formation and crystallization of chiral salts, or prepared by asymmetric syntheses. See, for example, Enantiomers, Racemates and Resolutions (Jacques, Ed., Wiley Interscience, New York, 1981); Wilen et al., Tetrahedron 33:2725 (1977); Stereochemistry of Carbon Compounds (E. L. Eliel, Ed., McGraw-Hill, N Y, 1962); and Tables of Resolving Agents and Optical Resolutions p. 268 (E. L. Eliel, Ed., Univ. of Notre Dame Press, Notre Dame, IN 1972).

It is further understood that reference to a compound as disclosed herein having one or more sterocenters without designating the specific chirality (e.g., R- or S-enantionmer) will be understood to refer to the compound as racemic mixture (or a mixture of diastereomers), while inclusion of R- or S-designations will be understood to refer to an enantiomer (or a diastereomer) form of the compound, such as an enantiomerically (or diastereomerically) enriched form of the compound, or an enantiomeric excess of the specified enantiomer form of the compound, in accordance with discussion above regarding enantiomeric enriched and enantiomeric excess. Notation of a compound with an R- or S-designation is understood to include an enantiomerically enriched or an enantiomeric excess of the specified enantiomer of the compound, and not limited to only 100% f the single specified enantiomer of the compound.

In certain embodiments, the pharmaceutically acceptable form is an isomer. "Isomers" are different compounds that have the same molecular formula. In some embodiments, the isomer may be a stereoisomer. In some embodiments, the isomer may be a tautomer. In some embodiments, the isomer may be a geometric isomer. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof, and other mixtures thereof, as falling within the scope of this disclosure.

Unless otherwise stated, structures depicted herein are also meant to include compounds which differ only in the presence of one or more isotopically enriched atoms. For example, compounds having the present structures except for the replacement or enrichment of a hydrogen by deuterium or tritium at one or more atoms in the molecule, or the replacement or enrichment of a carbon by $^{13}C$ or $^{14}C$ at one or more atoms in the molecule, are within the scope of this disclosure. In one embodiment, provided herein are isotopically labeled compounds having one or more hydrogen atoms replaced by or enriched by deuterium. In one embodiment, provided herein are isotopically labeled compounds having one or more hydrogen atoms replaced by or enriched by tritium. In one embodiment, provided herein are isotopically labeled compounds having one or more carbon atoms replaced or enriched by $^{13}C$. In one embodiment, provided herein are isotopically labeled compounds having one or more carbon atoms replaced or enriched by $^{14}C$.

The term "isotopologue" refers to isotopically-enriched compounds which are identical to those recited herein, but for the fact that one or more atoms are replaced by an atom having an atomic mass or mass number different from the atomic mass or mass number usually found in nature. Unless otherwise stated, structures depicted herein are also meant to include compounds which differ only in the presence of one or more isotopically enriched atoms. Examples of isotopes that can be incorporated into compounds described herein include isotopes of hydrogen, carbon, nitrogen, oxygen, phosphorus, fluorine and chlorine, such as $^{2}H$, $^{3}H$, $^{13}C$, $^{14}C$ $^{15}N$, $^{18}O$, $^{17}O$, $^{32}P$, $^{33}P$, $^{33}S$, $^{34}S$, $^{36}S$, $^{18}F$, $^{35}Cl$, $^{36}Cl$, and $^{37}Cl$, respectively, each of which is also within the scope of this description. For example, compounds having the present structures except for the replacement or enrichment of a hydrogen by deuterium or tritium at one or more atoms in the molecule, are within the scope of this disclosure. In one embodiment, provided herein are isotopically labeled compounds having one or more hydrogen atoms replaced by or enriched by deuterium. In one embodiment, provided herein are isotopically labeled compounds having one or more hydrogen atoms replaced by or enriched by tritium. Further, substitution with heavier isotopes such as deuterium (i.e., $^2$H) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. Isotopically-enriched compounds of Formula (I), (II), (III), or (IV), or a pharmaceutically acceptable form thereof, or of Formula (V) or (VI), or a pharmaceutically acceptable form thereof, for example a compound of Formula (Ia), (Ib), (IIa), (IIb), (IIIa), (IIIb), (IVa), or (IVb), such as a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or a pharmaceutically acceptable form thereof, or of Formula (III-3), (IIIa-3), (IIIb-3), (Va), (Vb), (V-1), (Va-1), (Vb-1), (VIa), (VIb), (VI-1), (VIa-1), or (VIb-1), or a pharmaceutically acceptable form thereof, can generally be prepared using procedures known to persons of ordinary skill in the art by substituting an appropriate isotopically-enriched reagent for a non-isotopically-enriched reagent.

When the compounds are enriched with deuterium, the deuterium-to-hydrogen ratio on the deuterated atoms of the molecule substantially exceeds the naturally occurring deuterium-to-hydrogen ratio.

An embodiment described herein may include an isotopologue form of the compound of Formula (I), (II), (III), or (IV), or a pharmaceutically acceptable form thereof, for example a compound of Formula (Ia), (Ib), (IIa), (IIb), (IIIa), (IIIb), (IVa), or (IVb), such as a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or a pharmaceutically acceptable form thereof, or of Formula (III-3), (IIIa-3), (IIIb-3), (Va), (Vb), (V-1), (Va-1), (Vb-1), (VIa), (VIb), (VI-1), (VIa-1), or (VIb-1), or a pharmaceutically acceptable form thereof, wherein the isotopologue is substituted on one or more atom members of said compound, or a pharmaceutically acceptable form thereof, with one or more deuterium atoms in place of one or more hydrogen atoms. An embodiment described herein may include a compound of Formula (I), (II), (III), or (IV), or a pharmaceutically acceptable form thereof, for example a compound of Formula (Ia), (Ib), (IIa), (IIb), (IIIa), (IIIb), (IVa), or (IVb), such as a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or a pharmaceutically acceptable form thereof, or of Formula (III-3), (IIIa-3), (IIIb-3), (Va), (Vb), (V-1), (Va-1), (Vb-1), (VIa), (VIb), (VI-1), (VIa-1), or (VIb-1), or a pharmaceutically acceptable form thereof, wherein a carbon atom may have from 1 to 3 hydrogen atoms optionally replaced with deuterium.

As used herein, a "pharmaceutically acceptable form" of compounds disclosed herein includes, but is not limited to, a pharmaceutically acceptable salt, solvate, isomer, and isotopologue (i.e., isotopically labeled derivative) of compounds disclosed herein. In one embodiment, a "pharmaceutically acceptable form" includes, but is not limited to, a pharmaceutically acceptable salt, solvate, isomer, and isotopologue (i.e., isotopically labeled derivative) of a compound of Formula (I), (II), (III), or (IV), or of Formula (V) or (VI), as disclosed herein, such as a pharmaceutically acceptable salt, hydrate, stereoisomer, and isotopologue of a compound of Formula (I), (II), (III), or (IV), or of Formula (V) or (VI), as disclosed herein. In one embodiment, a pharmaceutically acceptable form includes, but is not limited to, a pharmaceutically acceptable salt, solvate, isomer, and isotopologue (i.e., isotopically labeled derivative) of a compound of Formula (Ia), (Ib), (IIa), (IIb), (IIIa), (IIIb), (IVa), or (IVb), or of Formula (Va), (Vb), (VIa), or (VIb), as disclosed herein, such as a pharmaceutically acceptable salt, hydrate, stereoisomer, and isotopologue of a compound of Formula (Ia), (Ib), (IIa), (IIb), (IIIa), (IIIb), (IVa), or (IVb), or of Formula (Va), (Vb), (VIa), or (VIb), as disclosed herein. In one embodiment, a pharmaceutically acceptable form includes, but is not limited to, a pharmaceutically acceptable salt, solvate, isomer, and isotopologue (i.e., isotopically labeled derivative) of a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or of Formula (III-3), (IIIa-3), (IIIb-3), (V-1), (Va-1), (Vb-1), (VI-1), (VIa-1), or (VIb-1), as disclosed herein. In one embodiment, a pharmaceutically acceptable form includes, but is not limited to, a pharmaceutically acceptable salt, hydrate, stereoisomer, and isotopologue of a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or of Formula (III-3), (IIIa-3), (IIIb-3), (V-1), (Va-1), (Vb-1), (VI-1), (VIa-1), or (VIb-1), as disclosed herein. One of ordinary skill will recognize that free forms and salt forms of a compound may be in solvate form.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases, such as suitable inorganic and organic addition acids and bases.

In certain embodiments, the pharmaceutically acceptable form is a solvate (e.g., a hydrate). As used herein, the term "solvate" refers to compounds (such as a free form of a compound, isomer, or isotopologue, or a pharmaceutically acceptable salt of any of the foregoing, e.g., a solvate of a free form or of a pharmaceutically acceptable salt form) that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". In some embodiments, the solvate is a hydrate. Pharmaceutically acceptable solvates and hydrates are complexes that, for example, can include 1 to about 100, or 1 to about 10, or one to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a double bond, or a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base or can occur without the action or presence of an external agent. Exemplary tautomerizations include, but are not limited to, keto-enol; amide-imide; lactam-lactim; enamine-imine; and enamine-(a different) enamine tautomerizations.

In certain embodiments, the pharmaceutically acceptable form of the compounds disclosed herein is exclusive of a salt form (i.e., is not a salt), sometimes referred to as a free base form, of the compounds disclosed herein. For example, in one embodiment, the pharmaceutically acceptable form of a compound of Formula (I), (II), (III), or (IV), or of Formula (V) or (VI), as disclosed herein, is exclusive of a salt form and includes a pharmaceutically acceptable solvate, isomer, and isotopologue (i.e., isotopically labeled derivative) of the compound of Formula (I), (II), (III), or (IV), or of Formula (V) or (VI), as disclosed herein, such as exclusive of a salt form and a hydrate, stereoisomer, and isotopologue of the compound of Formula (I), (II), (III), or (IV), or of Formula (V) or (VI), as disclosed herein. In one embodiment, the pharmaceutically acceptable form is exclusive of a salt form and includes a pharmaceutically acceptable solvate, isomer, and isotopologue (i.e., isotopically labeled derivative) of the compound of Formula (Ia), (Ib), (IIa), (IIb), (IIIa), (IIIb), (IVa), or (IVb), or of Formula (Va), (Vb), (VIa), or (VIb), as disclosed herein, such as exclusive of a salt form and a hydrate, stereoisomer, and isotopologue of the compound of Formula (Ia), (Ib), (IIa), (IIb), (IIIa), (IIIb), (IVa), or (IVb), or of Formula (Va), (Vb), (VIa), or (VIb), as disclosed herein. In one embodiment, the pharmaceutically acceptable form is exclusive of a salt form and includes a pharmaceutically acceptable solvate, isomer, and isotopologue (i.e., isotopically labeled derivative) of the compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or of Formula (III-3), (IIIa-3), (IIIb-3), (V-1), (Va-1), (Vb-1), (VI-1), (VIa-1), or (VIb-1), as disclosed herein, such as exclusive of a salt form and a hydrate, stereoisomer, and isotopologue of the compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or of Formula (III-3), (IIIa-3), (IIIb-3), (V-1), (Va-1), (Vb-1), (VI-1), (VIa-1), or (VIb-1), as disclosed herein.

As used herein, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which a therapeutic agent is administered. Such pharmaceutical carriers can be sterile liquids, such as water and oils, including those of petroleum, animal, vegetable or synthetic origin, such as peanut oil, soybean oil, mineral oil, sesame oil and the like. Water is a specific carrier for intravenously administered pharmaceutical compositions. Saline solutions and aqueous dextrose and glycerol solutions can also be employed as liquid carriers, particularly for injectable solutions. For example, the term pharmaceutically acceptable carrier, excipient or diluent includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions as disclosed herein is contemplated. Supplementary active ingredients can also be incorporated into the pharmaceutical compositions.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. Further provided herein are anhydrous pharmaceutical compositions and dosage forms comprising one or more compounds of Formula (I), (II), (III), or (IV), or a pharmaceutically acceptable form thereof, or of Formula (V) or (VI), or a pharmaceutically acceptable form, as described herein, for example a compound of Formula (Ia), (Ib), (IIa), (IIb), (IIIa), (IIIb), (IVa), or (IVb), such as a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or a pharmaceutically acceptable form thereof, or of Formula (III-3), (IIIa-3), (IIIb-3), (V-1), (Va-1), (Vb-1), (VI-1), (VIa-1), or (VIb-1), or a pharmaceutically acceptable form, as described herein. The compositions and single unit dosage forms can take the form of solutions or syrups (optionally with a flavoring agent), suspensions (optionally with a flavoring agent), emulsions, tablets (e.g., chewable tablets), pills, capsules, granules, powder (optionally for reconstitution), taste-masked or sustained-release formulations, and the like.

Pharmaceutical compositions provided herein that are suitable for oral administration can be presented as discrete dosage forms, such as, but are not limited to, tablets, caplets, capsules, granules, powder, and liquids. Such dosage forms contain predetermined amounts of active ingredients, and may be prepared by methods of pharmacy well known to those skilled in the art.

Examples of excipients that can be used in oral dosage forms provided herein include, but are not limited to, binders, fillers, disintegrants, and lubricants.

As used herein, the terms "prevention" and "preventing" are used herein to refer to an approach for obtaining beneficial or desired results including, but not limited to, prophylactic benefit. For prophylactic benefit, the compounds and pharmaceutical compositions disclosed herein can be administered to a patient at risk of developing a particular disease, or to a patient reporting one or more of the physiological symptoms of a disease or disorder, even though a diagnosis of this disease or disorder may not have been made.

As used herein, the term "stereoisomers" is understood to mean isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof, and other mixtures thereof, as falling within the scope of this disclosure.

In certain embodiments, the symbol ═════ denotes a bond that can be a single or double as described herein.

In certain embodiments, provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of the plane of the ring are designated "cis trans."

As used herein, the term "subject" to which administration is contemplated includes, but is not limited to, humans (e.g., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, dogs, rabbits, and/or rodents; and/or birds, including commercially relevant birds such as chickens, ducks, geese, quail, and/or turkeys. The subject can be a patient, for example, a patient having a cancer dependent on a farnesylated protein.

A "therapeutic effect," as that term is used herein, encompasses a therapeutic benefit and/or a prophylactic benefit as described herein. A prophylactic effect includes delaying or eliminating the appearance of a disease or disorder, delaying, or eliminating the onset of symptoms of a disease or disorder, slowing, halting, or reversing the progression of a disease or disorder, or any combination thereof.

As used herein, the terms "treat," "treating," "treatment," and "ameliorating" are used interchangeably herein. These terms refer to an approach for obtaining beneficial or desired results including, but not limited to, therapeutic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disease or disorder. For example, when used in reference to a patient having cancer dependent on a farnesylated protein, refers to an action that reduces the severity of the cancer, or retards or slows the progression of the cancer, including (a) inhibiting the cancer growth, or arresting development of the cancer, and (b) causing regression of the cancer, or delaying or minimizing one or more symptoms associated with the presence of the cancer.

Definitions of specific functional groups and chemical terms are described in more detail below. The chemical elements are identified in accordance with the Periodic Table of the Elements, CAS version, Handbook of Chemistry and Physics, 75th ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th ed., John Wiley & Sons, Inc., New York, 2001; Larock, *Comprehensive Organic Transformations*, VCH Publishers, Inc., New York, 1989; and Carruthers, Some *Modern Methods of Organic Synthesis*, 3rd ed., Cambridge University Press, Cambridge, 1987.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a straight or branched hydrocarbon chain radical consisting solely of carbon and hydrogen atoms, containing no unsaturation, having, in some embodiments, from one to ten carbon atoms (e.g., $C_1$-$C_{10}$ alkyl). Linear or straight alkyl refers to an alkyl with no branching, e.g., methyl, ethyl, n-propyl. Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, 4 carbon atoms, etc., up to and including 10 carbon atoms, although the present definition also covers the occurrence of the term "alkyl" where no numerical range is designated. In some embodiments, an alkyl is a $C_1$-$C_6$ alkyl group. In some embodiments, alkyl groups have 1 to 10, 1 to 6, 1 to 4, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C (NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Alkenyl" refers to a straight or branched hydrocarbon chain radical group consisting solely of carbon and hydrogen atoms, containing at least one double bond, and in some embodiments, having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, 4 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless stated otherwise in the specification, an alkenyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Alkynyl" refers to a straight or branched hydrocarbon chain radical group consisting solely of carbon and hydrogen atoms, containing at least one triple bond, having, in some embodiments, from two to ten carbon atoms (i.e., $C_2$-$C_{10}$ alkynyl). Whenever it appears herein, a numerical range such as "2 to 10" refers to each integer in the given range; e.g., "2 to 10 carbon atoms" means that the alkynyl group can consist of 2 carbon atoms, 3 carbon atoms, 4 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the parent molecular structure by a single bond, for example, ethynyl, propynyl, butynyl, pentynyl, hexynyl, and the like. Unless stated otherwise in the specification, an alkynyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

The term "alkoxy" refers to the group —O-alkyl (in some embodiments, including from 1 to 10 carbon atoms), of a straight, branched, cyclic configuration and combinations thereof, attached to the parent molecular structure through an oxygen. Examples include methoxy, ethoxy, propoxy, isopropoxy, cyclopropyloxy, cyclohexyloxy, and the like. "Lower alkoxy" refers to alkoxy groups containing one to six carbons. In some embodiments, $C_1$-$C_4$ alkoxy is an alkoxy group which encompasses both straight and branched chain alkyls of from 1 to 4 carbon atoms. Unless stated otherwise in the specification, an alkoxy group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "alkenoxy" and "alkynoxy" mirror the above description of "alkoxy" wherein the prefix "alk" is replaced with "alken" or "alkyn" respectively, and the parent "alkenyl" or "alkynyl" terms are as described herein.

"Aryl" refers to a radical with six to fourteen ring atoms (e.g., $C_6$-$C_{14}$ or $C_6$-$C_{10}$ aryl) which has at least one carbocyclic ring having a conjugated pi electron system which is aromatic (e.g., having 6, 10, or 14 π electrons shared in a cyclic array) (e.g., phenyl, fluorenyl, and naphthyl). In one embodiment, bivalent radicals formed from substituted benzene derivatives and having the free valences at ring atoms are named as substituted phenylene radicals. In other embodiments, bivalent radicals derived from univalent monocyclic or polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10 aryl" refers to each integer in the given range; e.g., "6 to 10 ring atoms" means that the aryl group can consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si$(R^a)_3$, —OR$^a$, —SR$^a$, —OC(O)—R$^a$, —N$(R^a)_2$, —C(O)R$^a$, —C(O)OR$^a$, —OC(O)N$(R^a)_2$, —C(O)N$(R^a)_2$, —N$(R^a)$C(O)OR$^a$, —N$(R^a)$C(O)R$^a$, —N$(R^a)$C(O)N$(R^a)_2$, —N$(R^a)$C(NR$^a$)N$(R^a)_2$, —N$(R^a)$S(O)$_t$R$^a$ (where t is 1 or 2), —S(O)$_t$OR$^a$ (where t is 1 or 2), —S(O)N$(R^a)_2$ (where t is 1 or 2), or —O—P(=O)(OR$^a)_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein. In one embodiment, unless stated otherwise, "aryl" also includes ring systems wherein the aryl ring, as defined above, is fused with one or more cycloalkyl or heterocyclyl groups wherein the point of attachment to the parent molecular structure is on the aryl ring.

"Cycloalkyl," or alternatively, "carbocyclyl," refers to a monocyclic or polycyclic radical that contains only carbon and hydrogen and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 10 ring atoms (e.g., $C_3$-$C_{10}$ cycloalkyl). Whenever it appears herein, a numerical range such as "3 to 10" refers to each integer in the given range; e.g., "3 to 10 carbon atoms" means that the cycloalkyl group can consist of 3 carbon atoms, 4 carbon atoms, 5 carbon atoms, etc., up to and including 10 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$), and the like. Examples of $C_{3-8}$ carbocyclyl groups include the aforementioned $C_{3-6}$ carbocyclyl groups as well as cycloheptyl ($C_7$), cycloheptadienyl ($C_7$), cycloheptatrienyl ($C_7$), cyclooctyl ($C_5$), bicyclo[2.2.1]heptanyl, bicyclo[2.2.2]octanyl, and the like. Examples of $C_{3-10}$ carbocyclyl groups include the aforementioned $C_{3-8}$ carbocyclyl groups as well as octahydro-1H-indenyl, decahydronaphthalenyl, spiro[4.5]decanyl, and the like. Unless stated otherwise in the specification, a cycloalkyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si$(R^a)_3$, —OR$^a$, —SR$^a$, —OC(O)—R$^a$, —N$(R^a)_2$, —C(O)R$^a$, —C(O)OR$^a$, —OC(O)N$(R^a)_2$, —C(O)N$(R^a)_2$, —N$(R^a)$C(O)OR$^a$, —N$(R^a)$C(O)R$^a$, —N$(R^a)$C(O)N$(R^a)_2$, —N$(R^a)$C(NR$^a$)N$(R^a)_2$, —N$(R^a)$S(O)$_t$R$^a$ (where t is 1 or 2), —S(O)$_t$OR$^a$ (where t is 1 or 2), —S(O)N$(R^a)_2$ (where t is 1 or 2), or —O—P(=O)(OR$^a)_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein. In one embodiment, unless stated otherwise, "cycloalkyl" or "carbocyclyl" also includes ring systems wherein the cycloalkyl or carbocyclyl ring, as defined above, is fused with one or more aryl or heteroaryl groups wherein the point of attachment to the parent molecular structure is on the cycloalkyl or carbocyclyl ring.

The term "halo", "halide", or, alternatively, "halogen" refers to fluoro, chloro, bromo, or iodo.

The terms "haloalkyl," "haloalkenyl," "haloalkynyl" and "haloalkoxy" include alkyl, alkenyl, alkynyl and alkoxy structures that are substituted with one or more halo groups or with combinations thereof. In certain embodiments, all hydrogen atoms of the alkyl group are substituted with halo atoms. In certain embodiments, the alkyl group is substituted by 1, 2, 3, 4, 5, or 6 halo atoms. In certain embodiments, the alkyl group is substituted by 1, 2, or 3 halo atoms. In certain other embodiments, the alkyl group is substituted with 2 halo atoms. In certain embodiments, the alkyl group is substituted with 1 halo atom. In certain embodiments, haloalkyl includes trifluoromethyl, fluoromethyl, perfluoroethyl, or chloromethyl. Certain other embodiments of haloalkyl include chloromethyl, fluoromethyl, difluoromethyl, trifluoromethyl, or 1, 1,1-trifluoroethany1. For example, the terms "fluoroalkyl" and "fluoroalkoxy" include haloalkyl and haloalkoxy groups, respectively, wherein the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

"Heteroalkyl", "heteroalkenyl" and "heteroalkynyl" include alkyl, alkenyl and alkynyl radicals, respectively, which have one or more skeletal chain atoms selected from an atom other than carbon, e.g., oxygen, nitrogen, sulfur, and phosphorus, or combinations thereof. A numerical range can be given, e.g., $C_1$-$C_4$ heteroalkyl which refers to the chain length in total, which in this example can be up to 4 atoms long. For example, a —CH$_2$OCH$_2$CH$_3$ radical is referred to as a "$C_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—CH$_2$CH$_2$OCH$_3$), ethoxymethanyl (—CH$_2$OCH$_2$CH$_3$), (methoxymethoxy)ethanyl (—CH$_2$CH$_2$—OCH$_2$OCH$_3$), (methoxymethoxy) methanyl (—CH$_2$OCH$_2$OCH$_3$), and (methoxyethoxy)methanyl(—CH$_2$OCH$_2$CH$_2$OCH$_3$), and the like; amines such as —CH$_2$CH$_2$NHCH$_3$, —CH$_2$CH$_2$N(CH$_3$)$_2$, —CH$_2$NHCH$_2$CH$_3$, —CH$_2$N(CH$_2$CH$_3$)(CH$_3$), and the like. Heteroalkyl, heteroalkenyl, and heteroalkynyl groups can each be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

"Heteroaryl", or alternatively, "heteroaromatic", refers to a radical of a 5- to 18-membered monocyclic or polycyclic (e.g., bicyclic or tricyclic) aromatic ring system (e.g., having 6, 10 or 14 π electrons shared in a cyclic array) having ring carbon atoms and 1 to 6 ring heteroatoms provided in the aromatic ring system, wherein each heteroatom is independently selected from nitrogen, oxygen, phosphorous, and sulfur ("5- to 18-membered heteroaryl"). Heteroaryl polycyclic ring systems can include one or more heteroatoms in one or more rings. Whenever it appears herein, a numerical range such as "5 to 18" refers to each integer in the given range; e.g., "5 to 18 ring atoms" means that the heteroaryl group can consist of 5 ring atoms, 6 ring atoms, 7 ring atoms, 8 ring atoms, 9 ring atoms, 10 ring atoms, etc., up to and including 18 ring atoms. In one embodiment, bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocyclyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either the ring bearing a heteroatom (e.g., 2-indolyl) or the ring that does not contain a heteroatom (e.g., 5-indolyl). In some embodiments, a heteroaryl group is a 5 to 10 membered aromatic ring system having ring carbon atoms and 1 to 4 ring heteroatoms provided in the aromatic ring system, wherein each heteroatom is independently selected from nitrogen, oxygen, phosphorous, and sulfur ("5- to 10-membered heteroaryl"). In some embodiments, a heteroaryl group is a 5- to 8-membered aromatic ring system having ring carbon atoms and 1 to 4 ring heteroatoms provided in the aromatic ring system, wherein each heteroatom is independently selected from nitrogen, oxygen, phosphorous, and sulfur ("5- to 8-membered heteroaryl"). In some embodiments, a heteroaryl group is a 5- to 6-membered aromatic ring system having ring carbon atoms and 1 to 4 ring heteroatoms provided in the aromatic ring system, wherein each heteroatom is independently selected from nitrogen, oxygen, phosphorous, and sulfur ("5- to 6-membered heteroaryl"). In some embodiments, the 5- to 6-membered heteroaryl has 1 to 3 ring heteroatoms independently selected from nitrogen, oxygen, phosphorous, and sulfur. In some embodiments, the 5- to 6-membered heteroaryl has 1 to 2 ring heteroatoms independently selected from nitrogen, oxygen, phosphorous, and sulfur. In some embodiments, the 5- to 6-membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl).

Unless stated otherwise in the specification, a heteroaryl moiety is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

"Heterocyclyl", "heterocycloalkyl" or "heterocarbocyclyl" each refer to any 3- to 18-membered non-aromatic radical monocyclic or polycyclic moiety comprising at least one ring heteroatom selected from nitrogen, oxygen, phosphorous, and sulfur. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or more rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "5 to 18" refers to each integer in the given range; e.g., "5 to 18 ring atoms" means that the heterocyclyl group can consist of 5 ring atoms, 6 ring atoms, 7 ring atoms, 8 ring atoms, 9 ring atoms, 10 ring atoms, etc., up to and including 18 ring atoms. In one embodiment, bivalent radicals derived from univalent heterocyclyl radicals whose names end in "-yl" by removal of one hydrogen atom from the atom with the free valence are named by adding "-idene" to the name of the corresponding univalent radical, e.g., a piperidyl group with two points of attachment is a piperidylidene.

An N-containing heterocyclyl moiety refers to a non-aromatic group in which at least one of the ring atoms is a nitrogen atom. The heteroatom(s) in the heterocyclyl radical can be optionally oxidized. One or more nitrogen atoms, if present, can be optionally quaternized. Heterocyclyl also includes ring systems substituted with one or more nitrogen oxide (—O—) substituents, such as piperidinyl N-oxides. The heterocyclyl is attached to the parent molecular structure through any atom of any of the ring(s).

"Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment to the parent molecular structure is on the heterocyclyl ring. In some embodiments, a heterocyclyl group is a 3- to 10-membered non-aromatic ring system having ring carbon atoms and 1 to 4 ring heteroatoms, wherein each heteroatom is independently selected from nitrogen, oxygen, phosphorous, and sulfur ("3- to 10-membered heterocyclyl"). In some embodiments, a heterocyclyl group is a 5- to 8-membered non-aromatic ring system having ring carbon atoms and 1 to 4 ring heteroatoms, wherein each heteroatom is independently selected from nitrogen, oxygen, phosphorous, and sulfur ("5- to 8-membered heterocyclyl"). In some embodiments, a heterocyclyl group is a 5- to 6-membered non-aromatic ring system having ring carbon atoms and 1 to 4 ring heteroatoms, wherein each heteroatom is independently selected from nitrogen, oxygen, phosphorous, and sulfur ("5- to 6-membered heterocyclyl"). In some embodiments, the 5- to 6-membered heterocyclyl has 1 to 3 ring heteroatoms independently selected from nitrogen, oxygen, phosphorous, and sulfur. In some embodiments, the 5- to 6-membered heterocyclyl has 1 to 2 ring heteroatoms independently selected from nitrogen, oxygen, phosphorous, and sulfur. In some embodiments, the 5- to 6-membered heterocyclyl has 1 ring heteroatom selected from nitrogen, oxygen, phosphorous, and sulfur.

Exemplary 3-membered heterocyclyls containing 1 heteroatom include, without limitation, azirdinyl, oxiranyl, thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

Unless stated otherwise, heterocyclyl moieties are optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein.

"Hydroxyalkyl" means a group of formula —R—(OH)$_z$, where R is an alkyl as defined herein and z is 1 or 2. In one embodiment, hydroxyalkyl is —ROH. In one embodiment, hydroxyalkyl includes —CH$_2$OH. In one embodiment, hydroxyalkyl is —R(OH)$_2$.

A "leaving group or atom" is any group or atom that will, under the reaction conditions, cleave from the starting material, thus promoting reaction at a specified site. Suitable non-limiting examples of such groups, unless otherwise specified, include halogen atoms, mesyloxy, o-nitrobenzensulphonyloxy, p-nitrobenzensulphonyloxy, trifluoromethyloxy, and tosyloxy groups.

"Protecting group" has the meaning conventionally associated with it in organic synthesis, e.g., a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, *Protective Groups in Organic Synthesis*, Fourth Edition, John Wiley & Sons, New York (2006), incorporated herein by reference in its entirety. For example, a hydroxy protected form is where at least one of the hydroxy groups present in a compound is protected with a hydroxy protecting group. Likewise, amines and other reactive groups can similarly be protected.

As used herein, the terms "substituted" or "substitution" mean that at least one hydrogen present on a group atom (e.g., a carbon or nitrogen atom) is replaced with a permissible substituent, e.g., a substituent which upon substitution for the hydrogen results in a stable compound, e.g., a compound which does not spontaneously undergo transformation such as by rearrangement, cyclization, elimination, or other reaction. Unless otherwise indicated, a "substituted" group can have a substituent at one or more substitutable positions of the group, and when more than one position in any given structure is substituted, the substituent is either the same or different at each position. Substituents, unless otherwise indicated, can include one or more group(s) individually and independently selected from acyl, alkyl, alkenyl, alkynyl, alkoxy, alkylaryl, cycloalkyl, aralkyl, aryl, aryloxy, amino, amido, azide, carbonate, carbonyl, heteroalkyl, heteroaryl, heteroarylalkyl, heterocycloalkyl, hydroxy, cyano, halo, haloalkoxy, haloalkyl, ester, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), and —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl, or heteroarylalkyl, and each of these moieties can be optionally substituted as defined herein. For example, a cycloalkyl substituent can have a halide substituted at one or more ring carbons, and the like. The protecting groups that can form the protective derivatives of the above substituents are known to those of skill in the art and can be found in references such as Greene and Wuts, above.

5.1 Compounds

In some embodiments, the compound is a compound of Formula (I), (Ia), or (Ib), as disclosed herein, wherein A$^1$ is N or NR$^{1a}$. In some embodiments, the compound of Formula (I), (Ia), or (Ib), as disclosed herein, wherein A$^2$ is CR$^{2b}$ or —C(=O)—. In some embodiments, the bond between A$^1$ and A$^2$ is a single bond, A$^1$ is NR$^{1a}$, and A$^2$ is —C(=O)—. In some embodiments, the bond between A$^1$ and A$^2$ is a double bond, A$^1$ is N, and A$^2$ is CR$^{2b}$.

In some embodiments, the compound is a compound of Formula (I), (Ia), or (Ib), as disclosed herein, wherein is

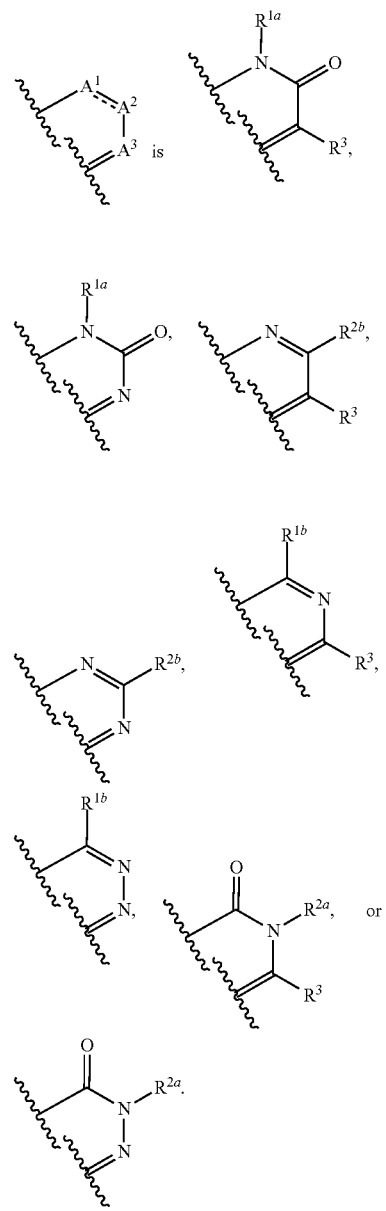

In some embodiments the compound is a compound of Formula (I), (Ia), or (Ib), as disclosed herein, wherein

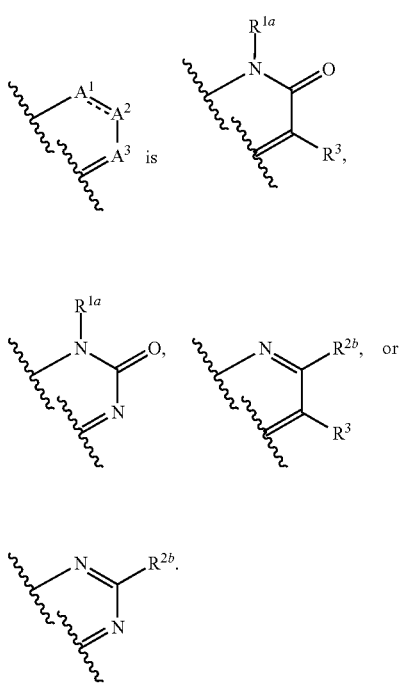

For example, in some embodiments, the

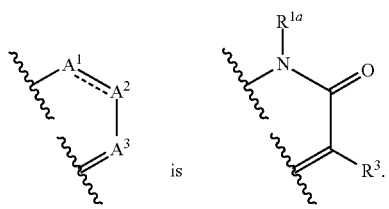

In some embodiments, the

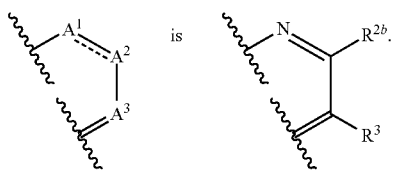

In some embodiments, the

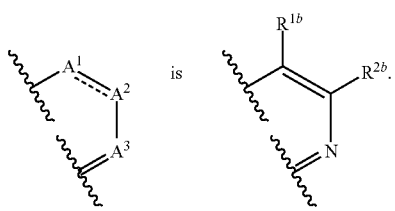

In some embodiments, the compound is a compound of Formula (I), (Ia), or (Ib), as disclosed herein, wherein

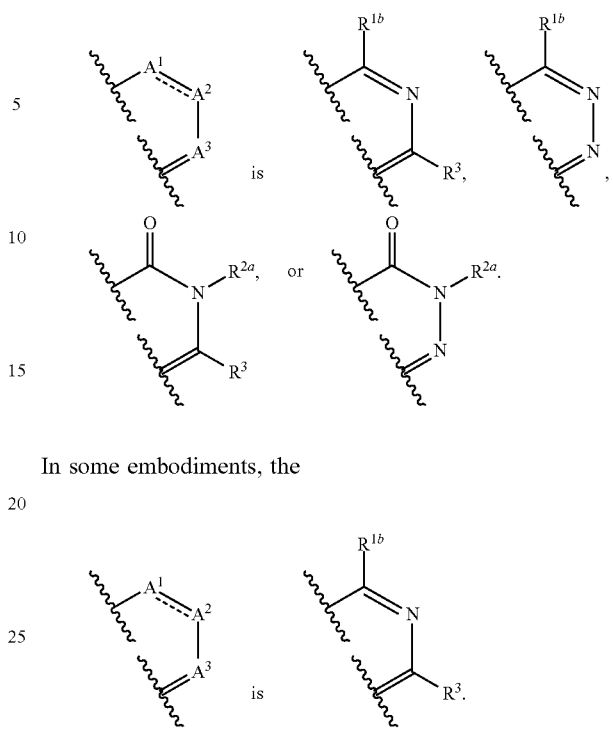

In some embodiments, the

In some embodiments, the compound is a compound of Formula (I), (Ia), or (Ib), as disclosed herein, wherein Y and the fused-ring system containing $A^1$, $A^2$, and $A^3$ are attached to W in a 1,2-relationship. In some embodiments, Y and the fused-ring system containing $A^1$, $A^2$, and $A^3$ are attached to W in a 1,3-relationship. In some embodiments, W is $C_{6-12}$ aryl. In some embodiments, W is phenyl. In some embodiments, W is 5-12 membered heteroaryl. In some embodiments, W is pyridyl. In some embodiments, W is substituted with one, two, three or four $R^4$ substituents. In some embodiments, W is substituted with two $R^4$ substituents. In some embodiments, W is substituted with one $R^4$ substituent. In some embodiments, $R^4$ is independently hydrogen, halo, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, or $-NR^{14}R^{15}$, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, or 3-6 membered heterocycloalkoxy, of the $R^4$ are optionally independently substituted with one, two, three, four, five, or six substituents selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O). For example, in some embodiments, $R^4$ is independently hydrogen, halo, $C_{1-6}$ alkyl, $C_{1-6}$ haloalkyl, $C_{3-6}$ cycloalkyl, $C_{1-6}$ alkoxy, or $C_{1-6}$ haloalkoxy, wherein each $C_{1-6}$ alkyl, $C_{1-6}$ haloalkyl, $C_{3-6}$ cycloalkyl, $C_{1-6}$ alkoxy, or $C_{1-6}$ haloalkoxy of the $R^4$ are optionally independently substituted with one, two, three, four, five, or six substituents selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O). In some embodiments, $R^4$ is independently hydrogen.

In some embodiments, the compound is a compound of Formula (I), (Ia), or (Ib), as disclosed herein, wherein the —C(R$^6$)(R$^7$)(fused-ring system containing A$^4$, A$^5$, and A$^6$)) group, and Y are attached to Z in a 1,2-relationship. In some embodiments, the —C(R$^6$)(R$^7$)(fused-ring system containing A$^4$, A$^5$, and A$^6$)) group, and Y are attached to Z in a 1,3-relationship. In some embodiments, Z is C$_{6-12}$ aryl. In some embodiments, Z is phenyl. In some embodiments, Z is 5-12 membered heteroaryl. In some embodiments, Z is pyridyl. In some embodiments, Z is substituted with one, two, three or four R$^5$ substituents. In some embodiments, Z is substituted with two R$^5$ substituents. In some embodiments, Z is substituted with one R$^5$ substituent. In some embodiments, R$^5$ independently is hydrogen, halo or CN. In some embodiments, R$^5$ independently is hydrogen. In some embodiments, R$^5$ is independently an electron-withdrawing group. In some embodiments, R$^5$ independently is chloro. In some embodiments, R$^5$ independently is CN.

In some embodiments, the compound is a compound of Formula (I) or (II), for example a compound of Formula (Ia), (Ib), (IIa), or (IIb), or a pharmaceutically acceptable form thereof, as disclosed herein, wherein R$^{1a}$ is independently R$^9$. For example, in some embodiments, R$^{1a}$ is hydrogen, C$_{1-6}$ alkyl, or C$_{3-6}$ cycloalkyl, wherein the C$_{1-6}$ alkyl, or C$_{3-6}$ cycloalkyl are optionally independently substituted with 1-6 substituents independently selected from halo, hydroxy, CN, NO$_2$, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, (O), —C(O)R$^{12}$, —C(O)OR$^{12}$, —OC(O)R$^{12}$, —OC(O) OR$^{12}$, —C(O)NR$^{10}$R$^{11}$, —NR$^{10}$R$^{11}$, —NR$^{10}$C(O)R$^{12}$, —NR$^{10}$C(O)OR$^{12}$, —NR$^{10}$C(O)NR$^{10}$R$^{11}$, —NR$^{10}$S(O)$_2$R$^{12}$, —S(O)$_p$R$^{12}$, and —S(O)$_2$NR$^{10}$R$^{11}$. In some embodiments, p is independently 0. In some embodiments, p is independently an integer of 1 or 2. For example, in some embodiments, R$^{1a}$ is hydrogen, C$_{1-3}$ alkyl, or C$_{3-4}$ cycloalkyl, wherein the C$_{1-3}$ alkyl, or C$_{3-4}$ cycloalkyl are optionally independently substituted with one, two, or three substituents independently selected from halo, hydroxy, CN, NO$_2$, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_3$-6 cycloalkyl, 3-6 membered heterocycloalkyl, C$_{1-6}$ alkoxy, C$_{1-6}$ haloalkoxy, (O), —C(O)R$^{12}$, —C(O)OR$^{12}$, —OC(O)R$^{12}$, —OC(O)OR$^{12}$, —C(O)NR$^{10}$R$^{11}$, —NR$^{10}$R$^{11}$, —NR$^{10}$C(O)R$^{12}$, —NR$^{10}$C(O)OR$^{12}$, —NR$^{10}$C(O)NR$^{10}$R$^{11}$, —NR$^{10}$S(O)$_2$R$^{12}$, —S(O)$_p$R$^{12}$, and —S(O)$_2$NR$^{10}$R$^{11}$. For example, in some embodiments, R$^{1a}$ is hydrogen, —CH$_3$, —CD$_3$, —CH$_2$CH$_3$, —CD$_2$CD$_3$, isopropyl, 2,3-dihydroxypropyl or cyclopropyl. In some embodiments, R$^{1a}$ is —CH$_3$, —CD$_3$, or cyclopropyl. In some embodiments, R$^{1a}$ is —CH$_3$ or —CD$_3$. In some embodiments, R$^{1a}$ is cyclopropyl. In some embodiments, the compound is a compound of Formula (II-1) or (II-2), such as a compound of Formula (IIa-1), (IIb-1), (IIa-2), or (IIb-2), or a pharmaceutically acceptable form thereof.

In some embodiments, the compound is a compound of Formula (I) or (III), for example a compound of Formula (Ia), (Ib), (IIIa), or (IIIb), or a pharmaceutically acceptable form thereof, or of Formula (V), (Va), (Vb), (VI), (VIa), or (VIb), or a pharmaceutically acceptable form thereof, as disclosed herein, wherein R$^{2b}$ is independently R$^9$, —OR$^9$, halo, CN, NO$_2$, —C(O)R$^9$, —C(O)OR$^9$, —C(O)NR$^{10}$R$^{11}$, —NR$^{10}$R$^{11}$, —NR$^{10}$C(O)R$^9$, —S(O)$_p$R$^9$, or —S(O)$_2$NR$^{10}$R$^{11}$. In some embodiments, p is independently 0. In some embodiments, p is independently an integer of 1 or 2. For example, in some embodiments, R$^{2b}$ is independently R$^9$, —OR$^9$, halo, CN, —C(O)NR$^{10}$R$^{11}$, or —NR$^{10}$R$^{11}$. In some embodiments, R$^{2b}$ is hydrogen, C$_{1-6}$ alkyl, C$_{3-6}$ cycloalkyl, hydroxy, C$_{1-6}$ alkoxy, C$_{3-6}$ cycloalkoxy, C$_{3-6}$ heterocycloalkoxy, halo, CN, —C(O) NR$^{10}$R$^{11}$, or —NR$^{10}$R$^{11}$; wherein R$^{10}$ and R$^{11}$, at each occurrence, are each independently hydrogen, C$_{1-6}$ alkyl, 3-6 membered heterocycloalkyl, or together with the N to which each is attached are combined to form a 3-6 membered heterocycloalkyl. In some embodiments, R$^{2b}$ is independently hydrogen, C$_{1-3}$ alkyl, C$_{3-4}$ cycloalkyl, C$_{1-3}$ alkoxy, C$_{3-4}$ cycloalkoxy, C$_{3-4}$ heterocycloalkoxy, halo, CN, —C(O) NR$^{10}$R$^{11}$, or —NR$^{10}$R$^{11}$; wherein R$^{10}$ and R$^{11}$, at each occurrence, are each independently hydrogen, C$_{1-3}$ alkyl, 3-4 membered heterocycloalkyl, or together with the N to which each is attached are combined to form a 4-6 membered heterocycloalkyl. In some embodiments, R$^{10}$ is H. In some embodiments, R$^{11}$ is C$_{1-3}$haloalkyl, such as chloroethyl or fluoroethyl. For example, in some embodiments, R$^{2b}$ is hydrogen, —CH$_3$, —CD$_3$, —CH$_2$CH$_3$, —CD$_2$CD$_3$, isopropyl, cyclopropyl, —OCH$_3$, —OCD$_3$, —OCH$_2$CH$_3$, —OCD$_2$CD$_3$, isopropoxy, cyclopropoxy, 3-oxetanylalkoxy, chloro, CN, morpholino, piperazinyl, 3-oxetanylamino, or —C(O)NH$_2$. In some embodiments, R$^{2b}$ is —NH$_2$. In some embodiments, R$^{2b}$ is independently an electron-withdrawing group. An electron-withdrawing group may include, for example, a halo, cyano, a nitro group, a carbonyl group, a carboxylic acid, a carboxylic ester, an amide, a sulfonyl group, a sulfonyl ester, or a sufonyl amide group. For example, in some embodiments, R$^{2b}$ is independently an electron-withdrawing group selected from halo, CN, NO$_2$, —C(O)R$^9$, —C(O)OR$^9$, —C(O)NR$^{10}$R$^{11}$, —S(O)$_p$R$^9$, or —S(O)$_2$NR$^{10}$R$^{11}$. In some embodiments, R$^{2b}$ is chloro, CN, —C(O)H, —C(O)CH$_3$, —C(O)OH, —C(O)OCH$_3$, —C(O) NH$_2$, —C(O)N(H)CH$_3$, —C(O)N(CH$_3$)$_2$, —S(O)CH$_3$, —S(O)$_2$CH$_3$, —S(O)$_2$NH$_2$, —S(O)$_2$N(H)CH$_3$, or —S(O)$_2$N (CH$_3$)$_2$. In some embodiments, the compound is a compound of Formula (III-1) or (III-2), such as a compound of Formula (IIIa-1), (IIIb-1), (IIIa-2), or (IIIb-2), or a pharmaceutically acceptable form thereof, or is a compound of Formula (III-3), (IIIa-3), or (IIIb-3), or a pharmaceutically acceptable form thereof.

In some embodiments, the compound is a compound of Formula (I), for example a compound of Formula (Ia) or (Ib), or a pharmaceutically acceptable form thereof, as disclosed herein, wherein A$^1$ is CR$^{1b}$ or —C(═O)—. In some embodiments, the compound of Formula (I), for example a compound of Formula (Ia) or (Ib), or a pharmaceutically acceptable form thereof, as disclosed herein, wherein A$^2$ is N or NR$^{2a}$. In some embodiments, the bond between A$^1$ and A$^2$ is a double bond, A$^1$ is CR$^{1b}$, and A$^2$ is N. In some embodiments, the bond between A$^1$ and A$^2$ is a single bond, A$^1$ is —C(═O)—, and A$^2$ is NR$^{2a}$. In some embodiments, the compound of Formula (I), (Ia), or (Ib), or pharmaceutically acceptable form thereof, is a compound of Formula (IV), (IVa), or (IVb), or a pharmaceutically acceptable form thereof, respectively. In some embodiments, the compound is a compound of Formula (IV-1), (IVa-1), (IVb-1), (IV-2), (IVa-2), or (IVb-2), or a pharmaceutically acceptable form thereof. In some embodiments, the compound is a compound of Formula (V), (Va), (Vb), (V-1), (Va-1), (Vb-1), (VI), (VIa), (VIb), (VIa-1), or (VIb-1), or a pharmaceutically acceptable form thereof.

In some embodiments, the compound is a compound of Formula (I) or (IV), for example a compound of Formula (Ia), (Ib), (IVa), or (IVb), or a pharmaceutically acceptable form thereof, or a compound of Formula (V) or (VI), for example a compound of Formula (Va), (Vb), (VIa), or (VIb), or a pharmaceutically acceptable form thereof, as disclosed herein, wherein R$^{1b}$ is independently R$^9$, —OR$^9$, halo, CN, $NO_2$, $-C(O)R^9$, $-C(O)OR^9$, $-C(O)NR^{10}R^{11}$, $-NR^{10}R^{11}$, $-NR^{10}C(O)R^9$, $-S(O)_pR^9$, or $-S(O)_2NR^{10}R^{11}$. For example, in some embodiments, $R^{1b}$ is $R^9$, $-OR^9$, halo, CN, $-C(O)R^9$, or $-C(O)OR^9$. In some embodiments, $R^{1b}$ is $R^9$, $-OR^9$, halo, or CN. For example, in some embodiments, $R^{1b}$ is hydrogen, $C_{1-6}$ alkyl, $C_{3-6}$ cycloalkyl, $C_{1-6}$ alkoxy, $C_{3-6}$ cycloalkoxy, halo or CN, wherein the $C_{1-6}$ alkyl, $C_{3-6}$ cycloalkyl, $C_{1-6}$ alkoxy, or $C_{3-6}$ cycloalkoxy, are optionally independently substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), $-C(O)R^{12}$, $-C(O)OR^{12}$, $-OC(O)R^{12}$, $-OC(O)OR^{12}$, $-C(O)NROR^{11}$, $-NR^{10}R^{11}$, $-NR^{10}C(O)R^{12}$, $-NR^{10}C(O)OR^{12}$, $-NR^{10}C(O)NR^{10}R^{11}$, $-NR^{10}S(O)_2R^{12}$, $-S(O)_pR^{12}$, and $-S(O)_2NR^{10}R^{11}$. In some embodiments, p is independently 0. In some embodiments, p is independently an integer of 1 or 2. For example, in some embodiments, $R^{1b}$ is hydrogen, $C_{1-3}$ alkyl, $C_{3-4}$ cycloalkyl, $C_{1-3}$ alkoxy, $C_{3-4}$ cycloalkoxy, halo or CN, wherein the $C_{1-3}$ alkyl, $C_{3-4}$ cycloalkyl, $C_{1-3}$ alkoxy, or $C_{3-4}$ cycloalkoxy are optionally independently substituted with one, two, or three substituents selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), $-C(O)R^{12}$, $-C(O)OR^{12}$, $-OC(O)R^{12}$, $-OC(O)OR^{12}$, $-C(O)NR^{10}R^{11}$, $-NR^{10}R^{11}$, $-NR^{10}C(O)R^{12}$, $-NR^{10}C(O)OR^{12}$, $-NR^{10}C(O)NR^{10}R^{11}$, $-NR^{10}S(O)_2R^{12}$, $-S(O)_pR^{12}$, and $-S(O)_2NR^{10}R^{11}$. For example, in some embodiments, $R^{1b}$ is hydrogen, $-CH_3$, $-CD_3$, $-CF_3$, $-CH_2CH_3$, $-CD_2CD_3$, isopropyl, 2,3-dihydroxypropyl, cyclopropyl, $-OCH_3$, $-OCD_3$, $-OCF_3$, $-OCH_2CH_3$, $-OCD_2CD_3$, isopropoxy, 2,3-dihydroxypropoxy, or cyclopropoxy. In some embodiments, the compound is a compound of Formula (IV-1) or (IV-2), such as a compound of Formula (IVa-1), (IVb-1), (IVa-2), or (IVb-2), or a pharmaceutically acceptable form thereof. In some embodiments, the compound is a compound of Formula (V-1), (Va-1), (Vb-1), (VI-1), (VIa-1), or (VIb-1), or a pharmaceutically acceptable form thereof.

In some embodiments, the compound is a compound of Formula (I), for example a compound of Formula (Ia) or (Ib), or a pharmaceutically acceptable form thereof, as disclosed herein, wherein $R^{2a}$ is independently $R^9$. For example, in some embodiments, $R^{2a}$ is hydrogen, $C_{1-6}$ alkyl, or $C_{3-6}$ cycloalkyl, wherein the $C_{1-6}$ alkyl, or $C_{3-6}$ cycloalkyl are optionally independently substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), $-C(O)R^{12}$, $-C(O)OR^{12}$, $-OC(O)R^{12}$, $-OC(O)OR^{12}$, $-C(O)NR^{10}R^{11}$, $-NR^{10}R^{11}$, $-NR^{10}C(O)R^{12}$, $-NR^{10}C(O)OR^{12}$, $-NR^{10}C(O)NR^{10}R^{11}$, $-NR^{10}S(O)_2R^{12}$, $-S(O)_pR^{12}$, and $-S(O)_2NR^{10}R^{11}$. For example, in some embodiments, $R^{2a}$ is hydrogen, $C_{1-3}$ alkyl, or $C_{3-4}$ cycloalkyl, wherein the $C_{1-3}$ alkyl, or $C_{3-4}$ cycloalkyl are optionally independently substituted with one, two, or three substituents selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), $-C(O)R^{12}$, $-C(O)OR^{12}$, $-OC(O)R^{12}$, $-OC(O)OR^{12}$, $-C(O)NR^{10}R^{11}$, $-NR^{10}R^{11}$, $-NR^{10}C(O)R^{12}$, $-NR^{10}C(O)OR^{12}$, $-NR^{10}C(O)NR^{10}R^{11}$, $-NR^{10}S(O)_2R^{12}$, $-S(O)_pR^{12}$, and $-S(O)_2NR^{10}R^{11}$. In some embodiments, p is independently 0. In some embodiments, p is independently an integer of 1 or 2. For example, in some embodiments, $R^{2a}$ is hydrogen, $-CH_3$, $-CD_3$, $-CH_2CH_3$, $-CD_2CD_3$, isopropyl, 2,3-dihydroxypropyl or cyclopropyl.

In some embodiments, the compound is a compound of Formula (I), (II), (III), or (IV), for example a compound of Formula (Ia), (Ib), (IIa), (IIb), (IIIa), (IIIb), (IVa), or (IVb), or a pharmaceutically acceptable form thereof, or a compound of Formula (VI), (VIa), or (VIb), as disclosed herein, wherein $A^3$ is $CR^3$. In some embodiments, $R^3$ is independently $R^9$, $-OR^9$, halo, or CN. In some embodiments, $R^3$ is hydrogen. In some embodiments, the compound is a compound of Formula (I), (II), (III), (IV), or (VI), for example a compound of Formula (Ia), (Ib), (IIa), (IIb), (IIIa), (IIIb), (IVa), (IVb), (VIa), or (VIb), wherein $A^3$ is N. In some embodiments, the compound is a compound of Formula (Ia), (Ib), (IIa), (IIb), (IIIa), (IIIb), (IVa), or (IVb), or a pharmaceutically acceptable form thereof, or is a compound of Formula (VIa) or (VIb), or a pharmaceutically acceptable salt thereof. In some embodiments, the compound is a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or a pharmaceutically acceptable form thereof, or a compound of Formula (III-3), (IIIa-3), (IIIb-3), (VIa-1), or (VIb-1), or a pharmaceutically acceptable form thereof.

In some embodiments, the compound is a compound of Formula (I), (II), (III), or (IV), for example a compound of Formula (Ia), (Ib), (IIa), (IIb), (IIIa), (IIIb), (IVa), or (IVb), or a pharmaceutically acceptable form thereof, or of Formula (V), (Va), (Vb), (VI), (VIa), or (VIb), or a pharmaceutically acceptable form thereof, as disclosed herein, wherein $A^4$ is $CR^8$. In some embodiments, $A^4$ is N. In some embodiments, $A^4$ is N, and no more than one of $A^5$ and $A^6$ is N. In some embodiments, $A^5$ is $CR^8$. In some embodiments, $A^5$ is N. In some embodiments, $A^5$ is N, and no more than one of $A^4$ and $A^6$ is N. In some embodiments, $A^6$ is $CR^8$. In some embodiments, $A^6$ is N. In some embodiments, $A^6$ is N, and no more than one of $A^4$ and $A^5$ is N. In some embodiments, $A^4$, $A^5$ and $A^6$ are each independently $CR^8$. In some embodiments, $R^8$ is independently $R^9$, $-OR^9$, halo, or CN. In some embodiments, $R^8$ is hydrogen. In some embodiments, $A^5$ and $A^6$ taken together is O, $NR^9$, or S. For example, as a representative example of $A^5$ and $A^6$ taken together replaced with O, $NR^9$, or S in a compound of Formula (I), is shown below as a compound of Formula (I-A1), Formula (I-A2), and Formula (I-A3), respectively:

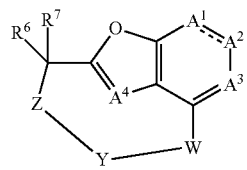

Formula (I-A1)

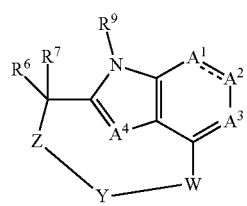

Formula (I-A2)

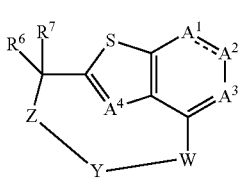

Formula (I-A3)

or a pharmaceutically acceptable form thereof.

In some embodiments, the compound is a compound of Formula (I), (II), (III), or (IV), for example a compound of Formula (Ia), (Ib), (IIa), (IIb), (IIIa), (IIIb), (IVa), or (IVb), or a pharmaceutically acceptable form thereof, or a compound of Formula (V) or (VI) such as Formula (Va), (Vb), (VIa), or (VIb), or a pharmaceutically acceptable form thereof, as disclosed herein, wherein Y is a bond or is a linker having a length of up to 5 atoms, up to 4 atoms, up to 3 atoms, or up to 2 atoms. In some embodiments, Y is a bond. In some embodiments, Y is a linker having a length of 5 atoms. In some embodiments, Y is a linker having a length of 4 atoms. In some embodiments, Y is a linker having a length of 3 atoms. In some embodiments, Y is a linker having a length of 2 atoms. In some embodiments, Y is a linker having a length of 1 atom. In some embodiments, Y is a $C_{1-6}$ alkylene, wherein one or more —$CH_2$— is optionally independently replaced by —O—, —C(O)—, —N($R^{10}$)—, —N($R^{10}$)C(O)—, —C(O)N($R^{10}$)—, —N($R^{10}$)C(O)N($R^{11}$)—, —S(O)$_p$—, —N($R^{10}$)S(O)$_2$—, —S(O)$_2$N($R^{10}$)—, or —N($R^{10}$)S(O)$_2$N($R^{11}$)—. In some embodiments, p is independently 0. In some embodiments, p is independently an integer of 1 or 2. In some embodiments, Y is in the direction of Z-Y-W (wherein Z refers to Z or the Z-containing ring and W refers to W or the W-containing ring as applicable in Formula (I), (II), (III), or (IV), and subformulae thereof). For example, as a representative example of Y written in the direction of Z-Y-W in a compound of Formula (I), wherein Y is —N($R^{10}$)C(O)— is shown below as a compound of Formula (I-A4):

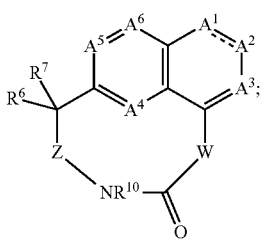

Formula (I-A4)

whereas Y is —C(O)N($R^{10}$)— is shown below as a compound of Formula (I-A5):

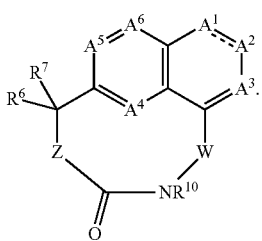

Formula (I-A5)

In some embodiments, the compound is a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or a pharmaceutically acceptable form thereof, as disclosed herein, or is a compound of Formula (III-3), (V-1), or (VI-1), such as Formula (IIIa-3), (IIIb-3), (Va-1), (Vb-1), (VIa-1), or (VIb-1), or a pharmaceutically acceptable form thereof.

In some embodiments, Y is —(CR$^{16}$R$^{17}$)$_q$—, —(CR$^{16}$R$^{17}$)$_m$O(CR$^{16}$R$^{17}$)$_n$—, —(CR$^{16}$R$^{17}$)$_m$C(O)(CR$^{16}$R$^{17}$)$_n$—, —(CR$^{16}$R$^{17}$)$_m$N(R$^{10}$)(CR$^{16}$R$^{17}$)$_n$—, —(CR$^{16}$R$^{17}$)$_m$N(R$^{10}$)C(O)(CR$^{16}$R$^{17}$)$_n$—, —(CR$^{16}$R$^{17}$)$_m$C(O)N(R$^{10}$)(CR$^{16}$R$^{17}$)$_n$—, —(CR$^{16}$R$^{17}$)$_m$N(R$^{10}$)C(O)N(R$^1$)(CR$^{16}$R$^{17}$)$_n$—, —(CR$^{16}$R$^{17}$)$_m$S(O)$_p$(CR$^{16}$R$^{17}$)$_n$—, —(CR$^{16}$R$^{17}$)$_m$N(R$^{10}$)S(O)$_2$(CR$^{16}$R$^{17}$)$_n$—, —(CR$^{16}$R$^{17}$)$_m$S(O)$_2$N(R$^{10}$)(CR$^{16}$R$^{17}$)$_n$—, or —(CR$^{16}$R$^{17}$)$_m$N(R$^{10}$)S(O)$_2$N(R$^1$)(CR$^{16}$R$^{17}$)$_n$—; wherein: R$^{16}$ and R$^{17}$, at each occurrence, are each independently hydrogen, halo, hydroxy, CN, NO$_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, or 3-6 membered heterocycloalkoxy, or together with the C to which each is attached are combined to form a C(O), $C_{3-6}$ cycloalkyl, or 3-6 membered heterocycloalkyl; each m is independently an integer of 0, 1, 2, or 3; each n is independently an integer of 0, 1, 2, or 3; wherein the sum of m and n is 0, 1, 2, 3, 4, 5, or 6; each p is independently an integer of 0, 1, or 2; and each q is independently an integer of 0, 1, 2, 3, 4, 5, or 6. In some embodiments, m is 0, 1, 2, or 3. In some embodiments, m is 0, 1, or 2. In some embodiments, n is 0, 1, or 2. In some embodiments, each m is independently an integer of 0 or 1; and each n is independently an integer of 1, 2 or 3; wherein the sum of m and n is 1, 2, 3, or 4. In some embodiments, each m is independently an integer of 0; and each n is independently an integer of 1, 2, or 3; wherein the sum of m and n is 1, 2, or 3. In some embodiments, each m is independently an integer of 0; and each n is independently an integer of 1 or 2; wherein the sum of m and n is 1 or 2. In some embodiments, each m is independently an integer of 1, 2, or 3; and each n is independently an integer of 0 or 1; wherein the sum of m and n is 1, 2, 3 or 4. In some embodiments, each m is independently an integer of 1, 2 or 3; and each n is independently an integer of 0; wherein the sum of m and n is 1, 2, or 3. In some embodiments, each m is independently an integer of 1 or 2; and each n is independently an integer of 0; wherein the sum of m and n is 1 or 2. In some embodiments, p is independently 0. In some embodiments, p is independently an integer of 1 or 2. In some embodiments, q is independently an integer of 1, 2, 3, 4, or 5. In some embodiments, q is independently an integer of 1, 2, 3, or 4. In some embodiments, q is independently an integer of 1, 2, or 3. In some embodiments, q is independently an integer of 2 or 3. In some embodiments, q is independently an integer of 1 or 2.

In some embodiments, Y is —(CR$^{16}$R$^{17}$)$_q$—, —(CR$^{16}$R$^{17}$)$_m$O(CR$^{16}$R$^{17}$)$_n$—, —(CR$^{16}$R$^{17}$)$_m$C(O)(CR$^{16}$R$^{17}$)$_n$—, —(CR$^{16}$R$^{17}$)$_m$N(R$^{10}$)(CR$^{16}$R$^{17}$)$_n$—, —(CR$^{16}$R$^{17}$)$_m$N(R$^{10}$)C(O)(CR$^{16}$R$^{17}$)$_n$—, —(CR$^{16}$R$^{17}$)$_m$C(O)N(R$^{10}$)(CR$^{16}$R$^{17}$)$_n$—, —(CR$^{16}$R$^{17}$)$_m$N(R$^{10}$)S(O)$_2$(CR$^{16}$R$^{17}$)$_n$—, or —(CR$^{16}$R$^{17}$)$_m$S(O)$_2$N(R$^{10}$)(CR$^{16}$R$^{17}$)$_n$—. For example, in some embodiments, Y is —(CR$^{16}$R$^{17}$)$_q$—, —(CR$^{16}$R$^{17}$)$_m$O(CR$^{16}$R$^{17}$)$_n$—, —(CR$^{16}$R$^{17}$)$_m$N(R$^{10}$)C(O)(CR$^{16}$R$^{17}$)$_n$—, or —(CR$^{16}$R$^{17}$)$_m$C(O)N(R$^{10}$)(CR$^{16}$R$^{17}$)$_n$—. For example, in some embodiments, Y is —(CR$^{16}$R$^{17}$)$_q$—. For example, in some embodiments, Y is —(CR$^{16}$R$^{17}$)$_m$O(CR$^{16}$R$^{17}$)$_n$—. For example, in some embodiments, Y is —(CR$^{16}$R$^{17}$)$_m$N(R$^{10}$)C(O)(CR$^{16}$R$^{17}$)$_n$—. For example, in some embodiments, Y is or —(CR$^{16}$R$^{17}$)$_m$C(O)N(R$^{10}$)(CR$^{16}$R$^{17}$)$_n$—. In some embodiments, m is 0, 1, 2, or 3. In some embodiments, m is 0, 1, or 2. In some embodiments, n is 0, 1, 2, or 3. In some embodiments, n is 0, 1, or 2. In some embodiments, q is independently an integer of 1, 2, 3, 4, or 5. In some embodiments, q is independently an integer of 1, 2, 3, or 4. In some embodiments, q is independently an integer of 1, 2, or 3. In some embodiments, q is independently an integer of 2 or 3. In some embodiments, q is independently an integer of 1 or 2. In some embodiments, Y is R$^{16}$ and R$^{17}$, at each occurrence, are each independently hydrogen, halo, hydroxy, CN, NO$_2$, C$_{1-3}$ alkyl, C$_{2-3}$ alkenyl, C$_{2-3}$ alkynyl, C$_{1-3}$ haloalkyl, C$_{1-3}$ hydroxyalkyl, C$_{1-3}$ heteroalkyl, C$_{3-5}$ cycloalkyl, 3-5 membered heterocycloalkyl, C$_{1-3}$ alkoxy, C$_{1-3}$ haloalkoxy, C$_{1-3}$ hydroxyalkoxy, C$_{1-3}$ heteroalkoxy, or 3-5 membered heterocycloalkoxy, or together with the C to which each is attached are combined to form a C(O), C$_{3-5}$ cycloalkyl, or 3-5 membered heterocycloalkyl. For example, in some embodiments, R$^{16}$ and R$^{17}$, at each occurrence, are each independently hydrogen, chloro, hydroxy, CN, NO$_2$, methyl, ethyl, isopropyl, —CF$_3$, —CH$_2$CF$_3$, —CH$_2$OH, —(CH$_2$)$_2$OH, —(CH$_2$)$_2$OCH$_3$, cyclopropyl, 3-oxetanyl, methoxy, ethoxy, isopropoxy, cyclopropoxy, —OCF$_3$, —OCH$_2$CF$_3$, —O(CH$_2$)$_2$OH, —O(CH$_2$)$_2$OCH$_3$, or 3-oxetanylalkoxy, or together with the C to which each is attached are combined to form a C(O), cyclopropyl, or 3-5 membered heterocycloalkyl. In some embodiments, R$^{16}$ and R$^{17}$ are each hydrogen. In some embodiments, Y is —(CH$_2$)O—, —O(CH$_2$)—, —(CH$_2$)$_2$O—, —O(CH$_2$)$_2$—, or —(CH$_2$)$_2$—. For example, in some embodiments, Y is —(CH$_2$)O—. In some embodiments, Y is —O(CH$_2$)—. In some embodiments, Y is —(CH$_2$)$_2$O—. In some embodiments, Y is —O(CH$_2$)$_2$—. In some embodiments, Y is —(CH$_2$)$_2$—. In some embodiments, the compound is a compound of Formula (I), (II), (III), or (IV), for example a compound of Formula (Ia), (Ib), (IIa), (IIb), (IIIa), (IIIb), (IVa), or (IVb), or a pharmaceutically acceptable form thereof, or of Formula (V), (Va), (Vb), (VI), (VIa), or (VIb), or a pharmaceutically acceptable form thereof, as disclosed herein. In some embodiments, the compound is a compound of Formula (II-1) or (II-2), such as a compound of Formula (IIa-1), (IIb-1), (IIa-2), or (IIb-2), or a pharmaceutically acceptable form thereof. In some embodiments, the compound is a compound of Formula (III-1) or (III-2), such as a compound of Formula (IIIa-1), (IIIb-1), (IIIa-2), or (IIIb-2), or a pharmaceutically acceptable form thereof, or a compound of Formula (III-3), (IIIa-3), or (IIIb-3), or a pharmaceutically acceptable form thereof. In some embodiments, the compound is a compound of Formula (IV-1) or (IV-2), such as a compound of Formula (IVa-1), (IVb-1), (IVa-2), or (IVb-2), or a pharmaceutically acceptable form thereof. In some embodiments, the compound is a compound of Formula (V-1), (Va-1), (Vb-1), (VI-1), (VIa-1), or (VIb-1), or a pharmaceutically acceptable form thereof.

In some embodiments, the compound is a compound of Formula (I), (II), (III), or (IV), for example a compound of Formula (Ia), (Ib), (IIa), (IIb), (IIIa), (IIIb), (IVa), or (IVb), or a pharmaceutically acceptable form thereof, or a compound of Formula (V), (Va), (Vb), (VI), (VIa), or (VIb), or a pharmaceutically acceptable form thereof, as disclosed herein, wherein W$^1$, W$^2$, W$^3$, and W$^4$ are each independently N or CR$^4$, or W$^1$ and W$^2$ taken together is O, NR$^{4A}$, or S, or W$^2$ and W$^3$ taken together is O, NR$^{4A}$, or S. In some embodiments, at least one of W$^1$, W$^2$, W$^3$, and W$^4$ is N. In some embodiments, W$^1$, W$^2$, and W$^3$ are each independently CR$^4$, and W$^4$ is N. In some embodiments, W$^1$, W$^2$, and W$^4$ are each independently CR$^4$, and W$^3$ is N. In some embodiments, W$^1$, W$^3$, and W$^4$ are each independently CR$^4$, and W$^2$ is N. In some embodiments, W$^2$, W$^3$, and W$^4$ are each independently CR$^4$, and W$^1$ is N. In some embodiments, W$^1$, W$^2$, W$^3$, and W$^4$ are each independently CR$^4$. In some embodiments, W$^2$ and W$^3$ are each independently CR$^4$, and W$^1$ and W$^4$ are each independently N. In some embodiments, W$^1$ and W$^2$ are each independently CR$^4$, and W$^3$ and W$^4$ are each independently N. In some embodiments, W$^1$ and W$^4$ are each independently CR$^4$, and W$^2$ and W$^3$ taken together is O, NR$^{4A}$, or S. In some embodiments, W$^3$ and W$^4$ are each independently CR$^4$, and W$^1$ and W$^2$ taken together is O, NR$^{4A}$ or S. In some embodiments, W$^1$ is CR$^4$, W$^4$ is N, and W$^2$ and W$^3$ taken together is O, NR$^{4A}$ or S. In some embodiments, W$^3$ is CR$^4$, W$^4$ is N, and W$^1$ and W$^2$ taken together is O, NR$^{4A}$, or S.

In some embodiments, R$^4$, at each occurrence, is independently hydrogen, halo, C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, C$_{1-6}$ hydroxyalkoxy, C$_{1-6}$ heteroalkoxy, C$_{3-6}$ cycloalkoxy, 3-6 membered heterocycloalkoxy, or —NR$^{14}$R$^{15}$, wherein each C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, C$_{1-6}$ hydroxyalkoxy, C$_{1-6}$ heteroalkoxy, C$_{3-6}$ cycloalkoxy, or 3-6 membered heterocycloalkoxy, of the R$^4$ are optionally independently substituted with 1-6 substituents independently selected from halo, hydroxy, C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, and (O). For example, in some embodiments, R$^4$ is independently hydrogen, halo, C$_{1-6}$ alkyl, C$_{1-6}$ haloalkyl, C$_{3-6}$ cycloalkyl, C$_{1-6}$ alkoxy, or C$_{1-6}$ haloalkoxy, wherein each C$_{1-6}$ alkyl, C$_{1-6}$ haloalkyl, C$_{3-6}$ cycloalkyl, C$_{1-6}$ alkoxy, or C$_{1-6}$ haloalkoxy of the R$^4$ are optionally independently substituted with 1-6 substituents independently selected from halo, hydroxy, C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, and (O). In some embodiments, R$^4$ is independently hydrogen, halo, C$_{1-3}$ alkyl, C$_{1-3}$ haloalkyl, C$_{3-5}$ cycloalkyl, C$_{1-3}$ alkoxy, or C$_{1-3}$ haloalkoxy. In some embodiments, R$^4$ is independently hydrogen.

In some embodiments, R$^{4A}$ is independently hydrogen, C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{6-12}$ aryl, or 5-12 membered heteroaryl, wherein each C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{6-12}$ aryl, or 5-12 membered heteroaryl of the R$^{4A}$ is optionally independently substituted with one, two, three, four, five, or six substituents selected from halo, hydroxy, C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, and (O). For example, in some embodiments, R$^{4A}$ is independently hydrogen, C$_{1-3}$ alkyl, C$_{1-3}$ haloalkyl, C$_{1-3}$ hydroxyalkyl, C$_{1-3}$ heteroalkyl, C$_{3-6}$ cycloalkyl, 3-6 membered heterocycloalkyl, phenyl, or 5-6 membered heteroaryl, wherein each C$_{1-3}$ alkyl, C$_{1-3}$ haloalkyl, C$_{1-3}$ hydroxyalkyl, C$_{1-3}$ heteroalkyl, C$_{3-6}$ cycloalkyl, 3-6 membered heterocycloalkyl, phenyl, or 5-6 membered heteroaryl of the R$^{4A}$ is optionally independently substituted with 1-6 substituents independently selected from halo, hydroxy, C$_{1-3}$ alkyl, C$_{1-3}$ haloalkyl, C$_{1-3}$ hydroxyalkyl, C$_{1-3}$ heteroalkyl, C$_{3-6}$ cycloalkyl, 3-6 membered heterocycloalkyl, C$_{1-3}$ alkoxy, C$_{1-3}$ haloalkoxy, and (O). In some embodiments, R$^{4A}$ is independently hydrogen, C$_{1-3}$ alkyl, C$_{1-3}$ haloalkyl, C$_{1-3}$ hydroxyalkyl, $C_{1-3}$ heteroalkyl, $C_{3-6}$ cycloalkyl, or 3-6 membered heterocycloalkyl. In some embodiments, $R^{4A}$ is independently hydrogen, $C_{1-3}$ alkyl, $C_{1-3}$ haloalkyl, $C_{1-3}$ hydroxyalkyl, $C_{1-3}$ heteroalkyl, or cyclopropyl.

In some embodiments, the compound is a compound of Formula (I), (II), (III), or (IV), for example a compound of Formula (Ia), (Ib), (IIa), (IIb), (IIIa), (IIIb), (IVa), or (IVb), or a pharmaceutically acceptable form thereof, or a compound of Formula (V), (Va), (Vb), (VI), (VIa), or (VIb), or a pharmaceutically acceptable form thereof, as disclosed herein, wherein $Z^1$, $Z^2$, $Z^3$, and $Z^4$ are each independently N or $CR^5$, or $Z^2$ and $Z^3$ taken together is O, $NR^{5A}$, or S, or $Z^3$ and $Z^4$ taken together is O, $NR^{5A}$, or S. In some embodiments, at least one of $Z^1$, $Z^2$, $Z^3$, and $Z^4$ is N. In some embodiments, $Z^1$, $Z^2$, and $Z^3$ are each independently $CR^5$, and $Z^4$ is N. In some embodiments, $Z^1$, $Z^2$, and $Z^4$ are each independently $CR^5$, and $Z^3$ is N. In some embodiments, $Z^1$, $Z^3$, and $Z^4$ are each independently $CR^5$, and $Z^2$ is N. In some embodiments, $Z^2$, $Z^3$, and $Z^4$ are each independently $CR^5$, and $Z^1$ is N. In some embodiments, $Z^1$, $Z^2$, $Z^3$, and $Z^4$ are each independently $CR^5$. In some embodiments, $Z^2$ and $Z^3$ are each independently $CR^5$, and $Z^1$ and $Z^4$ are each independently N. In some embodiments, $Z^3$ and $Z^4$ are each independently $CR^5$, and $Z^1$ and $Z^2$ are each independently N. In some embodiments, $Z^1$ and $Z^4$ are each independently $CR^5$, and $Z^2$ and $Z^3$ taken together is O, $NR^{5A}$, or S. In some embodiments, $Z^1$ and $Z^2$ are each independently $CR^5$, and $Z^3$ and $Z^4$ taken together is O, $NR^{5A}$, or S. In some embodiments, $Z^1$ is N, $Z^2$ and $Z^3$ taken together is O, $NR^{5A}$, or S, and $Z^4$ is $CR^5$. In some embodiments, $Z^1$ is N, $Z^2$ is $CR^5$, and $Z^3$ and $Z^4$ taken together is O, $NR^{5A}$, or S. In some embodiments, $R^5$, at each occurrence, is independently $R^9$, —$OR^9$, halo, CN, $NO_2$, —$C(O)R^9$, —$C(O)OR^9$, —$C(O)NR^{10}R^{11}$, —$S(O)_pR^9$, or —$S(O)_2NR^{10}R^{11}$. In some embodiments, p is independently 0. In some embodiments, p is independently an integer of 1 or 2. For example, in some embodiments, $R^5$, at each occurrence, is independently hydrogen halo, CN, $NO_2$, —$C(O)(C_{1-6}$ alkyl), —$C(O)OH$, —$C(O)O(C_{1-6}$ alkyl), —$C(O)NR^{10}R^{11}$, —$S(O)_p(C_{1-6}$ alkyl), or —$S(O)_2NR^{10}R^{11}$. In some embodiments, $R^5$, at each occurrence, is independently halo, CN, $NO_2$, —$C(O)CH_3$, —$C(O)OH$, —$C(O)OCH_3$, —$C(O)N(CH_3)_2$, —$S(O)_2CH_3$, or —$S(O)_2N(CH_3)_2$. In some embodiments, $R^5$ independently is hydrogen, halo or CN. In some embodiments, $R^5$ independently is hydrogen. In some embodiments, $R^5$ is independently an electron-withdrawing group. In some embodiments, $R^5$ independently is chloro. In some embodiments, $R^5$ independently is CN.

In some embodiments, $R^{5A}$ is independently hydrogen, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{5A}$ is optionally independently substituted with 1-6 substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O). For example, in some embodiments, $R^{5A}$ is independently hydrogen, $C_{1-3}$ alkyl, $C_{1-3}$ haloalkyl, $C_{1-3}$ hydroxyalkyl, $C_{1-3}$ heteroalkyl, $C_{3-6}$ cycloalkyl, 3-6 membered heterocycloalkyl, phenyl, or 5-6 membered heteroaryl, wherein each $C_{1-3}$ alkyl, $C_{1-3}$ haloalkyl, $C_{1-3}$ hydroxyalkyl, $C_{1-3}$ heteroalkyl, $C_{3-6}$ cycloalkyl, 3-6 membered heterocycloalkyl, phenyl, or 5-6 membered heteroaryl of the $R^{5A}$ is optionally independently substituted with 1-6 substituents selected from halo, hydroxy, $C_{1-3}$ alkyl, $C_{1-3}$ haloalkyl, $C_{1-3}$ hydroxyalkyl, $C_{1-3}$ heteroalkyl, $C_{3-6}$ cycloalkyl, 3-6 membered heterocycloalkyl, $C_{1-3}$ alkoxy, $C_{1-3}$ haloalkoxy, and (O). In some embodiments, $R^{5A}$ is independently hydrogen, $C_{1-3}$ alkyl, $C_{1-3}$ haloalkyl, $C_{1-3}$ hydroxyalkyl, $C_{1-3}$ heteroalkyl, $C_{3-6}$ cycloalkyl, or 3-6 membered heterocycloalkyl. In some embodiments, $R^{5A}$ is independently hydrogen, $C_{1-3}$ alkyl, $C_{1-3}$ haloalkyl, $C_{1-3}$ hydroxyalkyl, $C_{1-3}$ heteroalkyl, or cyclopropyl.

In some embodiments, the compound is a compound of Formula (I), (II), (III), or (IV), for example a compound of Formula (Ia), (Ib), (IIa), (IIb), (IIIa), (IIIb), (IVa), or (IVb), or a pharmaceutically acceptable form thereof, or a compound of Formula (V), (Va), (Vb), (VI), (VIa), or (VIb), or a pharmaceutically acceptable form thereof, as disclosed herein, wherein $R^6$ is CN, $R^9$, —$OR^9$, —$C(O)R^9$, —$C(O)OR^9$, —$OC(O)R^9$, —$OC(O)OR^9$, —$C(O)NROR^{11}$, —$NR^{10}R^{11}$, —$NR^{10}OR^9$, —$NR^{10}C(O)R^9$, —$NR^{10}C(O)OR^9$, —$NR^{10}C(O)NR^{10}R^{11}$, —$NR^{10}S(O)_2R^9$, —$NR^{10}C(NR^{10})NROR^{11}$, —$S(O)_pR^9$, —$S(O)_2NR^{10}R^{11}$ or —$NR^{10}S(O)_2NR'OR^{11}$. In some embodiments, p is independently 0. In some embodiments, p is independently an integer of 1 or 2. For example, in some embodiments, $R^6$ is CN, $R^9$, —$OR^9$, —$OC(O)R^9$, —$OC(O)OR^9$, —$NR^{10}R^{11}$, —$NR^{10}OR^9$, —$NR^{10}C(O)R^9$ or —$NR^{10}C(NR^{10})NR^{10}R^{11}$. In some embodiments, $R^6$ is CN, $R^9$, —$OR^9$, —$OC(O)R^9$, —$OC(O)OR^9$, —$NR^{10}R^{11}$, —$NR^{10}R^9$, or —$NR^{10}C(O)R^9$. In some embodiments, $R^6$ is CN, $R^9$, —$OR^9$, —$NR^{10}R^{11}$, or —$NR^{10}R^9$. In some embodiments, $R^6$ is CN, $R^9$, —$OR^9$, or —$NR^{10}R^{11}$. For example, in some embodiments, $R^9$ is independently hydrogen or $C_{1-3}$ alkyl, wherein the $C_{1-3}$ alkyl is optionally substituted with CN. In some embodiments, $R^{10}$ and $R^{11}$ are each independently hydrogen, $C_{1-6}$ alkyl or $C_{1-6}$ alkoxy. In some embodiments, $R^{10}$ and $R^{11}$ together is a divalent group, such as —$(CH_2)_x$—, wherein x=2-5, —$CH_2CH_2OCH_2CH_2$—, or —$CH_2CH_2NR^{18}CH_2CH_2$—, wherein $R^{18}$ is independently hydrogen, $C_{1-6}$ alkyl, $C_{1-6}$ haloalkyl, $C_{1-6}$ hydroxyalkyl, $C_{1-6}$ heteroalkyl, 3-6 membered heterocycloalkyl, or 5-12 membered heteroaryl. In some embodiments, $R^6$ is hydroxy, —$OCH_3$, CN, hydrogen, —$CH_3$, —$CH_2CN$, —$NH_2$, —$NHCH_3$, or —$NH(OCH_3)$. In some embodiments, $R^6$ is hydrogen, —$CH_3$, hydroxy, —$OCH_3$, —$OCD_3$, —$NH_2$, —$NHCH_3$, or —$NH(OCH_3)$. In some embodiments, $R^6$ is hydrogen, hydroxy, —$OCH_3$, —$OCD_3$, —$NH_2$, or —$NHCH_3$. In some embodiments, $R^6$ is —$NH(CH_2CH_2)Cl$, —$NH(CH_2CH_2)F$, or N-linked morpholino. In some embodiments, $R^6$ is hydroxy. In some embodiments, $R^6$ is hydrogen. In some embodiments, $R^6$ is $NH_2$. In some embodiments, the compound is a compound of Formula (II-1) or (II-2), such as a compound of Formula (IIa-1), (IIb-1), (IIa-2), or (IIb-2), or a pharmaceutically acceptable form thereof. In some embodiments, the compound is a compound of Formula (III-1) or (III-2), such as a compound of Formula (IIIa-1), (IIIb-1), (IIIa-2), or (IIIb-2), or a pharmaceutically acceptable form thereof, or is a compound of Formula (III-3), (IIIa-3), or (IIIb-3), or a pharmaceutically acceptable form thereof. In some embodiments, the compound is a compound of Formula (IV-1) or (IV-2), such as a compound of Formula (IVa-1), (IVb-1), (IVa-2), or (IVb-2), or a pharmaceutically acceptable form thereof. In some embodiments, the compound is a compound of Formula (V-1), (Va-1), (Vb-1), (VI-1), (VIa-1), or (VIb-1), or a pharmaceutically acceptable form thereof.

In some embodiments, the compound is a compound of Formula (I), (II), (III), or (IV), for example a compound of Formula (Ia), (Ib), (IIa), (IIb), (IIIa), (IIIb), (IVa), or (IVb), or a pharmaceutically acceptable form thereof, or a compound of Formula (V), (Va), (Vb), (VI), (VIa), or (VIb), or a pharmaceutically acceptable form thereof, as disclosed herein, wherein $R^7$ is a 5-12 membered heteroaryl, optionally substituted with 1-4 substituents independently selected from halo, CN, $NO_2$, $R^9$, —$OR^9$, —$C(O)R^9$, —$C(O)OR^9$, —$OC(O)R^9$, —$OC(O)OR^9$, —$C(O)NR^{10}R^{11}$, —$NR^{10}R^{11}$, —$NR^{10}C(O)R^9$, —$NR^{10}C(O)OR^9$, —$NR^{10}C(O)NR^{10}R^{11}$, —$NR^{10}S(O)_2R^9$, —$S(O)_pR^9$, —$S(O)_2NR^{10}R^{11}$ or —$NR^{10}S(O)_2NR^{10}R^{11}$. For example, in some embodiments, $R^7$ is an imidazolyl, a triazolyl, a tetrazolyl, an oxazolyl, a thiazolyl, an oxadiazolyl, a thiadiazolyl, a pyridyl, or a pyrimidinyl, optionally substituted with 1-4 substituents independently selected from halo, CN, $NO_2$, $R^9$, —$OR^9$, —$C(O)R^9$, —$C(O)OR^9$, —$OC(O)R^9$, —$OC(O)OR^9$, —$C(O)NR^{10}R^{11}$, —$NR^{10}R^{11}$, —$NR^{10}C(O)R^9$, —$NR^{10}C(O)OR^9$, —$NR^{10}C(O)NR^{10}R^{11}$, —$NR^{10}S(O)_2R^9$, —$S(O)_pR^9$, —$S(O)_2NR^{10}R^{11}$, or —$NR^{10}S(O)_2NR^{10}R^{11}$. In some embodiments, p is independently 0. In some embodiments, p is independently an integer of 1 or 2. For example, in some embodiments, $R^7$ is imidazolyl or triazolyl, optionally substituted with 1-4 substituents independently selected from halo, CN, $NO_2$, $R^9$, —$OR^9$, —$C(O)R^9$, —$C(O)OR^9$, —$C(O)NR^{10}R^{11}$, —$NR^{10}R^{11}$, —$NR^{10}C(O)R^9$, —$S(O)_pR^9$, or —$S(O)_2NR^{10}R^{11}$. In some embodiments, $R^7$ is a C-linked imidazolyl or a C-linked triazolyl, optionally substituted with 1-4 substituents independently selected from halo, CN, $NO_2$, $R^9$, —$OR^9$, —$C(O)R^9$, —$C(O)OR^9$, —$C(O)NROR^{11}$, —$NR^{10}R^{11}$, —$NR^{10}C(O)R^9$, —$S(O)_pR^9$, or —$S(O)_2NR^{10}R^{11}$. In some embodiments, $R^7$ is an N-linked imidazolyl or an N-linked triazolyl, optionally substituted with 1-4 substituents independently selected from halo, CN, $NO_2$, $R^9$, —$OR^9$, —$C(O)R^9$, —$C(O)OR^9$, —$C(O)NR^{10}R^{11}$, —$NR^{10}R^{11}$, —$NR^{10}C(O)R^9$, —$S(O)_pR^9$, or —$S(O)_2NR^{10}R^{11}$. In some embodiments, $R^7$ is a methyl-substituted imidazolyl or a methyl-substituted triazolyl. In some embodiments, $R^7$ is a C-methyl-substituted imidazolyl or a C-methyl-substituted triazolyl. In some embodiments, $R^7$ is an N-methyl-substituted imidazolyl or an N-methyl-substituted triazolyl. In some embodiments, $R^7$ is

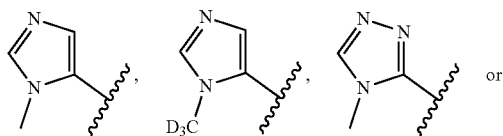

In some embodiments, $R^7$ is

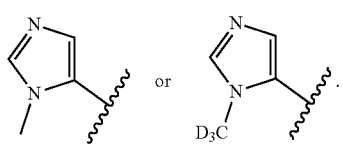

In some embodiments, $R^7$ is

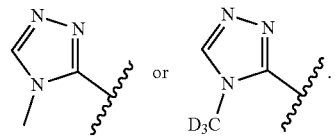

In some embodiments, $R^7$ is

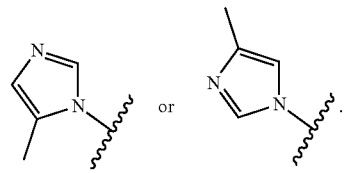

In some embodiments, $R^7$ is

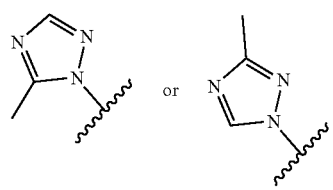

the compound is a compound of Formula (II-1) or (II-2), such as a compound of Formula (IIa-1), (IIb-1), (IIa-2), or (IIb-2), or a pharmaceutically acceptable form thereof. In some embodiments, the compound is a compound of Formula (III-1) or (III-2), such as a compound of Formula (IIIa-1), (IIIb-1), (IIIa-2), or (IIIb-2), or a pharmaceutically acceptable form thereof, or a compound of Formula (III-3), (IIIa-3), or (IIIb-3), or a pharmaceutically acceptable form thereof. In some embodiments, the compound is a compound of Formula (IV-1) or (IV-2), such as a compound of Formula (IVa-1), (IVb-1), (IVa-2), or (IVb-2), or a pharmaceutically acceptable form thereof. In some embodiments, the compound is a compound of Formula (V-1), (Va-1), (Vb-1), (VI-1), (VIa-1), or (VIb-1), or a pharmaceutically acceptable form thereof.

In some embodiments, the compound disclosed herein is a compound of Formula (I), such as a compound of Formula (Ia), or (Ib), or pharmaceutically acceptable form thereof. In some embodiments, the pharmaceutically acceptable form of the compound of Formula (I), such as a compound of Formula (Ia), or (Ib), is exclusive of a salt form (i.e., is not a salt), and includes a pharmaceutically acceptable solvate, isomer, and isotopologue (i.e., isotopically labeled derivative) of the compound of Formula (I), such as a compound of Formula (Ia), or (Ib), respectively.

In some embodiments, the compound of Formula (I), (Ia), or (Ib), or pharmaceutically acceptable form thereof, is a compound of Formula (II), (IIa), or (IIb), or a pharmaceutically acceptable form thereof, respectively. In some embodiments, the compound is a compound of Formula (II-1) or (II-2), or pharmaceutically acceptable form thereof, such as a compound of Formula (IIa-1), (IIb-1), (IIa-2), or (IIb-2), or pharmaceutically acceptable form thereof, respectively. In some embodiments, the pharmaceutically acceptable form of the compound of Formula (II), (IIa), or (IIb), for example the compound of Formula (II-1) or (II-2), such as the compound of Formula (IIa-1), (IIb-1), (IIa-2), or (IIb-2), is exclusive of a salt form (i.e., is not a salt), and includes a pharmaceutically acceptable solvate, isomer, and isotopologue (i.e., isotopically labeled derivative) of the compound of Formula (II), (IIa), or (IIb), for example the compound of Formula (II-1) or (II-2), such as the compound of Formula (IIa-1), (IIb-1), (IIa-2), or (IIb-2), respectively.

In some embodiments, the compound of Formula (I), (Ia), or (Ib), or pharmaceutically acceptable form thereof, is a compound of Formula (III), (IIIa), or (IIIb), or a pharmaceutically acceptable form thereof, respectively. In some embodiments, the compound is a compound of Formula (III-1) or (III-2), or pharmaceutically acceptable form thereof, such as a compound of Formula (IIIa-1), (IIIb-1), (IIIa-2), or (IIIb-2), or pharmaceutically acceptable form thereof, respectively, or a compound of Formula (III-3), (IIIa-3), or (IIIb-3), or a pharmaceutically acceptable form thereof. In some embodiments, the pharmaceutically acceptable form of the compound of Formula (III), (IIIa), or (IIIb), for example the compound of Formula (III-1) or (III-2), such as the compound of Formula (IIIa-1), (IIIb-1), (IIIa-2), or (IIIb-2), or of Formula (III-3), (IIIa-3), or (IIIb-3), is exclusive of a salt form (i.e., is not a salt), and includes a pharmaceutically acceptable solvate, isomer, and isotopologue (i.e., isotopically labeled derivative) of the compound of Formula (III), (IIIa), or (IIIb), for example the compound of Formula (III-1) or (III-2), such as the compound of Formula (IIIa-1), (IIIb-1), (IIIa-2), or (IIIb-2), respectively, or of Formula (III-3), (IIIa-3), or (IIIb-3).

In some embodiments, the compound of Formula (I), (Ia), or (Ib), or pharmaceutically acceptable form thereof, is a compound of Formula (IV), (IVa), or (IVb), or a pharmaceutically acceptable form thereof, respectively. In some embodiments, the compound is a compound of Formula (IV-1) or (IV-2), or pharmaceutically acceptable form thereof, such as a compound of Formula (IVa-1), (IVb-1), (IVa-2), or (IVb-2), or pharmaceutically acceptable form thereof, respectively. In some embodiments, the pharmaceutically acceptable form of the compound of Formula (IV), (IVa), or (IVb), for example the compound of Formula (IV-1) or (IV-2), such as the compound of Formula (IVa-1), (IVb-1), (IVa-2), or (IVb-2), is exclusive of a salt form (i.e., is not a salt), and includes a pharmaceutically acceptable solvate, isomer, and isotopologue (i.e., isotopically labeled derivative) of the compound of Formula (IV), (IVa), or (IVb), for example the compound of Formula (IV-1) or (IV-2), such as the compound of Formula (IVa-1), (IVb-1), (IVa-2), or (IVb-2), respectively.

In some embodiments, the compound of Formula (I), (Ia), or (Ib), or pharmaceutically acceptable form thereof, is a compound of Formula (V), (Va), or (Vb), or a pharmaceutically acceptable form thereof, respectively. In some embodiments, the compound is a compound of Formula (V-1), or pharmaceutically acceptable form thereof, such as a compound of Formula (Va-1) or (Vb-1), or pharmaceutically acceptable form thereof, respectively. In some embodiments, the pharmaceutically acceptable form of the compound of Formula (V), (Va), or (Vb), for example the compound of Formula (V-1), such as the compound of Formula (Va-1) or (Vb-1), is exclusive of a salt form (i.e., is not a salt), and includes a pharmaceutically acceptable solvate, isomer, and isotopologue (i.e., isotopically labeled derivative) of the compound of Formula (V), (Va), or (Vb), for example the compound of Formula (V-1), such as the compound of Formula (Va-1) or (Vb-1).

In some embodiments, the compound of Formula (I), (Ia), or (Ib), or pharmaceutically acceptable form thereof, is a compound of Formula (VI), (VIa), or (VIb), or a pharmaceutically acceptable form thereof, respectively. In some embodiments, the compound is a compound of Formula (VI-1), or pharmaceutically acceptable form thereof, such as a compound of Formula (VIa-1) or (VIb-1), or pharmaceutically acceptable form thereof, respectively. In some embodiments, the pharmaceutically acceptable form of the compound of Formula (VI), (VIa), or (VIb), for example the compound of Formula (VI-1), such as the compound of Formula (VIa-1) or (VIb-1), is exclusive of a salt form (i.e., is not a salt), and includes a pharmaceutically acceptable solvate, isomer, and isotopologue (i.e., isotopically labeled derivative) of the compound of Formula (VI), (VIa), or (VIb), for example the compound of Formula (VI-1), such as the compound of Formula (VIa-1) or (VIb-1).

In some embodiments, the compound is a compound of Formula (II-1), Formula (II-2), Formula (III-1), or Formula (III-2), or a pharmaceutically acceptable form thereof, or of Formula (III-3), or a pharmaceutically acceptable form thereof, wherein:

Y is $-(CR^{16}R^{17})_q-$ or $-(CR^{16}R^{17})_mO(CR^{16}R^{17})_n-$;

$R^{1a}$ is independently $R^9$, $-OR^9$, $-C(O)R^9$, $-C(O)OR^9$, $-C(O)NR^{10}R^{11}$, $-S(O)_pR^9$, or $-S(O)_2NR^{10}R^{11}$;

$R^{2b}$ and $R^5$, at each occurrence, are each independently $R^9$, $-OR^9$, halo, CN, $NO_2$, $-C(O)R^9$, $-C(O)OR^9$, $-OC(O)R^9$, $-OC(O)OR^9$, $-C(O)NR^{10}R^{11}$, $-NR^{10}R^{11}$, $-NR^{10}C(O)R^9$, $-NR^{10}C(O)OR^9$, $-NR^{10}C(O)NR^{10}R^{11}$, $-NR^{10}S(O)_2R^9$, $-S(O)_pR^9$, $-S(O)_2NR^{10}R^{11}$ or $-NR^{10}S(O)_2NR^{10}R^{11}$;

$R^6$ is CN, $R^9$, $-OR^9$, $-C(O)R^9$, $-C(O)OR^9$, $-OC(O)R^9$, $-OC(O)OR^9$, $-C(O)NR^{10}R^{11}$, $-NR^{10}R^{11}$, $-NR^{10}OR^9$, $-NR^{10}C(O)R^9$, $-NR^{10}C(O)OR^9$, $-NR^{10}C(O)NR^{10}R^{11}$, $-NR^{10}S(O)_2R^9$, $-NR^{10}C(NR^{10})NR^{10}R^{11}$, $-S(O)_pR^9$, $-S(O)_2NR^{10}R^{11}$ or $-NR^{10}S(O)_2NR^{10}R^{11}$;

$R^7$ is a 5-12 membered heteroaryl, optionally substituted with 1-4 substituents independently selected from halo, CN, $NO_2$, $R^9$, $-OR^9$, $-C(O)R^9$, $-C(O)OR^9$, $-OC(O)R^9$, $-OC(O)OR^9$, $-C(O)NR^{10}R^{11}$, $-NR^{10}R^{11}$, $-NR^{10}C(O)R^9$, $-NR^{10}C(O)OR^9$, $-NR^{10}C(O)NR^{10}R^{11}$, $-NR^{10}S(O)_2R^9$, $-S(O)_pR^9$, $-S(O)_2NR^{10}R^{11}$ or $-NR^{10}S(O)_2NR^{10}R^{11}$;

$R^9$, at each occurrence, is independently hydrogen, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-5}$ cycloalkyl, 3-6 membered heterocycloalkyl, phenyl, or 5-9 membered heteroaryl, wherein each $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-5}$ cycloalkyl, 3-6 membered heterocycloalkyl, phenyl, or 5-9 membered heteroaryl is optionally independently substituted with 1-6 substituents independently selected from halo, hydroxy, CN, $NO_2$, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-5}$ cycloalkyl, 3-6 membered heterocycloalkyl, $C_{1-4}$ alkoxy, $C_{1-4}$ haloalkoxy, (O), $-C(O)R^{12}$, $-C(O)OR^{12}$, $-OC(O)R^{12}$, $-OC(O)OR^{12}$, $-C(O)NR^{10}R^{11}$, $-NR^{10}R^{11}$, $-NR^{10}C(O)R^{12}$, $-NR^{10}C(O)OR^{12}$, $-NR^{10}C(O)NR^{10}R^{11}$, $-NR^{10}S(O)_2R^{12}$, $-S(O)_pR^{12}$, $-S(O)_2NR^{10}R^{11}$ and $-NR^{10}S(O)_2NR^{10}R^{11}$;

$R^{10}$ and $R^{11}$, at each occurrence, are each independently hydrogen, hydroxy, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-6}$ cycloalkyl, 3-6 membered heterocycloalkyl, $C_{1-4}$ alkoxy, phenyl, or 5-9 membered heteroaryl, or together with the N to which each is attached are combined to form a 3-6 membered heterocycloalkyl, wherein each $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-5}$ cycloalkyl, 3-6 membered heterocycloalkyl, $C_{1-4}$ alkoxy, phenyl, or 5-9 membered heteroaryl of the $R^{10}$ and $R^{11}$ are each optionally independently substituted with 1-6 substituents independently selected from halo, hydroxy, CN, $NO_2$, $C_{1-4}$ alkyl, $C_{2-4}$ alkenyl, $C_{2-4}$ alkynyl, $C_{1-4}$ haloalkyl, $C_{1-4}$ heteroalkyl, $C_{3-5}$ cycloalkyl, 3-6 membered heterocycloalkyl, $C_{1-4}$ alkoxy, $C_{1-4}$ haloalkoxy, (O), —C(O)$R^{13}$, —C(O)O$R^{13}$, —OC(O)$R^{13}$, —OC(O)O$R^{13}$, —C(O)N$R^{14}R^{15}$, —N$R^{14}R^{15}$, —N$R^{14}$C(O)$R^{13}$, —N$R^{14}$C(O)O$R^{13}$, —N$R^{14}$C(O)N$R^{14}R^{15}$, —N$R^{14}$S(O)$_2R^{13}$, —S(O)$_pR^{13}$, —S(O)$_2$N$R^{14}R^{15}$ and —N$R^{14}$S(O)$_2$N$R^{14}R^{15}$;

$R^{12}$, at each occurrence, is independently hydrogen, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-5}$ cycloalkyl, 3-6 membered heterocycloalkyl, phenyl, or 5-9 membered heteroaryl, wherein each $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-5}$ cycloalkyl, 3-6 membered heterocycloalkyl, phenyl, or 5-9 membered heteroaryl, of the $R^{12}$ are optionally independently substituted with 1-6 substituents independently selected from halo, hydroxy, CN, $NO_2$, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-5}$ cycloalkyl, 3-6 membered heterocycloalkyl, $C_{1-4}$ alkoxy, $C_{1-4}$ haloalkoxy, (O), —C(O)$R^{13}$, —C(O)O$R^{13}$, —OC(O)$R^{13}$, —OC(O)O$R^{13}$, —C(O)N$R^{10}R^{11}$, —N$R^{10}R^{11}$, —N$R^{10}$C(O)$R^{13}$, —N$R^{10}$C(O)O$R^{13}$, —N$R^{10}$C(O)N$R^{10}R^{11}$, —N$R^{10}$S(O)$_2R^{13}$, —S(O)$_pR^{13}$, —S(O)$_2$N$R^{10}R^{11}$; and —N$R^{10}$S(O)$_2$N$R^{10}R^{11}$;

$R^{13}$, at each occurrence, is independently hydrogen, $C_{1-3}$ alkyl, $C_{2-3}$ alkenyl, $C_{2-3}$ alkynyl, $C_{1-3}$ haloalkyl, $C_{1-3}$ hydroxyalkyl, $C_{1-3}$ heteroalkyl, $C_{3-5}$ cycloalkyl, or 3-6 membered heterocycloalkyl;

$R^{14}$ and $R^{15}$, at each occurrence, are each independently hydrogen, hydroxy, $C_{1-3}$ alkyl, $C_{2-3}$ alkenyl, $C_{2-3}$ alkynyl, $C_{1-3}$ haloalkyl, $C_{1-3}$ hydroxyalkyl, $C_{1-3}$ heteroalkyl, $C_{3-5}$ cycloalkyl, 3-6 membered heterocycloalkyl, or $C_{1-4}$ alkoxy, or together with the N to which each is attached are combined to form a 3-6 membered heterocycloalkyl;

$R^{16}$ and $R^{17}$, at each occurrence, are each independently hydrogen, halo, hydroxy, CN, $NO_2$, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-6}$ cycloalkyl, 3-6 membered heterocycloalkyl, $C_{1-4}$ alkoxy, $C_{1-4}$ haloalkoxy, $C_{1-4}$ hydroxyalkoxy, $C_{1-4}$ heteroalkoxy, or 3-6 membered heterocycloalkoxy, or together with the C to which each is attached are combined to form a C(O), $C_{3-5}$ cycloalkyl, or 3-6 membered heterocycloalkyl;

each m is independently an integer of 0, 1, 2, or 3;
each n is independently an integer of 0, 1, 2, or 3;
wherein the sum of m and n is 0, 1, 2, 3, 4, 5, or 6;
each p is independently an integer of 0, 1, or 2; and
each q is independently an integer of 0, 1, 2, 3, 4, 5, or 6.

In some embodiments, the compound is a compound of Formula (II-1), Formula (II-2), Formula (III-1), or Formula (III-2), or a pharmaceutically acceptable form thereof, or of Formula (III), or a pharmaceutically acceptable form thereof, wherein:

Y is —(CH$_2$)$_q$— or —(CH$_2$)$_m$O(CH$_2$)$_n$—;
$R^{1a}$ is independently $R^9$;
$R^{2b}$ is independently $R^9$, —O$R^9$, halo, CN, —C(O)N$R^{10}R^{11}$, or —N$R^{10}R^{11}$;

$R^5$ is independently $R^9$, —O$R^9$, halo, CN, $NO_2$, —C(O)$R^9$, —C(O)O$R^9$, —C(O)N$R^{10}R^{11}$, —S(O)$_pR^9$, or —S(O)$_2$N$R^{10}R^{11}$;
$R^6$ is CN, $R^9$, —O$R^9$, —N$R^{10}R^{11}$, or —N$R^{10}$O$R^9$;
$R^7$ is a 5-12 membered heteroaryl, optionally substituted with 1-4 substituents independently selected from halo, CN, $NO_2$, $R^9$, —O$R^9$, —C(O)$R^9$, —C(O)O$R^9$, —C(O)N$R^{10}R^{11}$, —N$R^{10}R^{11}$, —N$R^{10}$C(O)$R^9$, —N$R^{10}$C(O)O$R^9$, —N$R^{10}$C(O)N$R^{10}R^{11}$, —N$R^{10}$S(O)$_2R^9$, —S(O)$_pR^9$, —S(O)$_2$N$R^{10}R^{11}$ or —N$R^{10}$S(O)$_2$N$R^{10}R^{11}$;

$R^9$, at each occurrence, is independently hydrogen, $C_{1-4}$ alkyl, $C_{1-4}$ hydroxyalkyl, $C_{1-4}$ heteroalkyl, $C_{3-5}$ cycloalkyl, or 3-6 membered heterocycloalkyl, wherein each $C_{1-4}$ alkyl, $C_{1-4}$ hydroxyalkyl, $C_{1-4}$ heteroalkyl, $C_{3-5}$ cycloalkyl, or 3-6 membered heterocycloalkyl, is optionally independently substituted with 1-5 substituents independently selected from halo, hydroxy, CN, $C_{1-3}$ alkyl, $C_{1-3}$ haloalkyl, $C_{1-3}$ hydroxyalkyl, $C_{1-3}$ heteroalkyl, $C_{3-5}$ cycloalkyl, 3-6 membered heterocycloalkyl, $C_{1-3}$ alkoxy, $C_{1-3}$ haloalkoxy, (O), and —N$R^{10}R^11$.

$R^{10}$ and $R^{11}$, at each occurrence, are each independently hydrogen, $C_{1-3}$ alkyl, $C_{1-3}$ haloalkyl, $C_{1-3}$ hydroxyalkyl, $C_{1-3}$ heteroalkyl, $C_{3-5}$ cycloalkyl, 3-6 membered heterocycloalkyl, or $C_{1-3}$ alkoxy, or together with the N to which each is attached are combined to form a 3-6 membered heterocycloalkyl, wherein each $C_{1-3}$ alkyl, $C_{1-3}$ haloalkyl, $C_{1-3}$ hydroxyalkyl, $C_{1-3}$ heteroalkyl, $C_{3-5}$ cycloalkyl, 3-6 membered heterocycloalkyl, or $C_{1-3}$ alkoxy, of the $R^{10}$ and $R^{11}$ are each optionally independently substituted with 1-5 substituents selected from halo, hydroxy, CN, $C_{1-3}$ alkyl, $C_{1-3}$ haloalkyl, $C_{1-3}$ heteroalkyl, $C_{3-5}$ cycloalkyl, 3-6 membered heterocycloalkyl, $C_{1-3}$ alkoxy, $C_{1-3}$ haloalkoxy, (O), and —N$R^{14}R^{15}$;

$R^{14}$ and $R^{15}$, at each occurrence, are each independently hydrogen, hydroxy, $C_{1-3}$ alkyl, $C_{1-3}$ hydroxyalkyl, $C_{1-3}$ heteroalkyl, $C_{3-5}$ cycloalkyl, 3-6 membered heterocycloalkyl, or $C_{1-3}$ alkoxy, or together with the N to which each is attached are combined to form a 3-6 membered heterocycloalkyl;

each m is independently an integer of 0, 1, 2, or 3;
each n is independently an integer of 0, 1, 2, or 3;
wherein the sum of m and n is 0, 1, 2, 3, 4, or 5;
each p is independently an integer of 0, 1, or 2; and
each q is independently an integer of 0, 1, 2, 3, 4, or 5.

In some embodiments, the compound is a compound of Formula (II-1), Formula (II-2), Formula (III-1), or Formula (III-2), or a pharmaceutically acceptable form thereof, or of Formula (III-3), or a pharmaceutically acceptable form, wherein:

Y is —(CH$_2$)$_q$— or —(CH$_2$)$_m$O(CH$_2$)$_n$—;
$R^{1a}$ is independently $R^9$;
$R^{2b}$ is independently $R^9$, —O$R^9$, halo, CN, —C(O)N$R^{10}R^{11}$, or —N$R^{10}R^{11}$;
$R^5$ is independently $R^9$, —O$R^9$, halo, CN, $NO_2$, —C(O)$R^9$, —C(O)O$R^9$, —C(O)N$R^{10}R^{11}$, —S(O)$_pR^9$, or —S(O)$_2$N$R^{10}R^{11}$;
$R^6$ is $R^9$, —O$R^9$, —NRO$R^{11}$, or —N$R^{10}$O$R^9R^7$ is a 5-12 membered heteroaryl, optionally substituted with 1-4 substituents independently selected from halo, CN, $NO_2$, $R^9$, —O$R^9$, —C(O)$R^9$, —C(O)O$R^9$, —C(O)N$R^{10}R^{11}$, —N$R^{10}R^{11}$, —N$R^{10}$C(O)$R^9$, —N$R^{10}$S(O)$_2R^9$, —S(O)$_pR^9$, or —S(O)$_2$N$R^{10}R^{11}$;

$R^9$, at each occurrence, is independently hydrogen, $C_{1-4}$ alkyl, $C_{1-4}$ hydroxyalkyl, $C_{1-4}$ heteroalkyl, $C_{3-5}$ cycloalkyl, or 3-6 membered heterocycloalkyl, wherein each $C_{1-4}$ alkyl, $C_{1-4}$ hydroxyalkyl, $C_{1-4}$ heteroalkyl, $C_{3-5}$ cycloalkyl, or 3-6 membered heterocycloalkyl, is optionally independently substituted with 1-5 substituents independently selected from halo, hydroxy, CN, $C_{1-3}$ alkyl, $C_{1-3}$ haloalkyl, $C_{1-3}$ hydroxyalkyl, $C_{1-3}$ heteroalkyl, $C_{3-5}$ cycloalkyl, 3-6 membered heterocycloalkyl, $C_{1-3}$ alkoxy, $C_{1-3}$ haloalkoxy, (O), and —$NR^{10}R^{11}$;

$R^{10}$ and $R^{11}$, at each occurrence, are each independently hydrogen, $C_{1-3}$ alkyl, $C_{1-3}$ haloalkyl, $C_{1-3}$ hydroxyalkyl, $C_{1-3}$ heteroalkyl, $C_{3-5}$ cycloalkyl, 3-6 membered heterocycloalkyl, or $C_{1-3}$ alkoxy, or together with the N to which each is attached are combined to form a 3-6 membered heterocycloalkyl, wherein each $C_{1-3}$ alkyl, $C_{1-3}$ haloalkyl, $C_{1-3}$ hydroxyalkyl, $C_{1-3}$ heteroalkyl, $C_{3-5}$ cycloalkyl, 3-6 membered heterocycloalkyl, or $C_{1-3}$ alkoxy, of the $R^{10}$ and $R^{11}$ are each optionally independently substituted with 1-5 substituents independently selected from halo, hydroxy, CN, $C_{1-3}$ alkyl, $C_{1-3}$ haloalkyl, $C_{1-3}$ heteroalkyl, $C_{3-5}$ cycloalkyl, 3-6 membered heterocycloalkyl, $C_{1-3}$ alkoxy, $C_{1-3}$ haloalkoxy, (O), and —$NR^{14}R^{15}$;

$R^{14}$ and $R^{15}$, at each occurrence, are each independently hydrogen, hydroxy, $C_{1-3}$ alkyl, $C_{1-3}$ hydroxyalkyl, $C_{1-3}$ heteroalkyl, $C_{3-5}$ cycloalkyl, 3-6 membered heterocycloalkyl, or $C_{1-3}$ alkoxy, or together with the N to which each is attached are combined to form a 3-6 membered heterocycloalkyl;

each m is independently an integer of 0, 1, 2, or 3;
each n is independently an integer of 0, 1, 2, or 3;
wherein the sum of m and n is 0, 1, 2, 3, 4, or 5;
each p is independently an integer of 0, 1, or 2; and
each q is independently an integer of 0, 1, 2, 3, 4, or 5.

In some embodiments, the compound is a compound of Formula (II-1), Formula (II-2), Formula (III-1), or Formula (III-2), or a pharmaceutically acceptable form thereof, or of Formula (III-3), or a pharmaceutically acceptable form thereof, wherein:

Y is —$(CH_2)_q$— or —$(CH_2)_mO(CH_2)_n$—;
$R^{1a}$ is independently $R^9$;
$R^{2b}$ is independently $R^9$, —$OR^9$, halo, CN, —$C(O)NR^{10}R^{11}$, or —$NR^{10}R^{11}$;
$R^5$ is independently $R^9$, halo, CN, $NO_2$, —$C(O)R^9$, —$S(O)_pR^9$, or —$S(O)_2NR^{10}R^{11}$;
$R^6$ is $R^9$, —$OR^9$, or —$NR^{10}R^{11}$;
$R^7$ is a 5-9 membered heteroaryl, optionally substituted with 1-4 substituents independently selected from halo, CN, $NO_2$, $R^9$, —$OR^9$, —$C(O)R^9$, —$C(O)NR^{10}R^{11}$, —$NR^{10}R^{11}$, —$NR^{10}C(O)R^9$, —$NR^{10}S(O)_2R^9$, —$S(O)_pR^9$, or —$S(O)_2NR^{10}R^{11}$;
$R^9$, at each occurrence, is independently hydrogen, $C_{1-3}$ alkyl, $C_{1-3}$ hydroxyalkyl, $C_{1-3}$ heteroalkyl, $C_{3-5}$ cycloalkyl, or 3-6 membered heterocycloalkyl, wherein each $C_{1-3}$ alkyl, $C_{1-3}$ hydroxyalkyl, $C_{1-3}$ heteroalkyl, $C_{3-5}$ cycloalkyl, or 3-6 membered heterocycloalkyl, is optionally independently substituted with one, two, or three substituents independently selected from halo, hydroxy, CN, $C_{1-3}$ alkyl, $C_{1-3}$ hydroxyalkyl, $C_{1-3}$ heteroalkyl, or $C_{1-3}$ alkoxy;
$R^{10}$ and $R^{11}$, at each occurrence, are each independently hydrogen, $C_{1-3}$ alkyl, $C_{1-3}$ heteroalkyl, or 3-6 membered heterocycloalkyl, or together with the N to which each is attached are combined to form a 3-6 membered heterocycloalkyl, wherein each $C_{1-3}$ alkyl, $C_{1-3}$ heteroalkyl, or 3-6 membered heterocycloalkyl, of the $R^{10}$ and $R^{11}$ are each optionally independently substituted with one, two or three substituents independently selected from halo, hydroxy, CN, $C_{1-3}$ alkyl, $C_{1-3}$ heteroalkyl, or 3-6 membered heterocycloalkyl; each m is independently an integer of 0, 1, 2, or 3;

each n is independently an integer of 0, 1, 2, or 3;
wherein the sum of m and n is 0, 1, 2, 3, 4, or 5;
each p is independently an integer of 0, 1, or 2; and
each q is independently an integer of 0, 1, 2, 3, 4, or 5.

In some embodiments, the compound is a compound of Formula (II-1), Formula (II-2), Formula (III-1), or Formula (III-2), or a pharmaceutically acceptable form thereof, or a compound of Formula (III-3), or a pharmaceutically acceptable form thereof, wherein:

Y is —$(CH_2)_q$— or —$(CH_2)_mO(CH_2)_n$—;
$R^{1a}$ is hydrogen, —$CH_3$, —$CD_3$, —$CH_2CH_3$, —$CD_2CD_3$, isopropyl, 2,3-dihydroxypropyl or cyclopropyl;
$R^{2b}$ is (a) hydrogen, —$CH_3$, —$CD_3$, —$CH_2CH_3$, —$CD_2CD_3$, isopropyl, cyclopropyl, —$OCH_3$, —$OCD_3$, —$OCH_2CH_3$, —$OCD_2CD_3$, isopropoxy, cyclopropoxy, 3-oxetanylalkoxy, chloro, CN, morpholino, piperazinyl, 3-oxetanylamino, or —$C(O)NH_2$; or $R^{2b}$ is (b) —$NH_2$;
$R^5$ is hydrogen, halo, CN, $NO_2$, —$C(O)CH_3$, —$S(O)CH_3$, —$S(O)_2CH_3$, —$S(O)_2NH_2$, —$S(O)_2NHCH_3$, or —$S(O)_2N(CH_3)_2$;
$R^6$ is hydrogen, —$CH_3$, hydroxy, —$OCH_3$, —$OCD_3$, —$NH_2$, —$NHCH_3$, or —$NH(OCH_3)$; or $R^6$ is —NH($CH_2CH_2$)Cl, —$NH(CH_2CH_2)F$, or N-linked morpholino.
$R^7$ is an imidazolyl, a triazolyl, a tetrazolyl, an oxazolyl, a thiazolyl, an oxadiazolyl, a thiadiazolyl, a pyridyl, or a pyrimidinyl, optionally substituted with 1-4 substituents independently selected from —$CH_3$, —$CD_3$, —$CH_2CH_3$, —$CD_2CD_3$, isopropyl, cyclopropyl, —$OCH_3$, —$OCD_3$, —$OCH_2CH_3$, —$OCD_2CD_3$, isopropoxy, cyclopropoxy, chloro, and CN;
each m is independently an integer of 0, 1, or 2;
each n is independently an integer of 0, 1, or 2;
wherein the sum of m and n is 0, 1, 2, 3, or 4; and
each q is independently an integer of 0, 1, 2, 3, 4, or 5.

In some embodiments, the compound is a compound of Formula (II-1), Formula (II-2), Formula (III-1), or Formula (III-2), or a pharmaceutically acceptable form thereof, or a compound of Formula (III-3), or a pharmaceutically acceptable form thereof, wherein:

Y is —$(CH_2)_2$—, —$O(CH_2)$—, —$O(CH_2)_2$—, —$(CH_2)O$—, or —$(CH_2)_2O$—;
$R^{1a}$ is hydrogen, —$CH_3$, —$CD_3$, 2,3-dihydroxypropyl, or cyclopropyl;
$R^{2b}$ is (a) —$OCH_3$, —$OCD_3$, 3-oxetanylalkoxy, chloro, CN, morpholino, piperazinyl, 3-oxetanylamino, or —$C(O)NH_2$; or $R^{2b}$ is (b) —$NH_2$;
$R^5$ is hydrogen, chloro, bromo, or CN;
$R^6$ is hydrogen, hydroxy, —$OCH_3$, —$OCD_3$, —$NH_2$, or —$NHCH_3$; and
$R^7$ is an imidazolyl, a triazolyl, a tetrazolyl, an oxazolyl, a thiazolyl, an oxadiazolyl, a thiadiazolyl, a pyridyl, or a pyrimidinyl, optionally substituted with 1-4 substituents independently selected from —$CH_3$, —$CD_3$, —$CH_2CH_3$, —$CD_2CD_3$, isopropyl, cyclopropyl, —$OCH_3$, —$OCD_3$, —$OCH_2CH_3$, —$OCD_2CD_3$, isopropoxy, cyclopropoxy, chloro, and CN.

In some embodiments, the compound is a compound of Formula (II-1), Formula (II-2), Formula (III-1), or Formula (III-2), or a pharmaceutically acceptable form thereof, or of Formula (III-3), or a pharmaceutically acceptable form thereof, wherein:

Y is —$(CH_2)_2$—, —$O(CH_2)$—, —$O(CH_2)_2$—, —$(CH_2)O$—, or —$(CH_2)_2O$—;
$R^{1a}$ is hydrogen, —$CH_3$, —$CD_3$, 2,3-dihydroxypropyl, or cyclopropyl;

R²ᵇ is (a) —OCH₃, —OCD₃, 3-oxetanylalkoxy, chloro, CN, morpholino, piperazinyl, 3-oxetanylamino, or —C(O)NH₂; or R²ᵇ is (b) —NH₂;
R⁵ is hydrogen, chloro, bromo, or CN;
R⁶ is hydrogen, hydroxy, —OCH₃, —OCD₃, —NH₂, or —NHCH₃; and
R⁷ is a methyl-substituted imidazolyl or a methyl-substituted triazolyl.

In some embodiments, the compound is a compound of Formula (II-1), Formula (II-2), Formula (III-1), or Formula (III-2), or a pharmaceutically acceptable form thereof, or of Formula (III-3), or a pharmaceutically acceptable form thereof, wherein:
Y is —(CH₂)₂—, —O(CH₂)—, —O(CH₂)₂—, —(CH₂)O—, or —(CH₂)₂O—;
R¹ᵃ is hydrogen, —CH₃, —CD₃, 2,3-dihydroxypropyl, or cyclopropyl;
R²ᵇ is (a) —OCH₃, —OCD₃, 3-oxetanylalkoxy, chloro, CN, morpholino, piperazinyl, 3-oxetanylamino, or —C(O)NH₂; or R²ᵇ is (b) —NH₂;
R⁵ is hydrogen, chloro, bromo, or CN;
R⁶ is hydrogen, hydroxy, —OCH₃, —OCD₃, —NH₂, or —NHCH₃; and
R⁷ is

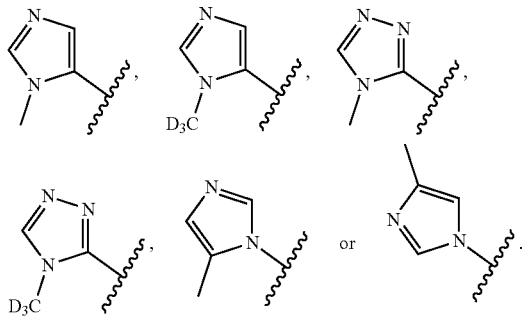

In some embodiments, the compound is a compound of Formula (II-1), Formula (II-2), Formula (III-1), or Formula (III-2), or a pharmaceutically acceptable form thereof, or of Formula (III-3), or a pharmaceutically acceptable form thereof, wherein:
Y is —(CH₂)₂—, —O(CH₂)—, —O(CH₂)₂—, —(CH₂)O—, or —(CH₂)₂O—;
R¹ᵃ is hydrogen, —CH₃, —CD₃, 2,3-dihydroxypropyl, or cyclopropyl;
R²ᵇ is (a) —OCH₃, —OCD₃, 3-oxetanylalkoxy, chloro, CN, morpholino, piperazinyl, 3-oxetanylamino, or —C(O)NH₂; or R²ᵇ is (b) —NH₂;
R⁵ is hydrogen, chloro, bromo, or CN;
R⁶ is hydrogen, hydroxy, —OCH₃, —OCD₃, —NH₂, or —NHCH₃; and
R⁷ is

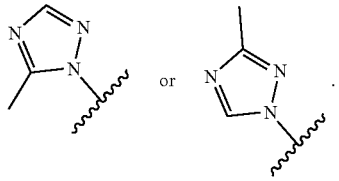

In some embodiments, the compound is a compound of Formula (II-1), such as a compound of Formula (II-1a) or Formula (II-1b), or a pharmaceutically acceptable form thereof. In some embodiments, the compound is a compound of Formula (II-2), such as a compound of Formula (II-2a) or Formula (II-2b), or a pharmaceutically acceptable form thereof. In some embodiments, the compound is a compound of Formula (III-1), such as a compound of Formula (III-1a) or Formula (III-1b), or a pharmaceutically acceptable form thereof. In some embodiments, the compound is a compound of Formula (III-2), such as a compound of Formula (III-2a) or Formula (III-2b), or a pharmaceutically acceptable form thereof. In some embodiments, the compound is a compound of Formula (III-3), such as a compound of Formula (III-3a) or Formula (III-3b), or a pharmaceutically acceptable form thereof. In some embodiments, the pharmaceutically acceptable form of the compound of Formula (II-1), Formula (II-2), Formula (III-1), or Formula (III-2), for example the compound of Formula (IIa-1), (IIb-1), (IIa-2), (IIb-2), (IIIa-1), (IIIb-1), (IIIa-2), (IIIb-2), or of Formula (III-3), (IIIa-3), or (IIIb-3), is exclusive of a salt form (i.e., is not a salt), and includes a pharmaceutically acceptable solvate, isomer, and isotopologue (i.e., isotopically labeled derivative) of the compound of Formula (II-1), Formula (II-2), Formula (III-1), or Formula (III-2), for example the compound of Formula (IIa-1), (IIb-1), (IIa-2), (IIb-2), (IIIa-1), (IIIb-1), (IIIa-2), (IIIb-2), respectively, or of Formula (III-3), (IIIa-3), or (IIIb-3).

In some embodiments, the compound is a compound of Formula (I), (II), (III), or (IV), for example a compound of Formula (Ia), (Ib), (IIa), (IIb), (IIIa), (IIIb), (IVa), or (IVb), or a pharmaceutically acceptable form thereof, or of Formula (V), (Va), (Vb), (VI), (VIa), or (VIb), or a pharmaceutically acceptable form thereof, as disclosed herein, wherein the compound has a MW of no more than 1,000 g/mol. In some embodiments, the compound has a MW of no more than 900 g/mol, no more than 800 g/mol, no more than 700 g/mol, no more than 600 g/mol, or no more than 500 g/mol. In some embodiments, the compound has a MW of no more than 600 g/mol. In some embodiments, the compound has a MW of no more than 500 g/mol. In some embodiments, the compound is a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or a pharmaceutically acceptable form thereof, or of Formula (III-3), (IIIa-3), (IIIb-3), (V-1), (Va-1), (Vb-1), (VI-1), (VIa-1), or (VIb-1), or a pharmaceutically acceptable form thereof, as disclosed herein.

In some embodiments, the compound is a compound of Formula (I), (II), (III), or (IV), for example a compound of Formula (II-1), (II-2), (III-1), (III-2), (IV-1), or (IV-2), or a pharmaceutically acceptable form thereof, or of Formula (III-3), (V), (V-1), (VI), or (VI-1), or a pharmaceutically acceptable form thereof, as disclosed herein, wherein the compound is a racemate or a mixture of diasteromers, or a mixture of stereoisomers. In some embodiments, the compound is a single enantiomer or a single diastereomer. In some embodiments, the compound is a single enantiomer. For example, in some embodiments, the compound is a compound of Formula (Ia), (Ib), (IIa), (IIb), (IIIa), (IIIb), (IVa), or (IVb), such as a compound of Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or a pharmaceutically acceptable form thereof, or of Formula (IIIa-1), (IIIb-1), (Va-1), (Vb-1), (VIa-1), or (VIb-1), or a pharmaceutically acceptable form thereof, as disclosed herein. In some embodiments, the compound is an (R)-enantiomer. In some embodiments, the compound has an enantiomeric excess of greater than 10% f the (R)-enantiomer. In some embodiments, the compound has an enantiomeric excess of 15% or more, 20% or more, 25% or more, 30% r more, 35% or more, 40% or more, 45% or more, 50% or more, 55% or more, 60% or more, 65% or more, 70% or more, 75% or more, 80% or more, 85% or more, 90% or more, 95% or more, 98% or more, 99% or more, of the (R)-enantiomer. In some embodiments, the compound has an enantiomeric excess of about 90%, about 91%, about 92%, about 93%, about 94%, about 95%, about 96%, about 97%, about 98%, or about 99%, of the (R)-enantiomer. In some embodiments, the compound is an (S)-enantiomer. In some embodiments, the compound has an enantiomeric excess of greater than 10% f the (S)-enantiomer. In some embodiments, the compound has an enantiomeric excess of 15% or more, 20% or more, 25% or more, 30% or more, 35% or more, 40% or more, 45% or more, 50% or more, 55% or more, 60% or more, 65% or more, 70% r more, 75% or more, 80% or more, 85% or more, 90% or more, 95% or more, 98% or more, 99% or more, of the (S)-enantiomer. In some embodiments, the compound has an enantiomeric excess of about 90%, about 91%, about 92%, about 93%, about 94%, about 95%, about 96%, about 97%, about 98%, or about 99%, of the (S)-enantiomer.

In some embodiments, the compound is a compound of Formula (I), (II), (III), or (IV), or of Formula (V) or (VI), as disclosed herein, wherein the compound is a racemate and is selected from Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, and 135, or a pharmaceutically acceptable form thereof. In some embodiments, the compound is a compound of Formula (I), (II), (III), or (IV), or of Formula (V) or (VI), as disclosed herein, wherein the compound is a single enantiomer. In some embodiments, the compound is an (R)-enantiomer of Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, and 135, or a pharmaceutically acceptable form thereof. For example, in some embodiments, the compound is an (R)-enantiomer of Compound 4, 6, 7, 8, 9, 14, 15, 18, 19, 20, 21, 25, 27, 28, 29, 30, 34, 35, 36, 37, 39, 46, 47, 48, 51, 55, 56, 57, 58, 66, 70, 76, 77, 78, 79, 80, 86, 89, 90, or 91, or a pharmaceutically acceptable form thereof. In some embodiments, the compound is an (S)-enantiomer of Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 86, 89, 90, or 91, or a pharmaceutically acceptable form thereof. For example, in some embodiments, the compound is an (S)-enantiomer of Compound 3, 4, 14, 15, 18, 19, 20, 21, 25, 27, 28, 29, 30, 34, 35, 36, 37, 39, 46, 47, 48, 51, 55, 56, 57, 58, 66, 69, or 70, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 1, 2, 3, 4, 6, 7, 8, 11, 13, 14, 15, 17, 18, 19, 20, 22, 23, 25, 26, 27, 28, 29, 30, 31, 32, 33, 34, 35, 36, 37, 38, 39, 41, 42, 43, 44, 45, 46, 47, 50, 51, 54, 55, 56, 57, 61, 62, 63, 65, 69, 76, 77, 79, 80, 92, 93, 94, 95, 96, 97, 98, 99, 100, 101, 102, 103, 104, 105, 106, 107, 108, 109, and 110, or a pharmaceutically acceptable form thereof. In some embodiments, the compound is an (R)-enantiomer of Compound 6, 7, 8, 76, 77, 79, or 80, or a pharmaceutically acceptable form thereof. In some embodiments, the compound is an (S)-enantiomer of Compound 3, 4, 14, 15, 18, 19, 20, 25, 27, 28, 29, 30, 34, 35, 36, 37, 39, 46, 47, 51, 55, 56, 57, 69, 79, or 80, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 5, 9, 10, 12, 16, 21, 24, 40, 43, 48, 49, 52, 53, 58, 59, 60, 64, 66, 67, 68, 70, 71, 72, 73, 74, 75, 78, 89, 90, and 91, or a pharmaceutically acceptable form thereof. In some embodiments, the compound is an (R)-enantiomer of Compound 9, 78, 89, 90, 91, or a pharmaceutically acceptable form thereof. In some embodiments, the compound is an (S)-enantiomer of Compound 21, 48, 58, 66, 70, 78, 89, 90, 91, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 36, 37, 40, 41, 42, 43, 44, 45, 46, 47, 48, 52, 53, 54, 55, 56, 57, 58, 59, 60, 61, 62, 63, 64, 65, 66, 67, 68, 69, 70, 71, 72, 73, 74, 75, 81, 82, 83, 84, 85, 86, 87, 88, 89, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, and 135, or a pharmaceutically acceptable form thereof. In some embodiments, the compound is an (R)-enantiomer of Compound 4, 6, 7, 8, 9, 14, 15, 18, 19, 20, 21, 25, 27, 28, 29, 30, 36, 37, 46, 47, 48, 55, 56, 57, 58, 66, 86, or 89, or a pharmaceutically acceptable form thereof. In some embodiments, the compound is an (S)-enantiomer of Compound 3, 4, 6, 7, 8, 9, 14, 15, 18, 19, 20, 21, 25, 27, 28, 29, 30, 36, 37, 46, 47, 48, 55, 56, 57, 58, 66, 69, 70, 76, 77, 86, or 89, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 31, 32, 33, 34, 35, 38, 39, 49, 50, and 51, or a pharmaceutically acceptable form thereof. In some embodiments, the compound is an (R)-enantiomer of Compound 34, 35, 39, or 51, or a pharmaceutically acceptable form thereof. In some embodiments, the compound is an (S)-enantiomer of Compound 34, 35, 39, or 51, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 1, 2, 3, 5, 6, 10, 11, 12, 13, 14, 16, 17, 18, 22, 23, 24, 25, 26, 28, 29, 31, 32, 36, 38, 40, 41, 42, 43, 44, 45, 49, 52, 53, 54, 55, 59, 60, 61, 63, 64, 65, 71, 72, 73, 78, 81, 83, 84, 85, 87, 88, 93, 94, 95, 112, 113, 114, 115, 117, 118, 119, and 120, or a pharmaceutically acceptable form thereof. In some embodiments, the compound is an (R)-enantiomer or Compound 6, 14, 18, 25, 28, 29, 36, 55, or 78, or a pharmaceutically acceptable form thereof. In some embodiments, the compound is an (S)-enantiomer of Compound 3, 6, 14, 18, 25, 28, 29, 36, 55, or 78, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 4, 7, 8, 9, 16, 19, 20, 21, 27, 30, 34, 35, 37, 39, 46, 47, 48, 51, 56, 57, 58, 62, 66, 67, 68, 69, 70, 74, 75, 82, 86, 89, and 92, or a pharmaceutically acceptable form thereof. In some embodiments, the compound is an (R)-enantiomer of Compound 4, 7, 8, 9, 15, 19, 20, 21, 27, 30, 34, 35, 37, 39, 46, 48, 51, 56, 57, 58, 66, 70, 86, or 89, or a pharmaceutically acceptable form thereof. In some embodiments, the compound is an (S)-enantiomer of Compound 4, 8, 9, 19, 20, 21, 27, 30, 34, 35, 37, 39, 46, 47, 48, 51, 56, 57, 58, 66, 69, 70, 86, or 89, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 3, 4, 12, 13, 14, 15, 24, 25, 26, 27, 28, 29, 30, 31, 32, 33, 34, 35, 43, 44, 45, 46, 47, 48, 49, 50, 51, 59, 64, 65, 76, 77, 80, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, and 135, or a pharmaceutically acceptable form thereof. In some embodiments, the compound is an (R)-enantiomer of Compound 4, 14, 15, 25, 27, 28, 29, 30, 34, 35, 46, 47, 48, 51, 76, 77, or 80, or a pharmaceutically acceptable form thereof. In some embodiments, the compound is an (S)-enantiomer of Compound 3, 4, 14, 15, 25, 27, 28, 29, 30, 34, 35, 46, 47, 48, 51, 71, 77, or 80, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 5, 6, 7, 8, 9, 16, 17, 18, 19, 20, 21, 36, 37, 38, 39, 53, 54, 55, 56, 57, 58, 60, 61, 62, 66, 67, 68, 69, 70, 72, 73, 78, 85, 86, 88, 89, 90, and 91, or a pharmaceutically acceptable form thereof. In some embodiments, the compound is an (R)-enantiomer of Compound 6, 7, 8, 9, 18, 19, 20, 21, 36, 37, 39, 55, 56, 57, 58, 66, 70, 78, 86, 89, 90, or 91, or a pharmaceutically acceptable form thereof. In some embodiments, the compound is an (S)-enantiomer of Compound 6, 7, 8, 9, 18, 19, 20, 21, 36, 37, 39, 55, 56, 57, 58, 66, 69, 70, 78, 86, 89, 90, or 91, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 1, 2, 3, 4, 5, 6, 7, 8, 9, 93, 98, 103, 108, 113, 118, 123, 128, and 133, or a pharmaceutically acceptable form thereof. In some embodiments, the compound is an (R)-enantiomer of Compound 4, 6, 7, 8, or 9, or a pharmaceutically acceptable form thereof. In some embodiments, the compound is an (S)-enantiomer of Compound 3, 4, 6, 7, 8, or 9, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 10, 11, 12, 13, 14, 15, 16, 17, 18, 19, 20, 21, 92, 96, 101, 106, 111, 116, 121, 126, and 131, or a pharmaceutically acceptable form thereof. In some embodiments, the compound is an (R)-enantiomer of Compound 14, 15, 18, 19, 20, or 21, or a pharmaceutically acceptable form thereof. In some embodiments, the compound is an (S)-enantiomer of Compound 14, 15, 18, 19, 20, or 21, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 22, 23, 24, 25, 26, 27, 28, 29, 30, 31, 32, 33, 34, 35, 36, 37, 38, 39, 97, 102, 107, 112, 117, 122, 127, and 132, or a pharmaceutically acceptable form thereof. In some embodiments, the compound is an (R)-enantiomer of Compound 25, 27, 28, 29, 30, 34, 35, 36, 37, or 39, or a pharmaceutically acceptable form thereof. In some embodiments, the compound is an (S)-enantiomer of Compound 25, 27, 28, 29, 30, 34, 35, 36, 37, or 39, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 40, 41, 42, 43, 44, 45, 46, 47, 48, 49, 50, 51, 52, 53, 54, 55, 56, 57, 58, 59, 60, 61, 62, 66, 67, 68, 69, 70, 71, 72, 73, 74, 75, 76, 77, 78, 79, 80, 81, 82, 83, 84, 85, 86, 87, 88, 89, 90, 91, 95, 100, 105, 110, 115, 120, 125, 130, and 135, or a pharmaceutically acceptable form thereof. In some embodiments, the compound is an (R)-enantiomer of Compound 46, 47, 48, 51, 55, 56, 57, 58, 66, 70, 76, 77, 78, 79, 80, 86, 89, 90, or 91, or a pharmaceutically acceptable form thereof. In some embodiments, the compound is an (S)-enantiomer of Compound 46, 47, 48, 51, 55, 56, 57, 58, 66, 69, 70, 76, 77, 78, 79, 80, 86, 89, 90, or 91, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 63, 64, 65, 94, 99, 104, 109, 114, 119, 124, 129, and 134, or a pharmaceutically acceptable form thereof.

In some embodiments, the compound is a compound of Formula (I), (II), (III), or (IV), or of Formula (V) or (VI), as disclosed herein, or a pharmaceutically acceptable form thereof, is a farnesyltransferase inhibitor. For example, in some embodiments, the compound disclosed herein has an $IC_{50}$ for inhibition of farnesyltransferase of 300 nM or less, for example, 250 nM or less, 200 nM or less, 150 nM or less, 125 nM or less, 100 nM or less, 90 nM or less, 80 nM or less, 70 nM or less, 60 nM or less, 50 nM or less, 40 nM or less, 30 nM or less, 25 nM or less, 20 nM or less, 15 nM or less, 10 nM or less, 9 nM or less, 8 nM or less, 7 nM or less, 6 nM or less, 5 nM or less, 4 nM or less, 3 nM or less, 2 nM or less, or 1 nM or less. In some embodiments, the compound disclosed herein is a selective farnesyltransferase inhibitor. In some embodiments, the compound disclosed herein selectively inhibits farnesyltransferase with greater potency (lower $IC_{50}$ value) relative to the level of inhibition of geranylgeranyl transferase type-1. For example, in some embodiments, the compound disclosed herein has an $IC_{50}$ for inhibition of geranylgeranyl transferase type-1 of 100 nM or more, for example, 300 nM or more, 500 nM or more, 750 nM or more, or 1,000 nM or more. For example, in some embodiments, the compound disclosed herein selectively inhibits farnesyltransferase relative to geranylgeranyl transferase type-1, wherein said compound has an $IC_{50}$ ratio of $IC_{50}$ (farnesyltransferase) to $IC_{50}$ (geranylgeranyl transferase type-1) of at least 1:5, for example an $IC_{50}$ ratio of 1:10, 1:25: 1:50, 1:100, 1:300, 1:500, 1:750, or 1:1000, or more.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 3, 4, 5, 6, 7, 8, 9, 11, 14, 15, 17, 18, 19, 20, 21, 23, 25, 27, 28, 29, 30, 34, 35, 36, 37, 38, 39, 42, 44, 45, 46, 47, 48, 50, 51, 53, 54, 55, 56, 57, 58, 61, 62, 65, 66, 69, 70, 72, 78, 82, 83, 86, 88, 89, and 91, or a pharmaceutically acceptable form thereof. In some embodiments, the compound is an (R)-enantiomer of Compound 6, 7, 8, 9, 66, or 91, or a pharmaceutically acceptable form thereof. In some embodiments, the compound is an (S)-enantiomer of Compound 3, 4, 14, 15, 18, 19, 20, 21, 25, 27, 28, 29, 30, 34, 35, 36, 37, 39, 46, 47, 48, 51, 55, 56, 57, 58, 66, 69, 78, 86, or 89, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 4, 6, 7, 8, 9, 18, 19, 20, 21, 23, 26, 27, 28, 36, 37, 39, 46, 55, 56, 57, and 58, or a pharmaceutically acceptable form thereof. In some embodiments, the compound is an (R)-enantiomer of Compound 6, 7, 8, or 9, or a pharmaceutically acceptable form thereof. In some embodiments, the compound is an (S)-enantiomer of Compound 4, 18, 19, 20, 21, 27, 28, 36, 37, 39, 46, 55, 56, 57, or 58, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 4, 6, 7, 8, 18, 27, 34, 37, 46, 47, 48, 55, 57, and 58, or a pharmaceutically acceptable form thereof. In some embodiments, the compound is an (R)-enantiomer of Compound 6, 7, or 8, or a pharmaceutically acceptable form thereof. In some embodiments, the compound is an (S)-enantiomer of Compound 4, 18, 27, 34, 37, 46, 47, 48, 55, 57, or 58, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from Compounds 4, 6, 7, 8, 18, 27, 37, 46, 55, 57, and 58, or a pharmaceutically acceptable form thereof. In some embodiments, the compound is an (R)-enantiomer of Compound 6, 7, or 8, or a pharmaceutically acceptable form thereof. In some embodiments, the compound is an (S)-enantiomer of Compound 4, 18, 27, 37, 46, 55, 57, or 58, or a pharmaceutically acceptable form thereof.

In some embodiments, the compound is a compound of Formula (I), (II), (III), or (IV), or of Formula (V) or (VI), as disclosed herein, wherein the compound is a racemate or a single enantiomer thereof, such as the (R)-enantiomer or the (S)-enantiomer thereof, and is selected from:

3-hydroxy-3-(1-methyl-1H-imidazol-5-yl)-$2^1$,$2^2$-dihydro-2(4,6)-quinolina-1,4(1,3)-dibenzenacyclohexaphan-$2^2$-one (001);

3-hydroxy-$2^1$-methyl-3-(1-methyl-1H-imidazol-5-yl)-$2^1$,$2^2$-dihydro-2(4,6)-quinolina-1,4(1,3)-dibenzenacyclohexaphan-$2^2$-one (002);

$4^4$-chloro-3-hydroxy-$2^1$-methyl-3-(1-methyl-1H-imidazol-5-yl)-$2^1$,$2^2$-dihydro-2(4,6)-quinolina-1,4(1,3)-dibenzenacyclohexaphan-$2^2$-one (003);

3-amino-$4^4$-chloro-$2^1$-methyl-3-(1-methyl-1H-imidazol-5-yl)-$2^1$,$2^2$-dihydro-2(4,6)-quinolina-1,4(1,3)-dibenzenacyclohexaphan-$2^2$-one (004);

3-hydroxy-$2^2$-methoxy-3-(1-methyl-1H-imidazol-5-yl)-2(4,6)-quinolina-1,4(1,3)-dibenzenacyclohexaphane-$4^4$-carbonitrile (005);

3-hydroxy-21-methyl-3-(1-methyl-1H-imidazol-5-yl)-$2^2$-oxo-$2^1$,$2^2$-dihydro-2(4,6)-quinolina-1,4(1,3)-dibenzenacyclohexaphane-$4^4$-carbonitrile (006);

3-amino-$2^1$-methyl-3-(1-methyl-1H-imidazol-5-yl)-$2^2$-oxo-$2^1$,$2^2$-dihydro-2(4,6)-quinolina-1,4(1,3)-dibenzenacyclohexaphane-$4^4$-carbonitrile (007);

3-amino-$2^1$-(methyl-$d_3$)-3-(1-methyl-1H-imidazol-5-yl)-$2^2$-oxo-$2^1$,$2^2$-dihydro-2(4,6)-quinolina-1,4(1,3)-dibenzenacyclohexaphane-$4^4$-carbonitrile (008);

3-amino-3-(1-methyl-1H-imidazol-5-yl)-2(4,6)-quinolina-1,4(1,3)-dibenzenacyclohexaphane-$2^2$, $4^4$-dicarbonitrile (009);

$2^2$-methoxy-3-(1-methyl-1H-imidazol-5-yl)-5-oxa-2(4,6)-quinolina-1,4(1,3)-dibenzenacyclohexaphan-3-ol (010);

3-hydroxy-$2^1$-methyl-3-(1-methyl-1H-imidazol-5-yl)-$2^1$,$2^2$-dihydro-5-oxa-2(4,6)-quinolina-1,4(1,3)-dibenzenacyclohexaphan-$2^2$-one (011);

$4^4$-chloro-$2^2$-methoxy-3-(1-methyl-1H-imidazol-5-yl)-5-oxa-2(4,6)-quinolina-1,4(1,3)-dibenzenacyclohexaphan-3-ol (012);

$4^4$-chloro-3-hydroxy-3-(1-methyl-1H-imidazol-5-yl)-$2^1$,$2^2$-dihydro-5-oxa-2(4,6)-quinolina-1,4(1,3)-dibenzenacyclohexaphan-$2^2$-one (013);

$4^4$-chloro-3-hydroxy-$2^1$-methyl-3-(1-methyl-1H-imidazol-5-yl)-$2^1$,$2^2$-dihydro-5-oxa-2(4,6)-quinolina-1,4(1,3)-dibenzenacyclohexaphan-$2^2$-one (014);

3-amino-$4^4$-chloro-$2^1$-methyl-3-(1-methyl-1H-imidazol-5-yl)-$2^1$,$2^2$-dihydro-5-oxa-2(4,6)-quinolina-1,4(1,3)-dibenzenacyclohexaphan-$2^2$-one (015);

3-hydroxy-$2^2$-methoxy-3-(1-methyl-1H-imidazol-5-yl)-5-oxa-2(4,6)-quinolina-1,4(1,3)-dibenzenacyclohexaphane-$4^4$-carbonitrile (016);

3-hydroxy-3-(1-methyl-1H-imidazol-5-yl)-$2^2$-oxo-$2^1$,$2^2$-dihydro-5-oxa-2(4,6)-quinolina-1,4(1,3)-dibenzenacyclohexaphane-$4^4$-carbonitrile (017);

3-hydroxy-$2^1$-methyl-3-(1-methyl-1H-imidazol-5-yl)-$2^2$-oxo-$2^1$,$2^2$-dihydro-5-oxa-2(4,6)-quinolina-1,4(1,3)-dibenzenacyclohexaphane-$4^4$-carbonitrile (018);

3-amino-$2^1$-methyl-3-(1-methyl-1H-imidazol-5-yl)-$2^2$-oxo-$2^1$,$2^2$-dihydro-5-oxa-2(4,6)-quinolina-1,4(1,3)-dibenzenacyclohexaphane-$4^4$-carbonitrile (019);

3-amino-$2^1$-(methyl-d$_3$)-3-(1-methyl-1H-imidazol-5-yl)-$2^2$-oxo-$2^1$,$2^2$-dihydro-5-oxa-2(4,6)-quinolina-1,4(1,3)-dibenzenacyclohexaphane-$4^4$-carbonitrile (020);

3-amino-3-(1-methyl-1H-imidazol-5-yl)-5-oxa-2(4,6)-quinolina-1,4(1,3)-dibenzenacyclohexaphane-$2^2$ $4^4$-dicarbonitrile (021);

3-hydroxy-3-(1-methyl-1H-imidazol-5-yl)-$2^1$,$2^2$-dihydro-5-oxa-2(4,6)-quinolina-1,4(1,3)-dibenzenacycloheptaphan-$2^2$-one (022);

3-hydroxy-$2^1$-methyl-3-(1-methyl-1H-imidazol-5-yl)-$2^1$,$2^2$-dihydro-5-oxa-2(4,6)-quinolina-1,4(1,3)-dibenzenacycloheptaphan-$2^2$-one (023);

$4^4$-chloro-$2^2$-methoxy-3-(1-methyl-1H-imidazol-5-yl)-5-oxa-2(4,6)-quinolina-1,4(1,3)-dibenzenacycloheptaphan-3-ol (024);

$4^4$-chloro-3-hydroxy-3-(1-methyl-1H-imidazol-5-yl)-$2^1$,$2^2$-dihydro-5-oxa-2(4,6)-quinolina-1,4(1,3)-dibenzenacycloheptaphan-$2^2$-one (025);

$4^4$-chloro-3-hydroxy-$2^1$-methyl-3-(1-methyl-1H-imidazol-5-yl)-$2^1$,$2^2$-dihydro-5-oxa-2(4,6)-quinolina-1,4(1,3)-dibenzenacycloheptaphan-$2^2$-one (026);

3-amino-$4^4$-chloro-$2^1$-methyl-3-(1-methyl-1H-imidazol-5-yl)-$2^1$,$2^2$-dihydro-5-oxa-2(4,6)-quinolina-1,4(1,3)-dibenzenacycloheptaphan-$2^2$-one (027);

$4^4$-chloro-3-hydroxy-$2^1$-(methyl-d$_3$)-3-(1-methyl-1H-imidazol-5-yl)-$2^1$,$2^2$-dihydro-5-oxa-2(4,6)-quinolina-1,4(1,3)-dibenzenacycloheptaphan-$2^2$-one (028);

$4^4$-chloro-$2^1$-cyclopropyl-3-hydroxy-3-(1-methyl-1H-imidazol-5-yl)-$2^1$,$2^2$-dihydro-5-oxa-2(4,6)-quinolina-1,4(1,3)-dibenzenacycloheptaphan-$2^2$-one (029);

3-amino-$4^4$-chloro-$2^1$-cyclopropyl-3-(1-methyl-1H-imidazol-5-yl)-$2^1$,$2^2$-dihydro-5-oxa-2(4,6)-quinolina-1,4(1,3)-dibenzenacycloheptaphan-$2^2$-one (030);

$4^4$-chloro-3-hydroxy-3-(4-methyl-4H-1,2,4-triazol-3-yl)-$2^1$,$2^2$-dihydro-5-oxa-2(4,6)-quinolina-1,4(1,3)-dibenzenacycloheptaphan-$2^2$-one (031);

$4^4$-chloro-3-hydroxy-$2^1$-(methyl-d$_3$)-3-(4-methyl-4H-1,2,4-triazol-3-yl)-$2^1$,$2^2$-dihydro-5-oxa-2(4,6)-quinolina-1,4(1,3)-dibenzenacycloheptaphan-$2^2$-one (032);

$4^4$-chloro-3-(methoxy-d$_3$)-$2^1$-(methyl-d$_3$)-3-(4-methyl-4H-1,2,4-triazol-3-yl)-$2^1$,$2^2$-dihydro-5-oxa-2(4,6)-quinolina-1,4(1,3)-dibenzenacycloheptaphan-$2^2$-one (033);

3-amino-$4^4$-chloro-$2^1$-(methyl-d$_3$)-3-(4-methyl-4H-1,2,4-triazol-3-yl)-$2^1$,$2^2$-dihydro-5-oxa-2(4,6)-quinolina-1,4(1,3)-dibenzenacycloheptaphan-$2^2$-one (034);

3-amino-$4^4$-chloro-$2^1$-cyclopropyl-3-(4-methyl-4H-1,2,4-triazol-3-yl)-$2^1$,$2^2$-dihydro-5-oxa-2(4,6)-quinolina-1,4(1,3)-dibenzenacycloheptaphan-$2^2$-one (035);

3-hydroxy-$2^1$-methyl-3-(1-methyl-1H-imidazol-5-yl)-$2^2$-oxo-$2^1$,$2^2$-dihydro-5-oxa-2(4,6)-quinolina-1,4(1,3)-dibenzenacycloheptaphane-$4^4$-carbonitrile (036);

3-amino-$2^1$-methyl-3-(1-methyl-1H-imidazol-5-yl)-$2^2$-oxo-$2^1$,$2^2$-dihydro-5-oxa-2(4,6)-quinolina-1,4(1,3)-dibenzenacycloheptaphane-$4^4$-carbonitrile (037);

3-hydroxy-$2^1$-methyl-3-(4-methyl-4H-1,2,4-triazol-3-yl)-$2^2$-oxo-$2^1$,$2^2$-dihydro-5-oxa-2(4,6)-quinolina-1,4(1,3)-dibenzenacycloheptaphane-$4^4$-carbonitrile (038);

3-amino-$2^1$-methyl-3-(4-methyl-4H-1,2,4-triazol-3-yl)-$2^2$-oxo-$2^1$,$2^2$-dihydro-5-oxa-2(4,6)-quinolina-1,4(1,3)-dibenzenacycloheptaphane-$4^4$-carbonitrile (039);

$2^2$-methoxy-3-(1-methyl-1H-imidazol-5-yl)-6-oxa-2(4,6)-quinolina-1,4(1,3)-dibenzenacyclohexaphan-3-ol (040);

3-hydroxy-3-(1-methyl-1H-imidazol-5-yl)-$2^1$,$2^2$-dihydro-6-oxa-2(4,6)-quinolina-1,4(1,3)-dibenzenacyclohexaphan-$2^2$-one (041);

3-hydroxy-$2^1$-methyl-3-(1-methyl-1H-imidazol-5-yl)-$2^1$,$2^2$-dihydro-6-oxa-2(4,6)-quinolina-1,4(1,3)-dibenzenacyclohexaphan-$2^2$-one (042);

$4^4$-chloro-$2^2$-methoxy-3-(1-methyl-1H-imidazol-5-yl)-6-oxa-2(4,6)-quinolina-1,4(1,3)-dibenzenacyclohexaphan-3-ol (043);

$4^4$-chloro-3-hydroxy-3-(1-methyl-1H-imidazol-5-yl)-$2^1$,$2^2$-dihydro-6-oxa-2(4,6)-quinolina-1,4(1,3)-dibenzenacyclohexaphan-$2^2$-one (044);

$4^4$-chloro-3-hydroxy-$2^1$-methyl-3-(1-methyl-1H-imidazol-5-yl)-$2^1$,$2^2$-dihydro-6-oxa-2(4,6)-quinolina-1,4(1,3)-dibenzenacyclohexaphan-$2^2$-one (045);

3-amino-$4^4$-chloro-$2^1$-methyl-3-(1-methyl-1H-imidazol-5-yl)-$2^1$,$2^2$-dihydro-6-oxa-2(4,6)-quinolina-1,4(1,3)-dibenzenacyclohexaphan-$2^2$-one (046);

3-amino-$4^4$-chloro-$2^1$-(methyl-d$_3$)-3-(1-methyl-1H-imidazol-5-yl)-$2^1$,$2^2$-dihydro-6-oxa-2(4,6)-quinolina-1,4(1,3)-dibenzenacyclohexaphan-$2^2$-one (047);

3-amino-$4^4$-chloro-3-(1-methyl-1H-imidazol-5-yl)-6-oxa-2(4,6)-quinolina-1,4(1,3)-dibenzenacyclohexaphane-$2^2$-carbonitrile (048);

$4^4$-chloro-$2^2$-methoxy-3-(4-methyl-4H-1,2,4-triazol-3-yl)-6-oxa-2(4,6)-quinolina-1,4(1,3)-dibenzenacyclohexaphan-3-ol (049);

$4^4$-chloro-$2^1$-methyl-3-(4-methyl-4H-1,2,4-triazol-3-yl)-3-(methylamino)-$2^1$,$2^2$-dihydro-6-oxa-2(4,6)-quinolina-1,4(1,3)-dibenzenacyclohexaphan-$2^2$-one (050);

3-amino-$4^4$-chloro-$2^1$-methyl-3-(4-methyl-4H-1,2,4-triazol-3-yl)-$2^1$,$2^2$-dihydro-6-oxa-2(4,6)-quinolina-1,4(1,3)-dibenzenacyclohexaphan-$2^2$-one (051); $4^4$-bromo-$2^2$-methoxy-3-(1-methyl-1H-imidazol-5-yl)-6-oxa-2(4,6)-quinolina-1,4(1,3)-dibenzenacyclohexaphan-3-ol (052);

3-hydroxy-$2^2$-methoxy-3-(1-methyl-1H-imidazol-5-yl)-6-oxa-2(4,6)-quinolina-1,4(1,3)-dibenzenacyclohexaphane-$4^4$-carbonitrile (053);

3-hydroxy-3-(1-methyl-1H-imidazol-5-yl)-$2^2$-oxo-$2^1$,$2^2$-dihydro-6-oxa-2(4,6)-quinolina-1,4(1,3)-dibenzenacyclohexaphane-$4^4$-carbonitrile (054);

3-hydroxy-21-(methyl-d$_3$)-3-(1-methyl-1H-imidazol-5-yl)-$2^2$-oxo-$2^1$,$2^2$-dihydro-6-oxa-2(4,6)-quinolina-1,4(1,3)-dibenzenacyclohexaphane-$4^4$-carbonitrile (055);

3-amino-$2^1$-(methyl-d$_3$)-3-(1-methyl-1H-imidazol-5-yl)-$2^2$-oxo-$2^1$,$2^2$-dihydro-6-oxa-2(4,6)-quinolina-1,4(1,3)-dibenzenacyclohexaphane-$4^4$-carbonitrile (056);

3-amino-$2^1$-cyclopropyl-3-(1-methyl-1H-imidazol-5-yl)-$2^2$-oxo-$2^1$,$2^2$-dihydro-6-oxa-2(4,6)-quinolina-1,4(1,3)-dibenzenacyclohexaphane-$4^4$-carbonitrile (057);

3-amino-3-(1-methyl-1H-imidazol-5-yl)-6-oxa-2(4,6)-quinolina-1,4(1,3)-dibenzenacyclohexaphane-$2^2$ $4^4$-dicarbonitrile (058);

$4^6$-chloro-$2^2$-methoxy-3-(1-methyl-1H-imidazol-5-yl)-6-oxa-2(4,6)-quinolina-4(3,5)-pyridina-1(1,3)-benzenacyclohexaphan-3-ol (059);

3-hydroxy-$2^2$-methoxy-3-(1-methyl-1H-imidazol-5-yl)-6-oxa-2(4,6)-quinolina-4(3,5)-pyridina-1(1,3)-benzenacyclohexaphane-$4^6$-carbonitrile (060);

3-hydroxy-21-(methyl-d$_3$)-3-(1-methyl-1H-imidazol-5-yl)-$2^2$-oxo-$2^1$,$2^2$-dihydro-6-oxa-2(4,6)-quinolina-4(3,5)-pyridina-1(1,3)-benzenacyclohexaphane-$4^6$-carbonitrile (061);

3-amino-$2^1$-(methyl-d$_3$)-3-(1-methyl-1H-imidazol-5-yl)-$2^2$-oxo-$2^1$,$2^2$-dihydro-6-oxa-2(4,6)-quinolina-4(3,5)-pyridina-1(1,3)-benzenacyclohexaphane-$4^6$-carbonitrile (062);

3-hydroxy-$2^1$-methyl-3-(1-methyl-1H-imidazol-5-yl)-$2^1$,$2^2$-dihydro-7-oxa-2(4,6)-quinolina-1,4(1,3)-dibenzenacycloheptaphan-$2^2$-one (063);

$4^4$-chloro-$2^2$-methoxy-3-(1-methyl-1H-imidazol-5-yl)-7-oxa-2(4,6)-quinolina-1,4(1,3)-dibenzenacycloheptaphan-3-ol (064);

$4^4$-chloro-3-hydroxy-$2^1$-methyl-3-(1-methyl-1H-imidazol-5-yl)-$2^1$,$2^2$-dihydro-7-oxa-2(4,6)-quinolina-1,4(1,3)-dibenzenacycloheptaphan-$2^2$-one (065);

3-amino-3-(1-methyl-1H-imidazol-5-yl)-$2^2$-morpholino-6-oxa-2(4,6)-quinolina-1,4(1,3)-dibenzenacyclohexaphane-$4^4$-carbonitrile (066);

3-amino-3-(1-methyl-1H-imidazol-5-yl)-$2^2$-(piperazin-1-yl)-6-oxa-2(4,6)-quinolina-1,4(1,3)-dibenzenacyclohexaphane-$4^4$-carbonitrile (067);

3-amino-3-(1-methyl-1H-imidazol-5-yl)-$2^2$-(oxetan-3-ylamino)-6-oxa-2(4,6)-quinolina-1,4(1,3)-dibenzenacyclohexaphane-$4^4$-carbonitrile (068);

3-amino-$2^1$-(2,3-dihydroxypropyl)-3-(1-methyl-1H-imidazol-5-yl)-$2^2$-oxo-$2^1$,$2^2$-dihydro-6-oxa-2(4,6)-quinolina-1,4(1,3)-dibenzenacyclohexaphane-$4^4$-carbonitrile (069);

3-amino-3-(1-(methyl-d$_3$)-1H-imidazol-5-yl)-6-oxa-2(4,6)-quinolina-1,4(1,3)-dibenzenacyclohexaphane-$2^2$ $4^4$-dicarbonitrile (070);

$4^4$-bromo-$2^2$-chloro-3-(1-methyl-1H-imidazol-5-yl)-6-oxa-2(4,6)-quinolina-1,4(1,3)-dibenzenacyclohexaphan-3-ol (071);

3-hydroxy-3-(1-methyl-1H-imidazol-5-yl)-6-oxa-2(4,6)-quinolina-1,4(1,3)-dibenzenacyclohexaphane-$2^2$ $4^4$-dicarbonitrile (072);

$4^4$-cyano-3-hydroxy-3-(1-methyl-1H-imidazol-5-yl)-6-oxa-2(4,6)-quinolina-1,4(1,3)-dibenzenacyclohexaphane-$2^2$-carboxamide (073);

$4^4$-bromo-$2^2$-chloro-3-(1-methyl-1H-imidazol-5-yl)-6-oxa-2(4,6)-quinolina-1,4(1,3)-dibenzenacyclohexaphan-3-amine (074);

$4^4$-bromo-3-(1-methyl-1H-imidazol-5-yl)-$2^2$-(oxetan-3-yloxy)-6-oxa-2(4,6)-quinolina-1,4(1,3)-dibenzenacyclohexaphan-3-amine (075);

$4^4$-chloro-$2^1$-(methyl-d$_3$)-3-(5-methyl-1H-imidazol-1-yl)-$2^1$,$2^2$-dihydro-6-oxa-2(4,6)-quinolina-1,4(1,3)-dibenzenacyclohexaphan-$2^2$-one (076); and $4^4$-chloro-$2^1$-(methyl-d$_3$)-3-(4-methyl-1H-imidazol-1-yl)-$2^1$,$2^2$-dihydro-6-oxa-2(4,6)-quinolina-1,4(1,3)-dibenzenacyclohexaphan-$2^2$-one (077);

or a pharmaceutically acceptable form thereof.

In some embodiments, the compound is selected from:

(R)-3-hydroxy-$2^1$-methyl-3-(1-methyl-1H-imidazol-5-yl)-$2^2$-oxo-$2^1$,$2^2$-dihydro-2(4,6)-quinolina-1,4(1,3)-dibenzenacyclohexaphane-$4^4$-carbonitrile ((R)-006);

(R)-3-amino-$2^1$-methyl-3-(1-methyl-1H-imidazol-5-yl)-$2^2$-oxo-$2^1$,$2^2$-dihydro-2(4,6)-quinolina-1,4(1,3)-dibenzenacyclohexaphane-$4^4$-carbonitrile ((R)-007);

(R)-3-amino-$2^1$-(methyl-d$_3$)-3-(1-methyl-1H-imidazol-5-yl)-$2^2$-oxo-$2^1$,$2^2$-dihydro-2(4,6)-quinolina-1,4(1,3)-dibenzenacyclohexaphane-$4^4$-carbonitrile ((R)-008);

(R)-3-amino-3-(1-methyl-1H-imidazol-5-yl)-2(4,6)-quinolina-1,4(1,3)-dibenzenacyclohexaphane-$2^2$ $4^4$-dicarbonitrile ((R)-009); and (R)-$4^4$-chloro-$2^1$-(methyl-d$_3$)-3-(4-methyl-1H-imidazol-1-yl)-$2^1$,$2^2$-dihydro-6-oxa-2(4,6)-quinolina-1,4(1,3)-dibenzenacyclohexaphan-$2^2$-one ((R)-077);

or a pharmaceutically acceptable form thereof.

In some embodiments, the compound is selected from:

(S)-$4^4$-chloro-3-hydroxy-$2^1$-methyl-3-(1-methyl-1H-imidazol-5-yl)-$2^1$,$2^2$-dihydro-2(4,6)-quinolina-1,4(1,3)-dibenzenacyclohexaphan-$2^2$-one ((S)-003);

(S)-3-amino-$4^4$-chloro-$2^1$-methyl-3-(1-methyl-1H-imidazol-5-yl)-$2^1$,$2^2$-dihydro-2(4,6)-quinolina-1,4(1,3)-dibenzenacyclohexaphan-$2^2$-one ((S)-004);

(S)-$4^4$-chloro-3-hydroxy-$2^1$-methyl-3-(1-methyl-1H-imidazol-5-yl)-$2^1$,$2^2$-dihydro-5-oxa-2(4,6)-quinolina-1,4(1,3)-dibenzenacyclohexaphan-$2^2$-one ((S)-014);

(S)-3-amino-$4^4$-chloro-$2^1$-methyl-3-(1-methyl-1H-imidazol-5-yl)-$2^1$,$2^2$-dihydro-5-oxa-2(4,6)-quinolina-1,4(1,3)-dibenzenacyclohexaphan-$2^2$-one ((S)-015);

(S)-3-hydroxy-$2^1$-methyl-3-(1-methyl-1H-imidazol-5-yl)-$2^2$-oxo-$2^1$,$2^2$-dihydro-5-oxa-2(4,6)-quinolina-1,4(1,3)-dibenzenacyclohexaphane-$4^4$-carbonitrile ((S)-018);

(S)-3-amino-$2^1$-methyl-3-(1-methyl-1H-imidazol-5-yl)-$2^2$-oxo-$2^1$,$2^2$-dihydro-5-oxa-2(4,6)-quinolina-1,4(1,3)-dibenzenacyclohexaphane-$4^4$-carbonitrile ((S)-019);

(S)-3-amino-$2^1$-(methyl-d$_3$)-3-(1-methyl-1H-imidazol-5-yl)-$2^2$-oxo-$2^1$,$2^2$-dihydro-5-oxa-2(4,6)-quinolina-1,4(1,3)-dibenzenacyclohexaphane-$4^4$-carbonitrile ((S)-020);

(S)-3-amino-3-(1-methyl-1H-imidazol-5-yl)-5-oxa-2(4,6)-quinolina-1,4(1,3)-dibenzenacyclohexaphane-$2^2$ $4^4$-dicarbonitrile ((S)-021);

(S)-$4^4$-chloro-3-hydroxy-3-(1-methyl-1H-imidazol-5-yl)-$2^1$,$2^2$-dihydro-5-oxa-2(4,6)-quinolina-1,4(1,3)-dibenzenacycloheptaphan-$2^2$-one ((S)-025);

(S)-3-amino-$4^4$-chloro-$2^1$-methyl-3-(1-methyl-1H-imidazol-5-yl)-$2^1$,$2^2$-dihydro-5-oxa-2(4,6)-quinolina-1,4(1,3)-dibenzenacycloheptaphan-$2^2$-one ((S)-027);

(S)-$4^4$-chloro-3-hydroxy-$2^1$-(methyl-d$_3$)-3-(1-methyl-1H-imidazol-5-yl)-$2^1$,$2^2$-dihydro-5-oxa-2(4,6)-quinolina-1,4(1,3)-dibenzenacycloheptaphan-$2^2$-one ((S)-028);

(S)-$4^4$-chloro-$2^1$-cyclopropyl-3-hydroxy-3-(1-methyl-1H-imidazol-5-yl)-$2^1$,$2^2$-dihydro-5-oxa-2(4,6)-quinolina-1,4(1,3)-dibenzenacycloheptaphan-$2^2$-one ((S)-029);

(S)-3-amino-$4^4$-chloro-$2^1$-cyclopropyl-3-(1-methyl-1H-imidazol-5-yl)-$2^1$,$2^2$-dihydro-5-oxa-2(4,6)-quinolina-1,4(1,3)-dibenzenacycloheptaphan-$2^2$-one ((S)-030);

(S)-3-amino-$4^4$-chloro-$2^1$-(methyl-d$_3$)-3-(4-methyl-4H-1,2,4-triazol-3-yl)-$2^1$,$2^2$-dihydro-5-oxa-2(4,6)-quinolina-1,4(1,3)-dibenzenacycloheptaphan-$2^2$-one ((S)-034);

(S)-3-amino-$4^4$-chloro-$2^1$-cyclopropyl-3-(4-methyl-4H-1,2,4-triazol-3-yl)-$2^1$,$2^2$-dihydro-5-oxa-2(4,6)-quinolina-1,4(1,3)-dibenzenacycloheptaphan-$2^2$-one ((S)-035);

(S)-3-hydroxy-$2^1$-methyl-3-(1-methyl-1H-imidazol-5-yl)-$2^2$-oxo-$2^1$,$2^2$-dihydro-5-oxa-2(4,6)-quinolina-1,4(1,3)-dibenzenacycloheptaphane-$4^4$-carbonitrile ((S)-036);

(S)-3-amino-$2^1$-methyl-3-(1-methyl-1H-imidazol-5-yl)-$2^2$-oxo-$2^1$,$2^2$-dihydro-5-oxa-2(4,6)-quinolina-1,4(1,3)-dibenzenacycloheptaphane-$4^4$-carbonitrile ((S)-037);

(S)-3-amino-$2^1$-methyl-3-(4-methyl-4H-1,2,4-triazol-3-yl)-$2^2$-oxo-$2^1$,$2^2$-dihydro-5-oxa-2(4,6)-quinolina-1,4(1,3)-dibenzenacycloheptaphane-$4^4$-carbonitrile ((S)-039);

(S)-3-amino-$4^4$-chloro-$2^1$-methyl-3-(1-methyl-1H-imidazol-5-yl)-$2^1$,$2^2$-dihydro-6-oxa-2(4,6)-quinolina-1,4(1,3)-dibenzenacyclohexaphan-$2^2$-one ((S)-046);

(S)-3-amino-$4^4$-chloro-$2^1$-(methyl-d$_3$)-3-(1-methyl-1H-imidazol-5-yl)-$2^1$,$2^2$-dihydro-6-oxa-2(4,6)-quinolina-1,4(1,3)-dibenzenacyclohexaphan-$2^2$-one ((S)-047);

(S)-3-amino-$4^4$-chloro-3-(1-methyl-1H-imidazol-5-yl)-6-oxa-2(4,6)-quinolina-1,4(1,3)-dibenzenacyclohexaphane-$2^2$-carbonitrile ((S)-048);

(S)-3-amino-$4^4$-chloro-$2^1$-methyl-3-(4-methyl-4H-1,2,4-triazol-3-yl)-$2^1$,$2^2$-dihydro-6-oxa-2(4,6)-quinolina-1,4(1,3)-dibenzenacyclohexaphan-$2^2$-one ((S)-051);

(S)-3-hydroxy-$2^1$-(methyl-d$_3$)-3-(1-methyl-1H-imidazol-5-yl)-$2^2$-oxo-$2^1$,$2^2$-dihydro-6-oxa-2(4,6)-quinolina-1,4(1,3)-dibenzenacyclohexaphane-$4^4$-carbonitrile ((S)-055);

(S)-3-amino-$2^1$-(methyl-$d_3$)-3-(1-methyl-1H-imidazol-5-yl)-$2^2$-oxo-$2^1$,$2^2$-dihydro-6-oxa-2(4,6)-quinolina-1,4(1,3)-dibenzenacyclohexaphane-$4^4$-carbonitrile ((S)-056);

(S)-3-amino-$2^1$-cyclopropyl-3-(1-methyl-1H-imidazol-5-yl)-$2^2$-oxo-$2^1$,$2^2$-dihydro-6-oxa-2(4,6)-quinolina-1,4(1,3)-dibenzenacyclohexaphane-$4^4$-carbonitrile ((S)-057);

(S)-3-amino-3-(1-methyl-1H-imidazol-5-yl)-6-oxa-2(4,6)-quinolina-1,4(1,3)-dibenzenacyclohexaphane-$2^2$ $4^4$-dicarbonitrile ((S)-058);

(S)-3-amino-3-(1-methyl-1H-imidazol-5-yl)-$2^2$-morpholino-6-oxa-2(4,6)-quinolina-1,4(1,3)-dibenzenacyclohexaphane-$4^4$-carbonitrile ((S)-066);

(S)-3-amino-$2^1$-(2,3-dihydroxypropyl)-3-(1-methyl-1H-imidazol-5-yl)-$2^2$-oxo-$2^1$,$2^2$-dihydro-6-oxa-2(4,6)-quinolina-1,4(1,3)-dibenzenacyclohexaphane-$4^4$-carbonitrile ((S)-069); and (S)-3-amino-3-(1-(methyl-$d_3$)-1H-imidazol-5-yl)-6-oxa-2(4,6)-quinolina-1,4(1,3)-dibenzenacyclohexaphane-$2^2$ $4^4$-dicarbonitrile ((S)-070);

or a pharmaceutically acceptable form thereof.

In some embodiments, the compound is selected from:

(R)-3-hydroxy-3-(1-(methyl-$d_3$)-1H-imidazol-5-yl)-6-oxa-2(4,6)-quinolina-1,4(1,3)-dibenzenacyclohexaphane-$2^2$ $4^4$-dicarbonitrile ((R)-078);

(S)-3-hydroxy-3-(1-(methyl-$d_3$)-1H-imidazol-5-yl)-6-oxa-2(4,6)-quinolina-1,4(1,3)-dibenzenacyclohexaphane-$2^2$ $4^4$-dicarbonitrile ((S)-078);

(R)-$4^4$-chloro-$2^1$-(methyl-$d_3$)-3-(5-methyl-1H-1,2,4-triazol-1-yl)-$2^1$,$2^2$-dihydro-6-oxa-2(4,6)-quinolina-1,4(1,3)-dibenzenacyclohexaphan-$2^2$-one ((R)-079);

(S)-$4^4$-chloro-$2^1$-(methyl-$d_3$)-3-(5-methyl-1H-1,2,4-triazol-1-yl)-$2^1$,$2^2$-dihydro-6-oxa-2(4,6)-quinolina-1,4(1,3)-dibenzenacyclohexaphan-$2^2$-one ((S)-079);

(R)-$4^4$-chloro-$2^1$-(methyl-$d_3$)-3-(3-methyl-1H-1,2,4-triazol-1-yl)-$2^1$,$2^2$-dihydro-6-oxa-2(4,6)-quinolina-1,4(1,3)-dibenzenacyclohexaphan-$2^2$-one ((R)-080);

(S)-$4^4$-chloro-$2^1$-(methyl-$d_3$)-3-(3-methyl-1H-1,2,4-triazol-1-yl)-$2^1$,$2^2$-dihydro-6-oxa-2(4,6)-quinolina-1,4(1,3)-dibenzenacyclohexaphan-$2^2$-one ((S)-080);

$4^4$-bromo-$2^2$-chloro-3-(1-methyl-1H-imidazol-5-yl)-6-oxa-2(4,6)-quinazolina-1,4(1,3)-dibenzenacyclohexaphan-3-ol (081);

$4^4$-bromo-3-(1-methyl-1H-imidazol-5-yl)-6-oxa-2(4,6)-quinazolina-1,4(1,3)-dibenzenacyclohexaphane-$2^2$,3-diamine (082);

$4^4$-bromo-3-(1-methyl-1H-imidazol-5-yl)-6-oxa-2(4,6)-isoquinolina-1,4(1,3)-dibenzenacyclohexaphan-3-ol (083);

$4^4$-bromo-3-(1-methyl-1H-imidazol-5-yl)-6-oxa-2(1,7)-isoquinolina-1,4(1,3)-dibenzenacyclohexaphan-3-ol (084);

3-hydroxy-3-(1-methyl-1H-imidazol-5-yl)-6-oxa-2(1,7)-isoquinolina-1,4(1,3)-dibenzenacyclohexaphane-$4^4$-carbonitrile (085);

3-amino-3-(1-methyl-1H-imidazol-5-yl)-6-oxa-2(1,7)-isoquinolina-1,4(1,3)-dibenzenacyclohexaphane-$4^4$-carbonitrile (086);

(R)-3-amino-3-(1-methyl-1H-imidazol-5-yl)-6-oxa-2(1,7)-isoquinolina-1,4(1,3)-dibenzenacyclohexaphane-$4^4$-carbonitrile ((R)-086);

(S)-3-amino-3-(1-methyl-1H-imidazol-5-yl)-6-oxa-2(1,7)-isoquinolina-1,4(1,3)-dibenzenacyclohexaphane-$4^4$-carbonitrile ((S)-086);

$4^4$-bromo-$2^7$-methoxy-3-(1-methyl-1H-imidazol-5-yl)-6-oxa-2(5,3)-quinolina-1,4(1,3)-dibenzenacyclohexaphan-3-ol (087);

3-hydroxy-$2^7$-methoxy-3-(1-methyl-1H-imidazol-5-yl)-6-oxa-2(5,3)-quinolina-1,4(1,3)-dibenzenacyclohexaphane-$4^4$-carbonitrile (088);

(R)-3-amino-3-(1-methyl-1H-imidazol-5-yl)-$2^2$-(oxetan-3-yloxy)-6-oxa-2(4,6)-quinolina-1,4(1,3)-dibenzenacyclohexaphane-$4^4$-carbonitrile ((R)-089);

(S)-3-amino-3-(1-methyl-1H-imidazol-5-yl)-$2^2$-(oxetan-3-yloxy)-6-oxa-2(4,6)-quinolina-1,4(1,3)-dibenzenacyclohexaphane-$4^4$-carbonitrile ((S)-089);

(S)-3-(4-methyl-1H-imidazol-1-yl)-6-oxa-2(4,6)-quinolina-1,4(1,3)-dibenzenacyclohexaphane-$2^2$ $4^4$-dicarbonitrile ((S)-090);

(R)-3-(4-methyl-1H-imidazol-1-yl)-6-oxa-2(4,6)-quinolina-1,4(1,3)-dibenzenacyclohexaphane-$2^2$ $4^4$-dicarbonitrile ((R)-090);

(S)-3-(5-methyl-1H-imidazol-1-yl)-6-oxa-2(4,6)-quinolina-1,4(1,3)-dibenzenacyclohexaphane-$2^2$ $4^4$-dicarbonitrile ((S)-091);

(R)-3-(5-methyl-1H-imidazol-1-yl)-6-oxa-2(4,6)-quinolina-1,4(1,3)-dibenzenacyclohexaphane-$2^2$ $4^4$-dicarbonitrile ((R)-091);

| | |
|---|---|
| (R)-3-amino-$4^4$-chloro-$2^1$-methyl-3-(1-methyl-1H-imidazol-5-yl)-$2^1$,$2^2$-dihydro-2(4,6)-quinolina-1,4(1,3)-dibenzenacyclohexaphan-$2^2$-one; | (R)-004 |
| (S)-3-hydroxy-$2^1$-methyl-3-(1-methyl-1H-imidazol-5-yl)-$2^2$-oxo-$2^1$,$2^2$-dihydro-2(4,6)-quinolina-1,4(1,3)-dibenzenacyclohexaphane-$4^4$-carbonitrile; | (S)-006 |
| (S)-3-amino-$2^1$-methyl-3-(1-methyl-1H-imidazol-5-yl)-$2^2$-oxo-$2^1$,$2^2$-dihydro-2(4,6)-quinolina-1,4(1,3)-dibenzenacyclohexaphane-$4^4$-carbonitrile; | (S)-007 |
| (S)-3-amino-$2^1$-(methyl-$d_3$)-3-(1-methyl-1H-imidazol-5-yl)-22-oxo-$2^1$,$2^2$-dihydro-2(4,6)-quinolina-1,4(1,3)-dibenzenacyclohexaphane-$4^4$-carbonitrile; | (S)-008 |
| (S)-3-amino-3-(1-methyl-1H-imidazol-5-yl)-2(4,6)-quinolina-1,4(1,3)-dibenzenacyclohexaphane-$2^2$,$4^4$-dicarbonitrile; | (S)-009 |
| (R)-$4^4$-chloro-3-hydroxy-$2^1$-methyl-3-(1-methyl-1H-imidazol-5-yl)-$2^1$,$2^2$-dihydro-5-oxa-2(4,6)-quinolina-1,4(1,3)-dibenzenacyclohexaphan-$2^2$-one; | (R)-014 |
| (R)-3-amino-$4^4$-chloro-$2^1$-methyl-3-(1-methyl-1H-imidazol-5-yl)-$2^1$,$2^2$-dihydro-5-oxa-2(4,6)-quinolina-1,4(1,3)-dibenzenacyclohexaphan-$2^2$-one; | (R)-015 |
| (R)-3-hydroxy-$2^1$-methyl-3-(1-methyl-1H-imidazol-5-yl)-$2^2$-oxo-$2^1$,$2^2$-dihydro-5-oxa-2(4,6)-quinolina-1,4(1,3)-dibenzenacyclohexaphane-$4^4$-carbonitrile; | (R)-018 |
| (R)-3-amino-$2^1$-methyl-3-(1-methyl-1H-imidazol-5-yl)-$2^2$-oxo-$2^1$,$2^2$-dihydro-5-oxa-2(4,6)-quinolina-1,4(1,3)-dibenzenacyclohexaphane-$4^4$-carbonitrile; | (R)-019 |
| (R)-3-amino-$2^1$-(methyl-$d_3$)-3-(1-methyl-1H-imidazol-5-yl)-$2^2$-oxo-$2^1$,$2^2$-dihydro-5-oxa-2(4,6)-quinolina-1,4(1,3)-dibenzenacyclohexaphane-$4^4$-carbonitrile; | (R)-020 |
| (R)-3-amino-3-(1-methyl-1H-imidazol-5-yl)-5-oxa-2(4,6)-quinolina-1,4(1,3)-dibenzenacyclohexaphane-$2^2$,$4^4$-dicarbonitrile; | (R)-021 |
| (R)-$4^4$-chloro-3-hydroxy-3-(1-methyl-1H-imidazol-5-yl)-$2^1$,$2^2$-dihydro-5-oxa-2(4,6)-quinolina-1,4(1,3)-dibenzenacycloheptaphan-$2^2$-one; | (R)-025 |

-continued

| | |
|---|---|
| (R)-3-amino-4⁴-chloro-2¹-methyl-3-(1-methyl-1H-imidazol-5-yl)-2¹,2²-dihydro-5-oxa-2(4,6)-quinolina-1,4(1,3)-dibenzenacycloheptaphan-2²-one; | (R)-027 |
| (R)-4⁴-chloro-3-hydroxy-2¹-(methyl-d₃)-3-(1-methyl-1H-imidazol-5-yl)-2¹,2²-dihydro-5-oxa-2(4,6)-quinolina-1,4(1,3)-dibenzenacycloheptaphan-2²-one; | (R)-028 |
| (R)-4⁴-chloro-2¹-cyclopropyl-3-hydroxy-3-(1-methyl-1H-imidazol-5-yl)-2¹,2²-dihydro-5-oxa-2(4,6)-quinolina-1,4(1,3)-dibenzenacycloheptaphan-2²-one; | (R)-029 |
| (R)-3-amino-4⁴-chloro-2¹-cyclopropyl-3-(1-methyl-1H-imidazol-5-yl)-2¹,2²-dihydro-5-oxa-2(4,6)-quinolina-1,4(1,3)-dibenzenacycloheptaphan-2²-one; | (R)-030 |
| (R)-3-amino-4⁴-chloro-2¹-(methyl-d₃)-3-(4-methyl-4H-1,2,4-triazol-3-yl)-2¹,2²-dihydro-5-oxa-2(4,6)-quinolina-1,4(1,3)-dibenzenacycloheptaphan-2²-one; | (R)-034 |
| (R)-3-amino-4⁴-chloro-2¹-cyclopropyl-3-(4-methyl-4H-1,2,4-triazol-3-yl)-2¹,2²-dihydro-5-oxa-2(4,6)-quinolina-1,4(1,3)-dibenzenacycloheptaphan-2²-one; | (R)-035 |
| (R)-3-hydroxy-2¹-methyl-3-(1-methyl-1H-imidazol-5-yl)-2²-oxo-2¹,2²-dihydro-5-oxa-2(4,6)-quinolina-1,4(1,3)-dibenzenacycloheptaphane-4⁴-carbonitrile; | (R)-036 |
| (R)-3-amino-2¹-methyl-3-(1-methyl-1H-imidazol-5-yl)-2²-oxo-2¹,2²-dihydro-5-oxa-2(4,6)-quinolina-1,4(1,3)-dibenzenacycloheptaphane-4⁴-carbonitrile; | (R)-037 |
| (R)-3-amino-21-methyl-3-(4-methyl-4H-1,2,4-triazol-3-yl)-2²-oxo-2¹,2²-dihydro-5-oxa-2(4,6)-quinolina-1,4(1,3)-dibenzenacycloheptaphane-4⁴-carbonitrile, | (R)-039 |
| (R)-3-amino-4⁴-chloro-2¹-methyl-3-(1-methyl-1H-imidazol-5-yl)-2¹,2²-dihydro-6-oxa-2(4,6)-quinolina-1,4(1,3)-dibenzenacyclohexaphan-2²-one; | (R)-046 |
| (R)-3-amino-4⁴-chloro-2¹-(methyl-d₃)-3-(1-methyl-1H-imidazol-5-yl)-2¹,2²-dihydro-6-oxa-2(4,6)-quinolina-1,4(1,3)-dibenzenacyclohexaphan-2²-one; | (R)-047 |
| (R)-3-amino-4⁴-chloro-3-(1-methyl-1H-imidazol-5-yl)-6-oxa-2(4,6)-quinolina-1,4(1,3)-dibenzenacyclohexaphane-2²-carbonitrile; | (R)-048 |
| (R)-3-amino-4⁴-chloro-2¹-methyl-3-(4-methyl-4H-1,2,4-triazol-3-yl)-2¹,2²-dihydro-6-oxa-2(4,6)-quinolina-1,4(1,3)-dibenzenacyclohexaphan-2²-one; | (R)-051 |
| (R)-3-hydroxy-21-(methyl-d₃)-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile; | (R)-055 |
| (R)-3-amino-2¹-(methyl-d₃)-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile; | (R)-056 |
| (R)-3-amino-21-cyclopropyl-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile; | (R)-057 |
| (R)-3-amino-3-(1-methyl-1H-imidazol-5-yl)-6-oxa-2(4,6)-quinolina-1,4(1,3)-dibenzenacyclohexaphane-2²,4⁴-dicarbonitrile; | (R)-058 |
| (R)-3-amino-3-(1-methyl-1H-imidazol-5-yl)-2²-morpholino-6-oxa-2(4,6)-quinolina-1,4(1,3)-dibenzenacyclohexaphane-4⁴-carbonitrile; | (R)-066 |
| (R)-3-amino-3-(1-(methyl-d₃)-1H-imidazol-5-yl)-6-oxa-2(4,6)-quinolina-1,4(1,3)-dibenzenacyclohexaphane-2²,4⁴-dicarbonitrile; | (R)-070 |
| (S)-4⁴-chloro-2¹-(methyl-d₃)-3-(5-methyl-1H-imidazol-1-yl)-2¹,2²-dihydro-6-oxa-2(4,6)-quinolina-1,4(1,3)-dibenzenacyclohexaphan-2²-one; and | (S)-076 |
| (S)-4⁴-chloro-2¹-(methyl-d₃)-3-(4-methyl-1H-imidazol-1-yl)-2¹,2²-dihydro-6-oxa-2(4,6)-quinolina-1,4(1,3)-dibenzenacyclohexaphan-2²-one; | (S)-077 | or a pharmaceutically acceptable form thereof.

In some embodiments, the compound is selected from: 3-amino-4⁴-chloro-2¹-cyclopropyl-3-(1-methyl-1H-imidazol-5-yl)-2¹,2²-dihydro-5-oxa-2(4,6)-quinolina-1,4(1,3)-dibenzenacyclohexaphan-2²-one; 092

| | |
|---|---|
| 3-amino-4⁴-chloro-21-cyclopropyl-3-(1-methyl-1H-imidazol-5-yl)-2¹,2²-dihydro-5-oxa-2(4,6)-quinolina-1,4(1,3)-dibenzenacyclohexaphan-2²-one; | 092 |
| 4⁴-chloro-2¹-cyclopropyl-3-hydroxy-3-(1-methyl-1H-imidazol-5-yl)-2¹,2²-dihydro-2(4,6)-quinolina-1,4(1,3)-dibenzenacyclohexaphan-2²-one; | 093 |
| 4⁴-chloro-2¹-cyclopropyl-3-hydroxy-3-(1-methyl-1H-imidazol-5-yl)-2¹,2²-dihydro-7-oxa-2(4,6)-quinolina-1,4(1,3)-dibenzenacycloheptaphan-2²-one; | 094 |
| 4⁴-chloro-2¹-cyclopropyl-3-hydroxy-3-(1-methyl-1H-imidazol-5-yl)-2¹,2²-dihydro-6-oxa-2(4,6)-quinolina-1,4(1,3)-dibenzenacyclohexaphan-2²-one; | 095 |
| 4⁴-chloro-2¹-cyclopropyl-3-((2-fluoroethyl)amino)-3-(1-methyl-1H-imidazol-5-yl)-2¹,2²-dihydro-5-oxa-2(4,6)-quinolina-1,4(1,3)-dibenzenacyclohexaphan-2²-one; | 096 |
| 4⁴-chloro-2¹-cyclopropyl-3-((2-fluoroethyl)amino)-3-(1-methyl-1H-imidazol-5-yl)-2¹,2²-dihydro-5-oxa-2(4,6)-quinolina-1,4(1,3)-dibenzenacycloheptaphan-2²-one; | 097 |
| 4⁴-chloro-2¹-cyclopropyl-3-((2-fluoroethyl)amino)-3-(1-methyl-1H-imidazol-5-yl)-2¹,2²-dihydro-2(4,6)-quinolina-1,4(1,3)-dibenzenacyclohexaphan-2²-one; | 098 |
| 4⁴-chloro-2¹-cyclopropyl-3-((2-fluoroethyl)amino)-3-(1-methyl-1H-imidazol-5-yl)-2¹,2²-dihydro-7-oxa-2(4,6)-quinolina-1,4(1,3)-dibenzenacycloheptaphan-2²-one; | 099 |

-continued

| Name | No. |
|---|---|
| 4⁴-chloro-2¹-cyclopropyl-3-((2-fluoroethyl)amino)-3-(1-methyl-1H-imidazol-5-yl)-2¹,2²-dihydro-6-oxa-2(4,6)-quinolina-1,4(1,3)-dibenzenacyclohexaphan-2²-one; | 100 |
| 4⁴-chloro-3-((2-chloroethyl)amino)-2¹-cyclopropyl-3-(1-methyl-1H-imidazol-5-yl)-2¹,2²-dihydro-5-oxa-2(4,6)-quinolina-1,4(1,3)-dibenzenacyclohexaphan-2²-one; | 101 |
| 4⁴-chloro-3-((2-chloroethyl)amino)-2¹-cyclopropyl-3-(1-methyl-1H-imidazol-5-yl)-2¹,2²-dihydro-5-oxa-2(4,6)-quinolina-1,4(1,3)-dibenzenacycloheptaphan-2²-one; | 102 |
| 4⁴-chloro-3-((2-chloroethyl)amino)-2¹-cyclopropyl-3-(1-methyl-1H-imidazol-5-yl)-2¹,2²-dihydro-2(4,6)-quinolina-1,4(1,3)-dibenzenacyclohexaphan-2²-one; | 103 |
| 4⁴-chloro-3-((2-chloroethyl)amino)-2¹-cyclopropyl-3-(1-methyl-1H-imidazol-5-yl)-2¹,2²-dihydro-7-oxa-2(4,6)-quinolina-1,4(1,3)-dibenzenacycloheptaphan-2²-one; | 104 |
| 4⁴-chloro-3-((2-chloroethyl)amino)-2¹-cyclopropyl-3-(1-methyl-1H-imidazol-5-yl)-2¹,2²-dihydro-6-oxa-2(4,6)-quinolina-1,4(1,3)-dibenzenacyclohexaphan-2²-one; | 105 |
| 4⁴-chloro-21-cyclopropyl-3-(1-methyl-1H-imidazol-5-yl)-3-morpholino-2¹,2²-dihydro-5-oxa-2(4,6)-quinolina-1,4(1,3)-dibenzenacyclohexaphan-2²-one; | 106 |
| 4⁴-chloro-2¹-cyclopropyl-3-(1-methyl-1H-imidazol-5-yl)-3-morpholino-2¹,2²-dihydro-5-oxa-2(4,6)-quinolina-1,4(1,3)-dibenzenacycloheptaphan-2²-one; | 107 |
| 4⁴-chloro-21-cyclopropyl-3-(1-methyl-1H-imidazol-5-yl)-3-morpholino-2¹,2²-dihydro-2(4,6)-quinolina-1,4(1,3)-dibenzenacyclohexaphan-2²-one; | 108 |
| 4⁴-chloro-2¹-cyclopropyl-3-(1-methyl-1H-imidazol-5-yl)-3-morpholino-2¹,2²-dihydro-7-oxa-2(4,6)-quinolina-1,4(1,3)-dibenzenacycloheptaphan-2²-one; | 109 |
| 4⁴-chloro-2¹-cyclopropyl-3-(1-methyl-1H-imidazol-5-yl)-3-morpholino-2¹,2²-dihydro-6-oxa-2(4,6)-quinolina-1,4(1,3)-dibenzenacyclohexaphane; | 110 |
| 4⁴-chloro-3-(1-methyl-1H-imidazol-5-yl)-5-oxa-2(4,6)-quinolina-1,4(1,3)-dibenzenacyclohexaphan-3-amine; | 111 |
| 4⁴-chloro-3-(1-methyl-1H-imidazol-5-yl)-5-oxa-2(4,6)-quinolina-1,4(1,3)-dibenzenacycloheptaphan-3-ol; | 112 |
| 4⁴-chloro-3-(1-methyl-1H-imidazol-5-yl)-2(4,6)-quinolina-1,4(1,3)-dibenzenacyclohexaphan-3-ol; | 113 |
| 4⁴-chloro-3-(1-methyl-1H-imidazol-5-yl)-7-oxa-2(4,6)-quinolina-1,4(1,3)-dibenzenacycloheptaphan-3-ol; | 114 |
| 4⁴-chloro-3-(1-methyl-1H-imidazol-5-yl)-6-oxa-2(4,6)-quinolina-1,4(1,3)-dibenzenacyclohexaphan-3-ol; | 115 |
| 4⁴-chloro-3-(1-methyl-1H-imidazol-5-yl)-5-oxa-2(1,7)-isoquinolina-1,4(1,3)-dibenzenacyclohexaphan-3-amine; | 116 |
| 4⁴-chloro-3-(1-methyl-1H-imidazol-5-yl)-5-oxa-2(1,7)-isoquinolina-1,4(1,3)-dibenzenacycloheptaphan-3-ol; | 117 |
| 4⁴-chloro-3-(1-methyl-1H-imidazol-5-yl)-2(1,7)-isoquinolina-1,4(1,3)-dibenzenacyclohexaphan-3-ol; | 118 |
| 4⁴-chloro-3-(1-methyl-1H-imidazol-5-yl)-7-oxa-2(1,7)-isoquinolina-1,4(1,3)-dibenzenacycloheptaphan-3-ol; | 119 |
| 4⁴-chloro-3-(1-methyl-1H-imidazol-5-yl)-6-oxa-2(1,7)-isoquinolina-1,4(1,3)-dibenzenacyclohexaphan-3-ol; | 120 |
| 4⁴-chloro-N-(2-fluoroethyl)-3-(1-methyl-1H-imidazol-5-yl)-5-oxa-2(1,7)-isoquinolina-1,4(1,3)-dibenzenacyclohexaphan-3-amine; | 121 |
| 4⁴-chloro-N-(2-fluoroethyl)-3-(1-methyl-1H-imidazol-5-yl)-5-oxa-2(1,7)-isoquinolina-1,4(1,3)-dibenzenacycloheptaphan-3-amine; | 122 |
| 4⁴-chloro-N-(2-fluoroethyl)-3-(1-methyl-1H-imidazol-5-yl)-2(1,7)-isoquinolina-1,4(1,3)-dibenzenacyclohexaphan-3-amine; | 123 |
| 4⁴-chloro-N-(2-fluoroethyl)-3-(1-methyl-1H-imidazol-5-yl)-7-oxa-2(1,7)-isoquinolina-1,4(1,3)-dibenzenacycloheptaphan-3-amine; | 124 |
| 4⁴-chloro-N-(2-fluoroethyl)-3-(1-methyl-1H-imidazol-5-yl)-6-oxa-2(1,7)-isoquinolina-1,4(1,3)-dibenzenacyclohexaphan-3-amine; | 125 |
| 4⁴-chloro-N-(2-chloroethyl)-3-(1-methyl-1H-imidazol-5-yl)-5-oxa-2(1,7)-isoquinolina-1,4(1,3)-dibenzenacyclohexaphan-3-amine; | 126 |
| 4⁴-chloro-N-(2-chloroethyl)-3-(1-methyl-1H-imidazol-5-yl)-5-oxa-2(1,7)-isoquinolina-1,4(1,3)-dibenzenacycloheptaphan-3-amine; | 127 |
| 4⁴-chloro-N-(2-chloroethyl)-3-(1-methyl-1H-imidazol-5-yl)-2(1,7)-isoquinolina-1,4(1,3)-dibenzenacyclohexaphan-3-amine; | 128 |
| 4⁴-chloro-N-(2-chloroethyl)-3-(1-methyl-1H-imidazol-5-yl)-7-oxa-2(1,7)-isoquinolina-1,4(1,3)-dibenzenacycloheptaphan-3-amine; | 129 |
| 4⁴-chloro-N-(2-chloroethyl)-3-(1-methyl-1H-imidazol-5-yl)-6-oxa-2(1,7)-isoquinolina-1,4(1,3)-dibenzenacyclohexaphan-3-amine; | 130 |
| 4⁴-chloro-3-(1-methyl-1H-imidazol-5-yl)-3-morpholino-5-oxa-2(1,7)-isoquinolina-1,4(1,3)-dibenzenacyclohexaphane; | 131 |
| 4⁴-chloro-3-(1-methyl-1H-imidazol-5-yl)-3-morpholino-5-oxa-2(1,7)-isoquinolina-1,4(1,3)-dibenzenacycloheptaphane; | 132 |
| 4-(4⁴-chloro-3-(1-methyl-1H-imidazol-5-yl)-2(1,7)-isoquinolina-1,4(1,3)-dibenzenacyclohexaphane-3-yl)morpholine; | 133 |
| 4⁴-chloro-3-(1-methyl-1H-imidazol-5-yl)-3-morpholino-7-oxa-2(1,7)-isoquinolina-1,4(1,3)-dibenzenacycloheptaphane; and | 134 |
| 4⁴-chloro-3-(1-methyl-1H-imidazol-5-yl)-3-morpholino-6-oxa-2(1,7)-isoquinolina-1,4(1,3)-dibenzenacyclohexaphane; | 135 |

5.2 Pharmaceutical Compositions

In some embodiments, provided herein is a pharmaceutical composition containing a therapeutically effective amount of a compound having a structure of any one of Formula (I), (II), (III), or (IV), or a pharmaceutically acceptable form thereof (e.g., pharmaceutically acceptable salt, solvate, isomer, or isotopologue thereof), or of Formula (V) or (VI), or a pharmaceutically acceptable form thereof, and a pharmaceutically acceptable carrier, diluent or excipient. For example, in some embodiments, the pharmaceutical composition provided herein contains a therapeutically effective amount of a compound having a structure of any one of Formula (Ia), (Ib), (IIa), (IIb), (IIIa), (IIIb), (IVa), or (IVb), or a pharmaceutically acceptable form thereof, or of Formula (Va), (Vb), (VIa), or (VIb), or a pharmaceutically acceptable form thereof, and a pharmaceutically acceptable carrier, diluent or excipient. For example, in some embodiments, the pharmaceutical composition provided herein contains a therapeutically effective amount of a compound having a structure of any one of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or a pharmaceutically acceptable form thereof, or of Formula (III-3), (IIIa-3), (IIIb-3), (V-1), (Va-1), (Vb-1), (VI-1), (VIa-1), or (VIb-1), or a pharmaceutically acceptable form thereof, and a pharmaceutically acceptable carrier, diluent or excipient.

The compound of any one of Formula (I), (II), (III), or (IV), or a pharmaceutically acceptable form thereof, or of Formula (V) or (VI), or a pharmaceutically acceptable form thereof, can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the compound disclosed herein is formulated into pharmaceutical compositions using techniques and procedures well known in the art (see, e.g., Ansel Introduction to Pharmaceutical Dosage Forms, Seventh Edition 1999).

The compositions can be formulated for single dosage administration. To formulate a composition, the weight fraction of the compound disclosed herein is dissolved, suspended, dispersed or otherwise mixed in a selected vehicle at an effective concentration such that the treated condition is relieved or ameliorated. Pharmaceutical carriers or vehicles suitable for administration of the compounds disclosed herein provided herein include any such carriers known to those skilled in the art to be suitable for the particular mode of administration.

In addition, the compound of any one of Formula (I), (II), (III), or (IV), or a pharmaceutically acceptable form thereof, or of Formula (V) or (VI), or a pharmaceutically acceptable form thereof, can be formulated as the sole pharmaceutically active ingredient in the composition or may be combined with other therapeutically active ingredients.

The compound of any one of Formula (I), (II), (III), or (IV), or a pharmaceutically acceptable form thereof, or of Formula (V) or (VI), or a pharmaceutically acceptable form thereof, is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The compound of any one of Formula (I), (II), (III), or (IV), or a pharmaceutically acceptable form thereof, or of Formula (V) or (VI), or a pharmaceutically acceptable form thereof, may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Thus, effective concentrations or amounts of one or more of the compounds described herein or pharmaceutically acceptable salts thereof are mixed with a suitable pharmaceutical carrier or vehicle for systemic, topical or local administration to form pharmaceutical compositions. Compounds are included in an amount effective for ameliorating one or more symptoms of, or for treating, retarding progression, or preventing. The concentration of active compound in the composition will depend on absorption, tissue distribution, metabolism, excretion rates of the active compound, the dosage schedule, amount administered, particular formulation as well as other factors known to those of skill in the art.

The compositions are intended to be administered by a suitable route, including but not limited to orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include iontophoresis patches, polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage forms or compositions containing active ingredient in the range of 0.001% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001% to 100% active ingredient, in certain embodiments, about 0.1-85%, about 75-95%, or about 80-98%.

The compound of any one of Formula (I), (II), (III), or (IV), or a pharmaceutically acceptable form thereof, or of Formula (V) or (VI), or a pharmaceutically acceptable form thereof, can be prepared with carriers that protect the compound against rapid elimination from the body, such as time release formulations or coatings.

The compositions can include other active compounds to obtain desired combinations of properties. The compounds provided herein, or pharmaceutically acceptable salts thereof as described herein, can also be administered together with another pharmacological agent known in the general art to be of value in treating one or more of the diseases or medical conditions referred to hereinabove, such as diseases related to oxidative stress.

Oral pharmaceutical dosage forms are either solid, gel or liquid. The solid dosage forms are tablets, capsules, granules, and bulk powders. Types of oral tablets include compressed, chewable lozenges and tablets which may be enteric coated, sugar coated or film coated. Capsules may be hard or soft gelatin capsules, while granules and powders may be provided in non effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non effervescent granules and effervescent preparations reconstituted from effervescent granules. Aqueous solutions include, for example, elixirs and syrups. Emulsions are either oil in-water or water in oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two phase system in which one liquid is dispersed in the form of small globules throughout another liquid. Pharmaceutically acceptable carriers used in emulsions are non aqueous liquids, emulsifying agents and preservatives. Suspensions use pharmaceutically acceptable suspending agents and preservatives. Pharmaceutically acceptable substances used in non effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Parenteral administration, generally characterized by injection, either subcutaneously, intramuscularly or intravenously is also provided herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound of any one of Formula (I), (II), (III), or (IV), or a pharmaceutically acceptable form thereof, or of Formula (V) or (VI), or a pharmaceutically acceptable form thereof, can be suspended in micronized or other suitable form produce a more soluble active product. The form of the resulting mixture depends upon a number of factors, including the intended mode of administration and the solubility of the compound in the selected carrier or vehicle. The effective concentration is sufficient for ameliorating the symptoms of the condition and may be empirically determined.

Topical mixtures are prepared as described for the local and systemic administration. The resulting mixture may be a solution, suspension, emulsion or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compound of any one of Formula (I), (II), (III), or (IV), or a pharmaceutically acceptable form thereof, or of Formula (V) or (VI), or a pharmaceutically acceptable form thereof, or pharmaceutical composition comprising the same, can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered. These solutions, particularly those intended for ophthalmic use, may be formulated as 0.01%-10% isotonic solutions, pH about 5-7, with appropriate salts.

Other routes of administration, such as transdermal patches, and rectal administration are also contemplated herein. For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin gelatin, carbowax (polyoxyethylene glycol) and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. An exemplary weight of a rectal suppository is about 2 to 3 grams. Tablets and capsules for rectal administration are manufactured using the same pharmaceutically acceptable substance and by the same methods as for formulations for oral administration.

The compound of any one of Formula (I), (II), (III), or (IV), or a pharmaceutically acceptable form thereof, or of Formula (V) or (VI), or a pharmaceutically acceptable form thereof, or pharmaceutical composition comprising the same, can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled release of the compounds disclosed herein using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

In certain embodiments, the compound of any one of Formula (I), (II), (III), or (IV), or a pharmaceutically acceptable form thereof, or of Formula (V) or (VI), or a pharmaceutically acceptable form thereof, can be administered using intravenous infusion, an implantable osmotic pump, a transdermal patch, liposomes, or other modes of administration. In one embodiment, a pump may be used (see, Sefton, CRC Crit. Ref Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984).

The compound of any one of Formula (I), (II), (III), or (IV), or a pharmaceutically acceptable form thereof, or of Formula (V) or (VI), or a pharmaceutically acceptable form thereof, or pharmaceutical composition comprising the same, can be packaged as articles of manufacture containing packaging material, a compound or pharmaceutically acceptable form thereof provided herein, which is used for treatment, prevention or amelioration of one or more symptoms or progression of cancer dependent on a farnesylated protein, and a label that indicates that the compound or pharmaceutically acceptable form thereof is used for treatment, prevention or amelioration of one or more symptoms or progression of cancer dependent on a farnesylated protein.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the compounds and compositions provided herein are contemplated.

In some embodiments, the article of manufacture is a kit. The kit can include a compound or pharmaceutical composition as described herein, in suitable packaging, and written material that can include instructions for use, discussion of clinical studies, listing of side effects, and the like. Such kits can also include information, such as scientific literature references, package insert materials, clinical trial results, and/or summaries of these and the like, which indicate or establish the activities and/or advantages of the pharmaceutical composition, and/or which describe dosing, administration, side effects, drug interactions, or other information useful to the health care provider. Such information can be based on the results of various studies, for example, studies using experimental animals involving in vivo models and studies based on human clinical trials.

In some embodiments, a memory aid is provided with the kit, e.g., in the form of numbers next to the tablets or capsules whereby the numbers correspond with the days of the regimen which the tablets or capsules so specified should be ingested. A "daily dose" can be a single tablet or capsule or several tablets or capsules to be taken on a given day.

Suitable packaging and additional articles for use (e.g., measuring cup for liquid preparations, foil wrapping to minimize exposure to air, and the like) are known in the art and can be included in the kit. In other embodiments, kits can further comprise devices that are used to administer the active agent. Examples of such devices include, but are not limited to, syringes, drip bags, patches, and inhalers. Kits described herein can be provided, marketed and/or promoted to health providers, including physicians, nurses, pharmacists, formulary officials, and the like. Kits can also, in some embodiments, be marketed directly to the consumer.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet is such that the tablets or capsules can be removed from the blister pack by manually applying pressure on the recesses whereby an opening is formed in the sheet at the place of the recess. The tablet or capsule can then be removed via said opening.

Kits can further comprise pharmaceutically acceptable vehicles that can be used to administer the active agent. For example, if an active agent is provided in a solid form that must be reconstituted for parenteral administration, the kit can comprise a sealed container of a suitable vehicle in which the active agent can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5.3 Uses and Methods

5.3.1 Therapeutic Uses and Methods

RAS isoforms associate with the inner surface of the plasma membrane to transduce extracellular signals. To become active, RAS undergoes several post-translational modifications. Among the first steps in becoming activated is the farnesylation of the cysteine in the CAAX box at the C-terminal end (where C represents cysteine, A represents an aliphatic amino acid, and X represents any amino acid).

Rowinsky, E. K., et al., J. Clin. Oncol. 1999, 17, 3631-3652. The enzyme farnesyltransferase (FTase) recognizes the CAAX motif and transfers a 15-carbon farnesyl isoprenoid from farnesyl diphosphate to the cysteine residue. The AAX amino acids subsequently are cleaved by Ras-converting enzyme I, and the farnesylated cysteine is carboxymethylated by isoprenylcysteine carboxyl methyltransferase. Prior, I. A., et al., J. Cell Sci. 2001, 114, 1603-1608. Further palmitoylation (KRAS4A, NRAS, and HRAS or the presence of a polybasic domain (KRAS4B) leads to anchoring of the protein in the plasma membrane. Hancock, J. F., et al., Cell 1990, 63, 133-139. The observations suggest prenylation is required for the function of all RAS isoforms, including their mutated forms. However, some farnesylated proteins—including KRAS and NRAS—can be rescued from membrane displacement in the presence of a farnesyltransferase inhibitor (FTI) by an alternative prenylation by the enzyme geranylgeranyltransferase (GGTase). Zhang, F. L., et al., J. Biol. Chem. 1997, 272, 10232-10239; Whyte, D. B., et al., J. Biol. Chem. 1997, 272, 14459-14464. Conversely, the third family member, HRAS, is not a GGTase substrate, and thus its membrane localization and cellular function are diminished by an FTI. Whyte, D. B., et al. Accordingly, the use of FTIs to target enriched patient populations of tumors, for example tumors dependent on farnesylated proteins, such as HRAS, for example tumors harboring HRAS mutations, should provide clinical benefit.

One particular FTI that is in clinical development is tipifarnib. The efficacy of tipifarnib was examined in a series of cell- and patient-derived xenograft models of head and neck squamous cell carcinoma (HNSCC). Gilardi, M., et al., Mol. Cancer Ther. 2020, 19, 1784-1796. Genomic analyses have revealed that HRAS mutations occur in 6% f HNSCC at initial diagnosis (Hoadley, K. A., et al., Cell 2018, 173, 291-304) and in 15% f patients during acquisition of resistance to cetuximab (Braig, F., et al., Oncotarget 2016, 7, 42988-42995), and HRAS mutations have been demonstrated to correlate with reduced response of HNSCC patients to cetuximab treatment. "Rampias, T., et al., Clin. Cancer Res. 2014, 20, 2933-2946.

HRAS is also recurrently mutated in other cancer types, including urothelial cell carcinoma and salivary gland tumors, and 24% f HRAS mutant metastatic urothelial carcinoma patients treated with tipifarnib experienced an objective response. In addition, of 13 pts with recurrent/metastatic salivary gland tumors (SGT) treated with tipifarnib, one experienced an objective response and an additional seven patients had stable disease as best response. Ho, A. L., et al., J. Clin. Oncol. 2020, 38, 6504. Other tumor types exhibiting recurrent HRAS driver mutations include lung squamous cell carcinoma, thyroid cancer, pheochromocytoma and paraganglioma. Hoadley, K. A., et al.

In certain embodiments, the compound as disclosed herein is a compound of Formula (Ia), (Ib), (IIa), (IIb), (IIIa), (IIIb), (IVa), or (IVb), for example a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or pharmaceutically acceptable form thereof, is a farnesyltransferase inhibitor. In some embodiments, the compound as disclosed herein is a compound of Formula (III-3), (IIIa-3), (IIIb-3), (Va), (Vb), (V-1), (Va-1), (Vb-1), (VIa), (VIb), (VIa-1), or (VIb-1), or a pharmaceutically acceptable form thereof, is a farnesyltransferase inhibitor. In certain embodiments, the compound, or pharmaceutically acceptable form thereof, as disclosed herein, is a selective farnesyltransferase inhibitor, relative to inhibition of geranylgeranyl transferase type-1, such as geranylgeranyl transferase type-1.

In some embodiments, provided herein is a method of inhibiting a farnesyltransferase, comprising contacting the farnesyltransferase with an effective amount of the compound of Formula (I), (II), (III), or (IV), as disclosed herein, or pharmaceutically acceptable form thereof. In some embodiments, provided herein is a method of inhibiting a farnesyltransferase, comprising contacting the farnesyltransferase with an effective amount of the compound of Formula (V) or (VI), as disclosed herein, or pharmaceutically acceptable form thereof. In some embodiments, the compound is a compound of Formula (Ia), (Ib), (IIa), (IIb), (IIIa), (IIIb), (IVa), or (IVb), for example a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or pharmaceutically acceptable form thereof. In some embodiments, the compound is a compound of Formula (III-3), (IIIa-3), (IIIb-3), (Va), (Vb), (V-1), (Va-1), (Vb-1), (VIa), (VIb), (VIa-1), or (VIb-1), or a pharmaceutically acceptable form thereof. In some embodiments, the method of inhibiting a farnesyltransferase comprises contacting the farnesyltransferase with an effective amount of a pharmaceutical composition, as disclosed herein, containing the compound of Formula (I), (II), (III), or (IV), or a pharmaceutically acceptable form thereof, and a pharmaceutically acceptable carrier, diluent or excipient. In some embodiments, the method of inhibiting a farnesyltransferase comprises contacting the farnesyltransferase with an effective amount of a pharmaceutical composition, as disclosed herein, containing the compound of Formula (V) or (VI), or a pharmaceutically acceptable form thereof, and a pharmaceutically acceptable carrier, diluent or excipient. In some embodiments, the pharmaceutical composition contains compound of Formula (Ia), (Ib), (IIa), (IIb), (IIIa), (IIIb), (IVa), or (IVb), for example a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or pharmaceutically acceptable form thereof. In some embodiments, the pharmaceutical composition contains compound of Formula (III-3), (IIIa-3), (IIIb-3), (Va), (Vb), (V-1), (Va-1), (Vb-1), (VIa), (VIb), (VIa-1), or (VIb-1), or a pharmaceutically acceptable form thereof. In some embodiments, the contacting of the farnesyltransferase takes place in a cell. In some embodiments, the farnesyltransferase is present in a cell. In some embodiments, the cell is in a subject. In some embodiments, the cell is a mammalian cell. In some embodiments, the cell a human cell. In some embodiments, the subject suffers from a cancer dependent on a farnesylated protein. In some embodiments, the subject is a human.

In some embodiments, the method inhibits farnesylation of H-Ras protein. In some embodiments, the H-Ras protein has a mutation. In some embodiments, the H Ras protein mutation is or comprises a modification in a codon that encodes an amino acid substitution at a specific position selected from G12, G13, Q61, Q22, K117, A146, and any combination thereof, in the corresponding mutant H-Ras protein. In some embodiments, the inhibiting of the farnesylation of the H-Ras protein, such as an H-Ras protein having a mutation, takes place in a cell. In some embodiments, the cell is in a subject. In some embodiments, the cell is a mammalian cell. In some embodiments, the cell a human cell. In some embodiments, the inhibition of the farnesyltransferase present in the cell takes place in a subject suffering from cancer dependent on a farnesylated protein.

In some embodiments, the cancer dependent on a farnesylated protein is a solid tumor. In some embodiments, the cancer dependent on a farnesylated protein is a cancer dependent on one or more farnesylated proteins. In some embodiments, the cancer dependent on a farnesylated protein is dependent on the farnesylated protein(s) for the progression and/or survival of said cancer. In some embodiments, the cancer dependent on a farnesylated protein is a cancer dependent on farnesylated H-Ras protein. In some embodiments, the cancer dependent on a farnesylated protein has an H-Ras protein mutation. In some embodiments, the H Ras protein mutation is or comprises a modification in a codon that encodes an amino acid substitution at a specific position selected from G12, G13, Q61, Q22, K117, A146, and any combination thereof, in the corresponding mutant H-Ras protein. In some embodiments, the cancer dependent on a farnesylated protein is head and neck cancer. In some embodiments, the head and neck cancer is head and neck squamous cell carcinoma (HNSCC). In some embodiments, the head and neck cancer, for example, HNSCC, is dependent on one or more farnesylated proteins, such as dependent on a farnesylated H-Ras protein. In some embodiments, the head and neck cancer, for example, HNSCC, has an H-Ras protein mutation. In some embodiments, the cancer dependent on a farnesylated protein is carcinoma, melanoma, sarcoma, or chronic granulomatous disease. For example, in some embodiments, the cancer dependent on a farnesylated protein is thyroid cancer, head and neck cancers, urothelial cancers, salivary cancers, cancers of the upper digestive tract, bladder cancer, breast cancer, ovarian cancer, brain cancer, gastric cancer, prostate cancer, lung cancer, colon cancer, skin cancer, liver cancer, or pancreatic cancer. In some embodiments, the cancer is Squamous Cell Carcinoma (SCC). For example, in some embodiments, the SCC is head and neck SCC (HNSCC), lung SCC (LSCC), thyroid SCC (TSCC), esophagus SCC (ESCC), bladder SCC (BSCC) or urothelial carcinoma (UC). In some embodiments, the SCC is HNSCC. In some embodiments, the SCC is human papillomavirus (HPV)-negative SCC. In some embodiments, the HNSCC is HPV-negative HNSCC. For example, in some embodiments, the HNSCC is HNSCC of the trachea, HNSCC of the maxilla, HNSCC of the oral cavity. In some embodiments, the SCC, for example, HNSCC, lung SCC, thyroid SCC, esophagus SCC, bladder SCC or urothelial carcinoma, is dependent on one or more farnesylated proteins, such as dependent on a farnesylated H-Ras protein. In some embodiments, the HNSCC is dependent on one or more farnesylated proteins, such as dependent on a farnesylated H-Ras protein. In some embodiments, the SCC, for example, HNSCC, lung SCC, thyroid SCC, esophagus SCC, bladder SCC or urothelial carcinoma, has an H-Ras protein mutation. In some embodiments, the HNSCC has an H-Ras protein mutation. In some embodiments, the subject is a human.

In some embodiments, the method inhibits farnesylation of N-Ras protein. In some embodiments, the N-Ras protein has a mutation. In some embodiments, the N Ras protein mutation is or comprises a modification in a codon that encodes an amino acid substitution at a specific position selected from G12, G13, Q61, Q22, K117, A146, and any combination thereof, in the corresponding mutant N-Ras protein. In some embodiments, the inhibiting of the farnesylation of the N-Ras protein, such as an N-Ras protein having a mutation, takes place in a cell. In some embodiments, the cell is in a subject. In some embodiments, the cell is a mammalian cell. In some embodiments, the cell a human cell. In some embodiments, the inhibition of the farnesyltransferase present in the cell takes place in a subject suffering from cancer dependent on a farnesylated protein. In some embodiments, the cancer dependent on a farnesylated protein is a solid tumor. In some embodiments, the cancer dependent on a farnesylated protein is a cancer dependent on one or more farnesylated proteins. In some embodiments, the cancer dependent on a farnesylated protein is dependent on the farnesylated protein(s) for the progression and/or survival of said cancer. In some embodiments, the cancer dependent on a farnesylated protein is a cancer dependent on farnesylated N-Ras protein. In some embodiments, the cancer dependent on a farnesylated protein has an N-Ras protein mutation. In some embodiments, the N-Ras protein mutation is or comprises a modification in a codon that encodes an amino acid substitution at a specific position selected from G12, G13, Q61, Q22, K117, A146, and any combination thereof, in the corresponding mutant N-Ras protein. In some embodiments, the cancer dependent on a farnesylated protein is melanoma, acute myeloid leukemia (AML), thyroid carcinoma, lung adenocarcinoma, rectal carcinoma, endometrial carcinoma, or colorectal carcinoma. In some embodiments, the melanoma, acute myeloid leukemia (AML), thyroid carcinoma, lung adenocarcinoma, rectal carcinoma, endometrial carcinoma, or colorectal carcinoma is dependent on one or more farnesylated proteins, such as dependent on a farnesylated N-Ras protein. In some embodiments, the melanoma, acute myeloid leukemia (AML), thyroid carcinoma, lung adenocarcinoma, rectal carcinoma, endometrial carcinoma, or colorectal carcinoma has an N-Ras protein mutation. In some embodiments, the subject is a human.

In some embodiments, provided herein is a method of treating cancer dependent on a farnesylated protein in a subject, comprising administering a therapeutically effective amount of the compound of Formula (I), (II), (III), or (IV), as disclosed herein, or pharmaceutically acceptable form thereof, to the subject having cancer dependent on a farnesylated protein. In some embodiments, provided herein is a method of treating cancer dependent on a farnesylated protein in a subject, comprising administering a therapeutically effective amount of the compound of Formula (V) or (VI), as disclosed herein, or pharmaceutically acceptable form thereof, to the subject having cancer dependent on a farnesylated protein. In some embodiments, the compound is a compound of Formula (Ia), (Ib), (IIa), (IIb), (IIIa), (IIIb), (IVa), or (IVb), for example a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or pharmaceutically acceptable form thereof. In some embodiments, the compound is a compound of Formula (III-3), (IIIa-3), (IIIb-3), (Va), (Vb), (V-1), (Va-1), (Vb-1), (VIa), (VIb), (VIa-1), or (VIb-1), or a pharmaceutically acceptable form thereof. In some embodiments, the method of treating cancer dependent on a farnesylated protein in a subject comprises administering a therapeutically effective amount of a pharmaceutical composition, as disclosed herein, containing the compound of Formula (I), (II), (III), or (IV), or a pharmaceutically acceptable form thereof, or of Formula (V) or (VI), or a pharmaceutically acceptable form thereof, and a pharmaceutically acceptable carrier, diluent or excipient, to the subject having cancer dependent on a farnesylated protein. In some embodiments, the pharmaceutical composition contains compound of Formula (Ia), (Ib), (IIa), (IIb), (IIIa), (IIIb), (IVa), or (IVb), for example a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or pharmaceutically acceptable form thereof. In some embodiments, the pharmaceutical composition contains compound of Formula (III-3), (IIIa-3), (IIIb-3), (Va), (Vb), (V-1), (Va-1), (Vb-1), (VIa), (VIb), (VIa-1), or (VIb-1), or a pharmaceutically acceptable form thereof. In some embodiments, the cancer dependent on a farnesylated protein is a solid tumor. In some embodiments, the cancer dependent on a farnesylated protein is a cancer dependent on one or more farnesylated proteins. In some embodiments, the cancer dependent on a farnesylated protein is dependent on the farnesylated protein(s) for the progression and/or survival of said cancer. In some embodiments, the cancer dependent on a farnesylated protein is a cancer dependent on farnesylated H-Ras protein. In some embodiments, the cancer dependent on a farnesylated protein has an H-Ras protein mutation. In some embodiments, the H Ras protein mutation is or comprises a modification in a codon that encodes an amino acid substitution at a specific position selected from G12, G13, Q61, Q22, K117, A146, and any combination thereof, in the corresponding mutant H-Ras protein. In some embodiments, the cancer dependent on a farnesylated protein is head and neck cancer. In some embodiments, wherein the head and neck cancer is head and neck squamous cell carcinoma (HNSCC). In some embodiments, the head and neck cancer, for example, HNSCC, is dependent on one or more farnesylated proteins, such as dependent on a farnesylated H-Ras protein. In some embodiments, the head and neck cancer, for example, HNSCC, has an H-Ras protein mutation. In some embodiments, the cancer dependent on a farnesylated protein is carcinoma, melanoma, sarcoma, or chronic granulomatous disease. For example, in some embodiments, the cancer dependent on a farnesylated protein is thyroid cancer, head and neck cancers, urothelial cancers, salivary cancers, cancers of the upper digestive tract, bladder cancer, breast cancer, ovarian cancer, brain cancer, gastric cancer, prostate cancer, lung cancer, colon cancer, skin cancer, liver cancer, or pancreatic cancer. In some embodiments, the cancer dependent on a farnesylated protein is Squamous Cell Carcinoma (SCC). For example, in some embodiments, the SCC is head and neck SCC (HNSCC), lung SCC (LSCC), thyroid SCC (TSCC), esophagus SCC (ESCC), bladder SCC (BSCC) or urothelial carcinoma (UC). In some embodiments, the SCC is HNSCC. In some embodiments, the SCC is human papillomavirus (HPV)-negative SCC. In some embodiments, the HNSCC is HPV-negative HNSCC. For example, in some embodiments, the HNSCC is HNSCC of the trachea, HNSCC of the maxilla, HNSCC of the oral cavity. In some embodiments, the SCC, for example, HNSCC, lung SCC, thyroid SCC, esophagus SCC, bladder SCC or urothelial carcinoma, is dependent on one or more farnesylated proteins, such as dependent on a farnesylated H-Ras protein. In some embodiments, the HNSCC is dependent on one or more farnesylated proteins, such as dependent on a farnesylated H-Ras protein. In some embodiments, the SCC, for example, HNSCC, lung SCC, thyroid SCC, esophagus SCC, bladder SCC or urothelial carcinoma, has an H-Ras protein mutation. In some embodiments, the HNSCC has an H-Ras protein mutation. In some embodiments, the subject is a human.

In some embodiments, provided herein is a method of treating cancer dependent on a farnesylated protein in a subject, comprising administering a therapeutically effective amount of the compound of Formula (I), (II), (III), or (IV), as disclosed herein, or pharmaceutically acceptable form thereof, to the subject having cancer dependent on a farnesylated protein. In some embodiments, provided herein is a method of treating cancer dependent on a farnesylated protein in a subject, comprising administering a therapeutically effective amount of the compound of Formula (V) or (VI), as disclosed herein, or pharmaceutically acceptable form thereof, to the subject having cancer dependent on a farnesylated protein. In some embodiments, the compound is a compound of Formula (Ia), (Ib), (IIa), (IIb), (IIIa), (IIIb), (IVa), or (IVb), for example a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or pharmaceutically acceptable form thereof. In some embodiments, the compound is a compound of Formula (III-3), (IIIa-3), (IIIb-3), (Va), (Vb), (V-1), (Va-1), (Vb-1), (VIa), (VIb), (VIa-1), or (VIb-1), or a pharmaceutically acceptable form thereof. In some embodiments, the method of treating cancer dependent on a farnesylated protein in a subject comprises administering a therapeutically effective amount of a pharmaceutical composition, as disclosed herein, containing the compound of Formula (I), (II), (III), or (IV), or a pharmaceutically acceptable form thereof, and a pharmaceutically acceptable carrier, diluent or excipient, to the subject having cancer dependent on a farnesylated protein. In some embodiments, the method of treating cancer dependent on a farnesylated protein in a subject comprises administering a therapeutically effective amount of a pharmaceutical composition, as disclosed herein, containing the compound of Formula (V) or (VI), or a pharmaceutically acceptable form thereof, and a pharmaceutically acceptable carrier, diluent or excipient, to the subject having cancer dependent on a farnesylated protein. In some embodiments, the pharmaceutical composition contains compound of Formula (Ia), (Ib), (IIa), (IIb), (IIIa), (IIIb), (IVa), or (IVb), for example a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or pharmaceutically acceptable form thereof. In some embodiments, the pharmaceutical composition contains compound of Formula (III-3), (IIIa-3), (IIIb-3), (Va), (Vb), (V-1), (Va-1), (Vb-1), (VIa), (VIb), (VIa-1), or (VIb-1), or a pharmaceutically acceptable form thereof. In some embodiments, the cancer dependent on a farnesylated protein is a solid tumor. In some embodiments, the cancer dependent on a farnesylated protein is dependent on one or more farnesylated proteins. In some embodiments, the cancer dependent on a farnesylated protein is dependent on the farnesylated protein(s) for the progression and/or survival of said cancer. In some embodiments, the cancer dependent on a farnesylated protein is a cancer dependent on farnesylated N-Ras protein. In some embodiments, the cancer dependent on a farnesylated protein has an N-Ras protein mutation. In some embodiments, the N Ras protein mutation is or comprises a modification in a codon that encodes an amino acid substitution at a specific position selected from G12, G13, Q61, Q22, K117, A146, and any combination thereof, in the corresponding mutant N-Ras protein. In some embodiments, the cancer dependent on a farnesylated protein is melanoma, acute myeloid leukemia (AML), thyroid carcinoma, lung adenocarcinoma, rectal carcinoma, endometrial carcinoma, or colorectal carcinoma. In some embodiments, the melanoma, acute myeloid leukemia (AML), thyroid carcinoma, lung adenocarcinoma, rectal carcinoma, endometrial carcinoma, or colorectal carcinoma is dependent on one or more farnesylated proteins, such as dependent on a farnesylated N-Ras protein. In some embodiments, the melanoma, acute myeloid leukemia (AML), thyroid carcinoma, lung adenocarcinoma, rectal carcinoma, endometrial carcinoma, or colorectal carcinoma has an N-Ras protein mutation. In some embodiments, the subject is a human.

In some embodiments, the method of treating cancer dependent on a farnesylated protein, as disclosed herein, wherein the method further comprises determining the presence or absence of the H-Ras mutation. In some embodiments, the method of treating cancer dependent on a farnesylated protein, as disclosed herein, wherein the method further comprises determining the presence or absence of the N-Ras mutation. In some embodiments, determining the presence or absence of the H-Ras mutation comprises analyzing nucleic acids obtained from a sample from the subject. In some embodiments, determining the presence or absence of the N-Ras mutation comprises analyzing nucleic acids obtained from a sample from the subject. In some embodiments, said sample is a tissue biopsy. In some embodiments, said sample is a tumor biopsy. In some embodiments, the H-Ras mutation or the N-Ras mutation is determined by sequencing, Polymerase Chain Reaction (PCR), DNA microarray, Mass Spectrometry (MS), Single Nucleotide Polymorphism (SNP) assay, denaturing high-performance liquid chromatography (DHPLC), or Restriction Fragment Length Polymorphism (RFLP) assay. In some embodiments, the H-Ras mutation is determined by PCR. In some embodiments, the N-Ras mutation is determined by PCR. In some embodiments, the H-Ras mutation is determined by sequencing. In some embodiments, the N-Ras mutation is determined by sequencing.

In some embodiments, the compound as disclosed herein is a compound of Formula (Ia), (Ib), (IIa), (IIb), (IIIa), (IIIb), (IVa), or (IVb), for example a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or pharmaceutically acceptable form thereof, or of Formula (III-3), (IIIa-3), (IIIb-3), (Va), (Vb), (V-1), (Va-1), (Vb-1), (VIa), (VIb), (VIa-1), or (VIb-1), or a pharmaceutically acceptable form thereof, and is metabolically stable, for example, metabolically stable to liver metabolism in a subject, such as metabolically stable to liver metabolism in a human.

5.3.2 Doses and Regimens

A compound described herein can be delivered in the form of a pharmaceutical composition which comprises a therapeutically effective amount of a compound of any one of Formula (I), (II), (III), or (IV), such as a compound of Formula (Ia), (Ib), (IIa), (IIb), (IIIa), (IIIb), (IVa), or (IVb), or a pharmaceutically acceptable form thereof, or a compound of Formula (V) or (VI), such as a compound of Formula (Va), (Vb), (VIa), or (VIb), or a pharmaceutically acceptable form thereof, and a pharmaceutically acceptable carrier, diluent or excipient. In some embodiments, the pharmaceutical composition comprises a therapeutically effective amount of a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or pharmaceutically acceptable form thereof, or a compound of Formula (III-3), (IIIa-3), (IIIb-3), (V-1), (Va-1), (Vb-1), (VIa-1), or (VIb-1), or a pharmaceutically acceptable form thereof. The pharmaceutical compositions disclosed herein are intended to be administered by a suitable route, including but not limited to orally, parenterally, rectally, topically and locally. In some embodiments, a selected dosage level will depend upon a variety of factors including, for example, the activity of the particular compound employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts A suitable daily dose of a compound described herein administered to a subject will be that amount of the compound which, in some embodiments, can be the lowest dose effective to produce a therapeutic effect. Such an effective dose will generally depend upon the factors described herein. In some embodiments, a therapeutically effective amount of the compound of any one of Formula (I), (II), (III), or (IV), such as a compound of Formula (Ia), (Ib), (IIa), (IIb), (IIIa), (IIIb), (IVa), or (IVb), or pharmaceutically acceptable form thereof, or a compound of Formula (V) or (VI), such as a compound of Formula (Va), (Vb), (VIa), or (VIb), or a pharmaceutically acceptable form thereof, as the active ingredient, is in an amount of from about 0.01 up to about 500 mg/kg daily, either as a single dose or subdivided into more than one dose, or more particularly in an amount of from about 0.01 to about 400 mg/kg daily, such as in an amount of from about 0.01 to about 300 mg/kg daily, about 0.01 to about 200 mg/kg daily, about 0.01 to 100 mg/kg daily, about 0.01 to about 50 mg/kg daily, about 0.01 to about 25 mg/kg daily, or about 0.01 to about 10 mg/kg daily, such as in an amount of about 0.01 mg/kg daily, about 0.025 mg/kg daily, about 0.05 mg/kg daily, about 0.075 mg/kg daily, about 0.1 mg/kg daily, about 0.25 mg/kg daily, about 0.5 mg/kg daily, about 0.75 mg/kg daily, about 1 mg/kg daily, about 2.5 mg/kg daily, about 5 mg/kg daily, about 7.5 mg/kg daily, about 10 mg/kg daily, about 15 mg/kg daily, about 20 mg/kg daily, about 25 mg/kg daily, about 50 mg/kg daily, about 75 mg/kg daily, about 100 mg/kg daily, about 100 mg/kg daily, about 200 mg/kg daily, about 300 mg/kg daily, about 400 mg/kg daily, or about 500 mg/kg daily. For example, in some embodiments, the dosage or therapeutically effective amount of the compound, or pharmaceutically acceptable form thereof, disclosed herein, is in an amount of from about 0.01 to about 25 mg/kg daily, about 0.01 to about 20 mg/kg daily, about 0.01 to about 15 mg/kg daily, about 0.01 to about 10 mg/kg daily, about 0.01 to about 7.5 mg/kg daily, about 0.01 to about 5 mg/kg daily, or about 0.01 to about 2.5 mg/kg daily, such as in an amount of about 0.01 mg/kg daily, about 0.025 mg/kg daily, about 0.05 mg/kg daily, about 0.075 mg/kg daily, about 0.1 mg/kg daily, about 0.25 mg/kg daily, about 0.5 mg/kg daily, about 0.75 mg/kg daily, about 1 mg/kg daily, about 2.5 mg/kg daily, about 5 mg/kg daily, about 7.5 mg/kg daily, about 10 mg/kg daily, about 15 mg/kg daily, about 20 mg/kg daily. In some embodiments, the compound is a compound of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or pharmaceutically acceptable form thereof, or a compound of Formula (III-3), (IIIa-3), (IIIb-3), (V-1), (Va-1), (Vb-1), (VIa-1), or (VIb-1), or a pharmaceutically acceptable form thereof. In some embodiments, the therapeutically effective amount of the compound of any one of Formula (I), (II), (III), or (IV), for example a compound of Formula (Ia), (Ib), (IIa), (IIb), (IIIa), (IIIb), (IVa), or (IVb), or pharmaceutically acceptable form thereof, or a compound of Formula (V) or (VI), such as a compound of Formula (Va), (Vb), (VIa), or (VIb), or a pharmaceutically acceptable form thereof, is contained in a pharmaceutical composition as described herein. In some embodiments, the therapeutically effective amount of the compound of any one of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or pharmaceutically acceptable form thereof, or a compound of Formula (III-3), (IIIa-3), (IIIb-3), (V-1), (Va-1), (Vb-1), (VIa-1), or (VIb-1), or a pharmaceutically acceptable form thereof, is contained in a pharmaceutical composition as described herein. Actual dosage levels of the active ingredients in the pharmaceutical compositions described herein can be varied so as to obtain an amount of the active ingredient which is effective to achieve the desired therapeutic response for a particular subject, such as a human patient, composition, and mode of administration, without being toxic to the subject. In some instances, dosage levels below the lower limit of the aforesaid range can be more than adequate, while in other cases still larger doses can be employed without causing any harmful side effect, e.g., by dividing such larger doses into several small doses for administration throughout the day. Dosages may reflect the amount of compound, or the amount of compound in a particular pharmaceutical form, or the free form equivalent of the particular pharmaceutical form.

In some embodiments, the treatment with a compound of any one of Formula (I), (II), (III), or (IV), for example a compound of Formula (Ia), (Ib), (IIa), (IIb), (IIIa), (IIIb), (IVa), or (IVb), or a pharmaceutically acceptable form thereof, or a compound of Formula (V) or (VI), such as a compound of Formula (Va), (Vb), (VIa), or (VIb), or a pharmaceutically acceptable form thereof, is administered in combination with radiotherapy, or radiation therapy. In some embodiments, the treatment with a compound of any one of Formula (II-1), (II-2), (III-1), (III-2), (IV-1), or (IV-2), such as Formula (IIa-1), (IIb-1), (IIa-2), (IIb-2), (IIIa-1), (IIIb-1), (IIIa-2), (IIIb-2), (IVa-1), (IVb-1), (IVa-2), or (IVb-2), or a pharmaceutically acceptable form thereof, or a compound of Formula (III-3), (IIIa-3), (IIIb-3), (V-1), (Va-1), (Vb-1), (VIa-1), or (VIb-1), or a pharmaceutically acceptable form thereof, is administered in combination with radiotherapy, or radiation therapy.

It is understood that subheadings throughout this document do not limit the subject matter discussed to only those sections, but apply, and are contemplated to apply, to each embodiment disclosed in the instant application.

It is understood that modifications which do not substantially affect the activity of the various embodiments of this invention are also provided within the definition of the invention provided herein. Accordingly, the following examples are intended to illustrate but not limit the present invention. The disclosed compounds herein, including exemplified compounds and intermediate compounds, were named using ChemDraw® version 18.1.4.4 or later. All of the references cited to herein are incorporated by reference in their entireties.

6. Examples

Abbreviations

ACN: Acetonitrile
AIBN: Azobisisobutyronitrile
BTEAC: Benzyltriethylammonium chloride
$Cu(OAc)_2$: Cupric acetate
DCE: 1,2-Dichloroethane
DCM: Dichloromethane
DEA: Diethylamine
DEAD: Diethyl azodicarboxylate
DIAD: Diisopropyl azodicarboxylate
DIBAL-H: Diisobutylaluminium hydride
DIPEA: N,N-Diisopropylethylamine
DMA: Dimethylacetamide
DMF: Dimethylformamide
DMI: 1,3-Dimethyl-2-imidazolidinone
DMSO: Dimethyl sulfoxide
DPPF: 1,1'-Bis(diphenylphosphino)ferrocene
$Et_3SiCl$: Chlorotriethylsilane
EtOAc: Ethyl acetate
EtOH: Ethanol
HATU: 1-[Bis(dimethylamino)methylene]-1H-1,2,3-triazolo[4,5-b]pyridinium 3-oxide hexafluorophosphate
MeOH: Methanol
NaOMe: Sodium methoxide
NBS: N-Bromosuccinimide
n-BuLi: n-Butyllithium
PCC: Pyridinium chlorochromate
$Pd(Ph_3)_4$: Tetrakis(triphenylphosphine)palladium(O)
$Pd_2(dba)_3$: Tris(dibenzylideneacetone)dipalladium(O)
$PPh_3$: Triphenylphosphine
SFC: Supercritical fluid chromatography
$T_3P$: Propanephosphonic acid anhydride
TBAF: Tetra-n-butylammonium fluoride
t-BuOK: Potassium tert-butoxide
TEA: Triethylamine
TFA: Trifluoroacetic acid
THF: Tetrahydrofuran
TIPSCl: Triisopropylsilyl chloride
TMEDA: Tetramethylethylenediamine LCMS Conditions:

Each LCMS conditions were conducted on instrument SHIMADZU LC20-MS2020 (except where indicated), at an oven temperature of 50° C., with an ESI mass spectrometry ionization, monitored at wavelengths 220 nm and 254 nm. It is understood that the molecular formula listed with the ESI calculated is the molecular formula of the detected ion (e.g., $[M+H]^+$). For example, the molecular formula of compound 1A-1 is $C_{17}H_{12}BrNO$ (i.e., [M]), while the molecular formula listed with the ESI calculated is the molecular formula of the detected ion, $C_{17}H_{13}BrNO$ (i.e., $[M+H]^+$).

The acidic LCMS methods are referred to with "AB" notation. Each of the acidic LCMS methods utilized a Xtimate C18 2.1×30 mm (3 μm particle size) column (except where indicated), mobile phase A (water (4 L) and TFA (1.5 mL)), and mobile phase B (ACN (4 L) and TFA (0.75 mL)) (except where indicated). The conditions for each of the acidic LCMS methods utilized includes the following: (1) 1.5 min method 5-95AB refers to using MERCK, RP-18e, 25×2 mm column, with a gradient starting at 5% B and ending at 95% B, over a total time of 1.5 min. and at a flow rate of 1.5 mL/min.; (2) 4.0 min method 0-60AB was conducted on instrument SHIMADZU LC20-MS2010 and refers to using a gradient starting at 0% B and ending at 60% B, over a total time of 4 min. and at a flow rate of 0.8 mL/min.; (3) 2.0 min method 10-80AB refers to using mobile phase A (water (4 L) and TFA (1.5 mL)) and B (ACN) and a gradient starting at 10% B and ending at 80% B, over a total time of 2 min. and at a flow rate of 1.2 mL/min.; (4) 3.0 min method 10-80AB refers to using mobile phase A (water (4 L) and TFA (1.5 mL)) and B (ACN) and a gradient starting at 10% B and ending at 80% B, over a total time of 3 min. and at a flow rate of 0.8 mL/min.; (5) 4.0 min method 10-80AB refers to using mobile phase A (water (4 L) and TFA (1.5 mL)) and B (ACN) and a gradient starting at 10% B and ending at 80% B, over a total time of 4 min. and at a flow rate of 0.8 mL/min.; and (6) 7.0 min method 10-80AB was conducted on instrument SHIMADZU LC20-MS2010 and refers to using a gradient starting at 10% B and ending at 80% B, over a total time of 7 min. and at a flow rate of 0.8 mL/min.

The basic LCMS methods are referred to with "CD" notation. Each of the basic LCMS methods utilized a Titank C18 2.1×50 mm (5 μm particle size) column, mobile phase A (water (4 L) and ammonium hydroxide (0.8 mL)), and mobile phase B (ACN). The conditions for each of the basic LCMS methods utilized includes the following: (1) 3.0 min method 10-80CD refers to a gradient starting at 10% B and ending at 80% B, over a total time of 3 min. and at a flow rate of 1.0 mL/min.; (2) 7.0 min method 10-80CD refers to a gradient starting at 10% B and ending at 80% B, over a total time of 7 min. and at a flow rate of 0.8 mL/min.; and (3) 3.0 min method 30-90CD refers to a gradient starting at 30% B and ending at 90% B, over a total time of 3 min. and at a flow rate of 1.0 mL/min.

SFC Chiral HPLC Conditions:

Each SFC Chiral HPLC methods was conducted on either (1) Waters UPCC with PDA detector and QDa detector or (2) Agilent 1260 with DAD detector.

"(SS)Whelk-O1_EtOH(DEA)_60" refers to using a (SS) Whelk-01 chiral column (10 cm column length), with $CO_2$ (mobile phase A) and ethanol having 0.05% f diethylamine (v/v) (mobile phase B), and using 60% B over a total time of 6 min. at a flow rate of 2.5 mL/min.

"OD_ETOH_DEA_40_2.8ML_10CM" refers to using a Chiralcel OD-3 chiral column (10 cm column length), with $CO_2$ (mobile phase A) and ethanol having 0.05% f diethylamine (v/v) (mobile phase B), and using 40% B over a total time of 10 min. at a flow rate of 2.8 mL/min.

"(SS)Whelk-01_MeOH(DEA)_40" refers to using a (SS) Whelk-O1 chiral column (10 cm column length), with $CO_2$ (mobile phase A) and methanol having 0.05% f diethylamine (v/v) (mobile phase B), and using 40% B over a total time of 10 min. at a flow rate of 2.5 mL/min.

"OD_3_EtOH_DEA_40_2.5ML" refers to using a Chiralcel OD-3 chiral column (15 cm column length), with $CO_2$ (mobile phase A) and ethanol having 0.05% f diethylamine (v/v) (mobile phase B), and using 40% B over a total time of 14 min. at a flow rate of 2.5 mL/min.

"AD_IPA_DEA_40_4ML_5CM" refers to using a Chiralpak AD-3 chiral column (5 cm column length), with $CO_2$ (mobile phase A) and isopropanol having 0.05% f diethylamine (v/v) (mobile phase B), and using 40% B over a total time of 2.5 min. at a flow rate of 4 mL/min.

"AD_ETOH_DEA_5_40_4ML_4MIN_5CM" refers to using a Chiralpak AD-3 chiral column (5 cm column length), with $CO_2$ (mobile phase A) and ethanol having 0.05% f diethylamine (v/v) (mobile phase B), and using a 5% B to 40% B gradient over a total time of 4 min. at a flow rate of 4 mL/min.

"AD_ETOH_DEA_40_4ML_5CM" refers to using a Chiralpak AD-3 chiral column (5 cm column length), with $CO_2$ (mobile phase A) and ethanol having 0.05% f diethylamine (v/v) (mobile phase B), and using 40% B over a total time of 2.5 min. at a flow rate of 4 mL/min.

"IG_ETOH_DEA_40_4ML_5CM" refers to using a Chiralpak IG-3 chiral column (5 cm column length), with $CO_2$ (mobile phase A) and ethanol having 0.05% f diethylamine (v/v) (mobile phase B), and using 40% B over a total time of 2 min. at a flow rate of 4 mL/min.

"OD_ETOH_DEA_40_4ML_5CM" refers to using a Chiralcel OD-3 chiral column (5 cm column length), with $CO_2$ (mobile phase A) and ethanol having 0.05% f diethylamine (v/v) (mobile phase B), and using 40% B over a total time of 2 min. at a flow rate of 4 mL/min.

"AD-3_EtOH(DEA)_5_40_2.5ML" refers to using a Chiralpak AD-3 chiral column (15 cm column length), with $CO_2$ (mobile phase A) and ethanol having 0.05% f diethylamine (v/v) (mobile phase B), and using a 5% B to 40% B gradient over a total time of 10 min. at a flow rate of 2.5 mL/min.

"AD_3_IPA_DEA_40_2.5ML" refers to using a Chiralpak AD-3 chiral column (15 cm column length), with $C_{O2}$ (mobile phase A) and isopropanol having 0.05% f diethylamine (v/v) (mobile phase B), and using 40% B over a total time of 9 min. at a flow rate of 2.5 mL/min.

"IG_3_EtOH_DEA_40_28ML" refers to using "Chiralpak IG-3" chiral column (10 cm column length), with $C_{O2}$ (mobile phase A) and ethanol (having 0.05% f diethylamine (v/v) (mobile phase B), using a 40% B over a total time of 8 min, and at a flow rate of 2.8 mL/min.

"OJ_MEOH_DEA_5_40_28ML_8MIN" using "Chiralcel OJ-3" chiral column (10 cm column length), with $C_{O2}$ (mobile phase A) and methanol (having 0.05% f diethylamine (v/v) (mobile phase B), using a 5% B to 40% B gradient over a total time of 8 min, and at a flow rate of 2.8 mL/min.

6.1 Synthetic Examples

Preparation of Intermediate Compounds

Example 1A: Preparation of Intermediate 1A

Scheme 1A—Synthesis of Intermediate 1A

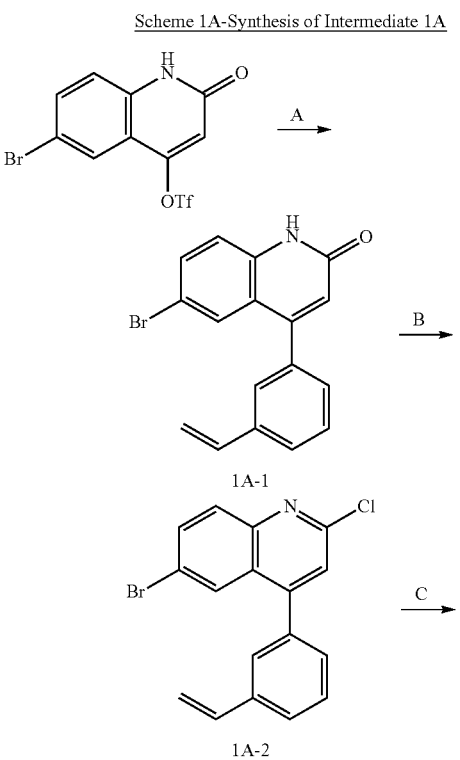

Step A: Preparation of (1A-1)

To a solution of 6-bromo-2-oxo-1,2-dihydroquinolin-4-yl trifluoromethanesulfonate (10 g, 26.87 mmol) in dioxane (300 mL) was added (3-vinylphenyl)boronic acid (3.98 g, 26.87 mmol) and TEA (8.16 g, 80.62 mmol, 11.22 mL). Pd(PPh$_3$)$_4$ (1.55 g, 1.34 mmol) was added to the mixture under N$_2$. The reaction was stirred at 100° C. for 8 h under N$_2$. The solvent was removed under reduced pressure. The mixture was blended with another batch prepared from 10 g of 6-bromo-2-oxo-1,2-dihydroquinolin-4-yl trifluoromethanesulfonate. The mixture was diluted with water (200 mL) and MeOH/DCM=1:10 (200 mL). The mixture was extracted with MeOH/DCM=1:10 (200 mL×3). The organic layer was separated and dried over Na$_2$SO$_4$ and concentrated. The crude product was triturated from EtOAc (100 mL) at 25° C. for 30 min to give 1A-1 (17 g, 52.12 mmol, 97.01% yield) as a white solid. $^1$H NMR (400 MHz, DMSO-d$_6$) δ=12.04 (s, 1H), 7.71-7.64 (m, 2H), 7.57-7.54 (m, 2H), 7.39-7.35 (m, 3H), 6.84-6.79 (m, 1H), 6.48 (s, 1H), 5.96 (d, J=17.6 Hz, 1H), 5.35 (d, J=11.2 Hz, 1H). LCMS Rt=0.86 min in 1.5 min chromatography, 5-95AB, ESI calcd. for C$_{17}$H$_{13}$BrNO [M+H]$^+$ 326.0, found 325.9.

Step B: Preparation of (1A-2)

A solution of 1A-1 (17 g, 52.12 mmol) in POCl$_3$ (226.14 g, 1.47 mol, 137.05 mL) was heated at 100° C. for 16 h. POCl$_3$ was removed under reduced pressure. The residue was diluted with water (500 mL) and EtOAc (500 mL). The mixture was extracted with EtOAc (500 mL×3). The organic layer was concentrated to dryness. The crude product was purified by flash chromatography on silica gel (EtOAc in petroleum ether=0 to 5%) to give 1A-2 (15 g, 43.52 mmol, 83.04% yield) as a light yellow solid. $^1$H NMR (400 MHz, CDCl$_3$) δ=8.00-7.96 (m, 2H), 7.83 (d, J=9.2 Hz, 1H), 7.59-7.53 (m, 3H), 7.48-7.27 (m, 2H), 6.84-6.77 (m, 1H), 5.86 (d, J=17.6 Hz, 1H), 5.38 (d, J=10.8 Hz, 1H). LCMS R$_t$=1.05 min in 1.5 min chromatography, 5-95AB, ESI calcd. for C$_{17}$H$_{12}$BrClN [M+H]$^+$ 344.0, found 343.7.

Step C. Preparation of 6-bromo-2-methoxy-4-(3-vinylphenyl)quinoline (1A)

To a solution of 1A-2 (15 g, 43.52 mmol) in MeOH (150 mL) and THF (150 mL) was added NaOMe (11.76 g, 217.62 mmol). The reaction was stirred at 80° C. for 16 h under N$_2$. The solvents were removed under reduced pressure to give a crude which was diluted with water (300 mL) and EtOAc (300 mL). The mixture was extracted with EtOAc (300 mL×3). The organic layer was separated and dried over anhydrous Na$_2$SO$_4$ and concentrated under reduced pressure. The crude product was purified by flash chromatography on silica gel (EtOAc in Petroleum ether=0 to 5%) to give 1A (9 g, 26.45 mmol, 60.78% yield) as a yellow oil. $^1$H NMR (400 MHz, CDCl$_3$) δ=7.87-7.86 (m, 1H), 7.80-7.78 (m, 1H), 7.71 (d, J=2.0 Hz, 1H), 7.55-7.49 (m, 3H), 7.47-7.27 (m, 1H), 6.88 (s, 1H), 6.81-6.76 (m, 1H), 5.84 (d, J=17.6 Hz, 1H), 5.35 (d, J=11.2 Hz, 1H), 4.10 (s, 3H). LCMS R$_t$=1.08 min in 1.5 min chromatography, 5-95AB, ESI calcd. for C$_{18}$H$_{15}$BrNO [M+H]$^+$ 340.0, found 339.9.

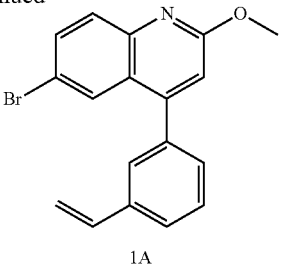

1A

Example 2A: Preparation of Intermediate 2A

Scheme 2A-Synthesis of Intermediate 2A

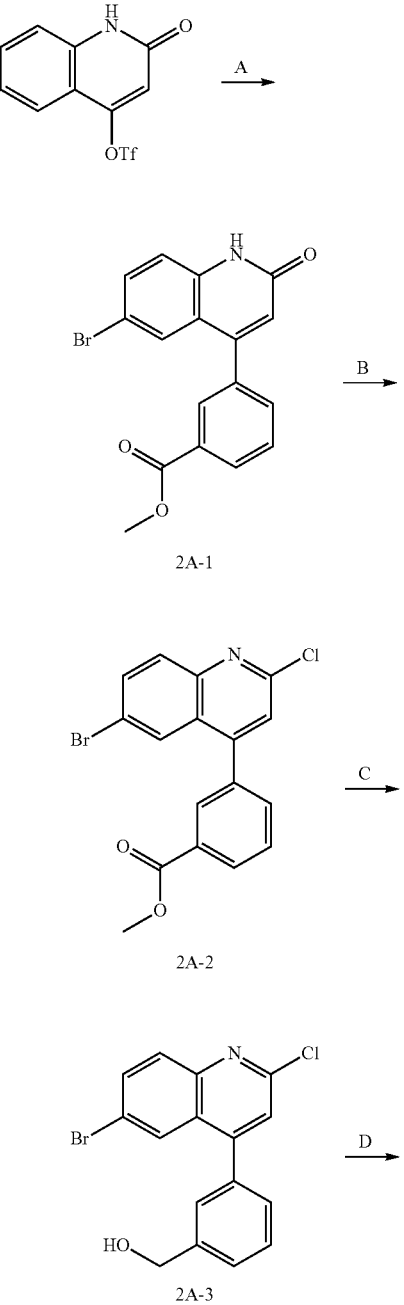

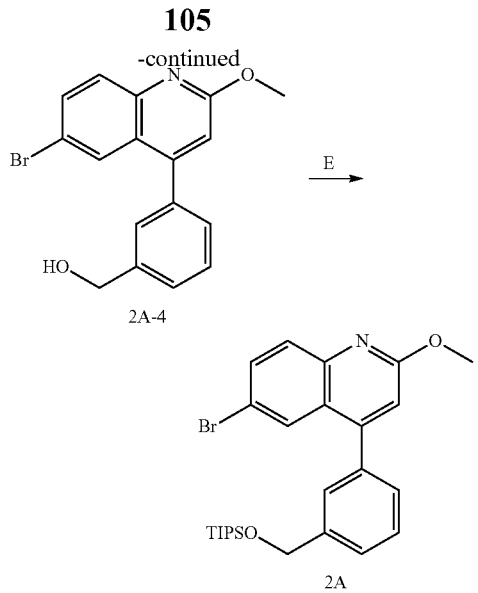

Step A: Preparation of (2A-1)

To a solution of 6-bromo-2-oxo-1,2-dihydroquinolin-4-yl trifluoromethanesulfonate (30 g, 80.62 mmol) and (3-(methoxycarbonyl)phenyl)boronic acid (14.51 g, 80.62 mmol) in dioxane (600 mL) was added Pd(PPh₃)₄ (4.66 g, 4.03 mmol) and TEA (24.47 g, 241.86 mmol, 33.66 mL). The reaction mixture was stirred at 100° C. under N₂ for 8 h. The reaction mixture was concentrated and the residue was triturated with EtOAc (100 mL) to give 2A-1 (27.4 g, 76.50 mmol, 94.89% yield) as a white solid. ¹H NMR (400 MHz, DMSO-d₆) δ=12.08 (s, 1H), 8.11 (d, J=7.6 Hz, 1H), 7.82-7.69 (m, 3H), 7.41-7.31 (m, 3H), 6.54-6.50 (m, 1H), 3.88 (s, 3H).

Step B: Preparation of (2A-2)

A mixture of 2A-1 (75 g, 209.39 mmol) in POCl₃ (300 mL) was stirred at 100° C. for 1 h. The solvent was removed under reduced pressure. The residue was dissolved in DCM (1500 mL) and adjusted pH=7-8 with the saturated NaHCO₃ solution. The organic layer was separated and washed with brine (300 mL), dried over anhydrous Na₂SO₄, filtered and concentrated. The residue was purified by flash chromatography on silica gel (EtOAc in DCM=0 to 30%) to give 2A-2 (70 g, 185.86 mmol, 88.76% yield) as a white solid. ¹H NMR (400 MHz, DMSO-d₆) δ=8.15 (d, J=7.6 Hz, 1H), 8.08 (d, J=1.2 Hz, 1H), 8.01 (s, 2H), 7.89-7.86 (m, 1H), 7.83 (s, 1H), 7.79 (t, J=7.6 Hz, 1H), 7.77 (s, 1H), 3.89 (s, 3H).

Step C: Preparation of (2A-3)

To a mixture of 2A-2 (24 g, 63.72 mmol) in THF (200 mL) was added DIBAL-H (1M in toluene, 140.19 mmol, 140.19 mL) at −78° C. and the reaction mixture was stirred at 25° C. for 1 h. The reaction mixture was added to saturated potassium sodium tartrate solution (200 mL) and the mixture was stirred for 16 h. The mixture was extracted with EtOAc (300 mL×3) and the combined organic layer was washed with brine (200 mL), dried over anhydrous Na₂SO₄, filtered and concentrated to give 2A-3 (22 g, 63.11 mmol, 99.04% yield) as an off-white solid. ¹H NMR (400 MHz, DMSO-d₆) δ=7.99 (s, 2H), 7.91 (s, 1H), 7.60-7.49 (m, 4H), 7.44 (d, J=7.2 Hz, 1H), 5.36 (t, J=6.0 Hz, 1H), 4.62 (d, J=6.0 Hz, 2H).

Step D: Preparation of (2A-4)

To a mixture of 2A-3 (500 mg, 1.43 mmol) in MeOH (5 mL) and THF (5 mL) was added NaOMe (154.96 mg, 2.87 mmol) and the reaction mixture was stirred at 80° C. for 1 h. The reaction mixture was added to water (20 mL), and HCl (5M in H₂O) was added to the mixture to adjust pH=7. The mixture was extracted with EtOAc (20 mL×2). The combined organic layer was washed with brine (50 mL), dried over anhydrous Na₂SO₄, filtered and concentrated to give 2A-4 (478 mg, 1.39 mmol, 97.20% yield) as a yellow solid. ¹H NMR (400 MHz, DMSO-d₆) δ=7.82 (s, 2H), 7.76 (s, 1H), 7.58-7.48 (m, 2H), 7.45 (s, 1H), 7.39 (d, J=7.2 Hz, 1H), 6.98 (s, 1H), 5.33 (t, J=5.6 Hz, 1H), 4.62 (d, J=5.6 Hz, 2H), 4.03 (s, 3H).

Step E: Preparation of 6-bromo-2-methoxy-4-(3-(((triisopropylsilyl)oxy)methyl) phenyl)quinoline (2A)

A solution of 2A-4 (12 g, 34.86 mmol), TIPSCl (6.05 g, 31.38 mmol, 6.71 mL) and imidazole (5.93 g, 87.16 mmol) in DCM (100 mL) was stirred at 25° C. for 1 h. The reaction mixture was added into water (100 mL) and extracted with EtOAc (100 mL×2). The combined organic layer was washed with brine (100 mL), dried over anhydrous Na₂SO₄ and concentrated. The residue was purified by flash chromatography on silica gel (EtOAc in petroleum ether=0 to 5%) to give 2A (13 g, 25.97 mmol, 74.50% yield). ¹H NMR (400 MHz, DMSO-d₆) δ=7.86 (d, J=2.0 Hz, 1H), 7.76 (d, J=8.8 Hz, 1H), 7.67 (dd, J=2.0 Hz, J=8.8 Hz, 1H), 7.47 (d, J=8.8 Hz, 2H), 7.43 (s, 1H), 7.34-7.29 (m, 1H), 6.84 (s, 1H), 4.91 (s, 2H), 4.08 (s, 3H), 1.23-1.13 (m, 3H), 1.11-1.07 (m, 18H).

Example 3A: Preparation of Intermediate 3A

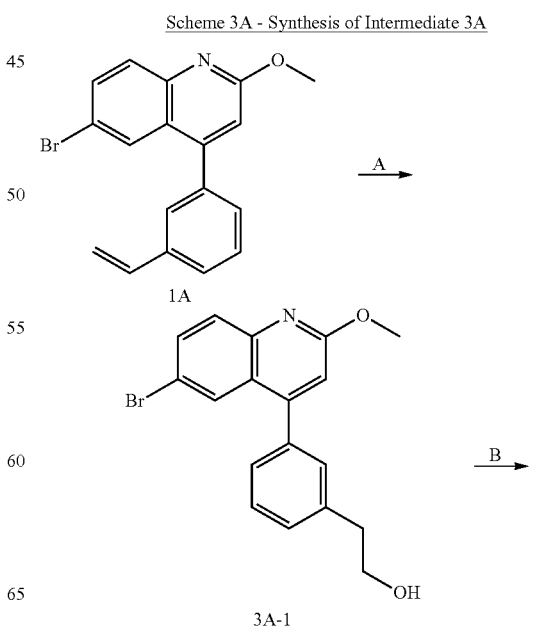

Scheme 3A - Synthesis of Intermediate 3A

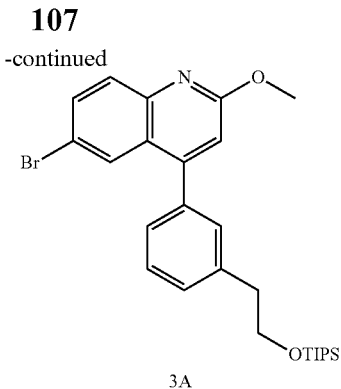

3A

Step A: Preparation of (3A-1)

To a solution of 1A (5 g, 14.70 mmol) in THF (50 mL) was added 9,9'-dibora-9,9'-bi(bicyclo[3.3.1]nonane) (5.34 g, 22.05 mmol) and the mixture was stirred at 20° C. for 12 h. EtOH (5 mL) was added to the above mixture. $H_2O_2$ (16.66 g, 146.97 mmol, 14.12 mL, 30% purity) was added to the above mixture, followed by NaOH (5M in $H_2O$, 29.39 mL) at 0° C. The resulting mixture was stirred at 80° C. for 30 min. After cooling to r.t., saturated $Na_2SO_3$ solution (100 mL) was added to the mixture and extracted with EtOAc (100 mL×2). The combined organic phase was washed with brine (100 mL), dried over anhydrous $Na_2SO_4$, filtered and concentrated. The crude was purified by flash chromatography on silica gel (EtOAc in petroleum ether=0 to 20%) to give 3A-1 (3.6 g, 10.05 mmol, 68.37% yield) as light yellow oil. $^1H$ NMR (400 MHz, $CD_3CN$) δ=7.83 (d, J=1.2 Hz, 1H), 7.73-7.66 (m, 2H), 7.47-7.41 (m, 1H), 7.40-7.32 (m, 2H), 7.31-7.26 (m, 1H), 6.87 (s, 1H), 4.02 (s, 3H), 3.80-3.73 (m, 2H), 2.85 (t, J=6.8 Hz, 2H), 2.79 (t, J=5.6 Hz, 1H).

Step B: Preparation of 6-bromo-2-methoxy-4-(3-(2-((triisopropylsilyl)oxy)ethyl) phenyl)quinoline (3A)

To a mixture of 3A-1 (3.6 g, 10.05 mmol) and imidazole (1.37 g, 20.10 mmol) in DMF (40 mL) was added TIPSCl (2.13 g, 11.05 mmol, 2.37 mL) dropwise at 0° C. and the mixture was stirred at 20° C. for 12 h. Water (100 mL) was added to the mixture and the mixture was extracted with EtOAc (150 mL×2). The combined organic phase was washed with brine (100 mL), dried over anhydrous $Na_2SO_4$, filtered and concentrated. The crude was purified by flash chromatography on silica gel (EtOAc in petroleum ether=0 to 10%) to give 3A (4.2 g, 8.16 mmol, 81.20% yield) as a colorless oil. $^1H$ NMR (400 MHz, $CDCl_3$) δ=7.85 (d, J=2.4 Hz, 1H), 7.75 (d, J=8.8 Hz, 1H), 7.68-7.63 (m, 1H), 7.44-7.38 (m, 1H), 7.37-7.32 (m, 1H), 7.30-7.25 (m, 2H), 6.83 (s, 1H), 4.07 (s, 3H), 3.93 (t, J=6.8 Hz, 2H), 2.92 (t, J=6.8 Hz, 2H), 1.10-1.04 (m, 3H), 1.01-0.98 (m, 18H).

Example 4A: Preparation of Intermediate 4A

Scheme 4A - Synthesis of Intermediate 4A

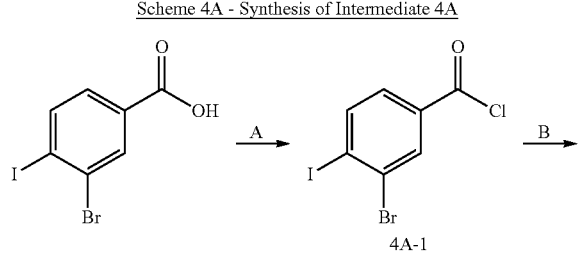

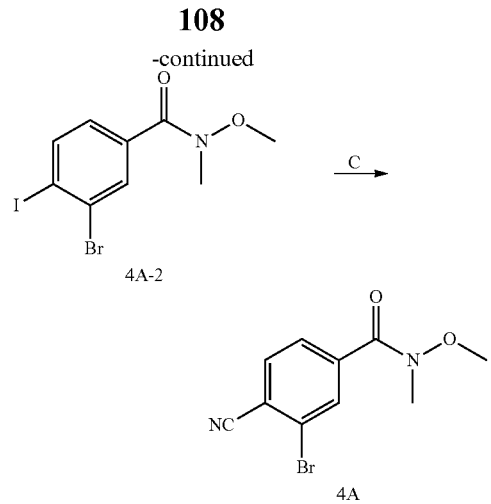

Step A: Preparation of (4A-1)

A solution of 3-bromo-4-iodobenzoic acid (50 g, 152.95 mmol) in $SOCl_2$ (200 mL) was warmed up to 80° C. and keep stirring for 16 h. The reaction mixture was blended with another batch prepared from 3-bromo-4-iodobenzoic acid (50 g, 152.95 mmol). The mixture was concentrated under reduced pressure to give 4A-1 (105 g, 304.03 mmol, 99.39% yield) as yellow solid, which was directly used for next step without purification.

Step B: Preparation of (4A-2)

To a solution of N,O-dimethylhydroxylamine hydrogen chloride (38.55 g, 395.24 mmol) in DCM (300 mL) was added TEA (153.82 g, 1.52 mol, 211.59 mL). A mixture of 4A-1 (105 g, 304.03 mmol) in DCM (300 mL) was added slowly into the above mixture. The mixture was stirred at 25° C. for 16 h. The residue was poured into $H_2O$ (300 mL) and stirred for 20 min. The aqueous phase was extracted with DCM (400 mL×3). The combined organic phase was washed with brine (500 mL×2), dried over anhydrous $Na_2SO_4$, filtered and concentrated under reduced pressure to give 4A-2 (110 g, 297.31 mmol, 97.79% yield) as yellow oil. The crude used directly for the next step. $^1H$ NMR (400 MHz, DMSO-$d_6$) δ=8.02 (d, J=8.0 Hz, 1H), 7.87 (d, J=2.0 Hz, 1H), 7.31 (dd, J=8.0, J=2.0 Hz, 1H), 3.54 (s, 3H), 3.25 (s, 3H). LCMS $R_t$=0.85 min in 1.5 min chromatography, 5-95AB, ESI calcd. for $C_9H_{10}BrINO_2$ [M+H]$^+$ 369.9, found 369.9.

Step C: Preparation of 3-bromo-4-cyano-N-methoxy-N-methylbenzamide (4A)

To a mixture of 4A-2 (55 g, 148.66 mmol) in DMSO (125 mL) was added CuCN (26.63 g, 297.31 mmol, 64.95 mL). The mixture was stirred at 70° C. for 3.5 h and then kept at 90° C. for 1 h. The reaction mixture was poured into $H_2O$ (500 mL), the aqueous layer was extracted with EtOAc (500 mL×2). The combined organic layers were dried over anhydrous $Na_2SO_4$, filtered and the filter cake was washed with EtOAc (200 mL). The combined filtrates were concentrated to give crude product, which was triturated with petroleum ether/EtOAc=3:1 (100 mL) at 25° C. for 30 min to give 4A (28.2 g, 104.80 mmol, 70.50% yield) as an off-white solid. HPLC $R_t$=7.39 min in 15 min chromatography, 220 nm, purity 92.36%.

Example 5A: Preparation of Intermediate 5A

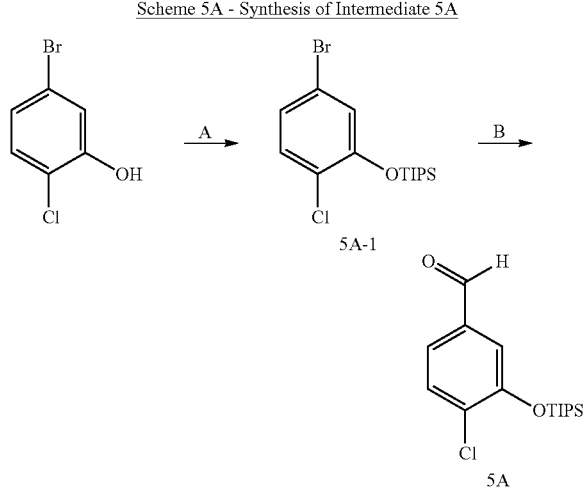

Step A: Preparation of (5A-1)

To a solution of 5-bromo-2-chlorophenol (5 g, 24.10 mmol) in DMF (50 mL) was added NaH (1.45 g, 36.15 mmol, 60% in oil) at 0° C. The mixture was stirred at 0° C. for 30 min. Then TIPSCl (6.97 g, 36.15 mmol, 7.74 mL) was added to the mixture at 0° C. The mixture was stirred at 15° C. for 3.5 h. The mixture was poured into water (500 mL) at 0° C. and stirred at 0° C. for 0.5 h. The aqueous layer was extracted with EtOAc (300 mL×2). The combined organic layers were washed with water (500 mL×2), brine (500 mL×2), dried over anhydrous $Na_2SO_4$, filtered and concentrated. The residue was purified by flash chromatography on silica gel (EtOAc in petroleum ether=0% to 1%) to afford 5A-1 (8.7 g, 23.91 mmol, 99.21% yield) as colorless oil. $^1$H NMR (400 MHz, $CDCl_3$) δ=7.19 (d, J=8.4 Hz, 1H), 7.03 (d, J=2.4 Hz, 1H), 7.00 (dd, J=2.4, 8.4 Hz, 1H), 1.33-1.27 (m, 3H), 1.16-1.10 (m, 18H).

Step B: Preparation of 4-chloro-3-((triisopropylsilyl)oxy)benzaldehyde (5A)

To a solution of 5A-1 (2 g, 5.50 mmol) and TMEDA (830.51 mg, 7.15 mmol, 1.08 mL) in redistillation THF (15 mL) was added n-BuLi (2.5M in n-hexane, 7.15 mmol, 2.86 mL) at −70° C. The mixture was stirred at −70° C. to −20° C. for 1 h. Then DMF (4.02 g, 54.98 mmol, 4.23 mL) was added to the mixture at −70° C. The mixture was stirred at −70° C. for 0.5 h and at 15° C. for 0.5 h. Saturated $NH_4Cl$ solution (100 mL) was added to the mixture at 15° C. The aqueous layer was extracted with EtOAc (80 mL×2). The combined organic layers were washed with water (150 mL×2), brine (150 mL×2), dried over anhydrous $Na_2SO_4$, filtered and concentrated. The residue was purified by flash silica gel chromatography (EtOAc in petroleum ether=0 to 1%) to afford 5A (1 g, 3.20 mmol, 58.18% yield) as colorless oil. $^1$H NMR (400 MHz, $CDCl_3$) δ=9.90 (s, 1H), 7.52 (d, J=8.4 Hz, 1H), 7.41-7.35 (m, 2H), 1.40-1.30 (m, 3H), 1.15-1.10 (m, 18H).

Example 6A: Preparation of Intermediate 6A

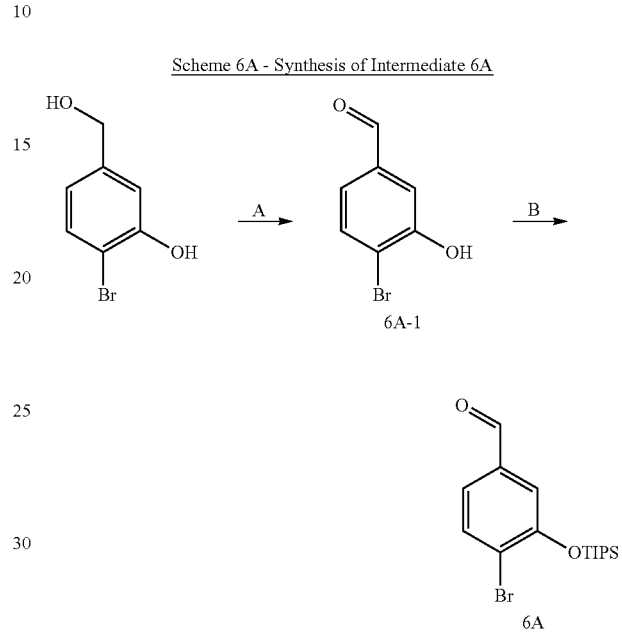

Step A: Preparation of (6A-1)

A mixture of 2-bromo-5-(hydroxymethyl)phenol (10 g, 49.25 mmol) and $MnO_2$ (42.82 g, 492.53 mmol) in DCM (150 mL) was stirred at 40° C. for 12 h. After cooling to r.t., the mixture was filtered through Celite. The cake was washed with MeOH (50 mL×2). The combined organic phase was concentrated to give 6A-1 (5 g, 24.87 mmol, 50.50% yield) as a yellow solid. $^1$H NMR (400 MHz, DMSO-$d_6$) δ=10.85 (s, 1H), 9.89 (s, 1H), 7.73 (d, J=8.0 Hz, 1H), 7.39 (d, J=2.0 Hz, 1H), 7.28 (dd, J=2.0, 8.0 Hz, 1H).

Step B: Preparation of 4-bromo-3-((triisopropylsilyl)oxy)benzaldehyde (6A)

To a mixture of 6A-1 (5 g, 24.87 mmol) and imidazole (5.08 g, 74.62 mmol) in DCM (60 mL) was added TIPSCl (4.80 g, 24.87 mmol, 5.32 mL) and the mixture was stirred at 25° C. for 1 h. Water (150 mL) was added to the mixture and the mixture was extracted with DCM (150 mL×2). The combined organic phase was washed with brine (100 mL), dried over anhydrous $Na_2SO_4$, filtered and concentrated. The crude was purified by flash chromatography on silica gel (EtOAc in petroleum ether=0 to 10%) to give 6A (8.2 g, 22.95 mmol, 92.28% yield) as light yellow oil. $^1$H NMR (400 MHz, $CDCl_3$) δ=9.90 (s, 1H), 7.71 (d, J=8.0 Hz, 1H), 7.35 (s, 1H), 7.30-7.28 (m, 1H), 1.41-1.33 (m, 3H), 1.17-1.13 (m, 18H).

Example 7A: Preparation of Intermediate 7A

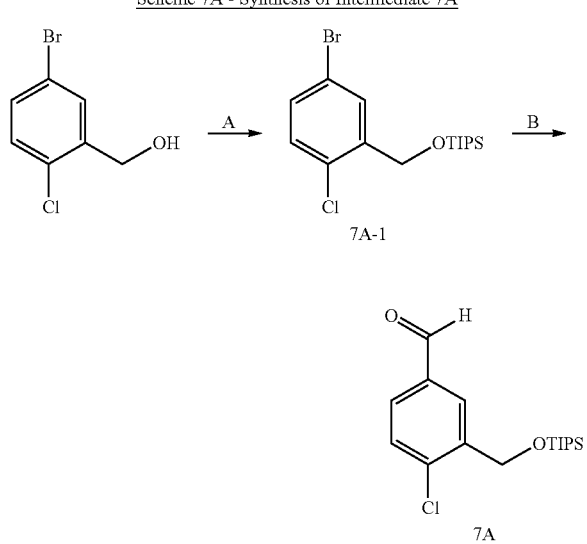

Step A: Preparation of (7A-1)

To a solution of (5-bromo-2-chlorophenyl)methanol (10 g, 45.15 mmol) in DCM (150 mL) was added imidazole (7.68 g, 112.88 mmol) and TIPSCl (9.58 g, 49.67 mmol, 10.63 mL). The reaction mixture was stirred at 25° C. for 16 h. The mixture was washed with water (100 mL). The aqueous layer was extracted with EtOAc (100 mL×2) and the combined organic layers were washed with brine (150 mL). The organic layer was dried over anhydrous $Na_2SO_4$ and concentrated. The crude was purified by flash column chromatography on silica gel (EtOAc in petroleum ether=0 to 3%) to give 7A-1 (17 g, 45.00 mmol, 99.58% yield) as colorless oil. $^1$H NMR (400 MHz, $CDCl_3$) δ=7.75 (d, J=2.4 Hz, 1H), 7.28 (dd, J=2.4 Hz, 8.4 Hz, 1H), 7.14 (d, J=8.4 Hz, 1H), 4.81 (s, 2H), 1.55-1.16 (m, 3H), 1.10-1.08 (m, 18H).

Step B: Preparation of 4-chloro-3-(((triisopropylsilyl)oxy)methyl)benzaldehyde (7A)

To a solution of 7A-1 (15 g, 39.70 mmol) in THF (200 mL) was added n-BuLi (2.5M in n-hexane, 47.64 mmol, 19.06 mL) dropwise by syringe at −78° C. under $N_2$. The mixture was stirred at −78° C. for 10 min under $N_2$. Then DMF (4.06 g, 55.58 mmol, 4.28 mL) was added to the above mixture by syringe dropwise. The reaction mixture was stirred at −78° C. for 2 h. The reaction was quenched with water (150 mL) and extracted with EtOAc (150 mL×3). The organic layer was dried over anhydrous $Na_2SO_4$ and concentrated. The crude was purified by flash chromatography on silica gel (EtOAc in petroleum ether=0 to 3%) to give 7A (4.69 g, 14.35 mmol, 36.15% yield) as colorless oil. $^1$H NMR (400 MHz, $CDCl_3$) δ=9.94 (s, 1H), 8.10 (d, J=8.0 Hz, 1H), 7.67 (dd, J=2.0 Hz, J=8.4 Hz, 1H), 7.40 (d, J=8.0 Hz, 1H), 4.85 (s, 2H), 1.21-1.15 (m, 3H), 1.13-1.04 (m, 18H).

Example 8A: Preparation of Intermediate 8A

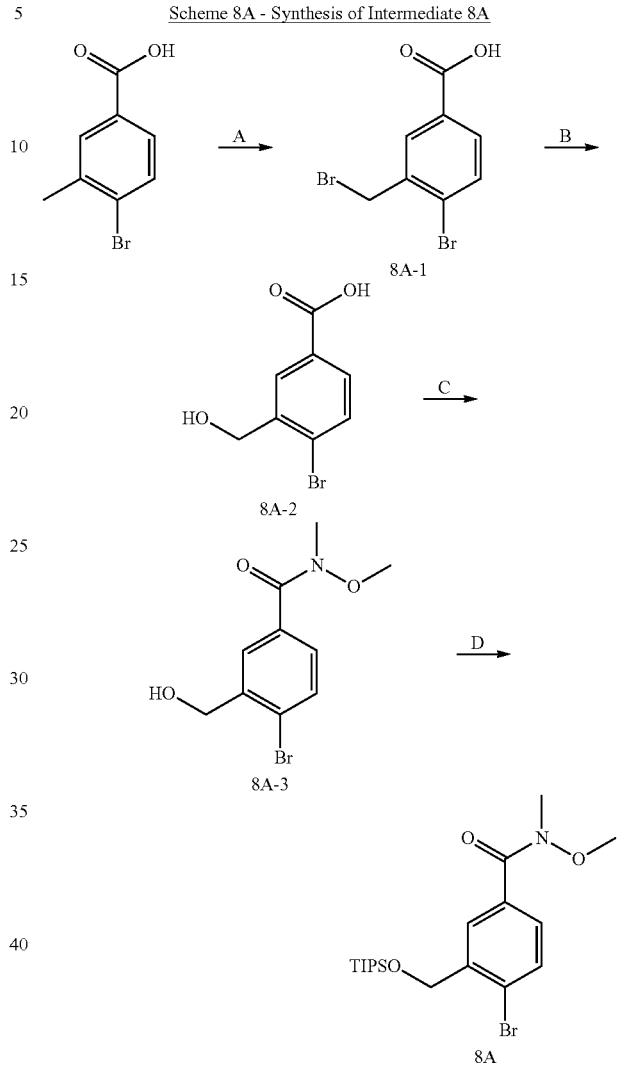

Step A: Preparation of (8A-1)

A mixture of 4-bromo-3-methylbenzoic acid (200 g, 930.04 mmol), NBS (248.29 g, 1.40 mol) and AIBN (30.54 g, 186.01 mmol) in $CCl_4$ (1600 mL) was degassed and purged with $N_2$ 3 times, and then the mixture was stirred at 85° C. for 12 h under $N_2$. The reaction mixture was filtered. The crude product was triturated by $CH_3CN$ (500 mL) to give a mixture of 8A-1 and the corresponding dibromomethyl compound (215 g, 731.44 mmol, 78.65% yield) as a yellow solid. $^1$H NMR (400 MHz, DMSO-$d_6$) δ=13.36 (br s, 1H), 8.17 (s, 1H) 7.78-7.82 (m, 2H), 4.82 (s, 2H).

Step B: Preparation of (8A-2)

To a solution of the mixture of 8A-1 and the corresponding dibromomethyl compound (160 g, 544.33 mmol) in $H_2O$ (1500 mL) was added $Na_2CO_3$ (230.77 g, 2.18 mol). The mixture was stirred at 75° C. for 12 h. The reaction mixture was treated with HCl (4M in $H_2O$) to give a white cake. The solvent was removed from the white cake. To the above product in MeOH (1000 mL) was added NaBH$_4$ (24.00 g, 634.42 mmol) under N$_2$, and then the mixture was stirred at 15° C. for 1 h under N$_2$. The reaction mixture was quenched with H$_2$O (400 mL) and acidified with HCl (1M in H$_2$O) to pH=2. The mixture was placed under reduced pressure to removed the solvent and then filtered. The white filter cake was placed under the reduced pressure to remove the surplus solvent to give 8A-2 (120 g, 519.38 mmol, 95.42% yield) as a yellow solid. $^1$H NMR (400 MHz, DMSO-d$_6$) δ=8.08-8.15 (m, 1H), 7.66-7.76 (m, 2H), 4.53 (s, 2H).

Step C: Preparation of (8A-3)

To a solution of 8A-2 (100 g, 432.90 mmol), N,O-dimethylhydroxylamine (57.97 g, 594.31 mmol, HCl) and DIPEA (223.76 g, 1.73 mol, 301.56 mL) in DCM (1000 mL) was added T$_3$P (275.43 g, 865.64 mmol, 257.41 mL). The mixture was stirred at 15° C. for 5 min. Water (200 mL) was added to the reaction mixture and the resulting mixture was extracted with DCM (500 mL×2). The organic layers were separated, and washed with brine (200 mL), dried over anhydrous Na$_2$SO$_4$, filtered and concentrated. The residue was purified by flash chromatography on silica gel (EtOAc in petroleum ether=0% to 35%) to give 8A-3 (83 g, 302.80 mmol, 69.95% yield) as a colorless oil. $^1$H NMR (400 MHz, DMSO-d$_6$) δ=7.92 (s, 1H), 7.72-7.76 (m, 1H), 7.64 (d, J=8.4 Hz, 1H), 7.41 (dd, J=8.4, 2.0 Hz, 1H), 4.53 (d, J=5.6 Hz, 2H), 3.54 (s, 3H), 3.26 (s, 3H).

Step D: Preparation of 4-bromo-N-methoxy-N-methyl-3-(((triisopropylsilyl)oxy) methyl)benzamide (8A)

A solution of 8A-3 (83 g, 302.80 mmol), TIPSCl (58.5 g, 303.42 mmol, 64.93 mL) and imidazole (51.54 g, 756.99 mmol) in DCM (800 mL) was stirred at 15° C. for 16 h. The reaction mixture was diluted with H$_2$O (500 mL) and extracted with DCM (600 mL×2). The combined organic layers were washed with brine (400 mL), dried over Na$_2$SO$_4$, filtered and concentrated under reduced pressure to give a residue. The crude was purified by flash chromatography on silica gel (EtOAc in petroleum ether=0 to 10%) to give 8A (104 g, 241.60 mmol, 79.79% yield) as a colorless oil. $^1$H NMR (400 MHz, DMSO-d$_6$) δ=7.81 (d, J=2.0 Hz, 1H), 7.67 (d, J=8.4 Hz, 1H), 7.46 (dd, J=8.4, 2.4 Hz, 1H), 4.80 (s, 2H), 3.51 (s, 3H), 3.23-3.29 (m, 3H), 1.12-1.23 (m, 3H), 1.03-1.08 (m, 18H).

Example 9A: Preparation of Intermediate 9A

Scheme 9A - Synthesis of Intermediate 9A

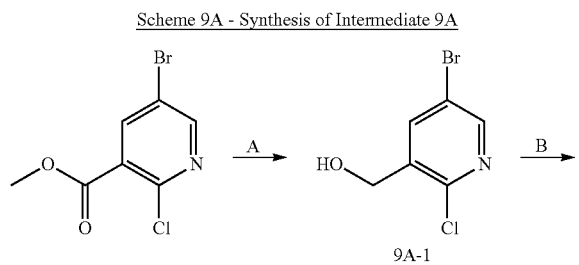

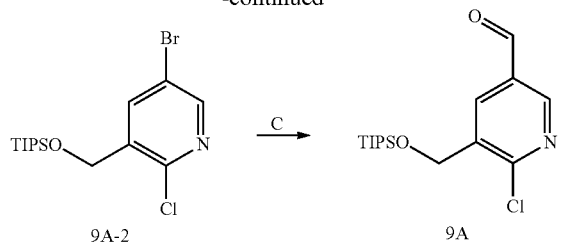

Step A: Preparation of (9A-1)

To a mixture of methyl 5-bromo-2-chloronicotinate (20 g, 79.85 mmol) in THF (200 mL) at −78° C., was slowly added DIBAL-H (1M in toluene, 175.66 mmol, 175.66 mL). The reaction mixture was stirred at 15° C. for 1 h. Saturated potassium sodium tartrate solution (200 mL) was added to the reaction mixture and the mixture was stirred for 2 h. The mixture was extracted with EtOAc (100 mL×3) and the combined organic layer was washed brine (100 mL), dried over anhydrous Na$_2$SO$_4$, filtered and concentrated. The residue was blended with another batch prepared from methyl 5-bromo-2-chloronicotinate (1 g, 3.99 mmol). The residue was purified by flash chromatography on silica gel (EtOAc in DCM=0 to 20%) to give 9A-1 (16.5 g, 74.17 mmol, 88.47% yield) as a white solid. $^1$H NMR (400 MHz, DMSO-d$_6$) δ=8.47 (d, J=2.4 Hz, 1H), 8.08 (d, J=2.8 Hz, 1H), 8.69 (t, J=5.6 Hz, 1H), 4.53 (d, J=5.6 Hz, 2H).

Step B: Preparation of (9A-2)

A solution of 9A-1 (16.5 g, 74.17 mmol), TIPSCl (14.30 g, 74.17 mmol, 15.87 mL) and imidazole (12.62 g, 185.42 mmol) in DCM (200 mL) was stirred at 25° C. for 16 h. The reaction mixture was washed with water (100 mL×3) and brine (100 mL), dried over anhydrous Na$_2$SO$_4$ and concentrated. The residue was purified by flash chromatography on silica gel (EtOAc in petroleum ether=0 to 5%) to give 9A-2 (19 g, 50.16 mmol, 67.63% yield) as colorless oil. $^1$H NMR (400 MHz, CDCl$_3$) δ=8.32 (d, J=2.4 Hz, 1H), 8.05 (d, J=2.4 Hz, 1H), 4.77 (s, 2H), 1.24-1.16 (m, 3H), 1.10-1.06 (m, 18H).

Step C: Preparation of 6-chloro-5-(((triisopropylsilyl)oxy)methyl)nicotinaldehyde (9A)

To a solution of 9A-2 (18 g, 47.52 mmol) in THF (200 mL) was added n-BuLi (2.5M in n-hexane, 47.52 mmol, 19.01 mL) at −70° C. and the mixture was stirred at −70° C. for 30 min. Then DMF (6.95 g, 95.04 mmol, 7.31 mL) was added to the above mixture at −70° C. for 30 min and the mixture was stirred at −70° C. for 30 min. The reaction mixture was poured into water (200 mL) and extracted with EtOAc (150 mL×3). The organic layer was washed with brine (50 mL), dried over anhydrous Na$_2$SO$_4$, filtered and concentrated. The residue was purified by flash chromatography on silica gel (EtOAc in petroleum ether=0 to 10%) to give 9A (11.2 g, 34.15 mmol, 71.86% yield) as brown oil. $^1$H NMR (400 MHz, CDCl$_3$) δ=10.13 (s, 1H), 8.76 (s, 1H), 8.44 (s, 1H), 4.89 (s, 2H), 1.27-1.23 (m, 3H), 1.21-1.11 (m, 18H).

Example 10A: Preparation of Intermediate 10A

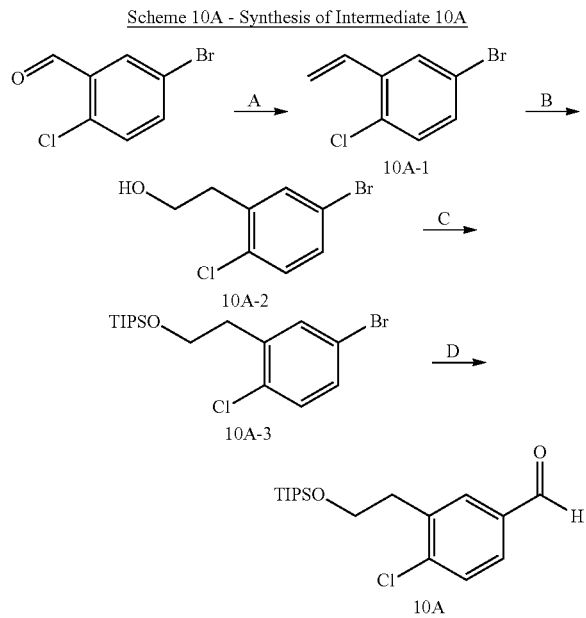

Scheme 10A - Synthesis of Intermediate 10A

Step A: Preparation of (10A-1)

To a solution of methyl(triphenyl)phosphonium bromide (42.32 g, 118.47 mmol) in THF (500 mL) was added t-BuOK (15.34 g, 136.70 mmol) at 0° C. under $N_2$. The mixture was stirred at 0° C. for 0.5 h. A solution of 5-bromo-2-chloro-benzaldehyde (20 g, 91.13 mmol) in THF (100 mL) was added dropwise to the reaction mixture. The reaction mixture was stirred at 25° C. for 2 h. The reaction mixture was diluted with $H_2O$ (500 mL) and extracted with EtOAc (300 mL×3). The combined organic layers were washed with brine (500 mL), dried over anhydrous $Na_2SO_4$, filtered and concentrated under reduced pressure. The residue was purified by flash chromatography on silica gel (EtOAc in petroleum ether=0 to 2%) to give 10A-1 (13.7 g, 62.99 mmol, 69.12% yield) as a colorless oil. $^1$H NMR (400 MHz, $CDCl_3$) δ=7.69 (d, J=2.4 Hz, 1H), 7.32 (dd, J=2.4, 8.4 Hz, 1H), 7.22 (d, J=8.4 Hz, 1H), 7.02 (dd, J=11.2, 17.6 Hz, 1H), 5.75 (d, J=17.6 Hz, 1H), 5.44 (d, J=11.2 Hz, 1H).

Step B: Preparation of (10A-2)

To a solution of 10A-1 (13.7 g, 62.99 mmol) in THF (280 mL) was added 9,9'-dibora-9,9'-bi(bicyclo[3.3.1]nonane) (15.24 g, 62.99 mmol). The mixture was stirred at 25° C. for 16 h. EtOH (10 mL) was added to the above mixture. NaOH (5M in $H_2O$, 629.91 mmol, 125.98 mL) was added to the reaction mixture at 0° C. and then $H_2O_2$ (71.42 g, 629.91 mmol, 60.53 mL, 30% purity) was added to the reaction mixture at 0° C. The reaction mixture was stirred at 80° C. for 30 min. The reaction mixture was added to saturated $Na_2SO_3$ solution (1000 mL) at 0° C. and then the mixture was extracted with EtOAc (300 mL×3). The combined organic layers were washed with brine (300 mL), dried over anhydrous $Na_2SO_4$, filtered and concentrated under reduced pressure. The residue was purified by flash chromatography on silica gel (EtOAc in petroleum ether=0 to 20%) to give 10A-2 (13.45 g, 57.11 mmol, 90.67% yield) as a colorless oil. $^1$H NMR (400 MHz, $CDCl_3$) δ=7.43 (d, J=2.4 Hz, 1H), 7.30 (dd, J=2.4, 8.4 Hz, 1H), 7.22 (d, J=8.8 Hz, 1H), 3.87 (t, J=6.4 Hz, 2H), 2.97 (t, J=6.8 Hz, 2H).

Step C: Preparation of (10A-3)

To a solution of 10A-2 (13.4 g, 56.90 mmol), imidazole (11.62 g, 170.70 mmol) in DMF (200 mL) was added TIPSCl (16.46 g, 85.35 mmol, 18.26 mL) at 0° C. The mixture was stirred at 25° C. for 16 h. The reaction mixture was diluted with $H_2O$ (500 mL) and extracted with EtOAc (100 mL×3). The combined organic layers were washed with brine (100 mL), dried over anhydrous $Na_2SO_4$, filtered and concentrated under reduced pressure. The residue was purified by flash chromatography on silica gel (EtOAc in petroleum ether=0 to 1%) to give 10A-3 (21 g, 53.59 mmol, 94.19% yield) as a colorless oil. $^1$H NMR (400 MHz, $CDCl_3$) δ=7.47 (d, J=2.4 Hz, 1H), 7.32-7.28 (m, 1H), 7.22 (d, J=8.8 Hz, 1H), 3.90 (t, J=6.4 Hz, 2H), 2.96 (t, J=6.8 Hz, 2H), 1.12-0.98 (m, 21H).

Step D: Preparation of (5-bromo-2-chlorophenethoxy)triisopropylsilane (10A)

To a solution of 10A-3 (5 g, 12.76 mmol) in THF (100 mL) was added n-BuLi (2.5M in n-hexane, 15.31 mmol, 6.12 mL) at −70° C. under $N_2$. The mixture was stirred at −70° C. for 0.5 h. DMF (4.75 g, 64.98 mmol, 5 mL) was added to the reaction mixture at −70° C. The reaction mixture was stirred at −70° C. for 2 h. The reaction mixture was poured into saturated $NH_4Cl$ solution (500 mL) at 0° C., and the mixture was extracted with EtOAc (100 mL×3). The combined organic layers were washed with brine (200 mL), dried over anhydrous $Na_2SO_4$, filtered and concentrated under reduced pressure. The residue was purified by flash chromatography on silica gel (EtOAc in petroleum ether=0 to 10%) to give 10A (1.72 g, 5.04 mmol, 39.50% yield) as a black oil. $^1$H NMR (400 MHz, $CDCl_3$) δ=9.96 (s, 1H), 7.83 (d, J=2.0 Hz, 1H), 7.68 (dd, J=2.0, 8.4 Hz, 1H), 7.51 (d, J=8.4 Hz, 1H), 3.96 (t, J=6.4 Hz, 2H), 3.08 (t, J=6.4 Hz, 2H), 1.03-0.98 (m, 21H).

Example 11A: Preparation of Intermediate 11A

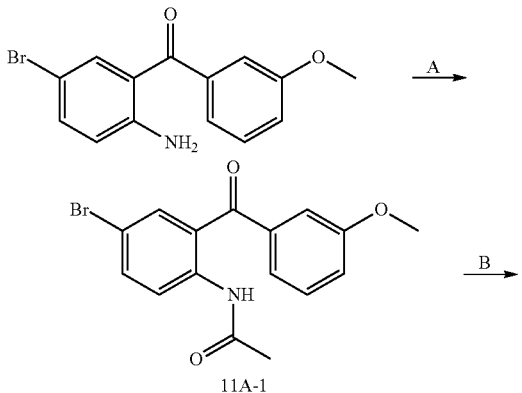

Scheme 11A - Synthesis of Intermediate 11A

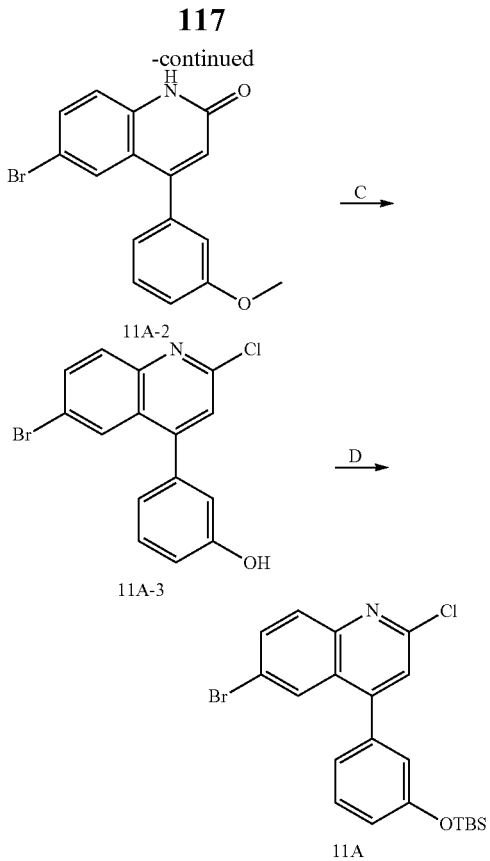

Step A: Preparation of 11A-1

To a mixture of (2-amino-5-bromophenyl)(3-methoxyphenyl)methanone (500 g, 1.63 mol) in toluene (3000 mL) was added Ac2O (333.46 g, 3.27 mol, 305.93 mL) and the mixture was stirred at 110° C. for 14 h. The reaction mixture was concentrated under reduced pressure to obtain 11A-1 (528 g, 1.52 mol, 92.85% yield) as a brown solid. LC-MS: Method: 5-95AB, $R_t$=0.88 min, M/Z calculated for $C_{16}H_{15}BrNO_3$ [M+H]$^+$ 350.0, found 349.9.

Step B: Preparation of 11A-2

To a solution of 11A-1 (528 g, 1.52 mol) in DME (2000 mL) under ice water was added t-BuOK (340.31 g, 3.03 mol) in portions, while maintaining the temperature at 20° C. under $N_2$. The resulting mixture was stirred at 20° C. for 12 h after which the reaction was quenched by water (200 mL). The mixture was concentrated under reduced pressure to remove DME. The residue was triturated with water (2000 mL, twice) then stirred with EtOAc (1000 mL) at 25° C. for 1 h to give 11A-2 (487 g, 1.47 mol, 97.27% yield) as yellow solid. $^1$H NMR (400 MHz, DMSO-d$_6$) δ=7.73-7.64 (m, 1H), 7.50-7.34 (m, 3H), 7.15-6.93 (m, 3H), 6.46 (s, 1H), 3.81 (s, 3H).

Step C: Preparation of 11A-3

To a solution of 11A-2 (50 g, 143.42 mmol) in DCM (500 mL) at −40° C. under $N_2$ was added BBr$_3$ (53.90 g, 215.13 mmol, 20.73 mL). The mixture was stirred at 25° C. for 4 h. The reaction mixture was poured into water (500 mL). The pH was adjusted to 7 with saturated NaHCO$_3$ solution. The aqueous layer was extracted with DCM (300 mL×2). The combined organic phase was washed with brine (300 mL), dried over anhydrous Na$_2$SO$_4$, filtered, and concentrated. The crude product was triturated with petroleum ether (300 mL) at 25° C. for 30 min and CH$_3$CN (200 mL) at 25° C. for 30 min to give 11A-3 (42 g, 125.53 mmol, 87.52% yield) as a yellow solid. $^1$H NMR (400 MHz, DMSO-d$_6$) δ=9.92 (br s, 1H), 8.03-7.91 (m, 3H), 7.56 (s, 1H), 7.43-7.37 (m, 1H), 6.99-6.91 (m, 3H).

Step D: Preparation of 6-bromo-4-(3-((tert-butyldimethylsilyl)oxy)phenyl)-2-chloroquinoline (11A)

To a solution of 11A-3 (40 g, 119.55 mmol) in DCM (400 mL) was added tert-butylchlorodimethylsilane (18.02 g, 119.55 mmol, 14.65 mL) under $N_2$ at 0° C., then 1H-imidazole (17.91 g, 263.00 mmol) was added dropwise, and the mixture was stirred at 0° C. for 1 h, the ice bath was removed and the mixture was stirred at 25° C. for 12 h. The residue was poured into water (400 mL) and then extracted with DCM (400 mL×2). The combined organic phase was washed with brine (400 mL), dried over anhydrous Na$_2$SO$_4$, filtered and concentrated under reduced pressure. The product was purified by flash chromatography on silica gel (EtOAc in petroleum ether=0 to 5%, twice) to give 11A (34 g, 75.75 mmol, 63.36% yield) as a yellow solid. $^1$H NMR (400 MHz, CDCl$_3$) δ=8.02 (d, J=2.0 Hz, 1H), 7.92 (d, J=8.8 Hz, 1H), 7.78 (dd, J=2.0, 8.8 Hz, 1H), 7.39 (t, J=8.0 Hz, 1H), 7.33 (s, 1H), 7.06-6.96 (m, 2H), 6.94-6.88 (m, 1H), 1.01-0.98 (m, 9H), 0.25-0.22 (m, 6H).

Example 12A: Preparation of Intermediate 12A

Scheme 12A - Synthesis of Intermediate 12A

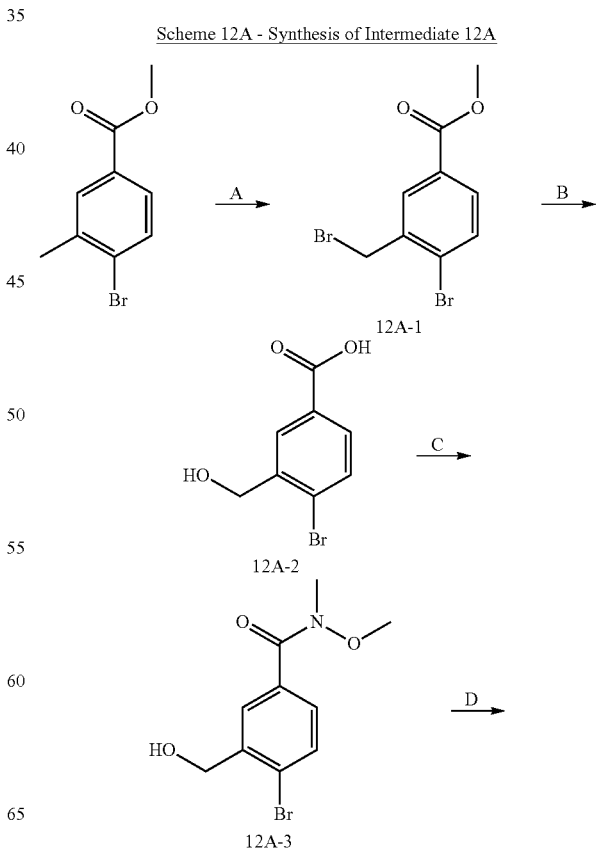

119

-continued

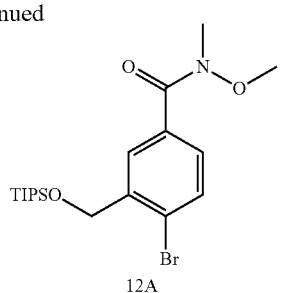

12A

Step A: Preparation of (12A-1)

A solution of methyl 4-bromo-3-methylbenzoate (20 g, 87.31 mmol) and NBS (18.65 g, 104.77 mmol) in $CH_3CN$ (400 mL) was flowed under blue ray at 25° C. for 1 h. The mixture was poured into saturated $NaHCO_3$ solution (200 mL) and then extracted with EtOAc (200 mL×3). The combined organic phase was washed with brine (200 mL), dried with anhydrous $Na_2SO_4$, filtered and concentrated under reduced pressure. The combined organic phase was concentrated under reduced pressure to give 12A-1 (26 g, 84.42 mmol, 96.70% yield) was obtained as a yellow solid. $^1H$ NMR (400 MHz, $CDCl_3$) δ=8.09 (d, J=2.0 Hz, 1H), 7.80-7.76 (m, 1H), 7.63 (d, J=8.0 Hz, 1H), 4.59 (s, 2H), 3.90 (s, 3H).

Step B: Preparation of (12A-2)

Step B. To a Solution of 12A-1 (50 g, 162.36 mmol) in $H_2O$ (750 mL) was added $LiOH \cdot H_2O$ (20.44 g, 487.07 mmol) at 25° C. The mixture was stirred at 50° C. for 12 h. The reaction mixture was adjusted pH=3 with HCl (12M) and then filtered to give 12A-2 (34 g, 147.16 mmol, 90.64% yield) was obtained as a yellow solid. $^1H$ NMR (400 MHz, DMSO-$d_6$) δ=13.21 (s, 1H), 8.12-8.08 (m, 1H), 7.76-7.66 (m, 2H), 6.23-5.13 (m, 1H), 4.53 (s, 2H).

Step C: Preparation of (12A-3)

A mixture of 12A-2 (34 g, 147.16 mmol), N,O-dimethylhydroxylamine (17.23 g, 176.59 mmol, HCl), DIEA (57.06 g, 441.48 mmol, 76.90 mL) and $T_3P$ (70.23 g, 220.74 mmol, 65.64 mL) in DCM (350 mL) was stirred at 25° C. for 0.5 h. The mixture was poured into water (500 mL) and the mixture was extracted with DCM (300 mL×2). The combined organic phase was washed with brine (500 mL), dried over anhydrous $Na_2SO_4$, filtered and concentrated to give 12A-3 (34 g, 124.04 mmol, 84.29% yield) as a yellow oil. LCMS $R_t$=1.97 min in 4.0 min chromatography, 0-60AB, ESI calcd. for $C_{10}H_{13}BrNO_3$ [M+H]$^+$ 274.0, found 273.6.

Step D: Preparation of 4-bromo-3-(((tert-butyldimethylsilyl)oxy)methyl)-N-methoxy-N-methylbenzamide (12A)

A mixture of 12A-3 (34 g, 124.04 mmol), TBSCl (22.43 g, 148.84 mmol, 18.24 mL) and imidazole (16.89 g, 248.07 mmol) in DCM (350 mL) was stirred at 25° C. for 1 h. The mixture was poured into water (100 mL) and the mixture was extracted with DCM (100 mL×2). The combined organic phase was washed with brine (100 mL), dried over anhydrous $Na_2SO_4$, filtered and concentrated. The crude was purified by flash chromatography on silica gel (EtOAc in

120 petroleum ether=0 to 10%) to give 12A (35 g, 90.12 mmol, 72.66% yield) as colorless oil. $^1H$ NMR (400 MHz, $CDCl_3$) δ=7.89 (d, J=1.2 Hz, 1H), 7.57-7.52 (m, 1H), 7.45 (dd, J=2.0, 8.0 Hz, 1H), 4.75 (s, 2H), 3.56 (s, 3H), 3.36 (s, 3H), 0.97 (s, 9H), 0.14 (s, 6H).

Example 13A: Preparation of Intermediate 13A

Scheme 13A - Synthesis of Intermediate 13A

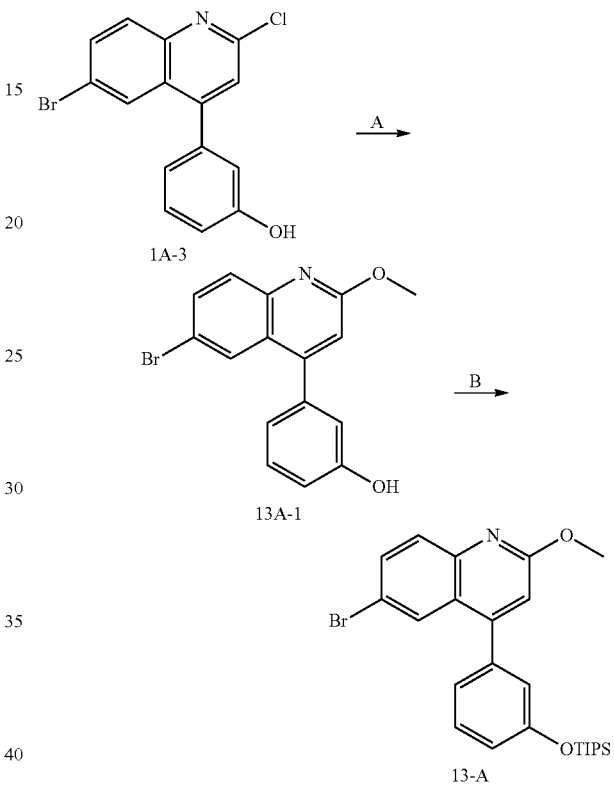

Step A: Preparation of (13A-1)

To a solution of 11A-3 (170 g, 508.08 mmol) in MeOH (800 mL) and THF (800 mL) at 25° C. was added $CH_3ONa$ (54.89 g, 1.02 mol), and the mixture was stirred at 80° C. for 12 h. The solvents were removed under reduced pressure. The mixture was poured into water (1000 mL), stirred for 30 min, then filtered. The filtrate was concentrated under reduced pressure. The crude product was triturated with $CH_3CN$ (500 mL) at 25° C. for 30 min to give 13A-1 (130 g, 393.73 mmol, 67.98% yield) as a yellow solid. $^1H$ NMR (400 MHz, DMSO-$d_6$) δ=7.79 (s, 3H), 7.43-7.29 (m, 1H), 6.99-6.84 (m, 4H), 4.01 (s, 3H), 3.64 (s, 1H).

Step B: Preparation of 6-bromo-2-methoxy-4-(3-((triisopropylsilyl)oxy)phenyl)-quinoline (13A)

Imidazole (58.97 g, 866.21 mmol) was added to a solution of 13A-1 (130 g, 393.73 mmol) in DCM (1500 mL) under $N_2$ at 0° C. The mixture was stirred until a clear solution appeared, TIPSCl (75.91 g, 393.73 mmol, 84.25 mL) was added dropwise, and the mixture was stirred at 0° C. for 1 h after which the ice bath was removed, and the mixture was stirred at 25° C. for 12 h. The residue was poured into water (1000 mL) and then extracted with DCM (1000 mL×3). The combined organic phase was washed with brine (1000 mL), dried over anhydrous Na$_2$SO$_4$, filtered, and concentrated under reduced pressure. The crude was purified by flash chromatography on silica gel (EtOAc in petroleum ether=0 to 5%) and then triturated with MeOH (300 mL) at 25° C. for 30 minutes to give 13A (160 g, 328.87 mmol, 83.52% yield) as a yellow solid. $^1$H NMR (400 MHz, CDCl$_3$) δ=7.88 (d, J=2.0 Hz, 1H), 7.79-7.73 (m, 1H), 7.67 (dd, J=2.4 Hz, J=9.2 Hz, 1H), 7.35 (t, J=8.0 Hz, 1H), 7.03-6.97 (m, 2H), 6.96-6.93 (m, 1H), 6.83 (s, 1H), 4.07 (s, 3H), 1.32-1.23 (m, 3H), 1.13-1.09 (m, 18H).

Scheme A - General Synthetic Method A

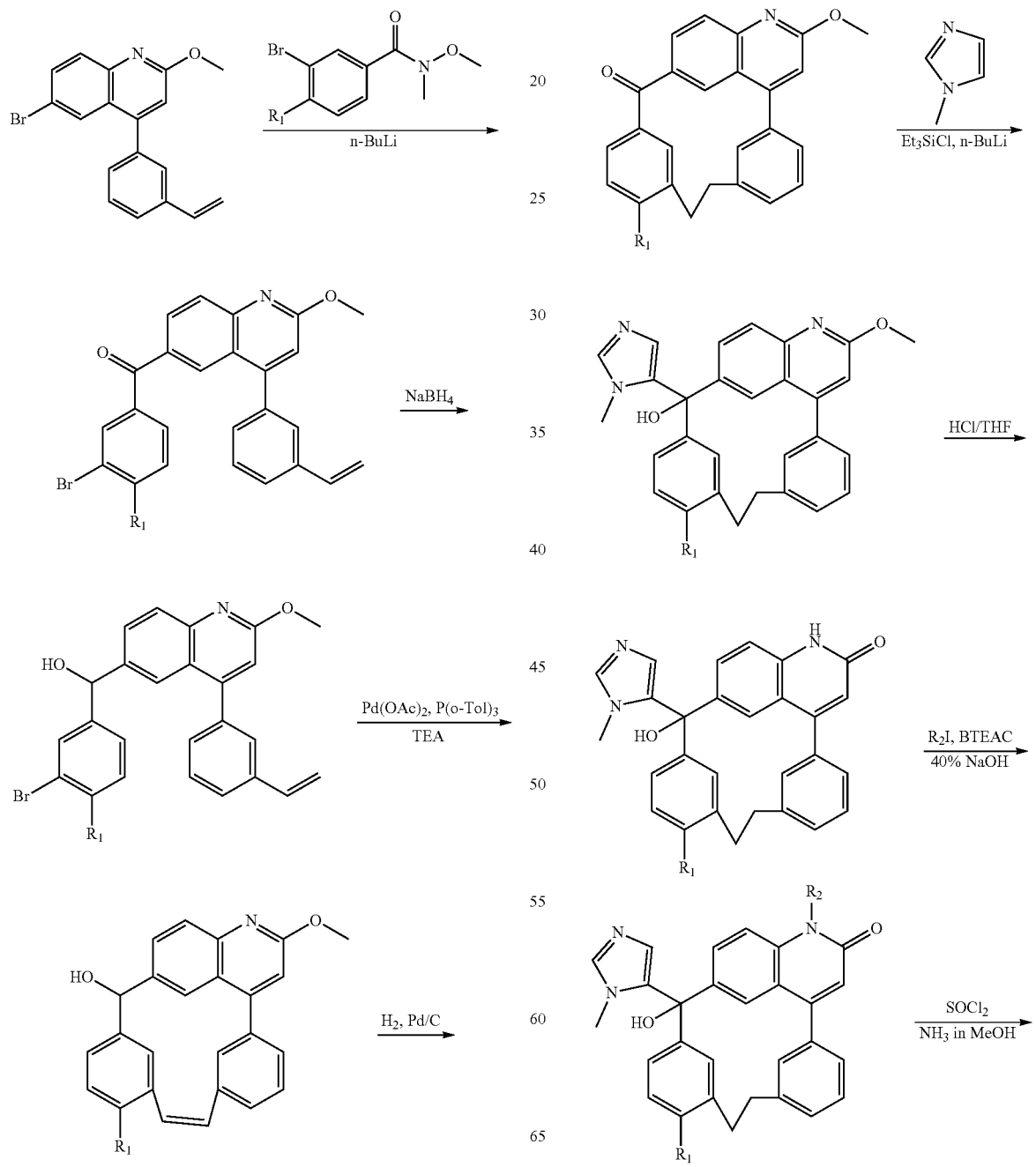

-continued

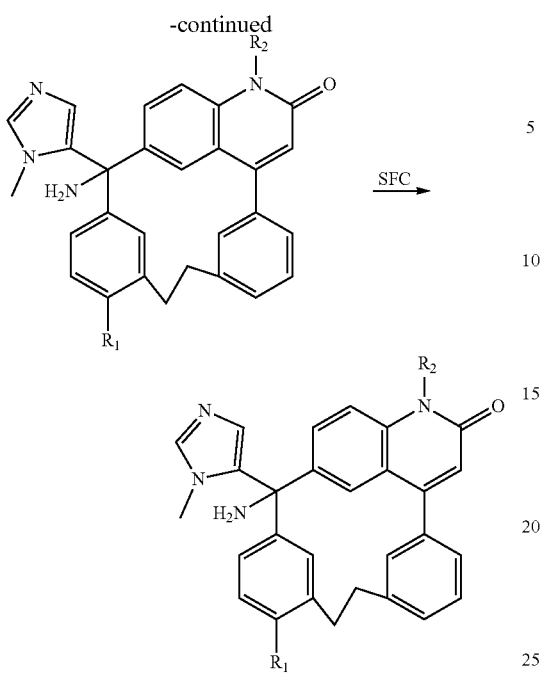

Preparation of Exemplary Compounds

It is understood that reference to a compound as disclosed herein by a number that includes one or two additional "0" prior to the compound number or without the one or two additional "0" prior to the compound number both refer to the same compound. For example, the final compound prepared in Example 1: 3-hydroxy-3-(1-methyl-1H-imidazol-5-yl)-$2^1$,$2^2$-dihydro-2(4,6)-quinolina-1,4(1,3)-dibenzenacyclohexaphan-$2^2$-one, is sometimes referred to as compound "001" is sometimes referred to as compound "1".

It is further understood that reference to a compound as disclosed herein having one or more sterocenters without designating the specific chirality (e.g., R- or S-enantionmer) will be understood to refer to the compound as racemic mixture (or a mixture of diastereomers), while inclusion of R- or S-designations will be understood to refer to an enantiomer (or a diastereomer) form of the compound, such as an enantiomerically (or diastereomerically) enriched form of the compound, or an enantiomeric excess of the specified enantiomer form of the compound, in accordance with discussion above regarding enantiomeric enriched and enantiomeric excess. Notation of a compound with an R- or S-designation is understood to include an enantiomerically enriched or an enantiomeric excess of the specified enantiomer of the compound, and not limited to only 100% f the single specified enantiomer of the compound. For example, reference to compound 3 (or compound 003 or compound rac-003 or compound rac-3) will be understood to refer to the compound prepared in Example 3 and in its racemic form: "$4^4$-chloro-3-hydroxy-$2^1$-methyl-3-(1-methyl-1H-imidazol-5-yl)-$2^1$,$2^2$-dihydro-2(4,6)-quinolina-1,4(1,3)-dibenzenacyclohexaphan-$2^2$-one". Similarly, reference to compound (S)-3 (or compound (S)-003) will be understood to refer to the compound prepared in Example 3 and in its single steroisomer (S) form: "(S)-$4^4$-chloro-3-hydroxy-$2^1$-methyl-3-(1-methyl-1H-imidazol-5-yl)-$2^1$,$2^2$-dihydro-2(4,6)-quinolina-1,4(1,3)-dibenzenacyclohexaphan-$2^2$-one".

Example 1: Preparation of Compound 1

Scheme 1 - Synthesis of Compound 1

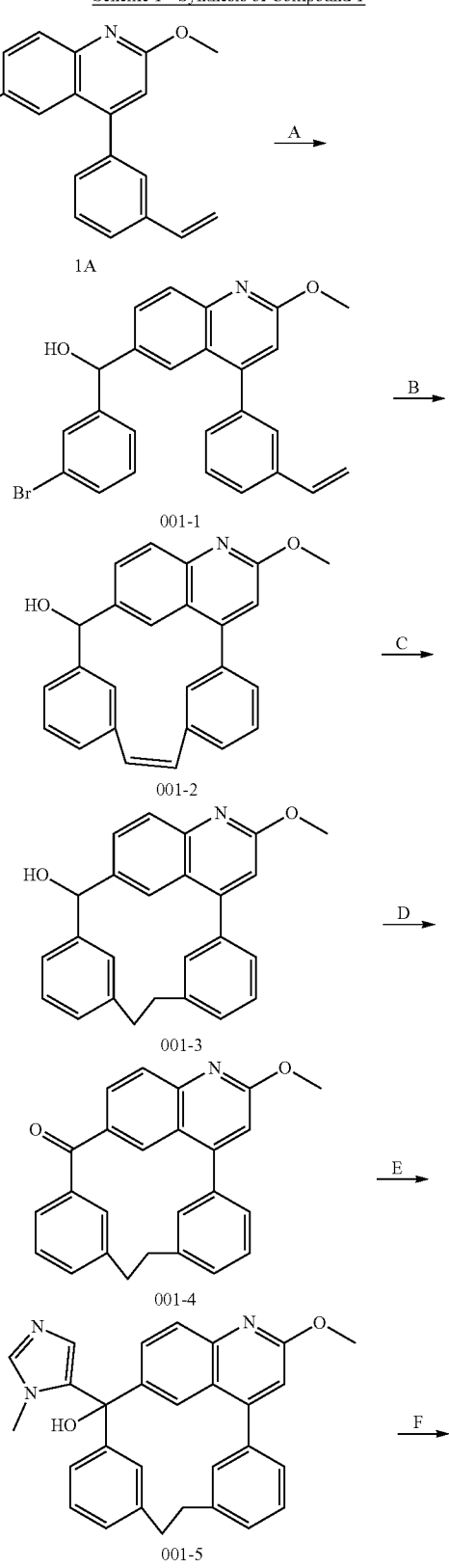

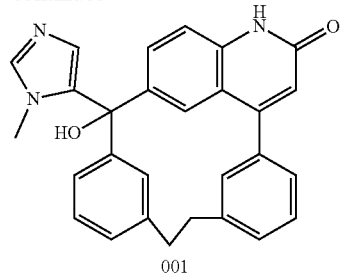

001

Step A: Preparation of (001-1)

To a solution of 1A (2 g, 5.88 mmol) in THF (30 mL) was added n-BuLi (2.5M in n-hexane, 6.47 mmol, 2.59 mL) dropwise by syringe at −78° C. under $N_2$. The mixture was stirred at −78° C. for 5 min under $N_2$. Then a solution of 3-bromobenzaldehyde (1.14 g, 6.17 mmol) (*J. Chem. Sci.* 2015, 175 (7), 1229-1234.) in THF (3 mL) was added to the above mixture by syringe dropwise and the reaction mixture was stirred at −78° C. for 1 h. The mixture was quenched with water (50 mL) and diluted with EtOAc (50 mL). The aqueous layer was extracted with EtOAc (50 mL×3). The organic layer was dried over $Na_2SO_4$ and concentrated under reduced pressure. The residue was purified by flash chromatography on silica gel (EtOAc in petroleum ether=0 to 16%) to give 001-1 (2.0 g, 4.48 mmol, 76.19% yield) as colorless oil. $^1$H NMR (400 MHz, $CDCl_3$) δ=7.90 (d, J=8.4 Hz, 1H), 7.79 (d, J=2.0 Hz, 1H), 7.59-7.55 (m, 3H), 7.51-7.48 (m, 2H), 7.40-7.36 (m, 2H), 7.29-7.27 (m, 1H), 7.21-7.17 (m, 1H), 6.89 (s, 1H), 6.80 (dd, J=10.8, 17.6 Hz, 1H), 5.86-5.80 (m, 2H), 5.37-5.34 (d, J=10.8 Hz, 1H), 4.10 (s, 3H), 2.39 (s, 1H). LCMS $R_t$=0.99 min in 1.5 min chromatography, 5-95AB, ESI calcd. for $C_{25}H_{21}BrNO_2$ [M+H]$^+$ 446.1, found 445.9.

Step B: Preparation of (001-2)

To a solution of 001-1 (2.0 g, 4.48 mmol) in $CH_3CN$ (120 mL) was added tri-o-tolylphosphane (272.77 mg, 896.19 μmol) and TEA (1.36 g, 13.44 mmol), $Pd_2(dba)_3$ (205.16 mg, 224.05 μmol) was added to the mixture under $N_2$. The reaction was stirred at 85° C. for 16 h under $N_2$. The solvent was removed under reduced pressure. The residue was purified by flash chromatography on silica gel (EtOAc in petroleum ether=0 to 17%) to give 001-2 (0.2 g, 547.31 mol, 12.21% yield) as a white solid. $^1$H NMR (400 MHz, $CDCl_3$) δ=7.99 (br s, 1H), 7.90 (br s, 1H), 7.79-7.76 (m, 2H), 7.56-7.47 (m, 2H), 7.41-7.39 (m, 1H), 7.31 (s, 1H), 7.23-7.15 (m, 2H), 7.09-7.08 (m, 1H), 6.88 (s, 1H), 6.73 (d, J=12.8 Hz, 1H), 6.64 (d, J=12.8 Hz, 1H), 6.05-5.95 (m, 1H), 4.07 (s, 3H), 2.45 (d, J=2.8 Hz, 1H). LCMS $R_t$=0.90 min in 1.5 min chromatography, 5-95AB, ESI calcd. for $C_{25}H_{20}NO_2$ [M+H]$^+$ 366.1, found 366.0.

Step C: Preparation of (001-3)

To a solution of 001-2 (0.2 g, 547.31 μmol) in EtOAc (30 mL) was added Pd/C (23.30 mg, 21.89 μmol, 10% purity). The reaction mixture was stirred at 25° C. for 2 h under $H_2$ balloon (15 psi). The solid was filtered off and washed with EtOAc (20 mL). The filtrate was concentrated under reduced pressure to give 001-3 (0.2 g, 544.31 μmol, 99.45% yield) as a white solid, which was used directly for the next step without further purification. LCMS $R_t$=0.90 min in 1.5 min chromatography, 5-95AB, ESI calcd. for $C_{25}H_{22}NO_2$ [M+H]$^+$ 368.2, found 368.0.

Step D: Preparation of (001-4)

To a solution of 001-3 (200 mg, 544.31 μmol) in DCM (40 mL) was added $MnO_2$ (236.61 mg, 2.72 mmol). The reaction mixture was stirred at 35° C. for 2 h. The solid was filtered off. The filtrate was concentrated to give 001-4 (198.9 mg, 544.30 μmol, 100% yield) as a white solid, which was used directly for the next step without further purification. $^1$H NMR (400 MHz, $CDCl_3$) δ=8.33-8.30 (m, 1H), 7.99-7.97 (m, 2H), 7.66-7.47 (m, 2H), 7.44 (s, 1H), 7.43-7.35 (m, 3H), 7.31-7.27 (m, 2H), 7.05 (s, 1H), 4.17 (s, 3H), 3.37-3.25 (m, 4H). LCMS $R_t$=1.00 min in 1.5 min chromatography, 5-95AB, ESI calcd. for $C_{25}H_{20}NO_2$ [M+H]$^+$ 366.1, found 366.0.

Step E: Preparation of (001-5)

Under dry $N_2$ flow, to a solution of 1-methyl-1H-imidazole (86.28 mg, 1.05 mmol) in THF (2 mL) was added n-BuLi (2.5M in n-hexane, 1.05 mmol, 420.33 μL) dropwise at −78° C. under $N_2$. The mixture was stirred at −78° C. for 1 h. $Et_3SiCl$ (158.38 mg, 1.05 mmol) in THF (1 mL) was added to the mixture dropwise at −78° C. and the mixture was stirred at −78° C. for 1 h. Then n-BuLi (2.5M in n-hexane, 1.05 mmol, 420.33 μL) was added to the mixture dropwise at −78° C. and the mixture was stirred at −78° C. for 1 h. A solution of 001-4 (320 mg, 875.70 μmol) in THF (4 mL) was added to the above mixture dropwise at −78° C. and the mixture was stirred at −78° C. for 1 h. Water (10 mL) was added to the mixture and extracted with EtOAc (20 mL×3). The combined organic phase was washed with brine (20 mL), dried over anhydrous $Na_2SO_4$, filtered and concentrated. The crude product was purified by flash chromatography on silica gel (MeOH in DCM=0 to 5%) to give 001-5 (0.25 g, 558.63 μmol, 63.79% yield) as white solid. $^1$H NMR (400 MHz, $CDCl_3$) δ=8.02-7.99 (m, 1H), 7.88 (d, J=8.8 Hz, 1H), 7.46-7.36 (m, 3H), 7.30-7.25 (m, 3H), 7.16-7.15 (m, 1H), 7.05 (s, 1H), 6.89-6.87 (m, 3H), 6.60-6.55 (m, 1H), 6.31 (s, 1H), 4.09 (s, 3H), 3.69 (s, 3H), 3.22-3.16 (m, 2H), 2.88-2.75 (m, 2H). LCMS $R_t$=0.78 min in 1.5 min chromatography, 5-95AB, ESI calcd. for $C_{29}H_{26}N_3O_2$ [M+H]$^+$ 448.2, found 448.0.

Step F: Preparation of 3-hydroxy-3-(1-methyl-1H-imidazol-5-yl)-2$^1$,2$^2$-dihydro-2(4,6)-quinolina-1,4(1,3)-dibenzenacyclohexaphan-2$^2$-one (001)

To a solution of 001-5 (0.25 g, 558.63 μmol) in THF (8 mL) was added HCl (4M in $H_2O$, 4.19 mL). The reaction mixture was stirred at 70° C. for 16 h. The reaction mixture was adjusted to pH=7 with NaOH (10M in $H_2O$) solution and the mixture was diluted with EtOAc (10 mL). The aqueous layer was extracted with EtOAc (20 mL×3). The organic layer was separated and dried over $Na_2SO_4$, filtered and concentrated. The residue was purified by flash chromatography on silica gel (MeOH in DCM=0 to 10%) and further purified by Prep-HPLC (Welch Xtimate $C_{18}$ 150×25 mm×5 m, water (0.04% $NH_3$-$H_2O$+10 mM $NH_4HCO_3$)-ACN as mobile phase, from 35-65%, Flow Rate (ml/min): 25) to give 001 (68.3 mg, 157.55 μmol, 28.20% yield) as a white solid. $^1$H NMR (400 MHz, DMSO-$d_6$) δ=11.49 (s, 1H), 7.90-7.87 (m, 1H), 7.49-7.41 (m, 1H), 7.39-7.34 (m, 1H), 7.27-7.24 (m, 5H), 7.16-7.14 (m, 2H), 6.71 (s, 1H), 6.56 (s, 1H), 6.48 (s, 1H), 6.42 (s, 1H), 6.08 (s, 1H), 3.23-3.18 (m, 2H), 3.15 (s, 3H), 3.04-2.86 (m, 1H), 2.85-2.72 (m, 1H). LCMS $R_t$=3.23 min in 7 min chromatography, 10-80CD, ESI calcd. for $C_{28}H_{24}N_3O_2$ [M+H]$^+$ 434.2, found 434.3. HPLC $R_t$=2.84 min in 8 min chromatography, 220 nm, purity 100%.

Example 2: Preparation of Compound 2

Scheme 2 - Synthesis of Compounds

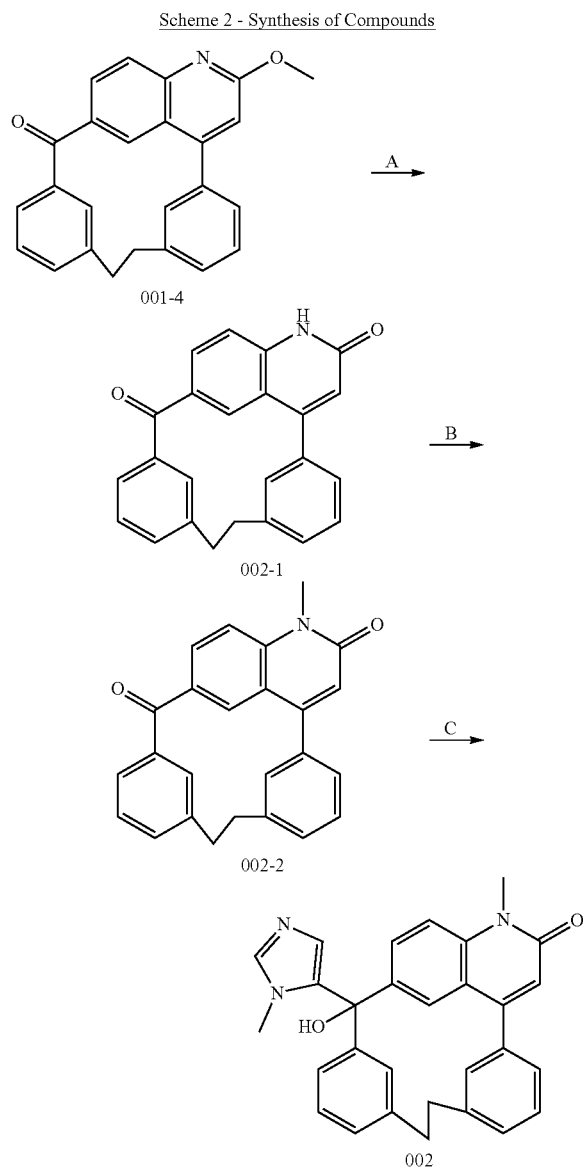

Step A: Preparation of (002-1)

To a solution of 001-4 (198.9 mg, 544.30 µmol) in THF (8 mL) was added HCl (4M in H$_2$O, 4.08 mL). The reaction mixture was stirred at 70° C. for 16 h. The reaction mixture was adjusted to pH=7 with NaOH (10M in H$_2$O) solution and diluted with EtOAc (50 mL). The mixture was extracted with EtOAc (50 mL×3). The organic layer was dried over Na$_2$SO$_4$ and concentrated under reduced pressure to give 002-1 (191.27 mg, 544.30 µmol, 100% yield) as a white solid, which was used directly for the next step without further purification. LCMS $R_t$=0.81 min in 1.5 min chromatography, 5-95AB, ESI calcd. for $C_{24}H_{18}NO_2$ [M+H]$^+$ 352.1, found 351.9.

Step B: Preparation of (002-2)

To a solution of 002-1 (191.27 mg, 544.30 µmol) in THF (6 mL) were added BTEAC (37.19 mg, 163.29 µmol) and NaOH (10M in H$_2$O, 54.43 mmol, 5.44 mL). The mixture was stirred at 25° C. for 5 min. Then iodomethane (0.25 g, 1.76 mmol) was added to the mixture and the reaction was stirred at 25° C. for 16 h. The reaction was diluted with water (5 mL) and extracted with EtOAc (5 mL×3). The organic layer was separated and dried over Na$_2$SO$_4$ and concentrated. The residue was purified by flash chromatography on silica gel (MeOH in DCM=0 to 10%) to give 002-2 (198.9 mg, 544.30 µmol, 100% yield) as yellow oil. LCMS $R_t$=0.85 min in 1.5 min chromatography, 5-95AB, ESI calcd. for $C_{25}H_{20}NO_2$ [M+H]$^+$ 366.1, found 366.0.

Step C: Preparation of 3-hydroxy-2$^1$-methyl-3-(1-methyl-1H-imidazol-5-yl)-2$^1$,2$^2$-dihydro-2(4,6)-quinolina-1,4(1,3)-dibenzenacyclohexaphan-2$^2$-one (002)

To a solution of 1-methyl-1H-imidazole (53.63 mg, 653.16 µmol) in THF (1 mL) was added n-BuLi (2.5M in n-hexane, 653.16 µmol, 261.26 µL) dropwise at −78° C. under N$_2$. The mixture was stirred at −78° C. for 1 h. Et$_3$SiCl (98.45 mg, 653.16 µmol) in THF (0.5 mL) was added to the mixture dropwise at −78° C. and the mixture was stirred at −78° C. for 1 h. Then n-BuLi (2.5M in n-hexane, 653.16 µmol, 261.26 µL) was added to the mixture dropwise at −78° C. and the mixture was stirred at −78° C. for 1 h. A solution of 002-2 (198.9 mg, 544.30 µmol) in THF (5 mL) was added to the above mixture dropwise at −78° C. and the mixture was stirred at −78° C. for 1 h. The reaction was quenched with water (0.4 mL). The solvents were removed in vacuum and the residue was purified by Prep-HPLC (Xtimate C$_{18}$ 100×30 mm×3 m, water (10 mM NH$_4$HCO$_3$)-ACN as mobile phase, from 43-83%, Flow Rate (ml/min): 30) to give 002 (0.021 g, 47.15 µmol, 8.66% yield) as a white solid. $^1$H NMR (400 MHz, DMSO-d$_6$) δ=8.02-8.00 (m, 1H), 7.60-7.55 (m, 2H), 7.42-7.41 (m, 1H), 7.35-7.33 (m, 2H), 7.28-7.27 (m, 3H), 7.26-7.17 (m, 1H), 6.65 (s, 1H), 6.54-6.53 (m, 2H), 6.48 (s, 1H), 6.11 (s, 1H), 3.66 (s, 3H), 3.38 (s, 3H), 3.25-3.18 (m, 2H), 2.79-2.77 (m, 1H), 2.69-2.67 (m, 1H). LCMS $R_t$=1.68 min in 3 min chromatography, 10-80CD, ESI calcd. for $C_{29}H_{26}N_3O_2$ [M+H]$^+$ 448.2, found 448.3. HPLC $R_t$=3.08 min in 8 min chromatography, 220 nm, purity 100%.

Example 3: Preparation of Compound 3

Scheme 3 - Synthesis of Compound 3

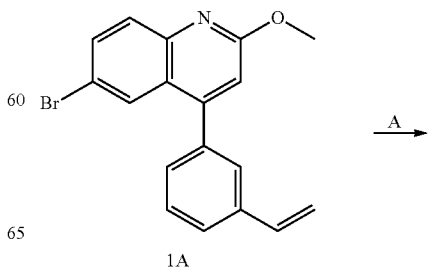

129
-continued

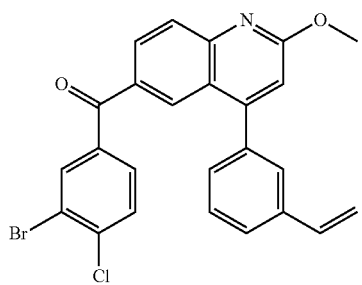
003-1

B →

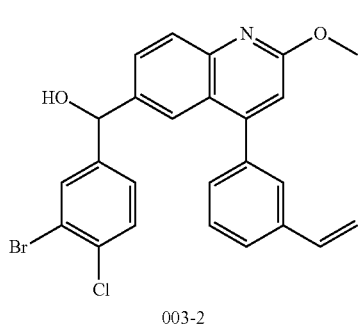
003-2

C →

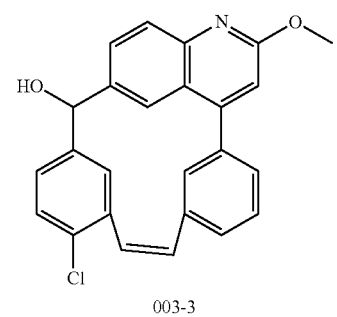
003-3

D →

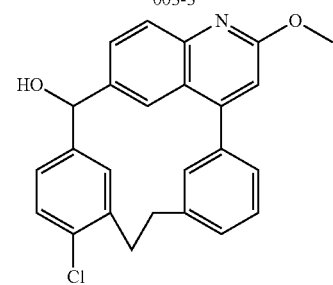
003-4

E →

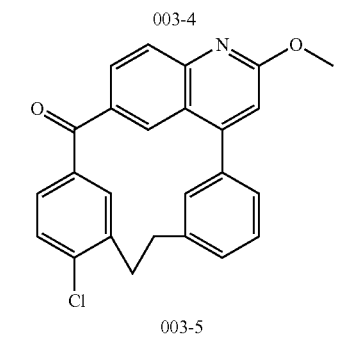
003-5

F →

130
-continued

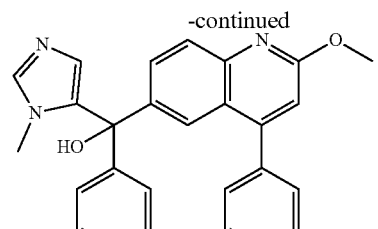
003-6

G →

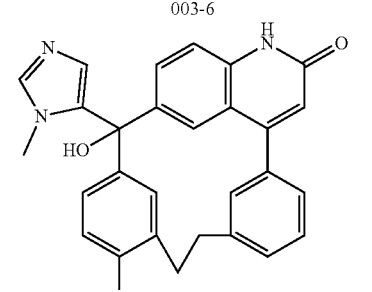
003-7

H →

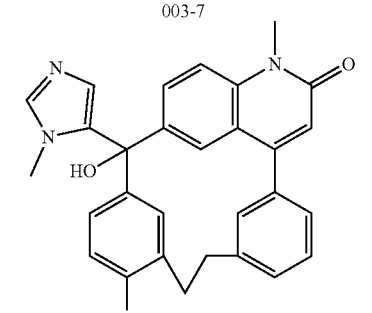
rac-003

I →

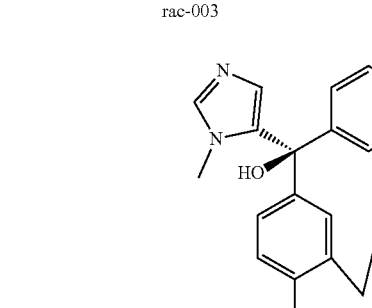
(S)-003

Step A: Preparation of (003-1)

To a solution of 1A (2 g, 5.88 mmol) in THF (20 mL) was added n-BuLi (2.5M in n-hexane, 6.47 mmol, 2.59 mL) dropwise at −70° C. The mixture was stirred at −70° C. for 30 min. Then a mixture of 3-bromo-4-chloro-N-methoxy-N-methylbenzamide (1.64 g, 5.88 mmol) (WO2009/152082, 2009, A1) in THF (5 mL) was added to the above mixture dropwise via syringe and the reaction mixture was stirred at −70° C. for 1.5 h. The reaction was quenched with water (20 mL) and diluted with EtOAc (50 mL). The aqueous layer was extracted with EtOAc (50 mL×3). The organic layer was dried over anhydrous $Na_2SO_4$ and concentrated under reduced pressure. The crude was purified by flash chromatography on silica gel (EtOAc in petroleum ether=0 to 4%) to give 003-1 (1.0 g, 2.09 mmol, 35.53% yield) as yellow oil. $^1$H NMR (400 MHz, CDCl$_3$) δ=8.17 (d, J=2.0 Hz, 1H), 8.03-7.99 (m, 3H), 7.63 (dd, J=1.6, 8.0 Hz, 1H), 7.52-7.43 (m, 4H), 7.33 (d, J=7.2 Hz, 1H), 6.93 (s, 1H), 6.73 (dd, J=10.8, 17.6 Hz, 1H), 5.77 (d, J=17.6 Hz, 1H), 5.31 (d, J=11.2 Hz, 1H), 4.13 (s, 3H). LCMS R$_t$=1.21 min in 1.5 min chromatography, 5-95AB, ESI calcd. for C$_{25}$H$_{18}$BrClNO$_2$ [M+H]$^+$ 478.0, found 478.1.

Step B: Preparation of (003-2)

To a solution of 003-1 (0.9 g, 1.88 mmol) in THF (20 mL) was added NaBH$_4$ (106.67 mg, 2.82 mmol). The reaction mixture was stirred at 25° C. for 16 h. The reaction mixture was quenched with water (1.0 mL). The solvents were removed under reduced pressure. The residue was purified by flash chromatography on silica gel (EtOAc in petroleum ether=0 to 12%) to give 003-2 (0.77 g, 1.60 mmol, 85.11% yield) as yellow oil. $^1$H NMR (400 MHz, CDCl$_3$) δ=7.86 (d, J=8.4 Hz, 1H), 7.72 (d, J=2.0 Hz, 1H), 7.62 (d, J=1.6 Hz, 1H), 7.51-7.46 (m, 4H), 7.45-7.34 (m, 2H), 7.23-7.21 (m, 1H), 6.86 (s, 1H), 6.75 (dd, J=10.8, 17.2 Hz, 1H), 5.82-5.76 (m, 2H), 5.31 (d, J=10.8 Hz, 1H), 4.08 (s, 3H), 2.28 (d, J=3.2 Hz, 1H). LCMS R$_t$=1.12 min in 1.5 min chromatography, 5-95AB, ESI calcd. for C$_{25}$H$_{20}$BrClNO$_2$ [M+H]$^+$ 480.0, found 480.0.

Step C: Preparation of (003-3)

To a solution of 003-2 (1.3 g, 2.70 mmol) in dioxane (250 mL) was added tri-o-tolylphosphane (164.60 mg, 540.79 μmol) and TEA (820.83 mg, 8.11 mmol, 1.13 mL). Pd(OAc)$_2$ (60.71 mg, 270.39 μmol) was added to the mixture under N$_2$. The reaction was stirred at 100° C. for 16 h. The solvent was removed under reduced pressure. The residue was purified by flash chromatography on silica gel (1$^{st}$: EtOAc in petroleum ether=0 to 12%; 2nd: EtOAc in petroleum ether=0 to 14%) to give 003-3 (0.24 g, 600.20 μmol, 22.20% yield) as a white solid. $^1$H NMR (400 MHz, CDCl$_3$) δ=7.90 (s, 1H), 7.77-7.69 (m, 3H), 7.53-7.44 (m, 2H), 7.39-7.36 (m, 1H), 7.22-7.20 (m, 2H), 7.06 (d, J=8.0 Hz, 1H), 6.87 (s, 1H), 6.77 (s, 2H), 5.94 (br s, 1H), 4.05 (s, 3H), 2.45 (d, J=2.8 Hz, 1H). LCMS R$_t$=1.05 min in 1.5 min chromatography, 5-95AB, ESI calcd. for C$_{25}$H$_{19}$ClNO$_2$ [M+H]$^+$ 400.1, found 400.0.

Step D: Preparation of (003-4)

To a solution of 003-3 (0.33 g, 825.27 μmol) in EtOAc (30 mL) was added Pd/C (17.57 mg, 16.51 μmol, 10% purity). The reaction mixture was stirred at 25° C. for 1 h under H$_2$ balloon (15 psi). The solid was filtered off and washed with EtOAc (30 mL). The filtrate was concentrated under reduced pressure to give 003-4 (0.35 g, 825.27 μmol, 100% yield) as a white solid, which was used directly for the next step without further purification. LCMS R$_t$=1.04 min in 1.5 min chromatography, 5-95AB, ESI calcd. for C$_{25}$H$_{21}$ClNO$_2$ [M+H]$^+$ 402.1, found 402.1.

Step E: Preparation of (003-5)

To a solution of 003-4 (0.35 g, 825.27 μmol) in DCM (40 mL) was added MnO$_2$ (378.58 mg, 4.35 mmol). The reaction mixture was stirred at 40° C. for 2 h. The solid was filtered off and washed with DCM (20 mL). The filtrate was concentrated. The crude was purified by flash chromatography on silica gel (EtOAc in petroleum ether=0 to 10%) to give 003-5 (0.33 g, 825.27 μmol, 100% yield) as a white solid. $^1$H NMR (400 MHz, CDCl$_3$) δ=8.44-8.24 (m, 1H), 8.04-7.95 (m, 2H), 7.73-7.71 (m, 1H), 7.64-7.61 (m, 1H), 7.55 (s, 1H), 7.49-7.28 (m, 3H), 7.23 (d, J=8.0 Hz, 1H), 7.15-6.89 (m, 1H), 4.14 (s, 3H), 3.42-3.34 (m, 4H). LCMS R$_t$=1.15 min in 1.5 min chromatography, 5-95AB, ESI calcd. for C$_{25}$H$_{19}$ClNO$_2$ [M+H]$^+$ 400.1, found 400.1.

Step F: Preparation of (003-6)

Under dry N$_2$ flow, to a solution of 1-methyl-1H-imidazole (81.31 mg, 990.33 μmol, 78.94 μL) in THF (10 mL) was added n-BuLi (2.5M in n-hexane, 990.33 μmol, 396.13 μL) dropwise at −78° C. under N$_2$. The mixture was stirred at −78° C. for 1 h. Et$_3$SiCl (149.26 mg, 990.33 μmol) in THF (1.0 mL) was added to the mixture dropwise at −78° C. and the mixture was stirred at −78° C. for 1 h. Then n-BuLi (2.5M in n-hexane, 990.33 μmol, 396.13 μL) was added to the mixture dropwise at −78° C. and the mixture was stirred at −78° C. for 1 h. A solution of 003-5 (0.33 g, 825.27 μmol) in THF (10 mL) was added to the above mixture dropwise at −78° C. and the mixture was stirred at −78° C. for 1 h. The reaction was quenched with water (10 mL), and the mixture was extracted with EtOAc (10 mL×3). The combined organic phase was washed with brine (10 mL), dried over anhydrous Na$_2$SO$_4$, filtered and concentrated. The crude was purified by flash chromatography on silica gel (MeOH in DCM=0 to 3%) to give 003-6 (0.22 g, 456.46 μmol, 55.31% yield) as white solid. $^1$H NMR (400 MHz, CDCl$_3$) δ=8.01-7.97 (m, 1H), 7.85-7.81 (m, 1H), 7.70-7.61 (m, 1H), 7.49-7.25 (m, 6H), 7.16-6.99 (m, 1H), 6.88-6.86 (m, 1H), 6.77-6.68 (m, 1H), 6.43-6.38 (m, 1H), 6.15 (s, 1H), 4.06 (s, 3H), 3.53-3.48 (m, 1H), 3.33 (s, 3H), 3.10-3.06 (m, 1H), 2.90-2.84 (m, 1H), 2.58-2.52 (m, 1H). LCMS R$_t$=0.90 min in 1.5 min chromatography, 5-95AB, ESI calcd. for C$_{29}$H$_{25}$ClN$_3$O$_2$ [M+H]$^+$ 482.2, found 482.2.

Step G: Preparation of (003-7)

To a solution of 003-6 (0.18 g, 373.47 μmol) in THF (8 mL) was added HCl (4M in H$_2$O, 16.06 mmol, 4.01 mL). The reaction mixture was stirred at 70° C. for 16 h. The reaction mixture was adjusted to pH=7 with NaOH (10M in H$_2$O) solution and diluted with EtOAc (50 mL). The aqueous layer was extracted with EtOAc (50 mL×3). The organic layer was dried over anhydrous Na$_2$SO$_4$, filtered and concentrated under reduced pressure to give 003-7 (0.17 g, 363.29 μmol, 97.27% yield) as a white solid, which was used directly for the next step without further purification. LCMS R$_t$=0.80 min in 1.5 min chromatography, 5-95AB, ESI calcd. for C$_{28}$H$_{23}$ClN$_3$O$_2$ [M+H]$^+$ 468.1, found 468.1.

Step H: Preparation of (rac)-4$^4$-chloro-3-hydroxy-2$^1$-methyl-3-(1-methyl-1H-imidazol-5-yl)-2$^1$,2$^2$-dihydro-2(4,6)-quinolina-1,4(1,3)-dibenzenacyclohexaphan-2$^2$-one (rac-003)

To a solution of 003-7 (0.17 g, 363.29 μmol) in THF (10 mL) were added BTEAC (41.37 mg, 181.65 μmol) and NaOH (10M in H$_2$O, 36.33 mmol, 3.63 mL). The mixture was stirred at 25° C. for 5 min. Then iodomethane (0.44 g, 3.10 mmol) was added to the mixture and the reaction was stirred at 25° C. for 2 h. The reaction was quenched water (10 mL) and extracted with EtOAc (10 mL×3). The organic layer was separated and dried over anhydrous Na$_2$SO$_4$, filtered and concentrated. The residue was purified by flash chromatography on silica gel (MeOH in DCM=0 to 10%) to give rac-003 (0.12 g, 248.98 μmol, 68.53% yield) as a white solid. LCMS $R_t$=0.81 min in 1.5 min chromatography, 5-95AB, ESI calcd. for $C_{29}H_{25}ClN_3O_2$ [M+H]$^+$ 482.2, found 482.2.

Step I: Preparation of (S)-4$^4$-chloro-3-hydroxy-2$^1$-methyl-3-(1-methyl-1H-imidazol-5-yl)-2$^1$, 2$^2$-dihydro-2(4,6)-quinolina-1,4(1,3)-dibenzenacyclohexaphan-2$^2$-one ((S)-003)

rac-003 (0.1 g, 207.48 μmol) was separated by SFC (column: (s,s) WHELK-01 (250 mm×30 mm, 5 m); mobile phase: [0.1% NH$_3$H$_2$O EtOH]; B %: 35%-65%, min) to give (S)-003 (0.0354 g, 73.45 μmol, 35.40% yield) as an off-white solid. $^1$H NMR (400 MHz, CD$_3$CN) δ=7.95-7.92 (m, 1H), 7.48-7.31 (m, 8H), 6.63-6.56 (m, 2H), 6.40-6.24 (m, 1H), 6.04 (s, 1H), 4.93 (br s, 1H), 3.65 (s, 3H), 3.52-3.46 (m, 1H), 3.33 (s, 3H), 3.16-3.11 (m, 1H) 2.91-2.71 (m, 1H), 2.66-2.45 (m, 1H). LCMS $R_t$=1.85 min in 3 min chromatography, 10-80CD, ESI calcd. for $C_{29}H_{25}ClN_3O_2$ [M+H]$^+$ 482.2, found 482.1. HPLC $R_t$=3.54 min in 8 min chromatography, 220 nm, purity 100%. Chiral HPLC (S)-003: $R_t$=3.55 min in 6 min (ee 100%) ((SS)Whelk-01_EtOH (DEA)_60), ((R)-003: $R_t$=2.23 min (ee 100%)).

Example 4: Preparation of Compound 4

Scheme 4 - Synthesis of Compound 4

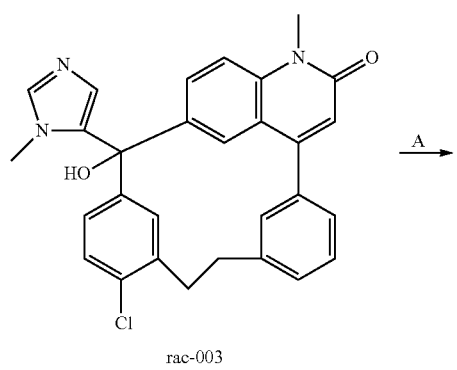

rac-003

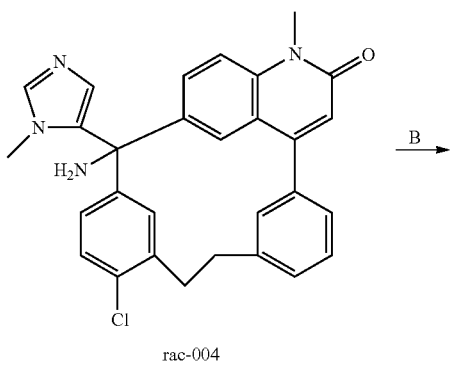

rac-004

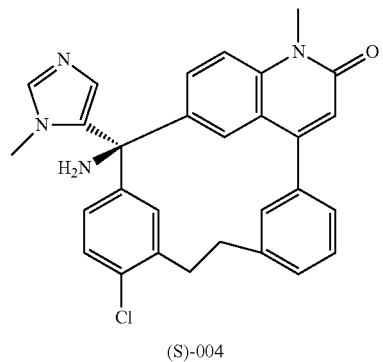

(S)-004

Step A: Preparation of (rac)-3-amino-4$^4$-chloro-2$^1$-methyl-3-(1-methyl-1H-imidazol-5-yl)-2$^1$,2$^2$-dihydro-2(4,6)-quinolina-1,4(1,3)-dibenzenacyclohexaphan-2$^2$-one (rac-004)

To a solution of rac-003 (0.1 g, 207.48 μmol) in DMI (3 mL) was added SOCl$_2$ (197.47 mg, 1.66 mmol, 120.41 μL) dropwise at 0° C. The mixture was stirred at 35° C. for 1.5 h. The above mixture was added to NH$_3$ in MeOH (7M, 14.27 mL) dropwise by syringe at 0° C. Then the mixture was stirred at 25° C. for 16 h. MeOH was removed under reduced pressure. The crude was purified by flash chromatography on silica gel (MeOH in DCM=0 to 5%) to give rac-004 (0.07 g, 145.53 μmol, 70.14% yield) as a white solid. LCMS $R_t$=0.78 min in 1.5 min chromatography, 5-95AB, ESI calcd. for $C_{29}H_{26}ClN_{4O}$ [M+H]$^+$ 481.2, found 481.1. HPLC $R_t$=6.59 min in 15 min chromatography, 220 nm, purity 93.82%.

Step B: Preparation of (S)-3-amino-4$^4$-chloro-2$^1$-methyl-3-(1-methyl-1H-imidazol-5-yl)-2$^1$,2$^2$-dihydro-2(4,6)-quinolina-1,4(1,3)-dibenzenacyclohexaphan-2$^2$-one ((S)-004)

rac-004 (0.07 g, 145.53 μmol) was separated by SFC (column: DAICEL CHIRALCEL OD-H (250 mm×30 mm, 5 m); mobile phase: [0.1% NH$_3$H$_2$O EtOH]; B %: 55%-55%, min) to give (S)-004 (33.0 mg, 68.61 μmol, 47.14% yield) as an off-white solid. $^1$H NMR (400 MHz, CD$_3$CN) δ=7.99-7.97 (m, 1H), 7.51-7.29 (m, 8H), 6.72-6.68 (m, 1H), 6.58 (s, 1H), 6.40-6.32 (m, 1H), 6.13-5.86 (m, 1H), 3.67 (s, 3H), 3.49-3.45 (m, 1H), 3.35 (s, 3H), 3.18-3.14 (m, 1H), 2.96-2.76 (m, 1H), 2.73-2.53 (m, 1H). LCMS $R_t$=1.79 min in 3 min chromatography, 10-80CD, ESI calcd. for $C_{29}H_{26}ClN_{4O}$ [M+H]$^+$ 481.2, found 481.1. HPLC $R_t$=3.33 min in 8 min chromatography, 220 nm, purity 100%. Chiral HPLC (S)-004: $R_t$=5.68 min in 10 min (ee 100%) (OD_ETOH_DEA_40_2.8ML_10CM), ((R)-004: $R_t$=2.94 min (ee 97.70%)).

Example 5: Preparation of Compound 5

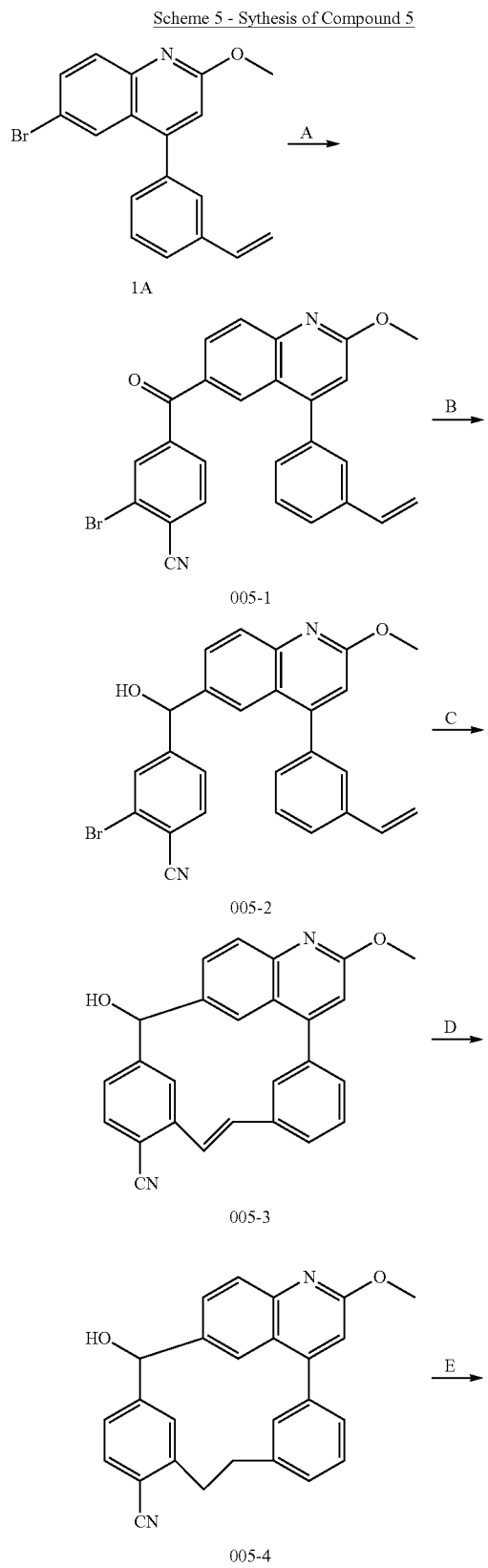

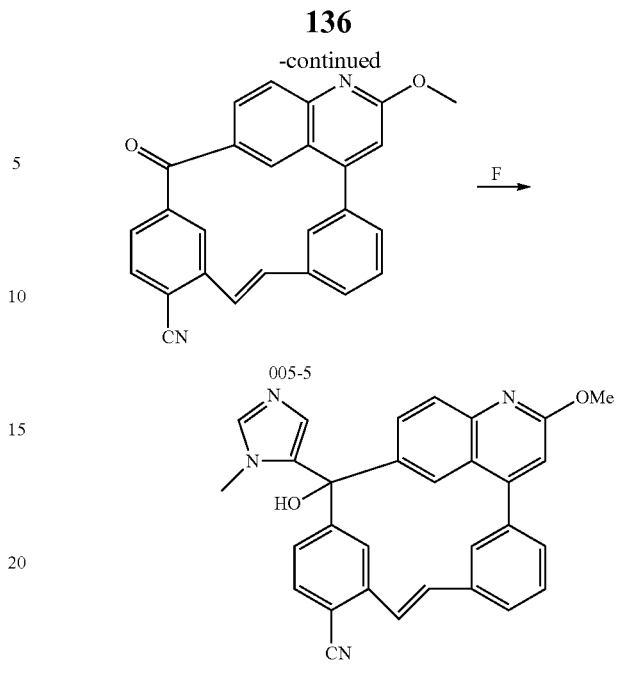

Step A: Preparation of (005-1)

To a solution of 1A (13 g, 38.21 mmol) in THF (170 mL) was added n-BuLi (2.5M in n-hexane, 16.81 mL, 49.67 mmol) dropwise at −78° C. under $N_2$. The mixture was stirred at −78° C. for 20 min. Then a solution of 4A (13.37 g, 49.67 mmol) in THF (30 mL) was added to the above mixture under $N_2$. The reaction mixture was stirred at −78° C. for 2 h. The reaction mixture was quenched with water (30 mL), and the mixture was extracted with EtOAc (30 mL×2). The combined organic phase was washed with brine (50 mL), dried over anhydrous $Na_2SO_4$, filtered and concentrated. The solvent was removed under reduced pressure. The crude was purified by flash chromatography on silica gel (EtOAc in petroleum ether=0 to 10%) to give 005-1 (6.5 g, 13.85 mmol, 36.24% yield) as a yellow solid. $^1$H NMR (400 MHz, CDCl$_3$) δ=8.14-8.13 (m, 1H), 8.05-8.00 (m, 3H), 7.73-7.72 (m, 2H), 7.49-7.43 (m, 3H), 7.40-7.32 (m, 1H), 6.94 (d, J=3.2 Hz, 1H), 6.74 (dd, J=10.8 Hz, J=17.2 Hz, 1H), 5.78 (d, J=17.2 Hz, 1H), 5.33 (d, J=10.8 Hz, 1H), 4.13 (s, 3H). LCMS $R_t$=1.08 min in 1.5 min chromatography, 5-95AB, ESI calcd. for $C_{26}H_{18}BrN_2O_2$ [M+H]$^+$ 469.1, found 468.8.

Step B: Preparation of (005-2)

To a solution of 005-1 (6.5 g, 13.85 mmol) in THF (120 mL) was added NaBH$_4$ (681.11 mg, 18.00 mmol) at 0° C. The reaction mixture was stirred at 25° C. for 2 h. The reaction mixture was quenched with water (0.5 mL). The solvents were removed under reduced pressure. The crude was purified by flash chromatography on silica gel (EtOAc in petroleum ether=0 to 20%) to give 005-2 (4.46 g, 9.46 mmol, 68.30% yield) as colorless oil. $^1$H NMR (400 MHz, CDCl$_3$) δ=7.88 (d, J=8.8 Hz, 1H), 7.72-7.68 (m, 2H), 7.56-7.52 (m, 6H), 7.51-7.31 (m, 2H), 6.75 (dd, J=10.4 Hz, J=17.2 Hz, 1H), 5.86-5.75 (m, 2H), 5.33 (d, J=10.8 Hz, 1H), 4.07 (s, 3H), 2.42 (d, J=3.6 Hz, 1H). LCMS $R_t$=1.01 min in 1.5 min chromatography, 5-95AB, ESI calcd. for $C_{26}H_{20}BrN_2O_2$ [M+H]$^+$ 471.1, found 471.0.

Step C: Preparation of (005-3)

To a solution of 005-2 (4 g, 8.49 mmol) in dioxane (400 mL) was added tri-o-tolylphosphane (516.59 mg, 1.70 mmol) and TEA (2.58 g, 25.46 mmol, 3.54 mL). Pd(OAc)$_2$ (190.53 mg, 848.64 µmol) was added to the mixture under N$_2$. The reaction was stirred at 100° C. for 16 h under N$_2$. The solvent was removed under reduced pressure. The crude was purified by flash chromatography on silica gel (1$^{st}$: EtOAc in petroleum ether=0 to 40%; 2$^{nd}$: EtOAc in petroleum ether=0 to 32%) to give 005-3 (1.1 g, 2.82 mmol, 33.23% yield) as a yellow solid. $^1$H NMR (400 MHz, CDCl$_3$) δ=7.99 (s, 1H), 7.77-7.75 (m, 1H), 7.70-7.66 (m, 2H), 7.56-7.46 (m, 2H), 7.43-7.39 (m, 1H), 7.30-7.28 (m, 1H), 7.22-7.20 (m, 1H), 7.15-7.04 (m, 3H), 6.88 (s, 1H), 5.99 (s, 1H), 4.05 (s, 3H), 2.76 (d, J=1.6 Hz, 1H). LCMS R$_t$=0.91 min in 1.5 min chromatography, 5-95AB, ESI calcd. for C$_{26}$H$_{19}$N$_2$O$_2$ [M+H]$^+$ 391.1, found 391.0. HPLC R$_t$=10.21 min in 15 min chromatography, 220 nm, purity 94.27%.

Step D: Preparation of (005-4)

To a mixture of 005-3 (1 g, 2.56 mmol) in THF (40 mL) and MeOH (20 mL) was added Pd/C (1.38 g, 1.28 mmol, 10% purity) at 25° C. under N$_2$. The suspension was degassed under vacuum and purged with H$_2$ three times. The mixture was stirred under H$_2$ (15 psi) at 25° C. for 10 h. The mixture was filtered and the filter liquid was concentrated under reduced pressure to afford 005-4 (0.9 g, 2.29 mmol, 89.45% yield) as a yellow solid, which was no purification and used into next step directly. $^1$H NMR (400 MHz, DMSO-d$_6$) δ=7.87 (d, J=8.0 Hz, 1H), 7.76 (d, J=8.4 Hz, 1H), 7.73-7.67 (m, 1H), 7.57-7.50 (m, 2H), 7.46-7.39 (m, 2H), 7.28-7.22 (m, 1H), 6.96-6.83 (m, 2H), 6.51 (s, 1H), 6.32 (s, 1H), 5.93 (d, J=4.4 Hz, 1H), 3.98 (s, 3H), 3.24-3.05 (m, 4H).

Step E: Preparation of (005-5)

To a mixture of 005-4 (0.9 g, 2.29 mmol) in DCM (20 mL) was added MnO$_2$ (3.99 g, 45.87 mmol) at 25° C. under N$_2$. The mixture was stirred at 40° C. for 10 h. The mixture was filtered. The filter liquid was concentrated under reduced pressure. The residue was purified by flash chromatography on silica gel (EtOAc in petroleum ether=0 to 20%) to afford 005-5 (0.6 g, 1.54 mmol, 67.25% yield) as a yellow solid. $^1$H NMR (400 MHz, DMSO-d$_6$) δ=8.28-8.18 (m, 2H), 8.02-7.93 (m, 2H), 7.84-7.91 (m, 2H), 7.64 (d, J=8.0 Hz, 1H), 7.51-7.29 (m, 3H), 7.22 (s, 1H), 4.16-4.01 (m, 3H), 3.60-3.38 (m, 4H).

Step F: Preparation of 3-hydroxy-2²-methoxy-3-(1-methyl-1H-imidazol-5-yl)-2(4,6)-quinolina-1,4(1,3)-dibenzenacyclohexaphane-4⁴-carbonitrile (005)

To a solution of 1-methyl-1H-imidazole (94.63 mg, 1.15 mmol, 91.87 µL) in THF (5 mL) was added n-BuLi (2.5M in n-hexane, 1.15 mmol, 461.03 µL) at −75° C. under N$_2$. The mixture was stirred at −75° C. for 30 min, then Et$_3$SiCl (173.72 mg, 1.15 mmol, 196.07 µL) was added dropwise at −75° C. The mixture stirred at −75° C. for 30 min. Then n-BuLi (2.5M in n-hexane, 1.15 mmol, 461.03 µL) was added dropwise at −75° C. and stirred at −75° C. for 1 h. A solution of 005-5 (300 mg, 768.38 µmol) in THF (5 mL) was added above reaction at −75° C., and this mixture was stirred at −75° C. for 1 h. The reaction mixture was poured into saturated NH$_4$Cl solution (50 mL). The aqueous layer was extracted with EtOAc (50 mL×2). The combined organic layers were washed with brine (50 mL×2), dried over anhydrous Na$_2$SO$_4$, filtered and the filter cake was washed with EtOAc (20 mL). The combined filtrates were concentrated. The crude product was purified by flash chromatography on silica gel (MeOH in DCM=0 to 3%) and Prep-HPLC (column: Welch Xtimate C$_{18}$ $_{150\times25}$ mm×5 m; mobile phase: [water (0.05% ammonia hydroxide v/v)-MeOH]; B %: 65%-95%, 7.8 min) to give 005 (114.6 mg, 242.52 µmol, 31.56% yield) as an off-white solid. $^1$H NMR (400 MHz, DMSO-d$_6$) δ=8.11-8.04 (m, 1H), 7.85 (d, J=8.8 Hz, 1H), 7.74 (d, J=8.4 Hz, 1H), 7.59-7.52 (m, 2H), 7.51-7.44 (m, 1H), 7.43-7.32 (m, 3H), 7.05-6.95 (m, 2H), 6.84 (s, 1H), 6.62 (s, 1H), 6.11 (s, 1H), 4.04 (s, 3H), 3.52-3.43 (m, 1H), 3.37 (s, 3H), 3.31-3.22 (m, 1H), 3.04-2.92 (m, 2H). LCMS R$_t$=1.94 min in 3.0 min chromatography, 10-80CD, ESI calcd. for C$_{30}$H$_{25}$N$_4$O$_2$ [M+H]$^+$ 473.2, found 473.2. HPLC R$_t$=3.77 min in 8 min chromatography, 220 nm, purity 99.68%.

Example 6: Preparation of Compound 6

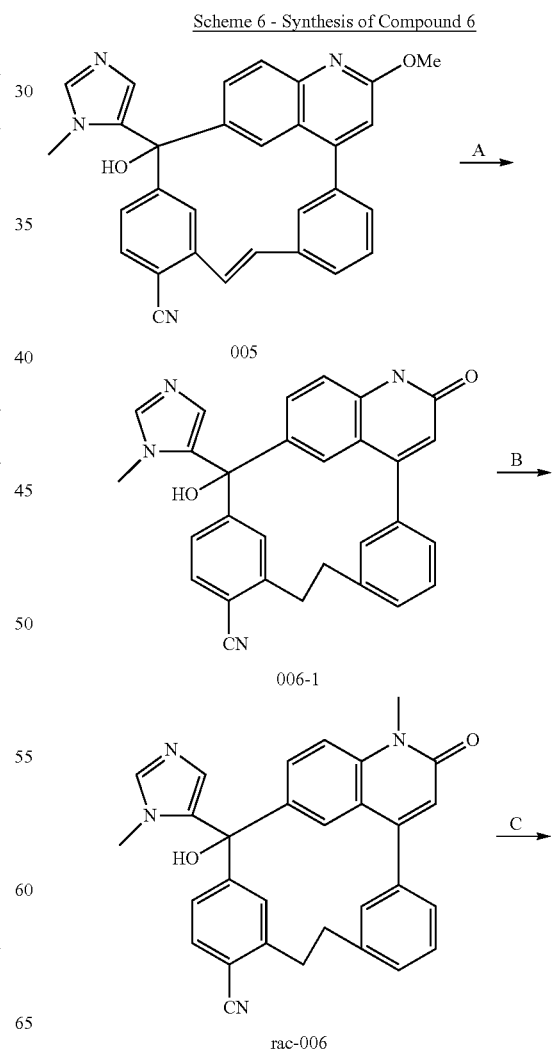

Scheme 6 - Synthesis of Compound 6

005

006-1 rac-006

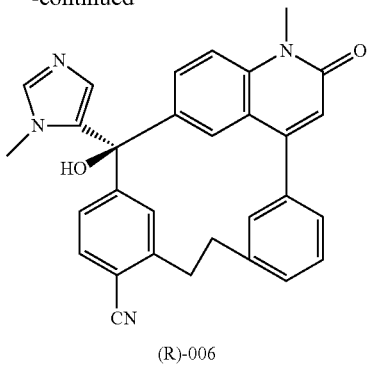

(R)-006

Step A: Preparation of (006-1)

To a solution of 005 (0.6 g, 1.27 mmol) in THF (20 mL) was added HCl (4M in H$_2$O, 40.01 mmol, 10 mL). The reaction mixture was stirred at 60° C. for 16 h. 006-1 (0.58 g, 1.26 mmol, 99.21% yield) was obtained as yellow liquid in THF, which was used directly for next step without further purification. LCMS R$_t$=0.67 min in 1.5 min chromatography, 5-95AB, ESI calcd. for C$_{29}$H$_{23}$N$_4$O$_2$ [M+H]$^+$ 459.2, found 459.0.

Step B: Preparation of (rac)-3-hydroxy-2$^1$-methyl-3-(1-methyl-1H-imidazol-5-yl)-2$^2$-oxo-2$^1$,2$^2$-dihydro-2(4,6)-quinolina-1,4(1,3)-dibenzenacyclohexaphane-4$^4$-carbonitrile (rac-006)

To a solution of 006-1 (0.58 g, 1.26 mmol) in THF (20 mL) were added BTEAC (143.50 mg, 630.00 μmol) and NaOH (10M in H$_2$O, 12.60 mmol, 1.26 mL) at 0° C. The mixture was stirred at 25° C. for 30 min. Then iodomethane (232.50 mg, 1.64 mmol) was added to the mixture and the reaction was stirred at 25° C. for 15.5 h. The reaction was diluted with water (10 mL) and extracted with EtOAc (10 mL×3). The organic layer was separated and dried over anhydrous Na$_2$SO$_4$ and concentrated. The residue was purified by flash chromatography on silica gel (MeOH in DCM=0 to 5%) to give rac-006 (0.59 g, 1.25 mmol, 99.21% yield) as a yellow solid. $^1$H NMR (400 MHz, CDCl$_3$) δ=8.02-7.97 (m, 1H), 7.77-7.62 (m, 2H), 7.52-7.44 (m, 3H), 7.38-7.29 (m, 3H), 7.03 (s, 1H), 6.83-6.78 (m, 1H), 6.66 (s, 1H), 6.21 (s, 1H), 3.65 (s, 3H), 3.62-3.56 (m, 1H), 3.35 (s, 3H), 3.24-3.21 (m, 1H), 2.89-2.63 (m, 2H). LCMS R$_t$=1.56 min in 1.5 min chromatography, 5-95AB, ESI calcd. for C$_{30}$H$_{25}$N$_4$O$_2$ [M+H]$^+$ 473.2, found 473.1. HPLC R$_t$=6.73 min in 15 min chromatography, 220 nm, purity 98.12%.

Step C: Preparation of (R)-3-hydroxy-2$^1$-methyl-3-(1-methyl-1H-imidazol-5-yl)-2$^2$-oxo-2$^1$,2$^2$-dihydro-2(4,6)-quinolina-1,4(1,3)-dibenzenacyclohexaphane-4$^4$-carbonitrile ((R)-006)

The rac-006 (90 mg, 190.46 μmol) was purified by SFC (column: (s,s) WHELK-01 (250 mm×30 mm, 5 m); mobile phase: [0.1% NH$_3$H$_2$O MeOH]; B %: 55%-55%, min) to give (R)-006 (12.5 mg, 26.45 μmol, 13.89% yield) as an off-white solid. $^1$H NMR (400 MHz, CD$_3$CN) δ=7.94 (d, J=8.4 Hz, 1H), 7.70 (d, J=8.4 Hz, 1H), 7.65-7.58 (m, 1H), 7.52-7.30 (m, 6H), 6.85-6.65 (m, 1H), 6.57 (s, 1H), 6.36-6.20 (m, 1H), 6.06 (s, 1H), 5.07 (s, 1H), 3.65 (s, 3H), 3.55-3.44 (m, 1H), 3.34-3.24 (m, 4H), 2.90-2.65 (m, 2H).

LCMS R$_t$=1.56 min in 3 min chromatography, 10-80CD, ESI calcd. for C$_{30}$H$_{25}$N$_4$O$_2$ [M+H]$^+$ 473.2, found 473.1. HPLC R$_t$=2.77 min in 8 min chromatography, 220 nm, purity 100%. Chiral HPLC (R)-006: R$_t$=7.55 min in 10 min (ee 99.67%) ((SS)Whelk-O1_MeOH(DEA)_40), ((S)-006: R$_t$=4.94 min (ee 100%)).

Example 7: Preparation of Compound 7

Scheme 7 - Synthesis of Compound 7

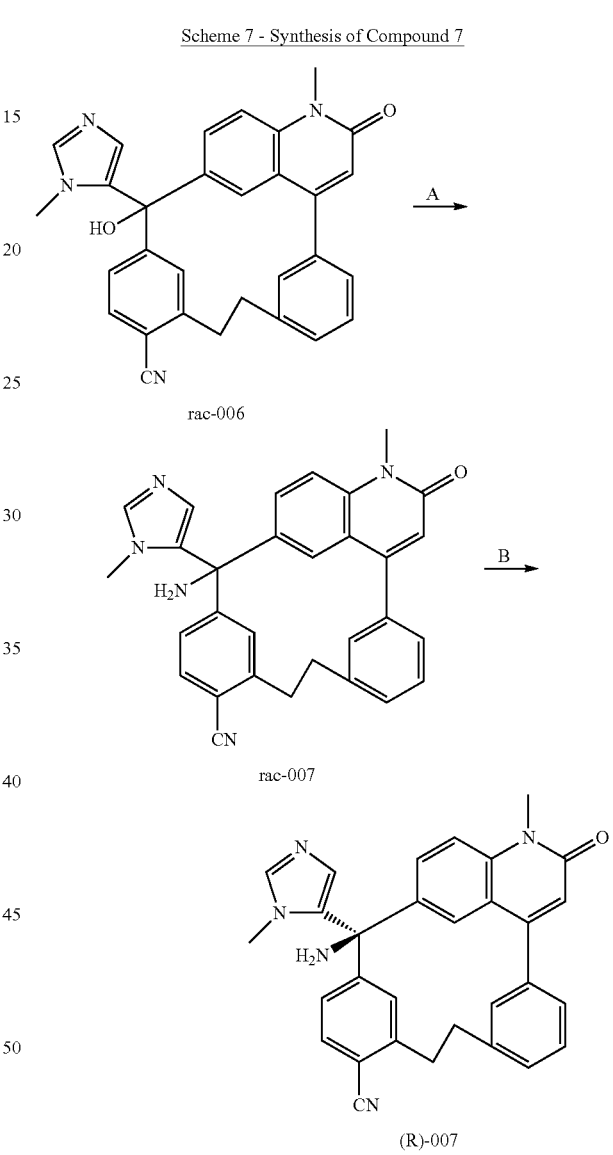

Step A: Preparation of (rac)-3-amino-2-methyl-3-(1-methyl-1H-imidazol-5-yl)-2$^2$-oxo-2$^1$,2$^2$-dihydro-2(4,6)-quinolina-1,4(1,3)-dibenzenacyclohexaphane-4$^4$-carbonitrile (rac-007)

To a solution of rac-006 (0.25 g, 529.06 μmol) in DMI (3 mL) was added SOCl$_2$ (629.42 mg, 5.29 mmol) dropwise at 0° C. The resulting mixture was stirred at 35° C. for 1 h. The mixture was added dropwise to NH$_3$ in MeOH (7M, 10.91 mL) at 0° C. The mixture was stirred at 25° C. for 2 h. The solvent was removed under reduced pressure. The crude was purified by flash chromatography on silica gel (MeOH in DCM=0 to 5%) to give rac-007 (160 mg, 339.30 μmol, 66.13% yield) as a white solid. LCMS $R_t$=0.68 min in 1.5 min chromatography, 5-95AB, ESI calcd. for $C_{30}H_{26}N_5O$ [M+H]⁺ 472.2, found 472.1. HPLC $R_t$=5.99 min in 15 min chromatography, 220 nm, purity 96.89%.

Step B: Preparation of (R)-3-amino-2¹-methyl-3-(1-methyl-1H-imidazol-5-yl)-2²-oxo-2¹,2²-dihydro-2(4,6)-quinolina-1,4(1,3)-dibenzenacyclohexaphane-4⁴-carbonitrile ((R)-007)

rac-007 (160 mg, 339.31 μmol) was separated by SFC (column: DAICEL CHIRALCEL OD-H (250 mm×30 mm, 5 m); mobile phase: [0.1% NH₃H₂O EtOH]; B %: 50%-50%, min) to give (R)-007 (37.9 mg, 80.37 μmol, 23.69% yield) as a white solid. ¹H NMR (400 MHz, DMSO-d₆) δ=8.08-8.06 (m, 1H), 7.71 (d, J=8.0 Hz, 1H), 7.58 (d, J=9.2 Hz, 1H), 7.49 (s, 1H), 7.43-7.35 (m, 3H), 7.28 (d, J=7.6 Hz, 1H), 7.07-7.03 (m, 2H), 6.63 (s, 1H), 6.56 (s, 1H), 6.10 (s, 1H), 3.67 (s, 3H), 3.47-3.43 (m, 1H), 3.33 (s, 3H), 3.28-3.25 (m, 1H), 3.06-2.99 (m, 4H). LCMS $R_t$=0.73 min in 1.5 min chromatography, 5-95AB, ESI calcd. for $C_{30}H_{26}N_5O$ [M+H]⁺ 472.2, found 472.2. HPLC $R_t$=5.99 min in 15 min chromatography, 220 nm, purity 100%. Chiral HPLC (R)-007: $R_t$=7.85 min in 14 min (ee 99.56%) (OD_3_EtOH_DEA_40_2.5ML), ((S)-007: $R_t$=4.85 min (ee 100%)).

Example 8: Preparation of Compound 8

Scheme 8 - Synthesis of Compound 8

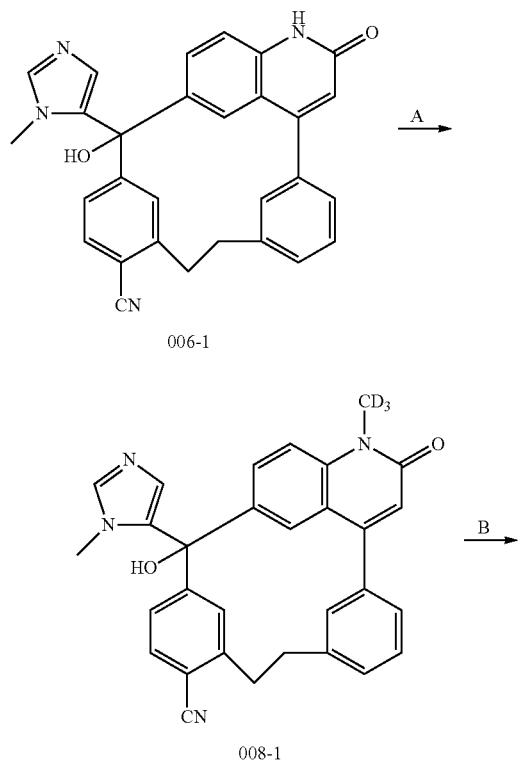

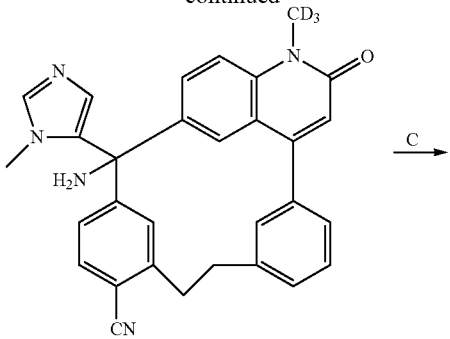

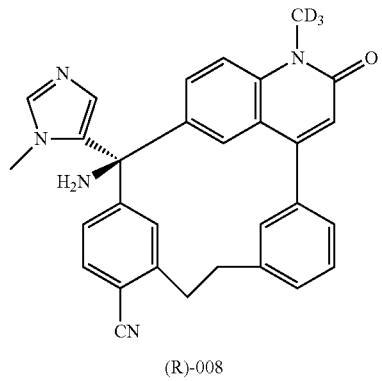

Step A: Preparation of (008-1)

To a mixture of 006-1 (0.2 g, 436.20 μmol) in DMF (2 mL) was added iodomethane-d₃ (123.83 mg, 872.39 μmol, 53.14 μL) and K2CO₃ (180.86 mg, 1.31 mmol) at 25° C. under N₂. The mixture was stirred at 25° C. for 3 h. The mixture was added into water (30 mL). The mixture was blended with another batch prepared from 0.2 g of 006-1. The aqueous phase was extracted with EtOAc (50 mL×3). The combined organic phase was washed with brine (80 mL), dried over anhydrous Na₂SO₄, filtered and concentrated under reduced pressure. The residue was purified by flash chromatography on silica gel (MeOH in DCM=0 to 15%) to afford 008-1 (300 mg, 630.84 μmol, 72.31% yield) as an off-white solid. ¹H NMR (400 MHz, DMSO-d₆) δ=8.05-7.94 (m, 1H), 7.81 (d, J=8.0 Hz, 1H), 7.64-7.53 (m, 3H), 7.52-7.24 (m, 4H), 7.10 (d, J=7.2 Hz, 1H), 6.93-6.67 (m, 1H), 6.57 (s, 1H), 6.45-6.00 (m, 2H), 3.42 (s, 3H), 3.32-3.19 (m, 4H).

Step B: Preparation of (rac)-3-amino-2¹-(methyl-d₃)-3-(1-methyl-1H-imidazol-5-yl)-2²-oxo-2¹,2²-dihydro-2(4,6)-quinolina-1,4(1,3)-dibenzenacyclohexaphane-4⁴-carbonitrile ((rac)-008)

To a solution of 008-1 (250 mg, 525.70 μmol) in DMI (3 mL) was added SOCl₂ (625.43 mg, 5.26 mmol, 381.36 μL) at 25° C. under N₂. Then the reaction mixture was stirred at 40° C. for 1 h. To NH₃ in MeOH (7M, 30 mL) was added the above mixture at −10° C. under N₂. The mixture was stirred at −10° C. for 0.5 h. The mixture was added into water (20 mL). The aqueous phase was extracted with EtOAc (50 mL×3). The combined organic phase was washed with brine (130 mL), dried over anhydrous Na₂SO₄, filtered and concentrated under reduced pressure. The residue was purified by flash chromatography on silica gel (MeOH in DCM=0 to 15%) to afford rac-008 (120 mg, 252.86 μmol, 48.10% yield) as an off-white solid. 1H NMR (400 MHz, DMSO-$d_6$) δ=8.16-7.91 (m, 1H), 7.76 (d, J=8.0 Hz, 1H), 7.65-7.22 (m, 7H), 7.11 (s, 1H), 6.88 (s, 1H), 6.57 (s, 1H), 5.97 (s, 1H), 3.36 (s, 3H), 3.28-3.19 (m, 2H), 3.11-2.78 (m, 2H).

Step C: Preparation of (R)-3-amino-$2^1$-(methyl-$d_3$)-3-(1-methyl-1H-imidazol-5-yl)-$2^2$-oxo-$2^1$,$2^2$-dihydro-2(4,6)-quinolina-1,4(1,3)-dibenzenacyclohexaphane-$4^4$-carbonitrile ((R)-008)

rac-008 (100 mg, 210.72 μmol) was separated by SFC (column: DAICEL CHIRALPAK AD (250 mm×30 mm, 10 m); mobile phase: [0.1% NH$_3$—H$_2$O IPA]; B %: 50%-50%, min) to afford (R)-008 (31.9 mg, 67.22 μmol, 31.90% yield) as an off-white solid. 1H NMR (400 MHz, DMSO-$d_6$) δ=8.07 (dd, J=2.0, 8.8 Hz, 1H), 7.71 (d, J=8.0 Hz, 1H), 7.58 (d, J=8.8 Hz, 1H), 7.52 (s, 1H), 7.46-7.40 (m, 2H), 7.40-7.33 (m, 1H), 7.29 (d, J=7.2 Hz, 1H), 7.10-7.00 (m, 2H), 6.63 (s, 1H), 6.57 (s, 1H), 6.12 (s, 1H), 3.51-3.43 (m, 1H), 3.33 (s, 3H), 3.30-3.22 (m, 1H), 3.09-2.95 (m, 4H). LCMS $R_t$=1.50 min in 3 min chromatography, 10-80CD, ESI calcd. for $C_{30}H_{23}D_3N_5O$ [M+H]$^+$ 475.2, found 475.2. HPLC $R_t$=2.57 min in 8 min chromatography, 220 nm, purity 100%. Chiral HPLC (R)-008: $R_t$=1.43 min in 2.5 min (ee 100%) (AD_IPA_DEA_40_4ML_5CM), ((S)-008: $R_t$=0.62 min (ee 100%)).

Example 9: Preparation of Compound 9

Scheme 9 - Synthesis of Compound 9

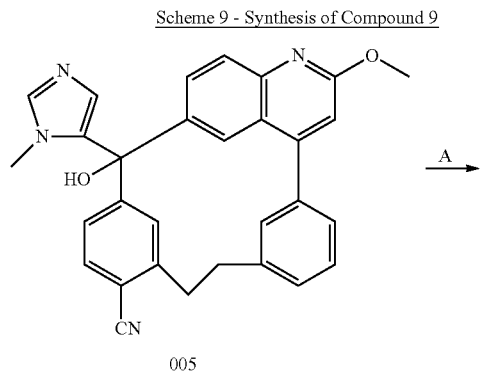

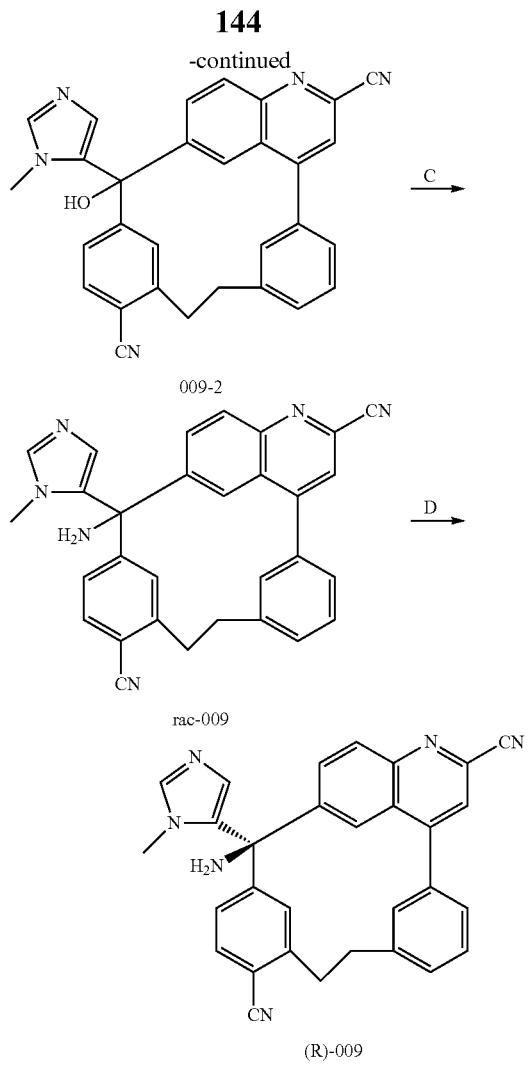

Step A: Preparation of (009-1)

To a mixture of 005 (0.25 g, 529.06 μmol) was added POCl$_3$ (811.21 mg, 5.29 mmol, 491.64 μL) at 25° C. under N$_2$. The mixture was stirred at 100° C. for 1 h. The mixture was cooled to 25° C. and NaOH solution (0.5M in H$_2$O) was added to adjust pH=8. The aqueous phase was extracted with DCM (50 mL×2). The combined organic phase was washed with brine (80 mL), dried over anhydrous Na$_2$SO$_4$, filtered and concentrated under reduced pressure. The residue was purified by flash chromatography on silica gel (MeOH in DCM=0 to 10%) to afford 009-1 (0.15 g, 314.49 μmol, 59.44% yield) as a yellow solid. $^1$H NMR (400 MHz, DMSO-$d_6$) δ=8.21 (d, J=8.8 Hz, 1H), 8.10-8.03 (m, 1H), 7.87-7.71 (m, 3H), 7.66-7.56 (m, 2H), 7.56-7.39 (m, 3H), 7.28 (s, 1H), 7.13-6.94 (m, 1H), 6.76-6.49 (m, 1H), 6.12 (s, 1H), 3.38 (s, 3H), 3.07-2.83 (m, 4H).

Step B: Preparation of (009-2)

To a mixture of 009-1 (0.15 g, 314.49 μmol) in DMF (2 mL) were added Zn(CN)$_2$ (0.74 g, 6.30 mmol, 400.00 μL) and Pd(PPh$_3$)$_4$ (72.68 mg, 62.90 μmol) in a 100 mL three-neck bottom flask at 25° C. under N$_2$. The mixture was stirred at 100° C. for 2 h. The mixture was cooled to 25° C. and added into water (50 mL). The aqueous phase was extracted with DCM (100 mL×3). The combined organic phase was washed with brine (250 mL), dried over anhydrous Na$_2$SO$_4$, filtered and concentrated under reduced pressure. The residue was purified by flash chromatography on silica gel (MeOH in DCM=0 to 15%) to afford 009-2 (120 mg, 256.67 μmol, 81.61% yield) as a pink solid. $^1$H NMR (400 MHz, DMSO-d$_6$) δ=8.38-8.19 (m, 2H), 8.10 (s, 1H), 7.84-7.75 (m, 2H), 7.61-7.43 (m, 5H), 7.38 (s, 1H), 7.21-6.96 (m, 1H), 6.68 (s, 1H), 6.15 (s, 1H), 3.48 (s, 1H), 3.41 (s, 3H), 3.27 (s, 1H), 3.02-2.88 (m, 2H).

Step C: Preparation of (rac)-3-amino-3-(1-methyl-1H-imidazol-5-yl)-2(4,6)-quinolina-1,4(1,3)-dibenzenacyclohexaphane-2$^2$ 4$^4$-dicarbonitrile ((rac)-009)

To a solution of 009-2 (100 mg, 213.89 μmol) in DMI (2 mL) was added SOCl$_2$ (254.47 mg, 2.14 mmol, 155.16 μL) at 25° C. under N$_2$. Then the reaction mixture was stirred at 40° C. for 1 h. To a mixture of NH$_3$ in MeOH (7M, 30 mL) was added the above mixture at −10° C. under N$_2$. The mixture was stirred at −10° C. for 0.5 h. The mixture was added into water (20 mL). The aqueous phase was extracted with EtOAc (50 mL×3). The combined organic phase was washed with brine (130 mL), dried over anhydrous Na$_2$SO$_4$, filtered and concentrated under reduced pressure. The residue was purified by flash chromatography on silica gel (MeOH in DCM=0 to 15%) to afford rac-009 (70 mg, 150.04 μmol, 70.15% yield) as a yellow solid. LCMS R$_t$=0.79 min in 3 min chromatography, 10-80CD, ESI calcd. for C$_{30}$H$_{23}$N$_6$ [M+H]$^+$ 467.2, found 467.3.

Step D: Preparation of (R)-3-amino-3-(1-methyl-1H-imidazol-5-yl)-2(4,6)-quinolina-1,4(1,3)-dibenzenacyclohexaphane-2$^2$ 4$^4$-dicarbonitrile ((R)-009)

rac-009 (70 mg, 150.04 μmol) was separated by SFC (column: DAICEL CHIRALPAK AD (250 mm×30 mm, 10 m); mobile phase: [0.1% NH$_3$H$_2$O EtOH]; B %: 40%-40%) to afford (R)-009 (20.1 mg, 43.08 μmol, 28.71% yield) as an off-white solid. 1H NMR (400 MHz, DMSO-d$_6$) δ=8.38 (dd, J=2.0, 8.8 Hz, 1H), 8.20 (d, J=8.8 Hz, 1H), 8.01 (s, 1H), 7.69 (d, J=8.0 Hz, 1H), 7.55 (s, 1H), 7.49-7.26 (m, 6H), 6.97 (s, 1H), 6.21 (s, 1H), 3.49-3.43 (m, 1H), 3.40-3.36 (m, 3H), 3.34-3.28 (m, 1H), 3.24-3.15 (m, 4H). LCMS R$_t$=1.76 min in 3 min chromatography, 10-80CD, ESI calcd. for C$_{30}$H$_{23}$N$_6$ [M+H]$^+$ 467.2, found 467.1. HPLC R$_t$=3.29 min in 8 min chromatography, 220 nm, purity 95.46%. Chiral HPLC (R)-009: R$_t$=2.15 min in 4 min (ee 99.34%) (AD_ETOH_DEA_5_40_4ML_4MIN_5CM), ((S)-009: R$_t$=1.81 min (ee 99.70%)).

Scheme B - General Synthetic Method B

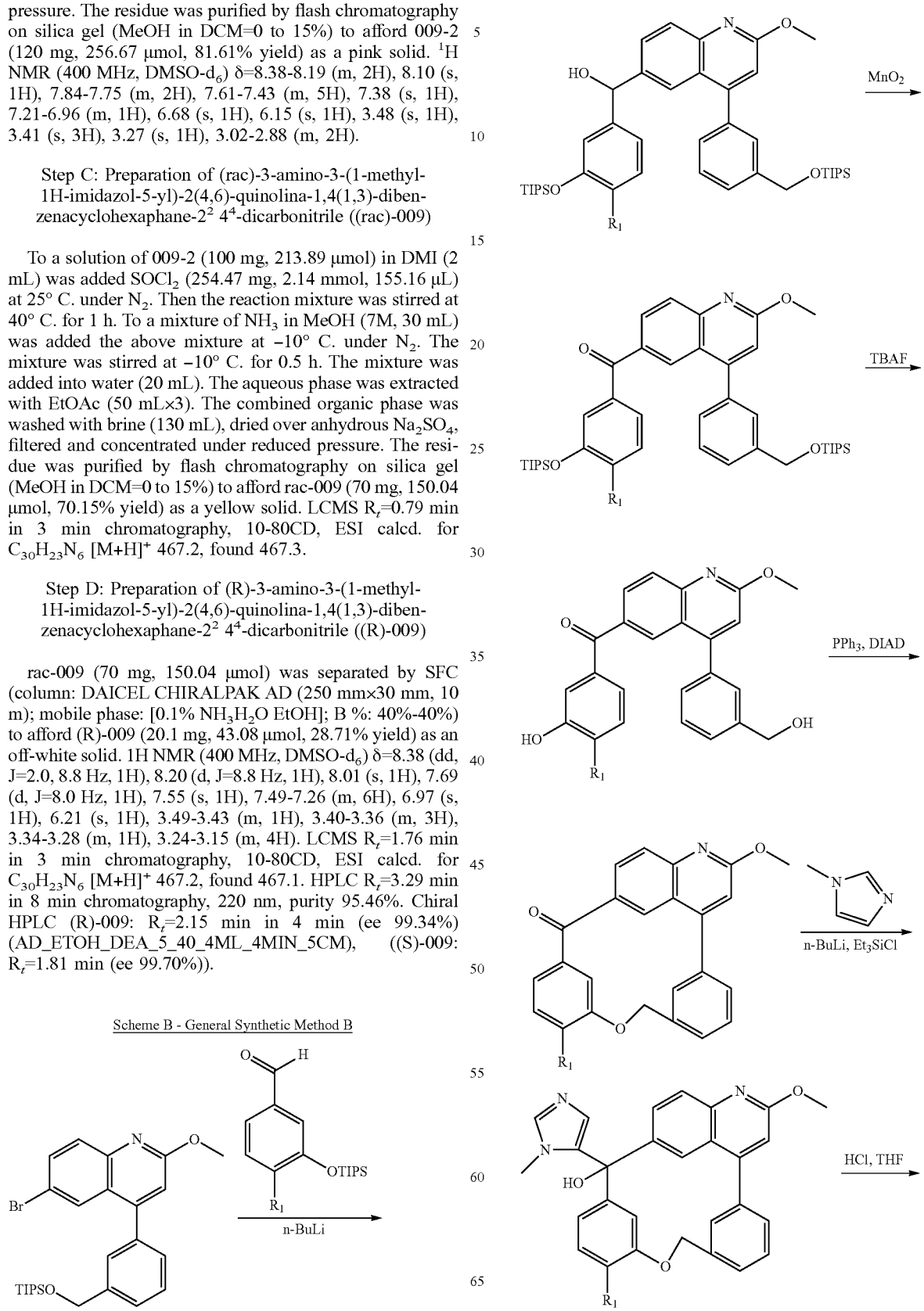

Example 10: Preparation of Compound 10
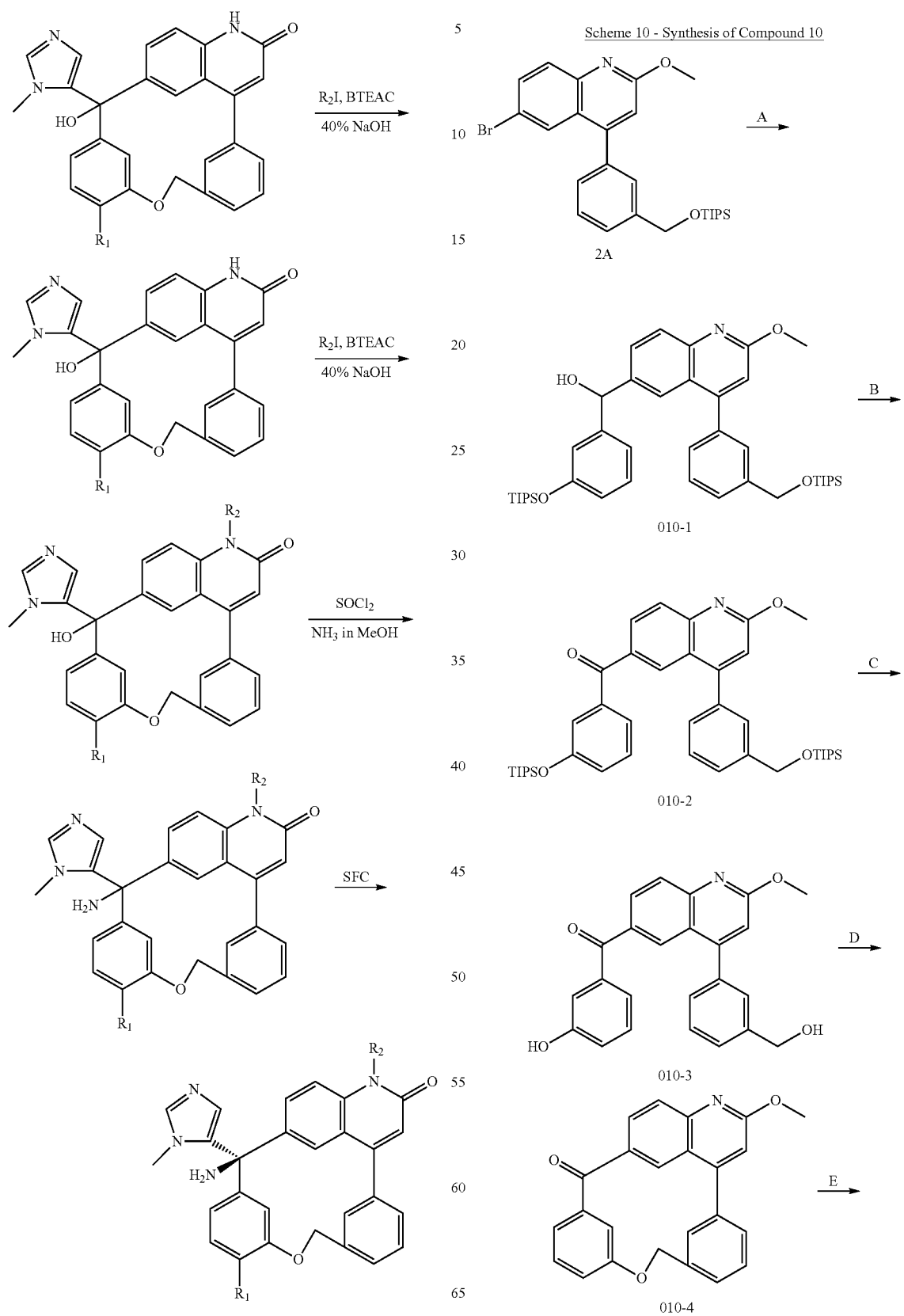
Scheme 10 - Synthesis of Compound 10

-continued

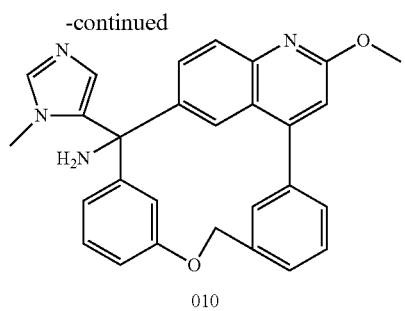

010

Step A: Preparation of (010-1)

To a mixture of 2A (3.19 g, 6.37 mmol) in THF (30 mL) was added n-BuLi (2.5M in n-hexane, 7.65 mmol, 3.06 mL) at −78° C. After stirring at −78° C. for 5 min, a solution of 3-((triisopropylsilyl)oxy)benzaldehyde (2.13 g, 7.65 mmol) (*J. Med. Chem.* 2017, 60 (11), 4636-4656.) in THF (10 mL) was added and stirring at −78° C. for 0.5 h. The reaction mixture was poured into saturated NH$_4$Cl solution (60 mL). The aqueous layer was extracted with EtOAc (60 mL×2). The combined organic layers were dried over anhydrous Na$_2$SO$_4$, filtered and concentrated. The residue was blended with another batch prepared from 3 g of 2A for purification. The combined crude product was purified by flash chromatography on silica gel (DCM in petroleum ether=0 to 80%) to give 010-1 (3.4 g, 4.86 mmol, 39.28% yield) as yellow oil. $^1$H NMR (400 MHz, CDCl$_3$) δ=7.77 (d, J=8.8 Hz, 2H), 7.46-7.59 (m, 5H), 7.39-7.33 (m, 1H), 7.15 (t, J=8.0 Hz, 1H), 6.94 (d, J=7.6 Hz, 1H), 6.89-6.85 (m, 1H), 6.70-6.75 (m, 2H), 5.77 (d, J=4.0 Hz, 1H), 4.93 (s, 2H), 4.03 (s, 2H), 3.86 (d, J=4.0 Hz, 1H), 1.22-1.14 (m, 6H), 1.11-1.09 (m, 18H), 0.99-0.95 (m, 18H).

Step B: Preparation of (010-2)

A mixture of 010-1 (3.4 g, 4.86 mmol) and MnO$_2$ (8.44 g, 97.13 mmol) in DCM (30 mL) was stirred at 35° C. for 12 h. The mixture was filtered through Celite and the filter cake was washed with DCM (200 mL×2). The filtrate was concentrated under reduced pressure. The residue was purified by flash chromatography on silica gel (EtOAc in petroleum ether=0 to 1%) to afford 010-2 (2.5 g, 3.58 mmol, 73.66% yield) as yellow oil. $^1$H NMR (400 MHz, CDCl$_3$) δ=8.14 (d, J=1.6 Hz, 1H), 8.04 (dd, J=2.0, 8.8 Hz, 1H), 7.94 (d, J=8.4 Hz, 1H), 7.51-7.44 (m, 3H), 7.42-7.29 (m, 3H), 7.20-7.15 (m, 1H), 7.15-7.09 (m, 1H), 6.98 (s, 1H), 4.87 (s, 2H), 4.11 (s, 3H), 1.30-1.16 (m, 6H), 1.06-1.02 (m, 36H).

Step C: Preparation of (010-3)

To a solution of 010-2 (2.5 g, 3.58 mmol) in THF (20 mL) was added TBAF (1M in THF, 17.91 mmol, 17.91 mL) at 25° C. The mixture was stirred at 25° C. for 2 h. Water (30 mL) was added to the mixture. The aqueous layer was extracted with EtOAc (30 mL×2). The combined organic layers were washed with water (30 mL×2), brine (30 mL), dried over anhydrous Na$_2$SO$_4$, filtered and concentrated. The residue was purified by flash chromatography on silica gel (EtOAc in petroleum ether=0 to 30%) to afford 010-3 (1.3 g, 3.37 mmol, 94.13% yield) as a white solid. $^1$H NMR (400 MHz, CD$_3$CN) δ=8.16-8.08 (m, 2H), 7.93 (d, J=8.4 Hz, 1H), 7.48-7.38 (m, 4H), 7.33 (t, J=7.6 Hz, 1H), 7.24-7.18 (m, 2H), 7.06-7.01 (m, 1H), 6.96 (s, 1H), 4.65 (d, J=5.2 Hz, 2H), 4.09 (s, 3H).

Step D: Preparation of (010-4)

A solution of DIAD (1.57 g, 7.78 mmol, 1.51 mL) and PPh$_3$ (2.04 g, 7.78 mmol) in THF (12 mL) was stirred at 0° C. for 1 h. Then a solution of 010-3 (500 mg, 1.30 mmol) in THF (100 mL) was added to the mixture at 0° C. The mixture was stirred at 25° C. for 2 h. Water (50 mL) was added to the mixture. The aqueous layer was extracted with EtOAc (50 mL×2). The combined organic layers were washed with water (50 mL×2), brine (50 mL), dried over anhydrous Na$_2$SO$_4$, filtered and concentrated. The residue was purified by flash chromatography on silica gel (EtOAc in petroleum ether=0 to 10%) to give 010-4 (0.14 g, 381.06 μmol, 29.31% yield) as a white solid. $^1$H NMR (400 MHz, DMSO-d$_6$) δ=8.26 (dd, J=2.0, 8.8 Hz, 1H), 8.19-8.16 (m, 1H), 7.95 (d, J=8.4 Hz, 2H), 7.84 (s, 1H), 7.68-7.55 (m, 3H), 7.42-7.34 (m, 1H), 7.30 (s, 1H), 7.21-7.11 (m, 2H), 5.52-5.38 (m, 2H), 4.09 (s, 3H).

Step E: Preparation of 2$^2$-methoxy-3-(1-methyl-1H-imidazol-5-yl)-5-oxa-2(4,6)-quinolina-1,4(1,3)-dibenzenacyclohexaphan-3-ol (010)

To a solution of 1-methyl-1H-imidazole (37.54 mg, 457.27 μmol, 36.45 μL) in THF (10 mL) was added n-BuLi (2.5M in n-hexane, 457.27 μmol, 182.91 μL) dropwise at −78° C. under N$_2$ and the mixture was stirred at −78° C. for 0.5 h. Then Et$_3$SiCl (68.92 mg, 457.27 μmol, 77.79 μL) was added to the mixture and the mixture was stirred at −78° C. for 0.5 h. Then n-BuLi (2.5M in n-hexane, 457.27 μmol, 182.91 μL) was added to the above mixture and the mixture was stirred at −78° C. for 0.5 h. Then a solution of 010-4 (0.14 g, 381.06 μmol) in THF (3 mL) was added to the above mixture and the mixture was stirred at −78° C. for 0.5 h. The residue was poured into water (40 mL). The aqueous phase was extracted with EtOAc (40 mL×2). The combined organic phase was washed with brine (40 mL), dried over anhydrous Na$_2$SO$_4$, filtered and concentrated in vacuum. The crude was purified by flash chromatography on silica gel (MeOH in DCM=0 to 10%) to give 010 (135.1 mg, 300.56 μmol, 78.87% yield) as an off-white solid. $^1$H NMR (400 MHz, DMSO-d$_6$) δ=8.10-8.00 (m, 1H), 7.86 (d, J=8.4 Hz, 1H), 7.66-7.43 (m, 4H), 6.72-7.33 (m, 8H), 6.18-6.00 (m, 1H), 5.43-5.24 (m, 2H), 4.02 (s, 3H), 3.47 (s, 3H). LCMS R$_t$=1.48 min in 3.0 min chromatography, 30-90CD, ESI calcd. for C$_{28}$H$_{24}$N$_3$O$_3$ [M+H]$^+$ 450.0, found 450.1. HPLC R$_t$=3.60 min in 8 min chromatography, 220 nm, purity 99.51%.

Example 11: Preparation of Compound 11

Scheme 11 - Synthesis of Compound 11

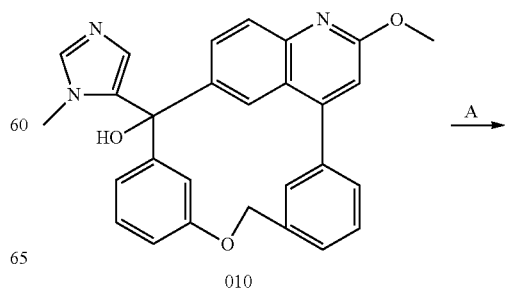

010

-continued

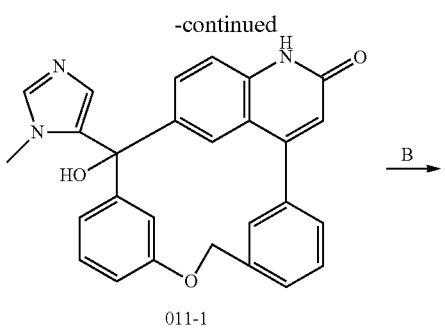

011-1

B →

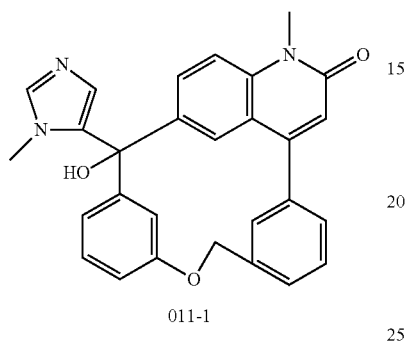

011-1

Step A: Preparation of (011-1)

To a solution of 010 (270 mg, 600.67 μmol) in THF (5 mL) was added HCl (4M in H$_2$O, 15.02 mmol, 3.75 mL) at 25° C. The mixture was stirred at 70° C. for 10 h. Saturated NaHCO$_3$ solution was added into the mixture to adjusted to pH=8. The aqueous layer was extracted with EtOAc (20 mL×3). The combined organic layers were washed with brine (30 mL), dried over anhydrous Na$_2$SO$_4$, filtered and concentrated. 011-1 (260 mg, 597.05 μmol, 99.40% yield) as an off-white solid was used into the next step without further purification. LCMS R$_t$=0.73 min in 1.5 min chromatography, 5-95AB, ESI calcd. for C$_{27}$H$_{22}$N$_3$O$_3$ [M+H]$^+$ 436.2, found 436.1.

Step B: Preparation of 3-hydroxy-2$^1$-methyl-3-(1-methyl-1H-imidazol-5-yl)-2$^1$,2$^2$-dihydro-5-oxa-2(4,6)-quinolina-1,4(1,3)-dibenzenacyclohexaphan-2$^2$-one (011)

To a solution of 011-1 (180 mg, 413.34 μmol) in THF (2 mL) and H$_2$O (2 mL) were added BTEAC (47.07 mg, 206.67 μmol) and NaOH (165.34 mg, 4.13 mmol) at 25° C. The mixture was stirred at 25° C. for 10 min. Then iodomethane-d$_3$ (58.67 mg, 413.34 μmol, 25.73 L) in THF (0.3 mL) was added to the above mixture at 25° C. The mixture was stirred at 25° C. for 2 h. Water (20 mL) was added to the mixture. The aqueous layer was extracted with EtOAc (15 mL×2). The combined organic layers were washed with brine (30 mL), dried over anhydrous Na$_2$SO$_4$, filtered and concentrated. The residue was blended with another batch prepared from 50 mg of 011-1 for further purification. The residue was purified by flash chromatography on silica gel (MeOH in DCM=0 to 3%) and triturated with CH$_3$CN (30 mL) and MeOH (10 mL), then was purified by Prep-HPLC (column: Phenomenex Gemini 150×25 mm×10 m; mobile phase: [water (0.05% NH$_3$H$_2$O+10 mM NH$_4$HCO$_3$)-ACN]; B %: 19%-49%, 7.8 min) to afford 011 (25.3 mg, 56.28 μmol, 10.66% yield) as an off-white solid. $^1$H NMR (400 MHz, DMSO-d$_6$) δ=8.01 (dd, J=2.4, 8.8 Hz, 1H), 7.61 (d, J=8.8 Hz, 1H), 7.54 (s, 1H), 7.51-7.47 (m, 2H), 7.44-7.39 (m, 1H), 7.22-7.15 (m, 1H), 7.13 (s, 1H), 6.98-6.91 (m, 3H), 6.78 (s, 1H), 6.64 (s, 1H), 6.45 (s, 1H), 6.15 (s, 1H), 5.35-5.21 (m, 2H), 3.69 (s, 3H), 3.43 (s, 3H). LCMS R$_t$=1.49 min in 3.0 min chromatography, 10-80CD, ESI calcd. for C$_{28}$H$_{24}$N$_3$O$_3$ [M+H]$^+$ 450.2, found 450.1. HPLC R$_t$=2.53 min in 8 min chromatography, 220 nm, purity 100%.

Example 12: Preparation of Compound 12

Scheme 12 - Synthesis of Compound 12

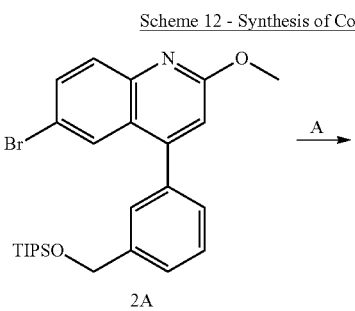

2A

A →

012-1

B →

012-2

C →

012-3

D →

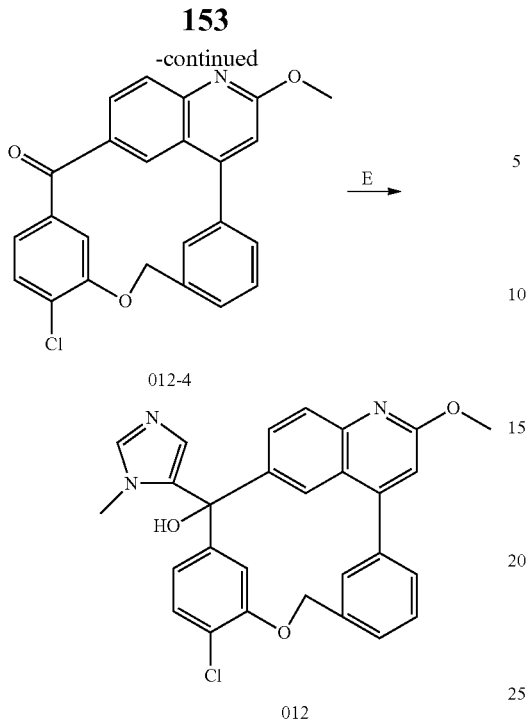

Step A: Preparation of (012-1)

To a solution of 2A (6 g, 11.99 mmol) in redistillation THF (60 mL) was added n-BuLi (2.5M in n-hexane, 14.38 mmol, 5.75 mL) at −78° C. The mixture was stirred at −78° C. for 10 min. Then a solution of 5A (4.50 g, 14.38 mmol) in redistillation THF (30 mL) was added the mixture at −78° C. The mixture was stirred at −78° C. for 1 h 50 min. Water (60 mL) was added to the mixture. The aqueous layer was extracted with EtOAc (40 mL×2). The combined organic layers were washed with brine (100 mL), dried over anhydrous $Na_2SO_4$, filtered and concentrated. The residue was purified by flash chromatography on silica gel (EtOAc in petroleum ether=0 to 10%) to afford 012-1 (2.7 g, 3.68 mmol, 30.69% yield) as yellow oil. $^1$H NMR (400 MHz, $CDCl_3$) δ=7.84 (d, J=8.8 Hz, 1H), 7.75 (d, J=2.0 Hz, 1H), 7.52-7.41 (m, 4H), 7.32-7.27 (m, 1H), 7.22 (s, 1H), 6.85-6.78 (m, 3H), 5.77 (d, J=3.2 Hz, 1H), 4.89 (s, 2H), 4.07 (s, 3H), 2.23-2.16 (m, 1H), 1.19-1.12 (m, 6H), 1.09-1.07 (m, 18H), 1.02-0.95 (m, 18H).

Step B: Preparation of (012-2)

A mixture of 012-1 (2.4 g, 3.27 mmol) and $MnO_2$ (2.84 g, 32.67 mmol) in DCM (30 mL) was stirred at 50° C. for 12 h. The mixture was filtered through Celite. The filter cake was washed with DCM (30 mL×3). The filtrate was concentrated under reduced pressure. The residue was blended with another batch prepared from 0.3 g of 012-1. The residue was purified by flash chromatography on silica gel (EtOAc in Petroleum ether=0 to 10%) to afford 012-2 (2.2 g, 3.00 mmol, 81.71% yield) as yellow oil. $^1$H NMR (400 MHz, $CDCl_3$) δ=8.26 (s, 1H), 8.00-7.96 (m, 1H), 7.95-7.92 (m, 1H), 7.47-7.36 (m, 4H), 7.35-7.28 (m, 2H), 7.27-7.25 (m, 1H), 6.91 (s, 1H), 4.87 (s, 2H), 4.13 (s, 3H), 1.32-1.15 (m, 6H), 1.08-1.03 (m, 36H).

Step C: Preparation of (012-3)

To a mixture of 012-2 (2.2 g, 3.00 mmol) in THF (20 mL) was added TBAF (1M in THF, 15.02 mmol, 15.02 mL) at 25° C. The mixture was stirred at 25° C. for 2 h. Water (40 mL) was added to the mixture. The aqueous layer was extracted with EtOAc (40 mL×2). The combined organic layers were washed with $H_2O$ (60 mL×3), brine (60 mL×2), dried over anhydrous $Na_2SO_4$, filtered and concentrated. The residue was purified by flash chromatography on silica gel (EtOAc in petroleum ether=0 to 70%) to afford 012-3 (1.2 g, 2.86 mmol, 95.33% yield) as an off-white solid. $^1$H NMR (400 MHz, DMSO-$d_6$) δ=10.68 (br s, 1H), 8.12 (s, 1H), 8.09-8.03 (m, 1H), 8.02-7.96 (m, 1H), 7.56-7.43 (m, 5H), 7.35 (s, 1H), 7.21 (d, J=8.0 Hz, 1H), 7.06 (s, 1H), 5.31 (br s, 1H), 4.58 (s, 2H), 4.08 (s, 3H). LCMS $R_t$=0.92 min in 1.5 min chromatography, 5-95AB, ESI calcd. for $C_{24}H_{19}ClNO_4$ $[M+H]^+$ 420.1, found 420.1.

Step D: Preparation of (012-4)

A solution of DIAD (192.64 mg, 952.71 μmol, 185.24 μL) and $PPh_3$ (249.89 mg, 952.71 μmol) in THF (4 mL) was stirred at 0° C. for 1 h. Then 012-3 (200 mg, 476.35 μmol) in THF (20 mL) was added to the mixture at 0° C. The mixture was stirred at 25° C. for 2 h. Water (20 mL) was added to the mixture. The aqueous layer was extracted with EtOAc (15 mL×2). The combined organic layers were washed with brine (30 mL), dried over anhydrous $Na_2SO_4$, filtered and concentrated. The residue was purified by flash chromatography on silica gel (EtOAc in petroleum ether=0 to 10%) to afford 012-4 (100 mg, 248.85 μmol, 52.24% yield) as an off-white solid. $^1$H NMR (400 MHz, DMSO-$d_6$) δ=8.25 (d, J=8.8 Hz, 1H), 8.12 (s, 1H), 8.03 (s, 1H), 7.98-7.91 (m, 2H), 7.68-7.57 (m, 3H), 7.54 (d, J=8.0 Hz, 1H), 7.31 (s, 1H), 7.18 (d, J=8.0 Hz, 1H), 5.56 (s, 2H), 4.09 (s, 3H). LCMS $R_t$=1.07 min in 1.5 min chromatography, 5-95AB, ESI calcd. for $C_{24}H_{17}ClNO_3$ $[M+H]^+$ 402.1, found 402.0.

Step E: Preparation of $4^4$-chloro-$2^2$-methoxy-3-(1-methyl-1H-imidazol-5-yl)-5-oxa-2(4,6)-quinolina-1,4(1,3)-dibenzenacyclohexaphan-3-ol (012)

To a solution of 1-methyl-1H-imidazole (98.07 mg, 1.19 mmol, 95.22 μL) in redistillation THF (5 mL) was added n-BuLi (2.5M in n-hexane, 1.19 mmol, 477.80 μL) at −78° C. The mixture was stirred at −78° C. for 0.5 h. Then $Et_3SiCl$ (180.04 mg, 1.19 mmol, 203.20 L) was added to the mixture at −78° C. The mixture was stirred at −78° C. for 0.5 h. Then n-BuLi (2.5M in n-hexane, 1.19 mmol, 477.80 μL) was added to the mixture at −78° C. The mixture was stirred at −78° C. for 0.5 h. Then a solution of 012-4 (400 mg, 995.42 μmol) in redistillation THF (5 mL) was added to the mixture at −78° C. The mixture was stirred at −78° C. for 1.5 h. Water (20 mL) was added to the mixture. The aqueous layer was extracted with EtOAc (15 mL×2). The combined organic layers were washed with brine (30 mL), dried over anhydrous $Na_2SO_4$, filtered and concentrated. The residue was purified by chromatography on silica gel (MeOH in DCM=0 to 2%) to afford 012 (330 mg, 681.90 μmol, 68.50% yield) as an off-white solid. 30 mg (61.99 μmol) of the product was purified by Prep-HPLC (column: Welch Xtimate $C_{18\ 150\times25}$ mm×5 m; mobile phase: [water (0.05% ammonia hydroxide v/v)-MeOH]; B %: 70%-100%, 7.8 min) to afford 012 (12.4 mg, 25.62 μmol, 41.33% yield) as an off-white solid. $^1$H NMR (400 MHz, DMSO-$d_6$) δ=8.03 (d, J=8.8 Hz, 1H), 7.85 (d, J=8.4 Hz, 1H), 7.63-7.58 (m, 1H), 7.56-7.52 (m, 3H), 7.33-7.22 (m, 3H), 7.10-7.00 (m, 3H), 6.60 (s, 1H), 6.15 (s, 1H), 5.35 (dd, J=12.0, 23.2 Hz, 2H), 4.06 (s, 3H), 3.39 (s, 3H). LCMS $R_t$=2.02 min in 3.0 min chromatography, 10-80CD, ESI calcd. for $C_{28}H_{23}ClN_3O_3$ $[M+H]^+$ 484.1, found 484.1. HPLC $R_t$=4.06 min in 8 min chromatography, 220 nm, purity 99.53%.

Example 13: Preparation of Compound 13

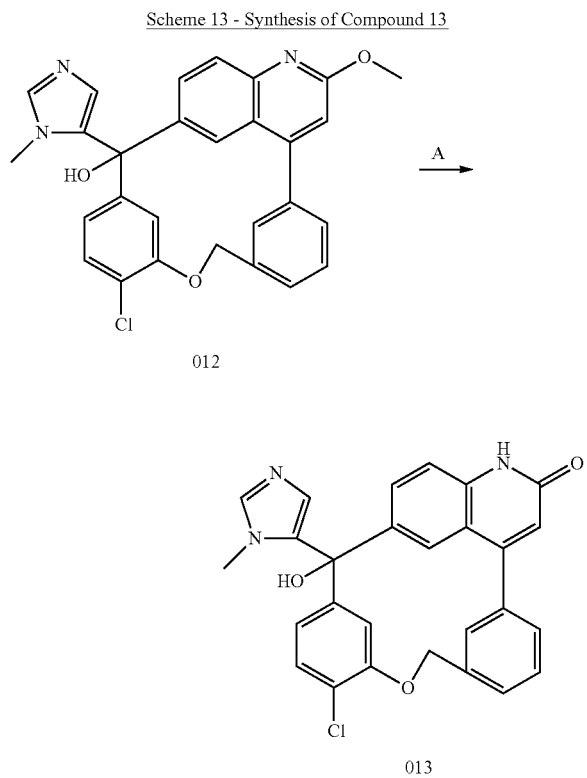

Step A: Preparation of $4^4$-chloro-3-hydroxy-3-(1-methyl-1H-imidazol-5-yl)-$2^1$,$2^2$-dihydro-5-oxa-2(4,6)-quinolina-1,4(1,3)-dibenzenacyclohexaphan-$2^2$-one (013)

To a solution of 012 (30 mg, 61.99 μmol) in THF (1 mL) was added HCl (4M in H$_2$O, 1.55 mmol, 387.44 μL) at 25° C. The mixture was stirred at 70° C. for 10 h. Saturated NaHCO$_3$ solution was added into the mixture to adjusted to pH=8. The aqueous layer was extracted with EtOAc (15 mL×2). The combined organic layers were washed with brine (30 mL), dried over anhydrous Na$_2$SO$_4$, filtered and concentrated. The residue was purified by Prep-HPLC (column: Welch Xtimate C$_{18}$ $_{150\times25}$ mm×5 μm; mobile phase: [water (0.05% ammonia hydroxide v/v)-MeOH]; B %: 60%-90%, 7.8 min) to afford 013 (9.8 mg, 20.85 μmol, 33.64% yield) as an off-white solid. $^1$H NMR (400 MHz, DMSO-d$_6$) δ=11.62 (br s, 1H), 7.86 (d, J=8.8 Hz, 1H), 7.62-7.56 (m, 1H), 7.55-7.44 (m, 3H), 7.39 (d, J=8.8 Hz, 1H), 7.30 (d, J=8.8 Hz, 1H), 7.20 (s, 1H), 7.09-6.89 (m, 3H), 6.59-6.46 (m, 2H), 6.16 (s, 1H), 5.39-5.23 (m, 2H), 3.36 (s, 3H). LCMS $R_t$=1.59 min in 3.0 min chromatography, 10-80CD, ESI calcd. for $C_{27}H_{21}ClN_3O_3$ $[M+H]^+$ 470.1, found 470.1. HPLC $R_t$=3.31 min in 8 min chromatography, 220 nm, purity 98.93%.

Example 14: Preparation of Compound 14

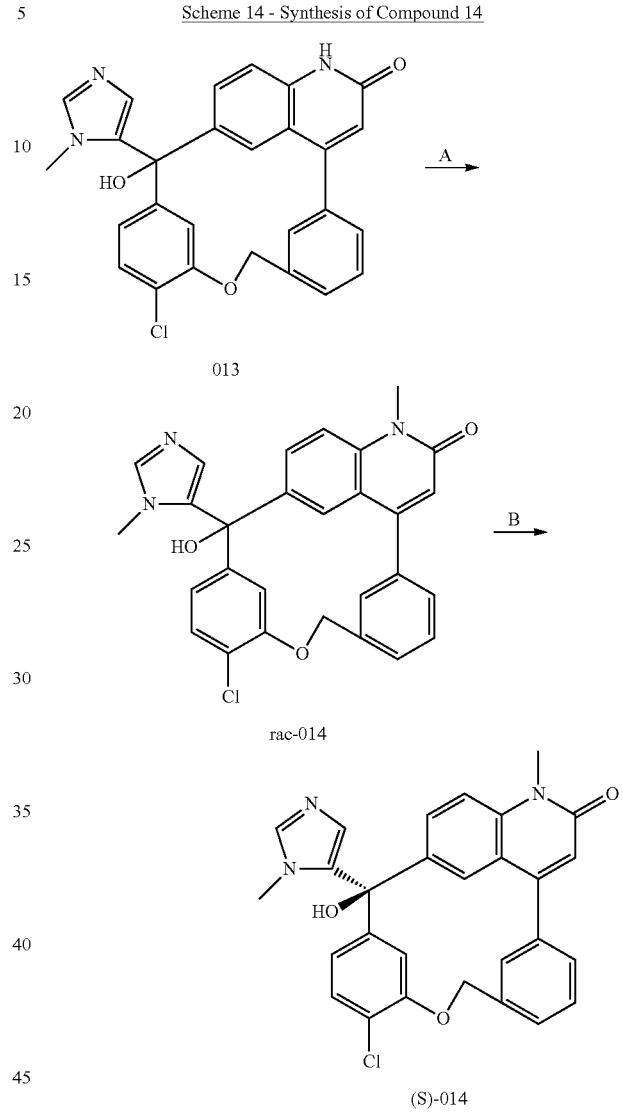

Step A: Preparation of (rac)-$4^4$-chloro-3-hydroxy-$2^1$-methyl-3-(1-methyl-1H-imidazol-5-yl)-$2^1$,$2^2$-dihydro-5-oxa-2(4,6)-quinolina-1,4(1,3)-dibenzenacyclohexaphan-$2^2$-one ((rac)-014)

To a solution of 013 (30 mg, 63.84 μmol) in THF (1 mL) and H$_2$O (1 mL) were added BTEAC (7.27 mg, 31.92 μmol) and NaOH (25.54 mg, 638.41 μmol) at 25° C. The mixture was stirred at 25° C. for 10 min. Then iodomethane-d$_3$ (13.59 mg, 95.76 μmol, 5.96 μL) in THF (0.5 mL) was added to the above mixture at 25° C. The mixture was stirred at 25° C. for 2 h. Water (20 mL) was added to the mixture. The aqueous layer was extracted with EtOAc (15 mL×2). The combined organic layers were washed with brine (30 mL), dried over anhydrous Na$_2$SO$_4$, filtered and concentrated. The residue was purified by Prep-HPLC (column: Welch Xtimate C$_{18}$ $_{150\times25}$ mm×5 m; mobile phase: [water (0.05% ammonia hydroxide v/v)-MeOH]; B %: 65%-95%, 7.8 min) to afford rac-014 (5.2 mg, 10.75 μmol, 16.84% yield) as an off-white solid. $^1$H NMR (400 MHz, DMSO-d$_6$) δ=7.99 (d, J=8.8 Hz, 1H), 7.65-7.58 (m, 2H), 7.56-7.46 (m, 3H), 7.32 (d, J=8.4 Hz, 1H), 7.19-6.95 (m, 3H), 6.88 (s, 1H), 6.68 (s, 1H), 6.58 (s, 1H), 6.15 (s, 1H), 5.38-5.19 (m, 2H), 3.69 (s, 3H), 3.36 (s, 3H). LCMS $R_t$=1.67 min in 3.0 min chromatography, 10-80CD, ESI calcd. for C$_{28}$H$_{23}$ClN$_3$O$_3$ [M+H]$^+$ 484.1, found 484.1. HPLC $R_t$=3.55 min in 8 min chromatography, 220 nm, purity 97.72%.

Step B: Preparation of (S)-4$^4$-chloro-3-hydroxy-2$^1$-methyl-3-(1-methyl-1H-imidazol-5-yl)-2$^1$,2$^2$-dihydro-5-oxa-2(4,6)-quinolina-1,4(1,3)-dibenzenacyclohexaphan-2$^2$-one ((S)-014)

rac-014 (50 mg, 103.32 μmol) was separated by SFC (column: DAICEL CHIRALPAK AD (250 mm×30 mm, 10 m); mobile phase: [0.1% NH$_3$H$_2$O EtOH]; B %: 55%-55%) to afford (S)-014 (13.8 mg, 28.52 μmol, 27.60% yield) as an off-white solid. $^1$H NMR (400 MHz, DMSO-d$_6$) δ=7.99 (d, J=8.8 Hz, 1H), 7.64-7.59 (m, 2H), 7.57-7.45 (m, 3H), 7.32 (d, J=8.4 Hz, 1H), 7.23-6.95 (m, 3H), 6.88 (s, 1H), 6.68 (s, 1H), 6.59 (s, 1H), 6.16 (s, 1H), 5.41-5.16 (m, 2H), 3.69 (s, 3H), 3.36 (s, 3H). LCMS $R_t$=1.67 min in 3.0 min chromatography, 10-80CD, ESI calcd. for C$_{28}$H$_{23}$ClN$_3$O$_3$ [M+H]$^+$ 484.1, found 484.1. HPLC $R_t$=3.56 min in 8 min chromatography, 220 nm, purity 97.36%. Chiral HPLC (S)-014: $R_t$=2.48 min in 4 min (ee 100%) (AD_ETOH_DEA_5_40_4ML_4MIN_5CM), ((R)-014: $R_t$=1.98 min (ee 100%)).

Example 15: Preparation of Compound 15

Scheme 15 - Synthesis of Compound 15

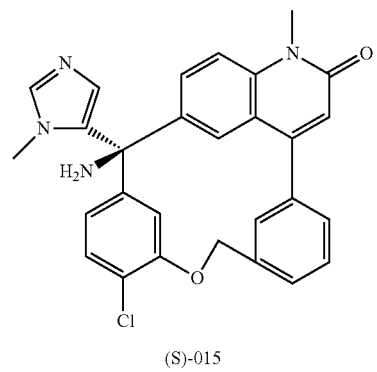

Step A: Preparation of (rac)-3-amino-4$^4$-chloro-2$^1$-methyl-3-(1-methyl-1H-imidazol-5-yl)-2$^1$,2$^2$-dihydro-5-oxa-2(4,6)-quinolina-1,4(1,3)-dibenzenacyclohexaphan-2$^2$-one ((rac)-015)

To a solution of rac-014 (30 mg, 61.99 μmol) in DMI (1 mL) was added SOCl$_2$ (59.00 mg, 495.92 μmol, 35.98 μL) at 0° C. The mixture was stirred at 0° C. for 0.5 h and 35° C. for 0.5 h. To a solution of NH$_3$ in MeOH (7M, 3 mL) was added the above mixture at −10° C. The mixture was stirred at −10° C. to 20° C. for 12 h. Water (20 mL) was added to the mixture. The aqueous layer was extracted with EtOAc (15 mL×2). The combined organic layers were washed with brine (30 mL), dried over anhydrous Na$_2$SO$_4$, filtered and concentrated. The residue was purified by Prep-HPLC (column: Welch Xtimate C$_{18}$ $_{150×25}$ mm×5 m; mobile phase: [water (0.05% ammonia hydroxide v/v)-MeOH]; B %: 55%-85%, 7.8 min) to afford rac-015 (4.6 mg, 9.52 μmol, 15.35% yield) as an off-white solid. 1H NMR (400 MHz, DMSO-d$_6$) δ=7.99 (d, J=8.8 Hz, 1H), 7.63-7.56 (m, 2H), 7.55-7.42 (m, 3H), 7.37-6.97 (m, 4H), 6.93-6.54 (m, 2H), 6.37-6.25 (m, 1H), 5.36 (s, 2H), 3.69 (s, 3H), 3.28 (s, 3H). LCMS $R_t$=1.64 min in 3.0 min chromatography, 10-80CD, ESI calcd. for C$_{28}$H$_{24}$ClN$_4$O$_2$ [M+H]$^+$ 483.2, found 483.0. HPLC $R_t$=2.97 min in 8 min chromatography, 220 nm, purity 98.48%.

Step B: Preparation of (S)-3-amino-4$^4$-chloro-2$^1$-methyl-3-(1-methyl-1H-imidazol-5-yl)-2$^1$,2$^2$-dihydro-5-oxa-2(4,6)-quinolina-1,4(1,3)-dibenzenacyclohexaphan-2$^2$-one ((S)-015)

rac-015 (70 mg, 144.94 μmol) was separated by SFC (column: DAICEL CHIRALPAK AD (250 mm×30 mm, 10 m); mobile phase: [0.1% NH$_3$H$_2$O IPA]; B %: 50%-50%) to afford (S)-015 (23.5 mg, 48.66 μmol, 33.57% yield) as an off-white solid. 1H NMR (400 MHz, DMSO-d$_6$) δ=7.99 (d, J=7.2 Hz, 1H), 7.62-7.55 (m, 2H), 7.54-7.42 (m, 3H), 7.35-6.97 (m, 4H), 6.95-6.50 (m, 2H), 6.28 (s, 1H), 5.36 (s, 2H), 3.68 (s, 3H), 3.28 (s, 3H), 2.94 (s, 2H). LCMS $R_t$=1.62 min in 3.0 min chromatography, 10-80CD, ESI calcd. for C$_{28}$H$_{24}$ClN$_4$O$_2$ [M+H]$^+$ 483.2, found 483.1. HPLC $R_t$=2.89 min in 8 min chromatography, 220 nm, purity 99.38%. Chiral HPLC (S)-015: $R_t$=1.65 min in 3 min (ee 100%) (AD_IPA_DEA_40-4ML 5CM), ((R)-015: $R_t$=1.02 min (ee 100%)).

Scheme C - General Synthetic Method C
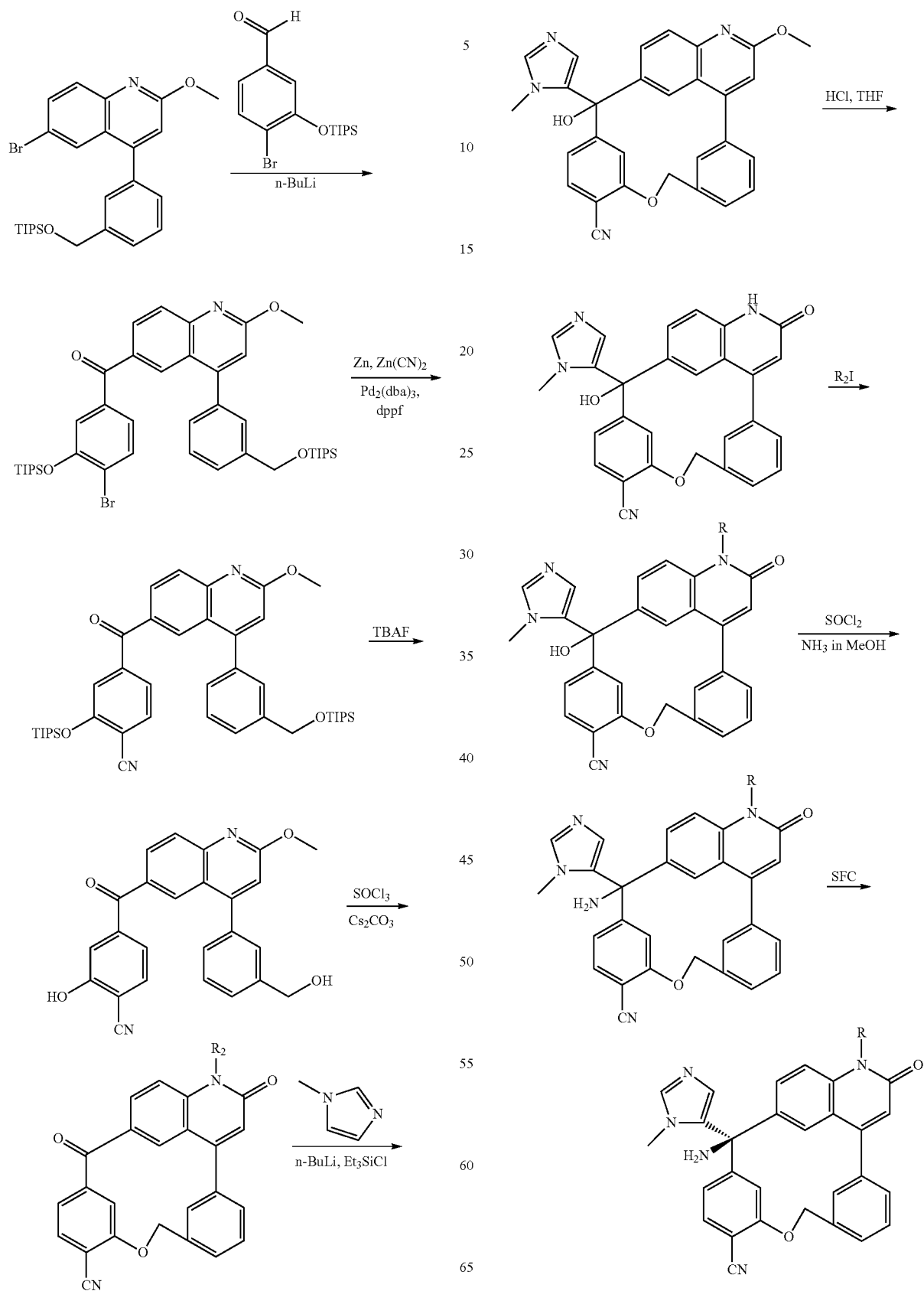

Example 16: Preparation of Compound 16

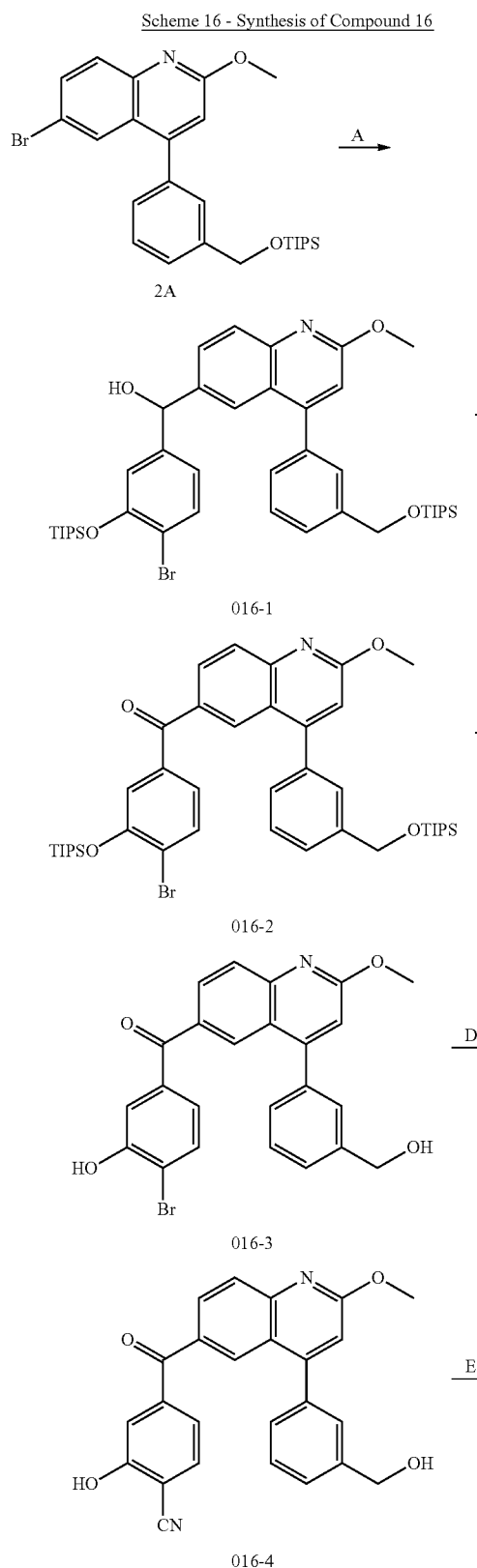

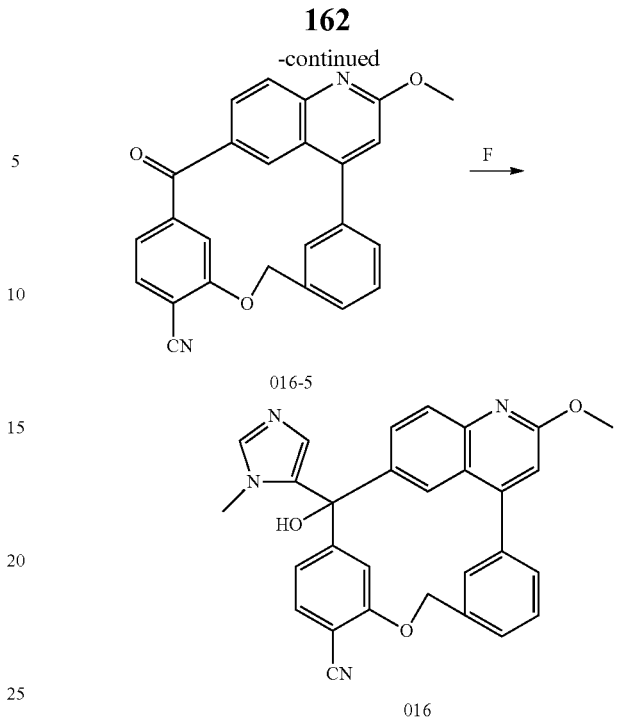

Step A: Preparation of (016-1)

To a solution of 2A (4.4 g, 8.79 mmol) in THF (80 mL) was added n-BuLi (2.5M in n-hexane, 8.79 mmol, 3.52 mL) dropwise at −78° C. under $N_2$. The reaction mixture was stirred at −78° C. for 15 min and then a solution of 6A (3.14 g, 8.79 mmol) in THE (8 mL) was added to the mixture dropwise and the reaction was stirred at −78° C. for 2 h. The reaction was quenched with water (10 mL). The solvent was removed under concentration. The crude was purified by flash chromatography on silica gel (EtOAc in petroleum ether=0 to 12%) to give 016-1 (4.4 g, 5.65 mmol, 64.28% yield) as a colorless oil. $^1$H NMR (400 MHz, CDCl$_3$) δ=7.84 (d, J=8.4 Hz, 1H), 7.75 (d, J=1.6 Hz, 1H), 7.51-7.39 (m, 5H), 7.31-7.28 (m, 1H), 6.83 (s, 1H), 6.77-6.75 (m, 2H), 5.76 (d, J=4.0 Hz, 1H), 4.89 (s, 2H), 4.07 (s, 3H), 2.21 (d, J=3.6 Hz, 1H), 1.20-1.11 (m, 6H), 1.08-1.07 (m, 18H), 0.99-0.98 (m, 18H).

Step B: Preparation of (016-2)

To a solution of 016-1 (4.4 g, 5.65 mmol) in THE (60 mL) was added MnO$_2$ (4.91 g, 56.48 mmol). The reaction mixture was stirred at 25° C. for 16 h. The solid was filtered off and the filtrate was concentrated to dryness. The crude was purified by flash chromatography on silica gel (EtOAc in petroleum ether=0 to 8%) to give 016-2 (3.6 g, 4.63 mmol, 81.95% yield) as a colorless oil. $^1$H NMR (400 MHz, CDCl$_3$) δ=8.26 (d, J=2.0 Hz, 1H), 7.79-7.92 (m, 2H), 7.57 (d, J=8.4 Hz, 1H), 7.44-7.43 (m, 3H), 7.33-7.30 (m, 2H), 7.17-7.14 (m, 1H), 6.91 (s, 1H), 4.88 (s, 2H), 4.13 (s, 3H), 1.29-1.11 (m, 6H), 1.08-1.04 (m, 36H).

Step C: Preparation of (016-3)

To a solution of 016-2 (3.6 g, 4.63 mmol) in THE (60 mL) was added TBAF (1M in THF, 13.90 mml, 13.90 mL). The reaction mixture was stirred at 25° C. for 1 h. The mixture was diluted with EtOAc (50 mL) and washed with water (50 mL). The organic layer was dried over anhydrous Na$_2$SO$_4$, filtered and concentrated. The crude was purified by flash chromatography on silica gel (EtOAc in petroleum ether=0 to 45%) to give 016-3 (1.5 g, 3.23 mmol, 69.76% yield) as a yellow solid. $^1$H NMR (400 MHz, CDCl$_3$) δ=8.19 (d, J=2.0 Hz, 1H), 8.13 (dd, J=2.0 Hz, J=8.8 Hz, 1H), 7.95 (d, J=8.8 Hz, 1H), 7.58-7.54 (m, 2H), 7.47-7.43 (m, 1H), 7.37-7.35 (m, 3H), 7.23-7.20 (m, 1H), 6.88 (s, 1H), 4.82 (s, 2H), 4.12 (s, 3H). LCMS R$_t$=0.89 min in 1.5 min chromatography, 5-95AB, ESI calcd. for C$_{24}$H$_{19}$BrNO$_4$ [M+H]$^+$ 464.0, found 463.9.

Step D: Preparation of (016-4)

A mixture of 016-3 (1.1 g, 2.37 mmol) and Zn(CN)$_2$ (2.72 g, 23.16 mmol) in DMA (20 mL) was added Pd$_2$(dba)$_3$ (216.94 mg, 236.91 μmol) and DPPF (262.68 mg, 473.82 μmol) and Zn (92.95 mg, 1.42 mmol). The mixture was stirred 120° C. for 16 h under N$_2$. The mixture was diluted with EtOAc (100 mL) and washed with water (100 mL×3). The combined organic layers were washed with brine (100 mL), dried over anhydrous Na$_2$SO$_4$, filtered and concentrated under reduced pressure. The crude was purified by flash chromatography on silica gel (EtOAc in petroleum ether=0 to 40%) to give 016-4 (0.46 g, 1.12 mmol, 47.26% yield) as a yellow oil. $^1$H NMR (400 MHz, CDCl$_3$) δ=8.28-8.20 (m, 1H), 7.97-7.95 (m, 1H), 7.62-7.25 (m, 8H), 6.88-6.87 (m, 1H), 4.93 (s, 2H), 4.12 (s, 3H). LCMS R$_t$=0.84 min in 1.5 min chromatography, 5-95AB, ESI calcd. for C$_{25}$H$_{19}$N$_2$O$_4$ [M+H]$^+$ 411.1, found 411.1.

Step E: Preparation of (016-5)

A solution of PPh$_3$ (63.91 mg, 243.65 μmol) and DIAD (49.27 mg, 243.65 μmol, 47.37 μL) in THF (1.5 mL) was stirred at 0° C. for 1 h under N$_2$. Then a solution of 016-4 (0.05 g, 121.83 μmol) in THF (10 mL) was added dropwise to above mixture and the reaction was stirred at 25° C. for 16 h. It was quenched with water (5 mL). The aqueous layer was extracted with EtOAc (5 mL×3). The combined organic layers were separated, dried over anhydrous Na$_2$SO$_4$, filtered and concentrated. The residue was purified by flash chromatography on silica gel (EtOAc in petroleum ether=0 to 20%) to afford 016-5 (0.005 g, 12.74 μmol, 10.46% yield) as a white solid. 1H NMR (400 MHz, CDCl$_3$) δ=8.34-8.31 (m, 1H), 8.05-7.94 (m, 2H), 7.75-7.72 (m, 1H), 7.65-7.50 (m, 5H), 6.39-6.37 (m, 1H), 7.10 (s, 1H), 5.63-5.31 (m, 2H), 4.16 (s, 3H). LCMS R$_t$=2.21 min in 3.0 min chromatography, 10-80CD, ESI calcd. for C$_{25}$H$_{17}$N$_2$O$_3$ [M+H]$^+$ 393.1, found 393.0.

Step F: Preparation of 3-hydroxy-2$^2$-methoxy-3-(1-methyl-1H-imidazol-5-yl)-5-oxa-2(4,6)-quinolina-1,4(1,3)-dibenzenacyclohexaphane-4$^4$-carbonitrile (016)

Under dry N$_2$ flow, to a solution of 1-methyl-1H-imidazole (301.29 mg, 3.67 mmol, 292.52 μL) in THF (15 mL) was added n-BuLi (2.5M in n-hexane, 3.67 mmol, 1.47 mL) dropwise at −78° C. under N$_2$. The mixture was stirred at −78° C. for 0.5 h. Et$_3$SiCl (553.09 mg, 3.67 mmol) was added to the mixture dropwise at −78° C. and the mixture was stirred at −78° C. for 0.5 h. Then n-BuLi (2.5M in n-hexane, 3.67 mmol, 1.47 mL) was added to the mixture dropwise at −78° C. and the mixture was stirred at −78° C. for 0.5 h. A solution of 016-5 (1.2 g, 3.06 mmol) in THF (20 mL) was added dropwise at −78° C. and the mixture was stirred at −78° C. for 0.5 h. The reaction was quenched with water (0.5 mL). The solvents were concentrated to dryness. The crude was purified by flash chromatography on silica gel (MeOH in DCM=0 to 7%) to give 016 (1.1 g, 2.32 mmol, 75.82% yield) as a brown solid. 50 mg (105.37 μmol) of the product was purified by Prep-HPLC (column: Welch Xtimate C$_{18\ 150×25}$ mm×5 m; mobile phase: [water (0.05% ammonia hydroxide v/v)-MeOH]; B %: 66%-96%, 7.8 min) to give 016 (10.5 mg, 22.13 μmol, 21.00% yield) as an off-white solid. $^1$H NMR (400 MHz, DMSO-d$_6$) δ=8.03 (dd, J=2.0, 8.8 Hz, 1H), 7.88 (d, J=8.8 Hz, 1H), 7.65-7.54 (m, 5H), 7.42 (s, 1H), 7.26-7.09 (m, 4H), 6.79 (s, 1H), 6.21 (s, 1H), 5.52-5.42 (m, 2H), 4.07 (s, 3H), 3.38 (s, 3H). LCMS R$_t$=1.79 min in 3.0 min chromatography, 10-80CD, ESI calcd. for C$_{29}$H$_{23}$N$_4$O$_3$ [M+H]$^+$ 475.2, found 475.2. HPLC R$_t$=3.36 min in 8 min chromatography, 220 nm, purity 100%.

Example 17: Preparation of Compound 17

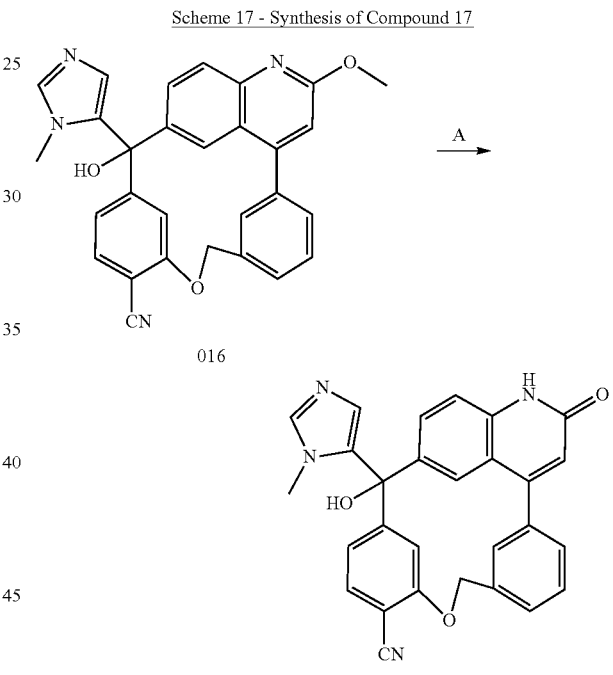

Scheme 17 - Synthesis of Compound 17

Step A: Preparation of 3-hydroxy-3-(1-methyl-1H-imidazol-5-yl)-2$^2$-oxo-2$^1$,2$^2$-dihydro-5-oxa-2(4,6)-quinolina-1,4(1,3)-dibenzenacyclohexaphane-4$^4$-carbonitrile (017)

To a solution of 016 (5.8 g, 12.22 mmol) in THF (200 mL) was added HCl (4M in H$_2$O, 76.39 mL). The reaction mixture was stirred at 70° C. for 12 h. The mixture was adjusted to pH=7 with saturated NaOH solution. The aqueous layer was extracted with EtOAc (50 mL×3). The combined organic layers were separated, dried over anhydrous Na$_2$SO$_4$, filtered and concentrated to give 017 (5.6 g, 12.16 mmol, 99.49% yield) as a white solid. 017 (60 mg, 130.30 mol) was purified by Prep-HPLC (column: Welch Xtimate C$_{18\ 150×25}$ mm×5 m; mobile phase: [water (0.05% ammonia hydroxide v/v)-MeOH]; B %: 48%-78%, 7.8 min) to give 017 (13.3 mg, 28.88 μmol, 22.17% yield) as an off-white solid. The product was lyophilized to remove solvent to give 017 (10.0 mg, 21.72 μmol, 75.19% yield) as an off-white solid. $^1$H NMR (400 MHz, DMSO-$d_6$) δ=8.05 (s, 1H), 7.83 (d, J=8.8 Hz, 1H), 7.66-7.49 (m, 4H), 7.47 (d, J=8.4 Hz, 2H), 7.34 (s, 1H), 7.08 (s, 1H), 6.84 (d, J=2.0 Hz, 2H), 6.61 (s, 1H), 6.42 (s, 1H), 5.46-5.37 (m, 2H), 3.40 (s, 3H). LCMS $R_t$=1.38 min in 3.0 min chromatography, 10-80CD, ESI calcd. for $C_{28}H_{21}N_4O_3$ [M+H]$^+$ 461.2, found 461.2. HPLC $R_t$=2.25 min in 8 min chromatography, 220 nm, purity 100%.

Example 18: Preparation of Compound 18

Scheme 18 - Synthesis of Compound 18

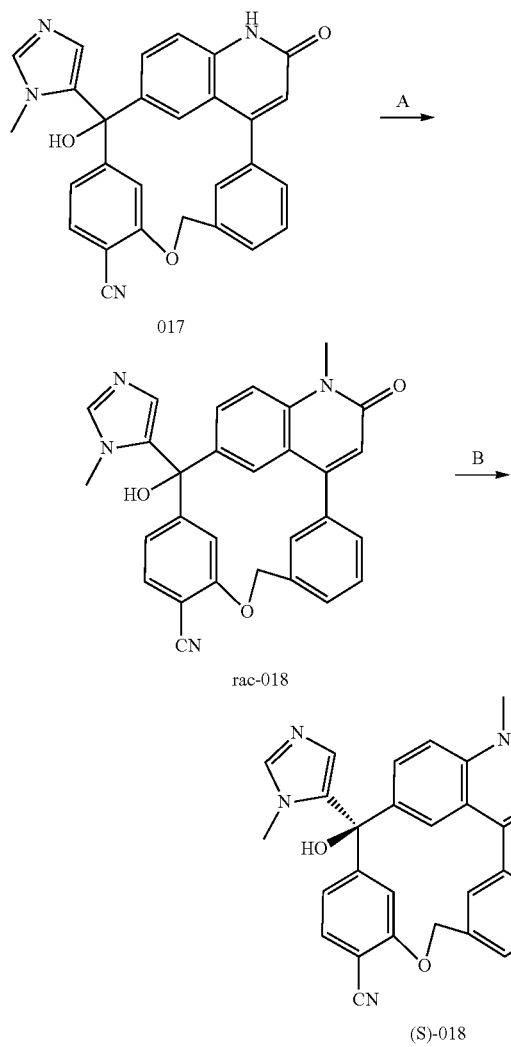

Step A: Preparation of (rac)-3-hydroxy-2$^1$-methyl-3-(1-methyl-1H-imidazol-5-yl)-2$^2$-oxo-2$^1$,2$^2$-dihydro-5-oxa-2(4,6)-quinolina-1,4(1,3)-dibenzenacyclohexaphane-4$^4$-carbonitrile ((rac)-018)

To a solution of 017 (0.115 g, 249.74 μmol) in THF (10 mL) was added NaOH (10M in H$_2$O, 499.48 μL) and BTEAC (28.44 mg, 124.87 μmol). The mixture was stirred at 0° C. for 30 min. Then iodomethane (38.99 mg, 274.71 μmol, 17.10 μL) was added to the mixture and the reaction was stirred at 25° C. for 16 h. The mixture was diluted with water (20 mL) and extracted with EtOAc (20 mL×3). The organic layer was separated, dried over anhydrous Na$_2$SO$_4$, filtered and concentrated. The crude was purified by flash chromatography on silica gel (MeOH in DCM=0 to 7%) to give rac-018 (0.115 g, 242.36 μmol, 97.04% yield) as a white solid. LCMS $R_t$=2.90 min in 7 min chromatography, 10-80CD, ESI calcd. for $C_{29}H_{23}N_4O_3$ [M+H]$^+$ 475.2, found 475.1. HPLC $R_t$=6.18 min in 15 min chromatography, 220 nm, purity 90.98%.

Step B: Preparation of (S)-3-hydroxy-2$^1$-methyl-3-(1-methyl-1H-imidazol-5-yl)-2$^2$-oxo-2$^1$,2$^2$-dihydro-5-oxa-2(4,6)-quinolina-1,4(1,3)-dibenzenacyclohexaphane-4$^4$-carbonitrile ((S)-018)

rac-018 (0.1 g, 210.74 μmol) was separated by SFC (column: DAICEL CHIRALPAK AD (250 mm×30 mm, 10 m); mobile phase: [0.1% NH$_3$H$_2$O EtOH]; B %: 50%-50%, min) to give (S)-018 (22.8 mg, 48.05 μmol, 22.80% yield) as a white solid. $^1$H NMR (400 MHz, DMSO-$d_6$) δ=8.02-7.99 (m, 1H), 7.67-7.48 (m, 6H), 7.32-7.08 (m, 3H), 6.95 (d, J=2.4 Hz, 1H), 6.77 (s, 1H), 6.71 (s, 1H), 6.21 (s, 1H), 5.49-5.38 (m, 2H), 3.70 (s, 3H), 3.36 (s, 3H). LCMS $R_t$=1.45 min in 3.0 min chromatography, 10-80CD, ESI calcd. for $C_{29}H_{23}N_4O_3$ [M+H]$^+$ 475.2, found 475.1. HPLC $R_t$=6.03 min in 15 min chromatography, 220 nm, purity 98.86%. Chiral HPLC (S)-018: $R_t$=2.39 min in 4 min (ee 99.72%) (AD_ETOH_DEA_5_40_4ML_4MIN_5CM), ((R)-018: $R_t$=1.80 min (ee 99.40%)).

Example 19: Preparation of Compound 19

Scheme 19 - Synthesis of Compound 19

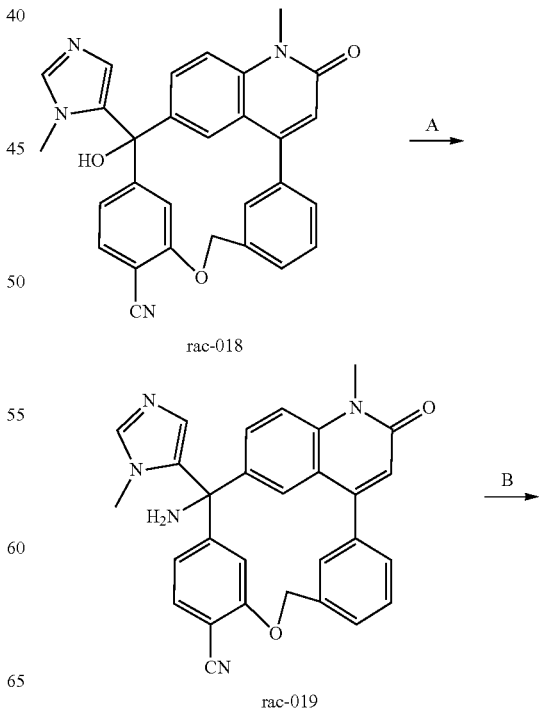

Example 20: Preparation of Compound 20

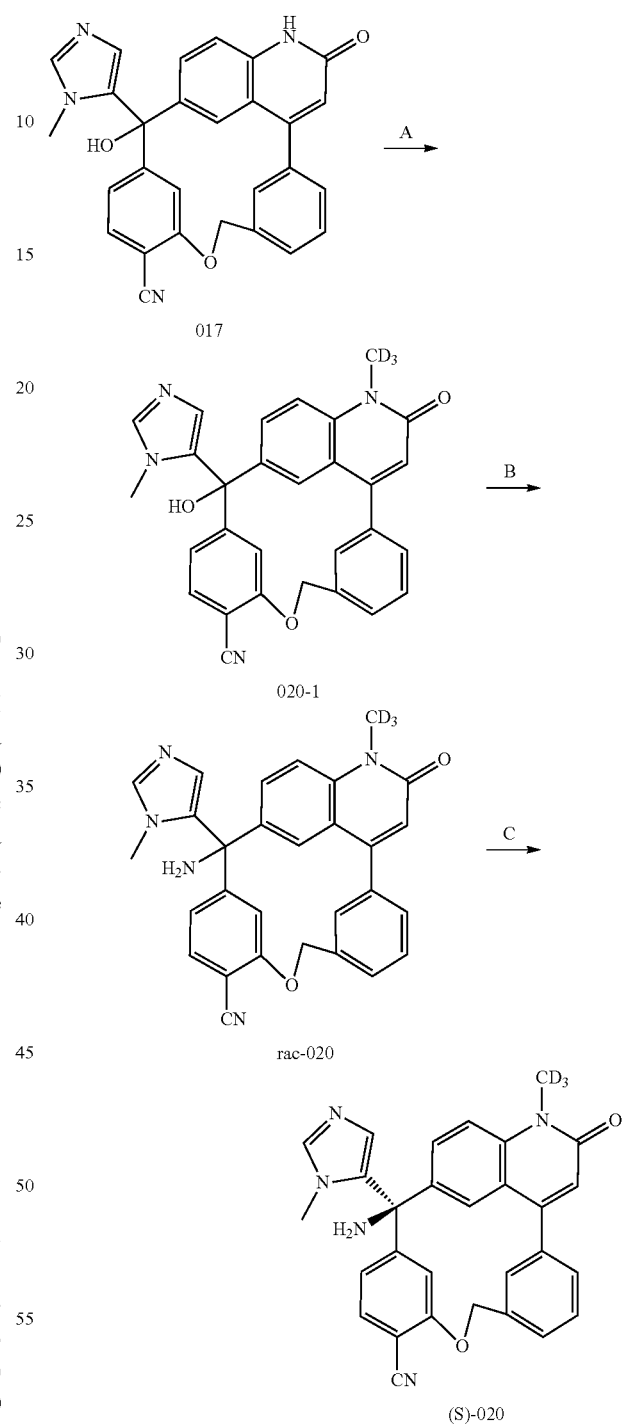

Scheme 20 - Synthesis of Compound 20

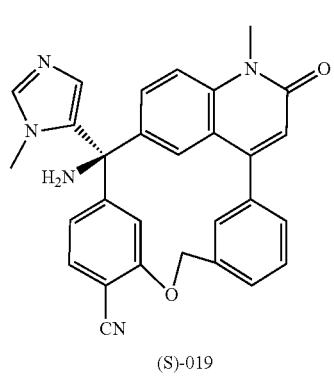

Step A: Preparation of (rac)-3-amino-2¹-methyl-3-(1-methyl-1H-imidazol-5-yl)-2²-oxo-2¹,2²-dihydro-5-oxa-2(4,6)-quinolina-1,4(1,3)-dibenzenacyclo-hexaphane-4⁴-carbonitrile ((rac)-018)

To a solution of rac-018 (0.11 g, 231.82 μmol) in DMI (3 mL) was added SOCl$_2$ (220.64 mg, 1.85 mmol, 134.53 μL) dropwise at 0° C. The mixture was stirred at 40° C. for 1 h. The above mixture was added dropwise to NH$_3$ in MeOH (7M, 6.38 mL) at 0° C. and the reaction mixture was stirred at 25° C. for 1 h. The mixture was diluted with water (20 mL) and extracted with EtOAc (10 mL×3). The organic layer was separated, dried over anhydrous Na$_2$SO$_4$, filtered and concentrated. The crude was purified by flash chromatography on silica gel (MeOH in DCM=0 to 7%) to give rac-019 (0.1 g, 211.18 μmol, 91.10% yield) as a white solid. LCMS R$_t$=0.70 min in 1.5 min chromatography, 5-95AB, ESI calcd. for C$_{29}$H$_{24}$N$_5$O$_2$ [M+H]⁺ 474.2, found 474.2.

Step B: Preparation of (S)-3-amino-2¹-methyl-3-(1-methyl-1H-imidazol-5-yl)-2²-oxo-2¹,2²-dihydro-5-oxa-2(4,6)-quinolina-1,4(1,3)-dibenzenacyclo-hexaphane-4⁴-carbonitrile ((S)-019)

rac-019 (100 mg, 211.18 μmol) was purified by SFC (column: DAICEL CHIRALCEL OD-H (250 mm×30 mm, 5 m); mobile phase: [0.1% NH$_3$H$_2$O EtOH]; B %: 55%-55%, min) to afford (S)-019 (22.0 mg, 46.46 μmol, 22.00% yield) as an off-white solid. ¹H NMR (400 MHz, DMSO-d$_6$) δ=7.93 (s, 1H), 7.73-7.33 (m, 9H), 6.90 (s, 1H), 6.69-6.20 (m, 2H), 5.48-5.38 (m, 2H), 3.66 (s, 3H), 3.22 (s, 3H). LCMS R$_t$=1.42 min in 3.0 min chromatography, 10-80CD, ESI calcd. for C$_{29}$H$_{24}$N$_5$O$_2$ [M+H]⁺ 474.2, found 474.1. HPLC R$_t$=2.36 min in 8 min chromatography, 220 nm, purity 100%. Chiral HPLC (S)-019: R$_t$=4.47 min in 6 min (ee 94.28%) (OD_ETOH_DEA_40_2.8ML_10CM), ((S)-013: R$_t$=3.26 min (ee 99.02%)).

Step A: Preparation of (020-1)

To a solution of 017 (0.15 g, 325.75 μmol) in THF (15 mL) was added BTEAC (37.10 mg, 162.87 μmol) and NaOH (10M in H$_2$O, 3.26 mL) and it was stirred at 25° C. for 30 min to form a clear solution. Then iodomethane-d$_3$ (50.86 mg, 358.32 µmol, 21.83 µL) was added to the above mixture dropwise and the reaction mixture was stirred at 25° C. for 8 h. The mixture was adjusted to pH=7 with HCl (1M in H$_2$O). The mixture was extracted with EtOAc (10 mL×3). The organic layer was separated, dried over anhydrous Na$_2$SO$_4$, filtered and concentrated. The crude was purified by flash chromatography on silica gel (MeOH in DCM=0 to 10%) to give 020-1 (0.13 g, 272.24 µmol, 83.57% yield) as a white solid. $^1$H NMR (400 MHz, DMSO-d$_6$) δ=8.02-8.00 (m, 1H), 7.68-7.52 (m, 8H), 7.05-6.97 (m, 3H), 6.75 (s, 1H), 6.17-6.07 (m, 1H), 5.50-5.47 (m, 2H), 3.32 (s, 3H). LCMS R$_t$=0.73 min in 1.5 min chromatography, 5-95AB, ESI calcd. for C$_{29}$H$_{20}$D$_3$N$_4$O$_3$ [M+H]$^+$ 478.2, found 478.4.

Step B: Preparation of (rac)-3-amino-2$^1$-(methyl-d$_3$)-3-(1-methyl-1H-imidazol-5-yl)-2$^2$-oxo-2$^1$,2$^2$-dihydro-5-oxa-2(4,6)-quinolina-1,4(1,3)-dibenzena-cyclohexaphane-4$^4$-carbonitrile ((rac)-020)

To a solution of 020-1 (0.13 g, 272.24 µmol) in DMI (2 mL) was added SOCl$_2$ (259.10 mg, 2.18 mmol, 157.99 µL) dropwise at 0° C. The mixture was stirred at 40° C. for 1 h. The above mixture was then added dropwise to NH$_3$ in MeOH (7M, 19.45 mL) at 0° C. The reaction mixture was stirred at 25° C. for 1 h. The solvent was removed under reduced pressure. The crude was purified by flash column chromatography on silica gel (MeOH in DCM=0 to 8%) to give rac-020 (0.1 g, 209.84 µmol, 77.08% yield) as a white solid. LCMS R$_t$=0.71 min in 1.5 min chromatography, 5-95AB, ESI calcd. for C$_{29}$H$_{21}$D$_3$N$_5$O$_2$ [M+H]$^+$ 477.2, found 477.3. HPLC R$_t$=2.35 min in 8 min chromatography, 220 nm, purity 100%.

Step C: Preparation of (S)-3-amino-2$^1$-(methyl-d$_3$)-3-(1-methyl-1H-imidazol-5-yl)-2$^2$-oxo-2$^1$,2$^2$-di-hydro-5-oxa-2(4,6)-quinolina-1,4(1,3)-dibenzenacy-clohexaphane-4$^4$-carbonitrile ((S)-020)

rac-020 (0.1 g, 209.84 µmol) was separated by SFC (column: DAICEL CHIRALPAK AD (250 mm×30 mm×10 m); mobile phase: [0.1% NH$_3$H$_2$O EtOH]; B %: 50%-50%, min) to give (S)-020 (34.7 mg, 72.82 µmol, 34.70% yield) as an off-white solid. 1H NMR (400 MHz, DMSO-d$_6$) δ=8.02-7.96 (m, 2H), 7.64-7.45 (m, 8H), 6.90 (s, 1H), 6.70 (s, 1H), 6.41-6.32 (m, 1H), 5.51-5.44 (m, 2H), 3.25 (s, 3H), 3.05 (br s, 2H). LCMS R$_t$=1.42 min in 3.0 min chromatography, 10-80CD, ESI calcd. for C$_{29}$H$_{21}$D$_3$N$_5$O$_2$ [M+H]$^+$ 477.2, found 477.2, C$_{25}$H$_{15}$D$_3$N$_3$O$_2$[M-C$_4$H$_5$N$_2$]$^+$ 395.2, found 395.1. HPLC R$_t$=2.01 min in 8 min chromatography, 220 nm, purity 99.03%. Chiral HPLC (S)-020: R$_t$=1.39 min in 2.5 min (ee 99.14%) (AD_ETOH_DEA_40-4ML_5CM), ((R)-020: R$_t$=0.70 min (ee 100%)).

Scheme D - General Synthetic Method D

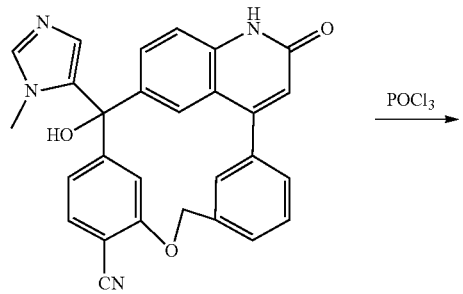

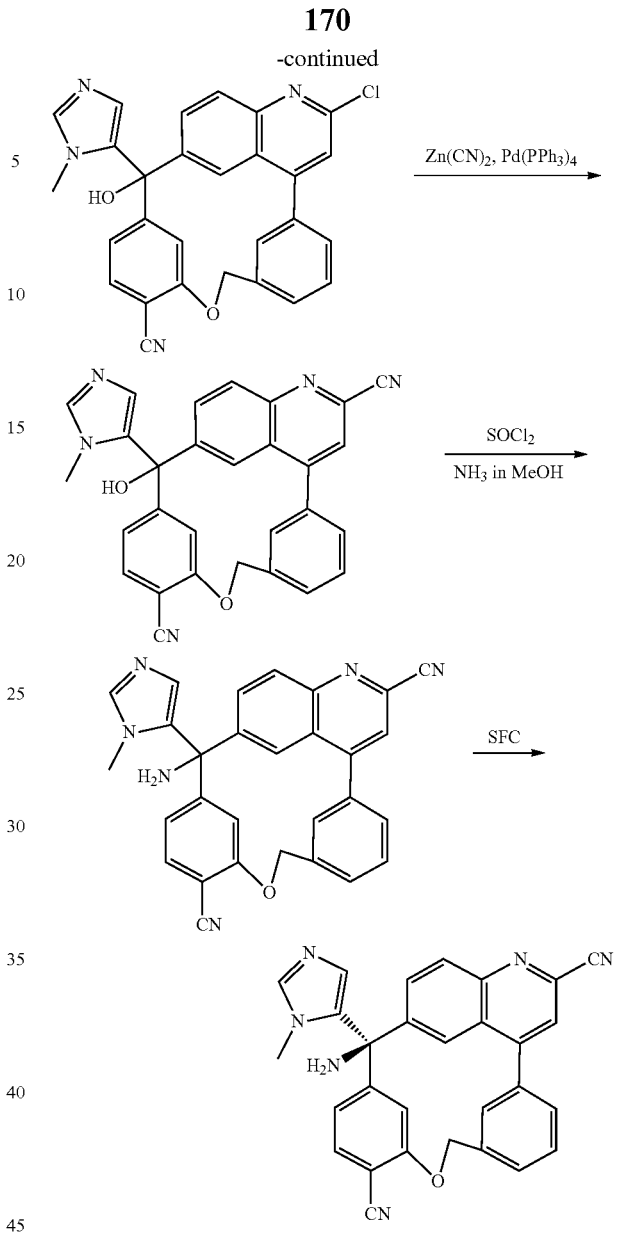

Example 21: Preparation of Compound 21

Scheme 21 - Synthesis of Compound 21

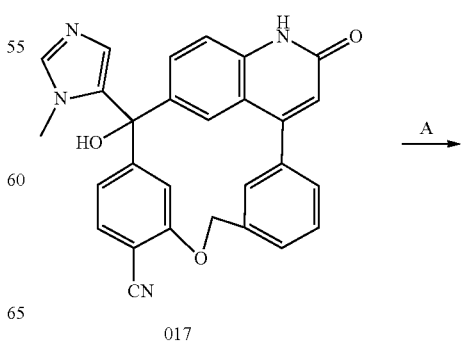

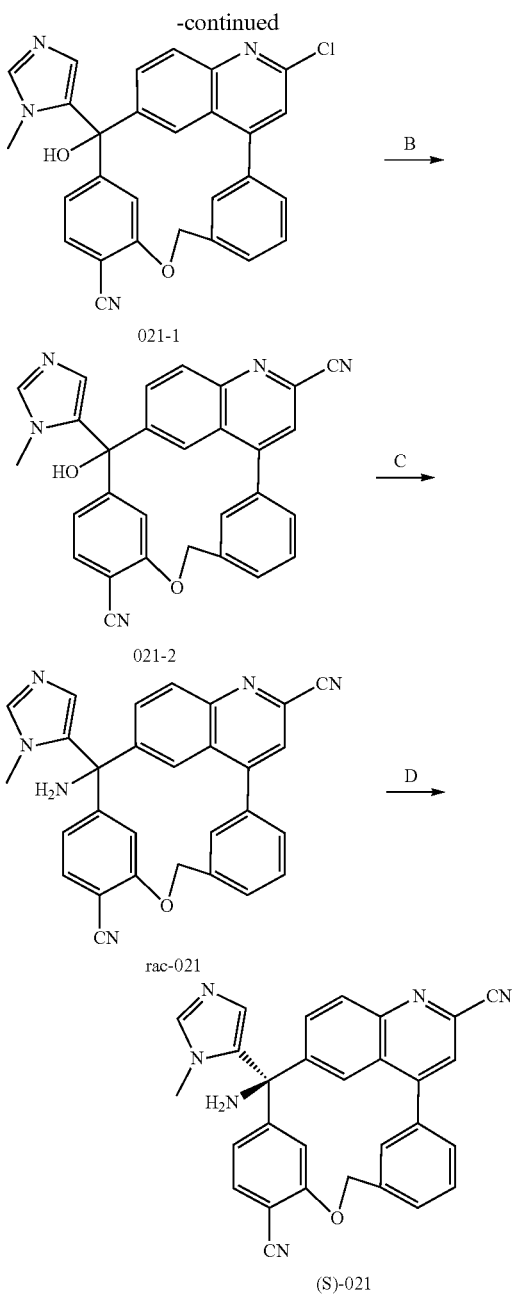

(s, 3H). LCMS $R_t$=1.79 min in 3.0 min chromatography, 10-80CD, ESI calcd. for $C_{28}H_{20}ClN_4O_2$ [M+H]$^+$ 479.1, found 479.1.

Step B: Preparation of (021-2)

To a solution of 021-1 (1.3 g, 2.71 mmol) and Zn(CN)$_2$ (4.78 g, 40.72 mmol) in DMF (20 mL) was added Pd(PPh$_3$)$_4$ (940.99 mg, 814.32 μmol) in a three-neck bottom flask at 25° C. under N$_2$. The mixture was stirred at 120° C. for 16 h. The mixture was cooled to 25° C. and added into water (70 mL). The aqueous phase was extracted with EtOAc (100 mL×2). The combined organic phase was washed with brine (50 mL×2), dried over anhydrous Na$_2$SO$_4$, filtered and concentrated under reduced pressure. The crude was blended with another batch from 1.3 g of 021-1, purified by flash chromatography on silica gel (MeOH in DCM=0 to 7%) to give 021-2 (1.1 g, 2.34 mmol, 43.13% yield) as a yellow solid. LCMS $R_t$=1.70 min in 3.0 min chromatography, 10-80CD, ESI calcd. for $C_{29}H_{20}N_5O_2$ [M+H]$^+$ 470.2, found 470.2.

Step C: Preparation of (rac)-3-amino-3-(1-methyl-1H-imidazol-5-yl)-5-oxa-2(4,6)-quinolina-1,4(1,3)-dibenzenacyclohexaphane-2$^2$ 4$^4$-dicarbonitrile ((rac)-021)

To a solution of 021-2 (1 g, 2.13 mmol) in DMI (5 mL) was added SOCl$_2$ (1.77 g, 14.91 mmol, 1.08 mL) at 0° C. by dropwise. The reaction mixture was stirred at 40° C. for 1 h. The above mixture was then added dropwise to NH$_3$ in MeOH (7M, 30.45 mL, 213.14 mmol) at 0° C. The reaction mixture was stirred at 25° C. for 1 h. Water (20 mL) was added to the mixture. The mixture was extracted with EtOAc (20 mL×3). The organic layer was separated, dried over anhydrous Na$_2$SO$_4$, filtered and concentrated. The solid was filtered and concentrated under pressure. The crude was purified by flash chromatography on silica gel (MeOH in DCM=0 to 7%) to give rac-021 (0.55 g, 1.17 mmol, 54.93% yield) as a yellow solid. LCMS $R_t$=1.69 min in 3.0 min chromatography, 10-80CD, ESI calcd. for $C_{29}H_{21}N_6O$ [M+H]$^+$ 469.2, found 469.2. HPLC $R_t$=6.77 min in 15 min chromatography, 215 nm, purity 93.86%.

Step D: Preparation of (S)-3-amino-3-(1-methyl-1H-imidazol-5-yl)-5-oxa-2(4,6)-quinolina-1,4(1,3)-dibenzenacyclohexaphane-2$^2$ 4$^4$-dicarbonitrile ((S)-021)

Step A: Preparation of (021-1)

A mixture of 017 (5.2 g, 11.29 mmol) in POCl$_3$ (173.15 g, 1.13 mol, 104.94 mL) was heated at 100° C. for 1 h. The reaction mixture was concentrated under reduced pressure to removed POCl$_3$. The residue was quenched by adding dropwise to saturated NaOH solution to pH=7. The mixture was extracted with DCM/MeOH=10:1 (50 mL×3). The organic layer was separated, dried over anhydrous Na$_2$SO$_4$, filtered and concentrated. The crude was purified by flash chromatography on silica gel (MeOH in DCM=0 to 10%) to give 021-1 (3.3 g, 6.89 mmol, 61.02% yield) as a white solid. $^1$H NMR (400 MHz, DMSO-d$_6$) δ=8.18-8.16 (m, 1H), 8.05 (d, J=8.8 Hz, 1H), 7.71 (s, 1H), 7.68-7.62 (m, 4H), 7.58 (s, 1H), 7.46 (s, 1H), 7.23 (d, J=2.0 Hz, 2H), 6.94 (s, 1H), 6.20 (br s, 1H), 5.52-5.44 (m, 2H), 3.83-3.82 (m, 1H), 3.39 rac-021 (0.55 g, 1.17 mmol) was separated by SFC (column: DAICEL CHIRALPAK AD (250 mm×30 mm, 10 m); mobile phase: [0.1% NH$_3$H$_2$O EtOH]; B %: 55%-55%, min) to give (S)-021 (213.5 mg, 455.70 μmol, 38.94% yield) as an off-white solid. 1H NMR (400 MHz, DMSO-d$_6$) δ=8.25-8.15 (m, 3H), 7.71-7.55 (m, 7H), 7.19 (s, 1H), 6.78-6.44 (m, 2H), 5.57-5.49 (m, 2H), 3.30-3.22 (m, 5H). LCMS $R_t$=1.67 min in 3 min chromatography, 10-80CD, ESI calcd. for: $C_{29}H_{21}N_6O$ [M+H]$^+$ 469.2, found 469.2. HPLC $R_t$=3.02 min in 8 min chromatography, 220 nm, purity 99.72%. Chiral HPLC (S)-021: $R_t$=1.08 min in 2 min (ee 99.74%) (AD_ETOH_DEA_40-4ML 5CM), ((R)-021: $R_t$=0.46 min (ee 99.74%)).

Scheme E - General Synthetic Method E
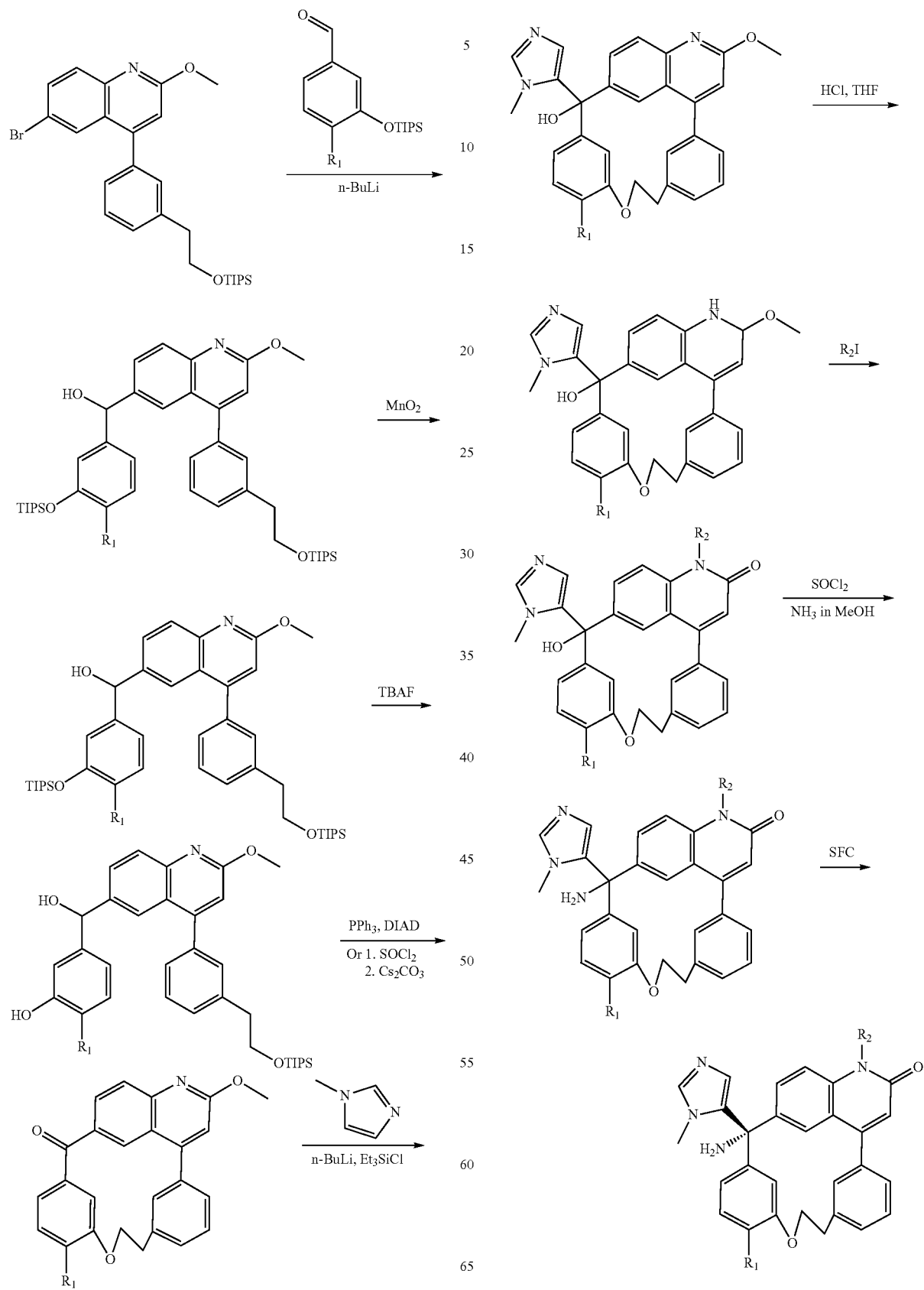

Example 22: Preparation of Compound 22

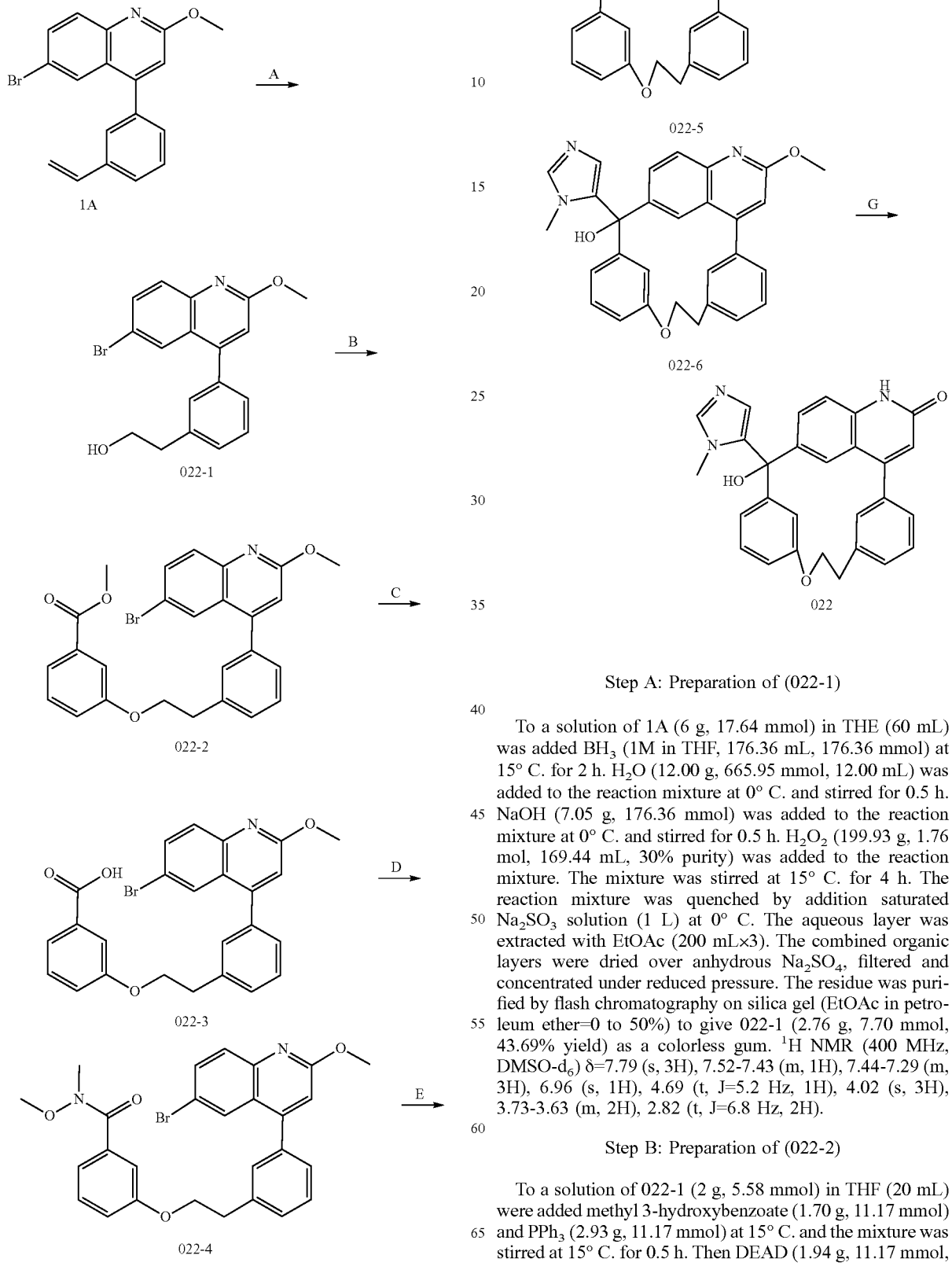

Step A: Preparation of (022-1)

To a solution of 1A (6 g, 17.64 mmol) in THF (60 mL) was added BH$_3$ (1M in THF, 176.36 mL, 176.36 mmol) at 15° C. for 2 h. H$_2$O (12.00 g, 665.95 mmol, 12.00 mL) was added to the reaction mixture at 0° C. and stirred for 0.5 h. NaOH (7.05 g, 176.36 mmol) was added to the reaction mixture at 0° C. and stirred for 0.5 h. H$_2$O$_2$ (199.93 g, 1.76 mol, 169.44 mL, 30% purity) was added to the reaction mixture. The mixture was stirred at 15° C. for 4 h. The reaction mixture was quenched by addition saturated Na$_2$SO$_3$ solution (1 L) at 0° C. The aqueous layer was extracted with EtOAc (200 mL×3). The combined organic layers were dried over anhydrous Na$_2$SO$_4$, filtered and concentrated under reduced pressure. The residue was purified by flash chromatography on silica gel (EtOAc in petroleum ether=0 to 50%) to give 022-1 (2.76 g, 7.70 mmol, 43.69% yield) as a colorless gum. $^1$H NMR (400 MHz, DMSO-d$_6$) δ=7.79 (s, 3H), 7.52-7.43 (m, 1H), 7.44-7.29 (m, 3H), 6.96 (s, 1H), 4.69 (t, J=5.2 Hz, 1H), 4.02 (s, 3H), 3.73-3.63 (m, 2H), 2.82 (t, J=6.8 Hz, 2H).

Step B: Preparation of (022-2)

To a solution of 022-1 (2 g, 5.58 mmol) in THF (20 mL) were added methyl 3-hydroxybenzoate (1.70 g, 11.17 mmol) and PPh$_3$ (2.93 g, 11.17 mmol) at 15° C. and the mixture was stirred at 15° C. for 0.5 h. Then DEAD (1.94 g, 11.17 mmol, 2.03 mL) was added to the mixture at 0° C. The mixture was stirred at 15° C. for 1.5 h. Water (20 mL) was added to the mixture. The aqueous layer was extracted with EtOAc (30 mL×2). The combined organic layers were washed with brine (80 mL), dried over anhydrous $Na_2SO_4$, filtered and concentrated. The residue was purified by flash chromatography on silica gel (EtOAc in petroleum ether=0 to 10%) to afford 022-2 (2.3 g, 4.67 mmol, 83.69% yield) as colorless oil. $^1$H NMR (400 MHz, $CDCl_3$) δ=7.89 (d, J=2.4 Hz, 1H), 7.79 (d, J=8.8 Hz, 1H), 7.70 (d, J=2.4, 8.8 Hz, 1H), 7.66-7.62 (m, 1H), 7.59-7.56 (m, 1H), 7.53-7.42 (m, 2H), 7.40-7.31 (m, 3H), 7.14-7.10 (m, 1H), 6.87 (s, 1H), 4.30 (t, J=6.8 Hz, 2H), 4.10 (s, 3H), 3.91 (s, 3H), 3.22 (t, J=6.8 Hz, 2H). LCMS $R_t$=1.18 min in 1.5 min chromatography, 5-95AB, ESI calcd. for $C_{26}H_{23}BrNO_4$ $[M+H]^+$ 492.1, found 491.9.

Step C: Preparation of (022-3)

To a solution of 022-2 (2.6 g, 5.28 mmol) in THF (25 mL) was added a solution of NaOH (1.06 g, 26.40 mmol) in $H_2O$ (20 mL) at 15° C. The mixture was stirred at 15° C. for 12 h and 70° C. for 8 h. HCl (1M in $H_2O$) was added to the mixture to adjust pH=3. The aqueous layer was extracted with EtOAc (30 mL×2). The combined organic layers were washed with brine (80 mL), dried over anhydrous $Na_2SO_4$, filtered and concentrated to afford 022-3 (2.5 g, 5.23 mmol, 99.05% yield) as colorless oil, which was used into the next step without further purification. LCMS $R_t$=1.09 min in 1.5 min chromatography, 5-95AB, ESI calcd. for $C_{25}H_{21}BrNO_4$ $[M+H]^+$ 478.1, found 478.0.

Step D: Preparation of (022-4)

To a solution of 022-3 (2.5 g, 5.23 mmol) in DCM (30 mL) were added HATU (2.38 g, 6.27 mmol), DIPEA (3.38 g, 26.13 mmol, 4.55 mL) and N,O-dimethylhydroxylamine hydrogen chloride (764.71 mg, 7.84 mmol) at 15° C. The mixture was stirred at 15° C. for 2 h. Water (20 mL) was added to the mixture. The aqueous layer was extracted with DCM (30 mL×2). The combined organic layers were washed with brine (90 mL), dried over anhydrous $Na_2SO_4$, filtered and concentrated. The residue was purified by flash chromatography on silica gel (EtOAc in petroleum ether=0 to 30%) to afford 022-4 (2.7 g, 5.18 mmol, 99.04% yield) as yellow oil. $^1$H NMR (400 MHz, $CDCl_3$) δ=7.88 (d, J=2.4 Hz, 1H), 7.78 (d, J=8.8 Hz, 1H), 7.69 (d, J=2.4, 8.8 Hz, 1H), 7.51-7.40 (m, 2H), 7.37 (s, 1H), 7.35-7.31 (m, 1H), 7.30-7.27 (m, 1H), 7.25-7.19 (m, 2H), 7.01-6.99 (m 1H), 6.86 (s, 1H), 4.27 (t, J=6.8 Hz, 2H), 4.09 (s, 3H), 3.55 (s, 3H), 3.32 (s, 3H), 3.20 (t, J=6.8 Hz, 2H). LCMS $R_t$=1.10 min in 1.5 min chromatography, 5-95AB, ESI calcd. for $C_{27}H_{26}BrN_2O_4$ $[M+H]^+$ 521.1, found 521.1.

Step E: Preparation of (022-5)

To a solution of 022-4 (1.8 g, 3.45 mmol) in redistillation THF (90 mL) was added n-BuLi (2.5M in n-hexane, 4.14 mmol, 1.66 mL) at −78° C. The mixture was stirred at −78° C. for 0.5 h. Water (20 mL) was added to the mixture. The aqueous layer was extracted with EtOAc (30 mL×2). The combined organic layers were washed with brine (100 mL), dried over anhydrous $Na_2SO_4$, filtered and concentrated. The residue was purified by flash chromatography on silica gel (EtOAc in petroleum ether=0 to 20%) to afford 022-5 (260 mg, 681.66 µmol, 19.75% yield) as an off-white solid. $^1$H NMR (400 MHz, $CDCl_3$) δ=8.38 (dd, J=2.0, 8.4 Hz, 1H), 8.00 (d, J=8.4 Hz, 1H), 7.95 (d, J=2.0 Hz, 1H), 7.48 (s, 1H), 7.43 (s, 1H), 7.42-7.33 (m, 3H), 7.33-7.27 (m, 2H), 7.07-7.01 (m, 1H), 6.94 (s, 1H), 4.67-4.56 (m, 2H), 4.16 (s, 3H), 3.11 (t, J=4.8 Hz, 2H). LCMS $R_t$=1.05 min in 1.5 min chromatography, 5-95AB, ESI calcd. for $C_{25}H_{20}NO_3$ $[M+H]^+$ 382.1, found 382.1.

Step F: Preparation of (022-6)

To a solution of 1-methyl-1H-imidazole (67.16 mg, 817.99 µmol, 65.20 µL) in re-distillation THF (5 mL) was added n-BuLi (2.5M in n-hexane, 817.99 µmol, 327.20 µL) at −78° C. The mixture was stirred at −78° C. for 0.5 h. Then $Et_3SiCl$ (123.29 mg, 817.99 µmol, 139.15 L) was added to the mixture at −78° C. The mixture was stirred at −78° C. for 0.5 h. Then n-BuLi (2.5M in n-hexane, 817.99 µmol, 327.20 µL) was added to the mixture at −78° C. The mixture was stirred at −78° C. for 0.5 h. Then 022-5 (260 mg, 681.66 µmol) in redistillation THF (3 mL) was added to the mixture at −78° C. The mixture was stirred at −78° C. for 1.5 h. Water (20 mL) was added to the mixture. The aqueous layer was extracted with EtOAc (30 mL×2). The combined organic layers were washed with brine (30 mL), dried over anhydrous $Na_2SO_4$, filtered and concentrated. The residue was purified by chromatography on silica gel (MeOH in DCM=0 to 10%) to afford 022-6 (150 mg, 323.61 µmol, 47.47% yield) as a pink solid. $^1$H NMR (400 MHz, DMSO-$d_6$) δ=8.09 (d, J=8.8 Hz, 1H), 7.87 (d, J=8.8 Hz, 1H), 7.57 (s, 2H), 7.47-7.40 (m, 1H), 7.27-16 (m, 2H), 7.10 (s, 1H), 7.03 (s, 1H), 6.94 (s, 1H), 6.91-6.86 (m, 2H), 6.80 (s, 1H), 6.42 (s, 1H), 5.94 (s, 1H), 4.76-4.48 (m, 2H), 4.01 (s, 3H), 3.37 (s, 3H), 3.03-2.93 (m, 1H), 2.92-2.83 (m, 1H). LCMS $R_t$=0.84 min in 1.5 min chromatography, 5-95AB, ESI calcd. for $C_{29}H_{26}N_3O_3$ $[M+H]^+$ 464.2, found 464.1.

Step G: Preparation of 3-hydroxy-3-(1-methyl-1H-imidazol-5-yl)-2$^1$,2$^2$-dihydro-5-oxa-2(4,6)-quinolina-1,4(1,3)-dibenzenacycloheptaphan-2$^2$-one (022)

A mixture of 022-6 (140 mg, 302.03 µmol) in THF (5 mL) and HCl (4M in $H_2O$, 7.55 mmol, 1.89 mL) was stirred at 70° C. for 12 h. After cooling to r.t, the mixture was adjusted to pH=7 with NaOH (5M in $H_2O$). The mixture was extracted with DCM (20 mL×3). The organic layer was separated, dried over anhydrous $Na_2SO_4$, filtered and concentrated the mixture was concentrated under reduced pressure to give 022 (130 mg, 289.21 µmol, 95.76% yield) as a yellow solid. 30 mg of the product was purified by Prep-HPLC (column: Welch Xtimate $C_{18}$ 150×25 mm×5×µm; mobile phase: [water (0.05% $NH_3H_2O$+10 mM $NH_4HCO_3$)-ACN]; B %: 36%-66%, 7.8 min) to afford 022 (6.8 mg, 15.13 µmol, 22.67% yield) as an off-white solid. $^1$H NMR (400 MHz, DMSO-$d_6$) δ=11.59 (br s, 1H), 8.02-7.65 (m, 2H), 7.45-7.33 (m, 3H), 7.20-7.12 (m, 2H), 7.02-6.78 (m, 3H), 6.68 (s, 1H), 6.55-6.42 (m, 2H), 6.35 (s, 1H), 4.79-4.45 (m, 2H), 3.39 (s, 3H), 3.03-2.93 (m, 2H). LCMS $R_t$=1.50 min in 3 min chromatography, 10-80CD, ESI calcd. for $C_{28}H_{24}N_3O_3$ $[M+H]^+$ 450.2, found 450.3. HPLC $R_t$=3.01 min in 8 min chromatography, 220 nm, purity 96.42%.

Example 23: Preparation of Compound 23

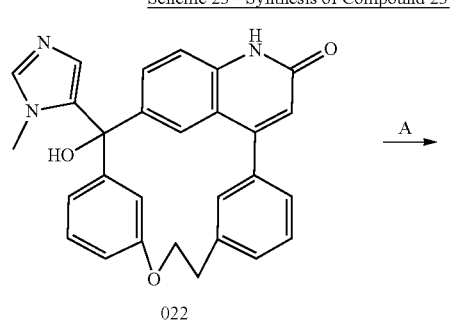

Scheme 23 - Synthesis of Compound 23

Step A: Preparation of (023)

To a solution of 022 (100 mg, 222.47 µmol) in THF (2 mL) and H$_2$O (1 mL) were added BTEAC (25.34 mg, 111.23 µmol), NaOH (88.98 mg, 2.22 mmol) and iodomethane (47.37 mg, 333.70 µmol, 20.77 µL) at 15° C. The mixture was stirred at 15° C. for 2 h. Water (15 mL) was added to the mixture. The aqueous layer was extracted with EtOAc (15 mL×2). The combined organic layers were washed with brine (30 mL), dried over anhydrous Na$_2$SO$_4$, filtered and concentrated. The residue was purified by Prep-HPLC (column: Waters Xbridge 150×25 mm×5 m; mobile phase: [water (0.05% NH$_3$H$_2$O)-ACN]; B %: 29%-59%, 7.8 min) to afford 023 (8.8 mg, 18.98 µmol, 8.53% yield) as an off-white solid. $^1$H NMR (400 MHz, DMSO-d$_6$) δ=8.05 (dd, J=2.4, 8.8 Hz, 1H), 7.63 (d, J=8.8 Hz, 1H), 7.59 (s, 1H), 7.44-7.35 (m, 2H), 7.19-7.13 (m, 2H), 6.96 (d, J=7.6 Hz, 1H), 6.89 (d, J=7.6 Hz, 1H), 6.81 (s, 1H), 6.76 (s, 1H), 6.48-6.43 (m, 3H), 6.08 (s, 1H), 4.74-4.63 (m, 1H), 4.61-4.52 (m, 1H), 3.69 (s, 3H), 3.38 (s, 3H), 2.99-2.96 (m, 1H), 2.94-2.91 (m, 1H). LCMS R$_t$=1.57 min in 3.0 min chromatography, 10-80CD, ESI calcd. for C$_{29}$H$_{26}$N$_3$O$_3$ [M+H]$^+$ 464.2, found 464.2. HPLC R$_t$=3.15 min in 8 min chromatography, 220 nm, purity 97.95%.

Example 24: Preparation of Compound 24

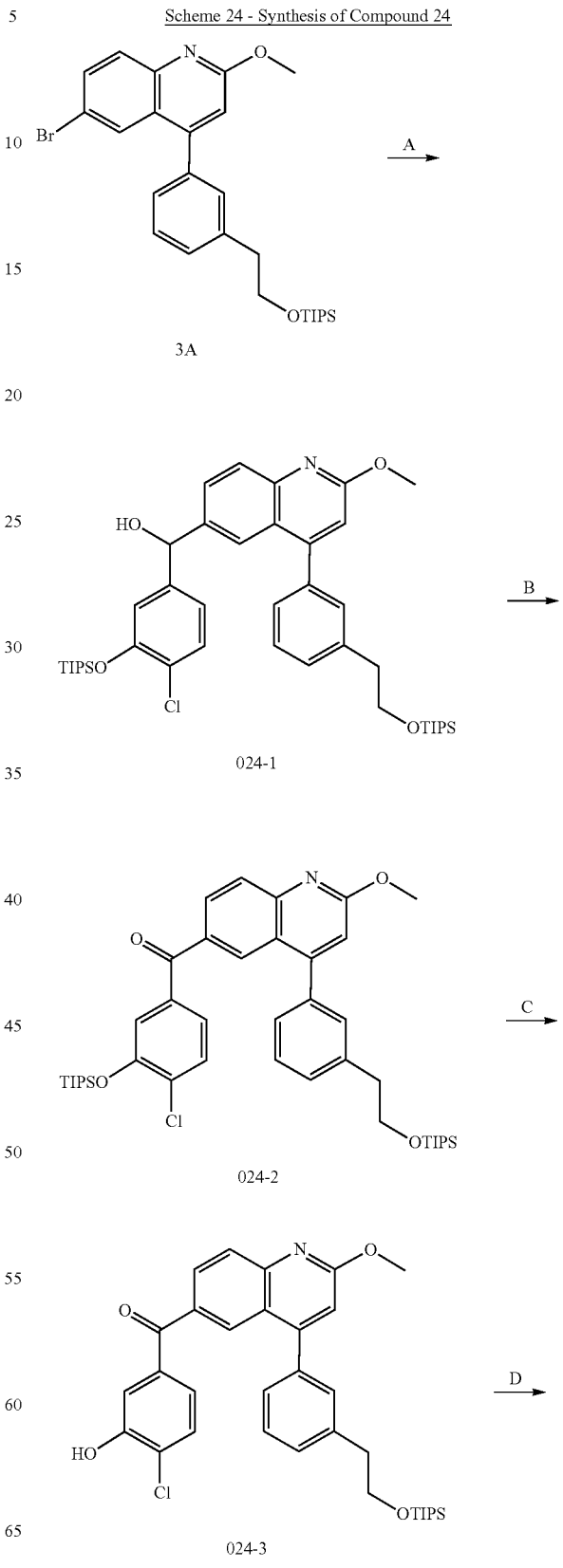

Scheme 24 - Synthesis of Compound 24

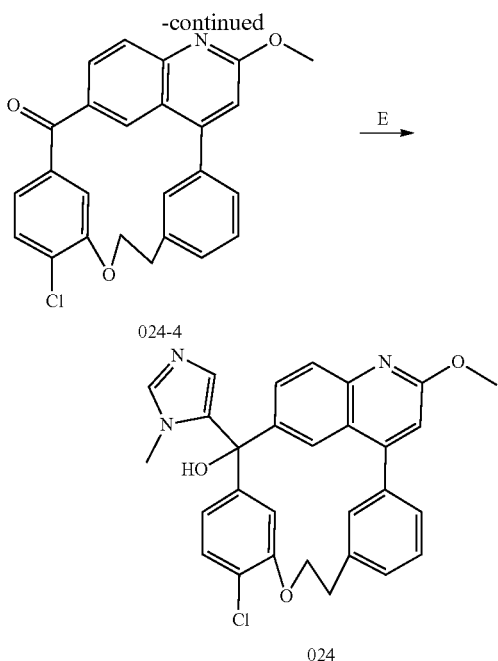

Step A: Preparation of (024-1)

To a solution of 3A (3 g, 5.83 mmol) in redistillation THF (30 mL) was added n-BuLi (2.5M in n-hexane, 7.00 mmol, 2.80 mL) at −78° C. The mixture was stirred at −78° C. for 10 min. Then a solution of 5A (2.01 g, 6.41 mmol) in redistillation THF (3 mL) was added to the mixture at −78° C. The mixture was stirred at −78° C. for 1 h and 15° C. for 2 h. Water (20 mL) was added to the mixture. The aqueous layer was extracted with EtOAc (20 mL×2). The combined organic layers were washed with brine (30 mL), dried over anhydrous $Na_2SO_4$, filtered and concentrated. The residue was purified by flash chromatography on silica gel (EtOAc in petroleum ether=0 to 20%) to afford 024-1 (2.8 g, 3.74 mmol, 64.16% yield) as yellow oil. $^1H$ NMR (400 MHz, $CDCl_3$) δ=7.84 (d, J=8.8 Hz, 1H), 7.76 (s, 1H), 7.50 (d, J=8.8 Hz, 1H), 7.41-7.35 (m, 1H), 7.35-7.31 (m, 1H), 7.30-7.26 (m, 3H), 6.85-6.78 (m, 3H), 5.78 (d, J=3.2 Hz, 1H), 4.08 (s, 3H), 3.92 (t, J=6.8 Hz, 2H), 2.91 (t, J=6.8 Hz, 2H), 2.14 (d, J=3.2 Hz, 1H), 1.19-1.02 (m, 6H), 1.02-0.96 (m, 36H).

Step B: Preparation of (024-2)

A mixture of 024-1 (2.8 g, 3.74 mmol) and $MnO_2$ (13.01 g, 149.62 mmol) in DCM (60 mL) was stirred at 35° C. for 6 h. The mixture was filtered through Celite and the filter cake was washed with DCM (15 mL×2). The filtrate was concentrated under reduced pressure. The residue was purified by flash chromatography on silica gel (EtOAc in petroleum ether=0 to 1%) to afford 024-2 (2.3 g, 3.08 mmol, 82.36% yield) as yellow oil. 1H NMR (400 MHz, $CDCl_3$) δ=8.26 (s, 1H), 8.00-7.95 (m, 1H), 7.95-7.91 (m, 1H), 7.41-7.38 (m, 1H), 7.37-7.35 (m, 1H), 7.34-7.32 (m, 1H), 7.33-7.28 (m, 3H), 7.28-7.25 (m, 1H), 6.90 (s, 1H), 4.13 (s, 3H), 3.89 (t, J=6.8 Hz, 2H), 2.89 (t, J=6.8 Hz, 2H), 1.30-1.25 (m, 3H), 1.10-1.05 (m, 18H), 1.03-0.99 (m, 3H), 0.98-0.95 (m, 18H).

Step C: Preparation of (024-3)

To a solution of 024-2 (2.3 g, 3.08 mmol) in THF (20 mL) was added TBAF (1M in THF, 30.81 mmol, 30.81 mL) at 15° C. The mixture was stirred at 15° C. for 2 h. Water (20 mL) was added to the mixture. The aqueous layer was extracted with EtOAc (15 mL×2). The combined organic layers were washed with water (30 mL×2), brine (30 mL), dried over anhydrous $Na_2SO_4$, filtered and concentrated. The residue was purified by flash chromatography on silica gel (MeOH in DCM=0 to 2%) to afford 024-3 (1 g, 2.30 mmol, 74.81% yield) as an off-white solid. $^1H$ NMR (400 MHz, $CDCl_3$) δ=8.23 (s, 1H), 8.05 (d, J=8.8 Hz, 1H), 7.96 (d, J=8.8 Hz, 1H), 7.44-7.37 (m, 4H), 7.34-7.27 (m, 4H), 6.91 (s, 1H), 6.38 (br s, 1H), 4.12 (s, 3H), 3.91 (t, J=6.4 Hz, 2H), 2.94 (t, J=6.4 Hz, 2H). LCMS $R_t$=0.92 min in 1.5 min chromatography, 5-95AB, ESI calcd. for $C_{25}H_{21}ClNO_4$ $[M+H]^+$ 434.1, found 434.0.

Step D: Preparation of (024-4)

A solution of DEAD (802.77 mg, 4.61 mmol, 837.97 μL) and $PPh_3$ (1.21 g, 4.61 mmol) in THF (12 mL) was stirred at 0° C. for 1 h. Then 024-3 (1 g, 2.30 mmol) in THF (100 mL) was added to the mixture at 0° C. The mixture was stirred at 15° C. for 12 h. Water (100 mL) was added to the mixture. The aqueous layer was extracted with EtOAc (50 mL×2). The combined organic layers were washed with brine (200 mL), dried over anhydrous $Na_2SO_4$, filtered and concentrated. The residue was purified by flash chromatography on silica gel (EtOAc in petroleum ether=0 to 20%) to afford 024-4 (700 mg, 1.68 mmol, 73.03% yield) as an off-white solid. $^1H$ NMR (400 MHz, $CDCl_3$) δ=8.34 (d, J=2.0, 8.8 Hz, 1H), 7.98 (d, J=8.8 Hz, 1H), 7.93 (d, J=2.0 Hz, 1H), 7.54 (s, 1H), 7.44 (s, 1H), 7.42-7.34 (m, 3H), 7.33-7.27 (m, 2H), 6.95 (s, 1H), 4.70-4.68 (m, 2H), 4.14 (s, 3H), 3.17 (t, J=4.8 Hz, 2H). LCMS $R_t$=1.10 min in 1.5 min chromatography, 5-95AB, ESI calcd. for $C_{25}H_{19}ClNO_3$ $[M+H]^+$ 416.1, found 416.1.

Step E: Preparation of 4⁴-chloro-2²-methoxy-3-(1-methyl-1H-imidazol-5-yl)-5-oxa-2(4,6)-quinolina-1,4(1,3)-dibenzenacycloheptaphan-3-ol (024)

To a solution of 1-methyl-1H-imidazole (153.99 mg, 1.88 mmol, 149.51 μL) in redistillation THF (5 mL) was added n-BuLi (2.5M in n-hexane, 1.88 mmol, 750.24 μL) at −78° C. The mixture was stirred at −78° C. for 0.5 h. Then $Et_3SiCl$ (282.69 mg, 1.88 mmol, 319.06 L) was added to the mixture at −78° C. The mixture was stirred at −78° C. for 0.5 h. Then n-BuLi (2.5M in n-hexane, 1.88 mmol, 750.24 μL) was added to the mixture at −78° C. The mixture was stirred at −78° C. for 0.5 h. Then 024-4 (650 mg, 1.56 mmol) in redistillation THF (5 mL) was added to the mixture at −78° C. The mixture was stirred at −78° C. for 1.5 h. Water (20 mL) was added to the mixture. The aqueous layer was extracted with EtOAc (15 mL×2). The combined organic layers were washed with brine (30 mL), dried over anhydrous $Na_2SO_4$, filtered and concentrated. The residue was purified by chromatography on silica gel (MeOH in DCM=0 to 2%) to afford 024 (650 mg, 1.31 mmol, 83.51% yield) as a yellow solid. 30 mg (60.24 μmol) of product was purified by Prep-HPLC (column: Waters Xbridge 150×25 mm×5 m; mobile phase: [water (0.05% $NH_3H_2O$+10 mM $NH_4HCO_3$)-ACN]; B %: 53%-83%, 7.8 min) to afford 024 (5.1 mg, 10.24 μmol, 17.00% yield) as an off-white solid. $^1H$ NMR (400 MHz, DMSO-$d_6$) δ=8.05 (dd, J=2.4, 8.8 Hz, 1H), 7.88

(d, J=8.8 Hz, 1H), 7.60 (s, 1H), 7.34-7.30 (m, 2H), 7.27 (s, 1H), 7.21-7.13 (m, 2H), 6.95-6.90 (m, 2H), 6.85-6.80 (m, 1H), 6.61 (d, J=2.0 Hz, 1H), 6.51 (s, 1H), 6.23 (s, 1H), 4.81-4.63 (m, 2H), 4.06 (s, 3H), 3.38 (s, 3H), 3.05-3.00 (m, 2H). LCMS $R_t$=2.05 min in 3.0 min chromatography, 10-80CD, ESI calcd. for $C_{29}H_{25}ClN_3O_3$ [M+H]$^+$ 498.2, found 498.2. HPLC $R_t$=4.15 min in 8 min chromatography, 220 nm, purity 98.85%.

Example 25: Preparation of Compound 25

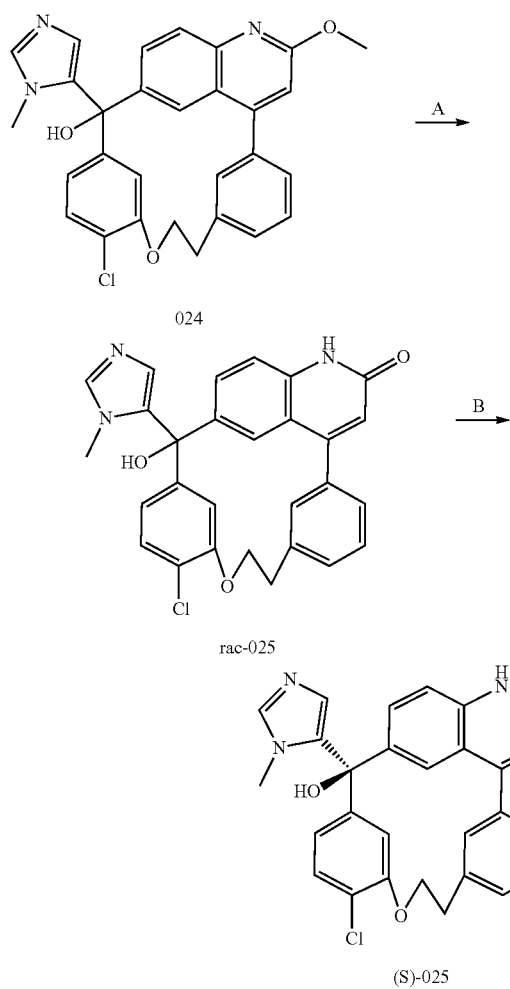

Scheme 25 - Synthesis of Compound 25 rac-025

Step A: Preparation of (rac)-4⁴-chloro-3-hydroxy-3-(1-methyl-1H-imidazol-5-yl)-2¹,2²-dihydro-5-oxa-2(4,6)-quinolina-1,4(1,3)-dibenzenacycloheptaphan-2²-one (rac-025)

To a solution of 024 (570 mg, 1.14 mmol) in THF (8 mL) was added HCl (4M in H$_2$O, 7.15 mL) at 15° C. The mixture was stirred at 70° C. for 12 h. Saturated NaHCO$_3$ solution was added into the mixture to adjusted to pH=8. The aqueous layer was filtered. The filtrate was extracted with DCM (30 mL×2). The combined organic layers were washed with brine (60 mL). The above organic layers and the filter cake dissolved in DCM/MeOH=10/1 (30 mL) were dried over anhydrous Na$_2$SO$_4$, filtered and concentrated to afford rac-025 (550 mg, 1.14 mmol, 100% yield) as a yellow solid, which was used into the next step without further purification. LCMS $R_t$=1.668 min in 3.0 min chromatography, 10-80CD, ESI calcd. for $C_{28}H_{23}ClN_3O_3$ [M+H]$^+$ 484.1, found 484.1.

Step B: Preparation of (S)-4⁴-chloro-3-hydroxy-3-(1-methyl-1H-imidazol-5-yl)-2¹,2²-dihydro-5-oxa-2(4,6)-quinolina-1,4(1,3)-dibenzenacycloheptaphan-2²-one ((S)-025)

rac-025 (100 mg, 206.64 μmol) was further separated by SFC (1$^{st}$: column: DAICEL CHIRALCEL OD-H (250 mm×30 mm, 5 m); mobile phase: [0.1% NH$_3$H$_2$O EtOH]; B %: 45%-45%; 2$^{nd}$: column: DAICEL CHIRALCEL OD (250 mm×30 mm, 10 m); mobile phase: [0.1% NH$_3$H$_2$O EtOH]; B %: 50%-50%) to afford (S)-025 (29.2 mg, 60.34 μmol, 29.20% yield) as an off-white solid. $^1$H NMR (400 MHz, DMSO-d$_6$) δ=11.61 (br s, 1H), 7.89 (dd, J=2.0, 8.8 Hz, 1H), 7.52 (s, 1H), 7.43 (d, J=8.8 Hz, 1H), 7.32-7.27 (m, 2H), 7.22 (s, 1H), 7.17 (d, J=8.8 Hz, 1H), 7.11-7.06 (m, 1H), 6.91-6.70 (m, 2H), 6.60-6.30 (s, 2H), 6.29 (s, 1H), 6.21 (s, 1H), 4.78-4.58 (m, 2H), 3.34 (s, 3H), 3.03-3.00 (m, 2H). LCMS $R_t$=1.6 min in 3.0 min chromatography, 10-80CD, ESI calcd. for $C_{28}H_{23}ClN_3O_3$ [M+H]$^+$ 484.1, found 484.0. HPLC $R_t$=3.52 min in 8 min chromatography, 220 nm, purity 99.00%. Chiral HPLC (S)-025: $R_t$=2.12 min in 8 min (ee 100%) (OD_ETOH_DEA_40_2.8ML_10CM), ((R)-025: $R_t$=1.48 min (ee 97.94%)).

Example 26: Preparation of Compound 26

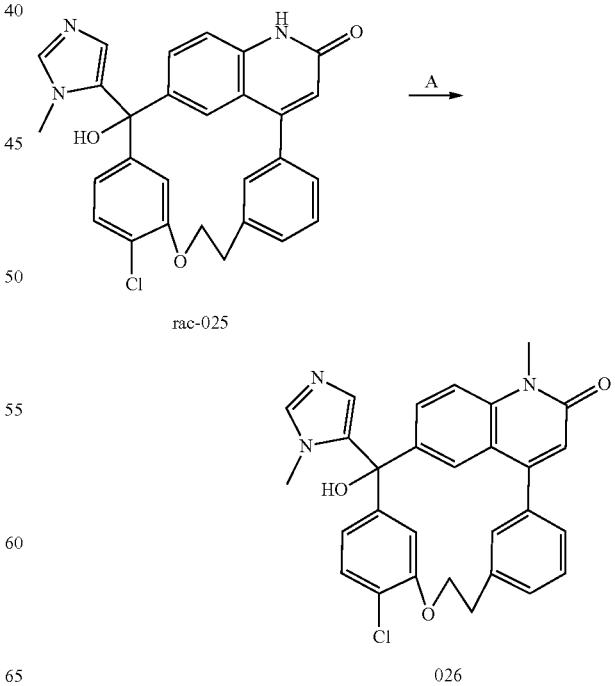

Scheme 26 - Synthesis of Compound 26

Step A: Preparation of 4⁴-chloro-3-hydroxy-2¹-methyl-3-(1-methyl-1H-imidazol-5-yl)-2¹,2²-dihydro-5-oxa-2(4,6)-quinolina-1,4(1,3)-dibenzenacycloheptaphan-2²-one (026)

To a solution of rac-025 (50 mg, 103.32 µmol) in THF (1 mL) and H$_2$O (1 mL) were added BTEAC (11.77 mg, 51.66 µmol) and NaOH (41.32 mg, 1.03 mmol) at 15° C. The mixture was stirred at 15° C. for 10 min. Then iodomethane (22.00 mg, 154.98 µmol, 9.65 µL) was added to the above mixture at 15° C. The mixture was stirred at 15° C. for 12 h. Water (20 mL) was added to the mixture. The aqueous layer was extracted with EtOAc (15 mL×2). The combined organic layers were washed with brine (30 mL), dried over anhydrous Na$_2$SO$_4$, filtered and concentrated to afford 026 (30 mg, 60.24 µmol, 58.31% yield) as a yellow solid. 80 mg (160.65 mol) of the product was triturated with CH$_3$CN (3 mL) at 20° C. for 30 min and purified by Prep-HPLC (column: Waters Xbridge 150×25 mm×5 m; mobile phase: [water (0.05% NH$_3$H$_2$O+10 mM NH$_4$HCO$_3$)-ACN]; B %: 37%-67%, 7.8 min) to afford 026 (32.5 mg, 65.26 µmol, 40.62% yield) as an off-white solid. $^1$H NMR (400 MHz, DMSO-d$_6$) δ=8.02 (dd, J=2.4, 8.8 Hz, 1H), 7.66 (d, J=8.8 Hz, 1H), 7.56 (s, 1H), 7.34-7.25 (m, 2H), 7.23-7.14 (m, 2H), 7.11-7.05 (m, 1H), 6.92-6.70 (m, 2H), 6.53-6.44 (m, 2H), 6.37 (d, J=2.0 Hz, 1H), 6.22 (s, 1H), 4.78-4.60 (m, 2H), 3.70 (s, 3H), 3.35 (s, 3H), 3.04-2.99 (m, 2H). LCMS R$_t$=1.70 min in 3.0 min chromatography, 10-80CD, ESI calcd. for C$_{29}$H$_{25}$ClN$_3$O$_3$ [M+H]$^+$ 498.2, found 498.1. HPLC R$_t$=3.54 min in 8 min chromatography, 220 nm, purity 98.13%.

Example 27: Preparation of Compound 27

Scheme 27 - Synthesis of Compound 27

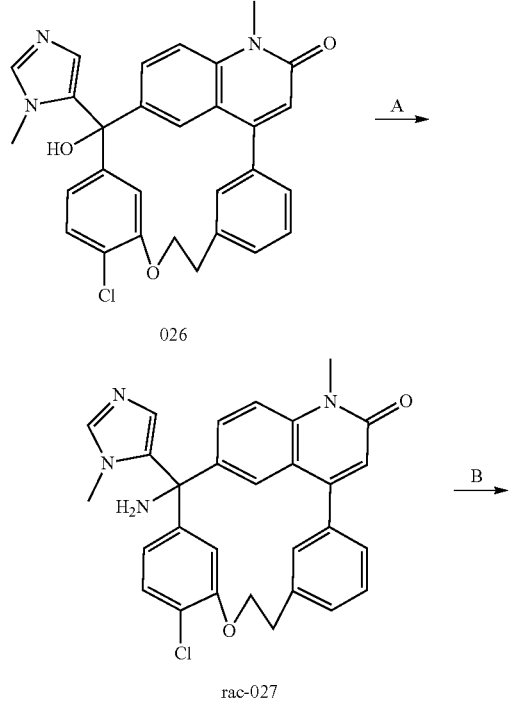

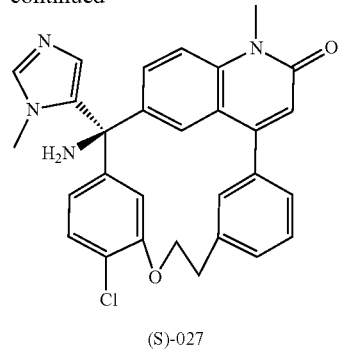

Step A: Preparation of (rac)-3-amino-4⁴-chloro-2¹-methyl-3-(1-methyl-1H-imidazol-5-yl)-2¹,2²-dihydro-5-oxa-2(4,6)-quinolina-1,4(1,3)-dibenzenacycloheptaphan-2²-one (rac-027)

To a solution of 026 (30 mg, 60.24 µmol) in DMI (2 mL) was added SOCl$_2$ (57.34 mg, 481.96 µmol, 34.96 µL) at 0° C. The mixture was stirred at 0° C. for 0.5 h and 35° C. for 0.5 h. To a solution of NH$_3$ in MeOH (7M, 7.00 mmol, 1 mL) was added the above mixture at −10° C. The resulting mixture was stirred at −10° C. to 20° C. for 12 h. Water (20 mL) was added to the mixture. The aqueous layer was extracted with EtOAc (15 mL×2). The combined organic layers were washed with brine (30 mL), dried over anhydrous Na$_2$SO$_4$, filtered and concentrated. The residue was purified by flash chromatography on silica gel (MeOH in DCM=0 to 2%) to afford rac-027 (5 mg, 10.06 µmol, 16.70% yield) as an off-white solid. $^1$H NMR (400 MHz, DMSO-d$_6$) δ=8.04 (dd, J=2.4, 8.8 Hz, 1H), 7.63 (d, J=8.8 Hz, 1H), 7.50 (s, 1H), 7.32-7.25 (m, 2H), 7.21 (s, 1H), 7.12 (d, J=8.4 Hz, 1H), 7.10-7.05 (m, 1H), 7.05-6.93 (m, 1H), 6.65-6.55 (m, 1H), 6.49 (s, 1H), 6.33 (d, J=2.0 Hz, 1H), 6.28 (s, 1H), 4.82-4.59 (m, 2H), 3.69 (s, 3H), 3.28 (s, 3H), 3.04-2.99 (m, 2H). LCMS R$_t$=1.69 min in 3.0 min chromatography, 10-80CD, ESI calcd. for C$_{29}$H$_{26}$ClN$_4$O$_2$ [M+H]$^+$ 497.2, found 497.1. HPLC R$_t$=3.04 min in 8 min chromatography, 220 nm, purity 98.40%.

Step B: Preparation of (S)-3-amino-4⁴-chloro-2¹-methyl-3-(1-methyl-1H-imidazol-5-yl)-2¹,2²-dihydro-5-oxa-2(4,6)-quinolina-1,4(1,3)-dibenzenacycloheptaphan-2²-one ((S)-027)

rac-027 (100 mg, 201.21 µmol) was separated by SFC (column: DAICEL CHIRALPAK AD (250 mm×30 mm, 10 m); mobile phase: [0.10% NH$_3$H$_2$O EtOH]; B %: 50%-50%) to afford (S)-027 (33.4 mg, 67.21 µmol, 33.40% yield) as an off-white solid. $^1$H NMR (400 MHz, DMSO-d$_6$) δ=8.05 (dd, J=2.4, 8.8 Hz, 1H), 7.63 (d, J=8.8 Hz, 1H), 7.50 (s, 1H), 7.33-7.25 (m, 2H), 7.22 (s, 1H), 7.13 (d, J=8.4 Hz, 1H), 7.09-7.05 (m, 1H), 7.05-6.95 (m, 1H), 6.65-6.53 (m, 1H), 6.49 (s, 1H), 6.33 (d, J=2.4 Hz, 1H), 6.28 (s, 1H), 4.85-4.59 (m, 2H), 3.69 (s, 3H), 3.29 (s, 3H), 3.03-3.00 (m, 2H). LCMS R$_t$=1.67 min in 3.0 min chromatography, 10-80CD, ESI calcd. for C$_{29}$H$_{26}$ClN$_4$O$_2$ [M+H]$^+$ 497.2, found 497.1. HPLC R$_t$=2.97 min in 8 min chromatography, 220 nm, purity 97.67%. Chiral HPLC (S)-027: R$_t$=2.81 min in 4 min (ee 99.72%) (AD_ETOH_DEA_5-40_4ML_4MIN_5CM), ((R)-027: R$_t$=2.35 min (ee 100%)).

Example 28: Preparation of Compound 28

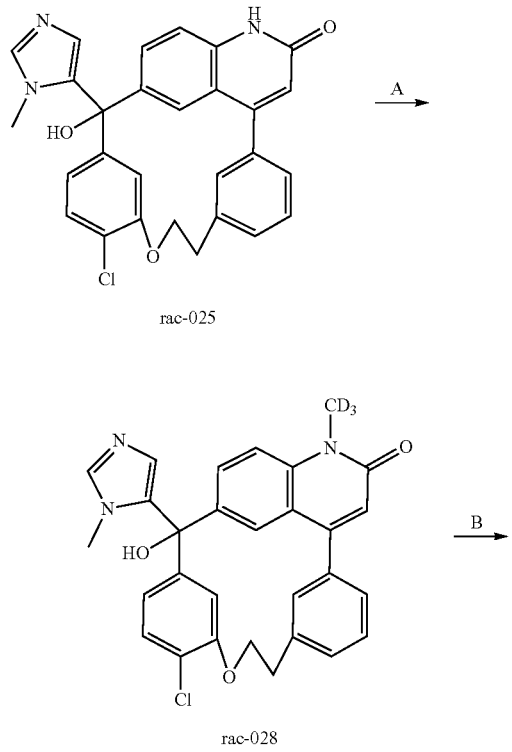

Step A: Preparation of (rac)-4⁴-chloro-3-hydroxy-2¹-(methyl-d₃)-3-(1-methyl-1H-imidazol-5-yl)-2¹,2²-dihydro-5-oxa-2(4,6)-quinolina-1,4(1,3)-dibenzenacycloheptaphan-2²-one (rac-028)

To a mixture of rac-025 (70 mg, 144.64 µmol) and BTEAC (16.47 mg, 72.32 µmol) in NaOH (5M in H₂O, 2 mL) and THF (4 mL) was added iodomethane-d₃ (16.42 mg, 115.72 mol, 7.05 µL) and the mixture was stirred at 20° C. for 12 h. Water (20 mL) was added and the mixture was extracted with EtOAc (20 mL×2). The combined organic phase was washed with brine (20 mL), dried over anhydrous Na₂SO₄, filtered and concentrated. The crude was purified by flash chromatography on silica gel (MeOH in DCM=0 to 10%) to give rac-028 (11.9 mg, 23.75 µmol, 16.42% yield) as an off-white solid. ¹H NMR (400 MHz, DMSO-d₆) δ=8.03 (dd, J=2.0, 8.8 Hz, 1H), 7.65 (d, J=9.2 Hz, 1H), 7.53 (s, 1H), 7.33-7.26 (m, 2H), 7.23-7.15 (m, 2H), 7.08 (d, J=6.4 Hz, 1H), 6.90-6.71 (m, 2H), 6.50 (m, 2H), 6.36 (s, 1H), 6.21 (s, 1H), 4.77-4.61 (m, 2H), 3.35 (s, 3H), 3.04-3.01 (m, 2H). LCMS $R_t$=1.72 min in 3 min chromatography, 10-80CD, ESI calcd. for $C_{29}H_{22}D_3ClN_3O_3$ [M+H]⁺ 501.2, found 501.1. HPLC $R_t$=3.17 min in 8 min chromatography, 220 nm, purity 100.00%.

Step B: Preparation of (S)-4⁴-chloro-3-hydroxy-2¹-(methyl-d₃)-3-(1-methyl-1H-imidazol-5-yl)-2¹,2²-dihydro-5-oxa-2(4,6)-quinolina-1,4(1,3)-dibenzenacycloheptaphan-2²-one ((S)-028)

rac-028 (100 mg, 199.60 µmol) was further separated by SFC (column: DAICEL CHIRALPAK IG (250 mm×50 mm, 10 m); mobile phase: [0.1% NH₃H₂O EtOH]; B %: 55%-55%) to afford (S)-028 (37.8 mg, 75.45 µmol, 37.80% yield) as an off-white solid. ¹H NMR (400 MHz, DMSO-d₆) δ=8.03 (dd, J=2.0, 8.8 Hz, 1H), 7.65 (d, J=8.8 Hz, 1H), 7.53 (s, 1H), 7.34-7.26 (m, 2H), 7.23-7.12 (m, 2H), 7.08 (d, J=6.8 Hz, 1H), 6.98-6.67 (m, 2H), 6.51 (s, 1H), 6.45 (s, 1H), 6.37 (s, 1H), 6.21 (s, 1H), 4.78-4.59 (m, 2H), 3.35 (s, 3H), 3.04-3.01 (m, 2H). LCMS $R_t$=1.70 min in 3 min chromatography, 10-80CD, ESI calcd. for $C_{29}H_{22}D_3ClN_3O_3$ [M+H]⁺ 501.2, found 501.1. HPLC $R_t$=3.48 min in 8 min chromatography, 220 nm, purity 98.16%. Chiral HPLC (S)-028: $R_t$=1.15 min in 2 min (ee 99.46%) (IG_ETOH_DEA_40-4ML_5CM), ((R)-028: $R_t$=0.66 min (ee 100%)).

Example 29: Preparation of Compound 29

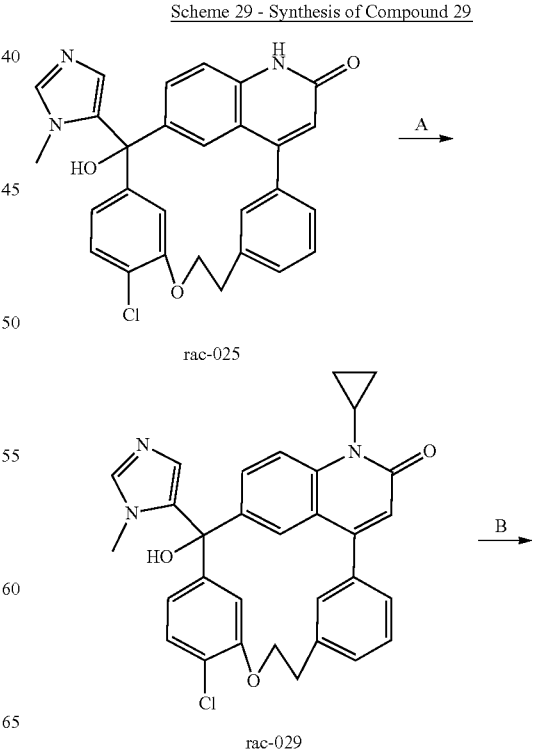

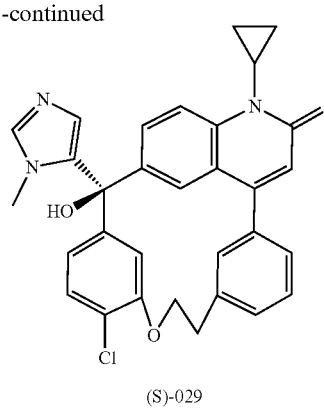

(S)-029

Step A: Preparation of (rac)-4⁴-chloro-2¹-cyclopropyl-3-hydroxy-3-(1-methyl-1H-imidazol-5-yl)-2¹,2²-dihydro-5-oxa-2(4,6)-quinolina-1,4(1,3)-dibenzena-cycloheptaphan-2²-one (rac-029)

A mixture of rac-025 (450 mg, 929.86 µmol), cyclopropylboronic acid (159.74 mg, 1.86 mmol), bipyridine (159.75 mg, 1.02 mmol), Cu(OAc)$_2$ (185.78 mg, 1.02 mmol) and Na$_2$CO$_3$ (246.39 mg, 2.32 mmol) in DCE (10 mL) was stirred at 70° C. for 5 h under 02 (15 psi). After cooling to r.t, saturated NH$_4$Cl (30 mL) solution was added to the mixture. The aqueous layer was extracted with DCM (30 mL×2). The combined organic layers were washed with brine (30 mL), dried over anhydrous Na$_2$SO$_4$, filtered and concentrated. The residue was purified by flash chromatography on silica gel (MeOH in DCM=0 to 2%) to afford rac-029 (270 mg, 515.26 µmol, 55.41% yield) as an off-white solid. $^1$H NMR (400 MHz, DMSO-d$_6$) δ=7.99 (s, 2H), 7.60 (s, 1H), 7.33-6.97 (m, 6H), 6.73 (s, 1H), 6.42 (s, 1H), 6.32-6.12 (m, 2H), 4.83-4.41 (m, 2H), 3.32 (s, 3H), 3.05-2.92 (m, 3H), 1.38-1.29 (m, 2H), 0.88-0.73 (m, 2H). LCMS R$_t$=1.74 min in 3 min chromatography, 10-80CD, ESI calcd. for C$_{31}$H$_{27}$ClN$_3$O$_3$ [M+H]$^+$ 524.2, found 524.1.

Step B: Preparation of (S)-4⁴-chloro-2¹-cyclopropyl-3-hydroxy-3-(1-methyl-1H-imidazol-5-yl)-2¹,2²-dihydro-5-oxa-2(4,6)-quinolina-1,4(1,3)-dibenzena-cycloheptaphan-2²-one ((S)-029)

rac-029 (100 mg, 190.84 µmol) was separated by SFC (column: DAICEL CHIRALCEL OD-H (250 mm×30 mm, 5 m); mobile phase: [0.1% NH$_3$H$_2$O EtOH]; B %: 55%-55%, min) to afford (S)-029 (18.6 mg, 35.50 µmol, 18.60% yield) as an off-white solid. $^1$H NMR (400 MHz, DMSO-d$_6$) δ=8.04-7.93 (m, 2H), 7.53 (s, 1H), 7.36-7.00 (m, 5H), 6.92-6.64 (m, 2H), 6.49 (s, 1H), 6.41 (s, 1H), 6.32 (s, 1H), 6.26 (s, 1H), 4.77-4.59 (m, 2H), 3.35 (s, 3H), 3.02-2.98 (m, 3H), 1.37-1.34 (m, 2H), 0.88-0.82 (m, 2H). LCMS R$_t$=1.73 min in 3.0 min chromatography, 10-80CD, ESI calcd. for C$_{31}$H$_{27}$ClN$_3$O$_3$ [M+H]$^+$ 524.2, found 524.1. HPLC R$_t$=3.26 min in 8 min chromatography, 220 nm, purity 100%. Chiral HPLC (S)-029: R$_t$=1.22 min in 2 min (ee 98.94%) (OD_ETOH_DEA_40-4ML_5CM), ((R)-029: R$_t$=0.72 min (ee 98.84%)).

Example 30: Preparation of Compound 30

Scheme 30 - Synthesis of Compound 30

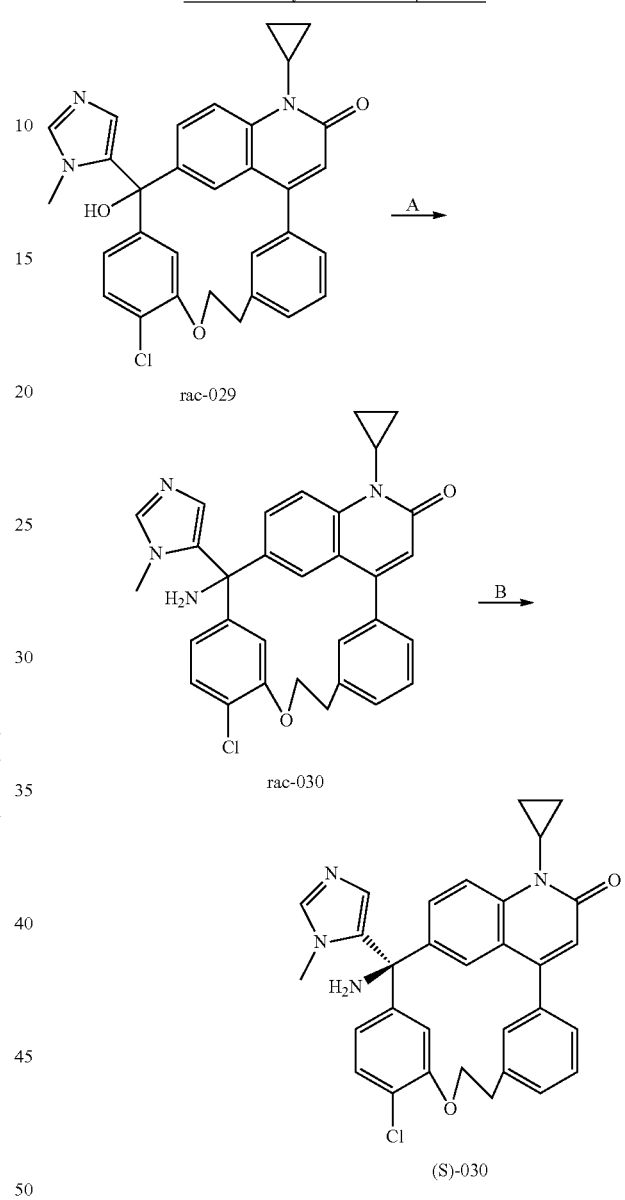

Step A: Preparation of (rac)-3-amino-4⁴-chloro-2¹-cyclopropyl-3-(1-methyl-1H-imidazol-5-yl)-2¹,2²-dihydro-5-oxa-2(4,6)-quinolina-1,4(1,3)-dibenzena-cycloheptaphan-2²-one (rac-030)

To a solution of rac-029 (140 mg, 267.17 µmol) in DMI (2 mL) was added SOCl$_2$ (254.28 mg, 2.14 mmol, 155.05 µL) at 20° C. The mixture was stirred at 40° C. for 4 h. To NH$_3$ in MeOH (7M, 326.63 mmol, 46.66 mL) was added the above mixture at −10° C. The mixture was stirred at 20° C. for 1 h. Water (40 mL) was added to the mixture. Then the aqueous layer was extracted with EtOAc (30 mL×2). The combined organic layers were washed with brine (50 mL), dried over anhydrous Na$_2$SO$_4$, filtered and concentrated. The residue was purified by flash chromatography on silica gel (MeOH in DCM=0 to 2%) to afford rac-030 (100 mg, 191.20 μmol, 71.56% yield) as an off-white solid. $^1$H NMR (400 MHz, DMSO-d$_6$) δ=8.24-7.86 (m, 2H), 7.79-6.93 (m, 6H), 6.68-5.93 (m, 3H), 5.05-4.02 (m, 2H), 3.06-2.89 (m, 3H), 1.39-1.30 (m, 2H), 0.90-0.69 (m, 2H). LCMS R$_t$=0.75 min in 1.5 min chromatography, 5-95AB, ESI calcd. for C$_{31}$H$_{28}$ClN$_4$O$_2$ [M+H]$^+$ 523.2, found 523.2.

Step B: Preparation of (S)-3-amino-4$^4$-chloro-2$^1$-cyclopropyl-3-(1-methyl-1H-imidazol-5-yl)-2$^1$,2$^2$-dihydro-5-oxa-2(4,6)-quinolina-1,4(1,3)-dibenzena-cycloheptaphan-2$^2$-one ((S)-030)

rac-030 (100 mg, 191.20 μmol) was further separated by SFC (column: DAICEL CHIRALPAK AD (250 mm×30 mm, 10 m); mobile phase: [0.1% NH$_3$H$_2$O EtOH]; B %: 50%-50%) to afford (S)-030 (33.1 mg, 63.29 μmol, 33.10% yield) as an off-white solid. $^1$H NMR (400 MHz, DMSO-d$_6$) δ=8.02 (d, J=8.8 Hz, 1H), 7.94 (d, J=8.8 Hz, 1H), 7.50 (s, 1H), 7.32-7.24 (m, 2H), 7.21 (s, 1H), 7.12 (d, J=8.0 Hz, 1H), 7.06 (d, J=6.8 Hz, 1H), 6.99 (s, 1H), 6.58 (s, 1H), 6.39 (s, 1H), 6.32-6.25 (m, 2H), 4.86-4.56 (m, 2H), 3.29 (s, 3H), 3.03-2.98 (m, 3H), 2.90 (br s, 2H), 1.38-1.31 (m, 2H), 0.93-0.77 (m, 2H). LCMS R$_t$=1.70 min in 3.0 min chromatography, 10-80CD, ESI calcd. for C$_{31}$H$_{28}$ClN$_4$O$_2$ [M+H]$^+$ 523.2, found 523.1. HPLC R$_t$=3.75 min in 8 min chromatography, 220 nm, purity 98.35%. Chiral HPLC (S)-030 R$_t$=1.73 min in 4 min (ee 100%) (AD_ETOH_DEA_40-4ML_5CM), ((R)-030: R$_t$=1.25 min (ee 100%)).

Scheme F - General Synthetic Method F

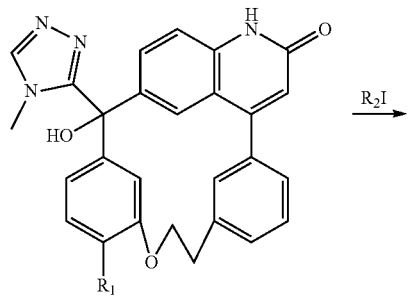

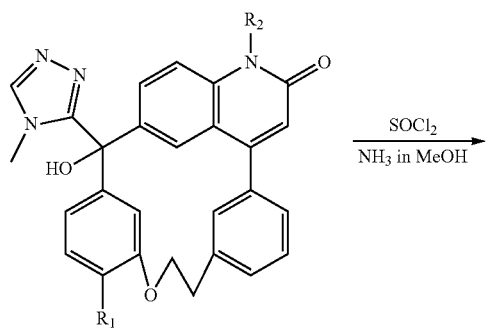

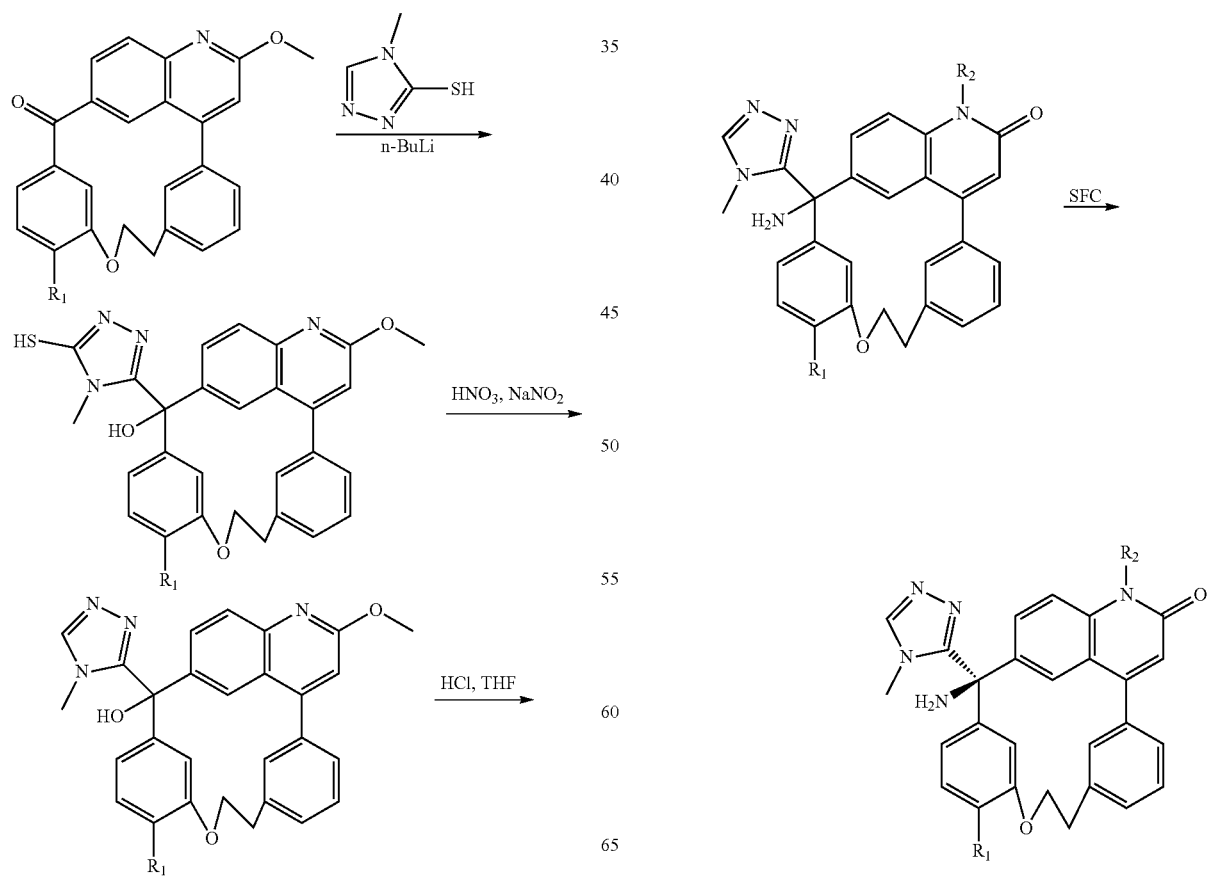

Example 31: Preparation of Compound 31

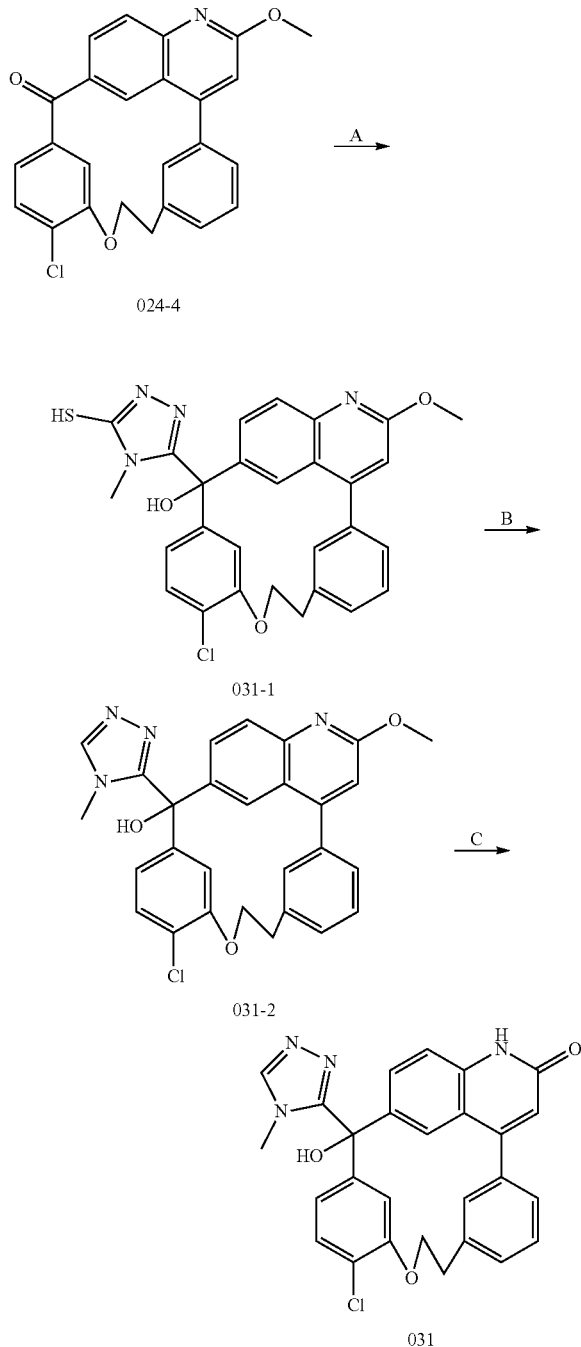

Step A: Preparation of (031-1)

To a solution of 4-methyl-4H-1,2,4-triazole-3-thiol (1.66 g, 14.43 mmol) in redistillation THF (30 mL) was added n-BuLi (2.5M in n-hexane, 21.64 mmol, 8.66 mL) at −78° C. The mixture was stirred at −78° C. for 0.5 h. Then the above mixture was added to a solution of 024-4 (1 g, 2.40 mmol) in redistillation THF (30 mL) at −78° C. The mixture was stirred at −78° C. for 1 h. Water (9 mL) was added to the mixture at −78° C. and brine (30 mL). The aqueous layer was extracted with EtOAc (40 mL×2). The combined organic layers were washed with brine (60 mL×3), dried over anhydrous $Na_2SO_4$, filtered and concentrated. The residue was purified by flash chromatography on silica gel (EtOAc in petroleum ether=0 to 15%) to afford 031-1 (1.2 g, 2.26 mmol, 93.98% yield) as an off-white solid. $^1$H NMR (400 MHz, DMSO-$d_6$) δ=13.77 (s, 1H), 7.97 (d, J=8.8 Hz, 1H), 7.86 (d, J=8.8 Hz, 1H), 7.43-7.24 (m, 5H), 7.20-7.09 (m, 1H), 7.01-6.80 (m, 2H), 6.49 (s, 1H), 4.94-4.55 (m, 2H), 4.02 (s, 3H), 3.26 (s, 3H), 3.07-2.94 (m, 2H). LCMS $R_t$=0.96 min in 1.5 min chromatography, 5-95AB, ESI calcd. for $C_{28}H_{24}ClN_4O_3S$ [M+H]$^+$ 531.0, found 531.0.

Step B: Preparation of (031-2)

To a solution of 031-1 (1.2 g, 2.26 mmol) in THF (16 mL) and $H_2O$ (4 mL) were added $NaNO_2$ (935.49 mg, 13.56 mmol) and $HNO_3$ (854.37 mg, 13.56 mmol, 610.27 μL). The mixture was stirred at 25° C. for 12 h. Water (20 mL) was added to the mixture. NaOH (0.5M in $H_2O$) was added to adjust pH=8. The aqueous layer was extracted with EtOAc (30 mL×2). The combined organic layers were washed with brine (60 mL), dried over anhydrous $Na_2SO_4$, filtered and concentrated. The residue was purified by flash chromatography on silica gel (MeOH in DCM=0 to 2%) to afford 031-2 (850 mg, 1.70 mmol, 75.39% yield) as an off-white solid. $^1$H NMR (400 MHz, DMSO-$d_6$) δ=8.46 (s, 1H), 7.94 (d, J=8.8 Hz, 1H), 7.85 (d, J=8.8 Hz, 1H), 7.37-7.20 (m, 5H), 7.18-7.12 (m, 2H), 7.03-6.80 (m, 2H), 6.54 (s, 1H), 4.87-4.57 (m, 2H), 4.03 (s, 3H), 3.44 (s, 3H), 3.06-2.95 (m, 2H). LCMS $R_t$=1.91 min in 3 min chromatography, 10-80CD, ESI calcd. for $C_{28}H_{24}ClN_4O_3$ [M+H]$^+$ 499.2, found 499.1. $C_{28}H_{22}ClN_4O_2$ [M-OH]$^+$ 481.1, found 481.1.

Step C: Preparation of 4$^4$-chloro-3-hydroxy-3-(4-methyl-4H-1,2,4-triazol-3-yl)-2$^1$,2$^2$-dihydro-5-oxa-2(4,6)-quinolina-1,4(1,3)-dibenzenacycloheptaphan-2$^2$-one (031)

To a solution of 031-2 (1 g, 2.00 mmol) in THF (25 mL) was added HCl (4M in $H_2O$, 50.10 mmol, 12.53 mL) at 25° C. The mixture was stirred at 60° C. for 10 h. Saturated $NaHCO_3$ solution was added into the mixture to adjusted to pH=8. The aqueous layer was extracted with EtOAc (60 mL×2). The combined organic layers were washed with brine (150 mL), dried over anhydrous $Na_2SO_4$, filtered and concentrated. The residue was purified by flash chromatography on silica gel (MeOH in DCM=0 to 10%) to afford 031 (680 mg, 1.40 mmol, 69.97% yield) as an off-white solid. 031 (30 mg, 61.86 μmol) was purified by flash chromatography on silica gel (MeOH in DCM=0 to 10%) to afford 031 (14.9 mg, 30.73 μmol, 49.67% yield) as an off-white solid. $^1$H NMR (400 MHz, DMSO-$d_6$) δ=11.62 (br s, 1H), 8.37 (s, 1H), 7.80 (d, J=8.8 Hz, 1H), 7.40 (d, J=8.8 Hz, 1H), 7.32-7.27 (m, 2H), 7.24-7.17 (m, 2H), 7.11-7.07 (m, 1H), 6.95-6.67 (m, 3H), 6.38 (s, 1H), 6.26 (s, 1H), 4.78-4.62 (m, 2H), 3.44 (s, 3H), 3.05-3.02 (m, 2H). LCMS $R_t$=1.55 min in 3.0 min chromatography, 10-80CD, ESI calcd. for $C_{27}H_{22}ClN_4O_3$ [M+H]$^+$ 485.1, found 485.1. $C_{27}H_2OClN_4O_2$ [M-OH]$^+$ 467.1, found 467.0. HPLC $R_t$=3.54 min in 8 min chromatography, 220 nm, purity 98.95%.

Example 32: Preparation of Compound 32

Scheme 32 - Synthesis of Compound 32

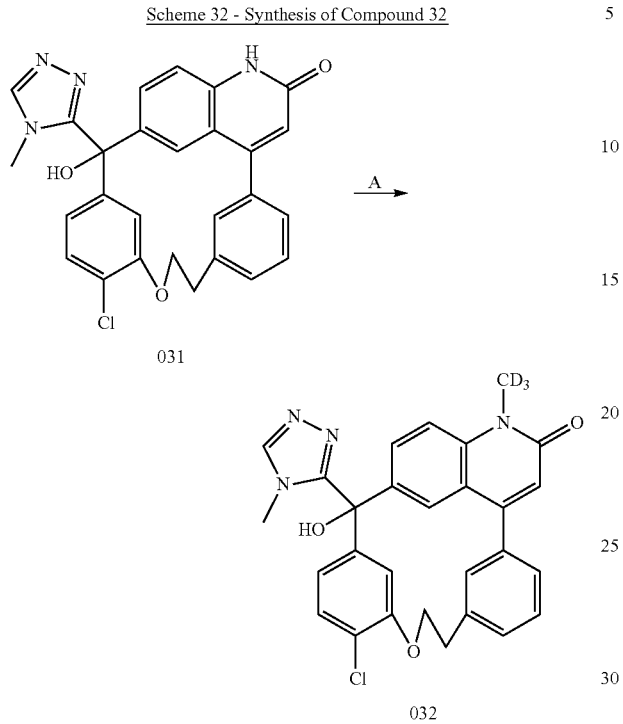

Step A: Preparation of 4⁴-chloro-3-hydroxy-2¹-(methyl-$d_3$)-3-(4-methyl-4H-1,2,4-triazol-3-yl)-2¹,2²-dihydro-5-oxa-2(4,6)-quinolina-1,4(1,3)-dibenzenacycloheptaphan-2²-one (032)

To a solution of 031 (280 mg, 577.40 μmol) in THF (3 mL) and H₂O (2 mL) were added BTEAC (65.76 mg, 288.70 μmol) and NaOH (230.96 mg, 5.77 mmol) at 25° C. Then iodomethane-$d_3$ (100.44 mg, 692.88 μmol, 43.11 μL) was added to the above mixture at 25° C. The mixture was stirred at 25° C. for 5 h. Water (20 mL) was added to the mixture. The aqueous layer was extracted with EtOAc (30 mL×2). The combined organic layers were washed with brine (60 mL), dried over anhydrous Na₂SO₄, filtered and concentrated. The residue was purified by flash chromatography on silica gel (MeOH in DCM=0 to 7%) to afford 032 (250 mg, 498.03 μmol, 86.25% yield) as an off-white solid. 50 mg (99.61 μmol) of the product was purified by Prep-HPLC (column: Welch Xtimate C₁₈ 150×25 mm×5 m; mobile phase: [water (0.05% ammonia hydroxide v/v)-MeOH]; B %: 60%-90%, 7.8 min) to afford 032 (14.0 mg, 27.89 μmol, 28.00% yield) as an off-white solid. ¹H NMR (400 MHz, DMSO-$d_6$) δ=8.38 (s, 1H), 7.94 (d, J=8.8 Hz, 1H), 7.62 (d, J=8.8 Hz, 1H), 7.33-7.27 (m, 2H), 7.23-7.18 (m, 2H), 7.11-7.07 (m, 1H), 7.01-6.58 (m, 3H), 6.50 (s, 1H), 6.34 (s, 1H), 4.75-4.62 (m, 2H), 3.44 (s, 3H), 3.05-3.00 (m, 2H). LCMS $R_t$=1.60 min in 3.0 min chromatography, 10-80CD, ESI calcd. for C₂₈H₂₁D₃ClN₄O₃ [M+H]⁺ 502.2, found 502.1. C₂₈H₁₉D₃ClN₄O₂ [M-OH]⁺484.2, found 484.1. HPLC $R_t$=4.04 min in 8 min chromatography, 220 nm, purity 97.89%.

Example 33: Preparation of Compound 33

Scheme 33 - Synthesis of Compound 33

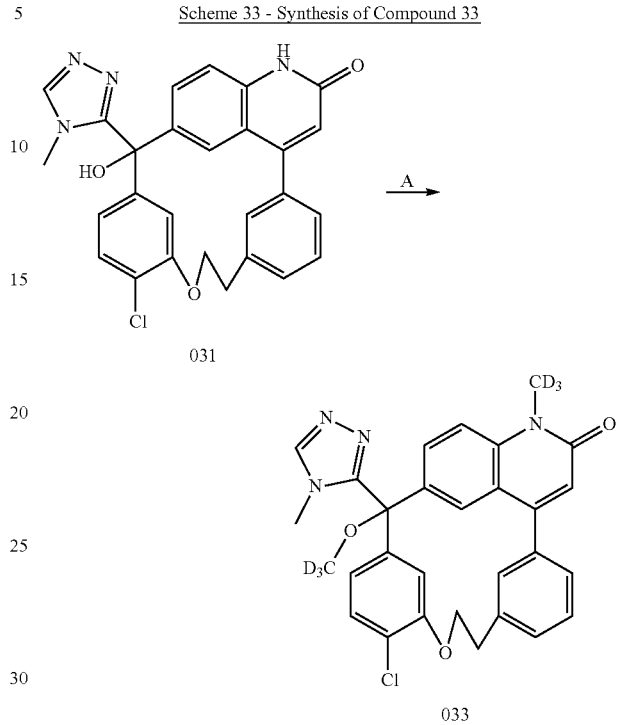

Step A: Preparation of 4⁴-chloro-3-(methoxy-$d_3$)-2¹-(methyl-$d_3$)-3-(4-methyl-4H-1,2,4-triazol-3-yl)-2¹,2²-dihydro-5-oxa-2(4,6)-quinolina-1,4(1,3)-dibenzenacycloheptaphan-2²-one (033)

To a solution of 031 (280 mg, 577.40 μmol) in THF (3 mL) and H₂O (2 mL) were added BTEAC (65.76 mg, 288.70 μmol) and NaOH (230.96 mg, 5.77 mmol) at 25° C. Then iodomethane-$d_3$ (100.44 mg, 692.88 μmol, 43.11 μL) was added to the above mixture at 25° C. The mixture was stirred at 25° C. for 5 h. Water (20 mL) was added to the mixture. The aqueous layer was extracted with EtOAc (30 mL×2). The combined organic layers were washed with brine (60 mL), dried over anhydrous Na₂SO₄, filtered and concentrated. The residue was purified by flash chromatography on silica gel (MeOH in DCM=0 to 7%) to afford 032 (250 mg, 498.03 μmol, 86.25% yield) as an off-white solid. 50 mg (99.61 μmol) of the product was purified by Prep-HPLC (column: Welch Xtimate C₁₈ 150×25 mm×5 m; mobile phase: [water (0.05% ammonia hydroxide v/v)-MeOH]; B %: 60%-90%, 7.8 min) to afford 032 (14.0 mg, 27.89 μmol, 28.00% yield) as an off-white solid. ¹H NMR (400 MHz, DMSO-$d_6$) δ=8.38 (s, 1H), 7.94 (d, J=8.8 Hz, 1H), 7.62 (d, J=8.8 Hz, 1H), 7.33-7.27 (m, 2H), 7.23-7.18 (m, 2H), 7.11-7.07 (m, 1H), 7.01-6.58 (m, 3H), 6.50 (s, 1H), 6.34 (s, 1H), 4.75-4.62 (m, 2H), 3.44 (s, 3H), 3.05-3.00 (m, 2H). LCMS $R_t$=1.60 min in 3.0 min chromatography, 10-80CD, ESI calcd. for C₂₈H₂₁D₃ClN₄O₃ [M+H]⁺ 502.2, found 502.1. C₂₈H₁₉D₃ClN₄O₂ [M-OH]⁺484.2, found 484.1. HPLC $R_t$=4.04 min in 8 min chromatography, 220 nm, purity 97.89%.

Example 34: Preparation of Compound 34

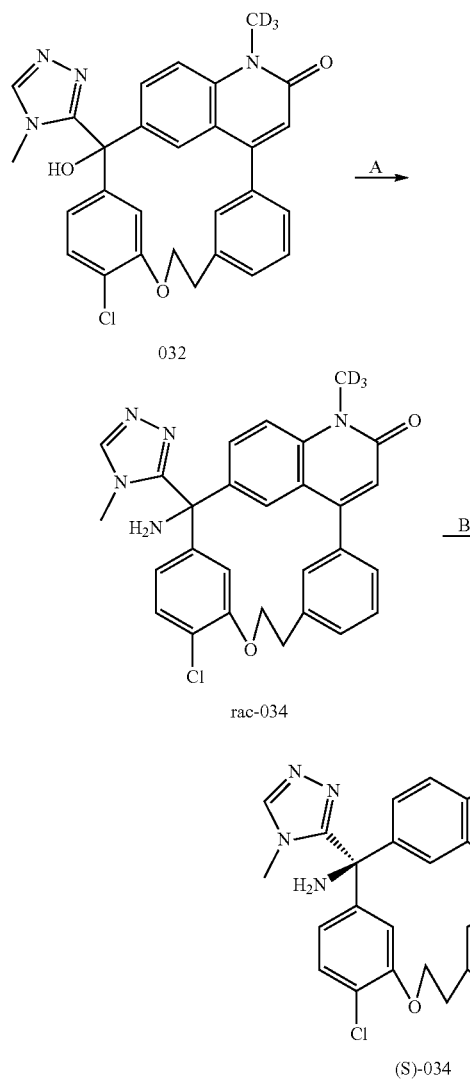

Step A: Preparation of (rac)-3-amino-4⁴-chloro-2¹-(methyl-d₃)-3-(4-methyl-4H-1,2,4-triazol-3-yl)-2¹,2²-dihydro-5-oxa-2(4,6)-quinolina-1,4(1,3)-dibenzenacycloheptaphan-2²-one (rac-034)

To a solution of 032 (50 mg, 99.61 μmol) in DMI (1 mL) was added SOCl₂ (94.80 mg, 796.85 μmol, 57.81 μL) at 0° C. The mixture was stirred at 0° C. for 0.5 h and at 40° C. for 0.5 h. To a solution of NH₃ in MeOH (7M, 35.00 mmol, 5 mL) was added the above mixture at −10° C. The mixture was stirred at 25° C. for 12 h. Water (20 mL) was added to the mixture. The aqueous layer was extracted with EtOAc (15 mL×2). The combined organic layers were washed with brine (20 mL), dried over anhydrous Na₂SO₄, filtered and concentrated. The residue was purified by flash chromatography on silica gel (MeOH in DCM=0 to 6%) to afford rac-034 (14.3 mg, 28.54 μmol, 28.66% yield) as an off-white solid. ¹H NMR (400 MHz, DMSO-d₆) δ=8.36 (s, 1H), 7.98 (d, J=8.8 Hz, 1H), 7.60 (d, J=9.2 Hz, 1H), 7.33-7.25 (m, 2H), 7.22 (s, 1H), 7.17-6.94 (m, 3H), 6.62-6.37 (m, 2H), 6.28 (s, 1H), 4.91-4.58 (m, 2H), 3.33 (s, 3H), 3.06-3.00 (m, 2H). LCMS R$_t$=1.58 min in 3.0 min chromatography, 10-80CD, ESI calcd. for C₂₈H₂₂D₃ClN₅O₂ [M+H]⁺ 501.2, found 501.1. C₂₈H₁₉D₃ClN₄O₂ [M-NH₂]⁺ 484.2, found 484.1. HPLC R$_t$=3.47 min in 8 min chromatography, 220 nm, purity 96.18%.

Step B: Preparation of (S)-3-amino-4⁴-chloro-2¹-(methyl-d₃)-3-(4-methyl-4H-1,2,4-triazol-3-yl)-2¹,2²-dihydro-5-oxa-2(4,6)-quinolina-1,4(1,3)-dibenzenacycloheptaphan-2²-one ((S)-034)

rac-034 (100 mg, 199.60 μmol) was separated by SFC (column: DAICEL CHIRALCEL OD (250 mm×30 mm, 10 m); mobile phase: [0.1% NH₃H₂O MeOH]; B %: 45%-45%) to afford (S)-034 (31.8 mg, 63.47 μmol, 31.80% yield) as an off-white solid. ¹H NMR (400 MHz, DMSO-d₆) δ=8.35 (s, 1H), 7.99 (d, J=8.8 Hz, 1H), 7.60 (d, J=9.2 Hz, 1H), 7.34-7.25 (m, 2H), 7.22 (s, 1H), 7.18-6.87 (m, 3H), 6.62-6.32 (m, 2H), 6.27 (s, 1H), 4.94-4.52 (m, 2H), 3.34 (s, 3H), 3.06-3.00 (m, 2H). LCMS R$_t$=1.55 min in 3.0 min chromatography, 10-80CD, ESI calcd. for C₂₈H₂₂D₃ClN₅O₂ [M+H]⁺ 501.2, found 501.1. C₂₈H₁₉D₃ClN₄O₂ [M-NH₂]⁺ 484.2, found 484.1. HPLC R$_t$=3.63 min in 8 min chromatography, 220 nm, purity 98.42%. Chiral HPLC (S)-034: R$_t$=1.49 min in 3 min (ee 100%) (OD_MEOH_DEA_40_4ML_5CM), ((R)-034: R$_t$=2.07 min (ee 95.52%)).

Example 35: Preparation of Compound 35

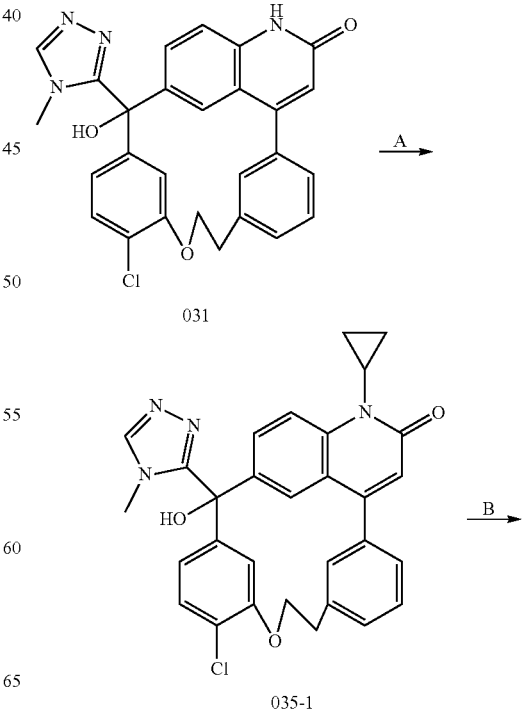

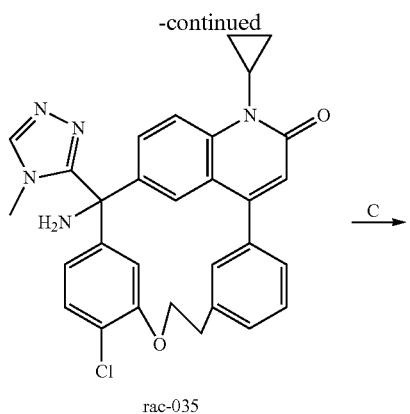

rac-035

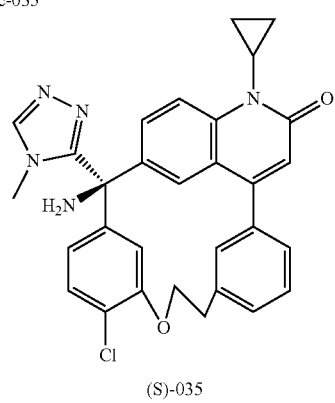

(S)-035

Step A: Preparation of (035-1)

A mixture of 031 (350 mg, 721.75 μmol), cyclopropylboronic acid (123.99 mg, 1.44 mmol), bipyridine (124.00 mg, 793.92 μmol), Cu(OAc)$_2$ (144.20 mg, 793.92 μmol) and Na$_2$CO$_3$ (191.25 mg, 1.80 mmol) in DCE (10 mL) was stirred at 70° C. for 16 h under O2(15 psi). After cooling to r.t, saturated NH$_4$Cl (40 mL) solution was added to the mixture. The aqueous layer was extracted with DCM/MeOH=10:1 (40 mL×2). The combined organic layers were washed with brine (50 mL), dried over anhydrous Na$_2$SO$_4$, filtered and concentrated. The residue was purified by flash chromatography on silica gel (MeOH in DCM=0 to 2%) to afford 035-1 (340 mg, 647.62 μmol, 89.73% yield) as a blue solid. $^1$H NMR (400 MHz, DMSO-d$_6$) δ=8.51 (s, 1H), 8.03-7.83 (m, 2H), 7.43-6.99 (m, 7H), 6.61-6.08 (m, 2H), 4.79-4.25 (m, 2H), 3.16 (s, 3H), 3.11-2.96 (m, 3H), 1.40-1.28 (m, 2H), 0.88-0.72 (m, 2H). LCMS R$_t$=0.81 min in 1.5 min chromatography, 5-95AB, ESI calcd. for C$_{30}$H$_{26}$ClN$_4$O$_3$ [M+H]$^+$ 525.2, found 525.1.

Step B: Preparation of (rac)-3-amino-4$^4$-chloro-2$^1$-cyclopropyl-3-(4-methyl-4H-1,2,4-triazol-3-yl)-2$^1$, 2$^2$-dihydro-5-oxa-2(4,6)-quinolina-1,4(1,3)-dibenzacycloheptaphan-2$^2$-one (rac-035)

To a solution of 035-1 (300 mg, 571.43 μmol) in DMI (3 mL) was added SOCl$_2$ (1.02 g, 8.57 mmol, 621.80 μL) at 20° C. The mixture was stirred at 40° C. for 16 h. To NH$_3$ in MeOH (7M, 349.98 mmol, 50 mL) was added the above mixture at −10° C. The mixture was stirred at 20° C. for 2 h. Water (20 mL) was added to the mixture. The aqueous layer was extracted with EtOAc (15 mL×2). The combined organic layers were washed with brine (30 mL), dried over anhydrous Na$_2$SO$_4$, filtered and concentrated. The residue was purified by flash chromatography on silica gel (MeOH in DCM=0 to 3%) to afford rac-035 (201 mg, 383.58 mol, 67.13% yield) as an off-white solid. rac-035 (100 mg, 190.84 μmol) was purified by flash chromatography on silica gel (MeOH in DCM=0 to 2%) to afford rac-035 (50.0 mg, 95.42 mol, 50.00% yield) as an off-white solid. $^1$H NMR (400 MHz, DMSO-d$_6$) δ=8.36 (s, 1H), 8.00-7.88 (m, 2H), 7.36-6.93 (m, 6H), 6.61-6.28 (m, 2H), 6.24 (s, 1H), 4.95-4.58 (m, 2H), 3.32 (s, 3H), 3.05-2.98 (m, 3H), 1.40-1.30 (m, 2H), 0.90-0.76 (m, 2H). LCMS R$_t$=1.10 min in 3.0 min chromatography, 30-90CD, ESI calcd. for C$_{30}$H$_{27}$ClN$_5$O$_2$ [M+H]$^+$ 524.2, found 524.1. C$_{30}$H$_{24}$ClN$_4$O$_2$ [M-NH$_2$]$^+$507.2, found 507.1. HPLC R$_t$=2.86 min in 8 min chromatography, 220 nm, purity 98.93%.

Step C: Preparation of (S)-3-amino-4$^4$-chloro-2$^1$-cyclopropyl-3-(4-methyl-4H-1,2,4-triazol-3-yl)-2$^1$, 2$^2$-dihydro-5-oxa-2(4,6)-quinolina-1,4(1,3)-dibenzacycloheptaphan-2$^2$-one ((S)-035)

rac-035 (100 mg, 190.84 μmol) was separated by SFC (column: DAICEL CHIRALPAK AD (250 mm×30 mm, 10 m); mobile phase: [0.1% NH$_3$H$_2$O EtOH]; B %: 50%-50%) to afford (S)-035 (34.4 mg, 65.65 μmol, 34.40% yield) as an off-white solid $^1$H NMR (400 MHz, DMSO-d$_6$) δ=8.36 (s, 1H), 8.02-7.86 (m, 2H), 7.35-6.97 (m, 6H), 6.72-6.32 (m, 2H), 6.23 (s, 1H), 4.96-4.58 (m, 2H), 3.32 (s, 3H), 3.05-3.00 (m, 3H), 1.38-1.31 (m, 2H), 0.92-0.76 (m, 2H). LCMS R$_t$=1.63 min in 3.0 min chromatography, 10-80CD, ESI calcd. for C$_{30}$H$_{27}$ClN$_5$O$_2$ [M+H]$^+$ 524.2, found 524.1. C$_{30}$H$_{24}$ClN$_4$O$_2$ [M-NH$_2$]$^+$507.2, found 507.1. HPLC R$_t$=3.98 min in 8 min chromatography, 220 nm, purity 97.60%. Chiral HPLC (S)-035: R$_t$=1.06 min in 3 min (ee 100%) (AD_ETOH_DEA_40-4ML_5CM), ((R)-035: R$_t$=1.30 min (ee 99.56%)).

Example 36: Preparation of Compound 36

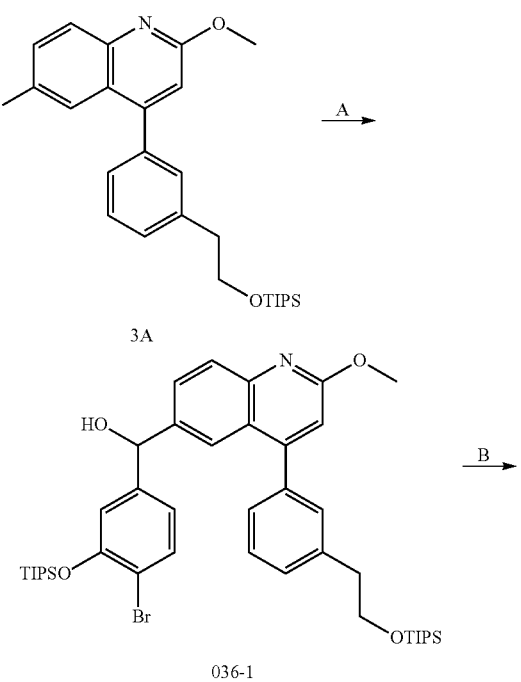

Scheme 36 - Synthesis of Compound 36

036-1

-continued

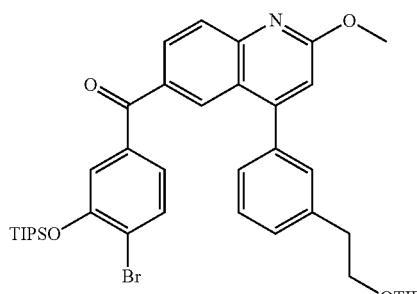

036-2

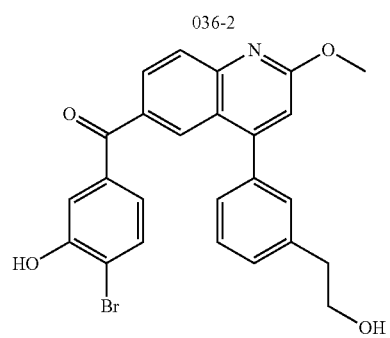

036-3

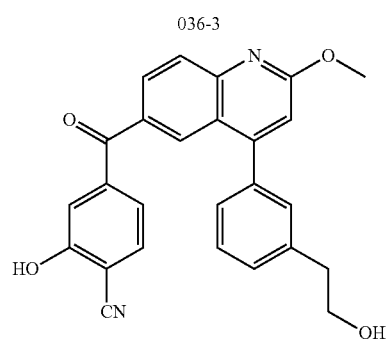

036-4

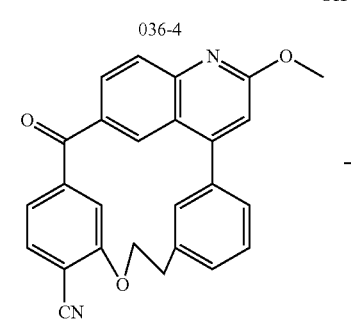

036-5

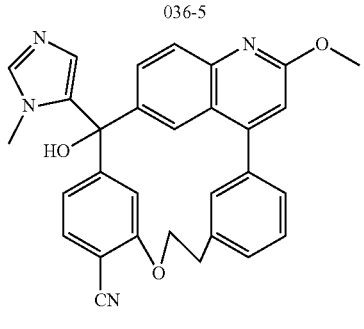

036-6

-continued


036-7

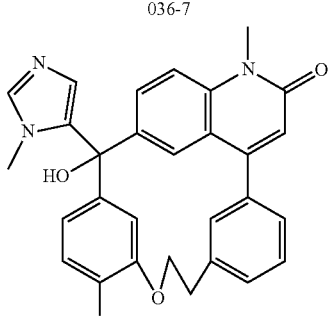

rac-036

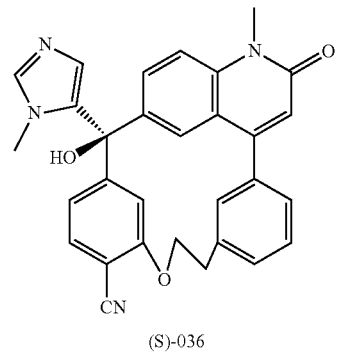 [SMILES: Cn1cncc1[C@@]1(O)c2ccc(C#N)c(c2)OCCc2cccc(c2)-c2cc(=O)n(C)c3ccc1cc23]

(S)-036

Step A: Preparation of (036-1)

To a solution of 3A (7 g, 13.60 mmol) in THF (50 mL) was added n-BuLi (2.5M in n-hexane, 14.96 mmol, 5.99 mL) and the mixture was stirred at −70° C. under $N_2$ for 10 min. Then a solution of 6A (5.60 g, 15.67 mmol) in THF (10 mL) was added to the above solution and the mixture was stirred at −70° C. under $N_2$ for 20 min. Water (300 mL) was added to the mixture and the mixture was extracted with EtOAc (250 mL×2). The combined organic phase was washed with brine (300 mL), dried over anhydrous $Na_2SO_4$, filtered and concentrated. The crude was purified by flash chromatography on silica gel (EtOAc in petroleum ether=0 to 30%) to give 036-1 (7 g, 8.83 mmol, 64.89% yield) as light yellow oil. $^1$H NMR (400 MHz, CDCl$_3$) δ=7.87 (d, J=8.4 Hz, 1H), 7.78 (s, 1H), 7.53 (dd, J=1.6, 8.4 Hz, 1H), 7.46-7.34 (m, 3H), 7.32-7.26 (m, 2H), 6.86 (s, 1H), 6.83-6.78 (m, 2H), 5.79 (d, J=2.8 Hz, 1H), 4.10 (s, 3H), 3.95 (t, J=6.8 Hz, 2H), 2.94 (t, J=6.8 Hz, 2H), 1.23-1.09 (m, 6H), 1.05-1.00 (m, 36H).

Step B: Preparation of (036-2)

A mixture of 036-1 (7 g, 8.83 mmol) and MnO$_2$ (7.67 g, 88.27 mmol) in DCM (100 mL) was stirred at 40° C. for 12 h. After cooling to r.t., the mixture was filtered through Celite and the filtrate was concentrated to give 036-2 (6.9 g, 8.72 mmol, 98.82% yield) as yellow oil. $^1$H NMR (400 MHz, CDCl$_3$) δ=8.30 (s, 1H), 8.04-7.93 (m, 2H), 7.61 (d, J=8.0 Hz, 1H), 7.43-7.30 (m, 5H), 7.19 (dd, J=1.6, 8.0 Hz, 1H), 6.93 (s, 1H), 4.15 (s, 3H), 3.92 (t, J=6.8 Hz, 2H), 2.92 (t, J=6.8 Hz, 2H), 1.34-1.15 (m, 6H), 1.13-1.08 (m, 18H), 1.02-0.97 (m, 18H).

Step C: Preparation of (036-3)

A mixture of 036-2 (6.8 g, 8.60 mmol) and TBAF (1M in THF, 17.19 mmol, 17.19 mL) in THF (50 mL) was stirred at 25° C. for 10 min. The solution was concentrated to give a residue. The residue was re-dissolved in EtOAc (100 mL). The organic phase was washed with water (100 mL×5), brine (100 mL×2), dried over anhydrous Na$_2$SO$_4$, filtered and concentrated. The crude was purified by flash chromatography on silica gel (EtOAc in petroleum ether=0 to 50%) to give 036-3 (4 g, 8.36 mmol, 97.28% yield) as an off-white solid. $^1$H NMR (400 MHz, CDCl$_3$) δ=8.25 (s, 1H), 8.08-8.03 (m, 1H), 7.96 (d, J=8.8 Hz, 1H), 7.57 (d, J=8.4 Hz, 1H), 7.46-7.37 (m, 3H), 7.35-7.29 (m, 2H), 7.22 (dd, J=2.0, 8.4 Hz, 1H), 6.92 (s, 1H), 4.14 (s, 3H), 3.93 (t, J=6.4 Hz, 2H), 2.95 (t, J=6.4 Hz, 2H). LCMS R$_t$=0.89 min in 1.5 min chromatography, 5-95AB, ESI calcd. for C$_{25}$H$_{21}$BrNO$_4$ [M+H]$^+$ 478.1, found 477.9.

Step D: Preparation of (036-4)

A mixture of 036-3 (4 g, 8.36 mmol), Zn(CN)$_2$ (9.82 g, 83.62 mmol, 5.31 mL) and Pd(PPh$_3$)$_4$ (966.32 mg, 836.24 µmol) in DMF (50 mL) was stirred at 120° C. for 12 h. After cooling to r.t., EtOAc (100 mL) was added to the mixture and the mixture was filtered through Celite. The cake was washed with EtOAc (50 mL×2). The combined organic phase was washed with water (300 mL×3), brine (300 mL), dried over anhydrous Na$_2$SO$_4$, filtered and concentrated. The crude was purified by flash chromatography on silica gel (EtOAc in petroleum ether=0 to 50%) to give 036-4 (2.6 g, 6.13 mmol, 73.25% yield) as a yellow oil. $^1$H NMR (400 MHz, CDCl$_3$) δ=8.15 (s, 1H), 8.06 (dd, J=2.0, 8.8 Hz, 1H), 7.92 (d, J=8.8 Hz, 1H), 7.51 (d, J=8.0 Hz, 1H), 7.42-7.40 (m, 1H), 7.38-7.35 (m, 1H), 7.30-7.24 (m, 3H), 7.23-7.19 (m, 1H), 6.87 (s, 1H), 4.12 (s, 3H), 3.96 (t, J=6.4 Hz, 2H), 2.99-2.95 (m, 2H). LCMS R$_t$=0.86 min in 1.5 min chromatography, 5-95AB, ESI calcd. for C$_{26}$H$_{21}$N$_2$O$_4$ [M+H]$^+$ 425.1, found 425.0.

Step E: Preparation of (036-5)

A mixture of DEAD (2.13 g, 12.25 mmol, 2.23 mL) and PPh$_3$ (3.21 g, 12.25 mmol) in THF (400 mL) was stirred at 0° C. for 1 h. Then a solution of 036-4 (2.6 g, 6.13 mmol) in THF (100 mL) was added to the above mixture and the mixture was stirred at 25° C. for 1.5 h. The mixture was poured into saturated NH$_4$Cl solution (500 mL) and the mixture was extracted with EtOAc (300 mL×2). The combined organic phase was washed with brine (300 mL), dried over anhydrous Na$_2$SO$_4$, filtered and concentrated. The crude was purified by flash chromatography on silica gel (EtOAc in DCM=0 to 30%) to give 036-5 (1.8 g, 4.43 mmol, 72.30% yield) as an off-white solid. LCMS R$_t$=1.01 min in 1.5 min chromatography, 5-95AB, ESI calcd. for C$_{26}$H$_{19}$N$_2$O$_3$ [M+H]$^+$ 407.1, found 407.0.

Step F: Preparation of (036-6)

To a solution of 1-methyl-1H-imidazole (121.21 mg, 1.48 mmol, 117.68 µL) in THF (5 mL) was added n-BuLi (2.5M in n-hexane, 1.48 mmol, 590.50 µL) at −70° C. under N$_2$ and the mixture was stirred at −70° C. for 10 min. Then Et$_3$SiCl (222.51 mg, 1.48 mmol, 251.13 µL) in THF (1 mL) was added to the above mixture and the mixture was stirred at −70° C. for 10 min. Then n-BuLi (2.5M in n-hexane, 1.48 mmol, 590.50 µL) was added to the above mixture and the mixture was stirred at −70° C. for 10 min. Then 036-5 (500 mg, 1.23 mmol) in THF (15 mL) was added to the above mixture and the mixture was stirred at −70° C. for 5 min. Water (50 mL) was added to the mixture and the mixture was extracted with EtOAc (50 mL×2). The combined organic phase was washed with brine (100 mL), dried over anhydrous Na$_2$SO$_4$, filtered and concentrated. The crude was purified by flash chromatography on silica gel (MeOH in DCM=0 to 10%) to give 036-6 (500 mg, 1.02 mmol, 83.19% yield) as an off-white solid. $^1$H NMR (400 MHz, DMSO-d$_6$) δ=8.13-7.99 (m, 1H), 7.91 (d, J=8.8 Hz, 1H), 7.62-7.53 (m, 2H), 7.39-7.29 (m, 3H), 7.16-7.12 (m, 1H), 7.02-6.87 (m, 3H), 6.48 (s, 1H), 6.21 (s, 1H), 4.96-4.51 (m, 2H), 4.02 (s, 3H), 3.35 (s, 3H), 3.05-2.99 (m, 2H). LCMS R$_t$=0.75 min in 1.5 min chromatography, 5-95AB, ESI calcd. for C$_{30}$H$_{25}$N$_4$O$_3$ [M+H]$^+$ 489.2, found 489.1.

Step G: Preparation of (036-7)

A mixture of 036-6 (700 mg, 1.43 mmol) in THF (20 mL) and HCl (4M, 10 mL) was stirred at 70° C. for 12 h. The mixture was poured into saturated NaHCO$_3$ (100 mL) solution to pH=8 and the mixture was extracted with EtOAc (100 mL×2). The combined organic phase was washed with brine (100 mL), dried over anhydrous Na$_2$SO$_4$, filtered and concentrated to give 036-7 (650 mg, 1.37 mmol, 95.60% yield) as an off-white solid. LCMS R$_t$=0.67 min in 1.5 min chromatography, 5-95AB, ESI calcd. for C$_{29}$H$_{23}$N$_4$O$_3$ [M+H]$^+$ 475.2, found 475.1.

Step H: Preparation of (rac)-3-hydroxy-2$^1$-methyl-3-(1-methyl-1H-imidazol-5-yl)-2$^2$-oxo-2$^1$,2$^2$-dihydro-5-oxa-2(4,6)-quinolina-1,4(1,3)-dibenzenacycloheptaphane-4$^4$-carbonitrile (rac-036)

A mixture of 036-7 (550 mg, 1.16 mmol), iodomethane (164.52 mg, 1.16 mmol, 72.16 µL), BTEAC (132.01 mg, 579.55 µmol) in THF (10 mL) and NaOH (5M, 5.50 mL) was stirred at 25° C. for 1 h. The mixture was filtered through filter paper and the filter cake was washed with water (30 mL) and CH$_3$CN (30 mL) to give rac-036 (500 mg, 1.02 mmol, 88.30% yield) as an off-white solid. $^1$H NMR (400 MHz, DMSO-d$_6$) δ=8.03 (dd, J=2.4, 8.8 Hz, 1H), 7.68 (d, J=8.8 Hz, 1H), 7.55 (s, 1H), 7.49 (d, J=8.0 Hz, 1H), 7.34-7.31 (m, 2H), 7.27 (s, 1H), 7.16-6.78 (m, 3H), 6.52 (s, 1H), 6.25-6.23 (m, 2H), 4.88-4.60 (m, 2H), 3.70 (s, 3H), 3.34 (s, 3H), 3.05-3.03 (m, 2H). LCMS R$_t$=1.50 min in 3.0 min chromatography, 10-80CD, ESI calcd. for C$_{30}$H$_{25}$N$_4$O$_3$ [M+H]$^+$ 489.2, found 489.1. HPLC R$_t$=2.57 min in 8 min chromatography, 220 nm, purity 99.20%.

Step I: Preparation of (S)-3-hydroxy-2$^1$-methyl-3-(1-methyl-1H-imidazol-5-yl)-2$^2$-oxo-2$^1$,2$^2$-dihydro-5-oxa-2(4,6)-quinolina-1,4(1,3)-dibenzenacycloheptaphane-4$^4$-carbonitrile ((S)-036)

rac-036 (100 mg, 204.69 µmol) was separated by SFC (column: DAICEL CHIRALPAK AD (250 mm×30 mm, 10 m); mobile phase: [0.1% NH$_3$H$_2$O ETOH]; B %: 45%-45%) to give (S)-036 (35.1 mg, 71.85 µmol, 35.10% yield) as an off-white solid. 1H NMR (400 MHz, DMSO-d$_6$) δ=8.03 (dd, J=2.4, 8.8 Hz, 1H), 7.73-7.65 (m, 1H), 7.55 (s, 1H), 7.49 (d, J=8.0 Hz, 1H), 7.35-7.31 (m, 2H), 7.27 (s, 1H), 7.14-6.82 (m, 3H), 6.67 (s, 1H), 6.54-6.51 (m, 1H), 6.25-6.23 (m, 2H), 4.88-4.63 (m, 2H), 3.71 (s, 3H), 3.35 (s, 3H), 3.06-3.03 (m, 2H). LCMS $R_t$=1.51 min in 3.0 min chromatography, 10-80CD, ESI calcd. for $C_{30}H_{25}N_4O_3$ [M+H]$^+$ 489.2, found 489.1. HPLC $R_t$=2.57 min in 8 min chromatography, 220 nm, purity 100%. Chiral HPLC (S)-036: $R_t$=0.42 min in 1 min (ee 99.20%) (AD_ETOH_DEA_40-4ML_5CM), ((R)-036: $R_t$=0.30 min (ee 100%)).

Example 37: Preparation of Compound 37

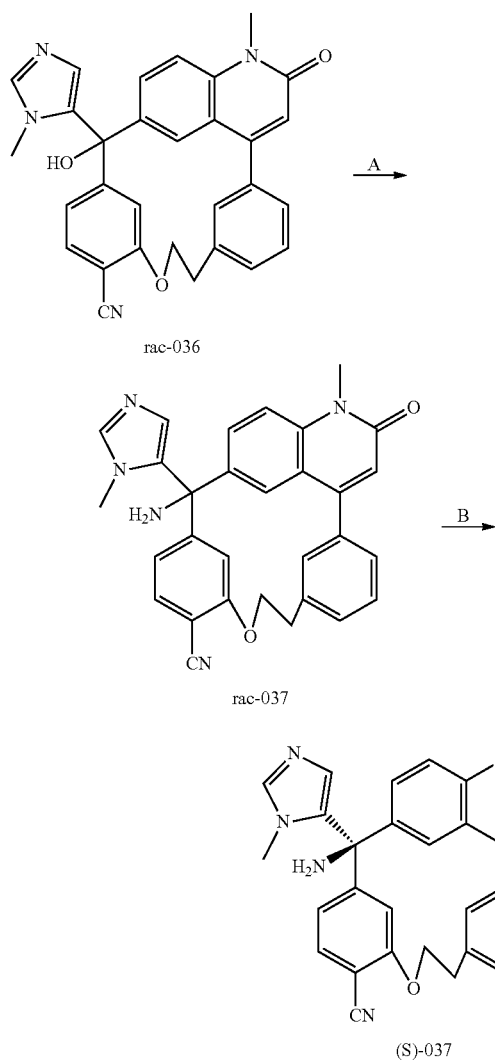

Step A: Preparation of (rac)-3-amino-2-methyl-3-(1-methyl-1H-imidazol-5-yl)-2²-oxo-2¹,2²-dihydro-5-oxa-2(4,6)-quinolina-1,4(1,3)-dibenzenacycloheptaphane-4⁴-carbonitrile (rac-037)

A mixture of rac-036 (180 mg, 368.45 μmol) and SOCl₂ (350.67 mg, 2.95 mmol, 213.83 μL) in DMI (8 mL) was stirred at 40° C. for 0.5 h, the above mixture was added to NH₃ in MeOH (7M, 30 mL) at 0° C. and the mixture was stirred at 0° C. for 15 min. The mixture was concentrated and re-dissolved in EtOAc (100 mL), washed with water (100 mL×3) and brine (100 mL), dried over anhydrous Na₂SO₄, filtered and concentrated. The crude was purified by flash chromatography on silica gel (MeOH in DCM=0 to 10%, twice) to give rac-037 (19.2 mg, 39.38 μmol, 10.69% yield) as an off-white solid. 1H NMR (400 MHz, DMSO-d₆) δ=8.07 (d, J=7.6 Hz, 1H), 7.65 (d, J=9.2 Hz, 1H), 7.55 (s, 1H), 7.44 (d, J=7.6 Hz, 1H), 7.34-7.24 (m, 4H), 7.15-7.01 (m, 2H), 6.50 (s, 1H), 6.32 (s, 1H), 6.19 (s, 1H), 4.87-4.68 (m, 2H), 3.70 (s, 3H), 3.29 (s, 3H), 3.06-3.04 (m, 2H). LCMS $R_t$=1.45 min in 3.0 min chromatography, 10-80CD, ESI calcd. for $C_{30}H_{26}N_5O_2$ [M+H]$^+$ 488.2, found 488.2. HPLC $R_t$=2.46 min in 8 min chromatography, 220 nm, purity 97.74%.

Step B: Preparation of (S)-3-amino-2¹-methyl-3-(1-methyl-1H-imidazol-5-yl)-2²-oxo-2¹,2²-dihydro-5-oxa-2(4,6)-quinolina-1,4(1,3)-dibenzenacycloheptaphane-4⁴-carbonitrile ((S)-037)

The rac-037 (100 mg, 205.11 μmol) was separated by SFC (column: DAICEL CHIRALPAK AD (250 mm×30 mm, 10 m); mobile phase: [0.1% NH₃H₂O EtOH]; B %: 45%-45%) to give (S)-037 (34.7 mg, 71.17 μmol, 34.70% yield) as an off-white solid. 1H NMR (400 MHz, DMSO-d₆) δ=8.07 (d, J=8.8 Hz, 1H), 7.65 (d, J=9.2 Hz, 1H), 7.53 (s, 1H), 7.44 (d, J=8.0 Hz, 1H), 7.36-7.22 (m, 4H), 7.15-6.95 (m, 2H), 6.50 (s, 1H), 6.31 (s, 1H), 6.19 (s, 1H), 4.88-4.67 (m, 2H), 3.70 (s, 3H), 3.29 (s, 3H), 3.06-3.03 (m, 2H). LCMS $R_t$=1.46 min in 3.0 min chromatography, 10-80CD, ESI calcd. for $C_{30}H_{26}N_5O_2$ [M+H]$^+$ 488.2, found 488.2. HPLC $R_t$=2.46 min in 8 min chromatography, 220 nm, purity 100%. Chiral HPLC (S)-037: $R_t$=2.49 min in 4 min (ee 99.94%) (AD_ETOH_DEA_5-40_4ML_4MIN_5CM), ((R)-037: $R_t$=2.06 min (ee 99.64%)).

Example 38: Preparation of Compound 38

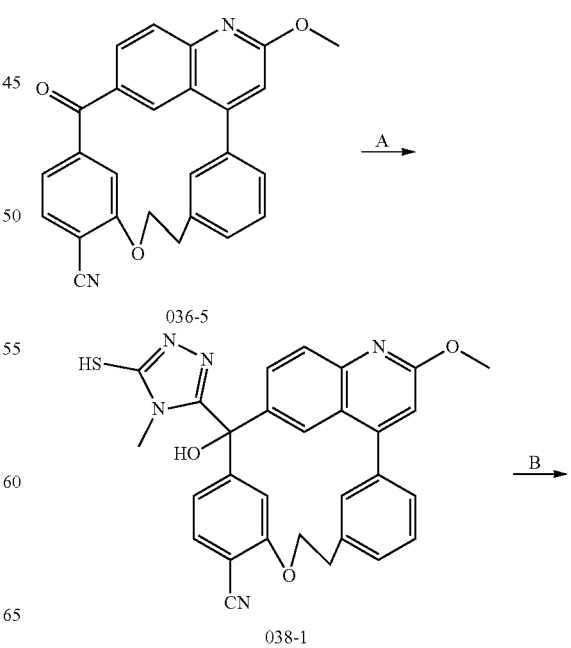

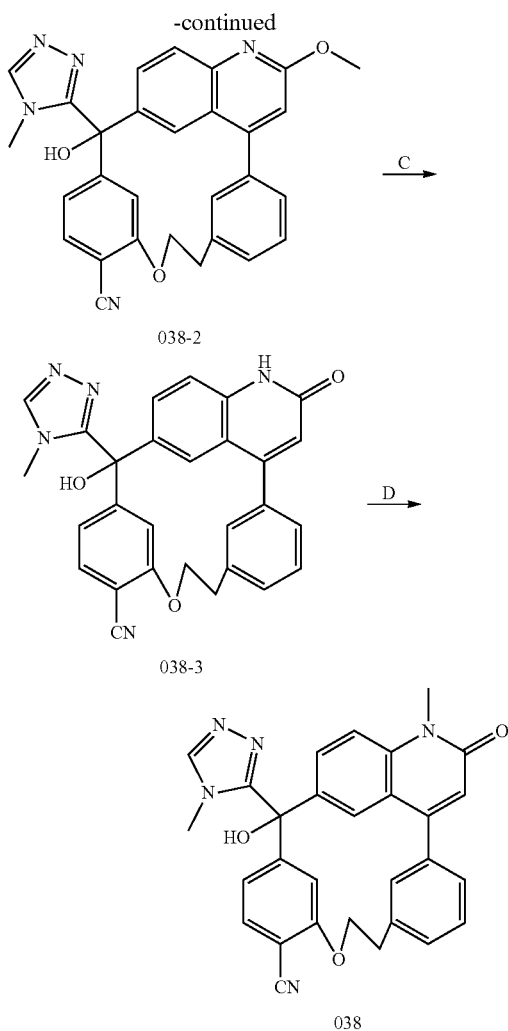

Step A: Preparation of (038-1)

To a solution of 4-methyl-4H-1,2,4-triazole-3-thiol (637.51 mg, 5.54 mmol) in THF (10 mL) was added n-BuLi (2.5M in n-hexane, 8.30 mmol, 3.32 mL) dropwise at −70° C. under $N_2$ for 0.5 h and the mixture was stirred at −70° C. for 10 min. The above suspension was added to a solution of 036-5 (750 mg, 1.85 mmol) in THF (10 mL) at −70° C. and the resulting mixture was stirred at −70° C. for 20 min. The mixture was poured into saturated $NH_4Cl$ aqueous (100 mL) and the mixture was extracted with EtOAc (100 mL×2). The combined organic phase was washed with brine (100 mL), dried over anhydrous $Na_2SO_4$, filtered and concentrated to give 038-1 (900 mg, 1.73 mmol, 93.51% yield) was obtained as an off-white solid. LCMS $R_t$=0.85 min in 1.5 min chromatography, 5-95AB, ESI calcd. for $C_{29}H_{24}N_5O_3S$ [M+H]$^+$ 522.2, found 522.0.

Step B: Preparation of (038-2)

To a solution of 038-1 (850 mg, 1.63 mmol) in THF (12 mL) and $H_2O$ (3 mL) was added $NaNO_2$ (1.12 g, 16.30 mmol) and $HNO_3$ (1.03 g, 16.30 mmol, 733.49 µL) and the mixture was stirred at 25° C. for 2 h. Water (50 mL) was added to the mixture and the mixture was extracted with EtOAc (50 mL). The organic phase was washed with saturated $NaHCO_3$ solution (50 mL), brine (50 mL), dried over anhydrous $Na_2SO_4$, filtered and concentrated. The crude was purified by flash chromatography on silica gel (MeOH in DCM=0 to 10%) to give 038-2 (630 mg, 1.29 mmol, 78.97% yield) as an off-white solid. $^1$H NMR (400 MHz, CDCl$_3$) δ=8.29 (s, 1H), 7.91-7.82 (m, 2H), 7.42-7.17 (m, 5H), 7.06 (d, J=7.2 Hz, 1H), 6.95-6.70 (m, 2H), 6.52 (s, 1H), 4.95-4.75 (m, 1H), 4.70-4.40 (m, 1H), 4.04 (s, 3H), 3.57 (s, 3H), 3.15-2.94 (m, 2H). LCMS $R_t$=0.78 min in 1.5 min chromatography, 5-95AB, ESI calcd. for $C_{29}H_{24}N_5O_3$ [M+H]$^+$ 490.2, found 490.1.

Step C: Preparation of (038-3)

A mixture of 038-2 (600 mg, 1.23 mmol) and HCl (4M in $H_2O$, 5 mL) in THF (10 mL) was stirred at 70° C. for 12 h. Saturated NaOH solution (50 mL) was added to the mixture to adjust pH=9 and the mixture was extracted with EtOAc (50 mL×2). The combined organic phase was washed with brine (50 mL), dried over anhydrous $Na_2SO_4$, filtered and concentrated to give 038-3 (550 mg, 1.16 mmol, 94.37% yield) as an off-white solid. LCMS $R_t$=0.70 min in 1.5 min chromatography, 5-95AB, ESI calcd. for $C_{28}H_{22}N_5O_3$ [M+H]$^+$ 476.2, found 476.0.

Step D: Preparation of 3-hydroxy-2$^1$-methyl-3-(4-methyl-4H-1,2,4-triazol-3-yl)-2$^2$-oxo-2$^1$,2$^2$-dihydro-5-oxa-2(4,6)-quinolina-1,4(1,3)-dibenzenacyclohep-taphane-4$^4$-carbonitrile (038)

A mixture of 038-3 (250 mg, 525.77 µmol), iodomethane (74.63 mg, 525.77 µmol, 32.73 µL) and K2CO$_3$ (217.99 mg, 1.58 mmol) in DMF (5 mL) was stirred at 25° C. for 12 h. Water (50 mL) was added to the mixture and the mixture was extracted with EtOAc (50 mL×2). The organic phase was washed with brine (50 mL), dried over anhydrous $Na_2SO_4$, filtered and concentrated. The crude was purified by flash chromatography on silica gel (MeOH in DCM=0 to 10%) and dried in oven to give 038 (20.8 mg, 42.49 µmol, 8.08% yield) as an off-white solid. $^1$H NMR (400 MHz, DMSO-d$_6$) δ=8.40 (s, 1H), 7.95 (dd, J=2.0, 8.8 Hz, 1H), 7.65 (d, J=8.8 Hz, 1H), 7.52 (d, J=8.0 Hz, 1H), 7.33 (d, J=4.4 Hz, 2H), 7.24 (s, 1H), 7.15-6.80 (m, 4H), 6.52 (s, 1H), 6.22 (s, 1H), 4.86-4.62 (m, 2H), 3.70 (s, 3H), 3.44 (s, 3H), 3.06-3.04 (m, 2H). LCMS $R_t$=1.40 min in 3.0 min chromatography, 10-80CD, ESI calcd. for $C_{29}H_{24}N_5O_3$ [M+H]$^+$ 490.2, found 490.2; $C_{29}H_{22}N_5O_2$ [M-OH]$^+$ 472.2, found 472.2. HPLC $R_t$=2.31 min in 8 min chromatography, 220 nm, purity 100%.

Example 39: Preparation of Compound 39

Scheme 39 - Synthesis of Compound 39

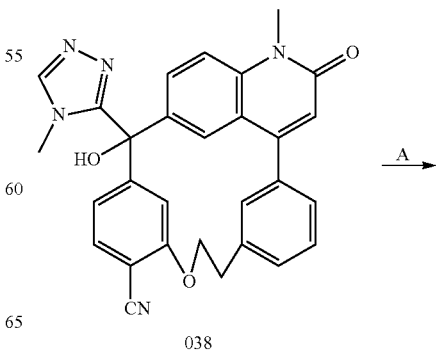

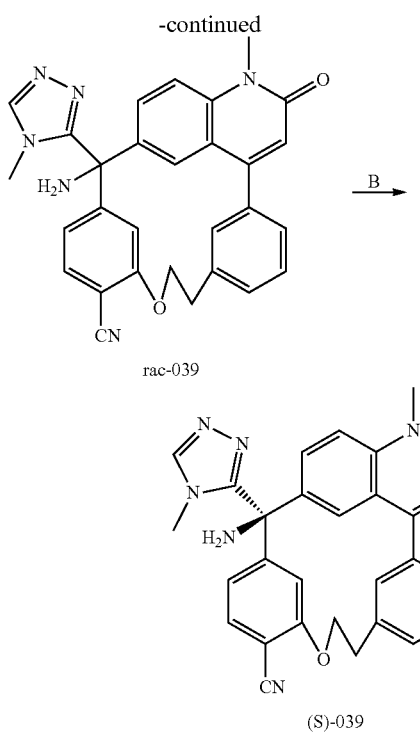

rac-039

(S)-039

Step A: Preparation of (rac)-3-amino-2¹-methyl-3-(4-methyl-4H-1,2,4-triazol-3-yl)-2²-oxo-2¹,2²-dihydro-5-oxa-2(4,6)-quinolina-1,4(1,3)-dibenzenacycloheptaphane-4⁴-carbonitrile (rac-039)

A mixture of 038 (100 mg, 204.28 μmol) and $SOCl_2$ (194.43 mg, 1.63 mmol, 118.55 L) in DMI (5 mL) was stirred at 40° C. for 1 h. The above solution was added to $NH_3$ in MeOH (7M, 10.00 mL) and the mixture was stirred at −10° C. for 10 min. The mixture was blended with another batch prepared from 50 mg of 038. Water (50 mL) was added to the mixture and the mixture was extracted with EtOAc (50 mL×2). The combined organic phase was washed with brine (100 mL), dried over anhydrous $Na_2SO_4$, filtered and concentrated. The crude was purified by flash chromatography on silica gel (MeOH in DCM=0 to 10%) to give rac-039 (100 mg, 204.69 μmol, 66.80% yield) as an off-white solid. LCMS $R_t$=0.67 min in 1.5 min chromatography, 5-95AB, ESI calcd. for $C_{29}H_{22}N_5O_2$ [M-NH$_2$]⁺472.2, found 472.0. $C_{26}H_{20}N_3O_2$[M-C$_3$H$_4$N$_3$]⁺406.2, found 406.0.

Step B: Preparation of (S)-3-amino-2¹-methyl-3-(4-methyl-4H-1,2,4-triazol-3-yl)-2²-oxo-2¹,2²-dihydro-5-oxa-2(4,6)-quinolina-1,4(1,3)-dibenzenacycloheptaphane-4⁴-carbonitrile ((S)-039)

rac-039 (100 mg, 204.69 μmol) was separated by SFC (column: DAICEL CHIRALCEL OD-H (250 mm×30 mm, 5 m); mobile phase: [0.1% NH$_3$H$_2$O EtOH]; B %: 55%-55%) to give (S)-039 (20.1 mg, 41.14 μmol, 20.10% yield) as an off-white solid. ¹H NMR (400 MHz, DMSO-d$_6$) δ=8.38 (s, 1H), 8.01 (d, J=8.8 Hz, 1H), 7.69-7.03 (m, 8H), 6.49 (s, 1H), 6.14 (d, J=2.4 Hz, 1H), 5.00-4.65 (m, 2H), 3.70 (s, 3H), 3.34 (s, 3H), 3.19 (s, 2H), 3.06-3.02 (m, 2H). LCMS $R_t$=1.37 min in 3.0 min chromatography, 10-80CD, ESI calcd. for $C_{29}H_{25}N_6O_2$ [M+H]⁺ 489.2, found 489.2; $C_{29}H_{22}N_5O_2$ [M-NH$_2$]⁺472.2, found 472.1. $C_{26}H_{20}N_3O_2$ [M-C$_3$H$_4$N$_3$]⁺406.2, found 406.1. HPLC $R_t$=2.22 min in 8 min chromatography, 220 nm, purity 98.80%. Chiral HPLC (S)-039: $R_t$=3.44 min in 8 min (ee 100%) (OD_ETOH_DEA_40-2.8ML_10CM), ((R)-039: $R_t$=5.70 min (ee 99.58%)).

Scheme G - General Synthetic Method G

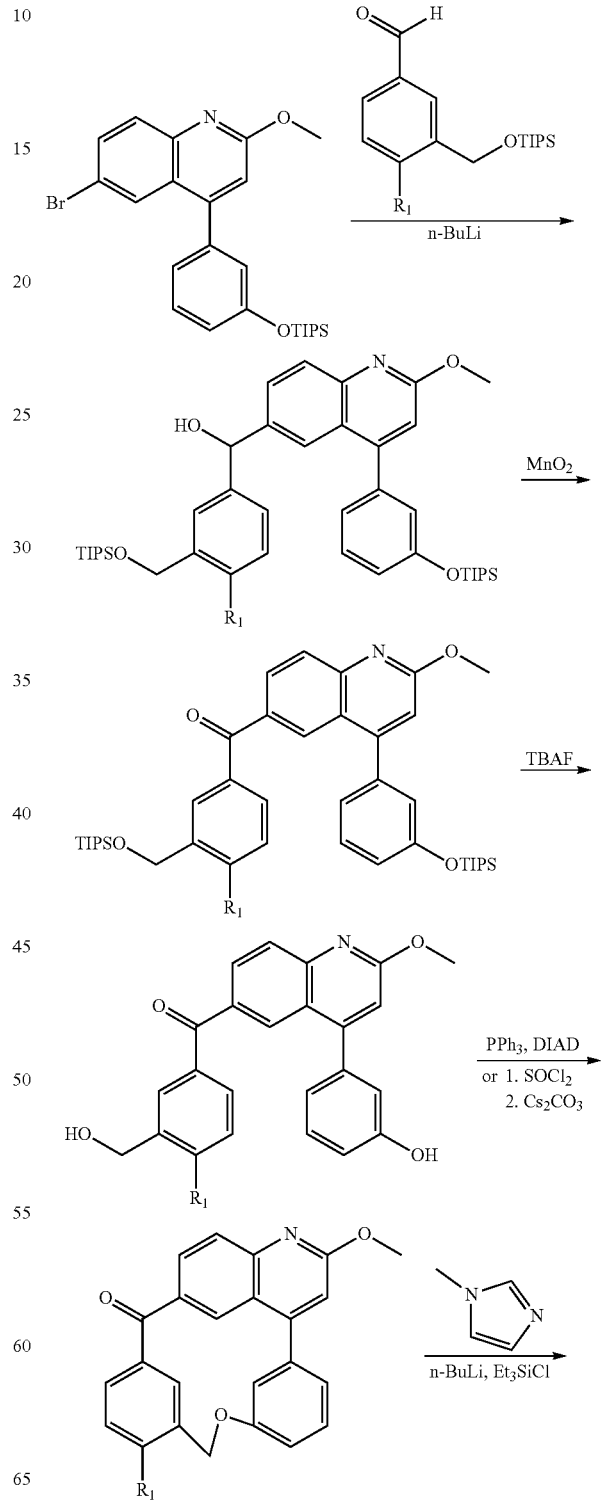

Example 40: Preparation of Compound 40
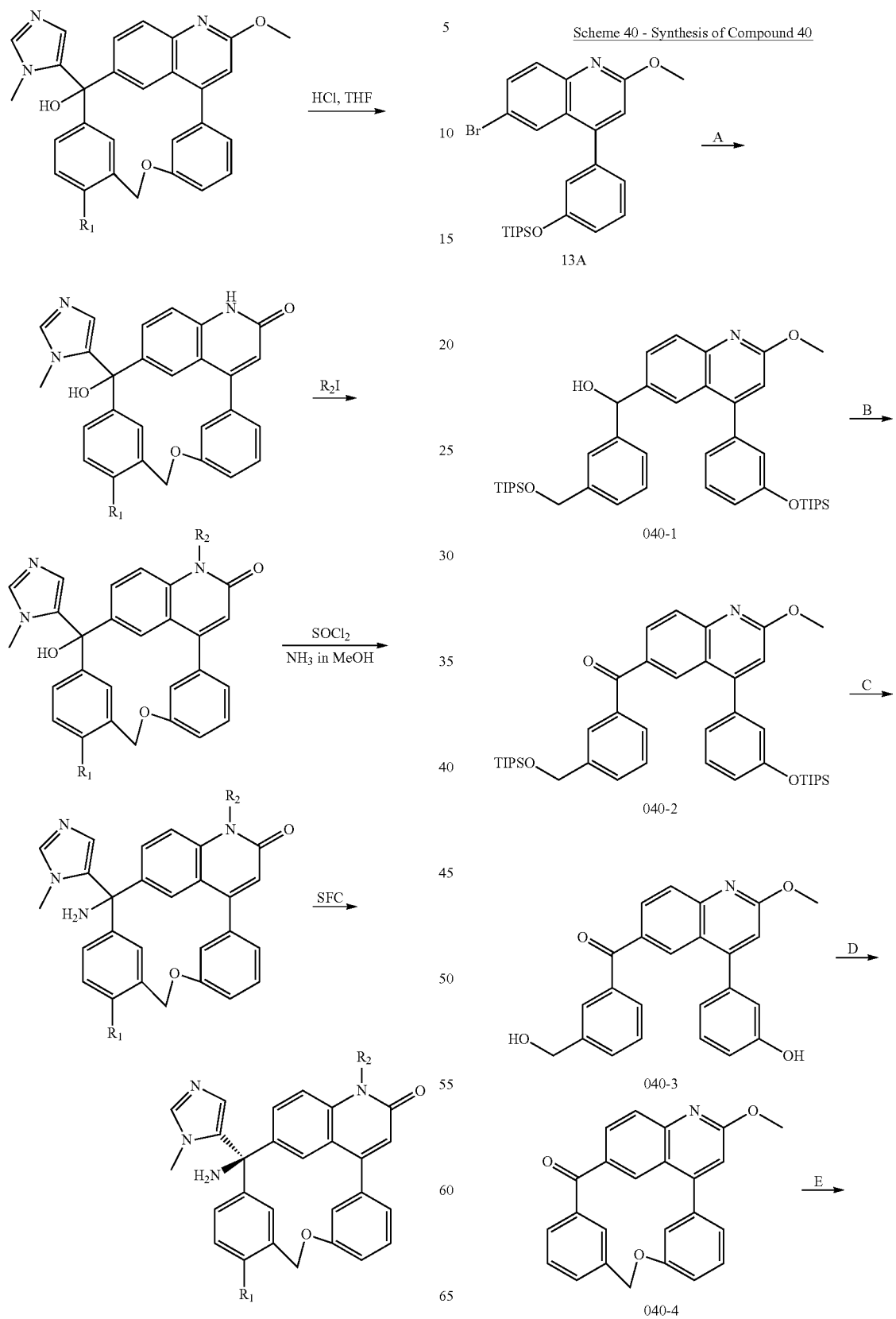

-continued

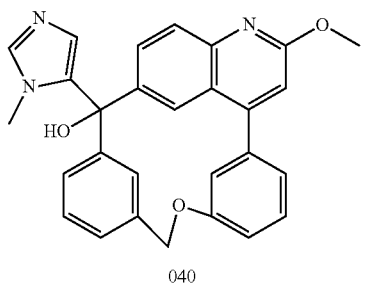 [SMILES: COc1cc2c3cc(ccc3n1)C(O)(c1cncn1C)c1cccc(c1)COc1cccc-2c1]

040

Step A: Preparation of (040-1)

To a mixture of 13A (5 g, 10.28 mmol) in THF (20 mL) was added n-BuLi (2.5M in n-hexane, 12.33 mmol, 4.93 mL) at −75° C. under N$_2$, the mixture was stirred at −75° C. for 5 min. Then 3-(((triisopropylsilyl)oxy)methyl)benzaldehyde (3.61 g, 12.33 mmol) (*J. Med. Chem.* 2000, 43 (22), 4084-4097.) was added at −75° C. The mixture was stirred at −75° C. for 55 min. The mixture was added into water (50 mL). The aqueous phase was extracted with DCM (50 mL×3). The combined organic phase was washed with brine (100 mL), dried over anhydrous Na$_2$SO$_4$, filtered and concentrated under reduced pressure. The residue was purified by flash chromatography on silica gel (EtOAc in petroleum ether=0 to 10%) to afford 040-1 (5.5 g, 7.86 mmol, 76.44% yield) as colorless oil. 1H NMR (400 MHz, DMSO-d$_6$) δ=7.80-7.74 (m, 2H), 7.56 (dd, J=2.0, 8.8 Hz, 1H), 7.45 (t, J=7.6 Hz, 1H), 7.28-7.23 (m, 2H), 7.17-7.01 (m, 4H), 6.96 (s, 1H), 6.86 (s, 1H), 5.95 (d, J=3.6 Hz, 1H), 5.71 (d, J=3.6 Hz, 1H), 4.70 (s, 2H), 4.01-3.97 (m, 3H), 1.20-1.14 (m, 3H), 1.08-1.05 (m, 18H), 1.03-0.97 (m, 3H), 0.94-0.90 (m, 18H).

Step B: Preparation of (040-2)

To a mixture of 040-1 (5.5 g, 7.86 mmol) in DCM (200 mL) was added MnO$_2$ (27.32 g, 314.24 mmol) at 20° C. under N$_2$. The mixture was stirred at 35° C. for 10 h. The mixture was filtered and the filtrate was concentrated under reduced pressure to afford 040-2 (5 g, 7.16 mmol, 91.17% yield) as yellow oil. $^1$H NMR (400 MHz, DMSO-d$_6$) δ=8.08 (s, 1H), 8.06-7.96 (m, 2H), 7.72 (s, 1H), 7.66-7.57 (m, 2H), 7.53-7.46 (m, 1H), 7.44-7.38 (m, 1H), 7.16 (d, J=8.0 Hz, 1H), 7.03 (s, 1H), 7.01-6.91 (m, 2H), 4.85 (s, 2H), 4.08 (s, 3H), 1.20-1.09 (m, 6H), 1.00-0.95 (m, 36H).

Step C: Preparation of (040-3)

To a mixture of 040-2 (5 g, 7.16 mmol) in THF (50 mL) was added TBAF (1M in THF, 71.62 mmol, 71.62 mL) at 0° C. under N$_2$. The mixture was stirred at 20° C. for 10 h. The mixture was added into water (50 mL). The aqueous phase was extracted with DCM (100 mL×2). The combined organic phase was washed with brine (150 mL), dried over anhydrous Na$_2$SO$_4$, filtered and concentrated under reduced pressure. The residue was purified by flash chromatography on silica gel (MeOH in DCM=0 to 10%) to afford 040-3 (2 g, 5.19 mmol, 72.45% yield) as an off-white solid. $^1$H NMR (400 MHz, DMSO-d$_6$) δ=9.74 (s, 1H), 8.19 (s, 1H), 8.14-8.01 (m, 1H), 8.01-7.94 (m, 1H), 7.73 (s, 1H), 7.68-7.57 (m, 2H), 7.55-7.48 (m, 1H), 7.32 (t, J=8.0 Hz, 1H), 7.04-6.82 (m, 4H), 5.41-5.29 (m, 1H), 4.60 (d, J=5.6 Hz, 2H), 4.07 (s, 3H).

Step D: Preparation of (040-4)

To a mixture of PPh$_3$ (2.04 g, 7.78 mmol) in THF (10 mL) was added DEAD (1.36 g, 7.78 mmol, 1.42 mL) at 0° C. under N$_2$. The mixture was stirred at 20° C. for 0.5 h. Then 040-3 (1.2 g, 3.11 mmol) in THF (200 mL) was added at 20° C. The mixture was stirred at 20° C. for 10 h. The mixture was blended with another batch prepared from 200 mg and 600 mg of 040-3. The mixture was added into water (200 mL). The aqueous phase was extracted with ethyl acetate (200 mL×3). The combined organic phase was washed with brine (500 mL), dried over anhydrous Na$_2$SO$_4$, filtered and concentrated under reduced pressure. The residue was purified by flash chromatography on silica gel (EtOAc in petroleum ether=0 to 5%) to afford 040-4 (900 mg, 2.45 mmol, 47.11% yield) as an off-white solid. $^1$H NMR (400 MHz, CD$_3$CN) δ=8.21 (d, J=8.8 Hz, 1H), 7.99-7.90 (m, 3H), 7.79 (d, J=7.6 Hz, 1H), 7.73-7.67 (m, 1H), 7.61-7.54 (m, 1H), 7.42-7.33 (m, 2H), 7.16-7.09 (m, 2H), 7.00-6.95 (m, 1H), 5.32 (s, 2H), 4.11 (s, 3H).

Step E: Preparation of 2$^2$-methoxy-3-(1-methyl-1H-imidazol-5-yl)-6-oxa-2(4,6)-quinolina-1,4(1,3)-dibenzenacyclohexaphan-3-ol (040)

To a mixture of 1-methyl-1H-imidazole (196.66 mg, 2.40 mmol, 190.93 µL) in THF (10 mL) was added n-BuLi (2.5M in hexane, 2.40 mmol, 958.09 µL) at −75° C. under N$_2$. The mixture was stirred at −75° C. for 30 min. Then Et$_3$SiCl (361.01 mg, 2.40 mmol, 407.46 µL) was added dropwise at −75° C. and stirred at −75° C. for 30 min. Then n-BuLi (2.5M in n-hexane, 2.40 mmol, 958.09 µL) was added dropwise at −75° C., and stirred for 1 h. A solution of 040-4 (800 mg, 2.18 mmol) in THF (5 mL) was added dropwise at −75° C. The mixture was stirred at −75° C. for 1 h. The mixture was added into water (30 mL). The mixture was blended with another batch prepared from 100 mg of 040-4. The aqueous phase was extracted with DCM (50 mL×3). The combined organic phase was washed with brine (130 mL), dried over anhydrous Na$_2$SO$_4$, filtered and concentrated under reduced pressure. The residue was purified by flash chromatography on silica gel (MeOH in DCM=0 to 20%) to afford 040 (900 mg, 2.00 mmol, 81.73% yield) as an off-white solid. 50 mg (111.23 µmol) of the product was purified by Prep-HPLC (column: Waters Xbridge 150×25 mm×5 m; mobile phase: [water (0.05% NH$_3$H$_2$O+10 mM NH$_4$HCO$_3$)-ACN]; B %: 44%-74%, 7.8 min) to give 040 (19.0 mg, 42.27 µmol, 38.00% yield) as an off-white solid. $^1$H NMR (400 MHz, CDCl$_3$) δ=8.00-7.80 (m, 2H), 7.46-7.16 (m, 6H), 7.05-6.87 (m, 4H), 6.77 (s, 1H), 6.45-6.25 (m, 1H), 5.42-5.25 (m, 2H), 4.07 (s, 3H), 3.59 (s, 3H). LCMS R$_t$=1.870 min in 3 min chromatography, 10-80CD, ESI calcd. for C$_{28}$H$_{24}$N$_3$O$_3$ [M+H]$^+$ 450.2, found 450.2. HPLC R$_t$=3.57 min in 8 min chromatography, 220 nm, purity 100%.

Example 41: Preparation of Compound 41

Scheme 41 - Synthesis of Compound 41

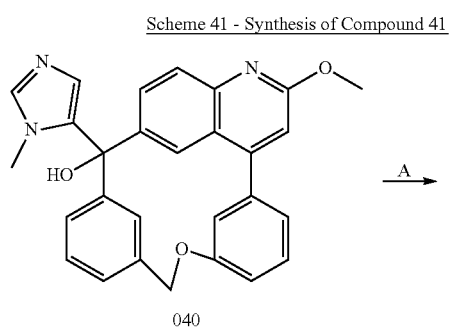

040

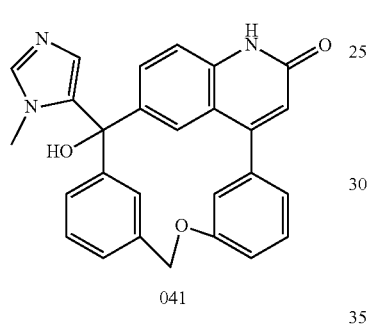

041

Step A: Preparation of 3-hydroxy-3-(1-methyl-1H-imidazol-5-yl)-$2^1,2^2$-dihydro-6-oxa-2(4,6)-quinolina-1,4(1,3)-dibenzenacyclohexaphan-$2^2$-one (041)

To a mixture of 040 (250 mg, 556.17 μmol) in THF (5 mL) was added HCl (4M in H$_2$O, 13.90 mmol, 3.48 mL) at 20° C. under N$_2$. The mixture was stirred at 70° C. for 10 h. The mixture was cooled to 20° C. and added into water (20 mL). Saturated NaHCO$_3$ solution was added to adjust pH=8. The aqueous phase was extracted with DCM (30 mL×2). The combined organic phase was washed with brine (50 mL), dried over anhydrous Na$_2$SO$_4$, filtered and concentrated under reduced pressure. The residue was purified by flash chromatography on silica gel (MeOH in DCM=0 to 30%) to afford 041 (200 mg, 459.27 μmol, 82.58% yield) as an off-white solid. 50 mg (114.82 μmol) of the product was purified by Prep-HPLC (column: Waters Xbridge 150×25 mm×5 m; mobile phase: [water (0.05% NH$_3$H$_2$O+10 mM NH$_4$HCO$_3$)-ACN]; B %: 23%-53%, 9.5 min) to give 041 (4.1 mg, 9.42 μmol, 8.20% yield) as an off-white solid. $^1$H NMR (400 MHz, DMSO-d$_6$) δ=11.94 (s, 1H), 7.98-7.90 (m, 1H), 7.70-7.55 (m, 1H), 7.45-7.23 (m, 5H), 7.05-6.89 (m, 3H), 6.86-6.60 (m, 1H), 6.61 (s, 1H), 6.50 (s, 1H), 6.32-6.15 (m, 1H), 5.34 (s, 2H), 3.54 (s, 3H). LCMS R$_t$=1.46 min in 3 min chromatography, 10-80CD, ESI calcd. for C$_{27}$H$_{22}$N$_3$O$_3$ [M+H]$^+$ 436.2, found 436.1. HPLC R$_t$=2.48 min in 8 min chromatography, 220 nm, purity 97.84%.

Example 42: Preparation of Compound 42

Scheme 42 - Synthesis of Compound 42

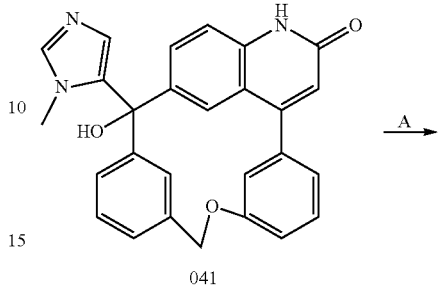

041

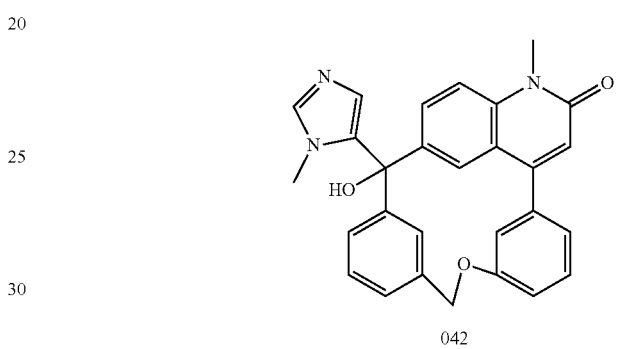

042

Step A: Preparation of 3-hydroxy-$2^1$-methyl-3-(1-methyl-1H-imidazol-5-yl)-$2^1,2^2$-dihydro-6-oxa-2(4,6)-quinolina-1,4(1,3)-dibenzenacyclohexaphan-$2^2$-one (042)

To a mixture of 041 (100 mg, 229.64 μmol) in THF (2 mL) and H$_2$O (1 mL) was added BTEAC (26.15 mg, 114.82 μmol) and NaOH (91.85 mg, 2.30 mmol) at 20° C. under N$_2$. Then iodomethane (65.19 mg, 459.27 μmol, 28.59 μL) in THF (0.5 mL) was added slowly. The mixture was stirred at 20° C. for 1 h. The mixture was blended with another batch prepared from 50 mg of 041. The mixture was added into water (20 mL) slowly. The aqueous phase was extracted with DCM (30 mL×2). The combined organic phase was washed with brine (50 mL), dried over anhydrous Na$_2$SO$_4$, filtered and concentrated under reduced pressure. The residue was purified by Prep-HPLC (column: Waters Xbridge 150×25 mm×5 m; mobile phase: [water (0.05% NH$_3$H$_2$O+10 mM NH$_4$HCO$_3$)-ACN]; B %: 29%-59%, 7.8 min) to afford 042 (39.9 mg, 88.77 μmol, 25.77% yield) as an off-white solid. $^1$H NMR (400 MHz, DMSO-d$_6$) δ=8.04 (dd, J=2.4, 8.8 Hz, 1H), 7.65 (d, J=9.2 Hz, 1H), 7.55 (s, 1H), 7.41-7.28 (m, 4H), 7.23-7.15 (m, 1H), 7.04-6.98 (m, 2H), 6.96-6.88 (m, 2H), 6.61 (s, 1H), 6.41 (s, 1H), 6.26 (s, 1H), 5.31 (dd, J=12.8, 21.6 Hz, 2H), 3.70 (s, 3H), 3.51 (s, 3H). LCMS R$_t$=1.52 min in 3 min chromatography, 10-80CD, ESI calcd. for C$_{28}$H$_{24}$N$_3$O$_3$ [M+H]$^+$ 450.2, found 450.2. HPLC R$_t$=2.65 min in 8 min chromatography, 220 nm, purity 100.00%.

Example 43: Preparation of Compound 43

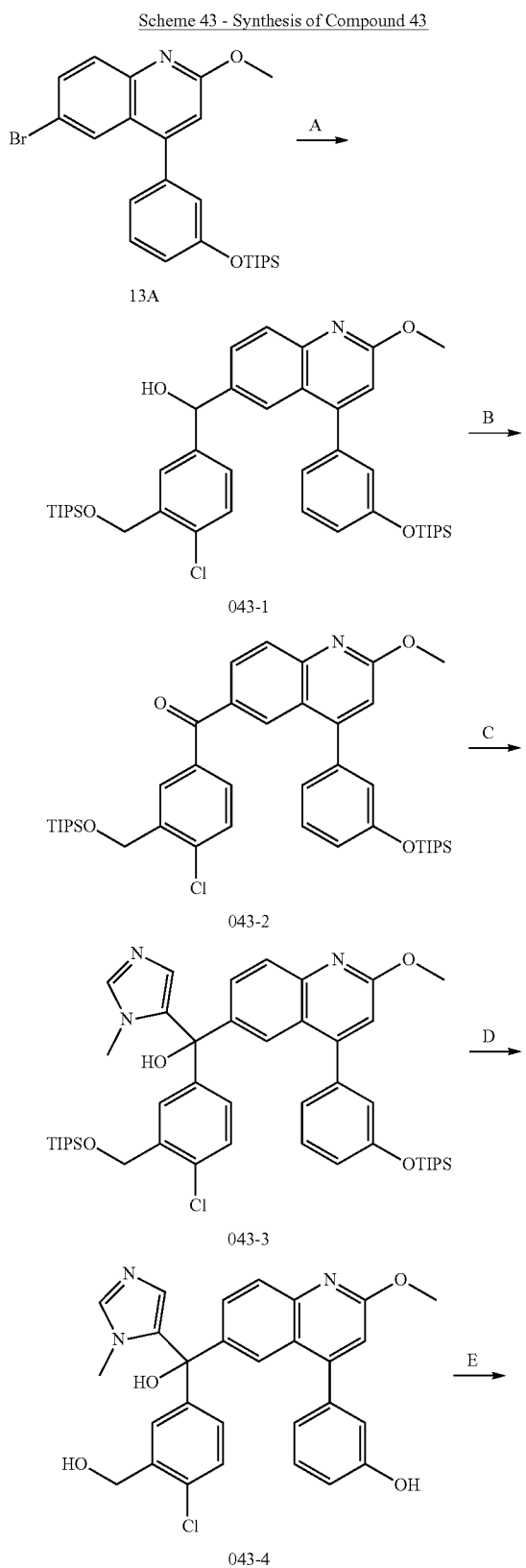

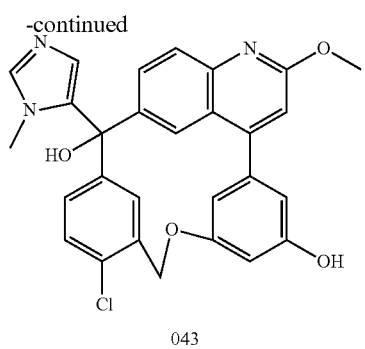

Step A: Preparation of (043-1)

To a solution of 13A (9.7 g, 19.94 mmol) in THF (100 mL) was added n-BuLi (2.5M in n-hexane, 21.93 mmol, 8.77 mL) at −70° C. during 30 min. Then a solution of 7A (6.52 g, 19.94 mmol) in THF (20 mL) was added dropwise to the above mixture at −70° C. during 30 min. The resulted mixture was stirred at −70° C. for 30 min. The mixture was poured into water (150 mL) and extracted with EtOAc (100 mL×3). The organic layer was washed brine (50 mL), dried over anhydrous $Na_2SO_4$, filtered and concentrated. The crude was blended with another batch prepared from 9.7 g of 6-bromo-2-methoxy-4-(3-((triisopropylsilyl)oxy)phenyl) quinoline. The residue was purified by flash chromatography on silica gel (EtOAc in petroleum ether=10% to 15%) to afford 043-1 (24.9 g, 33.90 mmol, 85.07% yield) as yellow oil. 1H NMR (400 MHz, DMSO-$d_6$) δ=7.81-7.75 (m, 2H), 7.55 (dd, J=2.0, 8.8 Hz, 1H), 7.44 (t, J=8.0 Hz, 1H), 7.39-7.31 (m, 2H), 7.26 (s, 1H), 7.07 (d, J=7.6 Hz, 1H), 7.05-6.99 (m, 1H), 6.95-6.92 (m, 1H), 6.87 (s, 1H), 6.05 (d, J=4.0 Hz, 1H), 5.76-5.75 (m, 1H), 5.74 (d, J=4.0 Hz, 1H), 4.70 (s, 2H), 4.00 (s, 1H), 4.01-3.98 (m, 1H), 1.25-1.15 (m, 3H), 1.05 (d, J=7.2 Hz, 18H), 0.98-0.92 (m, 3H), 0.87-0.82 (m, 18H).

Step B: Preparation of (043-2)

To a mixture of 043-1 (24.9 g, 33.90 mmol) in DCM (300 mL) was added $MnO_2$ (58.94 g, 677.96 mmol) at 25° C. and the mixture was stirred at 40° C. for 12 h. The mixture was cooled and filtered. The filter cake was washed with DCM (100 mL×2). The filtrated was concentrated to give 043-2 (23.6 g, 32.22 mmol, 95.04% yield) as yellow oil. 1H NMR (400 MHz, DMSO-$d_6$) δ=8.06 (s, 1H), 8.00-7.96 (m, 2H), 7.92-7.90 (m, 1H), 7.71 (dd, J=1.6, 8.4 Hz, 1H), 7.59 (d, J=8.0 Hz, 1H), 7.43 (t, J=8.0 Hz, 1H), 7.15 (d, J=7.6 Hz, 1H), 7.05 (s, 1H), 7.00 (dd, J=2.0, 6.4 Hz, 1H), 6.92-6.90 (m, 1H), 4.84 (s, 2H), 4.08 (s, 3H), 1.21-1.11 (m, 3H), 1.09-1.03 (m, 3H), 0.97-0.95 (m, 18H), 0.92-0.90 (m, 18H).

Step C: Preparation of (043-3)

To a mixture of 1-methyl-1H-imidazole (1.36 g, 16.52 mmol, 1.32 mL) in THF (55 mL) was added n-BuLi (2.5M in n-hexane, 16.52 mmol, 6.61 mL) at −75° C. under $N_2$. The mixture was stirred at −75° C. for 30 min, then $Et_3SiCl$ (2.49 g, 16.52 mmol, 2.81 mL) in THF (25 mL) was added dropwise at −75° C. The mixture was stirred at −75° C. for 30 min. Then n-BuLi (2.5M in n-hexane, 16.52 mmol, 6.61 mL) was added dropwise at −75° C., and stirred at 75° C. for 1 h. A solution of 043-2 (11 g, 15.02 mmol) in THF (110 mL) was added dropwise at −75° C., and this mixture was stirred at −75° C. for 1 h. The residue was blended with another batch prepared from 2 g, 10 g of 043-2. The mixture was added into water (200 mL). The aqueous phase was extracted with EtOAc (500 mL×2). The combined organic phase was washed with brine (800 mL), dried over anhydrous $Na_2SO_4$, filtered and concentrated under reduced pressure. The residue was purified by flash chromatography on silica gel (MeOH in DCM=0 to 15%) to afford 043-3 (20 g, 24.55 mmol, 78.23% yield) as a yellow solid. $^1$H NMR (400 MHz, DMSO-$d_6$) δ=7.80 (d, J=8.8 Hz, 1H), 7.61 (d, J=2.0 Hz, 1H), 7.59-7.51 (m, 2H), 7.48-7.43 (m, 1H), 7.42-7.37 (m, 1H), 7.35-7.30 (m, 1H), 7.15-7.08 (m, 1H), 6.97-6.89 (m, 2H), 6.87-6.83 (m, 2H), 6.79 (s, 1H), 6.00 (s, 1H), 4.73-4.64 (m, 2H), 4.00 (s, 3H), 3.31 (s, 3H), 1.25-1.16 (m, 3H), 1.05-0.95 (m, 18H), 0.92-0.87 (m, 3H), 0.84-0.78 (m, 18H).

Step D: Preparation of (043-4)

To a mixture of 043-3 (2 g, 2.46 mmol) in THF (20 mL) was added TBAF (1M in THF, 3.68 mmol, 3.68 mL) at 25° C. under $N_2$. The mixture was stirred at 25° C. for 0.5 h. The mixture was added into water (30 mL). The aqueous phase was extracted with EtOAc (50 mL×2). The combined organic phase was washed with brine (80 mL), dried over anhydrous $Na_2SO_4$, filtered and concentrated under reduced pressure. The crude product was triturated with EtOAc: petroleum ether=1:5 at 25° C. for 20 min to afford 043-4 (1 g, 1.99 mmol, 81.15% yield) as a white solid. 50 mg (99.61 μmol) of the product was purified by Prep-HPLC (column: Welch Xtimate $C_{18\ 150\times 25}$ mm×5 m; mobile phase: [water (0.05% ammonia hydroxide v/v)-MeOH]; B %: 62%-92%, 9.5 min) to give 043-4 (10.2 mg, 20.32 μmol, 20.40% yield) as an off-white solid. $^1$H NMR (400 MHz, DMSO-$d_6$) δ=9.39 (s, 1H), 7.80 (d, J=8.4 Hz, 1H), 7.68 (d, J=2.0 Hz, 1H), 7.63-7.57 (m, 2H), 7.51 (d, J=2.4 Hz, 1H), 7.32-7.22 (m, 2H), 7.09 (dd, J=2.4, 8.4 Hz, 1H), 6.91-6.74 (m, 4H), 6.59 (s, 1H), 6.11 (s, 1H), 5.07 (s, 1H), 4.58-4.44 (m, 2H), 4.04 (s, 3H), 3.35 (s, 3H). LCMS $R_t$=1.67 min in 3 min chromatography, 10-80CD, ESI calcd. for $C_{28}H_{25}ClN_3O_4$ [M+H]$^+$ 502.2, found 502.2. HPLC $R_t$=3.04 min in 8 min chromatography, 220 nm, purity 100%.

Step E: Preparation of 4$^4$-chloro-2$^2$-methoxy-3-(1-methyl-1H-imidazol-5-yl)-6-oxa-2(4,6)-quinolina-1,4(1,3)-dibenzenacyclohexaphan-3-ol (043)

To a mixture of 043-4 (4 g, 7.97 mmol) in THF (32 mL) and DMF (8 mL) was added $SOCl_2$ (2.84 g, 23.91 mmol, 1.73 mL) at 25° C. under $N_2$. The mixture was stirred at 25° C. for 1 h. The above mixture (4.15 g, 7.97 mmol) in DMF (200 mL) and THF (600 mL) was added $Cs_2CO_3$ (51.97 g, 159.49 mmol) at 0° C. under $N_2$. The mixture was stirred at 105° C. for 10 h. The mixture was filtered and the filtrate was concentrated under reduced pressure. The mixture was dissolve with EtOAc (300 mL). The combined organic phase was washed with $H_2O$ (300 mL), brine (300 mL), dried over anhydrous $Na_2SO_4$, filtered and concentrated under reduced pressure. The crude product was triturated with petroleum ether:EtOAc=1:1 (100 mL) at 25° C. for 20 min to afford 043 (3.5 g, 7.23 mmol, 90.69% yield) as a brown solid, which was purified by flash chromatography on silica gel (MeOH in DCM=0 to 15%) to afford 043 (3.2 g, 6.61 mmol, 91.43% yield) as a yellow solid. 40 mg (82.65 μmol) of the product was further purified by Prep-HPLC (column: Phenomenex Gemini 150×25 mm×10 m; mobile phase: [water (0.05% $NH_3H_2O$+10 mM $NH_4HCO_3$)-ACN]; B %: 42%-72%, 7.8 min) to afford 043 (15.7 mg, 32.44 μmol, 39.25% yield) as a white solid. $^1$H NMR (400 MHz, DMSO-$d_6$) δ=8.06-8.03 (m, 1H), 7.88 (d, J=8.0 Hz, 1H), 7.65 (s, 1H), 7.55 (s, 1H), 7.41-7.34 (m, 2H), 7.27-7.23 (m, 2H), 7.15-7.11 (m, 2H), 7.04-7.01 (m, 2H), 6.55 (s, 1H), 6.29 (s, 1H), 5.48-5.39 (m, 2H), 4.06 (s, 3H), 3.50 (s, 3H). LCMS $R_t$=1.89 min in 3 min chromatography, 10-80CD, ESI calcd. for $C_{28}H_{23}ClN_3O_3$ [M+H]$^+$ 484.1, found 484.1. HPLC $R_t$=3.87 min in 8 min chromatography, 220 nm, purity 100%.

Example 44: Preparation of Compound 44

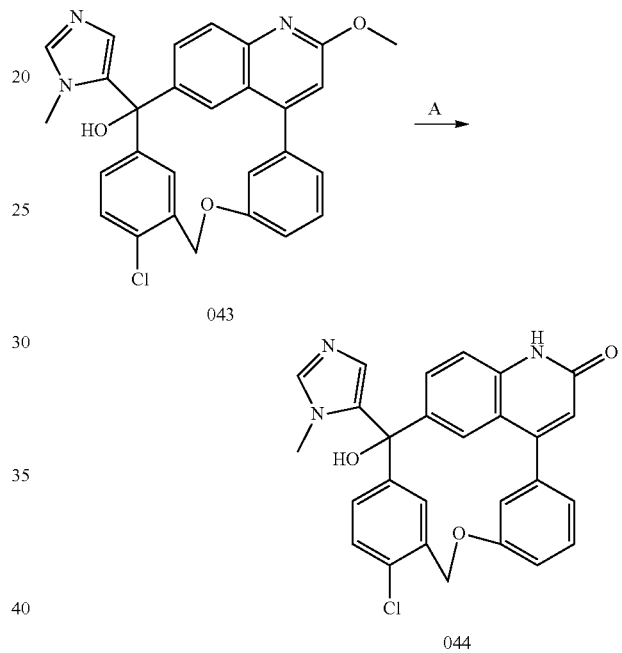

Scheme 44 - Synthesis of Compound 44

Step A: Preparation of 4$^4$-chloro-3-hydroxy-3-(1-methyl-1H-imidazol-5-yl)-2$^1$,2$^2$-dihydro-6-oxa-2(4,6)-quinolina-1,4(1,3)-dibenzenacyclohexaphan-2$^2$-one (044)

To a solution of 043 (150 mg, 309.95 μmol) in THF (6 mL) was added HCl (4M in $H_2O$, 11.78 mmol, 2.94 mL). The mixture was stirred at 70° C. for 16 h. The mixture was adjusted to pH=7 with saturated NaOH solution. The solvent was removed under concentration. The crude was lyophilized to give 044 (140 mg, 297.92 μmol, 96.12% yield) as a white solid. 40 mg (85.12 μmol) of 044 was further purified by Prep-HPLC (column: Welch Xtimate $C_{18\ 150}$×25 mm×5 m; mobile phase: [water (0.05% ammonia hydroxide v/v)-MeOH]; B %: 60%-90%, 7.8 min) to give 044 (12.4 mg, 26.39 μmol, 31.00% yield) as an off-white solid. $^1$H NMR (400 MHz, DMSO-$d_6$) δ=11.66 (s, 1H), 7.88-7.85 (m, 1H), 7.56-7.52 (m, 2H), 7.44-7.31 (m, 3H), 7.25-7.23 (m, 1H), 7.09-6.99 (m, 4H), 6.51 (s, 1H), 6.43 (s, 1H), 6.29 (s, 1H), 5.47-5.37 (m, 2H), 3.47 (s, 3H). LCMS $R_t$=1.59 min in 3 min chromatography, 10-80CD, ESI calcd. for $C_{27}H_{21}ClN_3O_3$ [M+H]$^+$ 470.1, found 470.0. HPLC $R_t$=2.81 min in 8 min chromatography, 220 nm, purity 98.49%.

Example 45: Preparation of Compound 45

Scheme 45 - Synthesis of Compound 45

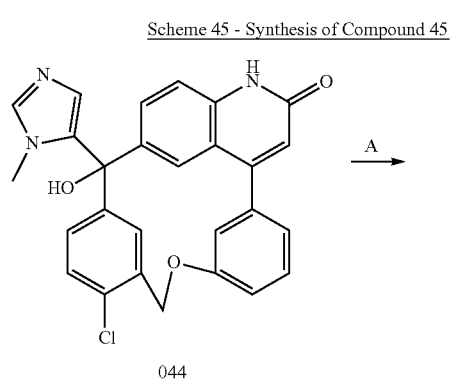

Step A: Preparation of 4⁴-chloro-3-hydroxy-2¹-methyl-3-(1-methyl-1H-imidazol-5-yl)-2¹,2²-dihydro-6-oxa-2(4,6)-quinolina-1,4(1,3)-dibenzenacyclohexaphan-2²-one (045)

A mixture of 044 (350 mg, 744.81 μmol), iodomethane (105.72 mg, 744.81 μmol, 46.37 μL) and BTEAC (84.82 mg, 372.41 μmol) in NaOH (5M in $H_2O$, 10 mL, 50.0 mmol) and THF (20 mL) was stirred at 20° C. for 1 h. Water (50 mL) was added to the mixture and the mixture was extracted with DCM:MeOH=10:1 (50 mL×2). The combined organic phase was washed with brine (100 mL), dried over anhydrous $Na_2SO_4$, filtered and concentrated. The crude was purified by flash chromatography on silica gel (MeOH in DCM=0 to 10%, twice) to give 045 (180 mg, 371.94 μmol, 49.94% yield) as an off-white solid. ¹H NMR (400 MHz, DMSO-$d_6$) δ=8.01 (dd, J=2.4, 8.8 Hz, 1H), 7.66 (d, J=9.2 Hz, 1H), 7.58-7.48 (s, 2H), 7.44-7.22 (m, 3H), 7.14-6.98 (m, 4H), 6.63 (s, 1H), 6.50 (s, 1H), 6.29 (s, 1H), 5.51-5.30 (m, 2H), 3.70 (s, 3H), 3.48 (s, 3H). LCMS $R_t$=1.66 min in 3 min chromatography, 10-80CD, ESI calcd. for $C_{28}H_{23}ClN_3O_3$ [M+H]⁺ 484.1, found 484.0. HPLC $R_t$=2.94 min in 8 min chromatography, 220 nm, purity 100%.

Example 46: Preparation of Compound 46

Scheme 46 - Synthesis of Compound 46

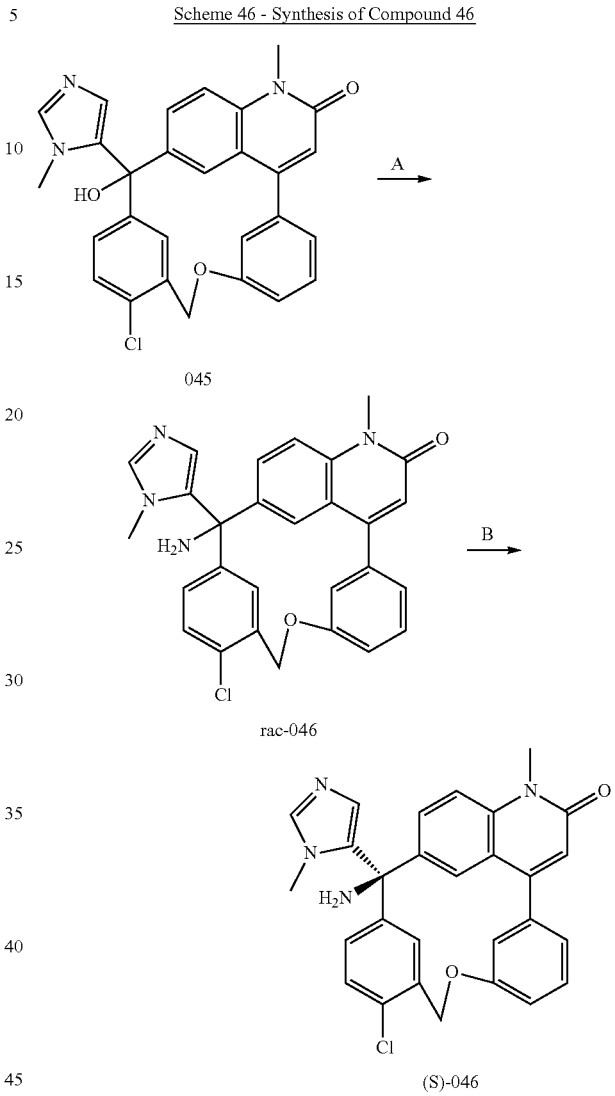

Step A: Preparation of (rac)-3-amino-4⁴-chloro-2¹-methyl-3-(1-methyl-1H-imidazol-5-yl)-2¹,2²-dihydro-6-oxa-2(4,6)-quinolina-1,4(1,3)-dibenzenacyclohexaphan-2²-one (rac-046)

To a mixture of 045 (155.8 mg, 321.94 μmol) in DMI (5 mL) was added $SOCl_2$ (306.41 mg, 2.58 mmol, 186.83 μL) at 0° C. and the mixture was stirred at 25° C. for 12 h. The above solution was added to $NH_3$ in MeOH (7M, 50 mL) at −10° C. and the mixture was stirred at 25° C. for 1 h. The mixture was poured into cold water and the mixture was extracted with EtOAc (50 mL×2). The combined organic phase was washed with brine (50 mL×2), dried over anhydrous $Na_2SO_4$, filtered and concentrated. The crude was purified by flash chromatography on silica gel (MeOH in DCM=0 to 10%, twice) to give rac-046 (60 mg, 124.23 μmol, 38.59% yield) as an off-white solid. ¹H NMR (400 MHz, DMSO-$d_6$) δ=7.97 (d, J=8.8 Hz, 1H), 7.64 (d, J=8.8 Hz, 2H), 7.50 (s, 1H), 7.39-7.28 (m, 2H), 7.15-6.93 (m, 5H), 6.63 (s, 1H), 6.44 (s, 1H), 5.43-5.33 (m, 2H), 3.67 (s, 3H), 3.30 (s, 3H). LCMS $R_t$=1.62 min in 3 min chromatography, 10-80CD, ESI calcd. for $C_{28}H_{24}ClN_4O_2$ [M+H]$^+$ 483.2, found 483.0. HPLC $R_t$=2.86 min in 8 min chromatography, 220 nm, purity 100%.

Step B: Preparation of (S)-3-amino-4⁴-chloro-2¹-methyl-3-(1-methyl-1H-imidazol-5-yl)-2¹,2²-dihydro-6-oxa-2(4,6)-quinolina-1,4(1,3)-dibenzenacyclohexaphan-2²-one ((S)-046)

rac-046 (50 mg, 103.53 μmol) was separated by SFC (column: DAICEL CHIRALPAK AD (250 mm×30 mm, 10 m); mobile phase: [0.1% NH₃H₂O ETOH]; B %: 55%-55%) to give (S)-046 (12.9 mg, 26.71 μmol, 25.80% yield) as an off-white solid. ¹H NMR (400 MHz, DMSO-d₆) δ=8.02 (d, J=8.8 Hz, 1H), 7.71 (s, 1H), 7.64 (d, J=8.8 Hz, 1H), 7.50 (s, 1H), 7.38-7.28 (m, 2H), 7.21-6.93 (m, 5H), 6.63 (s, 1H), 6.45 (s, 1H), 5.48-5.37 (m, 2H), 3.70 (s, 3H), 3.35 (s, 3H). LCMS $R_t$=1.61 min in 3 min chromatography, 10-80CD, ESI calcd. For $C_{28}H_{24}ClN_4O_2$ [M+H]$^+$ 483.2, found 483.1. HPLC $R_t$=2.87 min in 8 min chromatography, 220 nm, purity 100%. Chiral HPLC (S)-046: $R_t$=1.50 min in 2.5 min (ee 99.22%) (AD_ETOH_DEA_40-4ML_5CM), ((R)-046: $R_t$=0.93 min (ee 100%)).

Example 47: Preparation of Compound 47

Scheme 47 - Synthesis of Compound 47

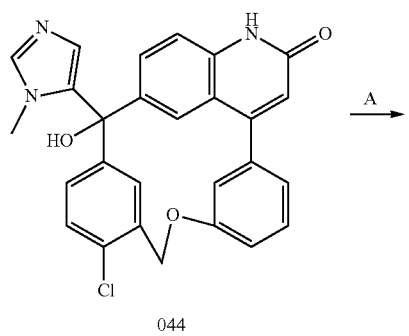

044

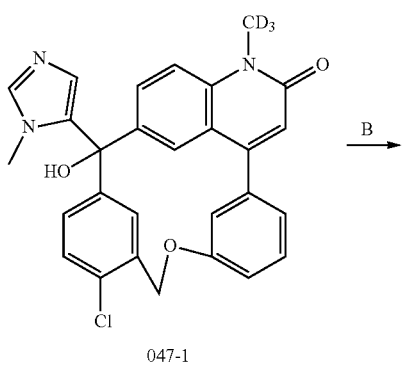

047-1

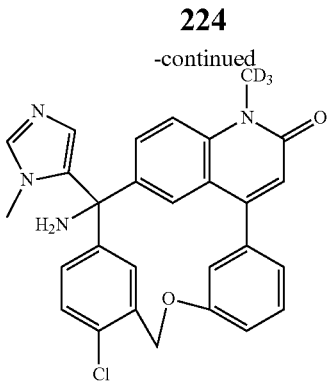

rac-047

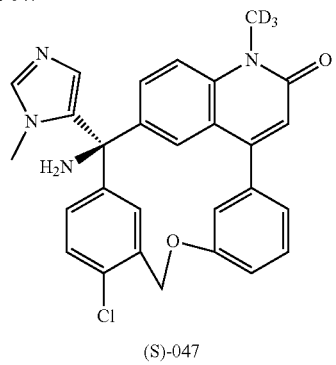

(S)-047

Step A: Preparation of (047-1)

To a mixture of 044 (1 g, 2.13 mmol) in DMF (10 mL) was added Cs₂CO₃ (2.08 g, 6.38 mmol), iodomethane-d₃ (604.11 mg, 4.26 mmol, 259.27 μL) at 25° C. under N₂. The mixture was blended with another batch prepared from 0.5 g, 1 g of 044. The mixture was added into water (50 mL). The aqueous phase was extracted with DCM (500 mL×2). The combined organic phase was washed with brine (800 mL), dried over anhydrous Na₂SO₄, filtered and concentrated under reduced pressure. The crude product was triturated with CH₃CN (100 mL) at 25° C. for 20 min to afford 047-1 (2.2 g, 4.52 mmol, 84.92% yield) as an off-white solid. ¹H NMR (400 MHz, DMSO-d₆) δ=8.10-7.87 (m, 1H), 7.84-7.54 (m, 3H), 7.47-7.27 (m, 2H), 7.23-6.94 (m, 4H), 6.79 (s, 1H), 6.71-6.59 (m, 1H), 6.21 (s, 1H), 5.50-5.31 (m, 2H), 3.51 (s, 3H).

Step B: Preparation of (rac)-3-amino-4⁴-chloro-2¹-(methyl-d₃)-3-(1-methyl-1H-imidazol-5-yl)-2¹,2²-dihydro-6-oxa-2(4,6)-quinolina-1,4(1,3)-dibenzenacyclohexaphan-2²-one (rac-047)

To a solution of 047-1 (2 g, 4.11 mmol) in DMI (10 mL) was added SOCl₂ (4.89 g, 41.07 mmol, 2.98 mL) at 25° C. under N₂. Then the reaction mixture was stirred at 40° C. for 1 h. The above solution was added to NH₃ in MeOH (7M, 50 mL) at −10° C. under N₂. Then the reaction mixture was stirred at −10° C. for 1 h. The mixture was blended with another batch prepared from 830.3 mg of 047-1. The mixture was added into water (30 mL). The aqueous phase was extracted with EtOAc (100 mL×3). The combined organic phase was washed with brine (250 mL), dried over anhydrous Na₂SO₄, filtered and concentrated under reduced pressure. The residue was purified by flash chromatography on silica gel (MeOH in DCM=0 to 20%) to afford rac-047

(1.15 g, 2.37 mmol, 41.07% yield) as an off-white solid. 100 mg (205.77 μmol) of rac-047 was purified by Prep-HPLC (column: Waters Xbridge BEH $C_{18\ 150\times25}$ mm×5 m; mobile phase: [water (0.05% ammonia hydroxide v/v)-MeOH]; B %: 58%-88%, 7.8 min) to give rac-047 (5.4 mg, 11.11 μmol, 5.40% yield) as an off-white solid. $^1$H NMR (400 MHz, DMSO-$d_6$) δ=8.01 (dd, J=2.0, 8.8 Hz, 1H), 7.80-7.58 (m, 3H), 7.42-7.27 (m, 2H), 7.16-7.10 (m, 2H), 7.08-6.97 (m, 3H), 6.63 (s, 1H), 6.52 (s, 1H), 5.49-5.36 (m, 2H), 3.36 (s, 3H). LCMS $R_t$=1.61 min in 3 min chromatography, 10-80CD, ESI calcd. for: $C_{28}H_{21}D_3ClN_4O_2$ [M+H]$^+$ 486.2, found 486.2. HPLC $R_t$=2.89 min in 8 min chromatography, 220 nm, purity 96.59%.

Step C: Preparation of (S)-3-amino-4$^4$-chloro-2$^1$-(methyl-$d_3$)-3-(1-methyl-1H-imidazol-5-yl)-2$^1$,2$^2$-dihydro-6-oxa-2(4,6)-quinolina-1,4(1,3)-dibenzena-cyclohexaphan-2$^2$-one ((S)-047)

rac-047 (1 g, 2.06 mmol) was separated by SFC (column: DAICEL CHIRALPAK AD (250 mm×50 mm, 10 m); mobile phase: [IPA-ACN]; B %: 55%-55%) to afford (S)-047 (332.2 mg, 683.57 μmol, 33.22% yield) as an off-white solid. $^1$H NMR (400 MHz, DMSO-$d_6$) δ=8.02 (dd, J=2.0, 8.8 Hz, 1H), 7.80-7.60 (m, 2H), 7.50 (s, 1H), 7.40-7.29 (m, 2H), 7.21-6.96 (m, 5H), 6.69-6.58 (m, 1H), 6.45 (s, 1H), 5.52-5.34 (m, 2H), 3.35 (s, 3H), 2.91 (s, 2H). LCMS $R_t$=1.61 min in 3 min chromatography, 10-80CD, ESI calcd. for $C_{28}H_{21}D_3ClN_4O_2$ [M+H]$^+$ 486.2, found 486.2. HPLC $R_t$=2.86 min in 8 min chromatography, 220 nm, purity 99.35%. Chiral HPLC (S)-047: $R_t$=1.32 min in 2.5 min (ee 97.10%) (AD_IPA_DEA_40-4ML_5CM), ((R)-047: $R_t$=0.81 min (ee 99.64%)).

Example 48: Preparation of Compound 48

Scheme 48 - Synthesis of Compound 48

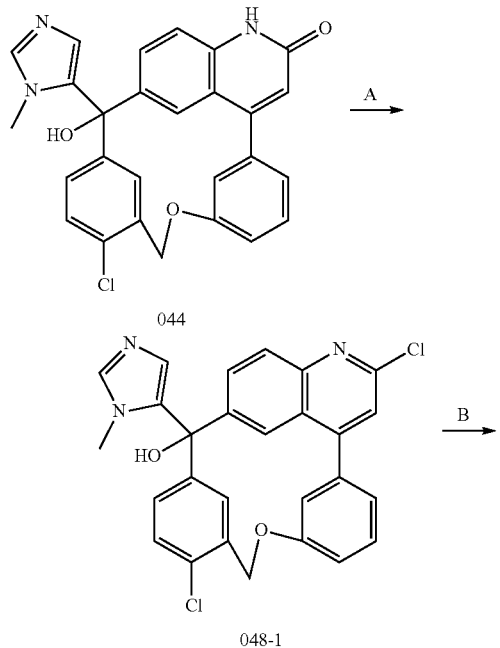

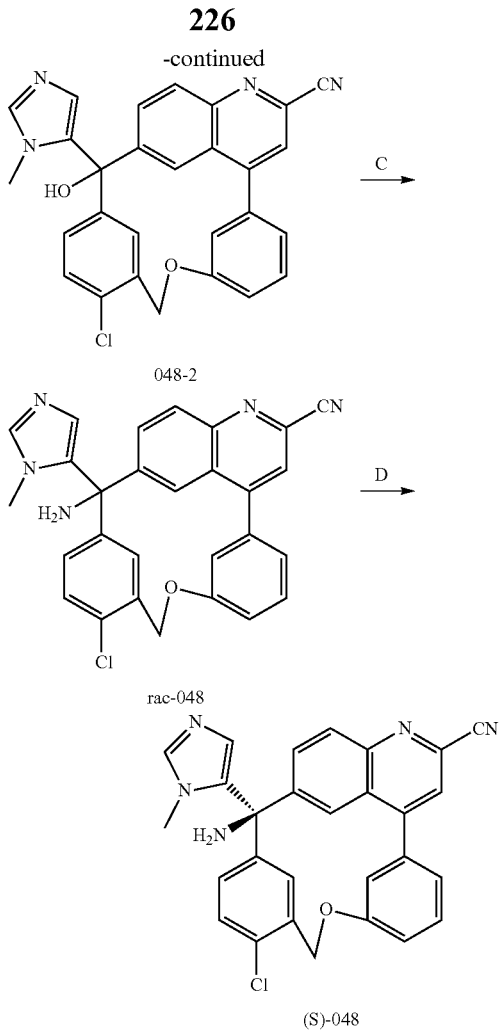

Step A: Preparation of (048-1)

044 (140 mg, 297.92 μmol) was dissolved in POCl$_3$ (4.62 g, 30.13 mmol, 2.80 mL). The resulting mixture was stirred at 100° C. for 0.5 h. The reaction mixture was poured into water (20 mL) slowly and stirred overnight. NaOH solution (1M) was added to the mixture to adjusted pH=7 and the aqueous was cooled to room temperature and extracted with EtOAc (20 mL×2). The combined organic layers were dried over anhydrous Na$_2$SO$_4$, filtered and concentrated. The residue was blended with another batch prepared from 350 mg of 044 and triturated with DCM (10 mL) to afford 048-1 (357 mg, 731.01 μmol, 70.11% yield) as an off-white solid. $^1$H NMR (400 MHz, DMSO-$d_6$) δ=8.19 (dd, J=2.0, 8.8 Hz, 1H), 8.06 (d, J=8.8 Hz, 1H), 7.68 (s, 1H), 7.62 (s, 1H), 7.57 (s, 1H), 7.45-7.36 (m, 2H), 7.33 (s, 1H), 7.30-7.16 (m, 3H), 7.07 (td, J=1.2, 8.4 Hz, 1H), 6.71 (s, 1H), 6.28 (s, 1H), 5.45 (d, J=8.8 Hz, 2H), 3.52 (s, 3H).

Step B: Preparation of (048-2)

To a solution of 048-1 (126 mg, 258.00 μmol) in DMF (1.5 mL) were added Zn(CN)$_2$ (240 mg, 2.04 mmol) under N$_2$. Then Pd(PPh$_3$)$_4$ (59.63 mg, 51.60 μmol) was added to the reaction mixture. The resulting mixture was stirred at 100° C. for 2 h. The reaction was cooled to room temperature then poured into water (15 mL), the aqueous layer was extracted with EtOAc (10 mL×2). The combined organic layers were washed with brine (10 mL), dried over anhydrous $Na_2SO_4$, filtered. The filtrate was concentrated under reduced pressure. The crude product was blended with another batch prepared from 357 mg of 048-1 and purified by flash chromatography on silica gel (MeOH in DCM=0 to 8%) to afford 048-2 (310 mg, 647.28 µmol, 65.45% yield) as an off-white solid. $^1$H NMR (400 MHz, DMSO-$d_6$) δ=8.33-8.18 (m, 2H), 8.08 (s, 1H), 7.70 (s, 1H), 7.58 (s, 1H), 7.46-7.34 (m, 3H), 7.29-7.19 (m, 3H), 7.12-7.05 (m, 1H), 6.81 (s, 1H), 6.28 (s, 1H), 5.46 (d, J=9.2 Hz, 2H), 3.53 (s, 3H).

Step C: Preparation of (rac)-3-amino-4$^4$-chloro-3-(1-methyl-1H-imidazol-5-yl)-6-oxa-2(4,6)-quinolina-1,4(1,3)-dibenzenacyclohexaphane-2$^2$-carbonitrile (rac-048)

To a solution of 048-2 (260 mg, 542.88 µmol) in DMI (3 mL) was added $SOCl_2$ (516.69 mg, 4.34 mmol, 315.06 µL) slowly at 0° C. The reaction mixture was stirred at 50° C. for 1 h. The above mixture was added into $NH_3$ in MeOH (7M, 15 mL) slowly at 0° C. The reaction mixture was stirred at 15° C. for 5 min. Water (20 mL) was added to the reaction mixture and the aqueous layer was extracted with EtOAc (20 mL×3). The combined organic layer were washed with brine (30 mL×2), dried over anhydrous $Na_2SO_4$, filtered. The filtrate was concentrated and purified by flash chromatography on silica gel (MeOH in DCM=0 to 5%) to afford rac-048 (140 mg, 292.92 µmol, 53.96% yield) as a yellow solid. $^1$H NMR (400 MHz, DMSO-$d_6$) δ=8.33 (d, J=8.0 Hz, 1H), 8.20 (d, J=9.2 Hz, 1H), 8.06 (s, 1H), 7.85 (s, 1H), 7.54 (s, 1H), 7.45-7.36 (m, 3H), 7.29 (s, 1H), 7.23 (d, J=7.6 Hz, 1H), 7.15-7.00 (m, 2H), 6.43 (s, 1H), 5.46 (d, J=4.4 Hz, 2H), 3.43 (d, J=3.2 Hz, 3H), 3.06-3.01 (m, 2H). LCMS $R_t$=1.89 min in 1.5 min chromatography, 5-95AB, ESI calcd. for $C_{28}H_{21}ClN_5O$ [M+H]$^+$ 478.1, found 478.0.

Step D: Preparation of (S)-3-amino-4$^4$-chloro-3-(1-methyl-1H-imidazol-5-yl)-6-oxa-2(4,6)-quinolina-1,4(1,3)-dibenzenacyclohexaphane-2$^2$-carbonitrile ((S)-048)

rac-048 (100 mg, 209.23 µmol) was purified by chiral SFC (column: DAICEL CHIRALPAK AD (250 mm×30 mm, 10 m); mobile phase: [0.1% $NH_3H_2O$ EtOH]; B %: 50%-50%, min) to afford (S)-048 (31.2 mg, 65.28 µmol, 31.20% yield) as an off-white solid. $^1$H NMR (400 MHz, DMSO-$d_6$) δ=8.33 (d, J=8.8 Hz, 1H), 8.20 (d, J=9.2 Hz, 1H), 8.06 (s, 1H), 7.86 (s, 1H), 7.54 (s, 1H), 7.45-7.35 (m, 3H), 7.29 (s, 1H), 7.23 (d, J=7.6 Hz, 1H), 7.19-7.02 (m, 2H), 6.43 (s, 1H), 5.52-5.40 (m, 2H), 3.44 (s, 3H), 3.07 (s, 2H). LCMS $R_t$=1.88 min in 3.0 min chromatography, 10-80CD, ESI calcd. for $C_{28}H_{21}ClN_5O$ [M+H]$^+$ 478.1, found 478.2. HPLC $R_t$=3.60 min in 8 min chromatography, 220 nm, purity 100%. Chiral HPLC (S)-048: $R_t$=1.20 min in 2 min (ee 99.70%) (AD_ETOH_DEA_40-4ML_5CM), ((R)-048: $R_t$=0.61 min (ee 100%)).

Example 49: Preparation of Compound 49

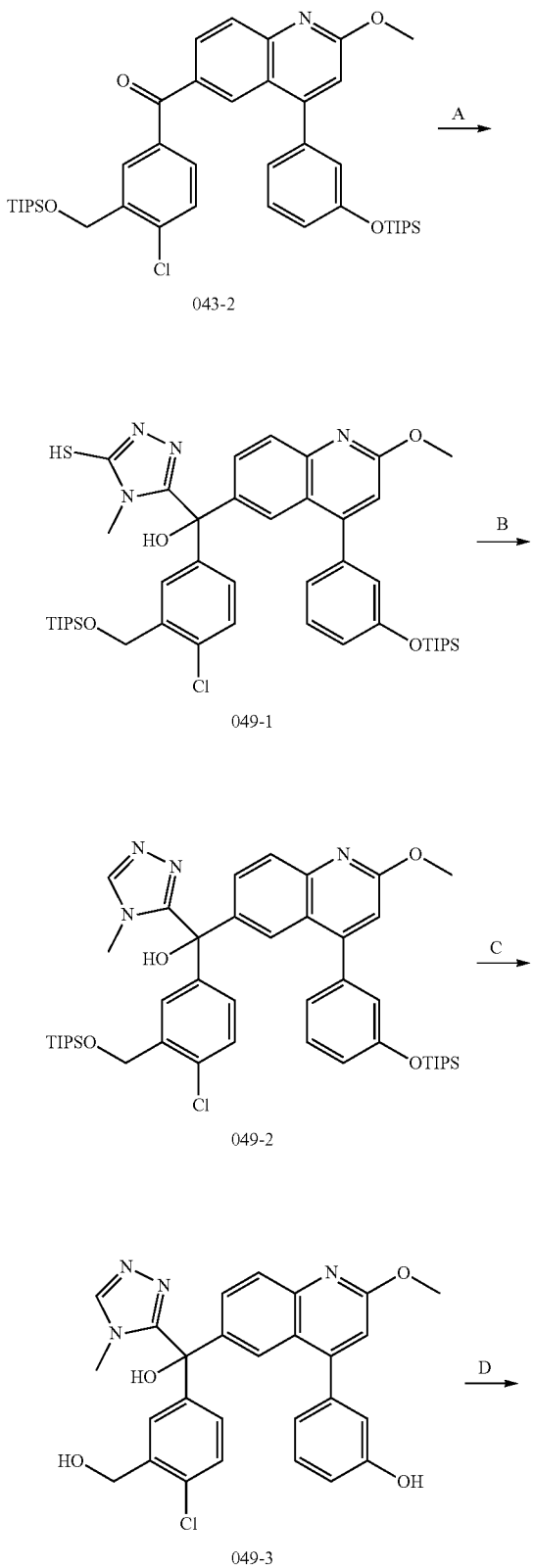

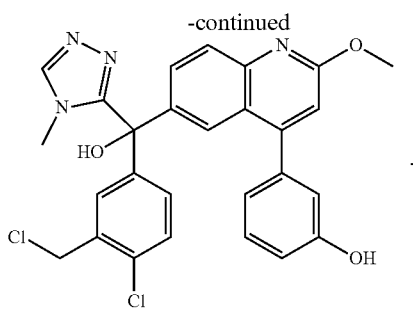

049-4

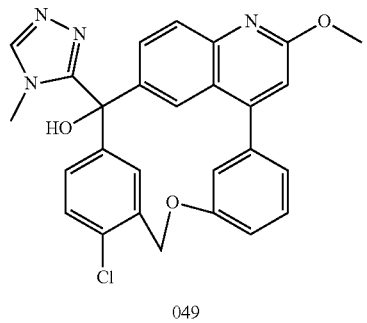 [SMILES: COc1cc2c3cc(ccc3n1)C(O)(c1nncn1C)c1ccc(Cl)c(c1)COc1cccc-2c1]

049

Step A: Preparation of (049-1)

To a mixture of 4-methyl-4H-1,2,4-triazole-3-thiol (94.32 mg, 819.07 μmol) in THF (5 mL) was added dropwise n-BuLi (2.5M in n-hexane, 1.23 mmol, 491.44 μL) at −70° C. during 10 min under $N_2$. Then the above white suspension mixture was added dropwise to a solution of 043-2 (0.2 g, 273.02 μmol) in THF (3 mL) at −70° C. for 10 min and the mixture was stirred −70° C. for 10 min. The reaction mixture was quenched with water (10 mL) and extracted with EtOAc (30 mL×2). The organic layer was washed with brine (10 mL), dried over anhydrous $Na_2SO_4$, filtered and concentrated. The residue was purified by Prep-TLC (EtOAc: petroleum ether=2:1) to give 049-1 (130 mg, 153.36 μmol, 56.17% yield) as a yellow oil. $^1$H NMR (400 MHz, DMSO-$d_6$) δ=13.67 (s, 1H), 7.82 (d, J=8.8 Hz, 1H), 7.63 (s, 1H), 7.64-7.62 (m, 1H), 7.45-7.41 (m, 3H), 7.38-7.36 (m, 1H), 7.10 (s, 1H), 6.98-6.97 (m, 1H), 6.88-6.86 (m, 3H), 4.70 (s, 2H), 4.01 (s, 3H), 3.19 (s, 3H), 1.22-1.20 (m, 3H), 1.04-1.02 (m, 18H), 0.84-0.83 (m, 3H), 0.82-0.80 (m, 18H).

Step B: Preparation of (049-2)

To a solution of 049-1 (0.13 g, 153.36 μmol) in THF (3 mL) and water (1 mL) was added $NaNO_2$ (63.49 mg, 920.14 μmol) and then $HNO_3$ (57.98 mg, 920.14 μmol, 41.41 μL) was added at 25° C. and the mixture was stirred at 25° C. for 12 h. The mixture was adjusted pH 8-9 by NaOH solution (0.5M) and the mixture was extracted with EtOAc (10 mL×2). The organic layer was washed with brine (10 mL), dried over anhydrous $Na_2SO_4$, filtered and concentrated to afford 049-2 (0.125 g, 153.26 μmol, 99.94% yield) as yellow oil. LCMS $R_t$=1.38 min in 1.5 min chromatography, 5-95AB, ESI calcd. for $C_{45}H_{64}ClN_4O_4Si_2$ [M+H]$^+$ 815.4, found 815.4.

Step C: Preparation of (049-3)

To a solution of 049-2 (0.125 g, 153.26 μmol) in THF (4 mL) was added TBAF (1M in THF, 0.2 mL) at 25° C. and the mixture was stirred at 25° C. for 30 min. The mixture was added into water (10 mL). The mixture was extracted with EtOAc (20 mL×2). The organic layer was dried over anhydrous $Na_2SO_4$, filtered and concentrated. The residue was purified by Prep-TLC (EtOAc/petroleum ether=2:1) to give 049-3 (50 mg, 99.41 μmol, 64.87% yield) as a white solid. $^1$H NMR (400 MHz, DMSO-$d_6$) δ=9.69 (s, 1H), 8.48 (s, 1H), 7.81 (d, J=8.4 Hz, 1H), 7.64-7.61 (m, 2H), 7.48 (s, 1H), 7.34-7.28 (m, 3H), 7.08-7.06 (m, 1H), 6.89-6.78 (m, 4H), 5.39-5.35 (m, 1H), 4.51 (d, J=4.0 Hz, 2H), 4.01 (s, 3H), 3.41 (s, 3H). LCMS $R_t$=0.74 min in 1.5 min chromatography, 5-95AB, ESI calcd. for $C_{27}H_{24}ClN_4O_4$ [M+H]$^+$ 503.1, found 503.0.

Step D: Preparation of (049-4)

To a solution of 049-3 (0.03 g, 59.65 μmol) in DCM (2 mL) was added $SOCl_2$ (35.48 mg, 298.24 μmol, 21.64 μL) at 25° C. and the mixture was stirred at 40° C. for 2 h. The solvent was removed under reduced pressure to afford 049-4 (31.1 mg, 59.65 μmol, 100.00% yield) as a white solid. LCMS $R_t$=0.82 min in 1.5 min chromatography, 5-95AB, ESI calcd. for $C_{27}H_{23}Cl_2N_4O_3$ [M+H]$^+$ 521.1, found 521.0.

Step E: Preparation of 4$^4$-chloro-2$^2$-methoxy-3-(4-methyl-4H-1,2,4-triazol-3-yl)-6-oxa-2(4,6)-quinolina-1,4(1,3)-dibenzenacyclohexaphan-3-ol (049)

To a solution of 049-4 (31.1 mg, 59.65 μmol) in DMF (2 mL) was added $K_2CO_3$ (82.44 mg, 596.48 μmol) and the mixture was stirred at 55° C. for 12 h. Water (10 mL) was added to the mixture and extracted with EtOAc (15 mL×2). The organic layer was dried over anhydrous $Na_2SO_4$ and filtered and concentrated. The residue was purified by Prep-TLC (DCM:MeOH=15:1) to give 049 (0.02 g, 41.24 μmol, 69.14% yield) as a white solid. The crude was purified by Prep-HPLC (column: Phenomenex Gemini-NX 80×40 mm×3 m; mobile phase: [water (10 mM $NH_4HCO_3$)-ACN]; B %: 31%-61%, 9.5 min) to give 049 (5.5 mg, 11.34 μmol, 27.50% yield) as a white solid. $^1$H NMR (400 MHz, DMSO-$d_6$) δ=8.45 (s, 1H), 7.92 (dd, J=2.4, 8.8 Hz, 1H), 7.86 (d, J=8.8 Hz, 1H), 7.68-7.66 (m, 1H), 7.47 (d, J=8.0 Hz, 1H), 7.35 (t, J=7.6 Hz, 1H), 7.28-7.20 (m, 3H), 7.11 (d, J=7.6 Hz, 1H), 7.06 (s, 1H), 6.99 (dd, J=2.0, 8.4 Hz, 1H), 5.52-5.49 (m, 1H), 5.48-5.42 (m, 1H), 4.04 (s, 3H), 3.62 (s, 3H). LCMS $R_t$=0.82 min in 1.5 min chromatography, 5-95AB, ESI calcd. for $C_{27}H_{22}ClN_4O_3$ [M+H]$^+$ 485.1, found 485.0. $C_{27}H_{20}ClN_4O_2$[M-OH]$^+$467.1, found 467.0. $C_{24}H_{17}ClNO_3$ [M-$C_3H_4N_3$]$^+$402.1, found 401.9. HPLC $R_t$=3.60 min in 8 min chromatography, 220 nm, purity 100%.

Example 50: Preparation of Compound 50

Scheme 50 - Synthesis of Compound 50

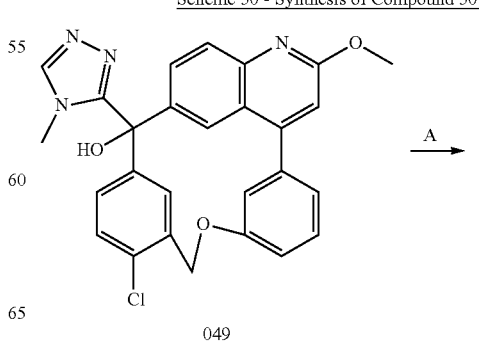

049

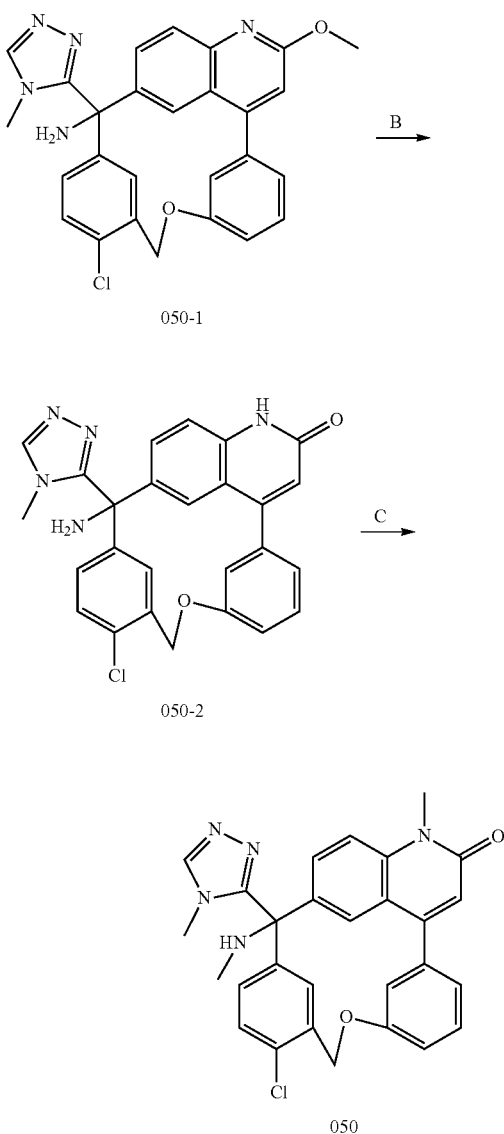

050-1

050-2

050

Step A: Preparation of (050-1)

To a mixture of 049 (600 mg, 1.24 mmol) in DMI (15 mL) was added SOCl$_2$ (1.31 g, 11.03 mmol, 0.8 mL). The mixture was stirred at 20° C. for 4 h. The above mixture was added to NH$_3$ in MeOH (7M, 20 mL) at 0° C. The mixture was stirred at 20° C. for 30 min. The reaction mixture was poured into H$_2$O (50 mL). The aqueous layer was extracted with EtOAc (100 mL×2). The combined organic layers were dried over anhydrous Na$_2$SO$_4$, filtered and the filter cake was washed with EtOAc (20 mL). The combined filtrates were concentrated to dryness. The crude product was purified by flash chromatography on silica gel (MeOH in DCM=0 to 10%) to give 050-1 (220 mg, 454.59 μmol, 36.74% yield) as a white solid. $^1$H NMR (400 MHz, DMSO-d$_6$) δ=8.42 (s, 1H), 8.03 (d, J=8.4 Hz, 1H), 7.90-7.60 (m 2H), 7.43 (d, J=7.6 Hz, 1H), 7.37-7.18 (m, 3H), 7.27 (s, 1H), 7.15-6.95 (m, 3H), 5.56-5.29 (m, 2H), 4.03 (s, 3H), 3.49 (s, 3H).

Step B: Preparation of (050-2)

To a mixture of 050-1 (220 mg, 454.59 μmol) in THF (10 mL) was added HCl (3M in H$_2$O, 5.50 mmol, 1.83 mL). The mixture was stirred at 75° C. for 16 h. The reaction mixture was concentrated to dryness. The crude product was blended with another batch prepared from 0.12 g of 050-1 was triturated with CH$_3$CN (10 mL) at 25° C. for 30 min to give 050-2 (250 mg, 532.00 μmol, 75.50% yield) as a white solid. $^1$H NMR (400 MHz, DMSO-d$_6$) δ=12.17 (s, 1H), 8.73 (s, 1H), 8.35 (s, 1H), 7.70-7.10 (m, 8H), 7.05-6.95 (m, 1H), 6.65 (s, 1H), 5.67-5.31 (m, 2H), 3.33-2.65 (m, 3H).

Step C: Preparation of 4$^4$-chloro-2$^1$-methyl-3-(4-methyl-4H-1,2,4-triazol-3-yl)-3-(methylamino)-2$^1$, 2$^2$-dihydro-6-oxa-2(4,6)-quinolina-1,4(1,3)-dibenzenacyclohexaphan-2$^2$-one (050)

To a mixture of 050-2 (200 mg, 425.60 μmol) and K2CO$_3$ (294.10 mg, 2.13 mmol) in DMF (10 mL) was added iodomethane (302.05 mg, 2.13 mmol, 132.48 μL). The mixture was stirred at 20° C. for 3 h. The reaction mixture was added into H$_2$O (50 mL). The aqueous layer was extracted with EtOAc (100 mL×2). The combined organic layers were dried over anhydrous Na$_2$SO$_4$, filtered and the filter cake was washed with EtOAc (20 mL). The combined filtrates were blended with another batch prepared from 0.05 g of 050-2 was concentrated to dryness. The crude product was purified by flash chromatography on silica gel (MeOH in DCM=0 to 10%) to give 050 (30 mg, 60.24 μmol, 11.32% yield) as a white solid. 30 mg (60.24 mol) of 050 was purified by Prep-HPLC (column: Welch Xtimate C$_{18\ 150\times25}$ mm×5 m; mobile phase: [water (0.05% ammonia hydroxide v/v)-MeOH]; B %: 67%-97%, 7.8 min) to give 050 (6.9 mg, 13.86 μmol, 23.00% yield) as a white solid. $^1$H NMR (400 MHz, DMSO-d$_6$) δ=8.30 (s, 1H), 7.91 (dd, J=2.4, 9.2 Hz, 1H), 7.69-7.39 (m, 4H), 7.37-7.23 (m, 2H), 7.19 (s, 1H), 7.08 (d, J=7.6 Hz, 1H), 6.97 (d, J=8.0 Hz, 1H), 6.63 (s, 1H), 5.45-5.31 (m, 2H), 3.70 (s, 3H), 3.48 (s, 3H), 3.37 (br s, 1H), 2.05 (s, 3H) LCMS R$_t$=0.73 min in 1.5 min chromatography, 5-95AB, ESI calcd. for C$_{28}$H$_{25}$ClN$_5$O$_2$ [M+H]$^+$ 498.2, found 498.2. C$_{27}$H$_{20}$ClN$_4$O$_2$+[M-CH$_3$NH]+467.1, found 467.1. HPLC R$_t$=5.96 min in 15 min chromatography, 220 nm, purity 98.16%.

Example 51: Preparation of Compound 51

Scheme 51 - Synthesis of Compound 51

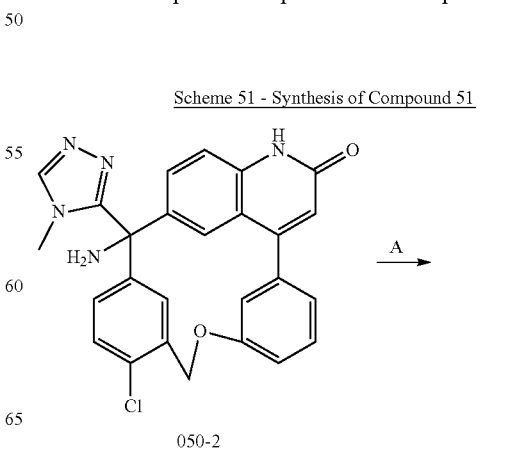

050-2

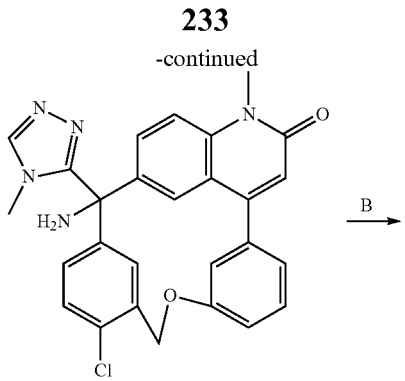

rac-051

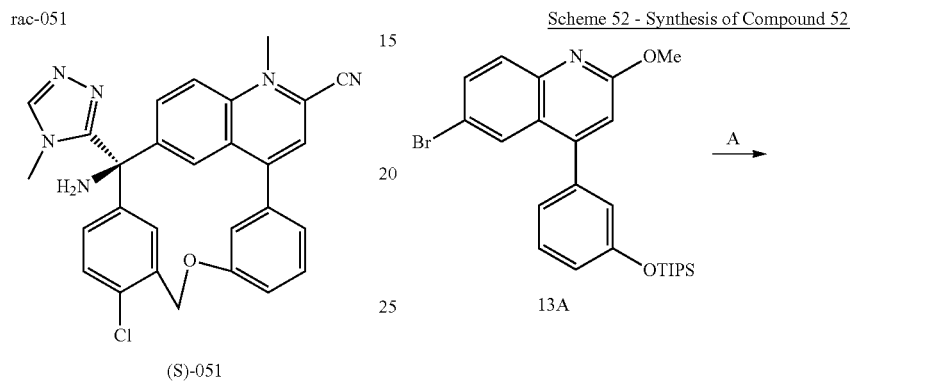

(S)-051

Step A: Preparation of (rac)-3-amino-4⁴-chloro-2¹-methyl-3-(4-methyl-4H-1,2,4-triazol-3-yl)-2¹,2²-dihydro-6-oxa-2(4,6)-quinolina-1,4(1,3)-dibenzena-cyclohexaphan-2²-one (rac-051)

To a mixture of 050-2 (200 mg, 425.60 μmol) and K2CO₃ (294.10 mg, 2.13 mmol) in DMF (10 mL) was added iodomethane (302.05 mg, 2.13 mmol, 132.48 μL). The mixture was stirred at 20° C. for 3 h. The reaction mixture was added into H₂O (50 mL). The aqueous layer was extracted with EtOAc (100 mL×2). The combined organic layers were dried over anhydrous Na₂SO₄, filtered and the filter cake was washed with EtOAc (20 mL). The combined filtrates were blended with another batch prepared from 0.05 g of 050-2 was concentrated to dryness. The crude product was purified by flash chromatography on silica gel (MeOH in DCM=0 to 10%) to give rac-051 (90 mg, 185.97 μmol, 34.96% yield) as a white solid. 1H NMR (400 MHz, DMSO-d₆) δ=8.40 (s, 1H), 8.03 (d, J=7.6 Hz, 1H), 7.64 (d, J=8.8 Hz, 2H), 7.33 (s, 1H), 7.41 (d, J=8.4 Hz, 1H), 7.31-7.20 (m, 1H), 7.22 (s, 1H), 7.07-6.96 (m, 3H), 6.29 (s, 1H), 5.49-5.37 (m, 2H), 3.70 (s, 3H), 3.48 (s, 3H), 3.20 (s, 2H).

Step B: Preparation of (S)-3-amino-4⁴-chloro-2¹-methyl-3-(4-methyl-4H-1,2,4-triazol-3-yl)-2¹,2²-dihydro-6-oxa-2(4,6)-quinolina-1,4(1,3)-dibenzena-cyclohexaphan-2²-one ((S)-051)

rac-051 (0.09 g, 185.97 μmol) was purified by SFC (column: DAICEL CHIRALPAK AD (250 mm×30 mm, 10 m); mobile phase: [0.1% NH₃H₂O IPA]; B %: 45%-45%, min) to afford (S)-051 (25.5 mg, 52.69 μmol, 28.33% yield) as an off-white solid. ¹H NMR (400 MHz, DMSO-d₆) δ=8.37 (s, 1H), 7.94 (dd, J=2.0, 8.8 Hz, 1H), 7.74 (s, 1H), 7.62 (d, J=8.8 Hz, 1H), 7.41 (d, J=8.4 Hz, 1H), 7.36-7.30 (m, 1H), 7.25-7.10 (m, 3H), 7.08-6.97 (m, 2H), 6.63 (s, 1H), 5.44 (s, 2H), 3.70 (s, 3H), 3.40 (s, 3H). LCMS R$_t$=1.51 min in 3 min chromatography, 10-80CD, ESI calcd. for C₂₇H₂₀ClN₄O₂ [M-NH₂]⁺ 467.1, found 467.1. C₂₇H₂₃ClN₅O₂ [M+H]⁺ 484.2, found 484.1. HPLC R$_t$=2.59 min in 8 min chromatography, 220 nm, purity 100%. Chiral HPLC (S)-051: R$_t$=1.25 min in 2.5 min (ee 99.42%) (AD_I-PA_DEA_40-4ML_5CM), ((R)-051: R$_t$=0.94 min (ee 100%)).

Example 52: Preparation of Compound 52

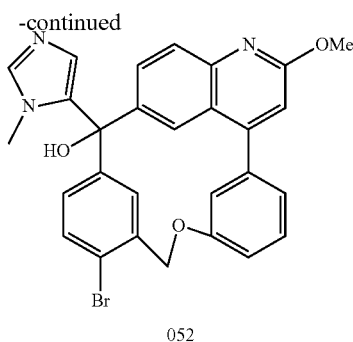

052

Step A: Preparation of (052-1)

To a solution of 13A (10 g, 20.55 mmol) in THF (100 mL) was added n-BuLi (2.5M in n-hexane, 22.61 mmol, 9.04 mL) and the mixture was stirred at −70° C. under $N_2$ for 0.5 h. A solution of 8A (9.00 g, 20.91 mmol) in THF (10 mL) was added to the above solution and the mixture was stirred at −70° C. for 0.5 h. Water (150 mL) was added to the mixture and the mixture was extracted with EtOAc (150 mL). The organic phase was washed with brine (150 mL), dried over anhydrous $Na_2SO_4$, filtered and concentrated. The mixture was blended with another batch prepared from 18 g of 6-bromo-2-methoxy-4-(3-((triisopropylsilyl)oxy) phenyl)quinoline. The crude was purified by flash chromatography on silica gel (EtOAc in petroleum ether=0 to 5%) to give 052-1 (40 g, 51.48 mmol, 83.50% yield) as a yellow oil. $^1$H NMR (400 MHz, $CDCl_3$) δ=8.28 (s, 1H), 8.09-7.95 (m, 3H), 7.62-7.54 (m, 2H), 7.35-7.29 (m, 1H), 7.09-7.04 (m, 1H), 7.00-6.95 (m, 2H), 6.92 (s, 1H), 4.85 (s, 2H), 4.16 (s, 3H), 1.28-1.21 (m, 3H), 1.16-1.13 (m, 3H), 1.11-1.07 (m, 18H), 1.04-1.01 (m, 18H).

Step B: Preparation of (052-2)

To a solution of 1-methyl-1H-imidazole (1.16 g, 14.16 mmol, 1.13 mL) in THF (50 mL) was added n-BuLi (2.5M in n-hexane, 14.16 mmol, 5.66 mL) and the mixture was stirred at −70° C. under $N_2$ for 20 min. Then $Et_3SiCl$ (2.13 g, 14.16 mmol, 2.41 mL) in THF (10 mL) was added to the above mixture and the mixture was stirred at −70° C. for 20 min. Then n-BuLi (2.5M in n-hexane, 14.16 mmol, 5.66 mL) was added to the above mixture and the mixture was stirred at −70° C. for 20 min. Then 052-1 (10 g, 12.87 mmol) in THF (40 mL) was added to the above mixture and the mixture was stirred at −70° C. for 20 min. Water (500 mL) was added to the mixture and the mixture was extracted with EtOAc (500 mL). The organic phase was washed with brine (250 mL), dried over anhydrous $Na_2SO_4$, filtered and concentrated. The mixture was blended with another batch prepared from 30 g of 052-1. The crude was purified by flash chromatography on silica gel (MeOH in DCM=0 to 10%) to give 052-2 (34 g, 39.58 mmol, 76.88% yield) as a light yellow solid. $^1$H NMR (400 MHz, $CDCl_3$) δ=7.70-7.63 (m, 2H), 7.36-7.32 (m, 1H), 7.30-7.25 (m, 2H), 7.11-7.04 (m, 3H), 6.81-6.76 (m, 2H), 6.75-6.71 (m, 1H), 6.69 (s, 1H), 6.14 (s, 1H), 4.63-4.54 (m, 2H), 3.96 (s, 3H), 3.18 (s, 3H), 1.13-1.06 (m, 3H), 0.96-0.92 (m, 18H), 0.89-0.84 (m, 3H), 0.80-0.77 (m, 18H).

Step C: Preparation of (052-3)

A mixture of 052-2 (26.5 g, 30.85 mmol) and TBAF (1M in THF, 46.27 mmol, 46.27 mL) in THF (250 mL) was stirred at 25° C. for 20 min. Water (500 mL) was added to the mixture and the mixture was extracted with EtOAc (500 mL). The organic phase was washed with brine (500 mL), dried over anhydrous $Na_2SO_4$, filtered and concentrated. The crude was purified by triturated from EtOAc: petroleum ether=1:5 (150 mL) to give 052-3 (16 g, 29.28 mmol, 94.93% yield) as an off-white solid. $^1$H NMR (400 MHz, DMSO-$d_6$) δ=9.69 (s, 1H), 7.81 (d, J=8.8 Hz, 1H), 7.74-7.68 (m, 1H), 7.64-7.54 (m, 2H), 7.53-7.44 (m, 2H), 7.29-7.21 (m, 1H), 7.04-6.96 (m, 1H), 6.91-6.84 (m, 3H), 6.83-6.75 (m, 2H), 6.05 (s, 1H), 5.42-5.35 (m, 1H), 4.52-4.41 (m, 2H), 4.03-3.98 (m, 3H), 3.35 (s, 3H). LCMS $R_t$=0.80 min in 1.5 min chromatography, 5-95AB, ESI calcd. for $C_{28}H_{25}BrN_3O_4$ [M+H]$^+$ 546.1, found 545.9.

Step D: Preparation of 4$^4$-bromo-2$^2$-methoxy-3-(1-methyl-1H-imidazol-5-yl)-6-oxa-2(4,6)-quinolina-1,4(1,3)-dibenzenacyclohexaphan-3-ol (052)

To a solution of 052-3 (5.7 g, 10.43 mmol) in DMF (85 mL) was added $SOCl_2$ (2.48 g, 20.86 mmol, 1.51 mL) and the mixture was stirred at 25° C. for 1 h. To the above solution was added $Cs_2CO_3$ (50.96 g, 156.41 mmol) and the mixture was stirred at 70° C. for 0.5 h. After cooling to room temperature, the mixture was filtered and the filtrate was concentrated. The crude product was blended with another batch prepared from 10.15 g of 052-3 and was triturated from water (150 mL) and filtered. The solid was re-dissolved in toluene (100 mL×2) and concentrated to give 052 (13 g, 24.60 mmol, 84.84% yield) as a light yellow solid. $^1$H NMR (400 MHz, DMSO-$d_6$) δ=8.09-8.01 (m, 1H), 7.92-7.87 (m, 1H), 7.69-7.53 (m, 4H), 7.38-7.34 (m, 1H), 7.26 (s, 1H), 7.19-7.10 (m, 3H), 7.07-7.00 (m, 2H), 6.29 (s, 1H), 5.49-5.37 (m, 2H), 4.05 (s, 3H), 3.50 (s, 3H). LCMS $R_t$=2.00 min in 3.0 min chromatography, 10-80CD, ESI calcd. for $C_{28}H_{23}BrN_3O_3$ [M+H]$^+$ 530.1, found 530.1.

Example 53: Preparation of Compound 53

Scheme 53 - Synthesis of Compound 53

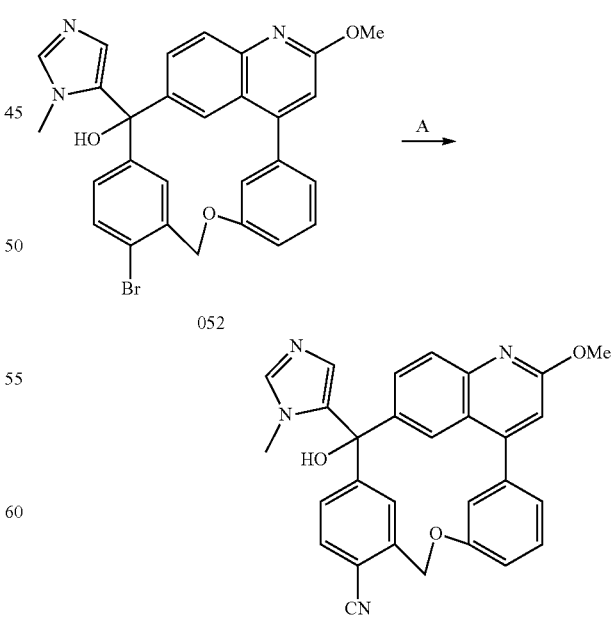

Step A: Preparation of 3-hydroxy-2²-methoxy-3-(1-methyl-1H-imidazol-5-yl)-6-oxa-2(4,6)-quinolina-1,4(1,3)-dibenzenacyclohexaphane-4⁴-carbonitrile (053)

A mixture of 052 (12 g, 22.71 mmol), Zn(CN)$_2$ (27.23 g, 231.89 mmol, 14.72 mL), Pd$_2$(dba)$_3$ (3.12 g, 3.41 mmol), dppf (3.78 g, 6.81 mmol) and Zn (891.01 mg, 13.63 mmol) in DMA (300 mL) was stirred at 120° C. under N$_2$ for 2 h. The mixture was filtered through Celite. The cake was washed with EtOAc (100 mL×2). The filtrate was concentrated. The crude was purified by flash chromatography on silica gel (EtOAc in petroleum ether=50% to 100%) and then triturated with MeOH (50 mL) to give 053 (6.55 g, 13.80 mmol, 60.78% yield) as a yellow solid. $^1$H NMR (400 MHz, DMSO-d$_6$) δ=8.05-8.01 (m, 1H), 7.95-7.90 (m, 1H), 7.85-7.78 (m, 2H), 7.63-7.44 (m, 2H), 7.40-7.32 (m, 2H), 7.18 (s, 1H), 7.12 (d, J=7.6 Hz, 1H), 7.07-7.01 (m, 3H), 6.94 (s, 1H), 5.52 (s, 2H), 4.06 (s, 3H), 3.62 (s, 3H). LCMS R$_t$=1.77 min in 3.0 min chromatography, 10-80CD, ESI calcd. for C$_{29}$H$_{23}$N$_4$O$_3$ [M+H]$^+$ 475.2, found 475.2.

Example 54: Preparation of Compound 54

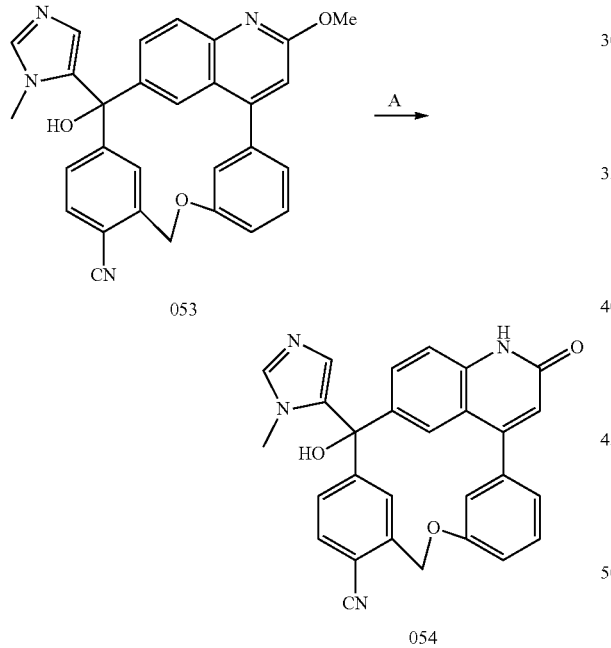

Scheme 54 - Synthesis of Compound 54

Step A: Preparation of 3-hydroxy-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile (054)

To a solution of 053 (0.12 g, 251.82 μmol) in THF (10 mL) was added HCl (4M in H$_2$O, 2.20 mL). The reaction mixture was stirred at 70° C. for 16 h. The mixture was cooled to 20° C. and added into water (20 mL). Saturated NaHCO$_3$ solution was added to adjust to pH=8. The aqueous phase was extracted with DCM (30 mL×2). The combined organic phase was washed with brine (50 mL), dried over anhydrous Na$_2$SO$_4$, filtered and concentrated under reduced pressure to give 054 (0.115 g, 249.74 μmol, 99.17% yield) as a colorless oil. 50 mg (108.58 μmol) of 054 was purified by Prep-HPLC (column: Phenomenex Gemini-NX 80×40 mm×3 m; mobile phase: [water (10 mM NH$_4$HCO$_3$)-ACN]; B %: 26%-56%, 7.8 min) to give 054 (12.4 mg, 26.93 μmol, 24.80% yield) as an off-white solid. $^1$H NMR (400 MHz, DMSO-d$_6$) δ=11.71 (br s, 1H), 7.89 (dd, J=2.0, 8.4 Hz, 1H), 7.81 (d, J=7.8 Hz, 1H), 7.69 (s, 1H), 7.57 (s, 1H), 7.45 (d, J=8.8 Hz, 2H), 7.38-7.31 (m, 1H), 7.10-7.02 (m, 3H), 6.75 (s, 1H), 6.65 (s, 1H), 6.52 (s, 1H), 6.34 (s, 1H), 5.55-5.46 (m, 2H), 3.49 (s, 3H). LCMS R$_t$=1.34 min in 3 min chromatography, 10-80CD, ESI calcd. for: C$_{28}$H$_{21}$N$_4$O$_3$ [M+H]$^+$ 461.2, found 461.1. HPLC R$_t$=2.22 min in 8 min chromatography, 220 nm, purity 100%.

Example 55: Preparation of Compound 55

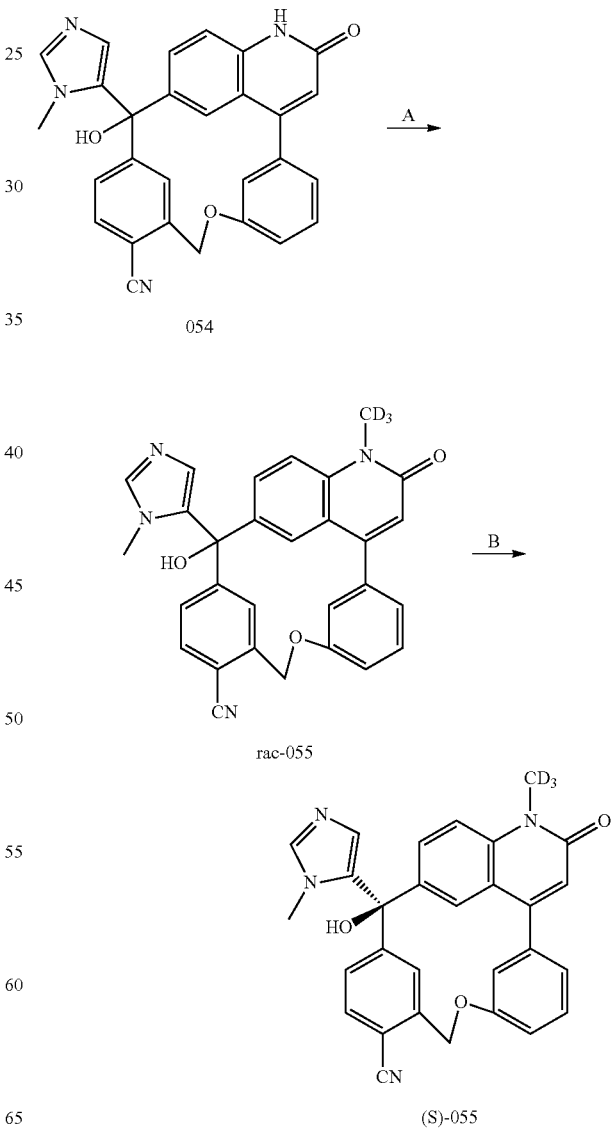

Scheme 55 - Synthesis of Compound 55

Step A: Preparation of (rac)-3-hydroxy-2¹-(methyl-d₃)-3-(1-methyl-1H-imidazol-5-yl)-2²-oxo-2¹,2²-dihydro-6-oxa-2(4,6)-quinolina-1,4(1,3)-dibenzena-cyclohexaphane-4⁴-carbonitrile (rac-055)

A mixture of 054 (800 mg, 1.61 mmol, HCl salt), iodomethane-d₃ (233.36 mg, 1.61 mmol, 100.15 μL) and Cs₂CO₃ (1.57 g, 4.83 mmol) in DMF (30 mL) was stirred at 25° C. for 2 h. Water (100 mL) was added to the mixture and the mixture was filtered. The cake was washed with water (50 mL×3) and dried to give rac-055 (750 mg, 1.57 mmol, 97.56% yield) as an off-white solid. ¹H NMR (400 MHz, DMSO-d₆) δ=8.03 (dd, J=2.4, 8.8 Hz, 1H), 7.85-7.79 (m, 1H), 7.71-7.64 (m, 2H), 7.58-7.43 (m, 2H), 7.39-7.31 (m, 1H), 7.08-7.03 (m, 3H), 6.89-6.83 (m, 1H), 6.72 (s, 1H), 6.64 (s, 1H), 6.32 (s, 1H), 5.53-5.43 (m, 2H), 3.49 (s, 3H). LCMS R$_t$=1.47 min in 3.0 min chromatography, 10-80CD, ESI calcd. for C₂₉H₂₀D₃N₄O₃ [M+H]⁺ 478.2, found 478.2.

Step B: Preparation of (S)-3-hydroxy-2¹-(methyl-d₃)-3-(1-methyl-1H-imidazol-5-yl)-2²-oxo-2¹,2²-dihydro-6-oxa-2(4,6)-quinolina-1,4(1,3)-dibenzena-cyclohexaphane-4⁴-carbonitrile ((S)-055)

rac-055 (100 mg, 209.41 μmol) was separated by SFC (column: DAICEL CHIRALPAK AD (250 mm×30 mm, 10 m); mobile phase: [0.1% NH₃H₂O EtOH]; B %: 45%-45%) to give (S)-055 (37.5 mg, 78.53 μmol, 37.50% yield) as an off-white solid. ¹H NMR (400 MHz, DMSO-d₆) δ=8.03 (dd, J=2.0, 8.8 Hz, 1H), 7.82 (d, J=7.6 Hz, 1H), 7.70-7.63 (m, 2H), 7.59-7.42 (m, 2H), 7.36 (t, J=8.0 Hz, 1H), 7.10-7.00 (m, 3H), 6.86 (s, 1H), 6.72 (s, 1H), 6.64 (s, 1H), 6.32 (s, 1H), 5.56-5.43 (m, 2H), 3.49 (s, 3H). LCMS R$_t$=1.45 min in 3 min chromatography, 10-80CD, ESI calcd. for C₂₉H₂₀D₃N₄O₃ [M+H]⁺ 478.2, found 478.2. HPLC R$_t$=2.44 min in 8 min chromatography, 220 nm, purity 99.13%. Chiral HPLC (S)-055: R$_t$=7.07 min in 10 min (ee 99.12%) (AD-3_EtOH(DEA)_5-40_2.5ML), ((R)-055: R$_t$=5.87 min (ee 100%)).

Example 56: Preparation of Compound 56

Scheme 56 - Synthesis of Compound 56

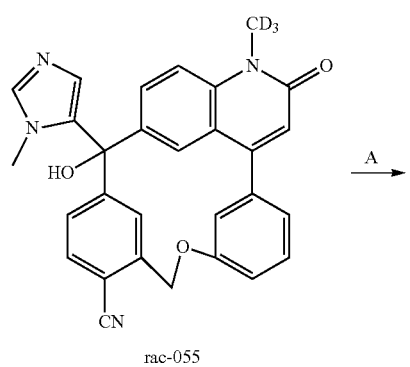

rac-055

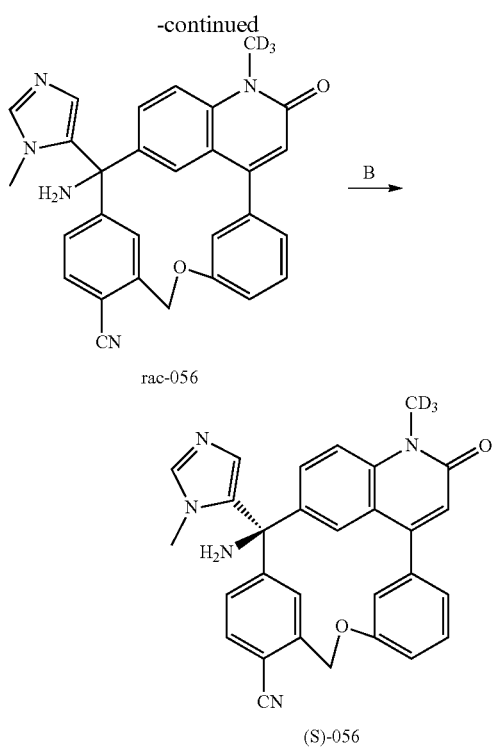

rac-056

(S)-056

Step A: Preparation of (rac)-3-amino-2¹-(methyl-d₃)-3-(1-methyl-1H-imidazol-5-yl)-2²-oxo-2¹,2²-dihydro-6-oxa-2(4,6)-quinolina-1,4(1,3)-dibenzena-cyclohexaphane-4⁴-carbonitrile (rac-056)

A mixture of rac-055 (600 mg, 1.26 mmol) and SOCl₂ (747.41 mg, 6.28 mmol, 455.74 μL) in DMI (10 mL) was stirred at 40° C. for 0.5 h. The above solution was added to NH₃ in MeOH (7M, 20 mL) at 0° C. and the mixture was stirred at 0° C. for 5 min. The crude product was blended with another batch prepared from 368.5 mg of rac-055. The mixture was poured into water (300 mL) and the mixture was filtered to give rac-056 (550 mg, 1.15 mmol, 55.00% yield) as a light yellow solid. ¹H NMR (400 MHz, DMSO-d₆) δ=8.06 (d, J=7.2 Hz, 1H), 7.86-7.75 (m, 2H), 7.66 (d, J=8.8 Hz, 1H), 7.52 (s, 1H), 7.42-7.26 (m, 2H), 7.13 (s, 1H), 7.06-6.99 (m, 2H), 6.85 (s, 1H), 6.63 (s, 1H), 6.45 (s, 1H), 5.54-5.45 (m, 2H), 3.40 (s, 3H), 2.98 (br s, 2H). LCMS R$_t$=1.43 min in 3.0 min chromatography, 10-80CD, ESI calcd. for C₂₉H₂₁D₃N₅O₂ [M+H]⁺ 477.2, found 477.2.

Step B: Preparation of (S)-3-amino-2¹-(methyl-d₃)-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile ((S)-056)

rac-056 (500 mg, 1.05 mmol) was separated by SFC (column: DAICEL CHIRALPAK IG (250 mm×30 mm, 10 m); mobile phase: [0.1% NH₃H₂O IPA]; B %: 60%-60%) to give (S)-056 (200 mg, 419.69 μmol, 40.00% yield) as a yellow solid. 380 mg (797.41 mol) of the product was dissolved with DCM (20 mL), the organic phase was washed with NaOH solution (1M, 20 mL). The aqueous phase was extracted with DCM (20 mL×2). The combined organic phase was washed with brine (30 mL), dried over anhydrous Na₂SO₄, filtered and concentrated under reduced pressure.

The product was lyophilized to afford (S)-056 (338.5 mg, 710.32 μmol, 89.08% yield) as an off-white solid. 1H NMR (400 MHz, DMSO-$d_6$) δ=8.06 (dd, J=2.0, 8.8 Hz, 1H), 7.89-7.72 (m, 2H), 7.66 (d, J=8.8 Hz, 1H), 7.52 (s, 1H), 7.36-7.32 (m, 2H), 7.13 (s, 1H), 7.10-6.96 (m, 2H), 6.85 (s, 1H), 6.63 (s, 1H), 6.45 (s, 1H), 5.57-5.45 (m, 2H), 3.39 (s, 3H), 2.97 (s, 2H). LCMS $R_t$=1.43 min in 3 min chromatography, 10-80CD, ESI calcd. for $C_{29}H_{21}D_3N_5O_2$ [M+H]$^+$ 477.2, found 477.2. HPLC $R_t$=2.34 min in 8 min chromatography, 220 nm, purity 98.45%. Chiral HPLC (S)-056: $R_t$=2.66 min in 4 min (ee 99.28%) (AD_EtOH_DEA_5-40_4ML_4MIN_5CM), ((R)-056: $R_t$=2.21 min (ee 99.00%)).

Example 57: Preparation of Compound 57

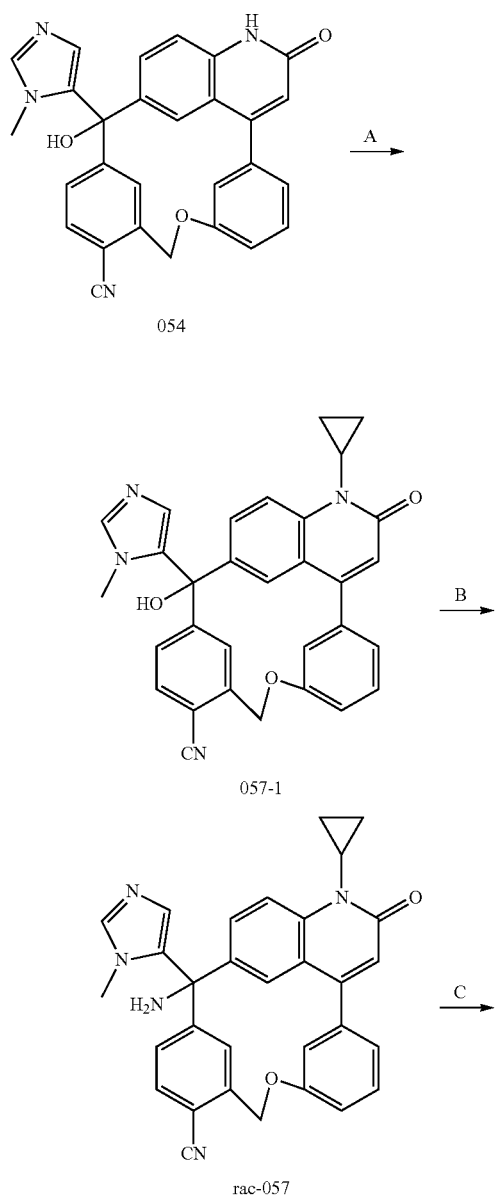

Scheme 57 - Synthesis of Compound 57

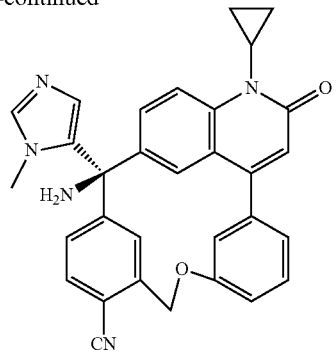

(S)-057

Step A: Preparation of (057-1)

To a mixture of 054 (100 mg, 217.16 μmol), cyclopropylboronic acid (55.96 mg, 651.49 μmol), Na$_2$CO$_3$ (115.08 mg, 1.09 mmol), Cu(OAc)$_2$ (86.78 mg, 477.76 μmol) in DCE (1 mL) was added bipyridine (74.62 mg, 477.76 μmol). The mixture was stirred at 70° C. for 16 h under O2 (15 psi). Water (30 mL) was added to the mixture and the mixture was extracted with DCM (50 mL×3). The combined organic phase was washed with brine (50 mL), dried over anhydrous Na$_2$SO$_4$, filtered and concentrated. The crude product was purified by flash chromatography on silica gel (MeOH in DCM=0 to 5%) to give 057-1 (28.5 mg, 56.94 μmol, 26.22% yield) as a white solid. LCMS $R_t$=1.49 min in 3 min chromatography, 10-80CD, ESI calcd. for $C_{31}H_{25}N_4O_3$ [M+H]$^+$ 501.2, found 501.1.

Step B: Preparation of (rac)-3-amino-2$^1$-cyclopropyl-3-(1-methyl-1H-imidazol-5-yl)-2$^2$-oxo-2$^1$,2$^2$-dihydro-6-oxa-2(4,6)-quinolina-1,4(1,3)-dibenzenacyclohexaphane-4$^4$-carbonitrile (rac-057)

To a solution of 057-1 (135 mg, 269.71 μmol) in DMI (1 mL) was added SOCl$_2$ (256.69 mg, 2.16 mmol, 156.52 μL) at 0° C. The mixture was stirred at 40° C. for 4 h. To NH$_3$ in MeOH (7M, 11.56 mL) was added the above mixture dropwise at 0° C. The reaction mixture was stirred at 25° C. for 1 h. The reaction mixture was added into H$_2$O (50 mL). The aqueous layer was extracted with EtOAc (50 mL×3). The combined organic layers were washed with brine (50 mL×3), dried over anhydrous Na$_2$SO$_4$, filtered and concentrated. The mixture was blended with another batch prepared from 28.5 mg and 126.39 mg of 057-1. The crude product was purified by flash chromatography on silica gel (MeOH in DCM=0 to 4%) to give rac-057 (85 mg, 170.15 μmol, 29.38% yield) as a yellow solid. LCMS $R_t$=1.46 min in 3 min chromatography, 10-80CD, ESI calcd. for $C_{31}H_{26}N_5O_2$ [M+H]$^+$ 500.2, found 500.2.

Step C: Preparation of (S)-3-amino-2$^1$-cyclopropyl-3-(1-methyl-1H-imidazol-5-yl)-2$^2$-oxo-2$^1$,2$^2$-dihydro-6-oxa-2(4,6)-quinolina-1,4(1,3)-dibenzenacyclohexaphane-4$^4$-carbonitrile ((S)-057)

rac-057 (84 mg, 168.15 μmol) was separated by SFC (column: DAICEL CHIRALPAK AD (250 mm×30 mm, 10 m); mobile phase: [0.1% NH$_3$H$_2$O EtOH]; B %: 55%-55%, min) to afford (S)-057 (26.8 mg, 53.65 μmol, 31.90% yield) as an off-white solid. $^1$H NMR (500 MHz, DMSO-$d_6$)

δ=8.07-7.86 (m, 4H), 7.74-7.86 (m, 3H), 7.11 (s, 1H), 7.06-6.92 (m, 2H), 6.82 (s, 1H), 6.57-6.41 (m, 2H), 5.50 (s, 2H), 3.38 (s, 3H), 3.03-2.94 (m, 3H), 1.40-1.32 (m, 2H), 0.91-0.79 (m, 2H). LCMS $R_t$=1.55 min in 3.0 min chromatography, 10-80CD, ESI calcd. for $C_{31}H_{26}N_5O_2$ [M+H]$^+$ 500.2, found 500.2. HPLC $R_t$=2.48 min in 8 min chromatography, 220 nm, purity 100%. Chiral HPLC (S)-057: $R_t$=1.15 min in 2.5 min (ee 99.82%) (AD_EtOH_DEA_40-4ML_5CM), ((R)-057: $R_t$=0.68 min (ee 100%)).

Example 58: Preparation of Compound 58

Synthesis 58 - Synthesis of Compound 58

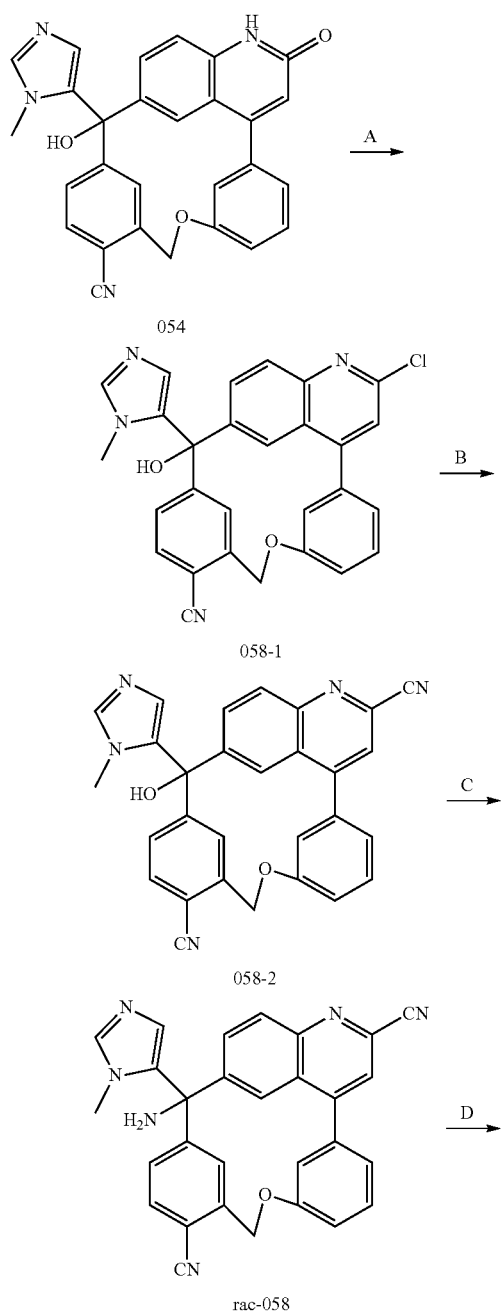

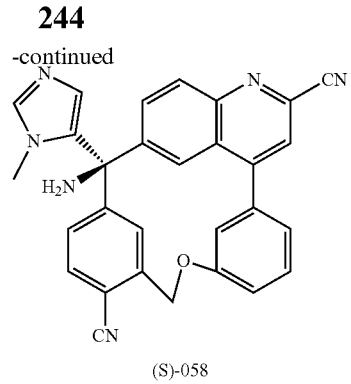

Step A: Preparation of (058-1)

Compound 054 (1.2 g, 2.61 mmol) was mixed with POCl$_3$ (19.80 g, 129.13 mmol, 12.00 mL) at 25° C. The mixture was stirred at 100° C. for 1 h. The mixture was concentrated. To the residue was added NaOH (1M in H$_2$O, 100 mL). The aqueous layer was extracted with EtOAc (200 mL×2). The combined organic layers were washed with brine (50 mL×2), dried over anhydrous Na$_2$SO$_4$, filtered and the filter cake was washed with EtOAc (20 mL). The combined filtrates were concentrated. The crude product was blended with another batch prepared from 0.5 g of 054. The crude product was purified by flash chromatography on silica gel (MeOH in DCM=0 to 10%) to give 058-1 (1.3 g, 2.71 mmol, 73.35% yield) as a yellow solid. LCMS $R_t$=1.79 min in 3.0 min chromatography, 10-80 CD, ESI calcd. for $C_{28}H_{20}ClN_4O_2$ [M+H]$^+$ 479.1, found 479.1.

Step B: Preparation of (058-2)

To a solution of 058-1 (1.2 g, 2.51 mmol) in DMF (10 mL) was added Zn(CN)$_2$ (2.69 g, 22.91 mmol, 1.45 mL) and Pd(PPh$_3$)$_4$ (579.07 mg, 501.12 µmol) in a three-neck bottom flask at 25° C. under N$_2$. The mixture was stirred at 100° C. for 2 h. The mixture was cooled to 25° C. and added into water (50 mL). The aqueous phase was extracted with EtOAc (50 mL×2). The combined organic phase was washed with brine (50 mL×2), dried over anhydrous Na$_2$SO$_4$, filtered and concentrated. The crude product was purified by flash chromatography on silica gel (MeOH in DCM=0 to 3%) to give 058-2 (900 mg, 1.92 mmol, 76.51% yield) as a yellow solid. $^1$H NMR (400 MHz, DMSO-d$_6$) δ=8.33-8.22 (m, 2H), 8.10 (s, 1H), 7.94-7.76 (m, 2H), 7.69 (s, 1H), 7.52-7.39 (m, 2H), 7.28-7.02 (m, 5H), 6.36 (s, 1H), 5.54 (s, 2H), 3.56 (s, 3H).

Step C: Preparation of (rac)-3-amino-3-(1-methyl-1H-imidazol-5-yl)-6-oxa-2(4,6)-quinolina-1,4(1,3)-dibenzenacyclohexaphane-2$^2$ 4$^4$-dicarbonitrile (rac-058)

To a solution of 058-2 (800 mg, 1.70 mmol) in DMI (8 mL) was added SOCl$_2$ (1.01 g, 8.52 mmol, 618.05 µL). The mixture was stirred at 40° C. for 1 h. To NH$_3$ in MeOH (7M, 100 mL) was added the above mixture at −10° C. The mixture was stirred at 25° C. for 30 min. The reaction mixture was poured into H$_2$O (100 mL). The aqueous layer was extracted with EtOAc (150 mL×2). The combined organic layers were washed with brine (50 mL×2), dried over anhydrous Na$_2$SO$_4$, filtered and the filter cake was washed with EtOAc (20 mL). The combined filtrates were concentrated. The crude product was purified by flash chromatography on silica gel (MeOH in DCM=0 to 8%) to give rac-058 (550 mg, 1.17 mmol, 68.89% yield) as a yellow solid. LCMS $R_t$=1.71 min in 3.0 min chromatography, 10-80CD, ESI calcd. for $C_{29}H_{21}N_6O$ [M+H]$^+$ 469.2, found 469.2.

Step D: Preparation of (S)-3-amino-3-(1-methyl-1H-imidazol-5-yl)-6-oxa-2(4,6)-quinolina-1,4(1,3)-dibenzenacyclohexaphane-2$^2$ 4$^4$-dicarbonitrile ((S)-058)

rac-058 (500 mg, 1.07 mmol) was purified by SFC (column: DAICEL CHIRALPAK AD (250 mm×30 mm, 10 m); mobile phase: [0.1% NH$_3$H$_2$O EtOH]; B %: 45%-45%) to give (S)-058 (229.5 mg, 489.85 μmol, 45.90% yield) as an off-white solid. $^1$H NMR (400 MHz, DMSO-d$_6$) δ=8.37 (d, J=8.4 Hz, 1H), 8.23 (d, J=9.2 Hz, 1H), 8.08 (s, 1H), 7.95 (s, 1H), 7.83 (d, J=8.0 Hz, 1H), 7.58 (s, 1H), 7.48-7.19 (m, 4H), 7.18-7.04 (m, 2H), 6.44 (s, 1H), 5.64-5.45 (m, 2H), 3.48 (s, 3H), 3.18 (s, 2H). LCMS $R_t$=1.68 min in 3.0 min chromatography, 10-80CD, ESI calcd. for $C_{29}H_{21}N_6O$ [M+H]$^+$ 469.2, found 469.2. HPLC $R_t$=3.03 min in 8 min chromatography, 220 nm, purity 100%. Chiral HPLC (S)-058: $R_t$=2.44 min in 4 min (ee 99.54%) (AD_ETOH_DEA_5-40_4ML_4MIN_5CM), ((R)-058: $R_t$=1.93 min (ee 99.44%)).

Example 59: Preparation of Compound 59

Scheme 59 - Synthesis of Compound 59

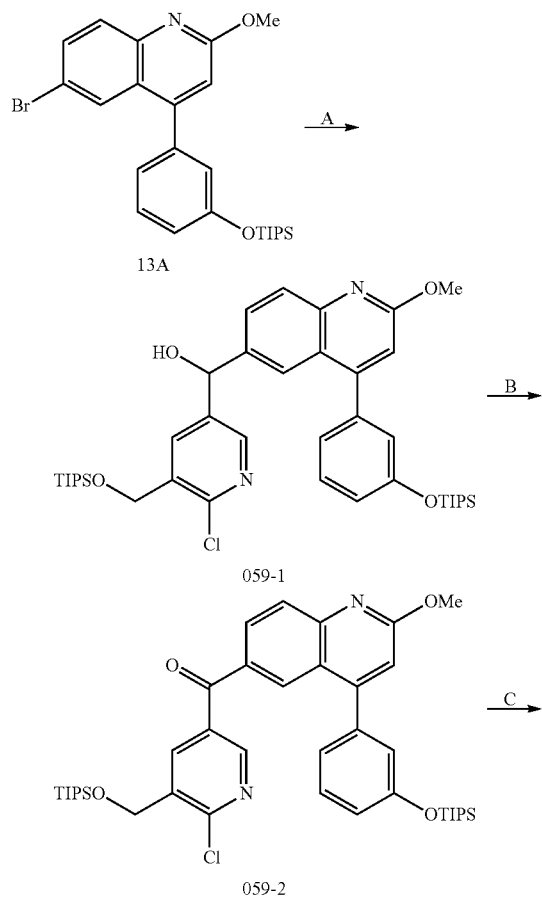

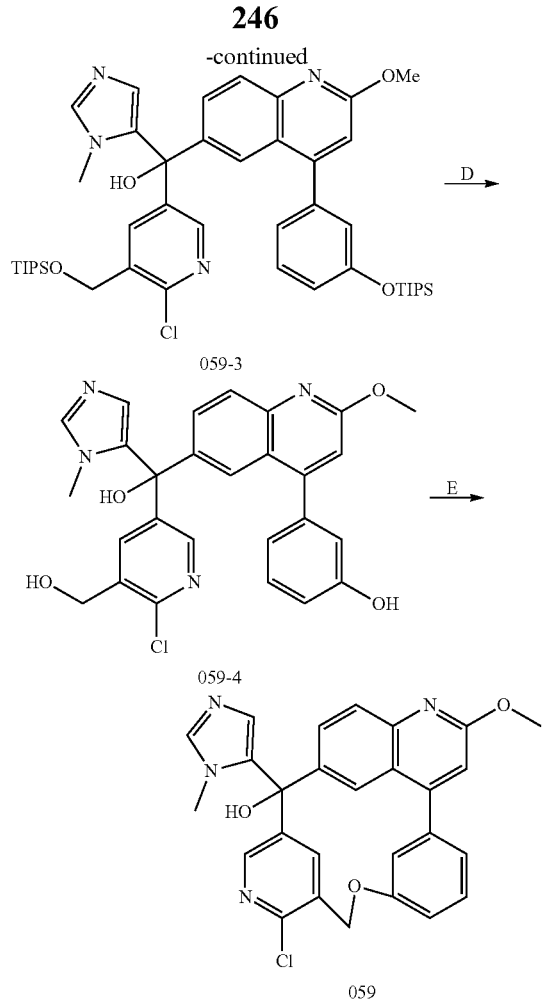

Step A: Preparation of (059-1)

To a solution of 13A (10 g, 20.55 mmol) in THF (100 mL) was added n-BuLi (2.5M in n-hexane, 22.61 mmol, 9.04 mL) at −70° C. during 5 min. To the above solution was added dropwise a solution of 9A (6.74 g, 20.55 mmol) in THF (10 mL) at −70° C. during 5 min and the mixture was stirred at −70° C. for 10 min. The mixture was poured into water (10 mL) and the mixture was extracted with EtOAc (20 mL×3). The organic layer was washed with brine (10 mL), dried over anhydrous Na$_2$SO$_4$, filtered and concentrated. The residue was purified by column chromatography on silica gel (EtOAc in petroleum ether=0 to 50%) to give 059-1 (6 g, 8.16 mmol, 39.69% yield) as yellow oil. $^1$H NMR (400 MHz, CDCl$_3$) δ=8.34 (s, 1H), 7.88 (d, J=8.4 Hz, 1H), 7.80-7.75 (m, 2H), 7.53 (d, J=7.2 Hz, 1H), 7.34 (t, J=7.6 Hz, 1H), 7.04-6.96 (m, 3H), 6.86 (s, 1H), 5.94 (s, 1H), 4.76 (s, 2H), 4.11 (s, 3H), 1.35-1.20 (m, 3H), 1.15-1.10 (m, 18H), 1.10-0.95 (m, 18H), 0.90-0.80 (m, 3H).

Step B: Preparation of (059-2)

To a mixture of 059-1 (5.5 g, 7.48 mmol) in DCM (100 mL) was added MnO$_2$ (13.00 g, 149.55 mmol) at 25° C. and the mixture was stirred at 40° C. for 16 h. The mixture was filtered and the filtrate was concentrated to give 059-2 (5 g, 6.82 mmol, 91.18% yield) as yellow oil. $^1$H NMR (400 MHz, CDCl$_3$) δ=8.64 (s, 1H), 8.39 (s, 1H), 8.30 (s, 1H), 8.03-7.97 (m, 2H), 7.40-7.32 (m, 1H), 7.15-7.05 (m, 1H), 6.99-6.92 (m, 3H), 4.88 (s, 2H), 4.16 (s, 3H), 1.29-1.12 (m, 6H), 1.10-1.00 (m, 36H).

Step C: Preparation of (059-3)

To a solution of 1-methyl-1H-imidazole (551.59 mg, 6.72 mmol, 535.53 µL) in THF (30 mL) was added n-BuLi (2.5M in n-hexane, 6.72 mmol, 2.69 mL) in THF (4 mL) at −70° C. and the mixture was stirred at −70° C. for 20 min. Et$_3$SiCl (1.01 g, 6.72 mmol, 1.14 mL) in THF (4 mL) was added to the above mixture at −70° C. and the mixture was stirred at −70° C. for 20 min. Then n-BuLi (2.5M in n-hexane, 6.72 mmol, 2.69 mL) was added to the above mixture at −70° C. and the mixture was stirred at −70° C. for 20 min. Then a solution of 059-2 (4.48 g, 6.11 mmol) in THF (20 mL) was added to the above mixture at −70° C. and the mixture was stirred at −70° C. for 20 min. The reaction mixture was poured into saturated NH$_4$Cl aqueous (100 mL). The aqueous layer was extracted with EtOAc (50 mL×3). The organic layer was washed with brine (30 mL), dried over anhydrous Na$_2$SO$_4$, filtered and concentrated to give 059-3 (4.98 g, 6.11 mmol, 100.00% yield) as a yellow oil, which was used in next step without further purification.

Step D: Preparation of (059-4)

To a solution of 059-3 (4.4 g, 5.39 mmol) in THF (60 mL) was added TBAF (1M in THF, 5.39 mmol, 5.39 mL) at 25° C. and the mixture was stirred at 25° C. for 4 h. Water (30 mL) was added to the mixture and the mixture was extracted with EtOAc (50 mL×3). The organic layer was dried over anhydrous Na$_2$SO$_4$, filtered and concentrated. The residue was purified by column chromatography on silica gel (MeOH in DCM=0 to 15%) to give 059-4 (1.5 g, 2.98 mmol, 55.29% yield) as a pale-yellow solid. 20 mg (39.77 µmol) of 059-4 was further purified by Prep-HPLC (column: Phenomenex Gemini-NX 80×40 mm×3 m; mobile phase: [water (10 mM NH$_4$HCO$_3$)-ACN]; B %: 24%-54%, 9.5 min) to give 059-4 (13.7 mg, 27.24 µmol, 68.50% yield) as a white solid. $^1$H NMR (400 MHz, DMSO-d$_6$) δ=9.41 (s, 1H), 8.11 (d, J=2.8 Hz, 1H), 7.85-7.81 (m, 2H), 7.67 (d, J=2.4 Hz, 1H), 7.61-7.59 (m, 2H), 7.27-7.23 (m, 1H), 6.88-6.79 (m, 5H), 6.12 (s, 1H), 5.28 (br s, 1H), 4.52-4.50 (m, 2H), 4.04 (s, 3H), 3.36 (s, 3H). LCMS R$_t$=1.49 min in 3 min chromatography, 10-80CD, ESI calcd. for C$_{27}$H$_{24}$ClN$_4$O$_4$ [M+H]$^+$ 503.1, found 503.1. HPLC R$_t$=2.55 min in 8 min chromatography, 220 nm, purity 98.65%.

Step E: Preparation of 4$^6$-chloro-2$^2$-methoxy-3-(1-methyl-1H-imidazol-5-yl)-6-oxa-2(4,6)-quinolina-4(3,5)-pyridina-1(1,3)-benzenacyclohexaphan-3-ol (059)

To a solution of 059-4 (1.3 g, 2.58 mmol) in DMF (40 mL) was added SOCl$_2$ (1.23 g, 10.34 mmol, 750.02 µL) at 25° C. and the mixture was stirred at 25° C. for 1 h. To the above mixture was added Cs$_2$CO$_3$ (16.87 g, 51.78 mmol) at 25° C. and the mixture was stirred at 70° C. for 1 h. After cooling to room temperature, the mixture was filtered and the filtrate was concentrated. Water (60 mL) was added to the residue and extracted with EtOAc (150 mL×3). The organic layer was washed with brine (100 mL), dried over anhydrous Na$_2$SO$_4$, filtered and concentrated to give 059 (1.0 g, 2.47 mmol, 95.57% yield) as a gray solid. 20 mg (41.24 µmol) of the product was further purified by Prep-HPLC (column: Phenomenex Gemini-NX 80×40 mm×3 m; mobile phase: [water (10 mM NH$_4$HCO$_3$)-ACN]; B %: 24%-54%, 9.5 min) to give 059 (0.01 g, 20.62 µmol, 50.00% yield) as a white solid. $^1$H NMR (400 MHz, DMSO-d$_6$) δ=8.20-8.10 (m, 1H), 8.06-8.03 (m, 1H), 7.95-7.92 (m, 1H), 7.64 (s, 1H), 7.40-7.36 (m, 1H), 7.29 (s, 1H), 7.15-7.01 (m, 6H), 6.27 (br s, 1H), 5.47 (br s, 2H), 4.04 (s, 3H), 3.59 (s, 3H). LCMS R$_t$=1.80 min in 3 min chromatography, 10-80CD, ESI calcd. for C$_{27}$H$_{22}$ClN$_4$O$_3$ [M+H]$^+$ 485.1, found 485.2. HPLC R$_t$=3.34 min in 8 min chromatography, 220 nm, purity 96.82%.

Example 60: Preparation of Compound 60

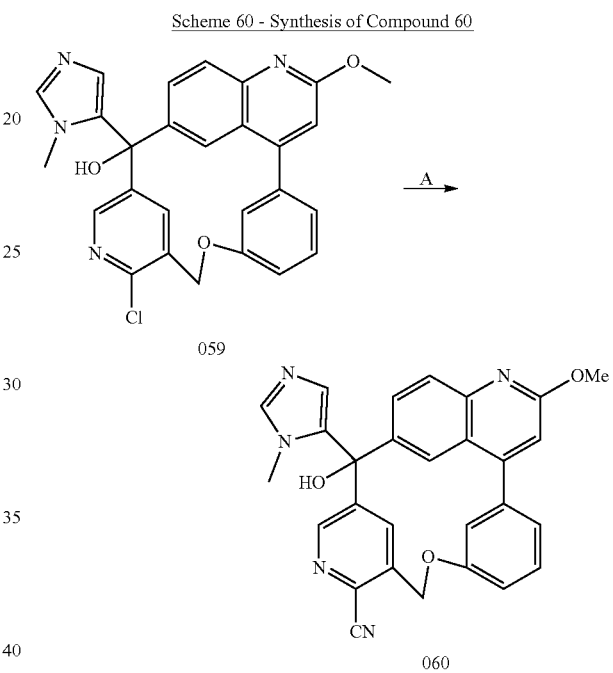

Scheme 60 - Synthesis of Compound 60

Step A: Preparation of 3-hydroxy-2$^2$-methoxy-3-(1-methyl-1H-imidazol-5-yl)-6-oxa-2(4,6)-quinolina-4(3,5)-pyridina-1(1,3)-benzenacyclohexaphane-4$^6$-carbonitrile (060)

To a mixture of 059 (0.85 g, 1.75 mmol) and Zn(CN)$_2$ (0.99 g, 8.43 mmol) in DMA (15 mL) were added Zn (68.77 mg, 1.05 mmol) and Pd$_2$(dba)$_3$ (160.51 mg, 175.28 µmol) and DPPF (194.35 mg, 350.56 µmol). The mixture was stirred 120° C. for 1 h under N$_2$. The reaction mixture was diluted with EtOAc (50 mL) and washed with water (50 mL×3). The organic layer was separated, dried over anhydrous Na$_2$SO$_4$, filtered and concentrated. The crude was purified by flash column chromatography on silica gel (MeOH in DCM=0 to 7%) to give 060 (0.62 g, 1.30 mmol, 74.39% yield) as a yellow solid. 20 mg (63.09 µmol) of the product was further purified by Prep-HPLC (column: Phenomenex Gemini-NX 80×40 mm×3 m; mobile phase: [water (10 mM NH$_4$HCO$_3$)-ACN]; B %: 35%-65%, 7.8 min) to give 060 (14.7 mg, 30.92 mol, 49.00% yield) as a white solid. $^1$H NMR (400 MHz, DMSO-d$_6$) δ=8.62 (s, 1H), 8.24-8.22 (m, 1H), 8.07-8.04 (m, 1H), 7.95-7.92 (m, 1H), 7.67-7.65 (m, 1H), 7.44-7.39 (m, 1H), 7.17-7.07 (m, 4H), 6.98-6.93 (m, 2H), 6.41 (br s, 1H), 5.63-5.55 (m, 2H), 4.07

(s, 3H), 3.58 (s, 3H). LCMS $R_t$=1.75 min in 3 min chromatography, 10-80CD, ESI calcd. for: $C_{28}H_{22}N_5O_3$ [M+H]$^+$ 476.1, found 476.1. HPLC $R_t$=3.15 min in 8 min chromatography, 220 nm, purity 99.25%.

Example 61: Preparation of Compound 61

Scheme 61 - Synthesis of Compound 61

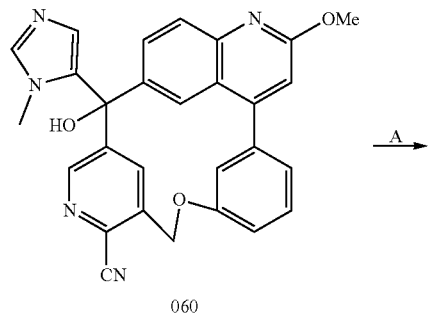

060

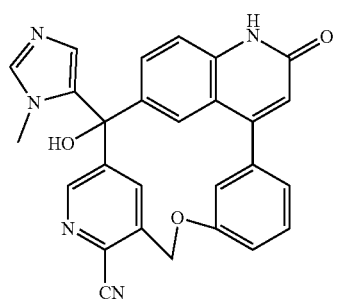

061-1

Step A: Preparation of (061-1)

To a solution of 060 (0.59 g, 1.24 mmol) in THF (6 mL) was added HCl (4M in H$_2$O, 4.65 mL). The reaction mixture was stirred at 70° C. for 8 h. The reaction mixture was adjusted to pH=7 by saturated NaOH solution. The solvent was removed under reduced pressure and the crude was purified by flash chromatography on silica gel (MeOH in DCM=0 to 12%) to give 061-1 (0.12 g, 260.04 μmol, 20.97% yield) as a yellow solid. LCMS $R_t$=1.01 min in 2 min chromatography, 10-80AB, ESI calcd. for $C_{27}H_{20}N_5O_3$ [M+H]$^+$ 462.1, found 462.2.

Step B: Preparation of 3-hydroxy-2$^1$-(methyl-d$_3$)-3-(1-methyl-1H-imidazol-5-yl)-2$^2$-oxo-2$^1$,2$^2$-dihydro-6-oxa-2(4,6)-quinolina-4(3,5)-pyridina-1(1,3)-benzenacyclohexaphane-4$^6$-carbonitrile (061)

To a solution of 061-1 (0.12 g, 260.04 μmol) in THF (2 mL) was added NaOH (10M, 1.04 mL) and BTEAC (29.61 mg, 130.02 μmol) at 0° C. The mixture was stirred at 0° C. for 30 min. Then iodomethane-d$_3$ (40.60 mg, 280.09 μmol) was added to the above mixture dropwise and the reaction mixture was stirred at 25° C. for 15.5 h. The mixture was diluted with water (10 mL) and extracted with EtOAc (10 mL×3). The organic layer was separated, dried over anhydrous Na$_2$SO$_4$, filtered and concentrated. The crude was purified by flash chromatography on silica gel (MeOH in DCM=0 to 10%) to give 061 (0.07 g, 146.29 μmol, 56.26% yield) as a brown solid. 20 mg (41.80 μmol) of the product was further purified by Prep-HPLC (column: Phenomenex Gemini-NX 80×40 mm×3 m; mobile phase: [water (10 mM NH$_4$HCO$_3$)-ACN]; B %: 19%-49%, 7.8 min) to give 061 (12.4 mg, 25.91 μmol, 62.00% yield) as a white solid. $^1$H NMR (400 MHz, DMSO-d$_6$) δ=8.64 (s, 1H), 8.13 (s, 1H), 8.03-8.00 (m, 1H), 7.70 (d, J=8.8 Hz, 1H), 7.59 (s, 1H), 7.42-7.38 (m, 1H), 7.11-7.07 (m, 3H), 6.96 (s, 1H), 6.79 (s, J=1.6 Hz, 1H), 6.66 (s, 1H), 6.34 (s, 1H), 5.60-5.51 (m, 2H), 3.54 (s, 3H). LCMS $R_t$=1.03 min in 2 min chromatography, 10-80AB, ESI calcd. for: $C_{28}H_{19}D_3N_5O_3$ [M+H]$^+$ 479.2, found 479.1. HPLC $R_t$=5.77 min in 15 min chromatography, 220 nm, purity 91.50%.

Example 62: Preparation of Compound 62

Scheme 62 - Synthesis of Compound 62

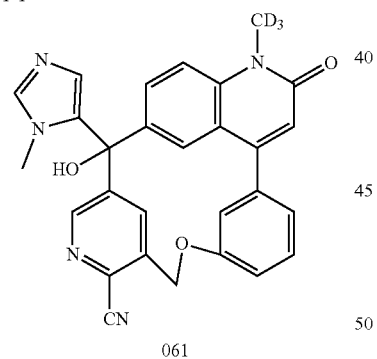

061

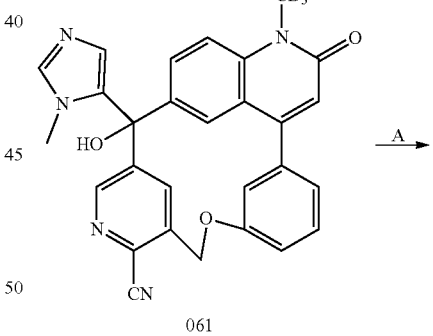

061

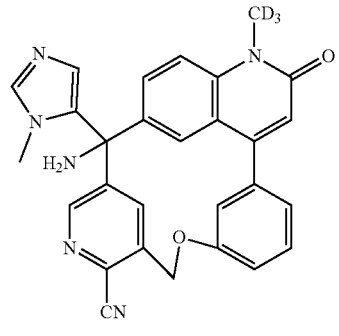

062

Step A: Preparation of 3-amino-2¹-(methyl-d₃)-3-(1-methyl-1H-imidazol-5-yl)-2²-oxo-2¹,2²-dihydro-6-oxa-2(4,6)-quinolina-4(3,5)-pyridina-1(1,3)-benzenacyclohexaphane-4⁶-carbonitrile (062)

To a solution of 061 (0.05 g, 104.49 μmol) in DMI (2 mL) was added SOCl₂ (99.45 mg, 835.92 μmol) at 0° C., the reaction mixture was stirred at 40° C. for 1 h. The resulting mixture was added dropwise to NH₃ in MeOH (7M, 2.99 mL) at 0° C. The reaction mixture was stirred at 25° C. for 1 h. The solvent was removed under reduced pressure. The crude was purified by flash chromatography on silica gel (MeOH in DCM=0 to 7%) to give 062 (49.9 mg, 104.50 μmol, 100.00% yield) as a white solid. The product was further purified by Prep-HPLC (column: Phenomenex Gemini-NX 80×40 mm×3 m; mobile phase: [water (10 mM NH₄HCO₃)-ACN]; B %: 33%-63%, 7.8 min) to give 062 (17.5 mg, 36.65 μmol, 35.07% yield) as a white solid. ¹H NMR (400 MHz, DMSO-d₆) δ=8.59 (br s, 1H), 8.25 (s, 1H), 8.07-8.04 (m, 1H), 7.67 (d, J=8.0 Hz, 1H), 7.54-7.52 (m, 1H), 7.40-7.36 (m, 1H), 7.14-7.05 (m, 3H), 6.78 (d, J=2.4 Hz, 1H), 6.65 (s, 1H), 6.48 (s, 1H), 5.60-5.52 (m, 2H), 3.46 (s, 3H), 3.14-3.10 (m, 2H). LCMS R$_f$=1.35 min in 3 min chromatography, 10-80CD, ESI calcd. for C₂₈H₂₀D₃N₆O₂ [M+H]⁺ 478.2, found 478.2. HPLC R$_f$=2.15 min in 8 min chromatography, 220 nm, purity 95.16%.

Scheme H - General Synthetic Method H

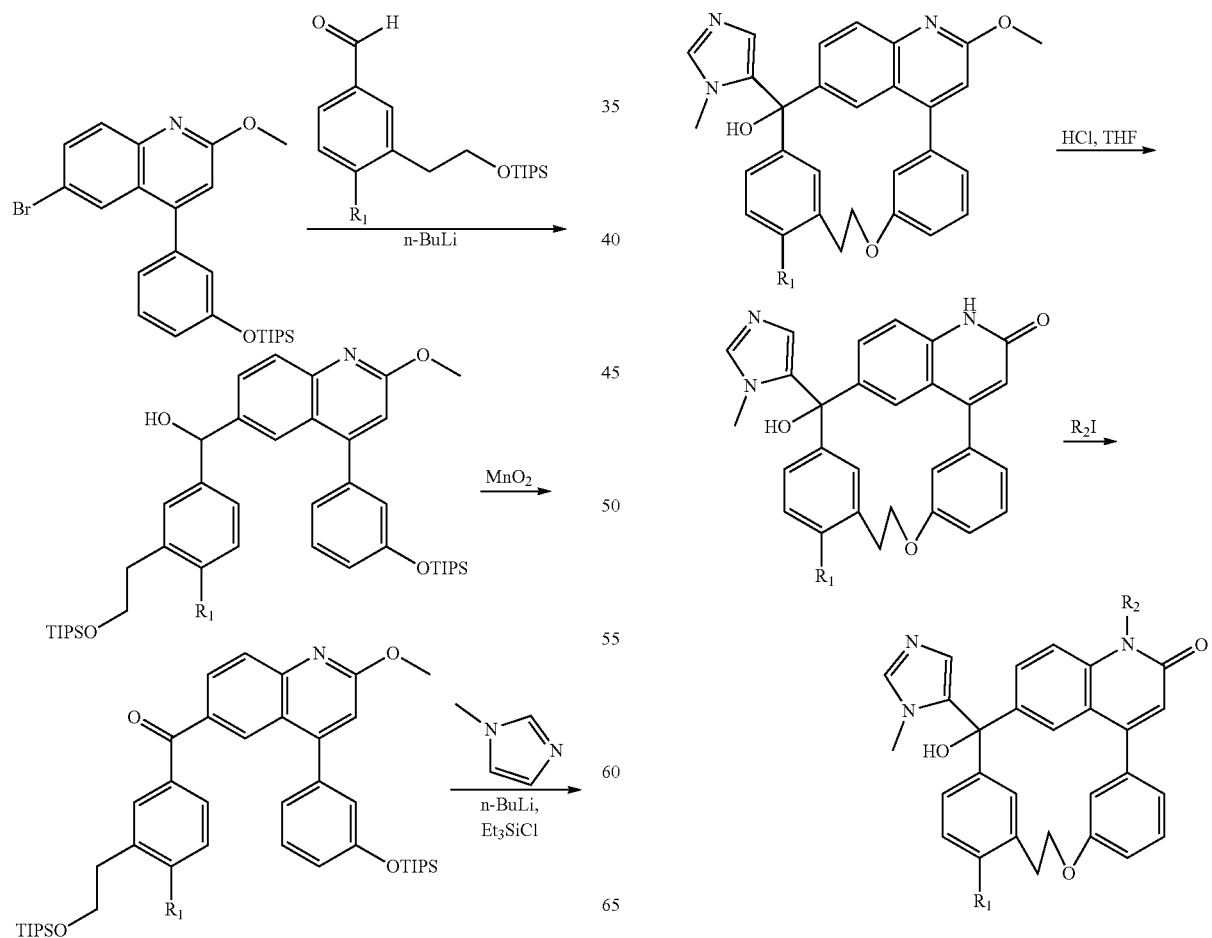

-continued

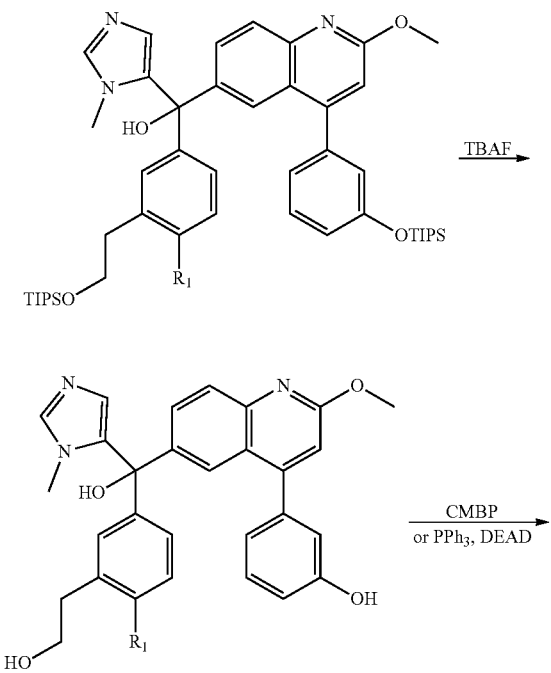

Example 63: Preparation of Compound 63

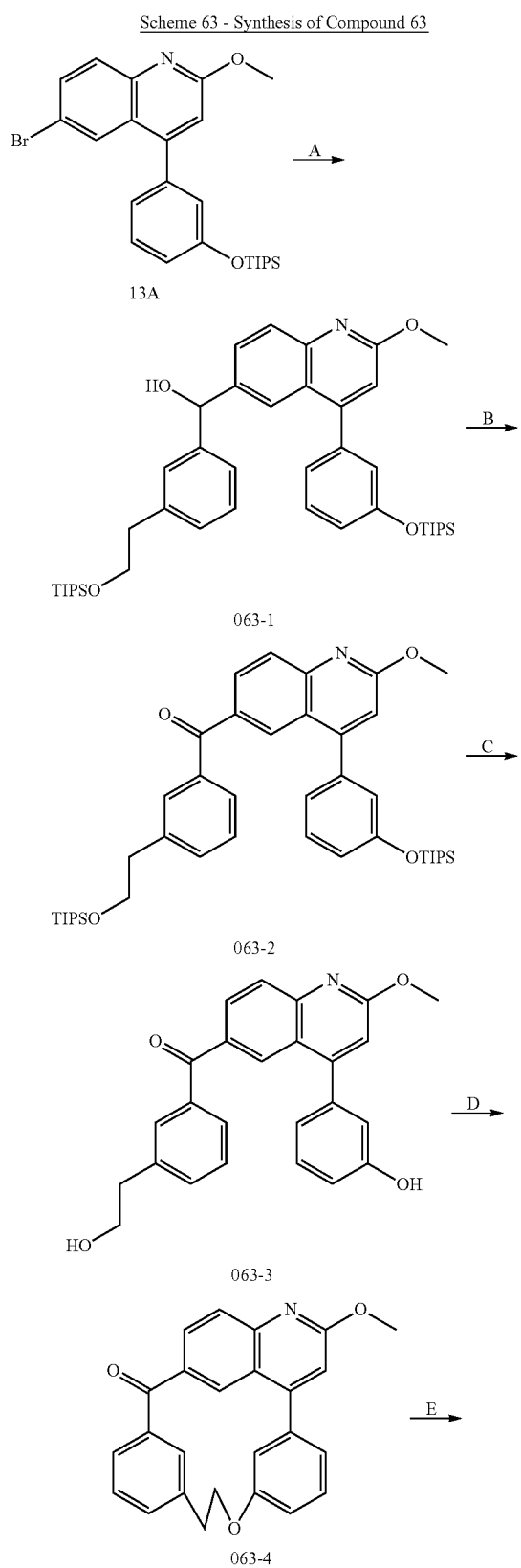

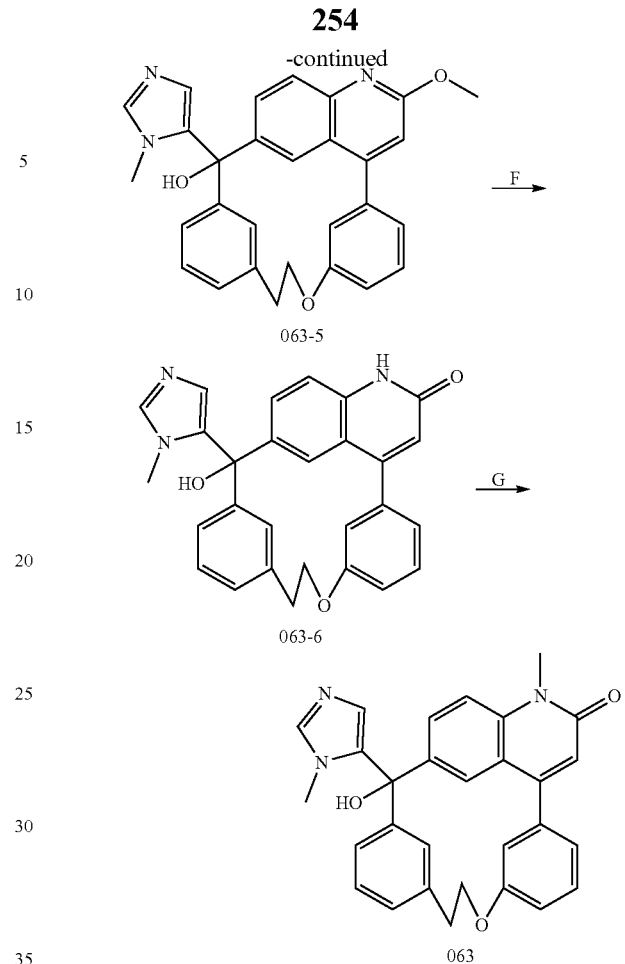

Step A: Preparation of (063-1)

To a solution of 13A (0.5 g, 1.03 mmol) in THF (5 mL) was added n-BuLi (2.5M in n-hexane, 1.23 mmol, 493.30 µL). The mixture was stirred at −70° C. for 5 min. 3-(2-((triisopropylsilyl)oxy)ethyl)benzaldehyde (315.01 mg, 1.03 mmol) (*J. Med. Chem.* 2011, 54 (19), 6969-6983.) was added to the reaction mixture. The reaction mixture was stirred at −70° C. for 25 min. The reaction mixture was quenched by addition $H_2O$ (20 mL) at −70° C. The aqueous layer was extracted with EtOAc (10 mL×3). The combined organic layers were washed with brine (10 mL), dried over anhydrous $Na_2SO_4$, filtered and concentrated. The residue was purified by flash chromatography on silica gel (EtOAc in petroleum ether=0 to 20%) to give 063-1 (340 mg, 476.10 µmol, 46.33% yield) as a brown gum. $^1$H NMR (400 MHz, DMSO-$d_6$) δ=7.80 (d, J=1.2 Hz, 1H), 7.76 (d, J=8.8 Hz, 1H), 7.56 (dd, J=2.0, 8.8 Hz, 1H), 7.45 (t, J=8.0 Hz, 1H), 7.20-7.16 (m, 2H), 7.12-7.01 (m, 4H), 6.99-6.95 (m, 1H), 6.86 (s, 1H), 5.89 (d, J=3.6 Hz, 1H), 5.67 (d, J=4.0 Hz, 1H), 3.99 (s, 3H), 3.75 (t, J=6.8 Hz, 2H), 2.69 (t, J=6.4 Hz, 2H), 1.34-1.21 (m, 3H), 1.10-1.06 (m, 18H), 1.02-0.95 (m, 3H), 0.88-0.76 (m, 18H).

Step B: Preparation of (063-2)

A mixture of 063-1 (330 mg, 462.10 µmol), $MnO_2$ (1.61 g, 18.48 mmol) in DCM (20 mL), and then the mixture was stirred at 35° C. for 16 h. The reaction mixture was filtered and the filtrate was concentrated to give 063-2 (0.32 g, 449.36 μmol, 97.24% yield) as a brown gum.

Step C: Preparation of (063-3)

To a solution of 063-2 (0.32 g, 449.36 μmol) in THF (20 mL) was added TBAF (1M in THF, 4.49 mmol, 4.49 mL). The mixture was stirred at 15° C. for 1 h. The reaction mixture was quenched with $H_2O$ (30 mL). The aqueous layer was extracted with EtOAc (30 mL×3). The combined organic layers were washed with brine (30 mL), dried over anhydrous $Na_2SO_4$, filtered and concentrated. The residue was purified by flash chromatography on silica gel (EtOAc in petroleum ether=0 to 60%) to give 063-3 (166 mg, 415.58 μmol, 92.48% yield) as a brown gum. $^1$H NMR (400 MHz, DMSO-$d_6$) δ=9.74 (s, 1H), 8.19 (d, J=1.8 Hz, 1H), 8.10-8.05 (m, 1H), 7.98 (d, J=8.4 Hz, 1H), 7.64-7.58 (m, 2H), 7.54-7.49 (m, 1H), 7.54-7.43 (m, 1H), 7.32 (t, J=7.8 Hz, 1H), 7.01 (s, 1H), 6.97 (d, J=7.8 Hz, 1H), 6.92-6.85 (m, 2H), 4.65 (t, J=4.8 Hz, 1H), 4.07 (s, 3H), 3.69-3.54 (m, 4H), 2.81 (t, J=6.8 Hz, 2H).

Step D: Preparation of (063-4)

To a solution of 063-3 (100 mg, 250.35 μmol) in THF (5 mL) was added $PPh_3$ (262.66 mg, 1.00 mmol) at 0° C. The mixture was stirred at 0° C. for 0.5 h. DEAD (174.40 mg, 1.00 mmol, 182.05 μL) was added to the reaction mixture. The reaction mixture was stirred at 15° C. for 15.5 h. The reaction mixture was quenched with $H_2O$ (10 mL). The aqueous layer was extracted with EtOAc (10 mL×3). The combined organic layers were washed with brine (10 mL), dried over anhydrous $Na_2SO_4$, filtered and concentrated. The residue was purified by flash chromatography on silica gel (EtOAc in petroleum ether=0 to 10%) to give 063-4 (54 mg, 141.58 μmol, 56.55% yield) as a white solid. $^1$H NMR (400 MHz, $CD_3CN$) δ=8.28 (dd, J=2.0, 8.8 Hz, 1H), 8.02 (d, J=2.0 Hz, 1H), 7.95 (d, J=8.8 Hz, 1H), 7.86 (s, 1H), 7.50-7.43 (m, 2H), 7.41 (s, 1H), 7.39-7.35 (m, 1H), 7.35-7.29 (m, 1H), 7.09 (s, 1H), 7.05 (d, J=7.2 Hz, 1H), 6.90 (dd, J=2.4, 8.0 Hz, 1H), 4.80-4.60 (m, 2H), 4.11 (s, 3H), 3.12 (t, J=5.2 Hz, 2H).

Step E: Preparation of (063-5)

To a solution of 1-methyl-1H-imidazole (23.25 mg, 283.15 μmol, 22.57 μL) in THF (3 mL) was added n-BuLi (2.5M in n-hexane, 283.15 μmol, 113.26 μL) at −78° C. The mixture was stirred at −78° C. for 0.5 h. $Et_3SiCl$ (42.68 mg, 283.15 μmol, 48.17 μL) was added to the mixture at −78° C. The mixture was stirred at −78° C. for 0.5 h. Then n-BuLi (2.5M in n-hexane, 283.15 μmol, 113.26 μL) was added to the mixture at −78° C. The mixture was stirred at −78° C. for 0.5 h. At last, a solution of 063-4 (90 mg, 235.96 μmol) in THF (2 mL) was added to the mixture at −78° C. The mixture was stirred at −78° C. for 1.5 h. The reaction mixture was quenched with $H_2O$ (10 mL) at −70° C., and then warmed to 15° C. The aqueous layer was extracted with EtOAc (10 mL×3). The combined organic layers were washed with brine (10 mL), dried over anhydrous $Na_2SO_4$, filtered and concentrated. The residue was purified by flash chromatography on silica gel (MeOH in DCM=0 to 5%) to afford 063-5 (55 mg, 118.66 μmol, 50.29% yield) as a brown gum. $^1$H NMR (400 MHz, DMSO-$d_6$) δ=8.10 (dd, J=1.6, 8.8 Hz, 1H), 7.89 (d, J=8.8 Hz, 1H), 7.61 (s, 1H), 7.56 (s, 1H), 7.33-7.25 (m, 1H), 7.14-7.08 (m, 3H), 6.97-6.85 (m, 4H), 6.78 (s, 1H), 6.69 (s, 1H), 6.17 (s, 1H), 4.69-4.43 (m, 2H), 4.02 (s, 3H), 3.38 (s, 3H), 3.02-2.83 (m, 2H).

Step F: Preparation of (063-6)

A mixture of 063-5 (40 mg, 86.30 μmol) and HCl (4M in $H_2O$, 2.16 mmol, 539.34 L) in THF (4 mL), and then the mixture was stirred at 70° C. for 16 h. The reaction mixture was blended with another batch prepared from 10 mg of 063-5. The reaction mixture was quenched with $H_2O$ (10 mL), and then extracted with EtOAc (10 mL×3). The combined organic layers were washed with brine (10 mL), dried over anhydrous $Na_2SO_4$, filtered and concentrated to give 063-6 (48 mg, 106.79 μmol, 99% yield) as a yellow oil, which was used into the next step without further purification. LCMS $R_t$=0.67 min in 1.5 min chromatography, 5-95AB, ESI calcd. for $C_{28}H_{24}N_3O_3$ [M+H]$^+$ 450.2, found 450.0.

Step G: Preparation of 3-hydroxy-2$^1$-methyl-3-(1-methyl-1H-imidazol-5-yl)-2$^1$,2$^2$-dihydro-7-oxa-2(4,6)-quinolina-1,4(1,3)-dibenzenacycloheptaphan-2$^2$-one (063)

A mixture of 063-6 (48 mg, 106.79 μmol), iodomethane (12.13 mg, 85.43 μmol, 5.32 L), NaOH (42.71 mg, 1.07 mmol) and BTEAC (9.73 mg, 42.71 μmol) in THF (4 mL) and $H_2O$ (2 mL) was stirred at 15° C. for 12 h under $N_2$. Water (5 mL) was added to the mixture. The aqueous layer was extracted with EtOAc (10 mL×2). The combined organic layers were washed with brine (3 mL), dried over anhydrous $Na_2SO_4$, filtered and concentrated. The residue was purified by flash chromatography on silica gel (MeOH in DCM=0 to 5%) and Prep-HPLC (column: Waters Xbridge 150×25 mm×5 m; mobile phase: [water (0.05% $NH_3H_2O$+ 10 mM $NH_4HCO_3$)-ACN]; B %: 38%-68%, 7.8 min) to give 063 (2.8 mg, 6.04 μmol, 7.07% yield) as an off-white solid. $^1$H NMR (400 MHz, $CD_3CN$) δ=8.00 (d, J=8.8 Hz, 1H), 7.60 (d, J=9.2 Hz, 1H), 7.54 (s, 1H), 7.26-7.22 (m, 1H), 7.18-6.91 (m, 5H), 6.83 (d, J=7.6 Hz, 1H), 6.65 (s, 1H), 6.57-6.50 (m, 2H), 6.30 (s, 1H), 4.77 (s, 1H), 4.60-4.48 (m, 2H), 3.69 (s, 3H), 3.40 (s, 3H), 3.05-2.87 (m, 2H). LCMS $R_t$=1.61 min in 3.0 min chromatography, 10-80CD, ESI calcd. for $C_{29}H_{26}N_3O_3$ [M+H]$^+$ 464.2, found 464.2. HPLC $R_t$=2.80 min in 8 min chromatography, 220 nm, purity 100%.

Example 64: Preparation of Compound 64

Scheme 64 - Synthesis of Compound 64

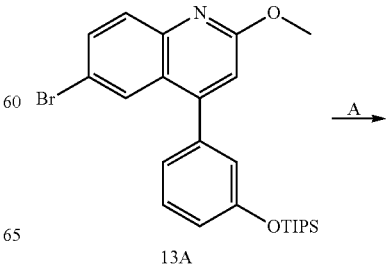

13A

-continued

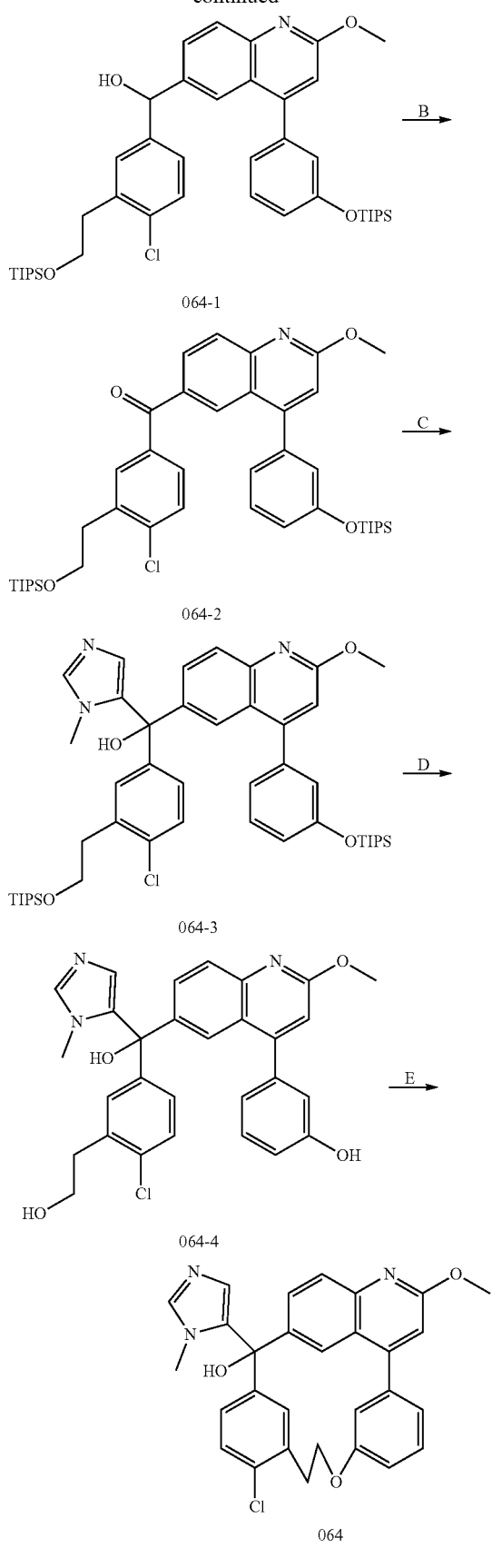

Step A: Preparation of (064-1)

To a solution of 13A (2.02 g, 4.15 mmol) in THF (20 mL) was added n-BuLi (2.5M in n-hexane, 4.57 mmol, 1.83 mL). The mixture was stirred at −70° C. for 5 min. The reaction mixture was added to a solution of 10A (1.7 g, 4.99 mmol) in THF (5 mL). The mixture was stirred at −70° C. for 25 min. The reaction mixture was quenched with H₂O (50 mL) at −70° C., and then warmed to 25° C. The mixture was extracted with EtOAc (20 mL×2). The combined organic layers were washed with brine (30 mL), dried over anhydrous Na₂SO₄, filtered and concentrated. The residue was purified by flash chromatography on silica gel (EtOAc in petroleum ether=0 to 5%) to give 064-1 (1.6 g, 2.14 mmol, 51.44% yield) as a black oil. ¹H NMR (400 MHz, CDCl₃) δ=7.90-7.82 (m, 2H), 7.49 (dd, J=2.0, 8.8 Hz, 1H), 7.35-7.32 (m, 1H), 7.30-7.25 (m, 2H), 7.08 (dd, J=2.0, 8.4 Hz, 1H), 7.04-6.96 (m, 3H), 6.85 (s, 1H), 5.82 (d, J=3.6 Hz, 1H), 4.10 (s, 3H), 3.86 (t, J=6.8 Hz, 2H), 2.95 (t, J=6.8 Hz, 2H), 2.18 (d, J=3.6 Hz, 1H), 1.32-1.24 (m, 3H), 1.15-1.10 (m, 18H), 1.00-0.94 (m, 21H).

Step B: Preparation of (064-2)

To a solution of 064-1 (3.6 g, 4.81 mmol) and silica gel (7.18 g, 119.51 mmol) in DCM (60 mL) was added PCC (2.07 g, 9.62 mmol) at 0° C. The mixture was stirred at 25° C. for 16 h. The reaction mixture was filtered and the filtrate was concentrated. The residue was purified by flash chromatography on silica gel (EtOAc in petroleum ether=0 to 3%) to give 064-2 (2.4 g, 3.21 mmol, 66.85% yield) as a light yellow oil. ¹H NMR (400 MHz, CDCl₃) δ=8.23 (d, J=1.6 Hz, 1H), 8.05-8.02 (m, 1H), 7.98-7.95 (m, 1H), 7.76 (d, J=2.0 Hz, 1H), 7.55 (dd, J=2.0, 8.0 Hz, 1H), 7.41 (d, J=8.4 Hz, 1H), 7.35-7.30 (m, 1H), 7.05-7.00 (m, 1H), 6.99-6.94 (m, 2H), 6.91 (s, 1H), 4.15 (s, 3H), 3.90 (t, J=6.8 Hz, 2H), 3.03 (t, J=6.8 Hz, 2H), 1.30-1.21 (m, 3H), 1.11-1.06 (m, 18H), 1.04-0.99 (m, 3H), 0.98-0.95 (m, 18H).

Step C: Preparation of (064-3)

To a solution of 1-methyl-1H-imidazole (184.76 mg, 2.25 mmol, 179.38 µL) in THF (11.57 mL) was added n-BuLi (2.5M in n-hexane, 2.25 mmol, 900.13 µL) at −70° C. under N₂. Then the reaction mixture was stirred at −70° C. for 0.5 h. Et₃SiCl (339.17 mg, 2.25 mmol, 382.81 µL) was added to the reaction mixture at −70° C. The reaction mixture was stirred −70° C. for 0.5 h. Then n-BuLi (2.5M in n-hexane, 2.25 mmol, 900.13 µL) was added to the reaction mixture at −70° C. The mixture was stirred at −70° C. for 0.5 h. A solution of 064-2 (1.4 g, 1.88 mmol) in THF (5 mL) was added to the reaction mixture at −70° C. The mixture was stirred at −70° C. for 0.5 h. The reaction mixture was quenched with H₂O (20 mL) at −70° C., and then warmed to 25° C. The mixture was extracted with EtOAc (20 mL×3). The combined organic layers were washed with brine (20 mL), dried over anhydrous Na₂SO₄, filtered and concentrated. The residue was purified by flash chromatography on silica gel (EtOAc in petroleum ether=0 to 100%) to give 064-3 (920 mg, 1.11 mmol, 59.20% yield) as a light yellow gum. ¹H NMR (400 MHz, DMSO-d₆) δ=7.79 (d, J=8.8 Hz, 1H), 7.67 (d, J=1.8 Hz, 1H), 7.60-7.53 (m, 2H), 7.38-7.29 (m, 2H), 7.14 (d, J=2.0 Hz, 1H), 7.12-7.06 (m, 1H), 7.02-6.93 (m, 2H), 6.90-6.83 (m, 2H), 6.73 (s, 1H), 6.04 (s, 1H), 4.00 (s, 3H), 3.75 (t, J=6.4 Hz, 2H), 3.29 (s, 3H), 2.84-2.78 (m, 2H), 1.30-1.20 (m, 3H), 1.10-0.98 (m, 18H), 0.88-0.78 (m, 21H).

Step D: Preparation of (064-4)

To a solution of 064-3 (920 mg, 1.11 mmol) in THF (20 mL) was added TBAF (1M in THF, 5.55 mmol, 5.55 mL). The mixture was stirred at 25° C. for 1 h. The reaction mixture was diluted with H$_2$O (50 mL) and extracted with EtOAc (20 mL×3). The combined organic layers were washed with brine (20 mL), dried over anhydrous Na$_2$SO$_4$, filtered and concentrated under reduced pressure. The residue was purified by flash chromatography on silica gel (MeOH in DCM=0 to 10%) to give 064-4 (537 mg, 1.04 mmol, 93.74% yield) as an off-white solid. $^1$H NMR (400 MHz, DMSO-d$_6$) δ=9.68 (s, 1H), 7.80 (d, J=8.8 Hz, 1H), 7.66 (d, J=2.0 Hz, 1H), 7.61-7.55 (m, 2H), 7.32 (d, J=8.4 Hz, 1H), 7.30-7.23 (m, 2H), 7.00 (dd, J=2.4, 8.4 Hz, 1H), 6.89-6.84 (m, 2H), 6.81-6.74 (m, 3H), 6.06 (s, 1H), 4.68 (t, J=5.2 Hz, 1H), 4.01 (s, 3H), 3.55-3.47 (m, 2H), 3.32 (s, 3H), 2.86-2.70 (m, 2H).

Step E: Preparation of 4$^4$-chloro-2$^2$-methoxy-3-(1-methyl-1H-imidazol-5-yl)-7-oxa-2(4,6)-quinolina-1,4(1,3)-dibenzenacycloheptaphan-3-ol (064)

To a mixture of 064-4 (0.35 g, 678.31 µmol) in toluene (16 mL) was added 2-(tributyl-λ$^5$-phosphaneylidene)acetonitrile (982.28 mg, 4.07 mmol) at 0° C. The mixture was stirred at 25° C. and the mixture was stirred at 120° C. for 4 h. The solvent was removed and the residue was dissolved with water (50 mL) and EtOAc (100 mL). The organic layer was separated and the aqueous layer was extracted with EtOAc (50 mL×2). The combined organic layer was washed with brine (30 mL), dried over anhydrous Na$_2$SO$_4$, filtered and concentrated. The residue was purified by Prep-HPLC (Phenomenex Gemini 150×25 mm×10 m, water (0.05% NH$_3$H$_2$O+10 mM NH$_4$HCO$_3$)-ACN, B % 54%-54%, flow-rate: 25 mL/min) to give 064 (0.065 g, 130.53 µmol, 19.24% yield) as a white solid. $^1$H NMR (400 MHz, DMSO-d$_6$) δ=8.06 (dd, J=2.0, 8.8 Hz, 1H), 7.89 (d, J=8.8 Hz, 1H), 7.63 (s, 1H), 7.36-7.20 (m, 3H), 6.98-6.83 (m, 5H), 6.63 (br s, 1H), 6.16 (s, 1H), 4.69-4.49 (m, 2H), 4.01 (s, 3H), 3.36 (s, 3H), 3.18-3.14 (m, 1H), 3.05-3.01 (m, 1H). LCMS R$_t$=2.07 min in 3.0 min chromatography, 10-80CD, ESI calcd. for C$_{29}$H$_{25}$ClN$_3$O$_3$ [M+H]$^+$ 498.2, found 498.1. HPLC R$_t$=4.07 min in 8 min chromatography, 220 nm, purity 94.33%.

Example 65: Preparation of Compound 65

Scheme 65 - Synthesis of Compound 65

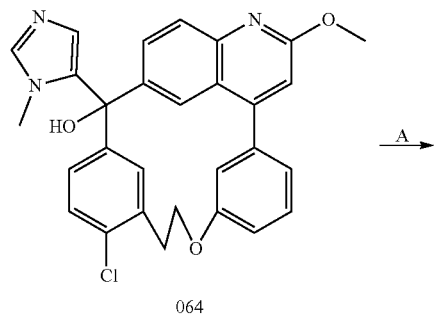

064

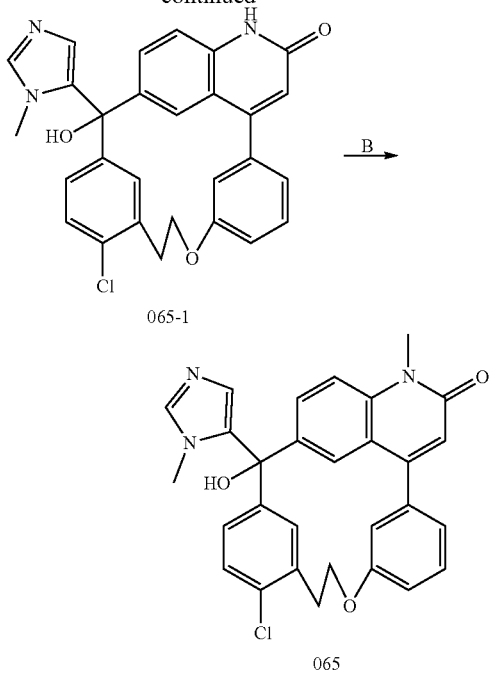

065-1

065

Step A: Preparation of (065-1)

A mixture of 064 (0.04 g, 80.33 µmol), HCl (4M in H$_2$O, 16.0 mmol, 4.00 mL) in THF (4 mL). Then the mixture was stirred at 60° C. for 10 h. The mixture was adjusted pH ~ 8 by saturated NaHCO$_3$ solution. The mixture was extracted with EtOAc (20 mL×3). The organic layer was washed with brine (15 mL), dried over anhydrous Na$_2$SO$_4$ and concentrated to give 065-1 (38.87 mg, 80.32 µmol, 100.00% yield) as a white solid. $^1$H NMR (400 MHz, CDCl$_3$) δ=11.92 (m, 1H), 7.93-7.91 (m, 1H), 7.60-7.55 (m, 1H), 7.43-7.41 (m, 1H), 7.30-7.27 (m, 1H), 7.27-7.25 (m, 2H), 6.85-6.84 (m, 2H), 6.70-6.68 (1H), 6.55-6.53 (m, 1H), 6.42-6.40 (m, 1H), 6.35-6.33 (m, 1H), 6.20-6.18 (m, 1H), 5.05 (s, 1H), 4.63-4.58 (m, 2H), 3.31 (s, 3H), 3.16-3.06 (m, 2H). LCMS R$_t$=1.64 min in 3.0 min chromatography, 10-80CD, ESI calcd. for C$_{28}$H$_{23}$ClN$_3$O$_3$ [M+H]$^+$ 484.1, found 484.1.

Step B: Preparation of 4$^4$-chloro-3-hydroxy-2$^1$-methyl-3-(1-methyl-1H-imidazol-5-yl)-2$^1$,2$^2$-dihydro-7-oxa-2(4,6)-quinolina-1,4(1,3)-dibenzenacycloheptaphan-2$^2$-one (065)

To a mixture of 065-1 (38.84 mg, 80.26 mmol) in THF (2 mL) and H$_2$O (2 mL) was added BTEAC (9.14 mg, 40.13 mmol), NaOH (32.10 mg, 802.57 mmol) and then iodomethane (11.39 mg, 80.26 µmol, 5.00 µL) was added at 25° C. and the mixture was stirred at 25° C. for 12 h. The solvent was removed and the residue was dissolved with EtOAc (20 mL) and water (10 mL). The organic layer was washed with brine (5 mL), dried over anhydrous Na$_2$SO$_4$ and concentrated. The residue was purified by Prep-HPLC (Column: Welch Xtimate C$_{18}$ 150×25 mm×5 m, Condition: water (0.05% ammonia hydroxide v/v)-MeOH, B %: 65%-95%, 7.8 min) to give 065 (16.5 mg, 33.13 µmol, 41.29% yield) as an off-white solid. 13.3 mg (26.71 µmol) of the product was purified by Prep-HPLC (column: Phenomenex Gemini 150×25 mm×10 m, condition: water(0.05% NH$_3$H$_2$O+10 mM NH$_4$HCO$_3$)-ACN, B: 33%-63%, 7.8 min) to give 065 (5.4 mg, 10.84 μmol, 40.60% yield) as an off-white solid. $^1$H NMR (400 MHz, DMSO-d$_6$) δ=8.06 (dd, J=2.0, 9.2 Hz, 1H), 7.72-7.68 (m, 2H), 7.36-7.14 (m, 3H), 6.95 (dd, J=2.0, 8.4 Hz, 1H), 6.85 (d, J=7.2 Hz, 1H), 6.80-6.78 (m, 2H), 6.55 (s, 1H), 6.44 (br s, 1H), 6.23 (s, 1H), 4.68-4.57 (m, 2H), 3.69 (s, 3H), 3.35 (s, 3H), 3.17-2.88 (m, 2H). LCMS R$_t$=1.72 min in 3.0 min chromatography, 10-80CD, ESI calcd. for C$_{29}$H$_{25}$ClN$_3$O$_3$ [M+H]$^+$ 498.2, found 498.0. HPLC R$_t$=3.16 min in 8 min chromatography, 220 nm, purity 100%.

Example 66: Preparation of Compound 66

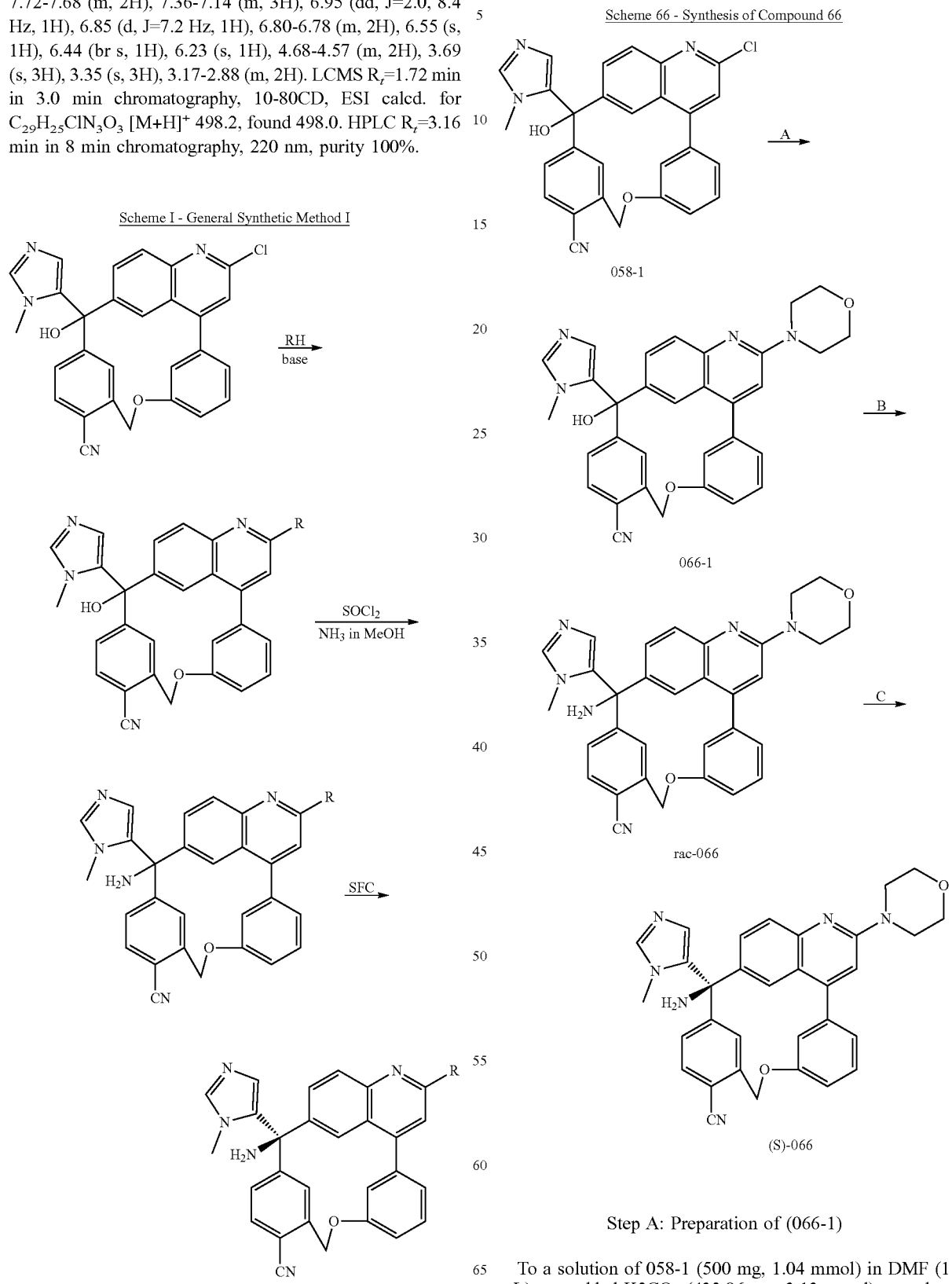

Step A: Preparation of (066-1)

To a solution of 058-1 (500 mg, 1.04 mmol) in DMF (1 mL) was added K2CO$_3$ (432.86 mg, 3.13 mmol), morpholine (727.63 mg, 8.35 mmol, 734.98 μL). The mixture was stirred at 100° C. for 12 h. The mixture was blended with another batch prepared from 50 mg of 058-1. Water (30 mL) was added to the mixture. The aqueous layer was extracted with DCM (30 mL×2). The combined organic layers were washed with brine (20 mL×2), dried over anhydrous Na$_2$SO$_4$, filtered and concentrated. The residue was purified by flash chromatography on silica gel (MeOH in DCM=0 to 6%) to afford 066-1 (300 mg, 566.48 μmol, 49.33% yield) as a yellow solid. $^1$H NMR (400 MHz, DMSO-d$_6$) δ=7.93 (dd, J=2.4, 8.8 Hz, 1H), 7.84-7.66 (m, 3H), 7.55 (s, 1H), 7.48-7.34 (m, 1H), 7.37 (s, 1H), 7.20-7.12 (m, 2H), 7.08-6.99 (m, 2H), 6.83 (s, 1H), 6.62 (s, 1H), 6.33 (s, 1H), 5.51 (s, 2H), 3.76-3.73 (m, 8H), 3.51 (s, 3H). LCMS R$_t$=1.80 min in 3.0 min chromatography, 10-80CD, ESI calcd. for C$_{32}$H$_{28}$N$_5$O$_3$ [M+H]$^+$ 530.2, found 530.1.

Step B: Preparation of (rac)-3-amino-3-(1-methyl-1H-imidazol-5-yl)-2$^2$-morpholino-6-oxa-2(4,6)-quinolina-1,4(1,3)-dibenzenacyclohexaphane-4$^4$-carbonitrile (rac-066)

To a solution of 066-1 (200 mg, 377.65 μmol) in DMI (1.5 mL) was added SOCl$_2$ (359.43 mg, 3.02 mmol, 219.16 μL). The mixture was stirred at 40° C. for 1 h. The above mixture was added to NH$_3$ in MeOH (7M, 20.00 mL) at 0° C. The mixture was stirred at 0° C. for 1 h. Water (30 mL) was added to the mixture. The aqueous layer was extracted with DCM (30 mL×3). The combined organic layers were washed with brine (30 mL×2), dried over anhydrous Na$_2$SO$_4$, filtered and concentrated. The mixture was blended with another batch prepared from 50 mg of 066-1. The residue was purified by flash chromatography on silica gel (MeOH in DCM=0 to 8%) to afford rac-066 (180 mg, 340.52 μmol, 72.13% yield) as a yellow solid. $^1$H NMR (400 MHz, DMSO-d$_6$) δ=8.01-7.84 (m, 2H), 7.80-7.65 (m, 2H), 7.52 (s, 1H), 7.44-7.27 (m, 2H), 7.18-7.09 (m, 3H), 7.02 (dd, J=1.6, 8.0 Hz, 1H), 6.82 (s, 1H), 6.47 (s, 1H), 5.56-5.44 (m, 2H), 3.78-3.69 (m, 8H), 3.09 (br s, 3H). LCMS R$_t$=0.70 min in 1.5 min chromatography, 5-95AB, ESI calcd. for C$_{32}$H$_{29}$N$_6$O$_2$ [M+H]$^+$ 529.2, found 529.2.

Step C: Preparation of (S)-3-amino-3-(1-methyl-1H-imidazol-5-yl)-2$^2$-morpholino-6-oxa-2(4,6)-quinolina-1,4(1,3)-dibenzenacyclohexaphane-4$^4$-carbonitrile ((S)-066)

rac-066 (100 mg, 189.18 μmol) was purified by SFC (column: DAICEL CHIRALPAK AD (250 mm×30 mm, 10 m); mobile phase: [0.1% NH$_3$H$_2$O EtOH]; B %: 50%-50%, min) to afford (S)-066 (33.3 mg, 63.00 μmol, 33.30% yield) as an off-white solid. $^1$H NMR (400 MHz, DMSO-d$_6$) δ=8.03-7.85 (m, 2H), 7.77 (d, J=7.6 Hz, 1H), 7.69 (d, J=8.8 Hz, 1H), 7.52 (s, 1H), 7.44-7.28 (m, 2H), 7.20-7.11 (m, 3H), 7.04-7.00 (m, 1H), 6.82 (br s, 1H), 6.47 (br s, 1H), 5.61-5.43 (m, 2H), 3.77-3.69 (m, 8H), 3.39 (br s, 2H), 3.01 (s, 3H). LCMS R$_t$=1.77 min in 3.0 min chromatography, 10-80CD, ESI calcd. for C$_{32}$H$_{29}$N$_6$O$_2$ [M+H]$^+$ 529.2, found 529.1. HPLC R$_t$=3.45 min in 8 min chromatography, 220 nm, purity 97.27%. Chiral HPLC (S)-066: R$_t$=1.62 min in 3 min (ee 100%) (AD_ETOH_DEA_40-4ML_5CM), ((R)-066: R$_t$=1.02 min (ee 100%)).

Example 67: Preparation of Compound 67

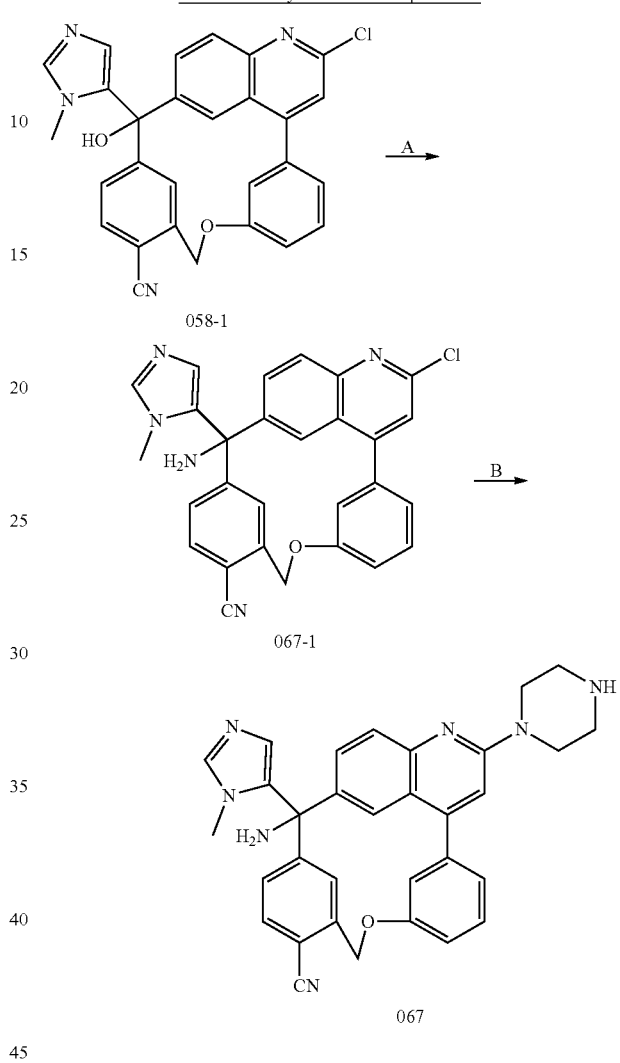

Scheme 67 - Synthesis of Compound 67

Step A: Preparation of (067-1)

To a solution of 058-1 (900 mg, 1.88 mmol) in DMI (10 mL) was added SOCl$_2$ (1.79 g, 15.03 mmol, 1.09 mL) dropwise at 0° C. The mixture was stirred at 40° C. for 0.5 h. The above mixture was added into NH$_3$ in MeOH (7M, 9 mL) at 0° C. The mixture was stirred at 20° C. for 5 min under N$_2$. Water (15 mL) was added to the mixture slowly at 0° C. and the aqueous phase was extracted with EtOAc (20 mL×2). The combined organic phase was washed with water (8 mL), brine (10 mL), dried over anhydrous Na$_2$SO$_4$, filtered and concentrated. The crude was purified by flash chromatography on silica gel (MeOH in DCM=0 to 10%) to give 067-1 (893.6 mg, 1.88 mmol, 100% yield) as a yellow solid. $^1$H NMR (400 MHz, DMSO-d$_6$) δ=8.25 (d, J=8.4 Hz, 1H), 8.05 (d, J=8.8 Hz, 1H), 7.92 (s, 1H), 7.81 (d, J=8.0 Hz, 1H), 7.61 (s, 1H), 7.55 (s, 1H), 7.41 (t, J=8.0 Hz, 1H), 7.22 (s, 1H), 7.18 (d, J=7.6 Hz, 1H), 7.11-7.02 (m, 2H), 6.43 (s, 1H), 5.68 (d, J=0.8 Hz, 1H), 5.59-5.47 (m, 2H), 3.44 (s, 3H).

Step B: Preparation of 3-amino-3-(1-methyl-1H-imidazol-5-yl)-2²-(piperazin-1-yl)-6-oxa-2(4,6)-quinolina-1,4(1,3)-dibenzenacyclohexaphane-4⁴-carbonitrile (067)

To a solution of 067-1 (50 mg, 104.61 μmol) in DMF (1 mL) was added K2CO₃ (43.38 mg, 313.84 μmol) and piperazine (54.07 mg, 627.69 μmol). The mixture was stirred at 100° C. for 12 h. Water (30 mL) was added to the mixture. The aqueous layer was extracted with DCM (30 mL×2). The combined organic layers were washed with brine (20 mL×2), dried over anhydrous Na₂SO₄, filtered and concentrated. The residue was purified by flash chromatography on silica gel (MeOH in DCM=0 to 20%) and then purified by Prep-HPLC (column: Phenomenex C$_{18}$ 75×30 mm×3 m; mobile phase: [water (NH₃H₂O+NH₄HCO₃)-ACN]; B %: 32%-62%, 7 min) to afford 067 (11.1 mg, 21.04 μmol, 20.11% yield) as an off-white solid. ¹H NMR (400 MHz, DMSO-d₆) δ=7.97-7.87 (m, 2H), 7.77 (d, J=8.0 Hz, 1H), 7.65 (d, J=8.8 Hz, 1H), 7.52 (s, 1H), 7.38-7.23 (m, 2H), 7.15-7.11 (m, 3H), 7.03-6.98 (m, 1H), 6.79 (s, 1H), 6.48 (s, 1H), 5.55-5.47 (m, 2H), 3.70-3.66 (m, 4H), 3.39 (s, 3H), 2.86-2.81 (m, 4H). LCMS R$_t$=1.65 min in 3.0 min chromatography, 10-80CD, ESI calcd. for C₃₂H₃₀N₇O [M+H]⁺ 528.2, found 528.2. HPLC R$_t$=3.21 min in 8 min chromatography, 220 nm, purity 99.85%.

Example 68: Preparation of Compound 68

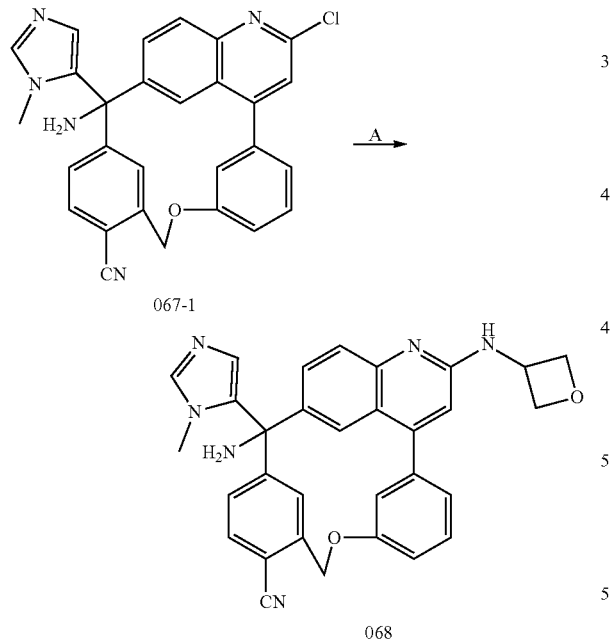

Scheme 68 - Synthesis of Compound 68

Step A: Preparation of 3-amino-3-(1-methyl-1H-imidazol-5-yl)-2²-(oxetan-3-ylamino)-6-oxa-2(4,6)-quinolina-1,4(1,3)-dibenzenacyclohexaphane-4⁴-carbonitrile (068)

A mixture of 067-1 (100 mg, 209.23 μmol) and oxetan-3-amine (1 mL) was stirred at 100° C. for 12 h. The reaction mixture was diluted with H₂O (5 mL) and the mixture was extracted with EtOAc (10 mL×2). The combined organic layers were washed with brine (10 mL×2), dried over anhydrous Na₂SO₄, filtered and concentrated. The residue was purified by Prep-HPLC (column: Welch Xtimate C$_{18}$ 150×25 mm×5 um; mobile phase: [water (ammonia hydroxide v/v)-MeOH]; B %: 58%-88%, 9.5 min) to give 068 (7.5 mg, 14.58 μmol, 6.97% yield) as a light yellow solid. ¹H NMR (400 MHz, DMSO-d₆) δ=7.94 (d, J=8.4 Hz, 1H), 7.78 (d, J=8.0 Hz, 2H), 7.51 (s, 1H), 7.37-7.19 (m, 3H), 7.09 (s, 1H), 7.08-6.98 (m, 2H), 6.72-6.64 (m, 2H), 6.45 (s, 1H), 5.49 (s, 2H), 4.68 (s, 1H), 4.40-4.31 (m, 1H), 4.26-4.20 (m, 1H), 4.15-4.02 (m, 1H), 3.70-3.58 (m, 1H), 3.55-3.50 (m, 1H), 3.38 (s, 3H). LCMS R$_t$=0.91 min in 2.0 min chromatography, 10-80AB, ESI calcd. for C₃₁H₂₇N₆O₂ [M+H]⁺ 515.2, found 515.1. HPLC R$_t$=4.04 min in 8 min chromatography, 220 nm, purity 99.74%.

Example 69: Preparation of Compound 69

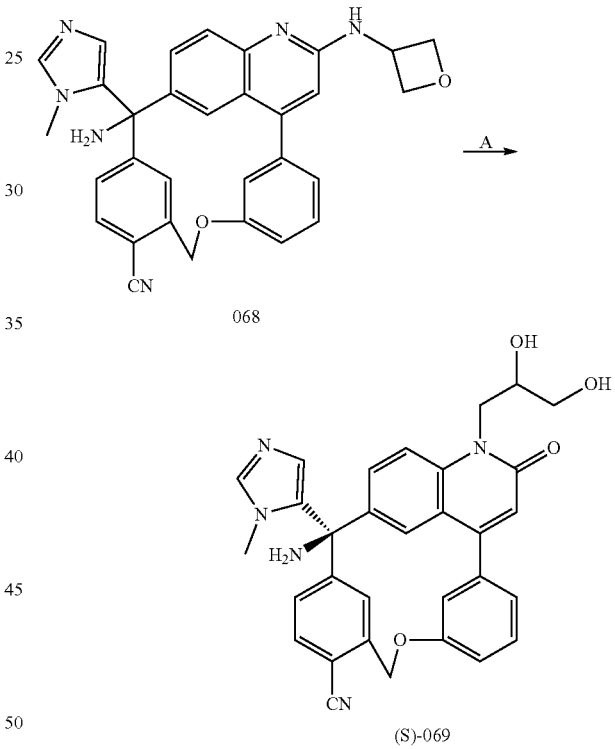

Scheme 69 - Synthesis of Compound 69

Step A: Preparation of (3S)-3-amino-2¹-(2,3-dihydroxypropyl)-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile ((S)-069)

Step A. 068 (100 mg, 193.96 μmol) was purified by SFC (column: DAICEL CHIRALPAK AD (250 mm×30 mm, 10 m); mobile phase: [0.1% NH₃H₂O EtOH]; B %: 40%-40%) and flash chromatography on silica gel (MeOH in DCM=0 to 20%) to give (S)-069 (42.5 mg, 82.43 μmol, 42.50% yield) as a light yellow solid. 40 mg (74.97 μmol) of the product was purified by Prep-HPLC (column: Welch Xtimate C$_{18}$ 150×25 mm×5 m; mobile phase: [water (ammonia hydroxide v/v)-MeOH]; B %: 45%-75%, 7.8 min) to give (S)-069 (3.6 mg, 6.75 μmol, 8.50% yield) as a white solid. $^1$H NMR (400 MHz, DMSO-$d_6$) δ=8.02 (d, J=8.8 Hz, 1H), 7.89-7.74 (m, 3H), 7.57 (s, 1H), 7.41-7.25 (m, 2H), 7.14 (s, 1H), 7.09-6.97 (m, 2H), 6.84 (s, 1H), 6.64 (s, 1H), 6.47 (s, 1H), 5.54-5.47 (m, 2H), 4.67 (s, 1H), 4.51 (s, 1H), 4.49-4.45 (m, 1H), 4.38-4.26 (m, 1H), 3.96 (s, 1H), 3.49 (s, 2H), 3.39 (s, 3H). LCMS $R_t$=1.48 min in 3.0 min chromatography, 10-80CD, ESI calcd. for $C_{31}H_{28}N_5O_4$ [M+H]$^+$ 534.2, found 534.3. HPLC $R_t$=2.28 min in 8 min chromatography, 220 nm, purity 99.46%.

Example 70: Preparation of Compound 70

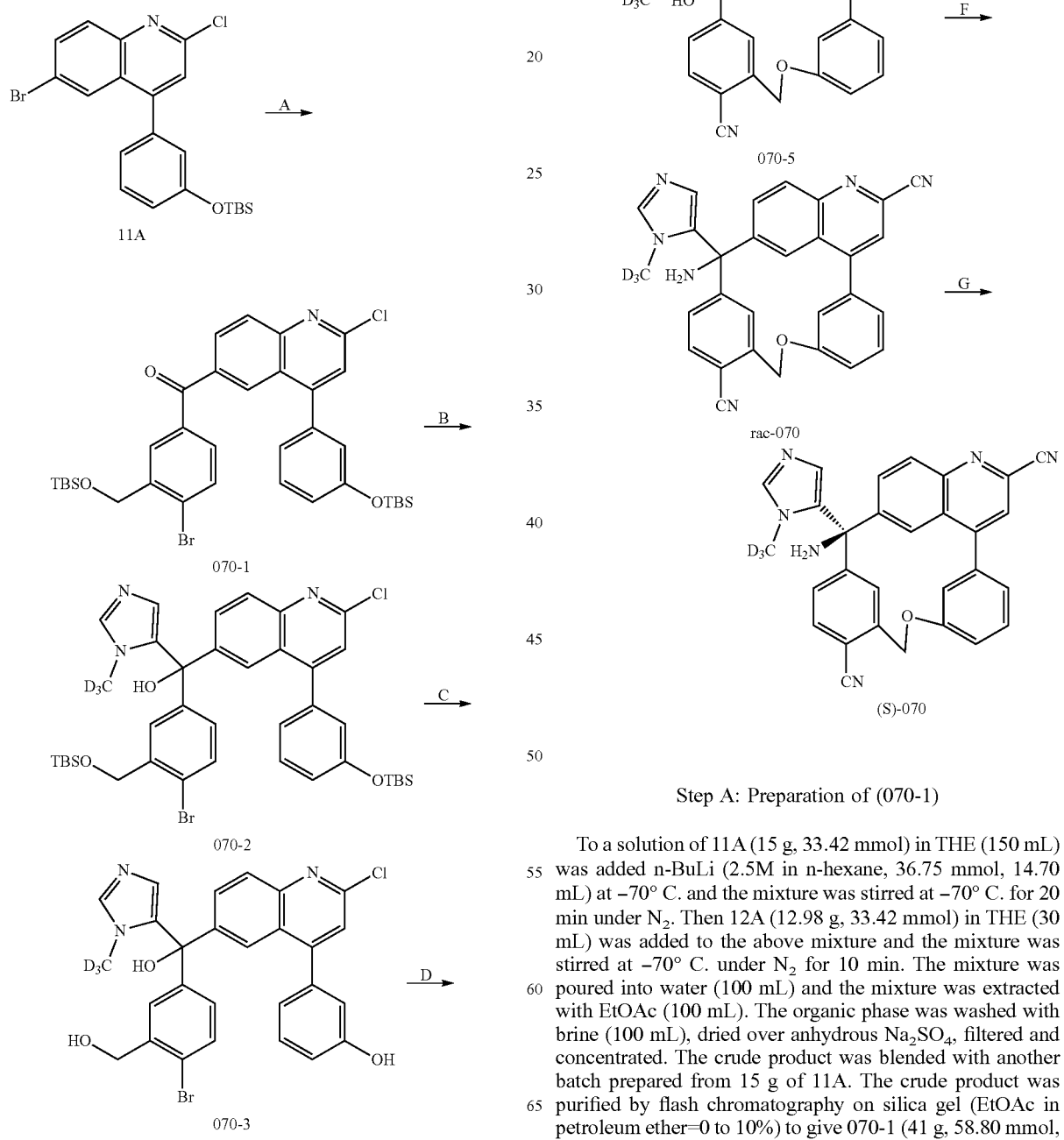

Step A: Preparation of (070-1)

To a solution of 11A (15 g, 33.42 mmol) in THF (150 mL) was added n-BuLi (2.5M in n-hexane, 36.75 mmol, 14.70 mL) at −70° C. and the mixture was stirred at −70° C. for 20 min under N$_2$. Then 12A (12.98 g, 33.42 mmol) in THF (30 mL) was added to the above mixture and the mixture was stirred at −70° C. under N$_2$ for 10 min. The mixture was poured into water (100 mL) and the mixture was extracted with EtOAc (100 mL). The organic phase was washed with brine (100 mL), dried over anhydrous Na$_2$SO$_4$, filtered and concentrated. The crude product was blended with another batch prepared from 15 g of 11A. The crude product was purified by flash chromatography on silica gel (EtOAc in petroleum ether=0 to 10%) to give 070-1 (41 g, 58.80 mmol, 87.98% yield) as a yellow oil. $^1$H NMR (400 MHz, CDCl$_3$)

δ=8.36 (d, J=1.6 Hz, 1H), 8.19-8.14 (m, 1H), 8.12-8.08 (m, 1H), 7.97 (d, J=1.6 Hz, 1H), 7.64-7.56 (m, 2H), 7.43 (s, 1H), 7.35 (d, J=8.0 Hz, 1H), 7.10-7.07 (m, 1H), 6.98-6.93 (m, 2H), 4.74 (s, 2H), 0.98 (s, 9H), 0.82 (s, 9H), 0.19 (s, 6H), 0.069 (s, 6H).

Step B: Preparation of (070-2)

To a solution of 1-(methyl-d$_3$)-1H-imidazole (1.34 g, 15.78 mmol) in THF (20 mL) was added n-BuLi (2.5M in n-hexane, 15.78 mmol, 6.31 mL) and the mixture was stirred at −70° C. under N$_2$ for 10 min. Then Et$_3$SiCl (2.38 g, 15.78 mmol, 2.68 mL) in THF (3 mL) was added to the above mixture and the mixture was stirred at −70° C. for 10 min. Then n-BuLi (2.5M in n-hexane, 6.31 mL, 15.78 mmol) was added to the above mixture and the mixture was stirred for 10 min. Then a solution of 070-1 (10 g, 14.34 mmol) in THF (50 mL) was added to the above mixture and the mixture was stirred for 10 min. The mixture was poured into water (300 mL) and the mixture was extracted with EtOAc (300 mL). The organic phase was washed with brine (300 mL), dried over anhydrous Na$_2$SO$_4$, filtered and concentrated. The crude product was blended with another batch prepared from 10 g×3 of 070-1. The crude product was purified by flash chromatography on silica gel (MeOH in DCM=0 to 10%) to give 070-2 (20 g, 25.56 mmol, 44.56% yield) as a yellow oil. $^1$H NMR (400 MHz, CDCl$_3$) δ=7.91 (d, J=8.8 Hz, 1H), 7.84 (d, J=2.0 Hz, 1H), 7.53 (dd, J=2.0, 8.8 Hz, 1H), 7.35 (d, J=8.4 Hz, 1H), 7.27 (d, J=2.4 Hz, 1H), 7.21-7.17 (m, 3H), 7.05 (dd, J=2.4, 8.4 Hz, 1H), 6.87-6.75 (m, 4H), 6.23 (d, J=1.2 Hz, 1H), 4.56-4.53 (m, 2H), 0.89 (s, 8H), 0.67-0.64 (m, 9H), 0.13-0.10 (m, 6H), 0.13 (s, 6H).

Step C: Preparation of (070-3)

To a solution of 070-2 (20 g, 25.56 mmol) in THF (200 mL) was added TBAF (1M in THF, 38.35 mmol, 38.35 mL) at 0° C. under N$_2$. The mixture was stirred at 25° C. for 1 h. The reaction mixture was poured into water (200 mL). The aqueous layer was extracted with EtOAc (200 mL×2). The combined organic phase was washed with brine (200 mL), dried over anhydrous Na$_2$SO$_4$, filtered and concentrated under reduced pressure. The crude product was triturated with petroleum ether (100 mL) at 25° C. for 30 min to give 070-3 (12 g, 21.67 mmol, 84.76% yield) as a yellow solid. $^1$H NMR (400 MHz, DMSO-d$_6$) δ=9.78 (s, 1H), 7.98 (d, J=8.8 Hz, 1H), 7.82 (d, J=2.0 Hz, 1H), 7.74 (dd, J=2.0, 8.8 Hz, 1H), 7.63 (s, 1H), 7.47-7.46 (m, 1H), 7.51-7.44 (m, 3H), 7.29 (t, J=8.0 Hz, 1H), 7.03-6.98 (m, 2H), 6.91 (dd, J=1.6, 8.4 Hz, 1H), 6.86-6.81 (m, 2H), 6.07 (s, 1H), 5.40 (t, J=5.6 Hz, 1H), 4.45 (d, J=2.8 Hz, 2H).

Step D: Preparation of (070-4)

To a solution of 070-3 (5 g, 9.03 mmol) in DMF (50 mL) was added SOCl$_2$ (2.15 g, 18.06 mmol, 1.31 mL) at 0° C. under N$_2$. To the above mixture was added Cs$_2$CO$_3$ (44.15 g, 135.51 mmol) at 25° C. The mixture was stirred at 70° C. for 2 h. After cooling to room temperature, the mixture was filtered and the filtrate was concentrated. The crude product was triturated with H$_2$O (30 mL) at 25° C. for 30 min and CH$_3$CN (50 mL) at 25° C. for 30 min to give 070-4 (4 g, 7.47 mmol, 82.64% yield) as a yellow solid. $^1$H NMR (400 MHz, DMSO-d$_6$) δ=8.19 (dd, J=2.0, 8.8 Hz, 1H), 8.06 (d, J=8.8 Hz, 1H), 7.66 (s, 1H), 7.62-7.56 (m, 3H), 7.42-7.37 (m, 2H), 7.22-7.19 (m, 2H), 7.18-7.16 (m, 1H), 7.08 (dd, J=1.6, 8.4 Hz, 1H), 6.97-6.93 (m, 1H), 6.73 (s, 1H), 5.43 (d, J=2.4 Hz, 2H).

Step E: Preparation of (070-5)

A mixture of 070-4 (3 g, 5.60 mmol), Zn(CN)$_2$ (1.31 g, 11.20 mmol, 710.77 μL), Zn (219.66 mg, 3.36 mmol), Pd$_2$(dba)$_3$ (769.03 mg, 839.81 μmol) and DPPF (931.15 mg, 1.68 mmol) in DMA (20 mL) was stirred at 120° C. under N$_2$ for 2 h. The mixture was filtered and the filter liquid was concentrated under reduced pressure. The crude product was triturated with petroleum ether (20 mL) at 25° C. for 30 min and purified by flash chromatography on silica gel (MeOH in DCM=0 to 10%) to give 070-5 (2.2 g, 4.66 mmol, 83.16% yield) as a brown solid. $^1$H NMR (400 MHz, DMSO-d$_6$) δ=8.25 (s, 2H), 8.09 (s, 1H), 7.77-7.74 (m, 2H), 7.59-7.57 (m, 2H), 7.50-7.48 (m, 2H), 7.43-7.41 (m, 2H), 7.25-7.21 (m, 2H), 7.10-7.07 (m, 1H), 5.61-5.43 (m, 2H).

Step F: Preparation of (rac-070)

To a solution of 070-5 (2 g, 4.23 mmol) in DMI (20 mL) was added SOCl$_2$ (2.52 g, 21.16 mmol, 1.54 mL) at 0° C. under N$_2$. The mixture was stirred at 40° C. for 1 h. To NH$_3$ in MeOH (7M, 90.78 mL) was added the above mixture dropwise at −10° C. The reaction mixture was stirred at 25° C. for 1 h. The mixture was blended with another batch prepared from 0.1 g of 070-5. The solvents were removed under reduced pressure. The mixture was poured into water (50 mL) and then extracted with EtOAc (50 mL×3). The combined organic phase was washed with brine (50 mL), dried over anhydrous Na$_2$SO$_4$, filtered and concentrated under reduced pressure. The crude was purified by flash chromatography on silica gel (1$^{st}$: MeOH in DCM=0 to 10%; 2$^{nd}$: MeOH in DCM=0 to 5%) to give rac-070 (1.1 g, 2.33 mmol, 52.46% yield) as a brown solid. LCMS R$_t$=3.75 min in 7.0 min chromatography, 10-80CD, ESI calcd. for C$_{29}$H$_{18}$D$_3$N$_6$O [M+H]$^+$ 472.2, found 472.1.

Step G: Preparation of (S)-3-amino-3-(1-(methyl-d$_3$)-1H-imidazol-5-yl)-6-oxa-2(4,6)-quinolina-1,4(1,3)-dibenzenacyclohexaphane-2$^2$ 4$^4$-dicarbonitrile ((S)-070)

rac-070 (200 mg, 424.15 μmol) was purified by SFC (column: DAICEL CHIRALPAK IG (250 mm×30 mm, 10 m); mobile phase: [0.1% NH$_3$H$_2$O EtOH]; B %: 55%-55%, min) to give (S)-070 (28.0 mg, 59.38 μmol, 14.00% yield) as an off-white solid. $^1$H NMR (400 MHz, DMSO-d$_6$) δ=8.36 (d, J=8.8 Hz, 1H), 8.22 (d, J=8.8 Hz, 1H), 8.08 (s, 1H), 7.95 (s, 1H), 7.83 (d, J=8.0 Hz, 1H), 7.56 (s, 1H), 7.52-7.33 (m, 2H), 7.27-7.21 (m, 2H), 7.16-7.06 (m, 2H), 6.42 (s, 1H), 5.59-5.48 (m, 2H), 3.15 (s, 2H). LCMS R$_t$=1.59 min in 3.0 min chromatography, 10-80CD, ESI calcd. for C$_{29}$H$_{18}$D$_3$N$_6$O [M+H]$^+$ 472.2, found 472.1. HPLC R$_t$=3.85 min in 8 min chromatography, 220 nm, purity 100%. Chiral HPLC (S)-070: R$_t$=2.52 min in 4 min (ee 100%) (AD_ETOH_DEA_5-40_4ML_4MIN_5CM), ((R)-070: R$_t$=1.99 min (ee 100%)).

Example 71: Preparation of Compound 71

Scheme 71 - Synthesis of Compound 71

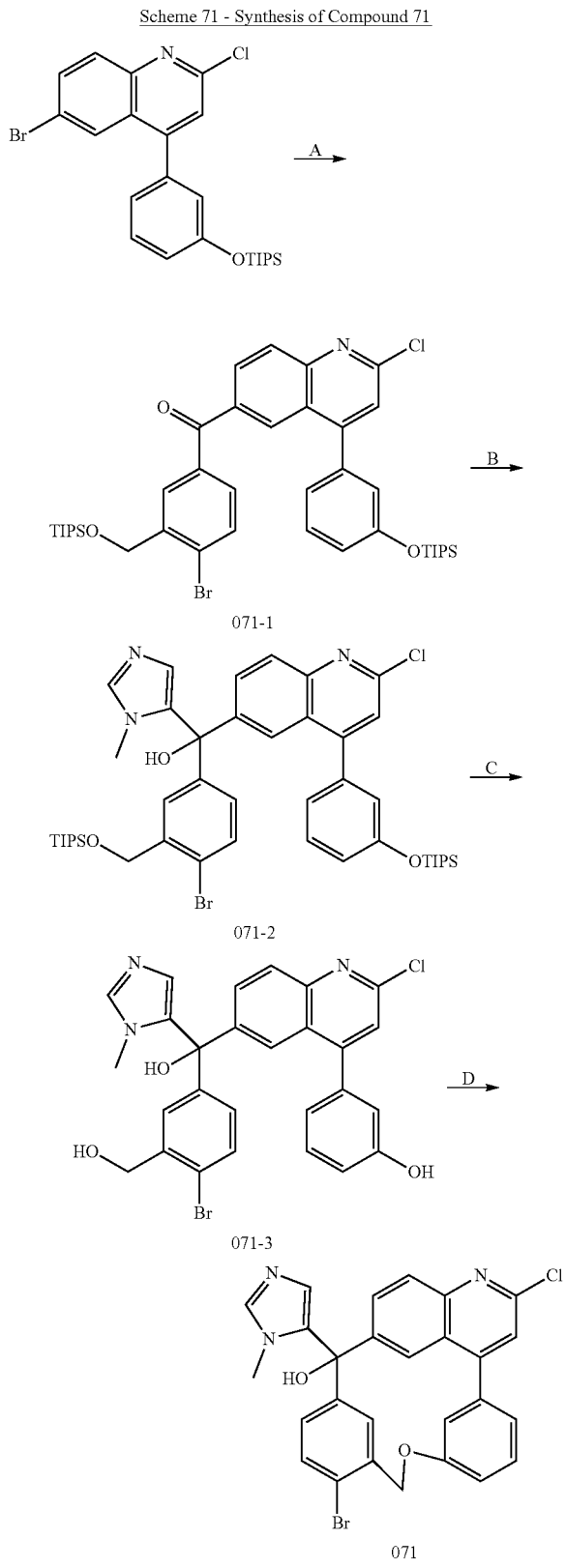

Step A: Preparation of (071-1)

To a solution of 6-bromo-2-chloro-4-(3-((triisopropylsilyl)oxy)phenyl)quinoline (13 g, 26.48 mmol; a TIPS analog of 11A) in THF (130 mL) was added n-BuLi (2.5M in n-hexane, 29.13 mmol, 11.65 mL) at −78° C., the mixture was stirred at −78° C. for 30 min, then 8A (11.51 g, 26.74 mmol) in THF (30 mL) was added at −78° C. The mixture was stirred at −78° C. for 30 min. The mixture was combined with another batch prepared from 10 g of 6-bromo-2-chloro-4-(3-((triisopropylsilyl)oxy) phenyl)quinolone. The reaction mixture was poured into water (100 mL). The aqueous layer was extracted with EtOAc (100 mL×2). The combined organic phase was washed with brine (100 mL), dried over anhydrous $Na_2SO_4$, filtered and concentrated under reduced pressure. The crude was purified by flash chromatography on silica gel (EtOAc in petroleum ether=0 to 5%, twice) to give 071-1 (24 g, 30.71 mmol, 65.55% yield) as yellow oil. $^1$H NMR (400 MHz, $CDCl_3$) δ=8.31 (s, 1H), 8.16-8.07 (m, 1H), 8.07-7.99 (m, 2H), 7.61-7.51 (m, 2H), 7.41-7.37 (m, 1H), 7.37-7.32 (m, 1H), 7.07-6.95 (m, 3H), 4.84-4.74 (m, 2H), 1.34-1.12 (m, 6H), 1.07-1.02 (m, 18H), 0.99-0.89 (m, 18H).

Step B: Preparation of (071-2)

To a solution of 1-methyl-1H-imidazole (2.77 g, 33.79 mmol, 2.69 mL) in redistillation THF (50 mL) was added n-BuLi (2.5M in n-hexane, 33.79 mmol, 13.51 mL) at −78° C. The mixture was stirred at −78° C. for 30 min. Then $Et_3SiCl$ (5.09 g, 33.79 mmol, 5.75 mL) in THF (50 mL) was added to the mixture at −78° C. The mixture was stirred at −78° C. for 30 min. Then n-BuLi (2.5M in n-hexane, 33.79 mmol, 13.51 mL) was added to the mixture at −78° C. The mixture was stirred at −78° C. for 30 min. At last, a solution of 071-1 (24 g, 30.71 mmol) in redistillation THF (200 mL) was added to the mixture at −78° C. The resulting mixture was stirred at −78° C. for 1.5 h. The reaction mixture was poured into water (200 mL). The aqueous layer was extracted with EtOAc (200 mL×2). The combined organic phase was washed with brine (200 mL), dried over anhydrous $Na_2SO_4$, filtered and concentrated under reduced pressure. The crude was purified by flash chromatography on silica gel (MeOH in DCM=0 to 5%, twice) to give 071-2 (16 g, 18.53 mmol, 60.33% yield) as a yellow solid. $^1$H NMR (400 MHz, $CDCl_3$) δ=7.92-7.86 (m, 2H), 7.55 (dd, J=2.0, 9.2 Hz, 1H), 7.37-7.30 (m, 2H), 7.24-7.22 (m, 1H), 7.20-7.06 (m, 4H), 6.87-6.79 (m, 3H), 6.18 (s, 1H), 4.63 (d, J=3.6 Hz, 2H), 3.23 (s, 3H), 1.20-1.14 (m, 3H), 1.03-0.98 (m, 18H), 0.93-0.89 (m, 3H), 0.85-0.81 (m, 18H).

Step C: Preparation of (071-3)

To a solution of 071-2 (16 g, 18.53 mmol) in THF (150 mL) was added TBAF (1M in THF, 27.79 mmol, 27.79 mL) at 0° C. under $N_2$. The mixture was stirred at 25° C. for 2 h The reaction mixture was poured into water (100 mL). The aqueous layer was extracted with EtOAc (100 mL×2). The combined organic phase was washed with brine (100 mL), dried over anhydrous $Na_2SO_4$, filtered and concentrated under reduced pressure. The crude product was triturated with petroleum ether (100 mL) at 25° C. for 30 min to give 071-3 (9 g, 16.34 mmol, 88.18% yield) as a yellow solid. $^1$H NMR (400 MHz, DMSO-$d_6$) δ=9.78 (s, 1H), 7.98 (d, J=8.8 Hz, 1H), 7.82 (d, J=2.0 Hz, 1H), 7.76-7.72 (m, 1H), 7.63 (s, 1H), 7.53-7.44 (m, 3H), 7.32-7.25 (m, 1H), 7.05-6.98 (m, 2H), 6.91 (dd, J=1.6, 8.0 Hz, 1H), 6.87-6.80 (m, 2H), 6.07 (d, J=0.8 Hz, 1H), 5.45-5.34 (m, 1H), 4.49-4.40 (m, 2H), 3.33 (s, 3H).

Step D: Preparation of $4^4$-bromo-$2^2$-chloro-3-(1-methyl-1H-imidazol-5-yl)-6-oxa-2(4,6)-quinolina-1,4(1,3)-dibenzenacyclohexaphan-3-ol (071)

To a solution of 071-3 (16 g, 29.05 mmol) in DMF (250 mL) was added $SOCl_2$ (6.91 g, 58.09 mmol, 4.21 mL) at 0° C. under $N_2$. The mixture was stirred at 25° C. for 2 h. To the above mixture was added $Cs_2CO_3$ (142.00 g, 435.82 mmol) at 25° C. The mixture was stirred at 70° C. for 2 h. After cooling to room temperature, the mixture was filtered and the filtrate was concentrated. The crude product was triturated with $H_2O$ (200 mL) and $CH_3CN$ (100 mL) at 25° C. for 30 min to give 071 (13 g, 24.40 mmol, 83.98% yield) as a yellow solid. 200 mg (375.36 mol) of the product was purified by Prep-HPLC (column: Phenomenex $C_{18\ 80\times40}$ mm×3 m; mobile phase: [water ($NH_3H_2O$)-ACN]; B %: 49%-79%, 8 min) to give 071 (51.0 mg, 95.72 mol, 25.50% yield) as an off-white solid. $^1H$ NMR (400 MHz, DMSO-$d_6$) δ=8.19 (dd, J=2.0, 8.8 Hz, 1H), 8.06 (d, J=9.2 Hz, 1H), 7.71-7.55 (m, 4H), 7.43-7.33 (m, 2H), 7.26-7.13 (m, 3H), 7.10-7.06 (m, 1H), 6.72 (s, 1H), 6.28 (s, 1H), 5.45-5.41 (m, 2H), 3.52 (s, 3H). LCMS $R_t$=2.20 min in 3.0 min chromatography, 10-80CD, ESI calcd. for $C_{27}H_{20}BrClN_3O_2$ $[M+H]^+$ 532.0, found 532.0. HPLC $R_t$=3.64 min in 8 min chromatography, 220 nm, purity 98.59%.

Examples 72 & 73: Preparation of Compound 72 & 73

Scheme 72-Synthesis of Compounds 72 & 73

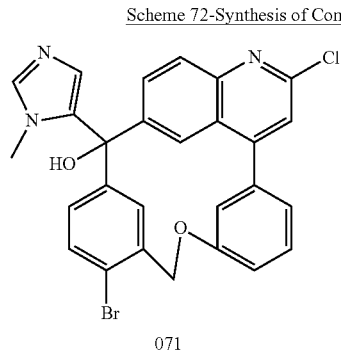

071

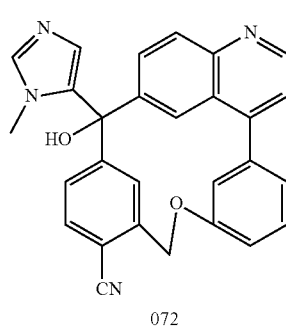

072

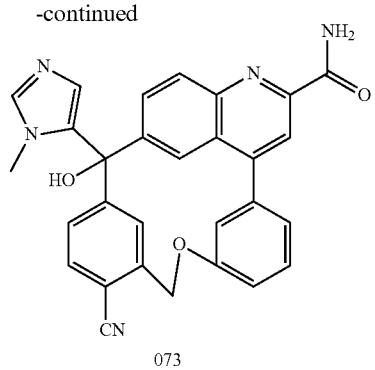

073

Step A: Preparation of 3-hydroxy-3-(1-methyl-1H-imidazol-5-yl)-6-oxa-2(4,6)-quinolina-1,4(1,3)-dibenzenacyclohexaphane-$2^2$ $4^4$-dicarbonitrile (072) & $4^4$-cyano-3-hydroxy-3-(1-methyl-1H-imidazol-5-yl)-6-oxa-2(4,6)-quinolina-1,4(1,3)-dibenzenacyclohexaphane-$2^2$-carboxamide (073)

To a solution of 071 (1 g, 1.88 mmol) in DMF (5 mL) was added $Zn(CN)_2$ (1.2 g, 10.22 mmol) and $Pd(PPh_3)_4$ (433.76 mg, 375.36 μmol) at 25° C. under $N_2$. The mixture was stirred at 100° C. for 12 h. The mixture was cooled to 25° C. and then the mixture was filtered and the filter liquid was concentrated under reduced pressure. The crude product was triturated with petroleum ether:EtOAC=5:1 (10 mL) at 25° C. for 30 min and then MeOH: $H_2O$=10:1 (20 mL) at 25° C. for 30 min to give 072 and 073 (500 mg, 1.03 mmol, 54.65% yield) as a yellow solid, which was purified by Prep-HPLC (column: Phenomenex $C_{18\ 80\times40}$ mm×3 m; mobile phase: [water ($NH_3H_2O$)-ACN]; B %: 37%-67%, 8 min) to give 072 (38.5 mg, 78.97 μmol, 7.70% yield) as an off-white solid and 073 (44.1 mg, 93.93 μmol, 9.16% yield) as an off-white solid. 072: $^1H$ NMR (400 MHz, DMSO-$d_6$) δ=8.36-8.22 (m, 2H), 8.10 (s, 1H), 7.88-7.79 (m, 2H), 7.60 (s, 1H), 7.51-7.40 (m, 2H), 7.27-7.21 (m, 2H), 7.16 (s, 1H), 7.14-7.09 (m, 1H), 7.01 (s, 1H), 6.32 (s, 1H), 5.59-5.49 (m, 2H), 3.54 (s, 3H). LCMS $R_t$=1.87 min in 3.0 min chromatography, 10-80CD, ESI calcd. for $C_{29}H_{20}N_5O_2$ $[M+H]^+$ 470.2, found 470.1. HPLC $R_t$=3.84 min in 8 min chromatography, 220 nm, purity 96.87%. 073: $^1H$ NMR (400 MHz, DMSO-$d_6$) δ=8.30-8.18 (m, 4H), 7.90-7.75 (m, 2H), 7.67-7.40 (m, 4H), 7.23-7.13 (m, 3H), 7.10 (dd, J=1.6, 8.0 Hz, 1H), 6.92 (s, 1H), 6.34 (s, 1H), 5.54 (s, 2H), 3.54 (s, 3H). LCMS $R_t$=1.62 min in 3.0 min chromatography, 10-80CD, ESI calcd. for $C_{29}H_{22}N_5O_3$ $[M+H]^+$ 488.2, found 488.1. HPLC $R_t$=3.07 min in 8 min chromatography, 220 nm, purity 98.18%.

Example 74: Preparation of Compound 74

Scheme 73-Synthesis of Compound 74

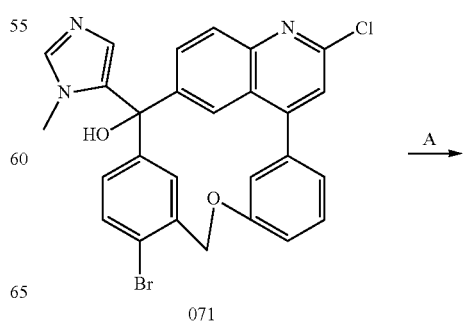

071

275

-continued

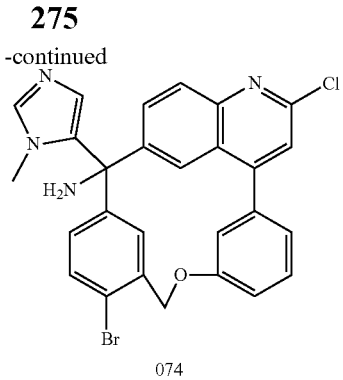

074

Step A: Preparation of 4⁴-bromo-2²-chloro-3-(1-methyl-1H-imidazol-5-yl)-6-oxa-2(4,6)-quinolina-1,4(1,3)-dibenzenacyclohexaphan-3-amine (074)

071 (100 mg, 187.68 µmol) in DMI (1 mL) was added SOCl₂ (111.64 mg, 938.41 mol, 68.07 µL) at 0° C. under N₂. The mixture was stirred at 35° C. for 1 h. To NH₃ in MeOH (7M, 4.02 mL) was added above mixture slowly at −10° C. under N₂. The reaction mixture was stirred at 25° C. for 10 min. The solvents were removed under reduced pressure. The mixture was poured into water (20 mL) and then extracted with EtOAc (20 mL×3). The combined organic phase was washed with brine (20 mL), dried over anhydrous Na₂SO₄, filtered and concentrated under reduced pressure. The crude product was triturated with petroleum ether (5 mL) at 25° C. for 30 min and Prep-HPLC (column: Boston Prime C₁₈ 150×30 mm×5 m; mobile phase: [water (NH₃H₂O+NH₄HCO₃)-ACN]; B %: 60%-90%, 7 min) to give 074 (18.5 mg, 34.79 µmol, 18.50% yield) as an off-white solid. ¹H NMR (400 MHz, DMSO-d₆) δ=8.21 (d, J=8.4 Hz, 1H), 8.03 (d, J=8.8 Hz, 1H), 7.83 (s, 1H), 7.60 (s, 1H), 7.57-7.51 (m, 2H), 7.44-7.32 (m, 2H), 7.27 (s, 1H), 7.18 (d, J=7.6 Hz, 1H), 7.15-6.95 (m, 2H), 6.44 (s, 1H), 5.44 (s, 2H), 3.41 (s, 3H), 2.99 (s, 2H). LCMS $R_t$=2.22 min in 3.0 min chromatography, 10-80CD, ESI calcd. for C₂₇H₂₁BrClN₄O [M+H]⁺ 531.1, found 531.0. HPLC $R_t$=4.63 min in 8 min chromatography, 220 nm, purity 95.10%.

Example 75: Preparation of Compound 75

276

-continued

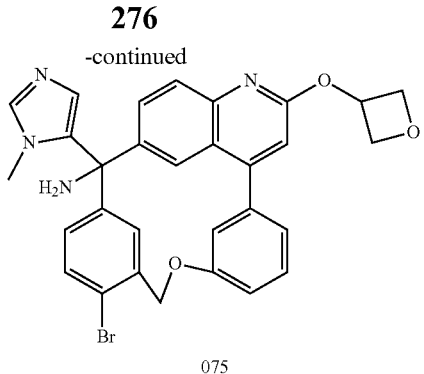

075

Step A: Preparation of 4⁴-bromo-3-(1-methyl-1H-imidazol-5-yl)-2²-(oxetan-3-yloxy)-6-oxa-2(4,6)-quinolina-1,4(1,3)-dibenzenacyclohexaphan-3-amine (075)

To a solution of oxetan-3-ol (73.13 mg, 987.16 µmol) in DMF (3 mL) was added NaH (52.64 mg, 1.32 mmol, 3.13 µL, 60% purity) at 0° C. Then 074 (350 mg, 658.10 µmol) was added to the mixture. The mixture was stirred at 0° C. for 1 h. Water (20 mL) was added to the mixture. The aqueous layer was extracted with EtOAc (15 mL×2). The combined organic layers were washed with brine (30 mL), dried over anhydrous Na₂SO₄, filtered and concentrated to afford 075 (360 mg, 632.19 µmol, 96.06% yield) as a yellow solid. 200 mg (351.22 µmol) of the product was purified by Pre-HPLC (column: Welch Xtimate C₁₈ 150×30 mm×5 m; mobile phase: [water (NH₃H₂O+NH₄HCO₃)-ACN]; B %: 45%-75%, 9 min) to afford 075 (15.4 mg, 27.04 µmol, 7.70% yield) as an off-white solid. ¹H NMR (400 MHz, DMSO-d₆) δ=8.10-8.00 (m, 1H), 7.85-7.76 (m, 2H), 7.57-7.50 (m, 2H), 7.36 (t, J=8.0 Hz, 1H), 7.28-7.20 (m, 2H), 7.17-7.09 (m, 2H), 7.08-6.87 (m, 2H), 6.56-6.35 (m, 1H), 5.84-5.78 (m, 1H), 5.42 (s, 2H), 5.00 (t, J=7.2 Hz, 2H), 4.69-4.64 (m, 2H), 3.35 (s, 3H), 2.89 (s, 2H). LCMS $R_t$=0.75 min in 1.5 min chromatography, 5-95AB, ESI calcd. for C₃₀H₂₆BrN₄O₃ [M+H]⁺ 569.1, found 569.1. HPLC $R_t$=3.78 min in 8 min chromatography, 220 nm, purity 94.48%.

Examples 76 & 77: Preparation of Compound 76 & 77

Scheme 74-Synthesis of Compound 75

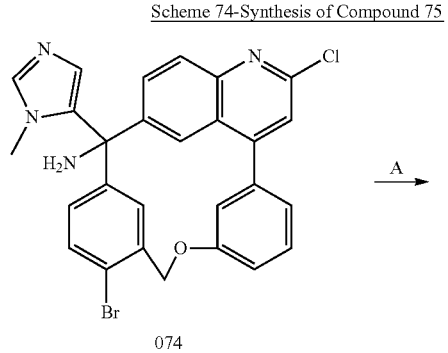

074

Scheme 75-Synthesis of Compounds 76 & 77

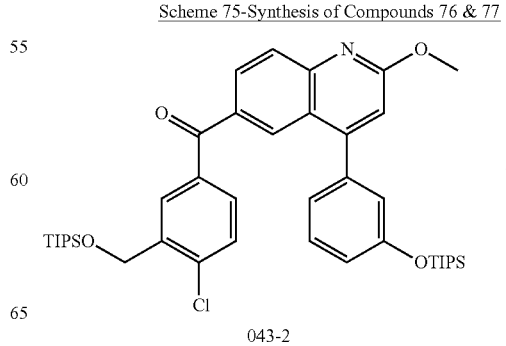

043-2

277
-continued
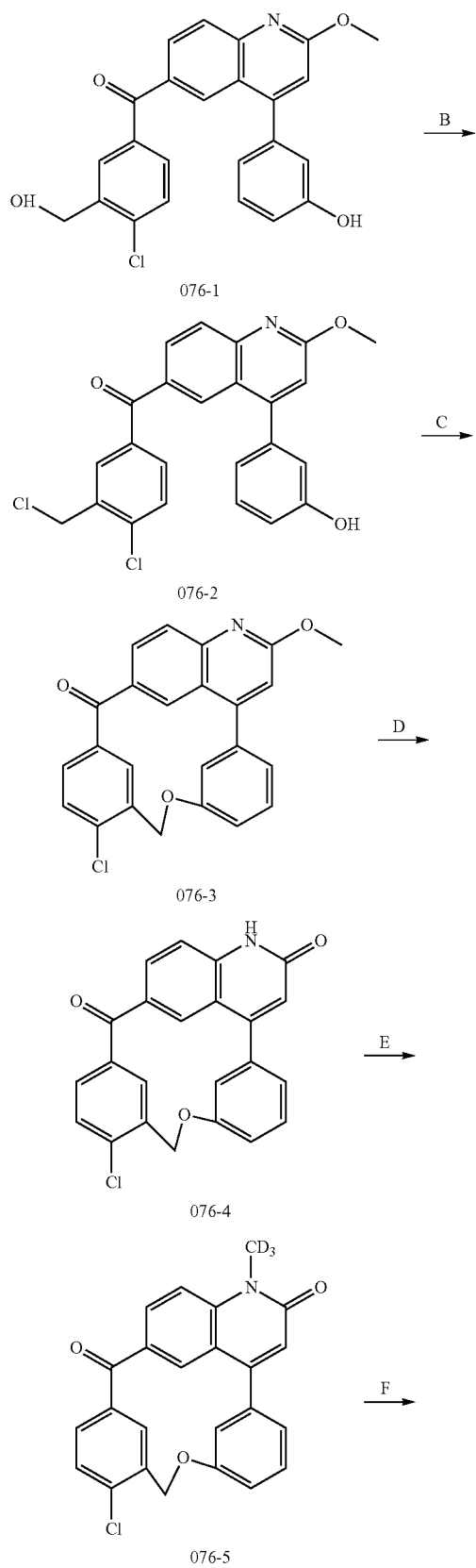
278
-continued
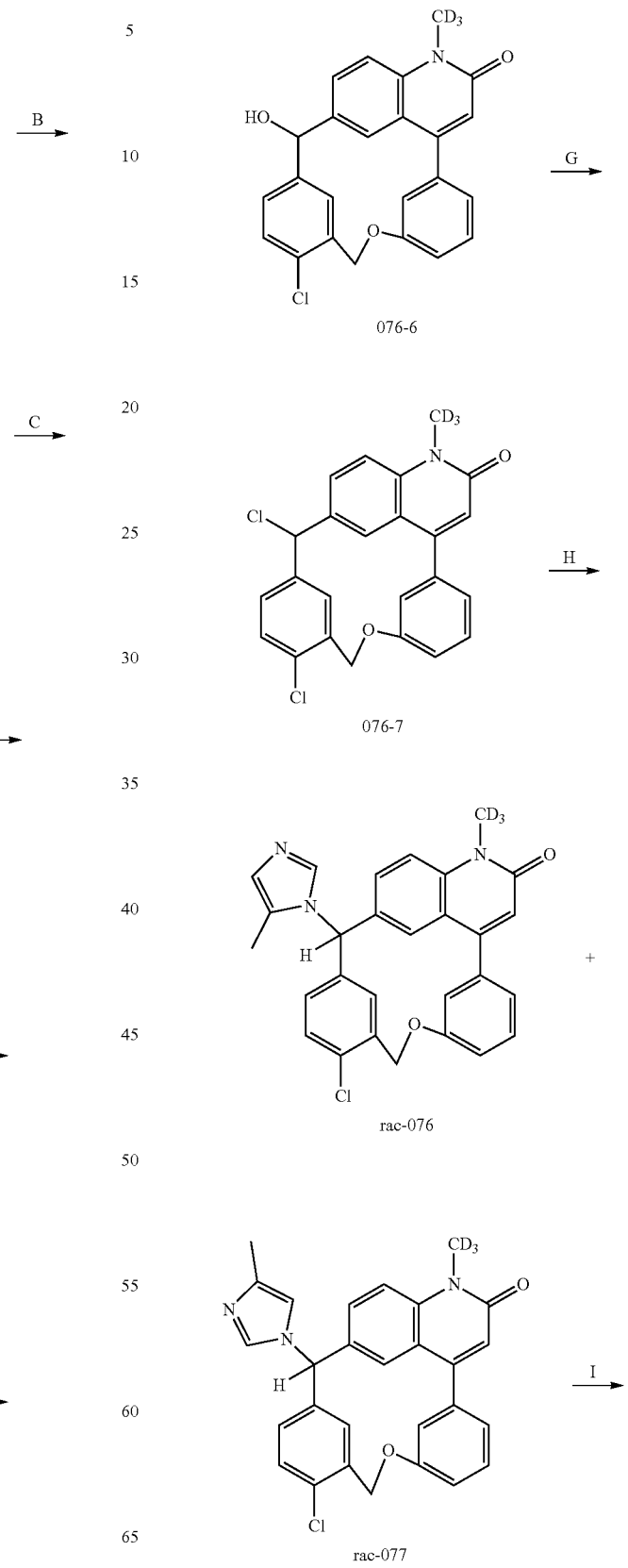

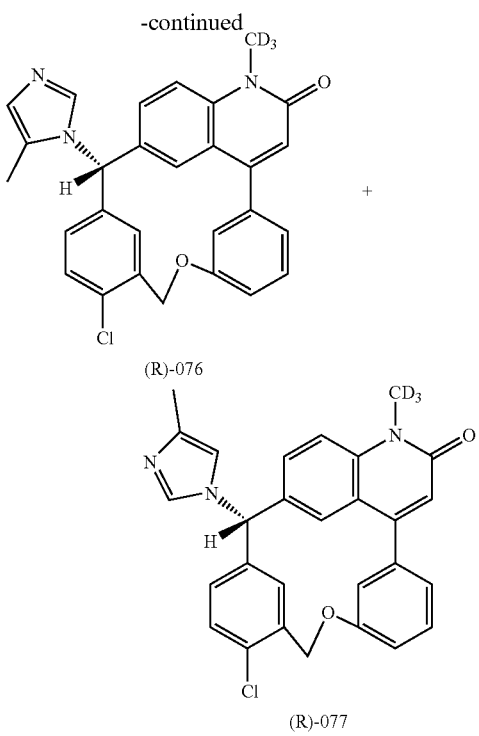

(R)-076

(R)-077

Step A: Preparation of (076-1)

To a solution of 043-2 (29.02 g, 39.62 mmol) in THF (200 mL) was added TBAF (1M in THF, 59.42 mmol, 59.42 mL). The mixture was stirred at 15° C. for 0.5 h. The reaction mixture was adjust pH=8-10 by addition NaOH solution (5M in $H_2O$). The aqueous layer was extracted with EtOAc (200 mL×2). The combined organic layers were washed with brine (100 mL×2), dried over anhydrous $Na_2SO_4$, filtered and the filter cake was washed with EtOAc (50 mL). The combined filtrates were concentrated. The crude product was purified by flash chromatography on silica gel (EtOAc in petroleum ether=0 to 1%) to give 076-1 (12.6 g, 30.01 mmol, 75.75% yield) as a yellow solid. $^1$H NMR (400 MHz, DMSO-$d_6$) δ=9.76 (s, 1H), 8.19 (d, J=1.6 Hz, 1H), 8.09-8.03 (m, 1H), 8.00-7.94 (m, 2H), 7.68 (dd, J=2.0, 8.0 Hz, 1H), 7.62-7.56 (m, 1H), 7.33 (t, J=8.0 Hz, 1H), 7.04-6.87 (m, 4H), 5.60 (s, 1H), 4.65 (s, 2H), 4.06 (s, 3H).

Step B: Preparation of (076-2)

To a solution of 076-1 (5 g, 11.91 mmol) in THF (50 mL) and DMF (10 mL) was added $SOCl_2$ (4.25 g, 35.73 mmol, 2.59 mL). The mixture was stirred at 25° C. for 2 h. The reaction mixture was adjusted pH=8-10 by saturated $NaHCO_3$ solution. The aqueous layer was extracted with EtOAc (100 mL×2). The combined organic layers were washed with brine (50 mL×2), dried over anhydrous $Na_2SO_4$, filtered and the filter cake was washed with EtOAc (20 mL). The combined filtrates were concentrated to afford 076-2 (5.22 g, 11.91 mmol, 100.00% yield) as a yellow solid. LCMS $R_t$=1.03 min in 1.5 min chromatography, 5-95AB, ESI calcd. for $C_{24}H_{18}Cl_2NO_3$ $[M+H]^+$ 438.1, found 438.1.

Step C: Preparation of (076-3)

To a solution of 076-2 (4 g, 9.13 mmol) in DMF (40 mL) and $CH_3CN$ (280 mL) was added $Cs_2CO_3$ (4.46 g, 13.69 mmol). The mixture was stirred at 60° C. for 16 h. The mixture was blended with another batch prepared from 1 g of 076-2. The reaction mixture was filtered through a pad of celite and the filter cake washed with EtOAc (50 mL×3). The filtrate was concentrated. The crude product was purified by flash chromatography on silica gel (EtOAc in DCM=0 to 3%) to give 076-3 (3.2 g, 7.96 mmol, 69.81% yield) as a yellow solid. $^1$H NMR (400 MHz, DMSO-$d_6$) δ=8.39 (d, J=1.6 Hz, 1H), 8.20 (dd, J=2.0, 8.8 Hz, 1H), 8.05 (d, J=2.0 Hz, 1H), 7.98 (d, J=8.4 Hz, 1H), 7.75 (s, 1H), 7.70-7.64 (m, 2H), 7.39 (t, J=8.0 Hz, 1H), 7.23 (s, 1H), 7.17 (d, J=7.2 Hz, 1H), 7.00 (dd, J=2.4, 8.4 Hz, 1H), 5.50 (s, 2H), 4.09 (s, 3H).

Step D: Preparation of (076-4)

To a mixture of 076-3 (3 g, 7.47 mmol) in HCl (4M in $H_2O$, 5.60 mL) and THF (35 mL) was stirred at 70° C. for 12 h. The mixture was concentrated to give 076-4 (2.90 g, 7.47 mmol, 100.00% yield) as an off-white solid. LCMS $R_t$=2.26 min in 4.0 min chromatography, 10-80AB, ESI calcd. for $C_{23}H_{15}ClNO_3$ $[M+H]^+$ 388.1, found 387.7.

Step E: Preparation of (076-5)

To a mixture of 076-4 (2.90 g, 7.47 mmol, 1.87 mL) in THF (30 mL) was added NaOH (4M in $H_2O$, 18.69 mL) and iodomethane-$d_3$ (1.27 g, 8.97 mmol, 546.64 μL) and the mixture was stirred at 25° C. for 1 h. The mixture was filtered. The cake was washed with water (50 mL). The crude was triturated from MeOH (20 mL) to give 076-5 (1.5 g, 3.70 mmol, 49.55% yield) as an off-white solid. LCMS $R_t$=2.53 min in 4.0 min chromatography, 10-80AB, ESI calcd. for $C_{24}H_{14}D_3ClNO_3$ $[M+H]^+$ 405.1, found 404.8.

Step F: Preparation of (076-6)

A mixture of 076-5 (1.5 g, 3.70 mmol) and $NaBH_4$ (280.34 mg, 7.41 mmol) in MeOH (30 mL) and THF (30 mL) was stirred at 25° C. for 1 h. The mixture was concentrated to give 076-6 (1.51 g, 3.70 mmol, 100.00% yield) as an off-white solid. LCMS $R_t$=2.31 min in 4.0 min chromatography, 10-80AB, ESI calcd. for $C_{24}H_{16}D_3ClNO_3$ $[M+H]^+$ 407.1, found 406.8.

Step G: Preparation of (076-7)

A mixture of 076-6 (1.3 g, 3.20 mmol) and $SOCl_2$ (760.24 mg, 6.39 mmol, 463.56 L) in DCM (20 mL) was stirred at 25° C. for 1 h. The mixture was concentrated to give 076-7 (1.36 g, 3.20 mmol, 100.00% yield) as an off-white solid. LCMS $R_t$=2.58 min in 4 min chromatography, 10-80AB, ESI calcd. for $C_{25}H_{18}D_3ClNO_3$ $[M-C_1+OCH_3+H]^+$ 421.1, found 420.8.

Step H: Preparation of (rac-076 and rac-077)

A mixture of 076-7 (500 mg, 1.18 mmol) and 5-methyl-1H-imidazole (4.83 g, 58.78 mmol) was stirred at 100° C. for 12 h. The mixture was poured into water (100 mL) and the mixture was extracted with EtOAc (100 mL). The organic phase was washed with brine (100 mL), dried over anhydrous $Na_2SO_4$, filtered and concentrated. The crude was purified by Pre-HPLC (Phenomenex $C_{18}$ 75×30 mm×3 m; mobile phase: [water($NH_3H_2O+NH_4HCO_3$)-ACN]; B %: 38%-68%, 7 min) to afford rac-076 and rac-077 (200 mg, 424.66 μmol, 36.00% yield) as an off-white solid. $^1$H NMR (400 MHz, DMSO-$d_6$) δ=8.03-7.91 (m, 1H), 7.71-7.47 (m, 2H), 7.45-7.28 (m, 4H), 7.27-7.15 (m, 2H), 7.11-7.05 (m, 1H), 7.00-6.95 (m, 1H), 6.90-6.75 (m, 2H), 6.67 (d, J=3.2 Hz, 1H), 5.47 (d, J=3.2 Hz, 2H), 2.08-2.05 (m, 3H). LCMS $R_t$=1.74 min in 1.5 min chromatography, 10-80CD, ESI calcd. for $C_{28}H_{20}D_3ClN_3O_2$ $[M+H]^+$ 471.2, found 471.3.

Step I: Preparation of (R)-4⁴-chloro-2¹-(methyl-d₃)-3-(5-methyl-1H-imidazol-1-yl)-2¹,2²-dihydro-6-oxa-2(4,6)-quinolina-1,4(1,3)-dibenzenacyclohexaphan-2²-one ((R)-076) & (R)-4⁴-chloro-2¹-(methyl-d₃)-3-(4-methyl-1H-imidazol-1-yl)-2¹,2²-dihydro-6-oxa-2(4,6)-quinolina-1,4(1,3)-dibenzenacyclohexaphan-2²-one ((R)-077)

rac-076 and rac-077 (100 mg, 212.33 μmol) was separated by SFC (column: DAICEL CHIRALPAK AD (250 mm×30 mm, 10 m); mobile phase: [0.1% NH₃H₂O IPA]; B %: 50%-50%, min) to afford (R)-076 (30 mg, 63.70 μmol, 30.00% yield) as an off-white solid, (R)-077 (20.8 mg, 44.16 μmol, 20.80% yield). (R)-076 (30 mg, 63.70 μmol) was purified again by SFC (column: DAICEL CHIRALPAK AD (250 mm×30 mm, 10 m); mobile phase: [0.1% NH₃H₂O IPA]; B %: 45%-45%) to afford (R)-076 (10.2 mg, 21.66 μmol, 34.00% yield) as an off-white solid. (R)-076: ¹H NMR (400 MHz, DMSO-d₆) δ=7.93 (d, J=1.6 Hz, 1H), 7.63 (d, J=8.8 Hz, 1H), 7.54-7.48 (m, 1H), 7.40 (d, J=8.0 Hz, 1H), 7.36-7.29 (m, 2H), 7.27-7.21 (m, 2H), 7.08 (d, J=7.6 Hz, 1H), 7.02-6.96 (m, 1H), 6.83 (s, 1H), 6.76 (s, 1H), 6.68 (s, 2H), 5.48 (s, 2H), 2.17 (s, 3H). LCMS $R_t$=0.72 min in 1.5 min chromatography, 5-95AB, ESI calcd. for $C_{24}H_{14}D_3ClNO_2$ $[M-C_4H_5N_2]^+$ 389.1, found 389.0, $C_{28}H_{19}D_3ClN_3NaO_2$ $[M+Na]^+$ 493.2, found 493.1. HPLC $R_t$=3.64 min in 8 min chromatography, 220 nm, purity 95.00%. Chiral HPLC (R)-076 $R_t$=6.51 min in 9 min (ee 100%), (AD_3_IPA_DEA_40-2.5ML), ((S)-076 $R_t$=3.31 min in 9 min (ee 100%)). (R)-077: ¹H NMR (400 MHz, DMSO-d₆) δ=7.99 (s, 1H), 7.67 (s, 1H), 7.61 (d, J=8.4 Hz, 1H), 7.46-7.38 (m, 2H), 7.37-7.30 (m, 2H), 7.19 (d, J=1.6 Hz, 1H), 7.08 (d, J=7.6 Hz, 1H), 7.00-6.89 (m, 2H), 6.87 (s, 1H), 6.77 (s, 1H), 6.67 (s, 1H), 5.47 (s, 2H), 2.07 (s, 3H). LCMS $R_t$=0.71 min in 1.5 min chromatography, 5-95AB, ESI calcd. for $C_{24}H_{14}D_3ClNO_2$ $[M-C_4H_5N_2]^+$ 389.1, found 389.0, $C_{28}H_{19}D_3ClN_3NaO_2$ $[M+Na]^+$493.2, found 493.1. HPLC $R_t$=3.62 min in 8 min chromatography, 220 nm, purity 99.70%. Chiral HPLC (R)-077 $R_t$=7.27 min in 9 min (ee 98.58%), (AD_3_IPA_DEA_40-2.5ML), ((S)-077 $R_t$=3.77 min in 9 min (ee 99.30%)).

Example 78—Preparation of Compound 78

Scheme 76-Synthesis of Compound 78

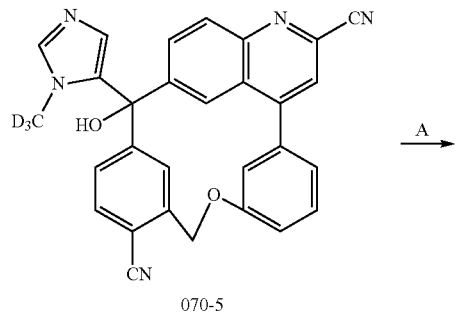

070-5

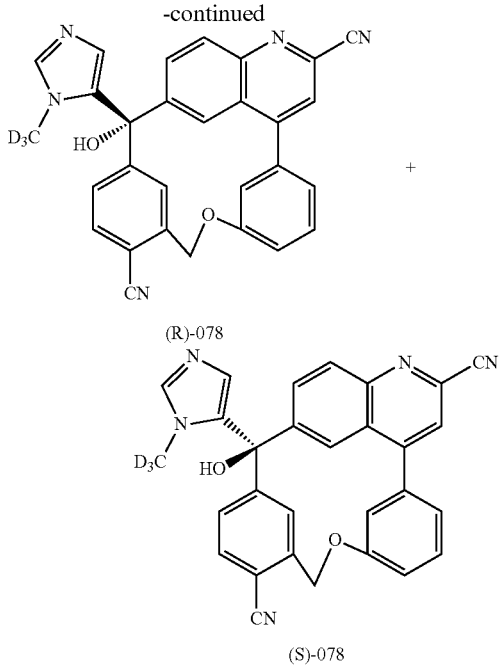

Step A: Preparation of (R)-3-hydroxy-3-(1-(methyl-d₃)-1H-imidazol-5-yl)-6-oxa-2(4,6)-quinolina-1,4(1,3)-dibenzenacyclohexaphane-2² 4⁴-dicarbonitrile ((R)-078) & (S)-3-hydroxy-3-(1-(methyl-d₃)-1H-imidazol-5-yl)-6-oxa-2(4,6)-quinolina-1,4(1,3)-dibenzenacyclohexaphane-2² 4⁴-dicarbonitrile ((S)-078)

070-5 (1.3 g, 2.76 mmol) was purified by SFC (column: DAICEL CHIRALPAK IG (250 mm×30 mm, 10 m); mobile phase: [0.1% NH₃H₂O EtOH]; B %: 55%-55%, min) to give (R)-078 (100 mg, 211.64 μmol, 7.68% yield) and (S)-078 (105 mg, 222.22 μmol, 8.06% yield) both as off-white solid. (R)-078 (100 mg, 211.64 μmol) in MeOH (2 mL) was decolorized by active carbon and purified by SFC (column: DAICEL CHIRALCEL OJ (250 mm×30 mm, 10 m); mobile phase: [0.1% NH₃H₂O EtOH]; B %: 40%-40%, min) to give (R)-078 (43.3 mg, 91.64 μmol, 43.30% yield) as an off-white solid. (S)-078 (105.00 mg, 222.22 μmol) in MeOH (5 mL) was decolorized by active carbon to obtain (S)-078 (54.1 mg, 114.49 μmol, 51.52% yield) as an off-white solid. (R)-078: ¹H NMR (400 MHz, DMSO-d₆) δ=8.33-8.23 (m, 2H), 8.10 (s, 1H), 7.88-7.79 (m, 2H), 7.60 (s, 1H), 7.51-7.39 (m, 2H), 7.28-7.21 (m, 2H), 7.16 (s, 1H), 7.11 (dd, J=2.0, 8.4 Hz, 1H), 7.00 (s, 1H), 6.32 (s, 1H), 5.54 (d, J=2.4 Hz, 2H). LCMS $R_t$=1.60 min in 3 min chromatography, 10-80CD, ESI calcd. for $C_{29}H_{17}D_3N_5O_2$ $[M+H]^+$ 473.2, found 473.1. HPLC $R_t$=3.39 min in 8 min chromatography, 220 nm, purity 98.95%. Chiral HPLC (R)-078 $R_t$=1.10 min in 8 min (ee 100%), (IG_3_EtOH_DEA_40-28ML). (S)-078: ¹H NMR (400 MHz, DMSO-d₆) δ=8.32-8.24 (m, 2H), 8.10 (s, 1H), 7.89-7.80 (m, 2H), 7.61 (s, 1H), 7.51-7.39 (m, 2H), 7.26-7.22 (m, 2H), 7.16 (s, 1H), 7.11 (dd, J=2.0, 8.4 Hz, 1H), 7.00 (s, 1H), 6.32 (s, 1H), 5.54 (d, J=2.4 Hz, 2H). LCMS $R_t$=1.60 min in 3 min chromatography, 10-80CD, ESI calcd. for $C_{29}H_{17}D_3N_5O_2$ $[M+H]^+$ 473.2, found 473.0. HPLC $R_t$=2.81 min in 8 min chromatography, 220 nm, purity 98.87%. Chiral HPLC (S)-078 $R_t$=1.69 min in 8 min (ee 98.52%), (IG_3_EtOH_DEA_40-28ML).

Examples 79 and 80—Preparation of Compounds 79 and 80

(R)-4⁴-chloro-2¹-(methyl-d₃)-3-(5-methyl-1H-1,2,4-triazol-1-yl)-2¹,2²-dihydro-6-oxa-2(4,6)-quinolina-1,4(1,3)-dibenzenacyclohexaphan-2²-one ((R)-079) & (S)-4⁴-chloro-2¹-(methyl-d₃)-3-(5-methyl-1H-1,2,4-triazol-1-yl)-2¹,2²-dihydro-6-oxa-2(4,6)-quinolina-1,4(1,3)-dibenzenacyclohexaphan-2²-one ((S)-079)

(R)-4⁴-chloro-2¹-(methyl-d₃)-3-(3-methyl-1H-1,2,4-triazol-1-yl)-2¹,2²-dihydro-6-oxa-2(4,6)-quinolina-1,4(1,3)-dibenzenacyclohexaphan-2²-one ((R)-080) & (S)-4⁴-chloro-2¹-(methyl-d₃)-3-(3-methyl-1H-1,2,4-triazol-1-yl)-2¹,2²-dihydro-6-oxa-2(4,6)-quinolina-1,4(1,3)-dibenzenacyclohexaphan-2²-one ((S)-080)

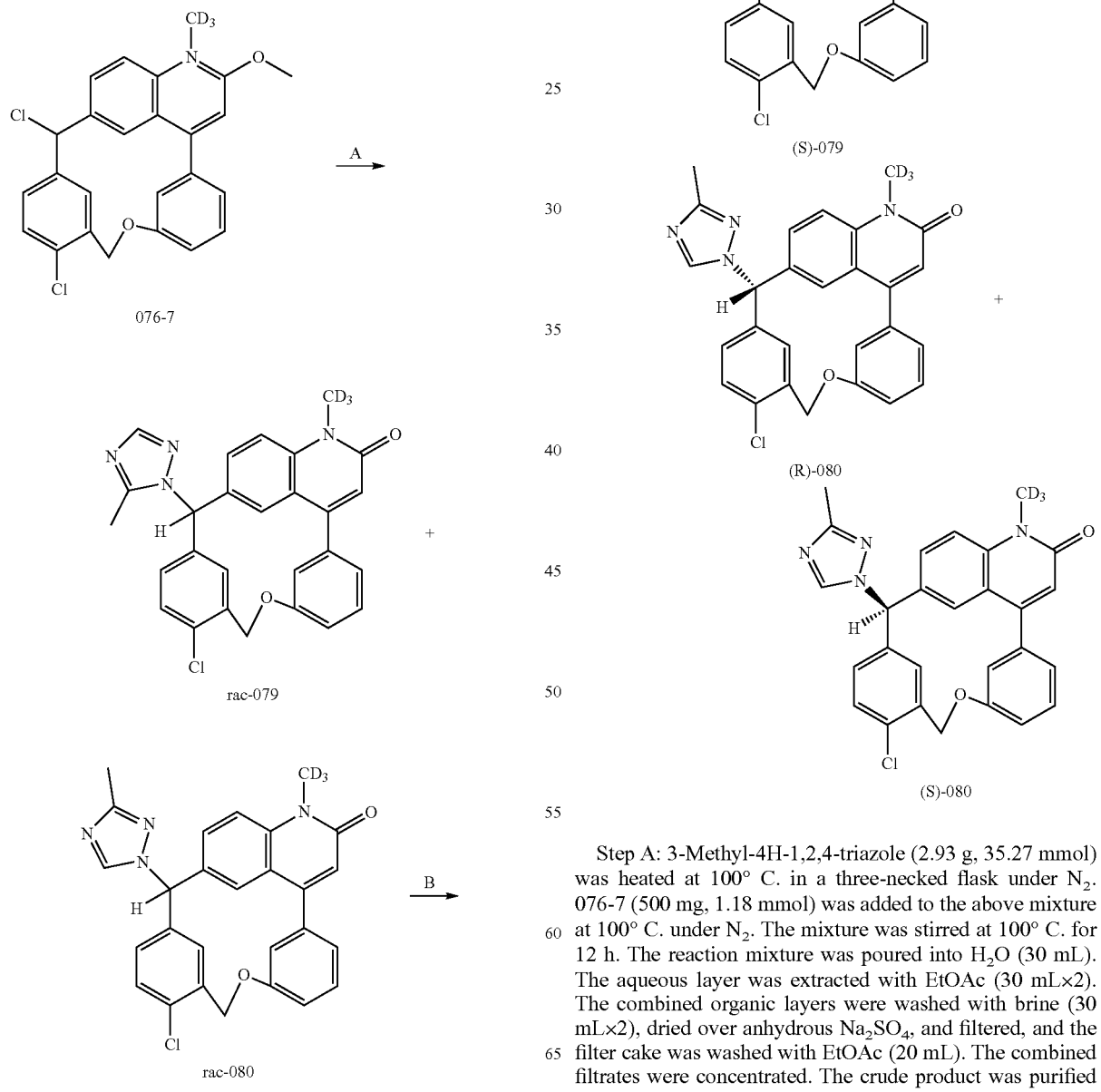

Step A: 3-Methyl-4H-1,2,4-triazole (2.93 g, 35.27 mmol) was heated at 100° C. in a three-necked flask under N₂. 076-7 (500 mg, 1.18 mmol) was added to the above mixture at 100° C. under N₂. The mixture was stirred at 100° C. for 12 h. The reaction mixture was poured into H₂O (30 mL). The aqueous layer was extracted with EtOAc (30 mL×2). The combined organic layers were washed with brine (30 mL×2), dried over anhydrous Na₂SO₄, and filtered, and the filter cake was washed with EtOAc (20 mL). The combined filtrates were concentrated. The crude product was purified by prep-HPLC (column: Xtimate C₁₈ 150×40 mm×10 m;

mobile phase: [water (NH$_3$H$_2$O+NH$_4$HCO$_3$)-ACN]; B %: 33%-63%, 7 min) to give rac-079 and rac-080 (200 mg, 423.77 μmol, 35.91% yield) as an off-white solid. LCMS R$_t$=1.64 min in 3 min chromatography, 10-80CD, ESI calcd. for C$_{27}$H$_{19}$D$_3$ClN$_4$O$_2$ [M+H]$^+$ 471.2, found 471.3.

Step B: rac-079 and rac-080 (200.00 mg, 423.77 μmol) were separated by SFC (column: DAICEL CHIRALCEL OJ (250 mm×30 mm, 10 m); mobile phase: [0.1% NH$_3$H$_2$O MeOH]; B %: 35%-35%) to give (S)-079 (20.9 mg, 44.28 μmol, 10.45% yield), (S)-080 and (R)-079 (60 mg, 127.13 μmol, 30.00% yield) and (R)-080 (60 mg, 127.13 μmol, 30.00% yield) both as off-white solid. (S)-080 and (R)-079 (50 mg, 105.94 μmol) were purified by SFC (column: DAICEL CHIRALPAK AD (250 mm×30 mm, 10 m); mobile phase: [0.1% NH$_3$H$_2$O EtOH]; B %: 55%-55%, min) to give (S)-080 (30.0 mg, 63.57 μmol, 60.00% yield) and (R)-079 (15.4 mg, 32.63 μmol, 30.80% yield) both as off-white solid. (R)-080 (50.00 mg, 105.94 μmol) was separated by SFC (column: DAICEL CHIRALCEL OD (250 mm×30 mm, 10 m); mobile phase: [0.1% NH$_3$H$_2$O EtOH]; B %: 50%-50%, 70 min) to give (R)-080 (30.7 mg, 65.05 μmol, 61.40% yield) as an off-white solid. (R)-079: $^1$H NMR (400 MHz, DMSO-d$_6$) δ=7.96 (s, 1H), 7.78 (s, 1H), 7.56 (d, J=8.8 Hz, 1H), 7.41 (d, J=8.0 Hz, 1H), 7.34 (t, J=8.0 Hz, 2H), 7.27 (s, 1H), 7.20 (s, 1H), 7.14-7.04 (m, 2H), 7.02-6.81 (m, 2H), 6.65 (s, 1H), 5.57-5.42 (m, 2H), 2.60 (s, 3H). LCMS R$_t$=1.90 min in 3 min chromatography, 10-80CD, ESI calcd. for C$_{27}$H$_{19}$D$_3$ClN$_4$O$_2$ [M+H]$^+$ 472.2, found 472.1. HPLC R$_t$=3.83 min in 8 min chromatography, 220 nm, purity 99.80%. Chiral HPLC (R)-079 R$_t$=4.00 min in 8 min (ee 100%), (OJ_MEOH_DEA_5-40_28ML_8MIN). (S)-079: $^1$H NMR (400 MHz, DMSO-d$_6$) δ=7.95 (s, 1H), 7.78 (s, 1H), 7.55 (d, J=8.8 Hz, 1H), 7.40 (d, J=8.4 Hz, 1H), 7.34 (t, J=8.0 Hz, 2H), 7.26 (s, 1H), 7.20 (s, 1H), 7.14-7.04 (m, 2H), 7.02-6.84 (m, 2H), 6.65 (s, 1H), 5.56-5.38 (m, 2H), 2.60 (s, 3H). LCMS R$_t$=1.91 min in 3 min chromatography, 10-80CD, ESI calcd. for C$_{27}$H$_{19}$D$_3$ClN$_4$O$_2$ [M+H]$^+$ 472.2, found 472.1. HPLC R$_t$=3.83 min in 8 min chromatography, 220 nm, purity 97.38%. Chiral HPLC (S)-079 R$_t$=3.56 min in 8 min (ee 96.65%), (OJ_MEOH_DEA_5-40_28ML_8MIN). (R)-080: $^1$H NMR (400 MHz, DMSO-d$_6$) δ=8.54 (s, 1H), 7.97 (s, 1H), 7.58 (d, J=8.8 Hz, 1H), 7.45-7.26 (m, 4H), 7.21 (s, 1H), 7.12-7.05 (m, 2H), 7.03-6.85 (m, 2H), 6.66 (s, 1H), 5.58-5.40 (m, 2H), 2.22 (s, 3H). LCMS R$_t$=1.94 min in 3 min chromatography, 10-80CD, ESI calcd. for C$_{27}$H$_{19}$D$_3$ClN$_4$O$_2$ [M+H]$^+$ 472.2, found 472.1. HPLC R$_t$=3.88 min in 8 min chromatography, 220 nm, purity 96.89%. Chiral HPLC (R)-080 R$_t$=5.13 min in 8 min (ee 99.62%), (OJ_MEOH_DEA_5-40_28ML_8MIN). (S)-080: $^1$H NMR (400 MHz, DMSO-d$_6$) δ=8.55 (s, 1H), 7.98 (s, 1H), 7.58 (d, J=8.8 Hz, 1H), 7.46-7.26 (m, 4H), 7.21 (d, J=1.2 Hz, 1H), 7.13-7.05 (m, 2H), 7.04-6.87 (m, 2H), 6.66 (s, 1H), 5.55-5.42 (m, 2H), 2.23 (s, 3H). LCMS R$_t$=1.91 min in 3 min chromatography, 10-80CD, ESI calcd. for C$_{27}$H$_{19}$D$_3$ClN$_4$O$_2$ [M+H]$^+$ 472.2, found 472.1. HPLC R$_t$=3.88 min in 8 min chromatography, 220 nm, purity 99.06%. Chiral HPLC (S)-080 R$_t$=4.03 min in 8 min (ee 99.62%), (OJ_MEOH_DEA_5-40_28ML_8MIN).

Example 81—Preparation of Compound 81

4$^4$-bromo-2$^2$-chloro-3-(1-methyl-1H-imidazol-5-yl)-6-oxa-2(4,6)-quinazolina-1,4(1,3)-dibenzenacyclohexaphan-3-ol (081)

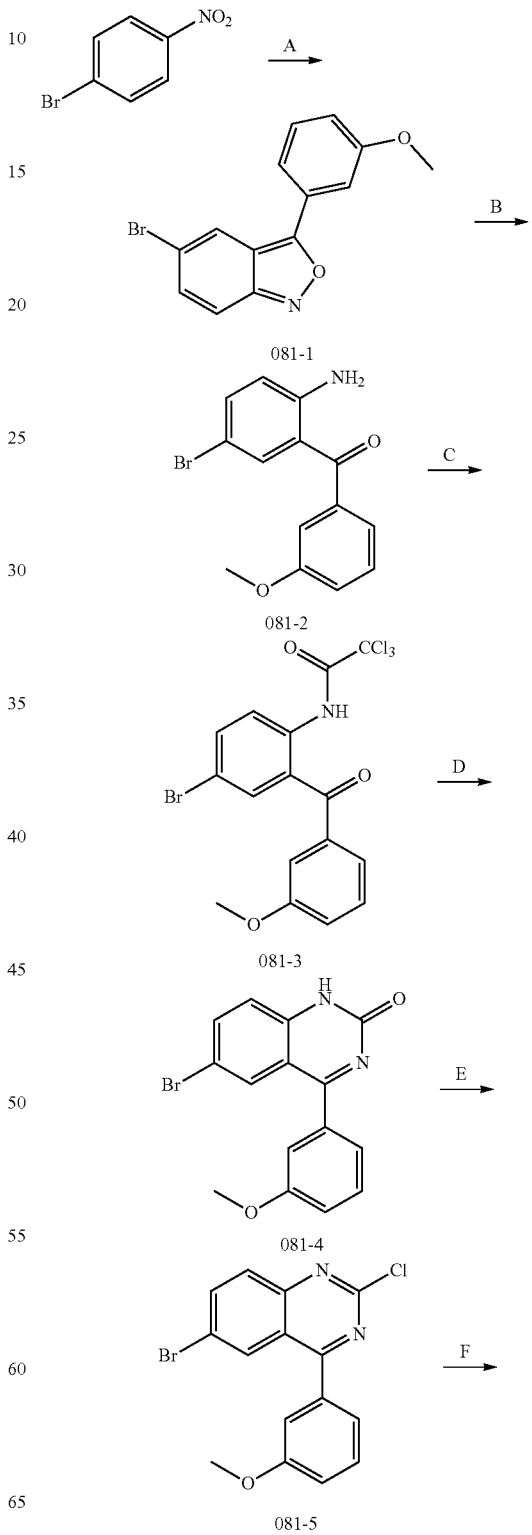

Scheme 78-Synthesis of Compound 081

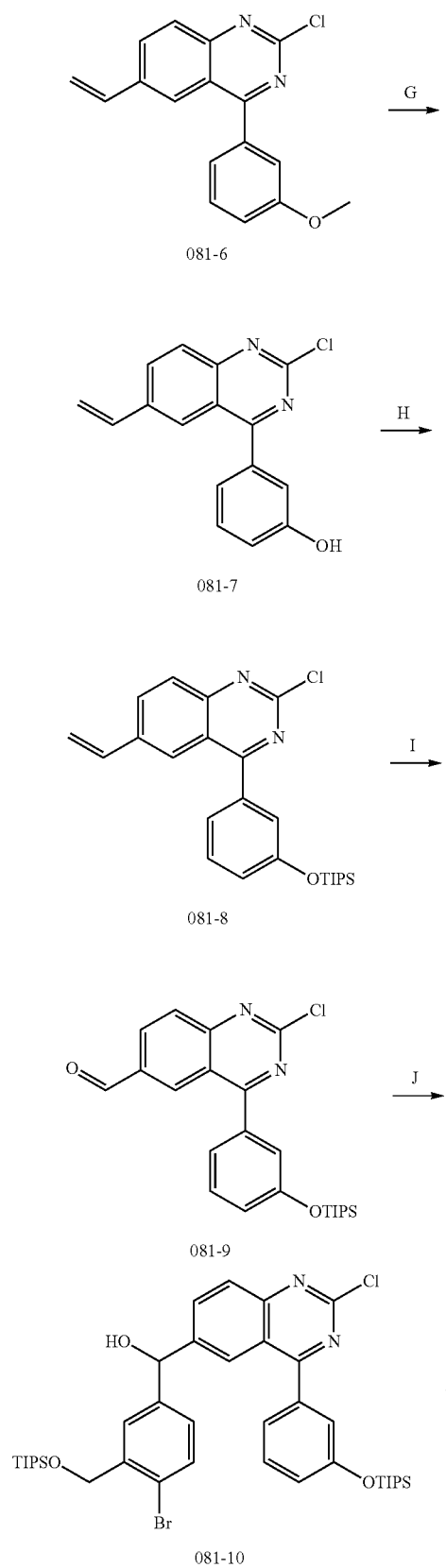
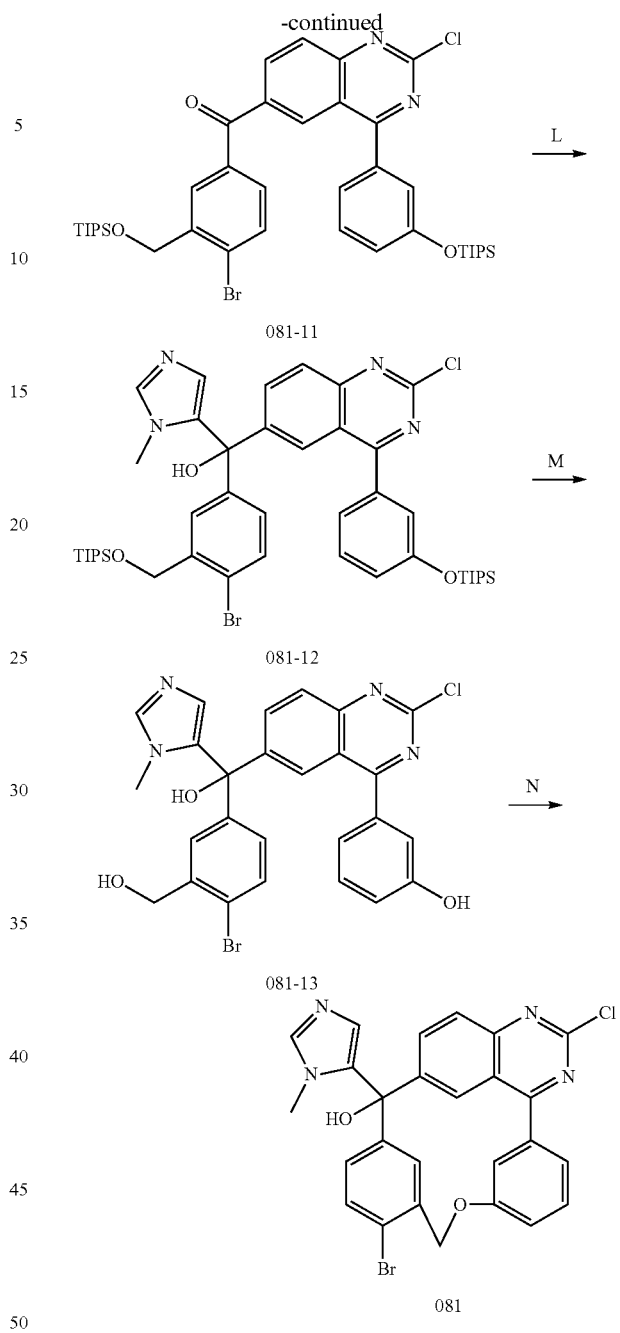

Step A: NaOH (99.00 g, 2.48 mol) was dissolved in MeOH (400 mL) and was stirred at 20° C. for 1 h under N$_2$. 1-Bromo-4-nitrobenzene (100 g, 495.04 mmol) was added, followed by 2-(3-methoxyphenyl)acetonitrile (145.71 g, 990.07 mmol, 134.92 mL) dropwise and the mixture was stirred vigorously at 20° C. for 16 h. The mixture was poured into ice-water (500 mL). The suspension was filtered. The product was triturated with water (300 mL) at 20° C. for 1 h and CH$_3$CN (400 mL, twice) at 20° C. for 2 h and then filtered and washed with CH$_3$CN (50 mL×2) to afford 081-1 (120 g, 394.56 mmol, 79.70% yield) as a yellow solid. $^1$H NMR (400 MHz, CDCl$_3$) δ=8.01 (s, 1H), 7.64-7.43 (m, 4H), 7.36 (dd, J=1.6, 9.6 Hz, 1H), 7.10-7.03 (m, 1H), 3.91 (s, 3H).

Step B: To a mixture of 081-1 (50 g, 164.40 mmol) in THF (300 mL) was added TiCl$_3$ (20% in HCl; 380.32 g, 493.20 mmol, 316.93 mL) in portions at 20° C. The mixture was stirred at 20° C. for 16 h. The mixture was poured into ice-water (200 mL). The aqueous layer was extracted with DCM (200 mL×3). The combined organic layers were washed with brine (100 mL×3), dried over anhydrous $Na_2SO_4$, filtered and concentrated to give 081-2 (50 g, 163.32 mmol, 99.34% yield) as a brown solid was used directly without further purification. $^1$H NMR (400 MHz, DMSO-$d_6$) δ=7.48-7.38 (m, 2H), 7.33-7.28 (m, 1H), 7.21-7.14 (m, 1H), 7.11-7.05 (m, 2H), 6.85 (dd, J=9.2, 1.2 Hz, 1H), 3.80 (s, 3H). LCMS $R_t$=0.87 min in 1.5 min chromatography, 5-95AB, ESI calcd. for $C_{14}H_{13}NO_2Br$ [M+H]$^+$ 306.0, found 305.9.

Step C: To a mixture of 081-2 (50 g, 163.32 mmol) in DCM (400 mL) were added 2,2,2-trichloroacetyl chloride (44.54 g, 244.97 mmol, 27.33 mL) and $Et_3N$ (33.05 g, 326.63 mmol, 45.46 mL). The mixture was stirred at 25° C. for 12 h. The mixture was poured into ice-water (200 mL). The aqueous layer was extracted with DCM (200 mL×2). The combined organic layers were washed with brine (50 mL×3), dried over anhydrous $Na_2SO_4$, filtered and concentrated. The product was blended with another batch prepared from 9 g of 081-2. The mixture was purified by flash chromatography on silica gel (EtOAc in petroleum ether=20% to 100%) to afford 081-3 (70 g, 155.03 mmol, 80.44% yield) as a yellow oil. $^1$H NMR (400 MHz, DMSO-$d_6$) δ=11.17 (s, 1H), 7.98-7.78 (m, 1H), 7.67 (d, J=2.4 Hz, 1H), 7.54 (d, J=8.4 Hz, 1H), 7.42 (s, 1H), 7.22 (dd, J=2.0, 7.6 Hz, 2H), 7.16 (d, J=1.6 Hz, 1H), 3.80-3.76 (m, 3H). LCMS $R_t$=1.0 min in 1.5 min chromatography, 5-95AB, ESI calcd. for $C_{16}H_{12}BrCl_3NO_3$ [M+H]$^+$ 449.9, found 449.8.

Step D: To a mixture of 081-3 (70 g, 155.03 mmol) in HMPA (500 mL) was added $NH_{40}Ac$ (23.90 g, 310.06 mmol) at 20° C. The mixture was stirred at 100° C. for 12 h. The mixture was poured into water (30 mL) and stirred at 20° C. for 20 min. The precipitate was filtered. The filter cake was triturated with water (200 mL) and $CH_3CN$ (50 mL×2) at 20° C. for 0.5 h, which was dried in oven at 50° C. for 24 h to afford 081-4 (48 g, 144.94 mmol, 93.49% yield) as a yellow solid. $^1$H NMR (400 MHz, DMSO-$d_6$) δ=12.1 (br s, 1H), 7.91 (dd, J=2.0, 8.8 Hz, 1H), 7.69 (d, J=2.0 Hz, 1H), 7.58-7.47 (m, 1H), 7.33 (d, J=8.8 Hz, 1H), 7.26-7.15 (m, 3H), 3.84 (s, 3H). LCMS $R_t$=0.80 min in 1.5 min chromatography, 5-95AB, ESI calcd. for $C_{15}H_{12}BrN_2O_2$ [M+H]$^+$ 331.0, found 331.0.

Step E: To a mixture of 081-4 (30 g, 90.59 mmol) in $CH_3CN$ (200 mL) was added $POCl_3$ (60 mL). The mixture was stirred at 100° C. for 18 h. After cooling to room temperature, the mixture was concentrated. The mixture was adjusted to pH=9. The aqueous layer was extracted with EtOAc (50 mL×3). The combined organic layers were washed with brine (50 mL×2), dried over anhydrous $Na_2SO_4$, filtered and concentrated. The residue was triturated by EtOAc (30 mL×2) to afford 081-5 (18 g, 51.49 mmol, 56.84% yield) as a yellow solid. $^1$H NMR (400 MHz, DMSO-$d_6$) δ=8.27-8.13 (m, 2H), 8.00 (d, J=9.2 Hz, 1H), 7.62-7.50 (m, 1H), 7.40-7.20 (m, 3H), 3.85 (s, 3H).

Step F: To a mixture of 081-5 (10 g, 28.60 mmol) in dioxane (100 mL) and $H_2O$ (20 mL) were added $K_2CO_3$ (11.86 g, 85.81 mmol), 4,4,5,5-tetramethyl-2-vinyl-1,3,2-dioxaborolane (4.41 g, 28.60 mmol, 4.85 mL) and Pd(dppf)$Cl_2$ (2.09 g, 2.86 mmol), and the mixture was stirred at 90° C. under $N_2$ for 2 h. The reaction mixture was concentrated. Brine (30 mL) was added. The aqueous phase was extracted with EtOAc (30 mL×2). The combined organic layers were dried over anhydrous $Na_2SO_4$, filtered and concentrated. The product was blended with another batch prepared from 10 g of 081-5. The mixture was purified by flash chromatography on silica gel (EtOAc in petroleum ether=0 to 10%) to afford 081-6 (12 g, 40.44 mmol, 70.67% yield) as a brown oil. $^1$H NMR (400 MHz, CDCl$_3$) δ=8.18-7.93 (m, 3H), 7.51 (d, J=8.0 Hz, 1H), 7.40-7.31 (m, 2H), 7.22-7.10 (m, 1H), 6.91-6.76 (m, 1H), 5.97-5.84 (m, 1H), 5.54-5.43 (m, 1H), 3.92 (s, 3H). LCMS $R_t$=5.21 min in 7 min chromatography, 10-80CD, ESI calcd. for $C_{17}H_{14}ClN_{20}$ [M+H]$^+$ 297.1, found 297.1.

Step G: To a solution of 081-6 (6 g, 20.22 mmol) in DCM (80 mL) were added $BCl_3$ (1M in DCM, 121.31 mmol, 121.31 mL) and TBAI (3.73 g, 10.11 mmol) at 0° C. The mixture was stirred at 20° C. for 12 h. The reaction mixture was added into $H_2O$ (100 mL), the aqueous layer was extracted with DCM (50 mL×2). The combined organic layers were washed with brine (50 mL×2), dried over anhydrous $Na_2SO_4$, filtered and concentrated. The product was blended with another batch prepared from 10 g of 081-6 to afford 081-7 (8 g, 28.30 mmol, 69.97% yield) as a yellow oil was used directly without further purification. LCMS $R_t$=0.89 min in 1.5 min chromatography, 5-95AB, ESI calcd. for $C_{16}H_{12}ClN_2O$ [M+H]$^+$ 283.1, found 283.0.

Step H: To a solution of 081-7 (8 g, 28.30 mmol) in DCM (100 mL) was added TIPSCl (6.55 g, 33.96 mmol, 7.27 mL) and 1H-imidazole (5.78 g, 84.89 mmol), and the mixture was stirred at 25° C. for 2 h. Water (50 mL) was added to the mixture. The aqueous layer was extracted with DCM (30 mL×3). The combined organic layers were washed with brine (30 mL×2), dried over anhydrous $Na_2SO_4$, filtered and concentrated. The mixture was purified by flash chromatography on silica gel (EtOAc in petroleum ether=0 to 10%) to afford 081-8 (10 g, 22.78 mmol, 80.52% yield) as a yellow oil. $^1$H NMR (400 MHz, CDCl$_3$) δ=8.11-8.06 (m, 1H), 8.02-7.97 (m, 2H), 7.47-7.40 (m, 1H), 7.37-7.33 (m, 1H), 7.25 (s, 1H), 7.14-7.07 (m, 1H), 6.85-6.74 (m, 1H), 5.93-5.82 (m, 1H), 5.44 (d, J=10.8 Hz, 1H), 1.31-1.27 (m, 3H), 1.16-1.11 (m, 18H).

Step I: To a solution of 081-8 (5 g, 11.39 mmol) in THF (200 mL) and $H_2O$ (70 mL) was added $K_2OsO_4 \cdot 2H_2O$ (209.80 mg, 569.39 μmol) and $NaIO_4$ (12.18 g, 56.94 mmol, 3.16 mL). The mixture was stirred at 25° C. for 0.5 h. The reaction mixture was added $H_2O$ (50 mL). The mixture was extracted with EtOAc (50 mL×2). The combined organic layer was washed with brine (50 mL), dried over anhydrous $Na_2SO_4$, filtered and concentrated. The product was blended with another batch prepared from 5 g of 081-8. The mixture was purified by flash chromatography on silica gel (EtOAc in petroleum ether=0 to 6%) to afford 081-9 (8 g, 18.14 mmol, 79.68% yield) as a yellow oil. $^1$H NMR (400 MHz, CDCl$_3$) δ=10.11 (s, 1H), 8.63 (d, J=1.6 Hz, 1H), 8.41 (dd, J=1.6, 8.8 Hz, 1H), 8.14 (d, J=8.8 Hz, 1H), 7.53-7.43 (m, 1H), 7.41-7.36 (m, 1H), 7.32-7.27 (m, 1H), 7.20-7.13 (m, 1H), 1.30-1.25 (m, 3H), 1.16-1.11 (m, 18H).

Step J: To a solution of ((2-bromo-5-iodobenzyl)oxy)triisopropylsilane (11.3 g, 24.08 mmol) in THF (100 mL) was added n-BuLi (2.5M in hexane, 22.72 mmol, 9.09 mL) at −70° C. and the mixture was stirred for 20 min. The above mixture was added into a solution of 081-9 (3 g, 6.80 mmol) in THF (30 mL) dropwise at −70° C. The mixture was stirred at 25° C. for 20 min. Saturated $NH_4Cl$ solution (100 mL) was added to the mixture. The aqueous layer was extracted with EtOAc (50 mL×2). The combined organic layers were washed with brine (30 mL×2), dried over anhydrous $Na_2SO_4$, filtered and concentrated. The residue was purified by flash chromatography on silica gel (EtOAc in petroleum ether=0 to 8%) to afford 081-10 (3.2 g, 4.08 mmol, 60.00% yield) as a yellow oil. $^1$H NMR (400 MHz, CDCl$_3$) δ=8.25

(s, 1H), 8.05-7.89 (m, 1H), 7.88-7.75 (m, 1H), 7.50-7.28 (m, 5H), 7.20-7.08 (m, 2H), 5.95 (s, 1H), 4.73 (s, 2H), 1.31-1.24 (m, 6H), 1.16-0.96 (m, 36H).

Step K: To a solution of 081-10 (3.2 g, 4.08 mmol) in DCM (32 mL) was added MnO$_2$ (3.55 g, 40.79 mmol) at 25° C. The mixture was stirred at 50° C. for 6 h. The reaction mixture was filtered and concentrated. The mixture was purified by flash chromatography on silica gel (EtOAc in petroleum ether=0 to 8%) to afford 081-11 (2.5 g, 3.20 mmol, 78.43% yield) as a yellow oil. $^1$H NMR (400 MHz, CDCl$_3$) δ=8.55 (d, J=1.6 Hz, 1H), 8.25 (dd, J=1.6, 8.4 Hz, 1H), 8.15-8.05 (m, 1H), 8.01 (s, 1H), 7.65 (d, J=1.2 Hz, 2H), 7.44-7.35 (m, 2H), 7.25-7.24 (m, 1H), 7.13-7.02 (m, 1H), 4.81 (s, 2H), 1.34-1.10 (m, 6H), 1.08-0.95 (m, 36H).

Step L: To a solution of 1-methyl-1H-imidazole (1.15 g, 14.06 mmol, 1.12 mL) in THF (30 mL) was added n-BuLi (2.5M in hexane, 14.06 mmol, 5.62 mL) at −78° C. The mixture was stirred at −78° C. for 0.5 h. Then Et$_3$SiCl (2.12 g, 14.06 mmol, 2.39 mL) in THF (30 mL) was added to the mixture at −78° C. The mixture was stirred at −78° C. for 0.5 h. n-BuLi (2.5M in hexane, 14.06 mmol, 5.62 mL) was added to the mixture. The mixture was stirred at −78° C. for 0.5 h. Then 081-11 (2 g, 2.56 mmol) in THF (30 mL) was added to the mixture at −78° C. The resulting mixture was stirred at −78° C. for 0.5 h. Saturated NH$_4$Cl solution (100 mL) was added to the mixture. The aqueous layer was extracted with EtOAc (40 mL×2). The combined organic layers were washed with brine (20 mL×2), dried over anhydrous Na$_2$SO$_4$, filtered and concentrated. The residue was by flash chromatography on silica gel (MeOH in DCM=0 to 8%) to afford 081-12 (2 g, 2.31 mmol, 90.50% yield) as a yellow oil. $^1$H NMR (400 MHz, CDCl$_3$) δ=7.90 (s, 1H), 7.51 (s, 1H), 7.45-7.35 (m, 3H), 7.25-7.23 (m, 1H), 7.15-7.08 (m, 2H), 7.00 (s, 3H), 6.86 (s, 2H), 5.30 (s, 2H), 3.69 (s, 3H), 1.28-0.95 (m, 6H), 0.94-0.62 (m, 36H).

Step M: To a solution of 081-12 (500 mg, 578.37 μmol) in THF (5 mL) was added TBAF (1M in THF, 1.16 mmol, 1.16 mL) and the mixture was stirred at 25° C. for 12 h. Water (20 mL) was added to the mixture. The aqueous layer was extracted with EtOAc (30 mL×2). The combined organic layers were washed with brine (30 mL×3), dried over anhydrous Na$_2$SO$_4$, filtered and concentrated to afford 081-13 (300 mg, 543.66 μmol, 94.00% yield) as a yellow oil was used directly without further purification. $^1$H NMR (400 MHz, DMSO-d$_6$) δ=9.86 (s, 1H), 8.00 (s, 3H), 7.67 (s, 1H), 7.51 (s, 2H), 7.35-7.30 (m, 1H), 7.13 (s, 2H), 7.07-6.96 (m, 3H), 6.11 (s, 1H), 5.10 (s, 1H), 4.47-4.43 (m, 2H), 3.35 (s, 3H).

Step N: To a solution of 081-13 (100 mg, 181.22 μmol) in DCM (1 mL) and DMF (0.2 mL) was added SOCl$_2$ (32.34 mg, 271.83 μmol, 19.72 μL) and the mixture was stirred at 25° C. for 2 h. The mixture was concentrated. The mixture in DMF (1 mL) was added Cs$_2$CO$_3$ (1.18 g, 3.62 mmol) and the mixture was stirred at 70° C. for 1 h. The mixture was added to water (30 mL) and extracted with DCM (50 mL×2). The combined organic layers were washed with brine (30 mL×2), dried over anhydrous Na$_2$SO$_4$, filtered and concentrated. The mixture was purified by prep-HPLC (column: Welch Xtimate C$_{18\ 150\times30}$ mm×5 μm; mobile phase: [water (NH$_3$H$_2$O+NH$_4$HCO$_3$)-ACN]; B %: 43%-73%, 8 min) to afford 081 (6.0 mg, 11.24 μmol, 6.20% yield) as an off-white solid. $^1$H NMR (400 MHz, DMSO-d$_6$) δ=8.50-8.32 (m, 1H), 8.07 (d, J=9.2 Hz, 1H), 7.74 (s, 1H), 7.65-7.57 (m, 2H), 7.51-7.40 (m, 2H), 7.35 (s, 2H), 7.21-7.09 (m, 2H), 6.86 (s, 1H), 6.29 (s, 1H), 5.52-5.42 (m, 2H), 3.55 (s, 3H). LCMS R$_t$=1.54 min in 3.0 min chromatography, 10-80CD, ESI calcd. for C$_{26}$H$_{19}$BrClN$_4$O$_2$ [M+H]$^+$ 533.0, found 533.0. HPLC R$_t$=3.67 min in 8 min chromatography, 220 nm, purity 100%.

Example 82—Preparation of Compound 82

4$^4$-bromo-3-(1-methyl-1H-imidazol-5-yl)-6-oxa-2(4, 6)-quinazolina-1,4(1,3)-dibenzenacyclohexaphane-2$^2$,3-diamine (082)

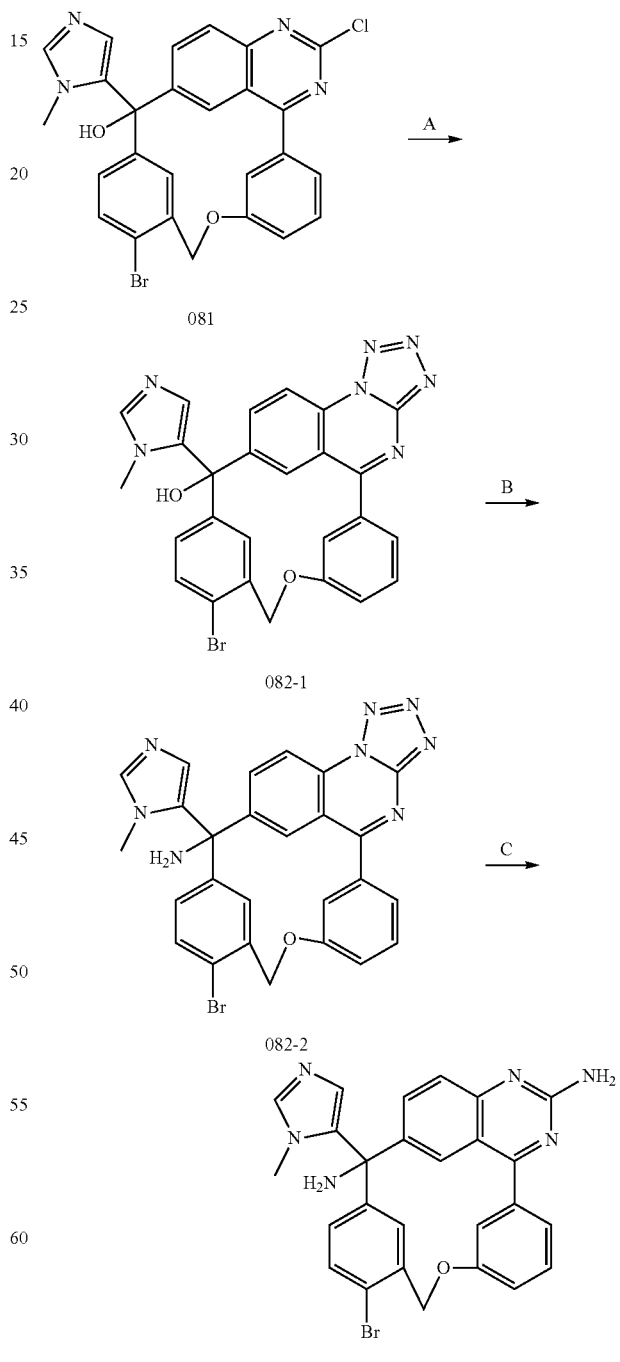

Step A: 081 (400 mg, 749.34 μmol), NaN$_3$ (560.00 mg, 8.61 mmol) in DMA (4 mL) was stirred at 20° C. and 50° C. for 12 h. The mixture was poured into ice water (50 mL) with stirring at 0° C. for 0.5 h. The mixture was purified by flash chromatography on silica gel (MeOH in DCM=0 to 5%) and prep-HPLC (column: Welch Xtimate C$_{18}$ $_{150\times30}$ mm×5 μm; mobile phase: [water (NH$_3$H$_2$O+NH$_4$HCO$_3$)-ACN]; B %: 35%-65%, 8 min) to afford 082-1 (5.9 mg, 10.92 μmol, 1.45% yield) as an off-white solid. $^1$H NMR (400 MHz, DMSO-d$_6$) δ=8.75 (d, J=8.4 Hz, 1H), 8.64-8.56 (m, 1H), 7.72-7.58 (m, 4H), 7.53-7.46 (m, 2H), 7.35 (s, 1H), 7.28-7.19 (m, 2H), 7.01 (s, 1H), 6.27 (s, 1H), 5.57-5.33 (m, 2H), 3.53 (s, 3H). LCMS R$_t$=1.59 min in 3 min chromatography, 10-80CD, ESI calcd. for C$_{26}$H$_{19}$BrN$_7$O$_2$ [M+H]$^+$ 540.1, found 540.2. HPLC R$_t$=3.72 min in 8 min chromatography, 220 nm, purity 97.60%.

Step B: To a solution of 082-1 (195.85 mg, 362.44 μmol) in DMI (2 mL) was added SOCl$_2$ (431.19 mg, 3.62 mmol, 262.92 μL) at 40° C. for 2 h. The above mixture was added into NH$_3$ (7M in MeOH, 30 mL) at 0° C., and the mixture was stirred at 0° C. for 0.5 h. Water (50 mL) was added to the mixture. The aqueous layer was extracted with EtOAc (40 mL×2). The combined organic layers were washed with brine (20 mL×2), dried over anhydrous Na$_2$SO$_4$, filtered and concentrated. The mixture was purified by flash chromatography on silica gel (MeOH in DCM=0 to 8%) to afford 082-2 (80 mg, 148.32 μmol, 40.92% yield) as a yellow solid. LCMS R$_t$=3.12 min in 7.0 min chromatography, 10-80CD, ESI calcd. for C$_{26}$H$_{20}$N$_8$BrO [M+H]$^+$ 539.1, found 539.2.

Step C: To a solution of 082-2 (80 mg, 148.32 μmol) in DMF (1 mL) was added Zn(CN)$_2$ (280 mg, 2.38 mmol, 151.35 μL) and Pd(PPh$_3$)$_4$ (27.34 mg, 74.16 μmol). The mixture was stirred at 100° C. for 2 h under N$_2$. The mixture was filtered. The filtrate was poured into H$_2$O (20 mL), diluted with EtOAc (20 mL) and the aqueous layer was extracted with EtOAc (20 mL×2). The combined organic layers were washed with brine (20 mL×2), dried over anhydrous Na$_2$SO$_4$, filtered and concentrated under reduced pressure. The product was purified by prep-HPLC (column: Boston Prime C$_{18}$ $_{150\times30}$ mm×5 μm; mobile phase: [water (NH$_3$H$_2$O+NH$_4$HCO$_3$)-ACN]; B %: 30%-60%, 10 min) to afford 082 (4.9 mg, 9.54 μmol, 6.44% yield) as an off-white solid. $^1$H NMR (400 MHz, DMSO-d$_6$) δ=8.05 (d, J=7.6 Hz, 1H), 7.86 (s, 1H), 7.57-7.50 (m, 3H), 7.40-7.28 (m, 3H), 7.12-6.94 (m, 3H), 6.68-6.43 (m, 3H), 5.44 (s, 2H), 3.40 (s, 3H). LCMS R$_t$=1.45 min in 3 min chromatography, 10-80CD, ESI calcd. for C$_{26}$H$_{22}$BrN$_6$O [M+H]$^+$ 513.1, found 513.2. HPLC R$_t$=3.36 min in 8 min chromatography, 220 nm, purity 90.32%.

Example 83—Preparation of Compound 83

4$^4$-bromo-3-(1-methyl-1H-imidazol-5-yl)-6-oxa-2(4,6)-isoquinolina-1,4(1,3)-dibenzenacyclohexaphan-3-ol (083)

Scheme 80-Synthesis of Compound 83

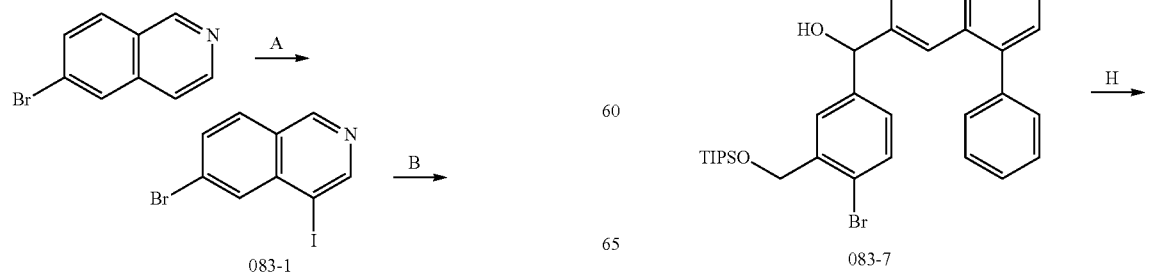

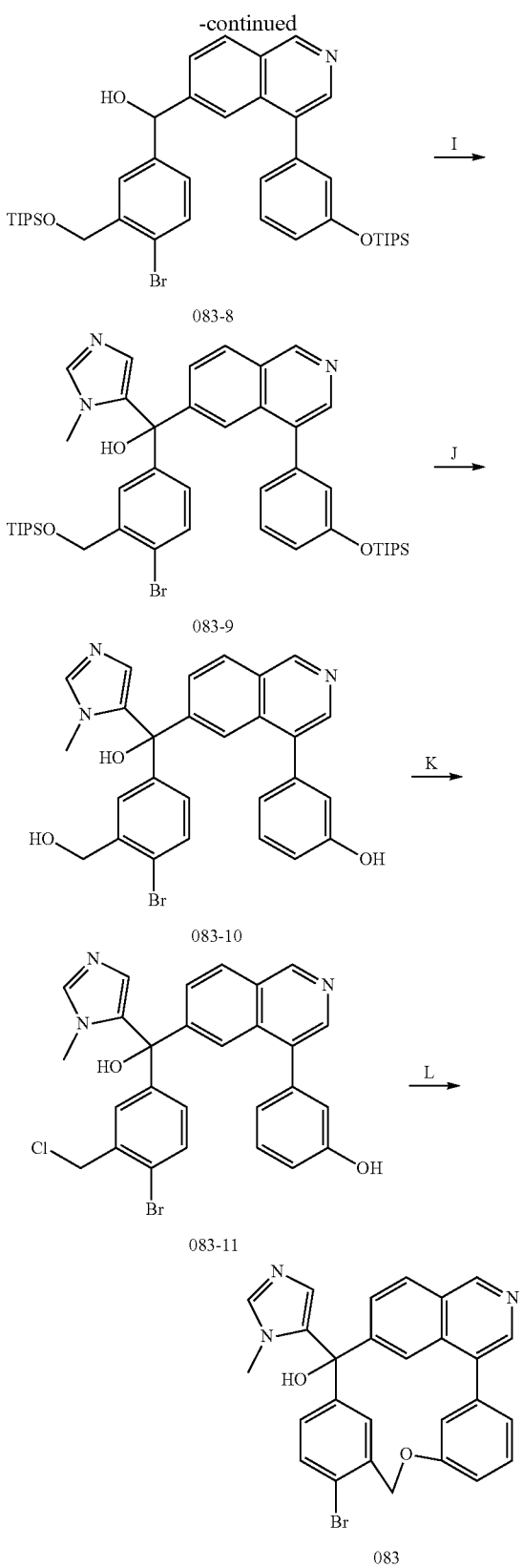

purified by flash chromatography on silica gel (EtOAc in petroleum ether=0 to 30%) to give 083-1 (50 g, 149.72 mmol, 62.30% yield) as yellow solid. $^1$H NMR (400 MHz, CDCl$_3$) δ=9.11 (s, 1H), 8.96 (s, 1H), 8.22 (s, 1H), 7.81-7.72 (m, 2H).

Step B: To a solution of 083-1 (15 g, 44.92 mmol) in DMF (150 mL) was added (3-methoxyphenyl)boronic acid (5.46 g, 35.93 mmol), K2CO$_3$ (12.42 g, 89.83 mmol), H$_2$O (30 mL) and Pd(dppf)Cl$_2$ (1.64 g, 2.25 mmol). The mixture was stirred at 80° C. for 1 h. The reaction mixture was filtered and concentrated. The residue was purified by flash chromatography on silica gel (EtOAc in DCM=0 to 30%) to give 083-2 (9 g, 28.65 mmol, 63.78% yield) as yellow oil. 1H NMR (400 MHz, DMSO-d$_6$) δ=9.35 (s, 1H), 8.48 (s, 1H), 8.17 (d, J=7.6 Hz, 1H), 7.93 (s, 1H), 7.84, (dd, J=1.6 Hz, 8.4 Hz, 1H), 7.49-7.45 (s, 1H), 7.10-7.05 (m, 3H), 3.81 (s, 3H).

Step C: To a solution of 083-2 (4 g, 12.73 mmol) in DCM (80 mL) was added BBr$_3$ (9.57 g, 38.20 mmol, 3.68 mL). The mixture was stirred at 20° C. for 2 h. Water (100 mL) was added to the mixture and the mixture was extracted with EtOAc (100 mL×2). The combined organic phase was washed with brine (100 mL), dried over anhydrous Na$_2$SO$_4$, filtered and concentrated to afford 083-3 (3.5 g, 11.66 mmol, 91.59% yield) as yellow solid was used into next step directly. LCMS R$_t$=0.67 min in 1.5 min chromatography, 5-95AB, ESI calcd. for C$_{15}$H$_{11}$BrNO [M+H]$^+$ 300.0, found 299.7.

Step D: To a solution of 083-3 (3.5 g, 11.66 mmol) in THF (10 mL) was added TIPSCl (6.74 g, 34.98 mmol, 7.49 mL) and 1H-imidazole (2.38 g, 34.98 mmol). The mixture was stirred at 25° C. for 8 h. The mixture was quenched with water (5 mL). The mixture was extracted with EtOAc (20 mL×2). The combined organic layers were washed with brine (10 mL×2), dried over anhydrous Na$_2$SO$_4$, filtered and concentrated. The residue was purified by flash chromatography on silica gel (EtOAc in Petroleum ether=0 to 10%) to give 083-4 (4.5 g, 9.86 mmol, 84.54% yield) as white oil. $^1$H NMR (400 MHz, DMSO-d$_6$) δ=9.37 (s, 1H), 8.47 (s, 1H), 8.20 (d, J=8.8 Hz, 1H), 7.93 (s, 1H), 7.87 (d, J=8.8 Hz, 1H), 7.49-7.45 (m, 1H), 7.12 (d, J=7.6 Hz, 1H), 7.02 (d, J=8.4 Hz, 1H), 6.96 (s, 1H), 1.34-1.20 (m, 3H), 1.07 (d, J=7.6 Hz, 18H).

Step E: To a solution of 083-4 (4.5 g, 9.86 mmol) in dioxane (40 mL) and H$_2$O (10 mL) was added K2CO$_3$ (4.09 g, 29.57 mmol), 4,4,5,5-tetramethyl-2-vinyl-1,3,2-dioxaborolane (2.28 g, 14.79 mmol, 2.51 mL) and Pd(dppf)Cl$_2$ (721.30 mg, 985.78 μmol). The mixture was stirred at 90° C. for 2 h. The mixture was quenched with water (50 mL). The aqueous layer was extracted with EtOAc (50 mL×3). The combined organic phase was washed with brine (50 mL), dried over anhydrous Na$_2$SO$_4$, filtered and concentrated. The residue was purified by flash chromatography on silica gel (EtOAc in petroleum ether=0 to 30%) to give 083-5 (3.5 g, 8.67 mmol, 87.96% yield) as yellow oil. $^1$H NMR (400 MHz, DMSO-d$_6$) δ=9.36-9.24 (m, 1H), 8.38 (s, 1H), 8.17 (d, J=8.4 Hz, 1H), 7.95 (dd, J=1.2, 8.4 Hz, 1H), 7.77-7.62 (m, 1H), 7.49-7.42 (m, 1H), 7.12 (d, J=7.6 Hz, 1H), 7.04-6.94 (m, 2H), 6.86-6.74 (m, 1H), 5.99 (d, J=17.6 Hz, 1H), 5.44 (d, J=11.2 Hz, 1H), 1.29-1.19 (m, 3H), 1.05 (d, J=7.2 Hz, 18H).

Step F: To a solution of 083-5 (3.5 g, 8.67 mmol) in THF (80 mL) and H$_2$O (20 mL) was added K$_2$OsO$_4$·2H$_2$O (319.50 mg, 867.13 umol) and NaIO$_4$ (7.42 g, 34.69 mmol, 1.92 mL). The mixture was stirred at 25° C. for 30 min. Water (50 mL) was added and the mixture was extracted with EtOAc (50 mL×2). The organic layer was dried over anhydrous Na$_2$SO$_4$, filtered and concentrated. The residue was purified by flash chromatography on silica gel (EtOAc Step A: To a solution of 6-bromoisoquinoline (50 g, 240.32 mmol) in AcOH (500 mL) was added NIS (81.10 g, 360.48 mmol). The mixture was stirred at 80° C. for 8 h. The mixture was filtered and concentrated. The residue was in petroleum ether=0 to 1%) to give 083-6 (2.5 g, 6.16 mmol, 71.08% yield) as yellow oil. $^1$H NMR (400 MHz, DMSO-$d_6$) δ=10.13 (s, 1H), 9.49 (s, 1H), 8.56 (s, 1H), 8.44-8.34 (m, 2H), 8.11 (d, J=8.4 Hz, 1H), 7.52-7.47 (m, 1H), 7.19 (d, J=7.2 Hz, 1H), 7.14-6.93 (m, 3H), 1.31-1.22 (m, 3H), 1.07 (d, J=7.2 Hz, 18H).

Step G: A mixture of (2-bromo-5-iodo-phenyl)methoxy-triisopropyl-silane (5.78 g, 12.33 mmol) in THF (50 mL) was degassed and purged with $N_2$ for 3 times. Then n-BuLi (2.5M in hexane, 12.33 mmol, 4.93 mL) was added under $N_2$ at −70° C. The mixture was stirred under $N_2$ at −70° C. for 0.5 h. Then to a solution of 083-6 (2.5 g, 6.16 mmol) in THF (20 mL) was added the above mixture under $N_2$ at −70° C. The mixture was stirred under $N_2$ at −70° C. for 0.5 h. Water (10 mL) was added to the mixture and the mixture was extracted with EtOAc (20 mL×2). The combined organic phase was washed with brine (10 mL), dried over anhydrous $Na_2SO_4$, filtered and concentrated to afford 083-7 (4 g, 5.34 mmol, 86.65% yield) as yellow oil used next step. LCMS $R_t$=1.16 min in 1.5 min chromatography, 5-95AB, ESI calcd. for $C_{41}H_{59}BrNO_3Si_2$ [M+H]$^+$ 748.3, found 748.4.

Step H. To a solution of 083-7 (4 g, 5.34 mmol) in DCM (50 mL) was added $MnO_2$ (4.64 g, 53.41 mmol). The mixture was stirred at 40° C. for 12 h. The mixture was filtered and the filtrate was concentrated under reduced pressure. The residue was purified by flash chromatography on silica gel (EtOAc in petroleum ether=0 to 30%) to give 083-8 (3 g, 4.02 mmol, 75.20% yield) as yellow oil. $^1$H NMR (400 MHz, DMSO-$d_6$) δ=9.50 (s, 1H), 8.58 (s, 1H), 8.46-8.35 (m, 1H), 8.08 (s, 1H), 7.96 (dd, J=1.2, 8.4 Hz, 1H), 7.88-7.76 (m, 2H), 7.71 (dd, J=2.4, 8.4 Hz, 1H), 7.51-7.39 (m, 1H), 7.17 (d, J=8.0 Hz, 1H), 7.02-6.89 (m, 2H), 4.76 (s, 2H), 1.19-1.08 (m, 6H), 0.88-0.84 (m, 36H).

Step I. To a solution of 1-methyl-1H-imidazole (329.75 mg, 4.02 mmol, 320.15 μL) in THF (10 mL) was added n-BuLi (2.5M in hexane, 4.03 mmol, 1.61 mL) dropwise under $N_2$ at −70° C. and the mixture was stirred at −70° C. for 30 min. A solution of $Et_3SiCl$ (605.33 mg, 4.02 mmol, 683.22 μL) in THF (20 mL) was added to the above mixture at −70° C. and the resulting mixture was stirred at −70° C. for 30 min. Then n-BuLi (2.5M in hexane, 4.03 mmol, 1.61 mL) was added to the mixture dropwise at −70° C. under $N_2$ and the mixture was stirred at −70° C. for 30 min. A solution of 083-8 (3 g, 4.02 mmol) in THF (30 mL) was added to the above mixture and the mixture was stirred at −70° C. for 1 h. Water (100 mL) was added to the mixture and the mixture was extracted with EtOAc (100 mL×2). The combined organic phase was washed with brine (50 mL), dried over anhydrous $Na_2SO_4$, filtered and concentrated. The residue was purified by flash chromatography on silica gel (MeOH in DCM=0 to 10%) to give 083-9 (3.1 g, 3.74 mmol, 93.10% yield) as yellow oil. $^1$H NMR (400 MHz, DMSO-$d_6$) δ=9.30 (s, 1H), 8.38 (s, 1H), 8.15 (d, J=8.8 Hz, 1H), 7.79 (s, 1H), 7.65-7.49 (m, 4H), 7.44-7.31 (m, 2H), 7.09 (s, 1H), 6.99-6.84 (m, 3H), 6.05 (s, 1H), 4.66-4.58 (m, 2H), 3.32 (s, 3H), 1.27-1.17 (m, 3H), 1.03 (d, J=7.6 Hz, 18H), 0.94-0.85 (m, 3H), 0.77 (dd, J=4.0 Hz, 18H).

Step J: To a solution of 083-9 (3.1 g, 3.74 mmol) in THF (10 mL) was added TBAF (1M in THF, 11.22 mmol, 11.22 mL). The mixture was stirred at 25° C. for 1 h. Water (10 mL) was added to the mixture and the mixture was extracted with EtOAc (20 mL×2). The combined organic phase was washed with brine (10 mL), dried over anhydrous $Na_2SO_4$, filtered and concentrated to give 083-10 (1.5 g, 2.90 mmol, 77.69% yield) as white solid which was used into next step directly. $^1$H NMR (400 MHz, DMSO-$d_6$) δ=9.63 (s, 1H), 9.28-9.16 (m, 1H), 8.40-8.34 (m, 1H), 8.14 (d, J=8.6 Hz, 1H), 7.87 (s, 1H), 7.67-7.57 (m, 2H), 7.54-7.46 (m, 2H), 7.35-7.23 (m, 1H), 7.12-6.94 (m, 2H), 6.91-6.80 (m, 3H), 6.09 (s, 1H), 5.39-5.36 (m, 1H), 4.44 (s, 2H), 3.30 (s, 3H).

Step K: To a solution of 083-10 (300 mg, 580.96 μmol) in DCM (5 mL) was added $SOCl_2$ (207.35 mg, 1.74 mmol, 126.43 μL). The mixture was stirred at 20° C. for 2 h. The mixture was concentrated under reduce pressure to give 083-11 (300 mg, 560.93 μmol, 96.55% yield) as yellow solid which was used into next step directly. LCMS $R_t$=1.92 min in 3 min chromatography, 10-80CD, ESI calcd. for $C_{27}H_{22}BrClN_3O_2$ [M+H]$^+$ 534.1, found 534.1.

Step L: To a solution of 083-11 (300 mg, 560.93 μmol) in DMF (5 mL) was added $Cs_2CO_3$ (548.28 mg, 1.68 mmol). The mixture was stirred at 70° C. for 1 h. Water (20 mL) was added the mixture and the mixture was filtrated and the filter residue was concentrated under reduce pressure. The residue was purified by prep-HPLC (column: Welch Xtimate $C_{18}$ 150×30 mm×5 m; mobile phase: [water ($NH_3H_2O$+$NH_4HCO_3$)-ACN]; B %: 50%-80%, 7 min) to give 083 (5.1 mg, 10.23 μmol, 10.20% yield) as a white solid. $^1$H NMR (400 MHz, DMSO-$d_6$) δ=9.33 (s, 1H), 8.60 (s, 1H), 8.23 (d, J=8.8 Hz, 1H), 8.05 (d, J=8.8 Hz, 1H), 7.65 (s, 1H), 7.62-7.54 (m, 2H), 7.44-7.30 (m, 2H), 7.22-7.10 (m, 3H), 7.06-6.94 (m, 1H), 6.74 (br s, 1H), 6.26 (br s, 1H), 5.42 (s, 2H), 3.52 (s, 3H). LCMS $R_t$=2.00 min in 3 min chromatography, 10-80CD, ESI calcd. for $C_{27}H_{21}BrN_3O_2$ [M+H]$^+$ 498.1, found 498.1. HPLC $R_t$=4.12 min in 8 min chromatography, 220 nm, purity 100%.

Example 84—Preparation of Compound 84

4$^4$-bromo-3-(1-methyl-1H-imidazol-5-yl)-6-oxa-2(1,7)-isoquinolina-1,4(1,3)-dibenzenacyclohexaphan-3-ol (084)

Scheme 81-Synthesis of Compound 84

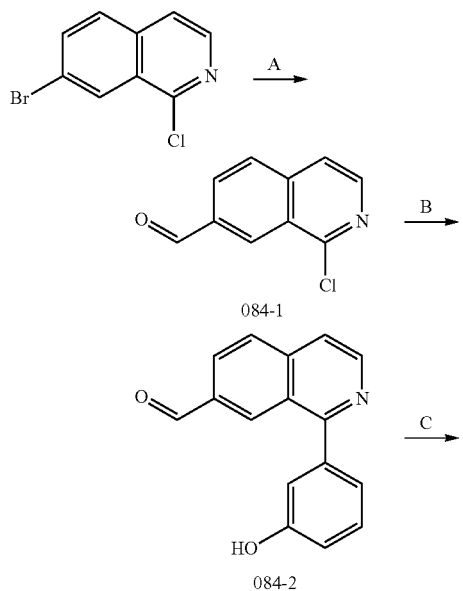

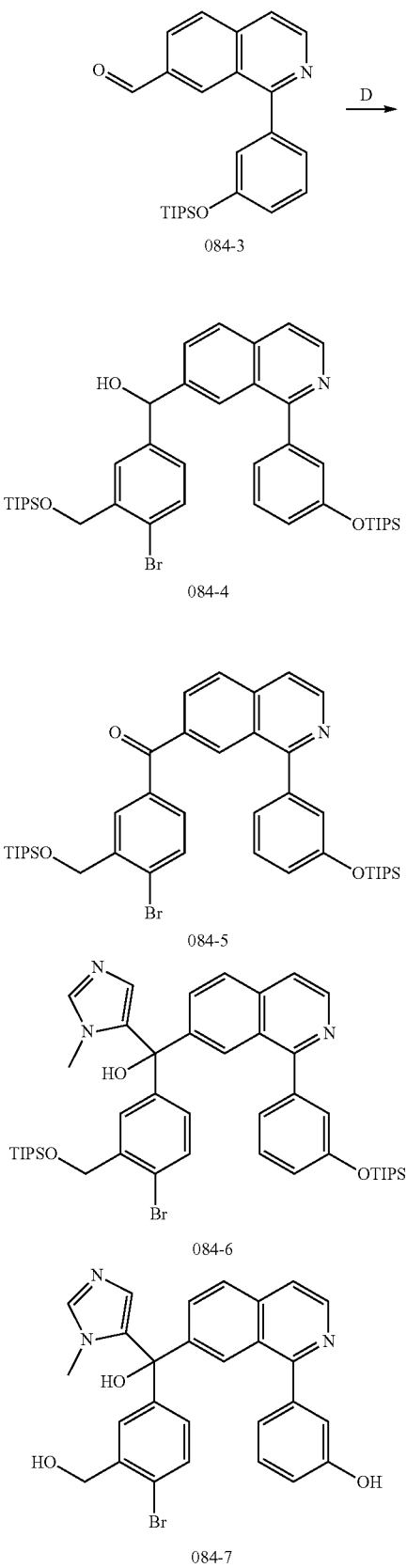

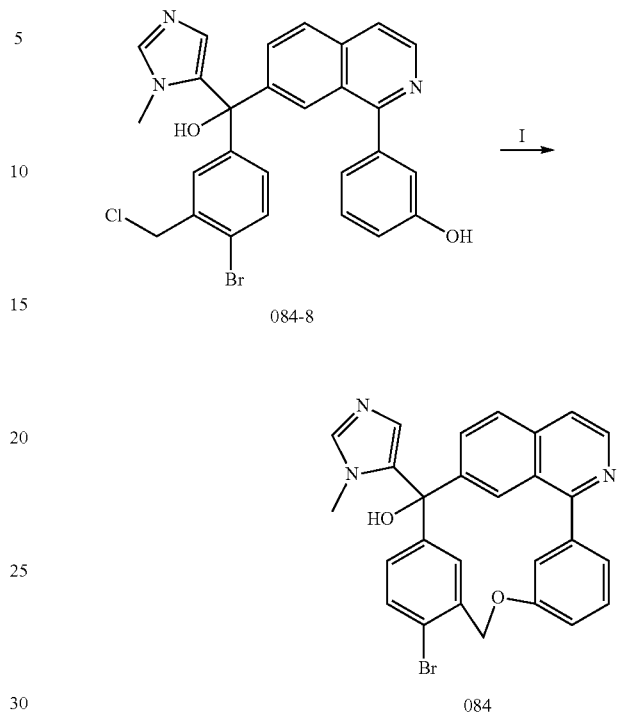

Step A: To a solution of 7-bromo-1-chloroisoquinoline (3.5 g, 14.43 mmol) in THF (30 mL) was added n-BuLi (2.5M in hexane, 15.88 mmol, 6.35 mL) at −75° C. and the mixture was stirred for 10 min under N₂. DMF (1.27 g, 17.32 mmol, 1.33 mL) in THF (5 mL) was added to the mixture under N₂. The mixture was stirred at −75° C. for 50 min under N₂. The mixture was blended with another batch prepared from 3.5 g of 7-bromo-1-chloroisoquinoline. The reaction mixture was poured into saturated NH₄Cl solution (50 mL). The aqueous layer was extracted with EtOAc (50 mL×2). The combined organic layers were washed with brine (50 mL×2), dried over anhydrous Na₂SO₄, filtered and the filter cake was washed with EtOAc (20 mL). The combined filtrates were concentrated. The crude was purified by flash chromatography on silica gel (EtOAc in petroleum ether=0 to 15%) to give 084-1 (4 g, 20.88 mmol, 72.32% yield) as a yellow solid. ¹H NMR (400 MHz, DMSO-d₆) δ=10.27 (s, 1H), 8.88 (s, 1H), 8.47 (d, J=5.6 Hz, 1H), 8.30-8.18 (m, 2H), 8.02 (d, J=4.8 Hz, 1H).

Step B: To a solution of 084-1 (3 g, 15.66 mmol) in dioxane (60 mL) and H₂O (5 mL) were added Pd(dppf)Cl₂—CH₂Cl₂ (1.28 g, 1.57 mmol) and DIPEA (4.05 g, 31.31 mmol, 5.45 mL) and (3-hydroxyphenyl)boronic acid (2.81 g, 20.35 mmol). The mixture was stirred at 85° C. for 12 h. The reaction was poured into H₂O (100 mL). The aqueous layer was extracted with EtOAc (100 mL×2). The combined organic layers were washed with brine (100 mL×2), dried over anhydrous Na₂SO₄, filtered and filter cake was washed with EtOAc (30 mL). The combined filtrate was concentrated and purified by flash chromatography on silica gel (EtOAc in DCM=0 to 50%) to give 084-2 (3.2 g, 12.84 mmol, 82.00% yield) as a brown solid. ¹H NMR (400 MHz, DMSO-d₆) δ=10.12 (s, 1H), 9.72 (s, 1H), 8.76-8.60 (m, 2H), 8.27-8.12 (m, 2H), 7.96 (d, J=5.6 Hz, 1H), 7.40-7.36 (m, 1H), 7.11 (s, 2H), 6.98 (d, J=8.4 Hz, 1H).

Step C: To a solution of 084-2 (2.5 g, 10.03 mmol) in THF (50 mL) was added 1H-imidazole (2.05 g, 30.09 mmol) and TIPSCl (5.80 g, 30.09 mmol, 6.44 mL). The mixture was stirred at 25° C. for 12 h. The reaction was poured into $H_2O$ (50 mL). The aqueous layer was extracted with EtOAc (100 mL×2). The combined organic layers were washed with brine (50 mL×2), dried over anhydrous $Na_2SO_4$, filtered and the filter cake was washed with EtOAc (20 mL). The filtrate was concentrated. The crude material was purified by flash chromatography on silica gel (EtOAc in petroleum ether=0 to 15%) to give 084-3 (2.5 g, 6.16 mmol, 61.46% yield) as yellow oil. $^1H$ NMR (400 MHz, DMSO-$d_6$) δ=10.09 (s, 1H), 8.74 (d, J=5.6 Hz, 1H), 8.58 (s, 1H), 8.29-8.11 (m, 2H), 7.97 (d, J=6.0 Hz, 1H), 7.54-7.42 (m, 1H), 7.32 (d, J=7.6 Hz, 1H), 7.17 (s, 1H), 7.13-7.03 (m, 1H), 1.31-1.23 (m, 3H), 1.11-1.05 (m, 18H).

Step D: To a solution of (2-bromo-5-iodo-phenyl) methoxy-triisopropyl-silane (4.34 g, 9.25 mmol) in THF (50 mL) was added n-BuLi (2.5M in hexane, 9.62 mmol, 3.85 mL) at −75° C. and the mixture was stirred for 15 min under $N_2$. 084-3 (1.5 g, 3.70 mmol) in THF (10 mL) was added to the mixture under $N_2$. The mixture was stirred at −75° C. for 45 min under $N_2$. The reaction mixture was poured into saturated $NH_4Cl$ solution (100 mL). The aqueous layer was extracted with EtOAc (100 mL×2). The combined organic layers were washed with brine (50 mL×2), dried over anhydrous $Na_2SO_4$, filtered and the filter cake was washed with EtOAc (20 mL). The filtrate was concentrated and purified by flash chromatography on silica gel (EtOAc in petroleum ether=0 to 10%) to give 084-4 (2 g, 2.67 mmol, 72.21% yield) as yellow oil. $^1H$ NMR (400 MHz, DMSO-$d_6$) δ=8.55 (d, J=5.6 Hz, 1H), 8.10 (s, 1H), 7.95 (d, J=8.4 Hz, 1H), 7.80 (d, J=6.0 Hz, 1H), 7.61 (d, J=8.4 Hz, 1H), 7.52 (d, J=8.4 Hz, 1H), 7.47-7.40 (m, 1H), 7.36 (d, J=8.0 Hz, 1H), 7.27-7.19 (m, 2H), 7.11 (s, 1H), 7.03 (d, J=8.0 Hz, 1H), 6.18 (d, J=4.0 Hz, 1H), 5.80 (d, J=4.4 Hz, 1H), 4.63 (s, 2H), 1.29-1.22 (m, 3H), 1.08-1.03 (m, 18H), 0.93-0.88 (m, 3H), 0.82-0.78 (m, 18H).

Step E: To a solution of 084-4 (2 g, 2.67 mmol) in DCM (30 mL) was added $MnO_2$ (2.32 g, 26.70 mmol). The mixture was stirred at 40° C. for 12 h. The reaction mixture was filtered through a pad of Celite and the filter cake washed with EtOAc (20 mL) and DCM (20 mL). The filtrate was concentrated to afford 084-5 (1.8 g, 2.41 mmol, 90.24% yield) as a yellow oil, which was used directly without further purification for the next step. 1H NMR (400 MHz, DMSO-$d_6$) δ=8.73 (d, J=5.6 Hz, 1H), 8.29 (s, 1H), 8.22 (d, J=8.4 Hz, 1H), 8.05 (d, J=8.4 Hz, 1H), 7.99 (d, J=5.6 Hz, 1H), 7.85 (s, 1H), 7.83-7.76 (m, 1H), 7.73-7.66 (m, 1H), 7.47-7.38 (m, 1H), 7.31 (d, J=7.6 Hz, 1H), 7.11-6.96 (m, 2H), 4.76 (s, 2H), 1.21-1.10 (m, 3H), 1.07-1.03 (m, 3H), 1.02-0.93 (m, 18H), 0.91-0.81 (m, 18H).

Step F: To a solution of 1-methyl-1H-imidazole (461.65 mg, 5.62 mmol, 448.20 μL) in THF (30 mL) was added n-BuLi (2.5M in n-hexane, 5.62 mmol, 2.25 mL) at −75° C. and the mixture was stirred for 30 min under $N_2$. $Et_3SiCl$ (847.48 mg, 5.62 mmol, 956.52 μL) in THF (10 mL) was added at −75° C. and the mixture was stirred for 30 min under $N_2$. n-BuLi (2.5M in n-hexane, 5.62 mmol, 2.25 mL) was added and the mixture was stirred at −75° C. for 1 h under $N_2$. 084-5 (2.8 g, 3.75 mmol) in THF (10 mL) was added at −75° C. and the mixture was stirred for 1 h under $N_2$. The reaction mixture was poured into saturated aqueous $NH_4Cl$ (100 mL). The aqueous layer was extracted with EtOAc (100 mL×2). The combined organic layers were washed with brine (50 mL×2), dried over anhydrous $Na_2SO_4$, filtered and the filter cake was washed with EtOAc (20 mL). The filtrate was concentrated and purified by flash chromatography on silica gel (MeOH in DCM=0 to 8%) to give 084-6 (2.6 g, 3.14 mmol, 83.66% yield) as a yellow oil. $^1H$ NMR (400 MHz, DMSO-$d_6$) δ=8.57 (d, J=5.6 Hz, 1H), 7.98 (d, J=8.4 Hz, 1H), 7.87-7.79 (m, 2H), 7.66 (d, J=8.8 Hz, 1H), 7.62-7.55 (m, 2H), 7.42 (d, J=6.0 Hz, 1H), 7.33-7.26 (m, 1H), 7.10-7.05 (m, 2H), 7.03-6.99 (m, 1H), 6.97-6.89 (m, 2H), 6.02 (s, 1H), 4.63 (d, J=4.8 Hz, 2H), 3.34 (s, 3H), 1.27-1.20 (m, 3H), 1.06-1.00 (m, 18H), 0.87-0.83 (m, 3H), 0.78-0.73 (m, 18H).

Step G: To a solution of 084-6 (2.6 g, 3.14 mmol) in THF (30 mL) was added TBAF (1M in hexane, 9.41 mL, 9.41 mmol). The mixture was stirred at 25° C. for 2 h. The reaction mixture was poured into $H_2O$ (50 mL). The aqueous layer was extracted with EtOAc (50 mL×2). The combined organic layers were washed with brine (50 mL×2), dried over anhydrous $Na_2SO_4$, filtered and the filter cake was washed with EtOAc (20 mL). The filtrate was concentrated and purified by flash chromatography on silica gel (MeOH in DCM=0 to 15%) to give 084-7 (1.3 g, 2.52 mmol, 80.28% yield) as a white solid. $^1H$ NMR (400 MHz, DMSO-$d_6$) δ=9.61 (s, 1H), 8.56 (d, J=5.6 Hz, 1H), 8.06-7.90 (m, 2H), 7.80 (d, J=5.6 Hz, 1H), 7.72 (dd, J=1.6, 8.8 Hz, 1H), 7.65 (s, 1H), 7.56-7.45 (m, 2H), 7.29-7.19 (m, 1H), 7.06-6.95 (m, 3H), 6.93-6.84 (m, 2H), 6.08 (s, 1H), 5.47-5.31 (m, 1H), 4.55-4.38 (m, 2H), 3.35 (s, 3H).

Step H: To a solution of 084-7 (1.2 g, 2.32 mmol) in DCM (20 mL) was added $SOCl_2$ (829.40 mg, 6.97 mmol, 505.73 μL). The mixture was stirred at 40° C. for 2 h. The reaction was concentrated to give 084-8 (1.24 g, 2.32 mmol, 100.00% yield) as a yellow solid, which was used directly without purification for the next step. LCMS $R_t$=1.42 min in 3 min chromatography, 5-95AB, ESI calcd. for $C_{27}H_{22}BrClN_3O_2$ [M+H]$^+$ 534.1, found 534.1.

Step I: To a solution of 084-8 (1.24 g, 2.32 mmol) in DMF (30 mL) was added $Cs_2CO_3$ (2.27 g, 6.96 mmol). The mixture was stirred at 50° C. for 12 h. The reaction mixture was poured into $H_2O$ (100 mL). The aqueous layer was extracted with EtOAc (100 mL×2). The combined organic layers were washed with brine (100 mL×2), dried over anhydrous $Na_2SO_4$, filtered and the filter cake was washed with EtOAc (20 mL). The filtrate was concentrated and purified by flash chromatography on silica gel (MeOH in DCM=0 to 10%) to give 084 (700 mg, 1.40 mmol, 60.58% yield) as a yellow solid. 084 (30 mg, 60.20 μmol) was purified by prep-HPLC (column: Boston Prime $C_{18}$ 150×30 mm×5 m; mobile phase: [water ($NH_3H_2O+NH_4HCO_3$)-ACN]; B %: 45%-75%, 7 min) to give 084 (22.2 mg, 44.55 μmol) as an off-white solid. $^1H$ NMR (400 MHz, DMSO-$d_6$) δ=8.60 (d, J=5.6 Hz, 1H), 8.18-8.03 (m, 2H), 7.82 (d, J=5.6 Hz, 1H), 7.70 (s, 1H), 7.63-7.53 (m, 2H), 7.50-7.34 (m, 3H), 7.29-7.13 (m, 2H), 7.09-7.00 (m, 1H), 6.67 (s, 1H), 6.27 (s, 1H), 5.43 (s, 2H), 3.52 (s, 3H). LCMS $R_t$=1.88 min in 3 min chromatography, 10-80CD, ESI calcd. for $C_{27}H_{21}BrN_3O_2$ [M+H]$^+$ 498.1, found 498.1. HPLC $R_t$=3.76 min in 8 min chromatography, 220 nm, purity 99.79%.

Example 85—Preparation of Compound 85

3-hydroxy-3-(1-methyl-1H-imidazol-5-yl)-6-oxa-2 (1,7)-isoquinolina-1,4(1,3)-dibenzenacyclohexaphane-4⁴-carbonitrile (085)

Example 86—Preparation of Compound 86

3-amino-3-(1-methyl-1H-imidazol-5-yl)-6-oxa-2(1, 7)-isoquinolina-1,4(1,3)-dibenzenacyclohexaphane-4⁴-carbonitrile (086), (R)-3-amino-3-(1-methyl-1H-imidazol-5-yl)-6-oxa-2(1,7)-isoquinolina-1,4(1,3)-dibenzenacyclohexaphane-4⁴-carbonitrile ((R)-086), (S)-3-amino-3-(1-methyl-1H-imidazol-5-yl)-6-oxa-2 (1,7)-isoquinolina-1,4(1,3)-dibenzenacyclohexaphane-4⁴-carbonitrile ((S)-086)

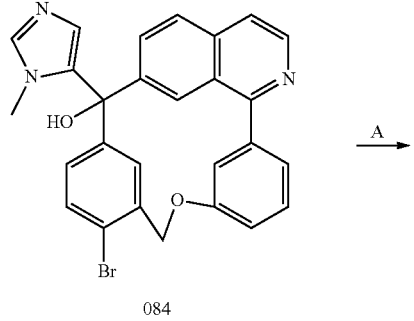

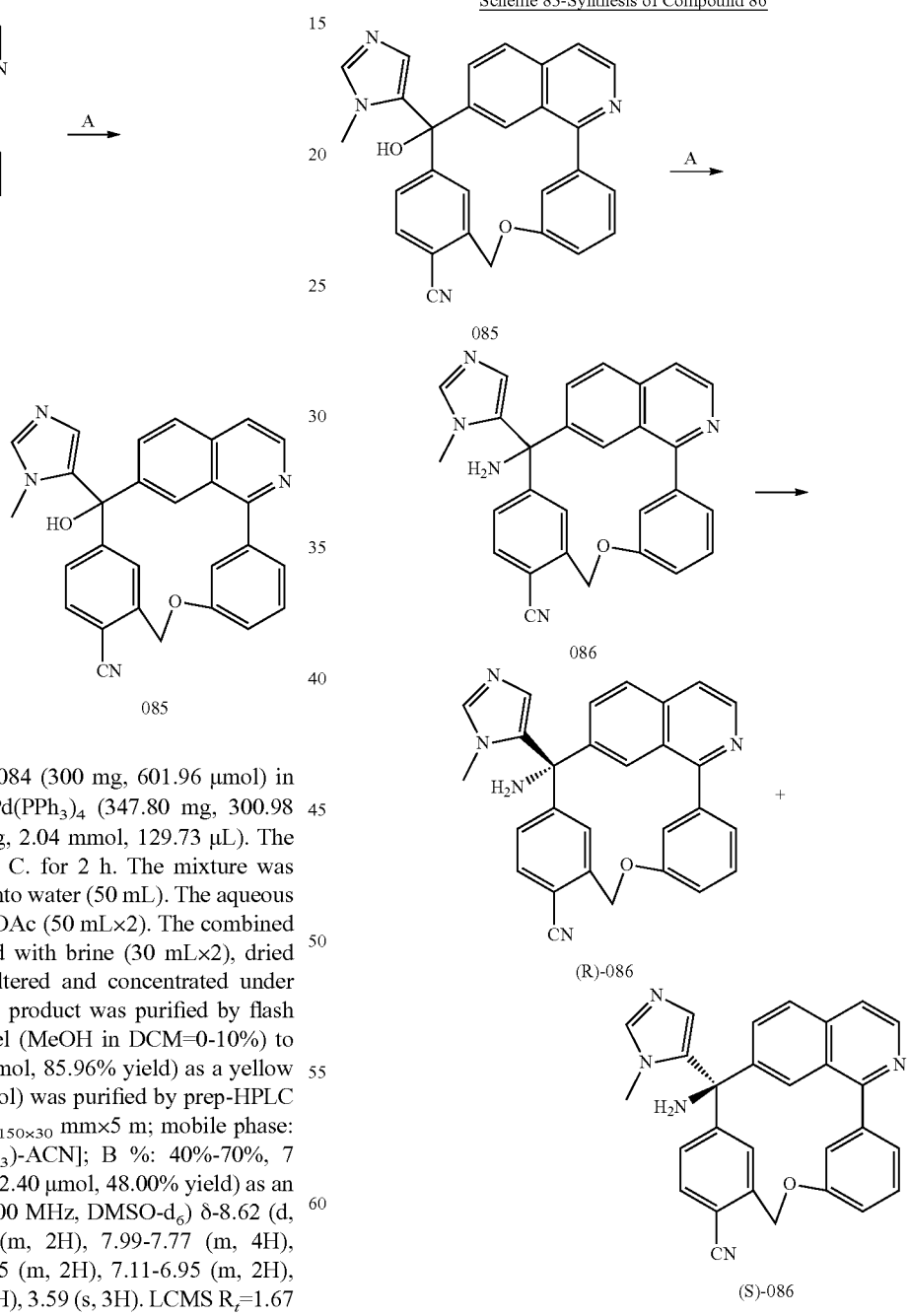

Step A: To a solution of 084 (300 mg, 601.96 μmol) in DMF (5 mL) was added Pd(PPh$_3$)$_4$ (347.80 mg, 300.98 μmol) and Zn(CN)$_2$ (240 mg, 2.04 mmol, 129.73 μL). The mixture was stirred at 100° C. for 2 h. The mixture was cooled to 25° C. and added into water (50 mL). The aqueous phase was extracted with EtOAc (50 mL×2). The combined organic phases were washed with brine (30 mL×2), dried over anhydrous Na$_2$SO$_4$, filtered and concentrated under reduced pressure. The crude product was purified by flash chromatography on silica gel (MeOH in DCM=0-10%) to give 085 (230 mg, 517.45 μmol, 85.96% yield) as a yellow solid. 085 (30 mg, 67.49 μmol) was purified by prep-HPLC (column: Boston Prime C$_{18}$ $_{150×30}$ mm×5 m; mobile phase: [water (NH$_3$H$_2$O+NH$_4$HCO$_3$)-ACN]; B %: 40%-70%, 7 min) to give 085 (14.4 mg, 32.40 μmol, 48.00% yield) as an off-white solid. $^1$H NMR (400 MHz, DMSO-d$_6$) δ-8.62 (d, J=5.6 Hz, 1H), 8.23-8.04 (m, 2H), 7.99-7.77 (m, 4H), 7.61-7.32 (m, 3H), 7.27-7.15 (m, 2H), 7.11-6.95 (m, 2H), 6.45 (s, 1H), 5.66-5.45 (m, 2H), 3.59 (s, 3H). LCMS R$_t$=1.67 min in 3 min chromatography, 10-80CD, ESI calcd. for C$_{28}$H$_{21}$N$_4$O$_2$ [M+H]$^+$ 445.2, found 445.2. HPLC R$_t$=3.19 min in 8 min chromatography, 220 nm, purity 99.23%.

Step A: To a solution of 085 (150 mg, 337.47 μmol) in DMI (5 mL) was added SOCl$_2$ (200.74 mg, 1.69 mmol, 122.41 μL). The mixture was stirred at 40° C. for 2 h. The mixture was added dropwise to NH₃ (7M in MeOH, 30 mL) at −10° C. The mixture was stirred at 20° C. for 30 min. The mixture was blended with another batch prepared from 50 mg of 085. The reaction mixture was poured into H₂O (50 mL). The aqueous layer was extracted with EtOAc (50 mL×2). The combined organic layers were washed with brine (50 mL×2), dried over anhydrous Na₂SO₄, filtered and the filter cake was washed with EtOAc (20 mL). The filtrate was concentrated and purified by flash chromatography on silica gel (MeOH in DCM=0 to 10%) to give 086 (120 mg, 270.58 μmol, 60.29% yield) as an off-white solid. ¹H NMR (400 MHz, DMSO-d₆) δ=8.60 (d, J=5.6 Hz, 1H), 8.20 (d, J=9.2 Hz, 1H), 8.07 (d, J=8.8 Hz, 1H), 7.97 (s, 1H), 7.87-7.78 (m, 2H), 7.56 (s, 1H), 7.46-7.11 (m, 5H), 7.05 (d, J=8.0 Hz, 1H), 6.44 (s, 1H), 5.64-5.43 (m, 2H), 3.45 (s, 3H), 3.08 (s, 2H). LCMS R$_t$=1.67 min in 3 min chromatography, 10-80CD, ESI calcd. for C₂₈H₂₂N₅O [M+H]⁺ 444.2, found 444.3. HPLC R$_t$=3.17 min in 8 min chromatography, 220 nm, purity 97.86%.

Step B: Racemic 086 (100 mg, 225.48 μmol) was purified by SFC (column: DAICEL CHIRALPAK AD (250 mm×30 mm, 10 m); mobile phase: [0.1% NH₃H₂O EtOH]; B %: 50%-50%, min) to give (R)-086 (35.8 mg, 80.72 μmol, 35.80% yield) as an off-white solid and (S)-086 (34.3 mg, 77.34 μmol, 34.30% yield) as an off-white solid. (R)-086: ¹H NMR (400 MHz, DMSO-d₆) δ=8.59 (d, J=5.6 Hz, 1H), 8.20 (d, J=8.4 Hz, 1H), 8.06 (d, J=8.8 Hz, 1H), 7.97 (s, 1H), 7.86-7.79 (m, 2H), 7.55 (s, 1H), 7.44-7.10 (m, 5H), 7.04 (d, J=7.6 Hz, 1H), 6.43 (s, 1H), 5.62-5.44 (m, 2H), 3.45 (s, 3H), 3.08 (s, 2H). LCMS R$_t$=1.70 min in 3 min chromatography, 10-80CD, ESI calcd. for C₂₈H₂₂N₅O [M+H]⁺ 444.2, found 444.2. HPLC R$_t$=3.20 min in 8 min chromatography, 220 nm, purity 98.56%. Chiral HPLC (R)-086 R$_t$=2.45 min in 4 min (ee 99.42%), (AD_ETOH_DEA_5-40_4ML_4MIN_5CM). (S)-086: ¹H NMR (400 MHz, DMSO-d₆) δ=8.60 (d, J=5.6 Hz, 1H), 8.21 (d, J=8.8 Hz, 1H), 8.07 (d, J=8.8 Hz, 1H), 7.97 (s, 1H), 7.86-7.78 (m, 2H), 7.56 (s, 1H), 7.43-7.10 (m, 5H), 7.05 (d, J=7.6 Hz, 1H), 6.43 (s, 1H), 5.62-5.44 (m, 2H), 3.45 (s, 3H), 3.08 (s, 2H). LCMS R$_t$=1.69 min in 3 min chromatography, 10-80CD, ESI calcd. for C₂₈H₂₂N₅O [M+H]⁺ 444.2, found 444.2. HPLC R$_t$=3.19 min in 8 min chromatography, 220 nm, purity 98.93%. Chiral HPLC (S)-086 R$_t$=2.11 min in 4 min (ee 98.90%), (AD_ETOH_DEA_5-40_4ML_4MIN_5CM).

Example 87—Preparation of Compound 87

4⁴-bromo-2⁷-methoxy-3-(1-methyl-1H-imidazol-5-yl)-6-oxa-2(5,3)-quinolina-1,4(1,3)-dibenzenacyclohexaphan-3-ol (087)

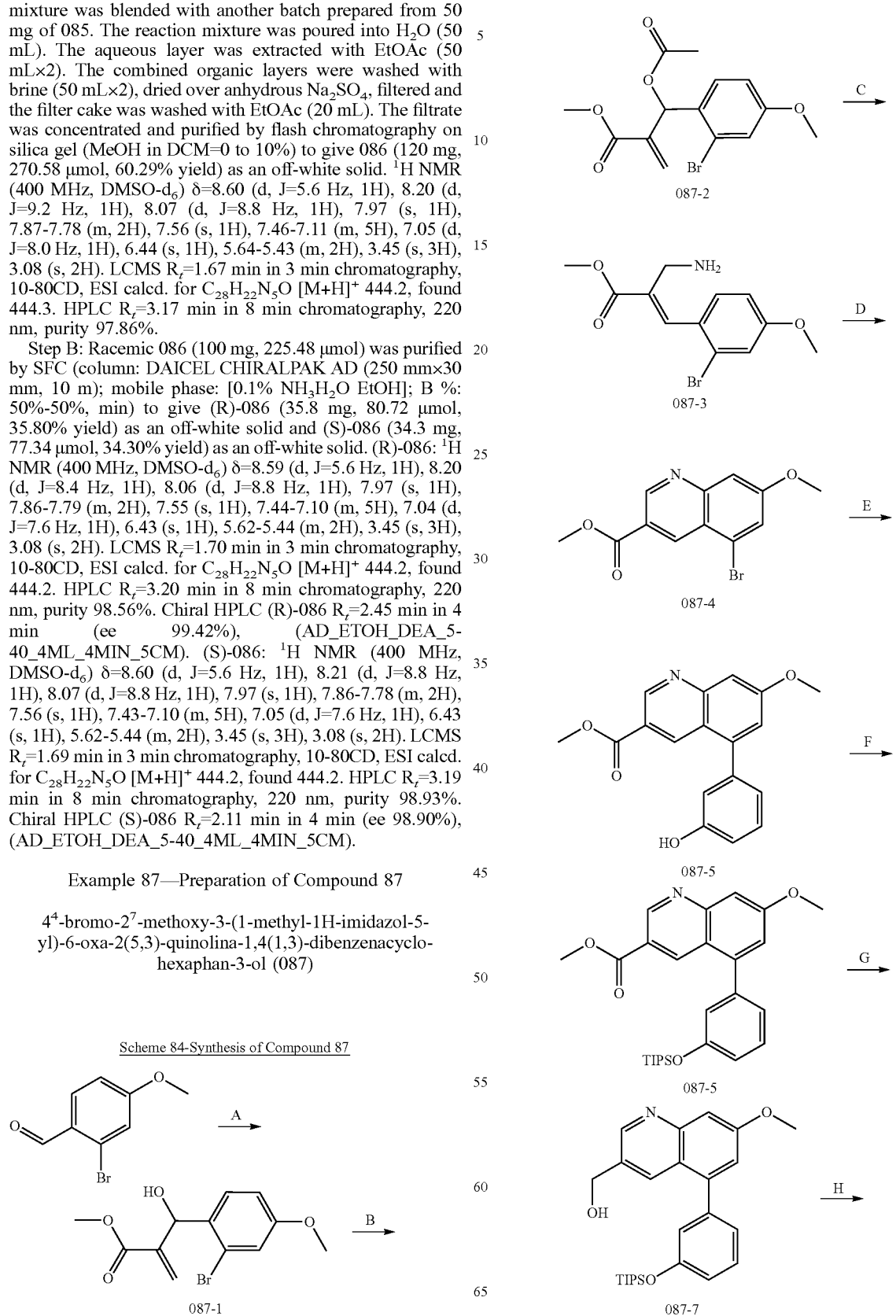

Scheme 84-Synthesis of Compound 87

-continued

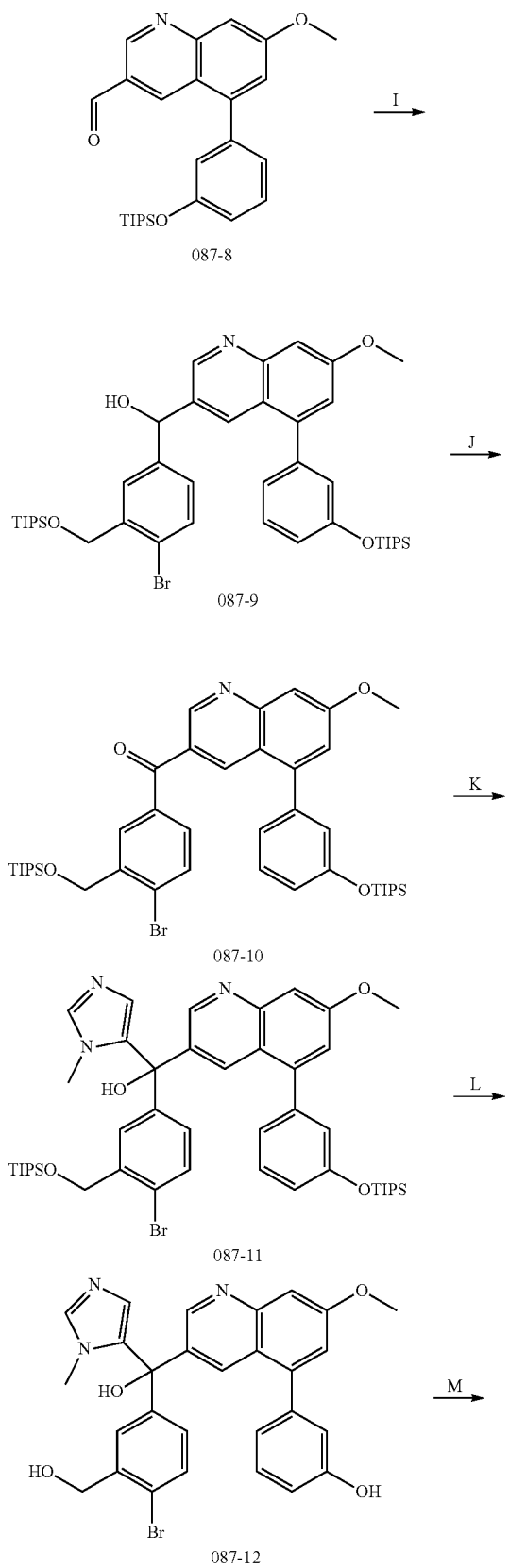

087-8

087-9

087-10

087-11

087-12

-continued

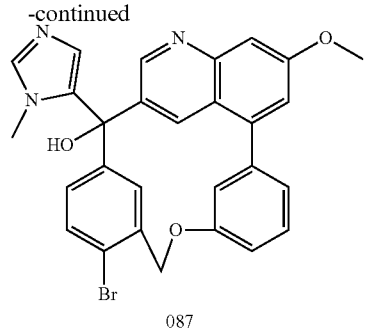

087

Step A: To a solution of 2-bromo-4-methoxybenzaldehyde (40 g, 186.01 mmol) in methyl acrylate (229.6 g, 2.67 mol, 240.17 mL) was added DABCO (10.43 g, 93.00 mmol, 10.23 mL) at 0° C., the mixture was stirred at 20° C. for 144 h. The solvents were removed under reduced pressure. The mixture was poured into water (300 mL), stirred for 30 min, and filtered. The crude was purified by flash chromatography on silica gel (EtOAc in petroleum ether=0 to 30%) to give 087-1 (35 g, 116.23 mmol, 62.49% yield) as a yellow solid. $^1$H NMR (400 MHz, DMSO-$d_6$) δ=7.28 (d, J=8.8 Hz, 1H), 7.15 (d, J=2.4 Hz, 1H), 6.96 (dd, J=2.8, 8.8 Hz, 1H), 6.21 (s, 1H), 5.79-5.66 (m, 3H), 3.76 (s, 3H), 3.63 (s, 3H).

Step B: To a solution of 087-1 (9 g, 29.89 mmol) in DCM (100 mL) was added DMAP (365.13 mg, 2.99 mmol), TEA (9.07 g, 89.66 mmol, 12.48 mL) and acetic anhydride (9.15 g, 89.66 mmol, 8.40 mL) at 0° C., the mixture was stirred at 20° C. for 1 h. The reaction mixture was poured into water (200 mL). The aqueous layer was extracted with DCM (200 mL×2). The combined organic phase was washed with brine (200 mL), dried over anhydrous Na$_2$SO$_4$, filtered and concentrated. The crude product was triturated with H$_2$O (100 mL) at 25° C. for 30 min to give 087-2 (8 g, 23.31 mmol, 78.00% yield) as a yellow solid. $^1$H NMR (400 MHz, CDCl$_3$) δ=7.20 (d, J=8.8 Hz, 1H), 7.10 (d, J=2.4 Hz, 1H), 6.91 (s, 1H), 6.81 (dd, J=2.8, 8.8 Hz, 1H), 6.43 (s, 1H), 5.64 (s, 1H), 3.76 (s, 3H), 3.70 (s, 3H), 2.08 (s, 3H).

Step C: A solution of 087-2 (8 g, 23.31 mmol) in NH$_3$ (7M in MeOH, 400 mL) was stirred at 20° C. for 2 h. The solvents were removed under reduced pressure. The crude was purified by flash chromatography on silica gel (MeOH in DCM=0 to 10%, twice) to give 087-3 (5 g, 16.66 mmol, 71.43% yield) as a yellow solid. $^1$H NMR (400 MHz, DMSO-$d_6$) δ=7.64 (d, J=8.4 Hz, 1H), 7.57 (s, 1H), 7.30 (d, J=2.8 Hz, 1H), 7.03 (dd, J=2.8, 8.8 Hz, 1H), 3.81 (s, 3H), 3.77 (s, 3H), 3.42 (s, 2H), 1.87 (s, 2H).

Step D: To a solution of 087-3 (5 g, 16.66 mmol) in CH$_3$CN (60 mL) was added 12 (12.68 g, 49.98 mmol, 10.07 mL) at 20° C., and the mixture was stirred at 20° C. for 5 min. K2CO$_3$ (6.91 g, 49.98 mmol) was added, and the mixture was stirred at 20° C. for 1 h. The reaction mixture was poured into saturated Na$_2$S$_2$O$_3$ solution (100 mL). The aqueous layer was extracted with DCM (100 mL×2). The combined organic phases were washed with brine (100 mL), dried over anhydrous Na$_2$SO$_4$, filtered and concentrated. The crude was purified by flash chromatography on silica gel (MeOH in DCM=0 to 10%, twice) to give 087-4 (3.5 g, 11.82 mmol, 70.99% yield) as a yellow solid. $^1$H NMR (400 MHz, CDCl$_3$) δ=9.34 (d, J=2.0 Hz, 1H), 9.02 (d, J=1.6 Hz, 1H), 7.55 (d, J=2.4 Hz, 1H), 7.41 (d, J=2.0 Hz, 1H), 4.00 (s, 3H), 3.95 (s, 3H).

Step E: To a solution of 087-4 (3.3 g, 11.14 mmol) in dioxane (30 mL) and H$_2$O (5 mL) was added (3-hydroxyphenyl)boronic acid (1.69 g, 12.26 mmol), Pd(dppf)Cl$_2$ (1.63 g, 2.23 mmol) and K2CO$_3$ (4.62 g, 33.43 mmol) at 25° C. under N$_2$. The mixture was stirred at 80° C. for 2 h. The mixture was filtered and the filtrate was concentrated and purified by flash chromatography on silica gel (MeOH in DCM=0 to 10%, twice) to give 087-5 (3 g, 9.70 mmol, 86.96% yield) as a brown solid. $^1$H NMR (400 MHz, DMSO-d$_6$) δ=9.75 (s, 1H), 9.26 (d, J=2.0 Hz, 1H), 8.62 (d, J=1.6 Hz, 1H), 7.58-7.56 (m, 1H), 7.51-7.48 (m, 2H), 7.37 (t, J=8.0 Hz, 1H), 7.25 (d, J=2.4 Hz, 1H), 6.87-6.84 (m, 1H), 4.00 (s, 3H), 3.87 (s, 3H).

Step F: To a solution of 087-5 (3 g, 9.70 mmol) in DCM (30 mL) was added 1H-imidazole (1.45 g, 21.34 mmol) and TIPSCl (2.80 g, 14.55 mmol, 3.11 mL) dropwise at 0° C., and the mixture was stirred at 0° C. for 1 h. The ice bath was removed and the mixture was stirred at 20° C. for 12 h. The residue was poured into water (100 mL) and then extracted with DCM (100 mL×2). The combined organic phases were washed with brine (100 mL), dried over anhydrous Na$_2$SO$_4$, filtered and concentrated. The crude product was purified by flash chromatography on silica gel (EtOAc in petroleum ether=0 to 40%, twice) to give 087-6 (4 g, 8.59 mmol, 88.50% yield) as a brown oil. LCMS R$_t$=1.21 min in 1.5 min chromatography, 5-95AB, ESI calcd. for C$_{27}$H$_{36}$NO$_4$Si [M+H]$^+$ 466.2, found 466.3.

Step G: To a solution of 087-6 (3.8 g, 8.16 mmol) in DCM (40 mL) was added DIBAL-H (1M in toluene, 20.40 mmol, 20.40 mL) at −78° C. under N$_2$, and the mixture was stirred at −78° C. for 2 h. The reaction mixture was quenched by adding to 20% f potassium sodium tartrate tetrahydrate solution (100 mL) at 0° C. and the mixture was stirred at 25° C. for 12 h. The mixture was extracted with DCM (100 mL×3). The combined organic phases were washed with brine (100 mL), dried over anhydrous Na$_2$SO$_4$, filtered and concentrated to afford 087-7 (3 g, 6.85 mmol, 84.00% yield) was obtained as a brown oil, which was used directly for the next step without purification. LCMS R$_t$=5.64 min in 7 min chromatography, 10-80CD, ESI calcd. for C$_{26}$H$_{36}$NO$_3$Si [M+H]$^+$ 438.2, found 438.3.

Step H: To a mixture of 087-7 (3 g, 6.85 mmol) in DCM (30 mL) was added MnO$_2$ (5.96 g, 68.55 mmol) at 20° C., and the mixture was stirred at 20° C. for 12 h. The mixture was filtered and the filter liquid was concentrated and purified by flash chromatography on silica gel (EtOAc in petroleum ether=0 to 30%, twice) to give 087-8 (1.8 g, 4.13 mmol, 60.28% yield) as a brown oil. $^1$H NMR (400 MHz, DMSO-d$_6$) δ=10.09 (s, 1H), 9.25 (d, J=2.0 Hz, 1H), 8.52 (d, J=1.6 Hz, 1H), 7.56 (d, J=2.4 Hz, 1H), 7.47 (t, J=8.0 Hz, 1H), 7.26 (d, J=2.4 Hz, 1H), 7.12 (d, J=7.6 Hz, 1H), 7.05 (dd, J=2.0, 8.0 Hz, 1H), 6.97-6.93 (m, 1H), 4.01 (s, 3H), 1.31-1.22 (m, 3H), 1.11-1.04 (m, 18H).

Step I: To a solution of ((2-bromo-5-iodobenzyl)oxy) triisopropylsilane (5.49 g, 11.71 mmol, 13.93 mL) in THF (40 mL) was added n-BuLi (2.5M in hexane, 11.51 mmol, 4.60 mL) at −78° C. under N$_2$, and the mixture was stirred at −78° C. for 20 min. The mixture was added into a solution of 087-8 (1.70 g, 3.90 mmol) in THF (20 mL) at −78° C. and the mixture was stirred at −78° C. for 1 h. The residue was poured into water (50 mL) and then extracted with EtOAc (50 mL×3). The combined organic phase was washed with brine (50 mL), dried over anhydrous Na$_2$SO$_4$, filtered and concentrated. The crude product was purified by flash chromatography on silica gel (EtOAc in petroleum ether=0 to 30%, twice) to give 087-9 (2.5 g, 3.21 mmol, 82.33% yield) as a yellow oil. LCMS R$_t$=1.29 min in 1.5 min chromatography, 5-95AB, ESI calcd. for C$_{42}$H$_{61}$BrNO$_4$Si$_2$ [M+H]$^+$ 778.3, found 777.8.

Step J. To a mixture of 087-9 (2.5 g, 3.21 mmol) in DCM (20 mL) was added MnO$_2$ (2.79 g, 32.09 mmol) at 20° C., and the mixture was stirred at 20° C. for 12 h. The mixture was filtered and the filtrate was concentrated and purified by flash chromatography on silica gel (EtOAc in petroleum ether=0 to 30%, twice) to give 087-10 (2.1 g, 2.70 mmol, 84.34% yield) as a yellow oil. $^1$H NMR (400 MHz, CDCl$_3$) δ=9.20-9.06 (m, 1H), 8.60-8.41 (m, 1H), 8.21-7.91 (m, 1H), 7.68-7.35 (m, 3H), 7.31-7.26 (m, 1H), 7.23-7.20 (m, 1H), 7.01-6.90 (m, 3H), 4.96-4.80 (m, 2H), 4.03-4.00 (m, 3H), 1.27-1.10 (m, 6H), 1.08-1.03 (m, 18H), 1.01-0.96 (m, 18H).

Step K: To a solution of 1-methyl-1H-imidazole (232.47 mg, 2.83 mmol, 225.70 μL) in THF (5 mL) was added n-BuLi (2.5M in hexane, 2.83 mmol, 1.13 mL) at −78° C. The mixture was stirred at −78° C. for 30 min. Et$_3$SiCl (426.76 mg, 2.83 mmol, 481.67 μL) in THF (5 mL) was added to the mixture at −78° C. The mixture was stirred at −78° C. for 30 min. n-BuLi (2.5M in hexane, 2.83 mmol, 1.13 mL) was added to the mixture at −78° C. The mixture was stirred at −78° C. for 30 min. A solution of 087-10 (2.00 g, 2.57 mmol) in THF (20 mL) was added to the mixture at −78° C. The resulting mixture was stirred at −78° C. for 1.5 h. The reaction mixture was poured into water (50 mL). The aqueous layer was extracted with EtOAc (50 mL×2). The combined organic phases were washed with brine (50 mL), dried over anhydrous Na$_2$SO$_4$, filtered and concentrated, and purified by flash chromatography on silica gel (MeOH in DCM=0 to 10%, twice) to give 087-11 (1.1 g, 1.28 mmol, 49.77% yield) as a yellow oil. LCMS R$_t$=1.24 min in 1.5 min chromatography, 5-95AB, ESI calcd. for C$_{46}$H$_{65}$BrN$_3$O$_4$Si$_2$ [M+H]$^+$ 858.4, found 858.1.

Step L: To a solution of 087-11 (1.1 g, 1.28 mmol) in THF (10 mL) was added TBAF (1M in THF, 1.92 mmol, 1.92 mL) at 0° C. under N$_2$. The mixture was stirred at 25° C. for 1 h. The reaction mixture was poured into water (50 mL). The aqueous layer was extracted with EtOAc (50 mL×2). The combined organic phase was washed with brine (50 mL), dried over anhydrous Na$_2$SO$_4$, filtered and concentrated. The crude product was triturated with PE (10 mL) at 25° C. for 30 min and purified by flash chromatography on silica gel (MeOH in DCM=0 to 10%) to give 087-12 (400 mg, 732.05 μmol, 57.17% yield) as a white solid. LCMS R$_t$=0.74 min in 1.5 min chromatography, 5-95AB, ESI calcd. for C$_{28}$H$_{25}$BrN$_3$O$_4$ [M+H]$^+$ 546.1, found 545.8.

Step M: A solution of 087-12 (300 mg, 549.04 μmol) in SOCl$_2$ (4.92 g, 41.35 mmol, 3.00 mL) was stirred at 25° C. for 2 h. The mixture was concentrated. To the residue in DMF (3 mL) was added Cs$_2$CO$_3$ (894.44 mg, 2.75 mmol) at 25° C. The resulting mixture was stirred at 70° C. for 2 h. After cooling to room temperature, the mixture was filtered and the filtrate was concentrated. The crude product was triturated with petroleum ether (5 mL) at 25° C. for 30 min and purified by flash chromatography on silica gel (MeOH in DCM=0 to 10%) to give 087 (200 mg, 378.50 μmol, 68.94% yield) as a yellow solid. 087 (20 mg, 37.85 μmol) was purified by Pre-TLC (DCM:MeOH=10:1) to give 087 (7.0 mg, 13.25 μmol, 35.00% yield) as an off-white solid. $^1$H NMR (400 MHz, DMSO-d$_6$) δ=9.16 (d, J=2.0 Hz, 1H), 7.65 (s, 1H), 7.61-7.58 (m, 2H), 7.50-7.47 (m, 2H), 7.36-7.32 (m, 2H), 7.18-7.09 (m, 3H), 6.99 (d, J=8.4 Hz, 1H), 6.76 (s, 1H), 6.32 (s, 1H), 5.42 (s, 2H), 3.99 (s, 3H), 3.56 (s, 3H). LCMS $R_t$=1.790 min in 3 min chromatography, 10-80CD, ESI calcd. for $C_{28}H_{23}BrN_3O_3$ [M+H]$^+$ 528.1, found 528.2. HPLC $R_t$=4.37 min in 8 min chromatography, 220 nm, purity 96.06%.

Example 88—Preparation of Compound 88

3-hydroxy-2$^7$-methoxy-3-(1-methyl-1H-imidazol-5-yl)-6-oxa-2(5,3)-quinolina-1,4(1,3)-dibenzenacyclohexaphane-4$^4$-carbonitrile (088)

Scheme 85-Synthesis of Compound 88

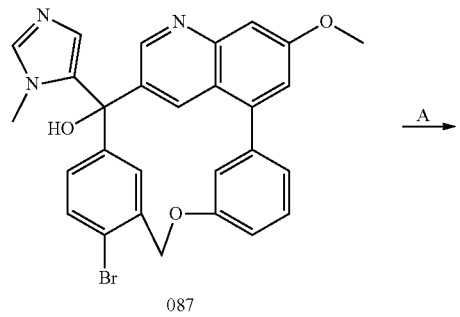

087

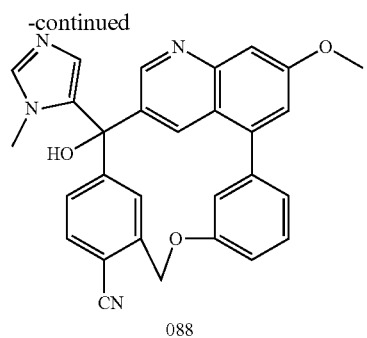

088

Step A: To a solution of 087 (80 mg, 151.40 μmol) in DMF (1 mL) was added Zn(CN)$_2$ (570 mg, 4.85 mmol) and Pd(PPh$_3$)$_4$ (87.48 mg, 75.70 μmol) at 25° C. under N$_2$. The mixture was stirred at 100° C. for 2 h. The mixture was filtered and the filtrate was concentrated and purified by flash chromatography on silica gel (MeOH in DCM=0 to 10%, twice) to give 088 (17.0 mg, 35.83 μmol, 23.66% yield) as an off-white solid. $^1$H NMR (400 MHz, DMSO-d$_6$) δ=9.18 (d, J=2.0 Hz, 1H), 7.84 (d, J=8.0 Hz, 1H), 7.78 (s, 1H), 7.64 (s, 1H), 7.58-7.44 (m, 2H), 7.44-7.26 (m, 3H), 7.23 (s, 1H), 7.14-7.07 (m, 2H), 7.00 (dd, J=2.4, 8.4 Hz, 1H), 6.36 (s, 1H), 5.52 (s, 2H), 3.99 (s, 3H), 3.58 (s, 3H). LCMS $R_t$=1.88 min 3 m chromatography, 10-80CD, ESI calcd. for $C_{29}H_{23}N_4O_3$ [M+H]$^+$ 475.2, found 475.2. HPLC $R_t$=3.74 min in 8 min chromatography, 220 nm, purity 94.75%.

The following compounds were obtained from chiral separations as described above for the respective enantiomer. Analytical data obtained compared appropriately with the racemic and/or enantiomeric analogs described above.

| Cmpd. | Structure | Name |
|---|---|---|
| (R)-004 | 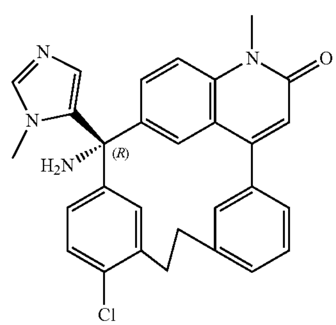 | (R)-3-amino-4$^4$-chloro-2$^1$-methyl-3-(1-methyl-1H-imidazol-5-yl)-2$^1$,2$^2$-dihydro-2(4,6)-quinolina-1,4(1,3)-dibenzenacyclohexaphan-2$^2$-one |
| (S)-006 | 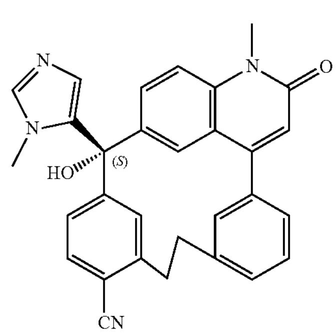 | (S)-3-hydroxy-2$^1$-methyl-3-(1-methyl-1H-imidazol-5-yl)-2$^2$-oxo-2$^1$,2$^2$-dihydro-2(4,6)-quinolina-1,4(1,3)-dibenzenacyclohexaphane-4$^4$-carbonitrile |

-continued

| Cmpd. | Structure | Name |
|---|---|---|
| (S)-007 | 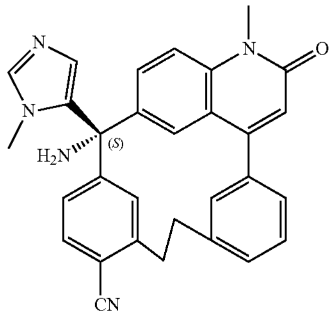 | (S)-3-amino-2¹-methyl-3-(1-methyl-1H-imidazol-5-yl)-22-oxo-2¹,2²-dihydro-2(4,6)-quinolina-1,4(1,3)-dibenzenacyclohexaphane-4⁴-carbonitrile |
| (S)-008 | 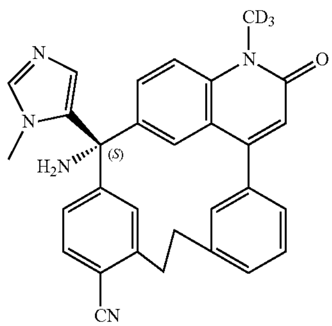 | (S)-3-amino-2¹-(methyl-d₃)-3-(1-methyl-1H-imidazol-5-yl)-22-oxo-2¹,2²-dihydro-2(4,6)-quinolina-1,4(1,3)-dibenzenacyclohexaphane-4⁴-carbonitrile |
| (S)-009 | 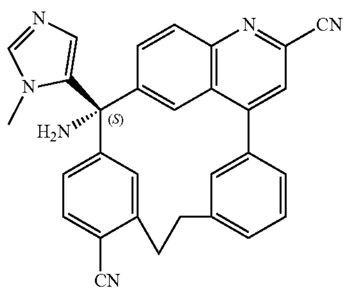 | (S)-3-amino-3-(1-methyl-1H-imidazol-5-yl)-2(4,6)-quinolina-1,4(1,3)-dibenzenacyclohexaphane-2²,4⁴-dicarbonitrile |
| (R)-014 | 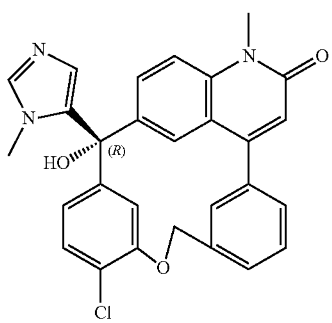 | (R)-4⁴-chloro-3-hydroxy-2¹-methyl-3-(1-methyl-1H-imidazol-5-yl)-2¹,2²-dihydro-5-oxa-2(4,6)-quinolina-1,4(1,3)-dibenzenacyclohexaphan-2²-one |
| (R)-015 | 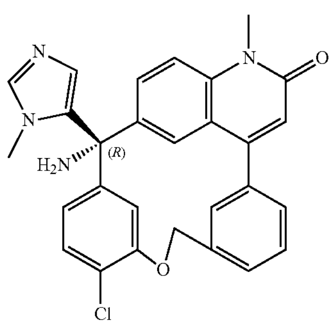 | (R)-3-amino-4⁴-chloro-2¹-methyl-3-(1-methyl-1H-imidazol-5-yl)-2¹,2²-dihydro-5-oxa-2(4,6)-quinolina-1,4(1,3)-dibenzenacyclohexaphan-2²-one |

-continued

| Cmpd. | Structure | Name |
|---|---|---|
| (R)-018 | 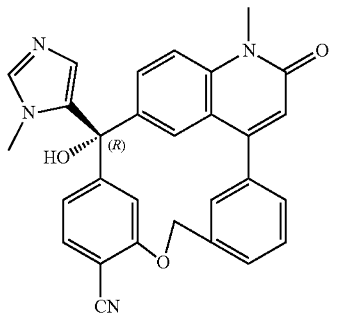 | (R)-3-hydroxy-2¹-methyl-3-(1-methyl-1H-imidazol-5-yl)-2²-oxo-2¹,2²-dihydro-5-oxa-2(4,6)-quinolina-1,4(1,3)-dibenzenacyclohexaphane-4⁴-carbonitrile |
| (R)-019 | 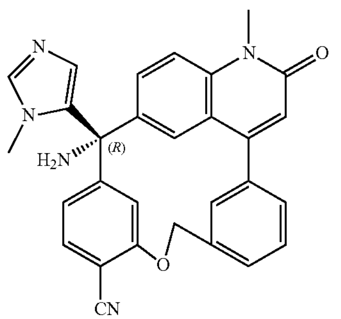 | (R)-3-amino-2¹-methyl-3-(1-methyl-1H-imidazol-5-yl)-2²-oxo-2¹,2²-dihydro-5-oxa-2(4,6)-quinolina-1,4(1,3)-dibenzenacyclohexaphane-4⁴-carbonitrile |
| (R)-020 | 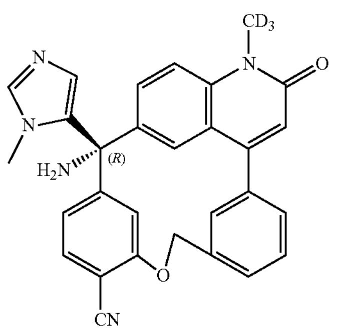 | (R)-3-amino-2¹-(methyl-d₃)-3-(1-methyl-1H-imidazol-5-yl)-2²-oxo-2¹,2²-dihydro-5-oxa-2(4,6)-quinolina-1,4(1,3)-dibenzenacyclohexaphane-4⁴-carbonitrile |
| (R)-021 | 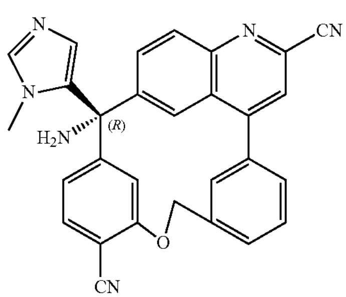 | (R)-3-amino-3-(1-methyl-1H-imidazol-5-yl)-5-oxa-2(4,6)-quinolina-1,4(1,3)-dibenzenacyclohexaphane-2²,4⁴-dicarbonitrile |
| (R)-025 | 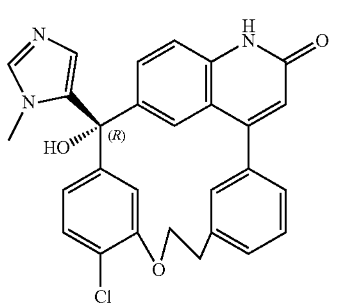 | (R)-4⁴-chloro-3-hydroxy-3-(1-methyl-1H-imidazol-5-yl)-2¹,2²-dihydro-5-oxa-2(4,6)-quinolina-1,4(1,3)-dibenzenacycloheptaphan-2²-one |

| Cmpd. | Structure | Name |
|---|---|---|
| (R)-027 | 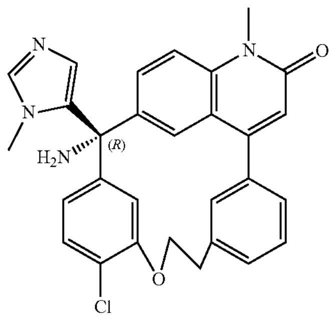 | (R)-3-amino-4⁴-chloro-2¹-methyl-3-(1-methyl-1H-imidazol-5-yl)-2¹,2²-dihydro-5-oxa-2(4,6)-quinolina-1,4(1,3)-dibenzenacycloheptaphan-2²-one |
| (R)-028 | 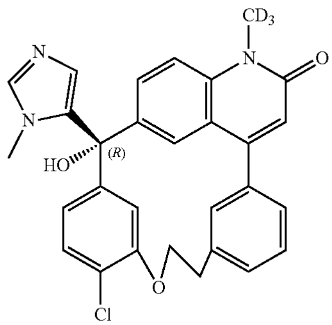 | (R)-4⁴-chloro-3-hydroxy-2¹-(methyl-d₃)-3-(1-methyl-1H-imidazol-5-yl)-2¹,2²-dihydro-5-oxa-2(4,6)-quinolina-1,4(1,3)-dibenzenacycloheptaphan-2²-one |
| (R)-029 | 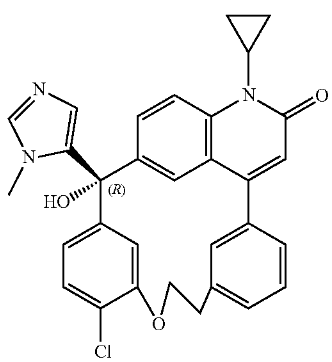 | (R)-4⁴-chloro-2¹-cyclopropyl-3-hydroxy-3-(1-methyl-1H-imidazol-5-yl)-2¹,2²-dihydro-5-oxa-2(4,6)-quinolina-1,4(1,3)-dibenzenacycloheptaphan-2²-one |
| (R)-030 | 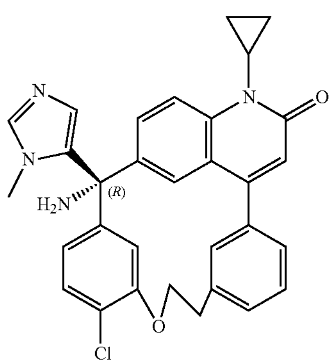 | (R)-3-amino-4⁴-chloro-2¹-cyclopropyl-3-(1-methyl-1H-imidazol-5-yl)-2¹,2²-dihydro-5-oxa-2(4,6)-quinolina-1,4(1,3)-dibenzenacycloheptaphan-2²-one |

| Cmpd. | Structure | Name |
|---|---|---|
| (R)-034 | 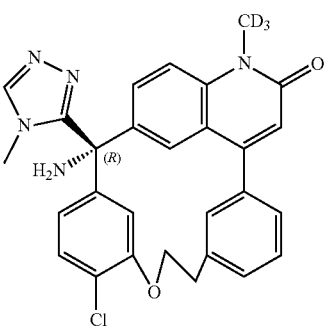 | (R)-3-amino-4⁴-chloro-2¹-(methyl-d₃)-3-(4-methyl-4H-1,2,4-triazol-3-yl)-2¹,2²-dihydro-5-oxa-2(4,6)-quinolina-1,4(1,3)-dibenzenacycloheptaphan-2²-one |
| (R)-035 | 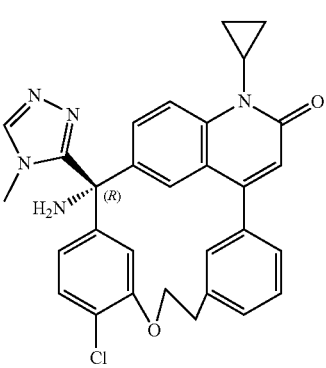 | (R)-3-amino-4⁴-chloro-2¹-cyclopropyl-3-(4-methyl-4H-1,2,4-triazol-3-yl)-2¹,2²-dihydro-5-oxa-2(4,6)-quinolina-1,4(1,3)-dibenzenacycloheptaphan-2²-one |
| (R)-036 | 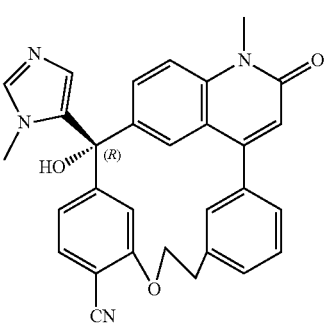 | (R)-3-hydroxy-2¹-methyl-3-(1-methyl-1H-imidazol-5-yl)-2²-oxo-2¹,2²-dihydro-5-oxa-2(4,6)-quinolina-1,4(1,3)-dibenzenacycloheptaphane-4⁴-carbonitrile |
| (R)-037 | 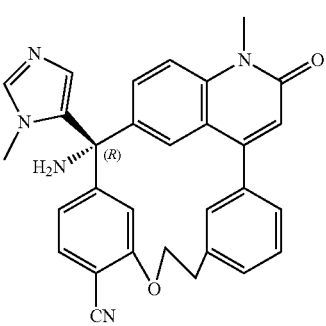 | (R)-3-amino-2¹-methyl-3-(1-methyl-1H-imidazol-5-yl)-2²-oxo-2¹,2²-dihydro-5-oxa-2(4,6)-quinolina-1,4(1,3)-dibenzenacycloheptaphane-4⁴-carbonitrile |

-continued

| Cmpd. | Structure | Name |
|---|---|---|
| (R)-039 | 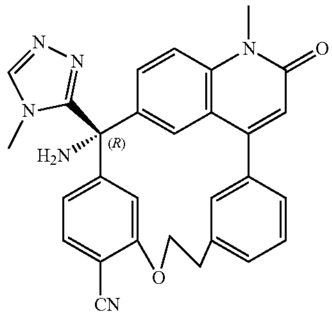 | (R)-3-amino-2¹-methyl-3-(4-methyl-4H-1,2,4-triazol-3-yl)-2²-oxo-2¹,2²-dihydro-5-oxa-2(4,6)-quinolina-1,4(1,3)-dibenzenacycloheptaphane-4⁴-carbonitrile |
| (R)-046 | 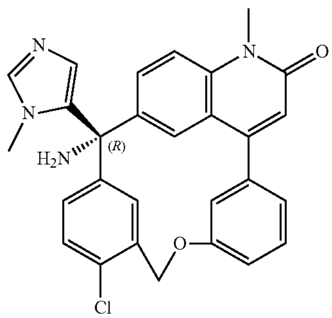 | (R)-3-amino-4⁴-chloro-2¹-methyl-3-(1-methyl-1H-imidazol-5-yl)-2¹,2²-dihydro-6-oxa-2(4,6)-quinolina-1,4(1,3)-dibenzenacyclohexaphan-2²-one |
| (R)-047 | 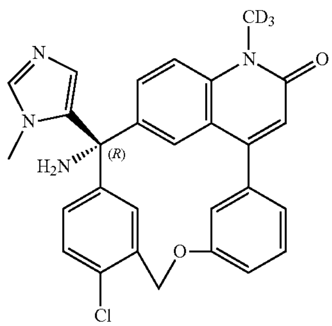 | (R)-3-amino-4⁴-chloro-2¹-(methyl-d₃)-3-(1-methyl-1H-imidazol-5-yl)-2¹,2²-dihydro-6-oxa-2(4,6)-quinolina-1,4(1,3)-dibenzenacyclohexaphan-2²-one |
| (R)-048 | 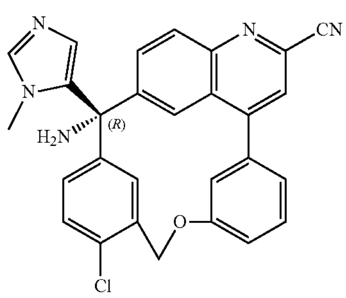 | (R)-3-amino-4⁴-chloro-3-(1-methyl-1H-imidazol-5-yl)-6-oxa-2(4,6)-quinolina-1,4(1,3)-dibenzenacyclohexaphane-2²-carbonitrile |
| (R)-051 | 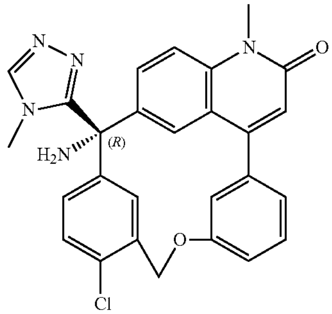 | (R)-3-amino-4⁴-chloro-2¹-methyl-3-(4-methyl-4H-1,2,4-triazol-3-yl)-2¹,2²-dihydro-6-oxa-2(4,6)-quinolina-1,4(1,3)-dibenzenacyclohexaphan-2²-one |

-continued

| Cmpd. | Structure | Name |
|---|---|---|
| (R)-055 | 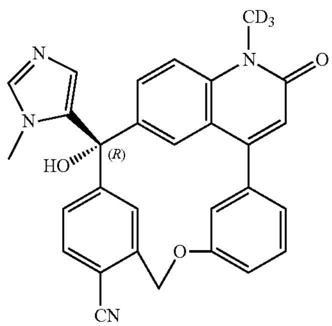 | (R)-3-hydroxy-2¹-(methyl-d₃)-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile |
| (R)-056 | 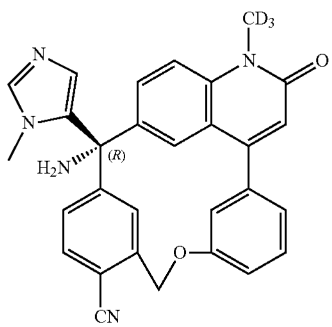 | (R)-3-amino-2¹-(methyl-d₃)-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile |
| (R)-057 | 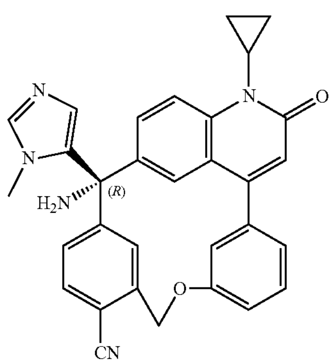 | (R)-3-amino-2¹-cyclopropyl-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile |
| (R)-058 | 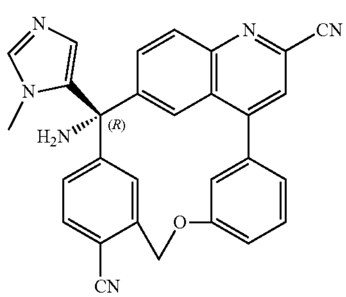 | (R)-3-amino-3-(1-methyl-1H-imidazol-5-yl)-6-oxa-2(4,6)-quinolina-1,4(1,3)-dibenzenacyclohexaphane-2²,4⁴-dicarbonitrile |

-continued

| Cmpd. | Structure | Name |
|---|---|---|
| (R)-066 | 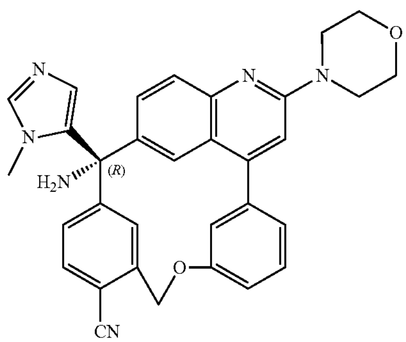 | (R)-3-amino-3-(1-methyl-1H-imidazol-5-yl)-2²-morpholino-6-oxa-2(4,6)-quinolina-1,4(1,3)-dibenzenacyclohexaphane-4⁴-carbonitrile |
| (R)-070 | 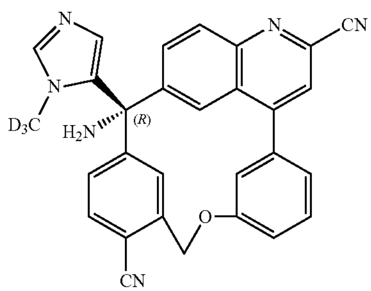 | (R)-3-amino-3-(1-(methyl-d₃)-1H-imidazol-5-yl)-6-oxa-2(4,6)-quinolina-1,4(1,3)-dibenzenacyclohexaphane-2²,4⁴-dicarbonitrile |
| (S)-076 | 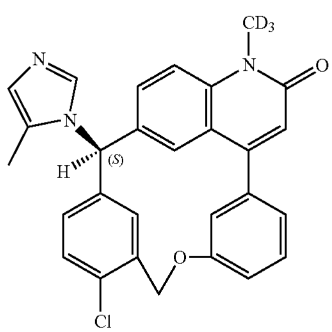 | (S)-4⁴-chloro-2¹-(methyl-d₃)-3-(5-methyl-1H-imidazol-1-yl)-2¹,2²-dihydro-6-oxa-2(4,6)-quinolina-1,4(1,3)-dibenzenacyclohexaphan-2²-one |
| (S)-077 | 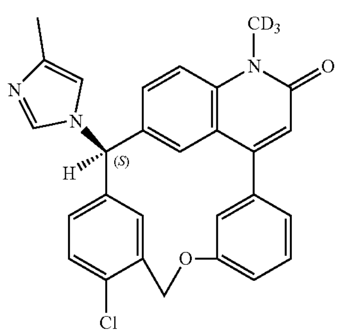 | (S)-4⁴-chloro-2¹-(methyl-d₃)-3-(4-methyl-1H-imidazol-1-yl)-2¹,2²-dihydro-6-oxa-2(4,6)-quinolina-1,4(1,3)-dibenzenacyclohexaphan-2²-one |

The following compounds were prepared using methods analogous to those described herein:

| Cmpd. | Structure | Name / Analytical Data |
|---|---|---|
| (R)-089 | 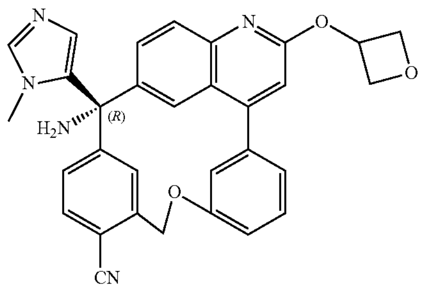 | (R)-3-amino-3-(1-methyl-1H-imidazol-5-yl)-2²-(oxetan-3-yloxy)-6-oxa-2(4,6)-quinolina-1,4(1,3)-dibenzenacyclohexaphane-4⁴-carbonitrile<br>¹H NMR (400 MHz, DMSO-d₆) δ = 8.13-8.06 (m, 1H), 7.91 (s, 1H), 7.84-7.77 (m, 2H), 7.53 (s, 1H), 7.43-7.26 (m, 2H), 7.19 (s, 1H), 7.15-7.11 (m, 2H), 7.05 (dd, J = 2.0, 8.0 Hz, 1H), 6.98 (s, 1H), 6.45 (s, 1H), 5.85-5.75 (m, 1H), 5.57-5.48 (m, 2H), 5.03-4.98 (m, 2H), 4.68-4.64 (m, 2H), 3.41 (s, 3H), 3.01 (s, 2H). LCMS R$_t$ = 1.90 min in 3.0 min chromatography, 10-80CD, ESI calcd. for C₃₁H₂₆N₅O₃ [M + H]⁺ 516.2, found 516.1. HPLC R$_t$ = 3.83 min in 8 min chromatography, 220 nm, purity 93.73%. Chiral HPLC R$_t$ = 0.86 min in 2 min (ee 99.48%), (AD_ETOH_DEA_40_4ML_5CM). |
| (S)-089 | 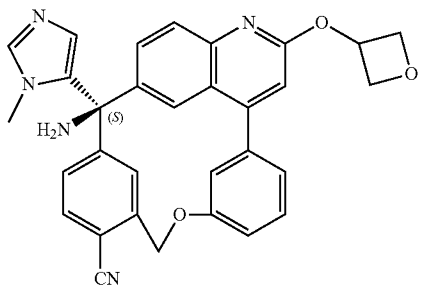 | (S)-3-amino-3-(1-methyl-1H-imidazol-5-yl)-2²-(oxetan-3-yloxy)-6-oxa-2(4,6)-quinolina-1,4(1,3)-dibenzenacyclohexaphane-4⁴-carbonitrile<br>¹H NMR (400 MHz, DMSO-d₆) δ = 8.09 (d, J = 8.8 Hz, 1H), 7.91 (s, 1H), 7.84-7.78 (m, 2H), 7.53 (s, 1H), 7.40-7.25 (m, 2H), 7.19 (s, 1H), 7.15-7.11 (m, 2H), 7.05 (dd, J = 1.6, 8.4 Hz, 1H), 6.98 (s, 1H), 6.44 (s, 1H), 5.85-5.78 (m, 1H), 5.57-5.48 (m, 2H), 5.02-4.98 (m, 2H), 4.68-4.65 (m, 2H), 3.41 (s, 3H), 3.01 (s, 2H). LCMS R$_t$ = 1.88 min in 3.0 min chromatography, 10-80CD, ESI calcd. for C₃₁H₂₆N₅O₃ [M + H]⁺ 516.2, found 516.2. HPLC R$_t$ = 3.82 min in 8 min chromatography, 220 nm, purity 97.94%. Chiral HPLC R$_t$ = 1.35 min in 2 min (ee 99.68%), (AD_ETOH_DEA_40_4ML_5CM). |
| (S)-090 | 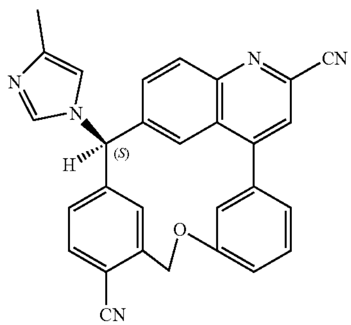 | (S)-3-(4-methyl-1H-imidazol-1-yl)-6-oxa-2(4,6)-quinolina-1,4(1,3)-dibenzenacyclohexaphane-2²,4⁴-dicarbonitrile<br>¹H NMR (400 MHz, DMSO-d₆) δ = 8.23-8.19 (m, 2H), 8.14 (s, 1H), 7.87 (d, J = 7.6 Hz, 1H), 7.77-7.71 (m, 2H), 7.48-7.43 (m, 1H), 7.35 (s, 1H), 7.32-7.28 (m, 2H), 7.20 (s, 1H), 7.08 (dd, J = 2.4, 8.4 Hz, 2H), 6.84 (s, 1H), 5.55 (s, 2H), 2.09 (s, 3H). LCMS R$_t$ = 2.01 min in 3 min chromatography, 10-80CD, ESI calcd. for C₂₉H₂₀N₅O [M + H]⁺ 454.2, found 454.2. HPLC R$_t$ = 4.13 min in 8 min chromatography, 220 nm, purity 97.75%. Chiral HPLC R$_t$ = 0.87 min in 5 min (ee 94.48%), (IG_ETOH_DEA_40_4ML_5CM). |
| (R)-090 | 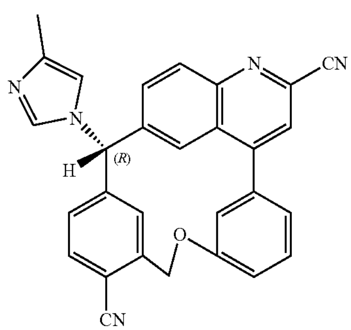 | (R)-3-(4-methyl-1H-imidazol-1-yl)-6-oxa-2(4,6)-quinolina-1,4(1,3)-dibenzenacyclohexaphane-2²,4⁴-dicarbonitrile<br>¹H NMR (400 MHz, DMSO-d₆) δ = 8.23-8.19 (m, 2H), 8.14 (s, 1H), 7.87 (d, J = 7.6 Hz, 1H), 7.77-7.71 (m, 2H), 7.48-7.43 (m, 1H), 7.35 (s, 1H), 7.32-7.28 (m, 2H), 7.20 (s, 1H), 7.08 (dd, J = 2.4, 8.4 Hz, 2H), 6.84 (s, 1H), 5.55 (s, 2H), 2.09 (s, 3H). LCMS R$_t$ = 2.01 min in 3 min chromatography, 10-80CD, ESI calcd. for C₂₉H₂₀N₅O [M + H]⁺ 454.2, found 454.2. HPLC R$_t$ = 4.13 min in 8 min chromatography, 220 nm, purity 94.10%. Chiral HPLC R$_t$ = 1.37 min in 5 min (ee 89.89%), (IG_ETOH_DEA_40_4ML_5CM). |
| (S)-091 | 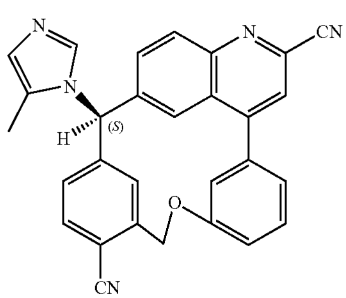 | (S)-3-(5-methyl-1H-imidazol-1-yl)-6-oxa-2(4,6)-quinolina-1,4(1,3)-dibenzenacyclohexaphane-2²,4⁴-dicarbonitrile<br>¹H NMR (400 MHz, DMSO-d₆) δ = 8.23 (d, J = 8.8 Hz, 1H), 8.15 (s, 2H), 7.89-7.81 (m, 2H), 7.46 (t, J = 7.6 Hz, 1H), 7.36-7.26 (m, 4H), 7.15-7.08 (m, 2H), 6.82 (s, 2H), 5.57 (s, 2H), 2.22 (s, 3H). LCMS R$_t$ = 1.98 min in 3 min chromatography, 10-80CD, ESI calcd. for C₂₉H₂₀N₅O [M + H]⁺ 454.2, found 454.2. HPLC R$_t$ = 4.03 min in 8 min chromatography, 220 nm, purity 97.18%. Chiral HPLC R$_t$ = 1.02 min in 5 min (ee 89.24%), (IG_ETOH_DEA_40_4ML_5CM). |

-continued

| Cmpd. | Structure | Name<br>Analytical Data |
|---|---|---|
| (R)-091 | 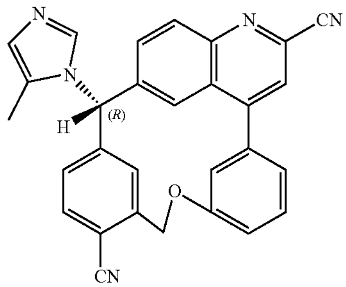 | (R)-3-(5-methyl-1H-imidazol-1-yl)-6-oxa-2(4,6)-quinolina-1,4(1,3)-dibenzenacyclohexaphane-$2^2$,$4^4$-dicarbonitrile<br>$^1$H NMR (400 MHz, DMSO-$d_6$) δ = 8.55 (s, 1H), 7.98 (s, 1H), 7.58 (d, J = 8.8 Hz, 1H), 7.46-7.26 (m, 4H), 7.21 (d, J = 1.2 Hz, 1H), 7.13-7.05 (m, 2H), 7.04-6.87 (m, 2H), 6.66 (s, 1H), 5.55-5.42 (m, 2H), 2.23 (s, 3H). LCMS $R_t$ = 1.91 min in 3 min chromatography, 10-80CD, ESI calcd. for $C_{27}H_{19}D_3ClN_4O_2$ [M + H]$^+$ 472.2, found 472.1. HPLC $R_t$ = 3.88 min in 8 min chromatography, 220 nm, purity 99.06%. Chiral HPLC ($R_t$ = 2.30 min in 5 min (ee 91.34%), (IG_ETOH_DEA_40_4ML_5CM). |

The following compounds can be prepared using methods analgous to those described herein.

| Cmpd. | Structure | Name |
|---|---|---|
| 092 | 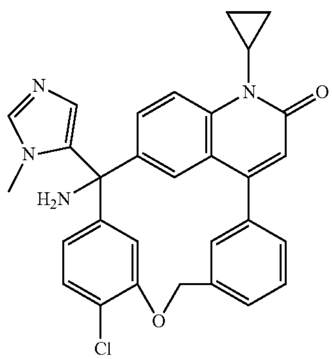 [SMILES: Cn1cncc1C1(N)c2ccc(Cl)c(c2)OCc2cccc(c2)-c2cc(=O)n(C3CC3)c3ccc1cc23] | 3-amino-$4^4$-chloro-$2^1$-cyclopropyl-3-(1-methyl-1H-imidazol-5-yl)-$2^1$,$2^2$-dihydro-5-oxa-2(4,6)-quinolina-1,4(1,3)-dibenzenacyclohexaphan-$2^2$-one |
| 093 | 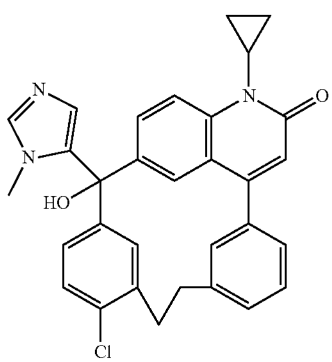 | $4^4$-chloro-$2^1$-cyclopropyl-3-hydroxy-3-(1-methyl-1H-imidazol-5-yl)-$2^1$,$2^2$-dihydro-2(4,6)-quinolina-1,4(1,3)-dibenzenacyclohexaphan-$2^2$-one |
| 094 | 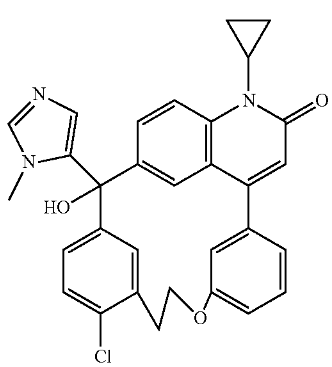 [SMILES: Cn1cncc1C1(O)c2ccc(Cl)c(c2)CCOc2cccc(c2)-c2cc(=O)n(C3CC3)c3ccc1cc23] | $4^4$-chloro-$2^1$-cyclopropyl-3-hydroxy-3-(1-methyl-1H-imidazol-5-yl)-$2^1$,$2^2$-dihydro-7-oxa-2(4,6)-quinolina-1,4(1,3)-dibenzenacycloheptaphan-$2^2$-one |

-continued

| Cmpd. | Structure | Name |
|---|---|---|
| 095 | 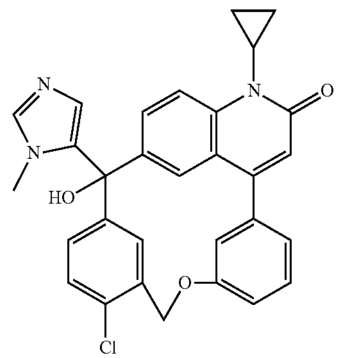 [SMILES: Cn1cncc1C1(O)c2ccc(Cl)c(c2)COc2cccc(c2)-c2cc(=O)n(C3CC3)c3ccc1cc23] | 4⁴-chloro-2¹-cyclopropyl-3-hydroxy-3-(1-methyl-1H-imidazol-5-yl)-2¹,2²-dihydro-6-oxa-2(4,6)-quinolina-1,4(1,3)-dibenzenacyclohexaphan-2²-one |
| 096 | 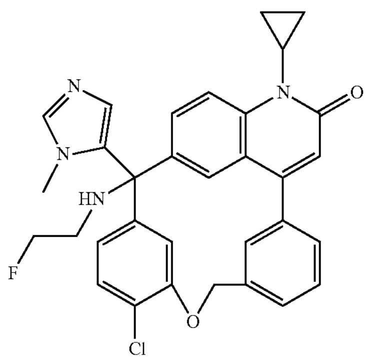 [SMILES: Cn1cncc1C1(NCCF)c2ccc(Cl)c(c2)OCc2cccc(c2)-c2cc(=O)n(C3CC3)c3ccc1cc23] | 4⁴-chloro-2¹-cyclopropyl-3-((2-fluoroethyl)amino)-3-(1-methyl-1H-imidazol-5-yl)-2¹,2²-dihydro-5-oxa-2(4,6)-quinolina-1,4(1,3)-dibenzenacyclohexaphan-2²-one |
| 097 | 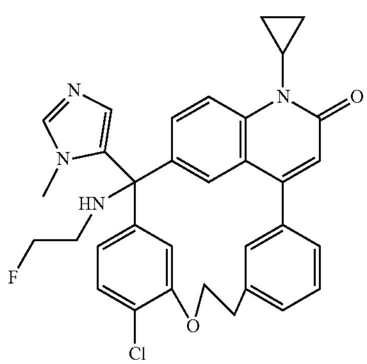 [SMILES: Cn1cncc1C1(NCCF)c2ccc(Cl)c(c2)OCCc2cccc(c2)-c2cc(=O)n(C3CC3)c3ccc1cc23] | 4⁴-chloro-2¹-cyclopropyl-3-((2-fluoroethyl)amino)-3-(1-methyl-1H-imidazol-5-yl)-2¹,2²-dihydro-5-oxa-2(4,6)-quinolina-1,4(1,3)-dibenzenacycloheptaphan-2²-one |
| 098 | 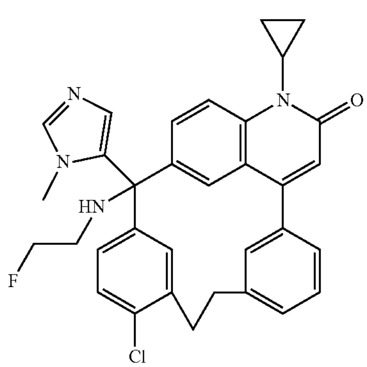 [SMILES: Cn1cncc1C1(NCCF)c2ccc(Cl)c(c2)CCc2cccc(c2)-c2cc(=O)n(C3CC3)c3ccc1cc23] | 4⁴-chloro-2¹-cyclopropyl-3-((2-fluoroethyl)amino)-3-(1-methyl-1H-imidazol-5-yl)-2¹,2²-dihydro-2(4,6)-quinolina-1,4(1,3)-dibenzenacyclohexaphan-2²-one |

| Cmpd. | Structure | Name |
|---|---|---|
| 099 | 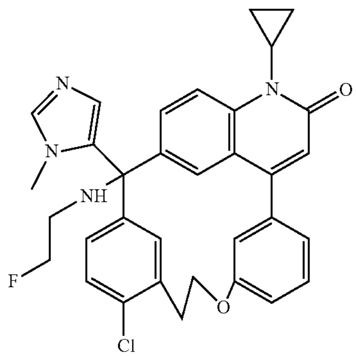 [SMILES: Cn1cncc1C1(NCCF)c2ccc(Cl)c(c2)CCOc2cccc(c2)-c2cc(=O)n(C3CC3)c3ccc1cc23] | 4⁴-chloro-2¹-cyclopropyl-3-((2-fluoroethyl)amino)-3-(1-methyl-1H-imidazol-5-yl)-2¹,2²-dihydro-7-oxa-2(4,6)-quinolina-1,4(1,3)-dibenzenacycloheptaphan-2²-one |
| 100 | 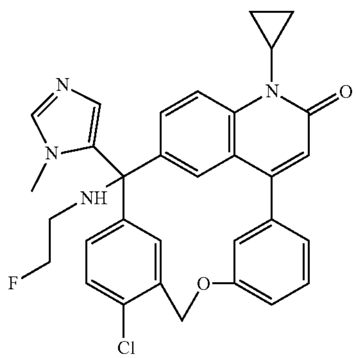 [SMILES: Cn1cncc1C1(NCCF)c2ccc(Cl)c(c2)COc2cccc(c2)-c2cc(=O)n(C3CC3)c3ccc1cc23] | 4⁴-chloro-2¹-cyclopropyl-3-((2-fluoroethyl)amino)-3-(1-methyl-1H-imidazol-5-yl)-2¹,2²-dihydro-6-oxa-2(4,6)-quinolina-1,4(1,3)-dibenzenacyclohexaphan-2²-one |
| 101 | 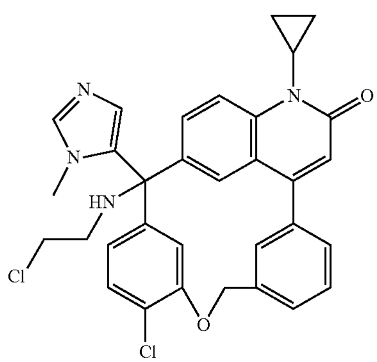 [SMILES: Cn1cncc1C1(NCCCl)c2ccc(Cl)c(c2)OCc2cccc(c2)-c2cc(=O)n(C3CC3)c3ccc1cc23] | 4⁴-chloro-3-((2-chloroethyl)amino)-2¹-cyclopropyl-3-(1-methyl-1H-imidazol-5-yl)-2¹,2²-dihydro-5-oxa-2(4,6)-quinolina-1,4(1,3)-dibenzenacyclohexaphan-2² one |
| 102 | 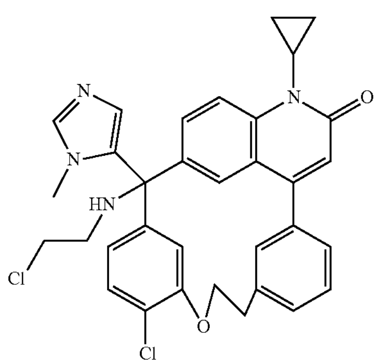 [SMILES: Cn1cncc1C1(NCCCl)c2ccc(Cl)c(c2)OCCc2cccc(c2)-c2cc(=O)n(C3CC3)c3ccc1cc23] | 4⁴-chloro-3-((2-chloroethyl)amino)-2¹-cyclopropyl-3-(1-methyl-1H-imidazol-5-yl)-2¹,2²-dihydro-5-oxa-2(4,6)-quinolina-1,4(1,3)-dibenzenacycloheptaphan-2²-one |

| Cmpd. | Structure | Name |
|---|---|---|
| 103 | 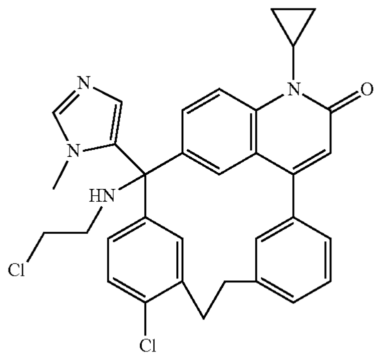 [SMILES: Cn1cncc1C1(NCCCl)c2ccc(Cl)c(c2)CCc2cccc(c2)-c2cc(=O)n(C3CC3)c3ccc1cc23] | $4^4$-chloro-3-((2-chloroethyl)amino)-$2^1$-cyclopropyl-3-(1-methyl-1H-imidazol-5-yl)-$2^1$,$2^2$-dihydro-2(4,6)-quinolina-1,4(1,3)-dibenzenacyclohexaphan-$2^2$-one |
| 104 | 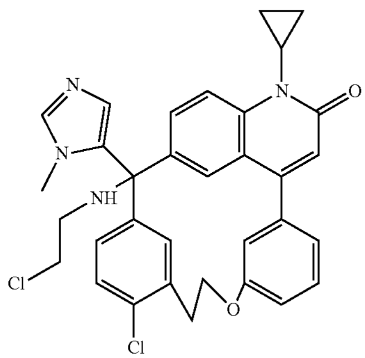 [SMILES: Cn1cncc1C1(NCCCl)c2ccc(Cl)c(c2)CCOc2cccc(c2)-c2cc(=O)n(C3CC3)c3ccc1cc23] | $4^4$-chloro-3-((2-chloroethyl)amino)-$2^1$-cyclopropyl-3-(1-methyl-1H-imidazol-5-yl)-$2^1$,$2^2$-dihydro-7-oxa-2(4,6)-quinolina-1,4(1,3)-dibenzenacycloheptaphan-$2^2$-one |
| 105 | 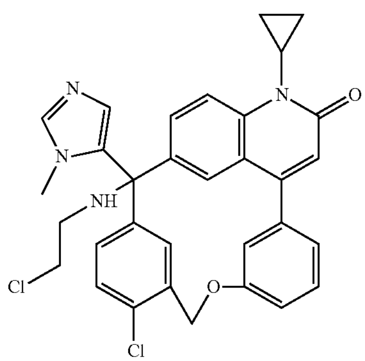 [SMILES: Cn1cncc1C1(NCCCl)c2ccc(Cl)c(c2)COc2cccc(c2)-c2cc(=O)n(C3CC3)c3ccc1cc23] | $4^4$-chloro-3-((2-chloroethyl)amino)-$2^1$-cyclopropyl-3-(1-methyl-1H-imidazol-5-yl)-$2^1$,$2^2$-dihydro-6-oxa-2(4,6)-quinolina-1,4(1,3)-dibenzenacyclohexaphan-$2^2$-one |
| 106 | 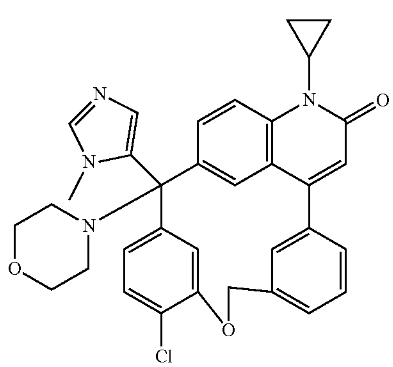 [SMILES: Cn1cncc1C1(N2CCOCC2)c2ccc(Cl)c(c2)OCc2cccc(c2)-c2cc(=O)n(C3CC3)c3ccc1cc23] | $4^4$-chloro-$2^1$-cyclopropyl-3-(1-methyl-1H-imidazol-5-yl)-3-morpholino-$2^1$,$2^2$-dihydro-5-oxa-2(4,6)-quinolina-1,4(1,3)-dibenzenacyclohexaphan-$2^2$-one |

-continued

| Cmpd. | Structure | Name |
|---|---|---|
| 107 | 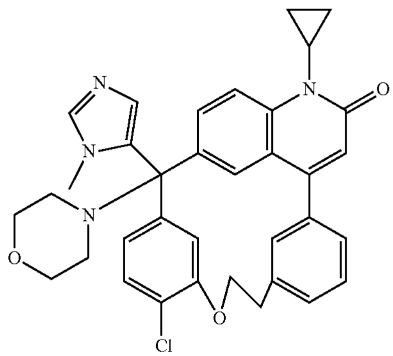 [SMILES: Cn1cncc1C1(N2CCOCC2)c2ccc(Cl)c(c2)OCCc2cccc(c2)-c2cc(=O)n(C3CC3)c3ccc1cc23] | 4⁴-chloro-2¹-cyclopropyl-3-(1-methyl-1H-imidazol-5-yl)-3-morpholino-2¹,2²-dihydro-5-oxa-2(4,6)-quinolina-1,4(1,3)-dibenzenacycloheptaphan-2²-one |
| 108 | 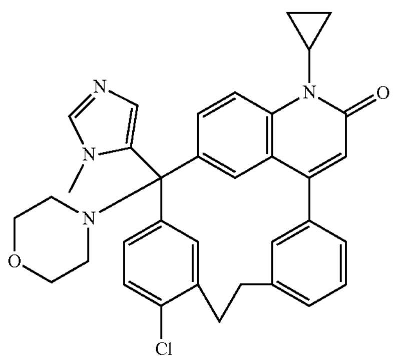 [SMILES: Cn1cncc1C1(N2CCOCC2)c2ccc(Cl)c(c2)CCc2cccc(c2)-c2cc(=O)n(C3CC3)c3ccc1cc23] | 4⁴-chloro-21-cyclopropyl-3-(1-methyl-1H-imidazol-5-yl)-3-morpholino-2¹,2²-dihydro-2(4,6)-quinolina-1,4(1,3)-dibenzenacyclohexaphan-2²-one |
| 109 | 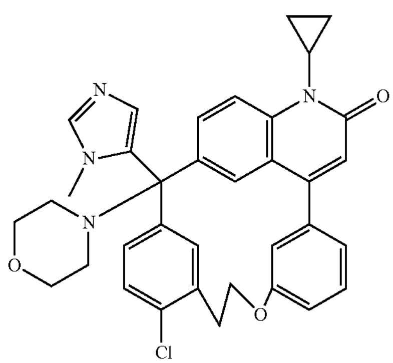 [SMILES: Cn1cncc1C1(N2CCOCC2)c2ccc(Cl)c(c2)CCOc2cccc(c2)-c2cc(=O)n(C3CC3)c3ccc1cc23] | 4⁴-chloro-2¹-cyclopropyl-3-(1-methyl-1H-imidazol-5-yl)-3-morpholino-2¹,2²-dihydro-7-oxa-2(4,6)-quinolina-1,4(1,3)-dibenzenacycloheptaphan-2²-one |
| 110 | 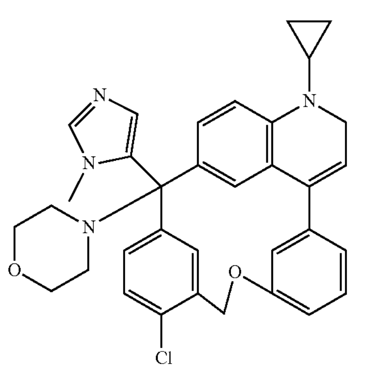 [SMILES: Cn1cncc1C1(N2CCOCC2)c2ccc(Cl)c(c2)COc2cccc(c2)C2=CCN(C3CC3)c3ccc1cc32] | 4⁴-chloro-2¹-cyclopropyl-3-(1-methyl-1H-imidazol-5-yl)-3-morpholino-2¹,2²-dihydro-6-oxa-2(4,6)-quinolina-1,4(1,3)-dibenzenacyclohexaphane |

| Cmpd. | Structure | Name |
|---|---|---|
| 111 | 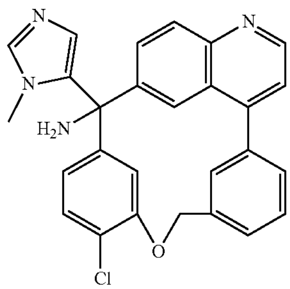 [SMILES: Cn1cncc1C1(N)c2ccc(Cl)c(c2)OCc2cccc(c2)-c2ccnc3ccc1cc23] | 4⁴-chloro-3-(1-methyl-1H-imidazol-5-yl)-5-oxa-2(4,6)-quinolina-1,4(1,3)-dibenzenacyclohexaphan-3-amine |
| 112 | 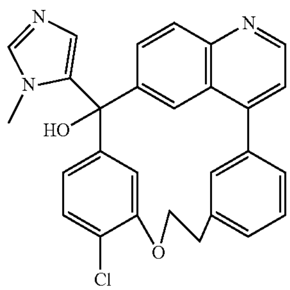 [SMILES: Cn1cncc1C1(O)c2ccc(Cl)c(c2)OCCc2cccc(c2)-c2ccnc3ccc1cc23] | 4⁴-chloro-3-(1-methyl-1H-imidazol-5-yl)-5-oxa-2(4,6)-quinolina-1,4(1,3)-dibenzenacycloheptaphan-3-ol |
| 113 | 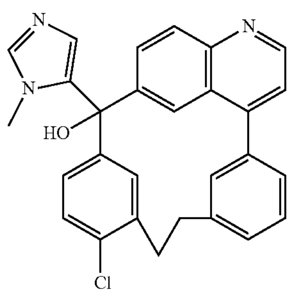 [SMILES: Cn1cncc1C1(O)c2ccc(Cl)c(c2)CCc2cccc(c2)-c2ccnc3ccc1cc23] | 4⁴-chloro-3-(1-methyl-1H-imidazol-5-yl)-2(4,6)-quinolina-1,4(1,3)-dibenzenacyclohexaphan-3-ol |
| 114 | 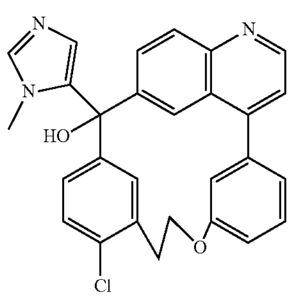 [SMILES: Cn1cncc1C1(O)c2ccc(Cl)c(c2)CCOc2cccc(c2)-c2ccnc3ccc1cc23] | 4⁴-chloro-3-(1-methyl-1H-imidazol-5-yl)-7-oxa-2(4,6)-quinolina-1,4(1,3)-dibenzenacycloheptaphan-3-ol |
| 115 | 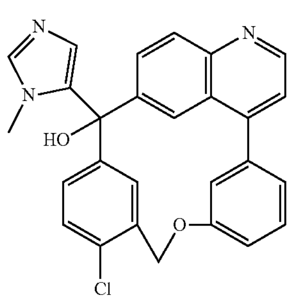 [SMILES: Cn1cncc1C1(O)c2ccc(Cl)c(c2)COc2cccc(c2)-c2ccnc3ccc1cc23] | 4⁴-chloro-3-(1-methyl-1H-imidazol-5-yl)-6-oxa-2(4,6)-quinolina-1,4(1,3)-dibenzenacyclohexaphan-3-ol |

-continued

| Cmpd. | Structure | Name |
|---|---|---|
| 116 | 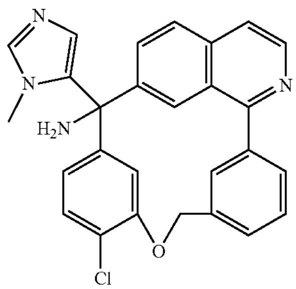 [SMILES: Cn1cncc1C1(N)c2ccc(Cl)c(c2)OCc2cccc(c2)-c2nccc3ccc1cc23] | 4[4]-chloro-3-(1-methyl-1H-imidazol-5-yl)-5-oxa-2(1,7)-isoquinolina-1,4(1,3)-dibenzenacyclohexaphan-3-amine |
| 117 | 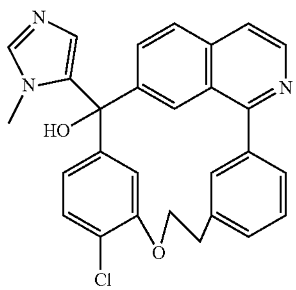 [SMILES: Cn1cncc1C1(O)c2ccc(Cl)c(c2)OCCc2cccc(c2)-c2nccc3ccc1cc23] | 4[4]-chloro-3-(1-methyl-1H-imidazol-5-yl)-5-oxa-2(1,7)-isoquinolina-1,4(1,3)-dibenzenacycloheptaphan-3-ol |
| 118 | 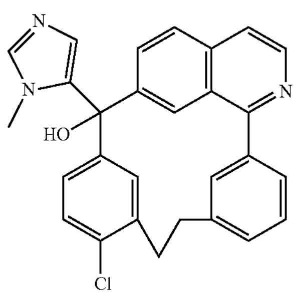 [SMILES: Cn1cncc1C1(O)c2ccc(Cl)c(c2)CCc2cccc(c2)-c2nccc3ccc1cc23] | 4[4]-chloro-3-(1-methyl-1H-imidazol-5-yl)-2(1,7)-isoquinolina-1,4(1,3)-dibenzenacyclohexaphan-3-ol |
| 119 | 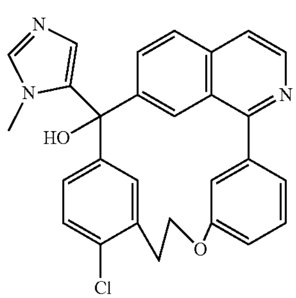 [SMILES: Cn1cncc1C1(O)c2ccc(Cl)c(c2)CCOc2cccc(c2)-c2nccc3ccc1cc23] | 4[4]-chloro-3-(1-methyl-1H-imidazol-5-yl)-7-oxa-2(1,7)-isoquinolina-1,4(1,3)-dibenzenacycloheptaphan-3-ol |
| 120 | 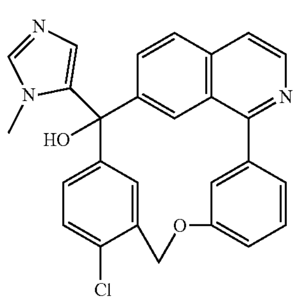 [SMILES: Cn1cncc1C1(O)c2ccc(Cl)c(c2)COc2cccc(c2)-c2nccc3ccc1cc23] | 4[4]-chloro-3-(1-methyl-1H-imidazol-5-yl)-6-oxa-2(1,7)-isoquinolina-1,4(1,3)-dibenzenacyclohexaphan-3-ol |

| Cmpd. | Structure | Name |
|---|---|---|
| 121 | 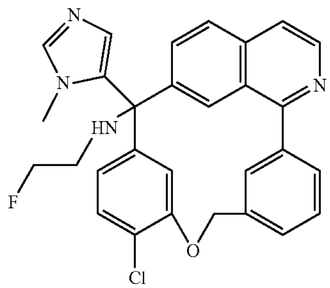 [SMILES: Cn1cncc1C1(NCCF)c2ccc(Cl)c(c2)OCc2cccc(c2)-c2nccc3ccc1cc23] | 4[4]-chloro-N-(2-fluoroethyl)-3-(1-methyl-1H-imidazol-5-yl)-5-oxa-2(1,7)-isoquinolina-1,4(1,3)-dibenzenacyclohexaphan-3-amine |
| 122 | 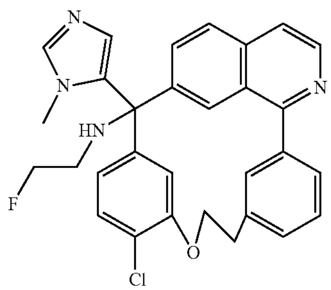 [SMILES: Cn1cncc1C1(NCCF)c2ccc(Cl)c(c2)OCCc2cccc(c2)-c2nccc3ccc1cc23] | 4[4]-chloro-N-(2-fluoroethyl)-3-(1-methyl-1H-imidazol-5-yl)-5-oxa-2(1,7)-isoquinolina-1,4(1,3)-dibenzenacycloheptaphan-3-amine |
| 123 | 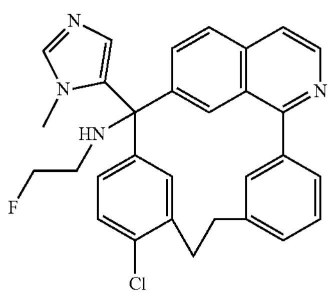 [SMILES: Cn1cncc1C1(NCCF)c2ccc(Cl)c(c2)CCc2cccc(c2)-c2nccc3ccc1cc23] | 4[4]-chloro-N-(2-fluoroethyl)-3-(1-methyl-1H-imidazol-5-yl)-2(1,7)-isoquinolina-1,4(1,3)-dibenzenacyclohexaphan-3-amine |
| 124 | 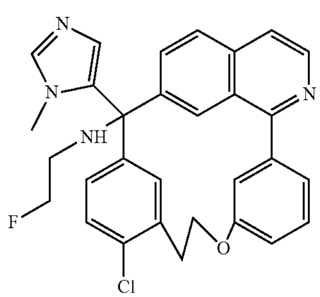 [SMILES: Cn1cncc1C1(NCCF)c2ccc(Cl)c(c2)CCOc2cccc(c2)-c2nccc3ccc1cc23] | 4[4]-chloro-N-(2-fluoroethyl)-3-(1-methyl-1H-imidazol-5-yl)-7-oxa-2(1,7)-isoquinolina-1,4(1,3)-dibenzenacycloheptaphan-3-amine |
| 125 | 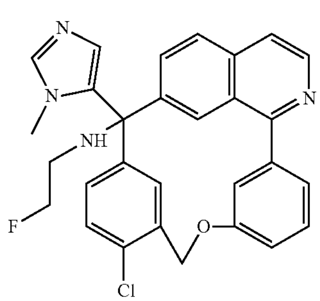 [SMILES: Cn1cncc1C1(NCCF)c2ccc(Cl)c(c2)COc2cccc(c2)-c2nccc3ccc1cc23] | 4[4]-chloro-N-(2-fluoroethyl)-3-(1-methyl-1H-imidazol-5-yl)-6-oxa-2(1,7)-isoquinolina-1,4(1,3)-dibenzenacyclohexaphan-3-amine |

-continued

| Cmpd. | Structure | Name |
|---|---|---|
| 126 | 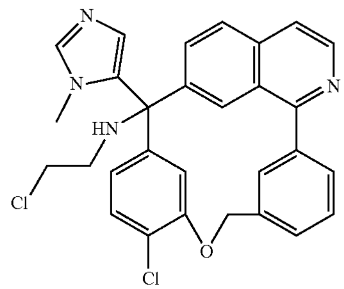 [SMILES: Cn1cncc1C1(NCCCl)c2ccc(Cl)c(c2)OCc2cccc(c2)-c2nccc3ccc1cc23] | 4⁴-chloro-N-(2-chloroethyl)-3-(1-methyl-1H-imidazol-5-yl)-5-oxa-2(1,7)-isoquinolina-1,4(1,3)-dibenzenacyclohexaphan-3-amine |
| 127 | 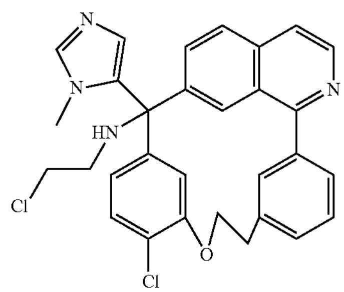 [SMILES: Cn1cncc1C1(NCCCl)c2ccc(Cl)c(c2)OCCc2cccc(c2)-c2nccc3ccc1cc23] | 4⁴-chloro-N-(2-chloroethyl)-3-(1-methyl-1H-imidazol-5-yl)-5-oxa-2(1,7)-isoquinolina-1,4(1,3)-dibenzenacycloheptaphan-3-amine |
| 128 | 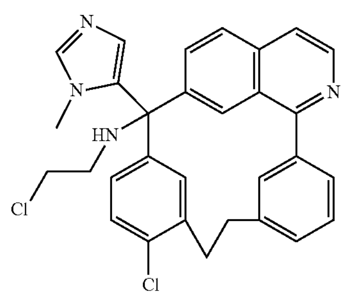 [SMILES: Cn1cncc1C1(NCCCl)c2ccc(Cl)c(c2)CCc2cccc(c2)-c2nccc3ccc1cc23] | 4⁴-chloro-N-(2-chloroethyl)-3-(1-methyl-1H-imidazol-5-yl)-2(1,7)-isoquinolina-1,4(1,3)-dibenzenacyclohexaphan-3-amine |
| 129 | 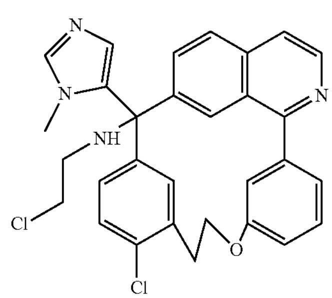 [SMILES: Cn1cncc1C1(NCCCl)c2ccc(Cl)c(c2)CCOc2cccc(c2)-c2nccc3ccc1cc23] | 4⁴-chloro-N-(2-chloroethyl)-3-(1-methyl-1H-imidazol-5-yl)-7-oxa-2(1,7)-isoquinolina-1,4(1,3)-dibenzenacycloheptaphan-3-amine |
| 130 | 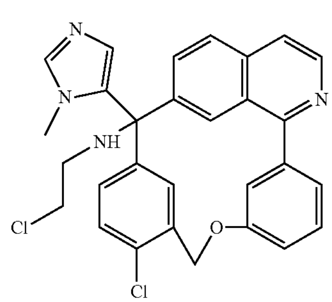 [SMILES: Cn1cncc1C1(NCCCl)c2ccc(Cl)c(c2)COc2cccc(c2)-c2nccc3ccc1cc23] | 4⁴-chloro-N-(2-chloroethyl)-3-(1-methyl-1H-imidazol-5-yl)-6-oxa-2(1,7)-isoquinolina-1,4(1,3)-dibenzenacyclohexaphan-3-amine |

-continued

| Cmpd. | Structure | Name |
|---|---|---|
| 131 | 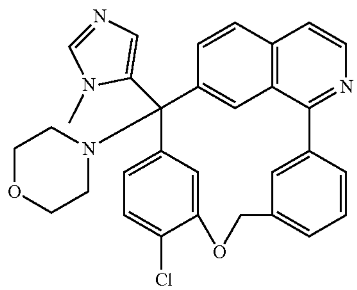 [SMILES: Cn1cncc1C1(N2CCOCC2)c2ccc(Cl)c(c2)OCc2cccc(c2)-c2nccc3ccc1cc23] | 4[4]-chloro-3-(1-methyl-1H-imidazol-5-yl)-3-morpholino-5-oxa-2(1,7)-isoquinolina-1,4(1,3)-dibenzenacyclohexaphane |
| 132 | 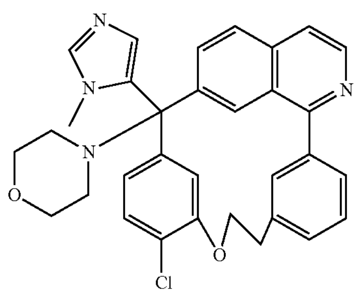 [SMILES: Cn1cncc1C1(N2CCOCC2)c2ccc(Cl)c(c2)OCCc2cccc(c2)-c2nccc3ccc1cc23] | 4[4]-chloro-3-(1-methyl-1H-imidazol-5-yl)-3-morpholino-5-oxa-2(1,7)-isoquinolina-1,4(1,3)-dibenzenacycloheptaphane |
| 133 | 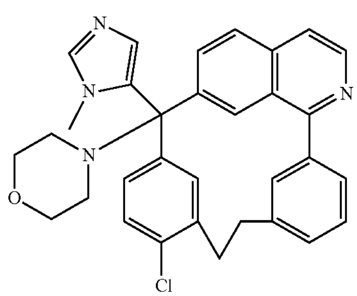 [SMILES: Cn1cncc1C1(N2CCOCC2)c2ccc(Cl)c(c2)CCc2cccc(c2)-c2nccc3ccc1cc23] | 4-(4[4]-chloro-3-(1-methyl-1H-imidazol-5-yl)-2(1,7)-isoquinolina-1,4(1,3)-dibenzenacyclohexaphane-3-yl)morpholine |
| 134 | 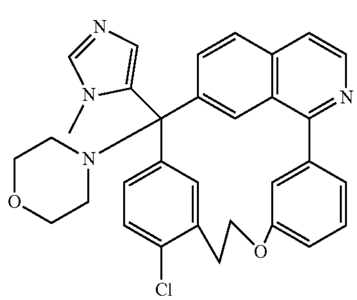 [SMILES: Cn1cncc1C1(N2CCOCC2)c2ccc(Cl)c(c2)CCOc2cccc(c2)-c2nccc3ccc1cc23] | 4[4]-chloro-3-(1-methyl-1H-imidazol-5-yl)-3-morpholino-7-oxa-2(1,7)-isoquinolina-1,4(1,3)-dibenzenacycloheptaphane |
| 135 | 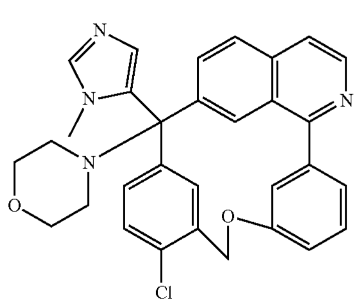 [SMILES: Cn1cncc1C1(N2CCOCC2)c2ccc(Cl)c(c2)COc2cccc(c2)-c2nccc3ccc1cc23] | 4[4]-chloro-3-(1-methyl-1/-imidazol-5-yl)-3-morpholino-6-oxa-2(1,7)-isoquinolina-1,4(1,3)-dibenzenacyclohexaphane |

Suitable exemplary compounds further include the (S)- or (R)-enantiomers of each of Compounds 92-135, which may be prepared by chiral separation of a racemic mixture.

6.2 Biological Examples

Biolgcical Example 1: In Vitro Potency ($IC_{50}$)

Materials $T_{24/83}$ cell line was purchased from the European Collection of Authenticated Cell Cultures (Salisbury, UK). Recombinant human farnesyl transferase (FTase) and geranylgeranyl transferase type-1 (GGTase) were obtained from Crelux (Martinsried, Germany). Dansyl labelled GCVLS peptide was purchased from Bachem (Torrance, CA), and Dansyl labelled GCVLL peptide was purchased from Bio Synthesis (Lewisville, TX). Farnesyl Pyrophosphate (FPP) and Geranylgeranyl pyrophosphate (GGPP) were purchased from Cayman (Ann Arbor, MI).

Fluorescence Assay

Specific biochemical activity of the compounds disclosed herein as FTase inhibitors was determined by measuring the ability of the compounds to block the farnesylation by recombinant FTase of fluorescent (i.e., dansyl-labeled) test substrates derived from the CAAX box of farnesylated proteins, such as the peptide GCVLS.

Geranylgeranyl transferase (GGTase) is a closely related enzyme to farnesyl transferase (FTase). The two enzymes share a common regulatory chain but have distinct individual enzymatic domains. GGTase catalyses the addition of an alternative prenylated side chain to some of the same proteins that may also be farnesylated. Thus, selective inhibitory activity against FTase relative to GGTase is a critical characteristic for FTase inhibitors.

The $IC_{50}$ value of the compounds disclosed herein as inhibitors of Ftase and/or GGTase, was determined by measuring the concentration (provided in nM) necessary to achieve inhibition of enzyme activity by 50% ($IC_{50}$). The lower an $IC_{50}$ value the more potent the inhibitor. Compounds having a low $IC_{50}$ value against FTase, for example an $IC_{50}$ (FTase)<100 nM, such as an $IC_{50}$ (FTase)<10 nM, are preferred. Compounds having a low $IC_{50}$ value against FTase and a high $IC_{50}$ value against GGTase, for example an $IC_{50}$ (FTase)<100 nM, such as an $IC_{50}$ (FTase)<10 nM, and an $IC_{50}$ (GGTase)>100 nM, are potent and selective inhibitors of FTase, and are particularly preferred.

The inhibition activities of the compounds disclosed herein against Ftase and GGTase were measured in the respective fluorescence assays as follows:

For the FTase assay, recombinant human FTase (2.5 nM), Dansyl labelled GCVLS peptide (85 nM), FPP (30 nM) and inhibitor were mixed in assay buffer (50 mM Tris, pH 7.5, 10 mM magnesium chloride, 10 μM zinc chloride, 0.08% CHAPS, 5 mM dithiothreitol) and incubated in a total volume of 20 μL at 30° C. for 50 minutes.

For the GGTase assay, GGTase (25 nM), Dansyl labelled GCVLL peptide (10 μM), GGPP (10 μM) and inhibitor were mixed in assay buffer (50 mM Tris, pH 7.5, 10 mM magnesium chloride, 10 μM zinc chloride, 0.08% CHAPS, 5 mM dithiothreitol) and incubated in a total volume of 20 μL at 30° C. for 120 minutes.

For both the FTase assay and GGTase assay, fluorescence intensity was detected (excitation at 340 nm and emission at 486 nm) using EnVision (PerkinElmer; Waltham, MA), $IC_{50}$ determinations were performed using a sigmoidal dose-response model with Xlfit software (IDBS, Inc.; Boston, MA), and tipifarnib was used as a positive control. All the assay plates for each assay passed the QC criteria (S/B, Z factor).

Cell Proliferation Assay

Mutant oncogenic HRAS was originally identified in a human bladder carcinoma cell line called T24. T24/83 is a subline of T24 established more recently that has more favorable growth characteristics for in vitro assays. Thus, T24/83 is a well-characterized mutant HRAS-dependent cell line that is an ideal model for quantifying the HRAS-dependent antitumor activity of farnesyltransferase inhibitors.

$T_{24/83}$ cells were inoculated into 384 well plates at 100 cells/well, and grown in the presence of inhibitor, 0.7% DMSO as a negative control, or 100 μM tipifarnib as a positive control, at 37° C. for 4 days. Cell viability was assessed using the CellTiter-Glo Kit (CTG) (Promega; Madison, WI). Luminescence was recorded using EnVision microplate reader (PerkinElmer; Waltham, MA). In this assay, tipifarnib was used as a positive control. All the assay plates passed the QC criteria (S/B, Z-factor).

Results

TABLE 1

In Vitro Potency data ($IC_{50}$) for tested compounds

| Compound No. | FTase (nM) | GGTase (nM) | $T_{24/83}$ (nM) |
|---|---|---|---|
| 1 | B | nt | nt |
| 2 | B | nt | B |
| (S)-3 | A | C | A |
| (S)-4 | A | C | A |
| (R)-4 | C | nt | nt |
| 5 | A | nt | nt |
| (R)-6 | A | C | A |
| (S)-6 | C | nt | nt |
| (R)-7 | A | C | A |
| (S)-7 | C | nt | nt |
| (R)-8 | A | C | A |
| (S)-8 | C | nt | nt |
| (R)-9 | A | B | A |
| (S)-9 | C | nt | nt |
| 10 | C | nt | nt |
| 11 | A | nt | C |
| 12 | C | nt | nt |
| 13 | B | nt | B |
| (S)-14 | A | C | B |
| (R)-14 | C | nt | nt |
| (S)-15 | A | C | B |
| (R)-15 | C | nt | nt |
| 16 | B | nt | nt |
| 17 | A | nt | nt |
| (S)-18 | A | C | A |
| (R)-18 | C | nt | nt |
| (S)-19 | A | nt | A |
| (R)-19 | C | nt | nt |
| (S)-20 | A | C | A |
| (R)-20 | C | nt | nt |
| (S)-21 | A | B | A |
| (R)-21 | C | nt | nt |
| 22 | B | nt | B |
| 23 | A | nt | A |
| 24 | C | nt | C |
| 25 | A | nt | B |
| (S)-25 | A | nt | B |
| (R)-25 | C | nt | nt |
| 26 | B | nt | B |
| (S)-27 | A | C | A |
| (R)-27 | C | nt | nt |
| 28 | A | nt | A |
| (S)-28 | A | nt | A |
| (R)-28 | C | nt | nt |
| (S)-29 | A | nt | B |
| (R)-29 | C | nt | nt |
| (S)-30 | A | nt | B |

TABLE 1-continued

In Vitro Potency data (IC$_{50}$) for tested compounds

| Compound No. | FTase (nM) | GGTase (nM) | T$_{24/83}$ (nM) |
|---|---|---|---|
| (R)-30 | C | nt | nt |
| 31 | B | nt | nt |
| 32 | B | nt | nt |
| 33 | B | nt | nt |
| (S)-34 | A | C | B |
| (R)-34 | C | nt | nt |
| (S)-35 | A | nt | B |
| (R)-35 | C | nt | nt |
| (S)-36 | A | nt | A |
| (R)-36 | C | nt | nt |
| (S)-37 | A | C | A |
| (R)-37 | C | nt | nt |
| 38 | A | nt | nt |
| (S)-39 | A | nt | A |
| (R)-39 | C | nt | nt |
| 40 | C | nt | B |
| 41 | B | nt | B |
| 42 | A | nt | A |
| 43 | B | nt | nt |
| 44 | A | nt | B |
| 45 | A | nt | A |
| (S)-46 | A | C | A |
| (R)-46 | C | nt | nt |
| (S)-47 | A | C | A |
| (R)-47 | C | nt | nt |
| (S)-48 | A | C | A |
| (R)-48 | B | nt | nt |
| 49 | C | nt | nt |
| 50 | A | nt | nt |
| (S)-51 | A | C | B |
| (R)-51 | C | nt | nt |
| 52 | B | nt | nt |
| 53 | A | nt | nt |
| 54 | A | nt | nt |
| (S)-55 | A | C | A |
| (R)-55 | C | nt | nt |
| (S)-56 | A | C | A |
| (R)-56 | C | nt | nt |
| (S)-57 | A | C | A |
| (R)-57 | C | nt | nt |
| (S)-58 | A | C | A |
| (R)-58 | B | nt | nt |
| 59 | C | nt | nt |
| 60 | B | nt | C |
| 61 | A | nt | B |
| 62 | A | nt | C |
| 63 | B | nt | nt |
| 64 | C | nt | nt |
| 65 | A | nt | B |
| (S)-66 | A | nt | C |
| (R)-66 | A | nt | nt |
| 67 | B | nt | nt |
| 68 | B | nt | nt |
| (S)-69 | A | nt | C |
| (S)-70 | A | nt | nt |
| (R)-70 | B | nt | nt |
| 71 | C | nt | nt |
| 72 | A | nt | B |
| 73 | B | nt | B |
| 74 | B | nt | nt |
| 75 | C | nt | nt |
| (R)-76 | B | nt | nt |
| (S)-76 | B | nt | nt |
| (R)-77 | B | nt | nt |
| (S)-77 | B | nt | nt |
| (R)-078 | B | nt | nt |
| (S)-078 | A | nt | nt |
| (R)-079 | B | nt | nt |
| (S)-079 | C | nt | nt |
| (R)-080 | B | nt | nt |
| (S)-080 | B | nt | nt |
| 82 | A | nt | nt |
| 83 | A | nt | nt |
| 84 | B | nt | nt |
| 85 | B | nt | nt |
| (R)-86 | C | nt | nt |
| (S)-86 | A | nt | nt |
| 87 | C | nt | nt |
| 88 | A | nt | nt |
| (R)-89 | B | nt | nt |
| (S)-89 | A | nt | nt |
| (S)-90 | B | nt | nt |
| (R)-90 | B | nt | nt |
| (S)-91 | C | nt | nt |
| (R)-91 | A | nt | nt |
| Tipifarnib | A | C | A |

Note:
nt = not tested. For FTase potency, A (IC$_{50}$ ≤ 10 nM), B (IC$_{50}$ 10-100 nM), C (IC$_{50}$ > 100 nM); for GGTase potency, A (IC$_{50}$ ≤ 100 nM), B (IC$_{50}$ 100-1000 nM), C (IC$_{50}$ > 1000 nM); for T$_{24/83}$ potency, A (IC$_{50}$ ≤ 50 nM), B (IC$_{50}$ 50-500 nM), C (IC$_{50}$ > 500 nM).

Biologcical Example 2: Metabolic Stability in Liver Microsomes

The metabolic stability of the compounds disclosed herein was determined by measuring half-life (T$_{1/2}$) of the compounds in the presence of mouse liver microsomes (MLM) or human liver microsomes (BILM). A longer T$_{1/2}$ value indicates the compound is more stable to metabolic degradation.

Test Compound and Control Working Solution Preparation:
Intermediate solution: 5 µL of compound and control stock solution (10 mM in dimethyl sulfoxide (DMSO)) were diluted with 495 µL of acetonitrile (ACN) (intermediate solution concentration: 100 µM, 99% ACN).

Working solution: 50 µL of compound and control intermediate solution (100 µM) were diluted with 450 µL of 100 mM potassium phosphate buffer (working solution concentration: 10 µM, 9.9% ACN).

Controls used in this assay: Testosterone, Diclofenac, and Propafenone.

NADPH Cofactor Preparation:
Materials: NADPH powder: β-Nicotinamide adenine dinucleotide phosphate reduced form, tetrasodium salt; NADPH·4Na (Vendor: Chem-Impex International, Cat. No. 00616).

Preparation Procedure: The appropriate amount of NADPH powder was weighed and diluted into a 10 mM MgCl$_2$ solution (working solution concentration: 10 unit/mL; final concentration in reaction system: 1 unit/mL).

Liver Microsomes Preparation:
The appropriate concentrations of microsome working solutions were prepared in 100 mM potassium phosphate buffer.

TABLE 2

Materials for Liver Microsomes Studies

| Species | Vendor | Abbreviation |
|---|---|---|
| Human | Corning | HLM |
| CD-1 Mouse | Xenotech | MLM |

Stop Solution Preparation:
Cold (4° C.) acetonitrile (CAN) containing 200 ng/mL tolbutamide and 200 ng/mL labetalol as internal standards (IS) was used as the stop solution.

Assay Procedure:
Using an Apricot automation workstation, 10 µL/well of compound working solution were added to all 96-well reaction plates except the blank (T0, T5, T10, T20, T30, T60, and NCF60).

An Apricot automation workstation was used to add 80 µL/well of microsome solution to all reaction plates (Blank, T0, T5, T10, T20, T30, T60, and NCF60).

All reaction plates containing mixtures of compound and microsomes were pre-incubated at 37° C. for 10 minutes.

An Apricot automation workstation was used to add 10 µL/well of 100 mM potassium phosphate buffer to reaction plate NCF60.

Reaction plate NCF60 was incubated at 37° C. for 60 minutes.

After pre-incubation, an Apricot automation workstation was used to add 10 µL/well of NADPH regenerating system to every reaction plate except NCF60 (Blank, T0, T5, T10, T20, T30, and T60) to start the reaction. Final concentration of each component in incubation medium: Microsome (0.5 mg protein/mL); Test Compound (1 µM); Control Compound (1 µM); Acetonitrile (0.99%); DMSO (0.01%).

The reaction plates were incubated at 37° C. for 0 minute (T0, stop solution was added prior to microsome and NADPH solutions), 5 minutes (T5), 10 minutes (T10), 20 minutes (T20), 30 minutes (T30), 60 minutes (T60).

An Apricot automation workstation was used to add 300 µL/well of stop solution to each reaction plate at its appropriate end time point to terminate the reaction.

Each plate was sealed and shaken for 10 minutes.

After shaking, each plate was centrifuged at 4000 rpm and 4° C. for 20 minutes.

During centrifugation, an Apricot automation workstation was used to add 300 L/well of HPLC grade water to eight new 96-well plates.

After centrifugation, an Apricot automation workstation was used to transfer 100 µL of supernatant from each reaction plate to its corresponding bioanaylsis plate.

Each bioanalysis plate was sealed and shaken for 10 minutes prior to LC-MS/MS analysis.

Data Analysis

The equation of first order kinetics was used to calculate $T_{1/2}$ and $CL_{int(mic)}$ (µL/min/mg).

$$C_f = C_0 * e^{-k_e * t}$$

when $C_f = \frac{1}{2} C_0$, $$T_{1/2} = \frac{Ln2}{k_e} = \frac{0.693}{k_e}$$

$$CL_{int(mic)} = \frac{0.693}{\text{In vitro } T_{1/2}} * \frac{1}{\text{mg/mL microsomal protein in reaction system}}$$

$$CL_{int(liver)} = CL_{int(mic)} * \frac{\text{mg microsomes}}{\text{g liver}} * \frac{\text{g liver}}{\text{kg body weight}}$$

Results:

TABLE 3

$T_{1/2}$ in Liver Microsomes for selected compounds

| Compound No. | $T_{1/2}$ in HLM (min) | $T_{1/2}$ in MLM (min) |
|---|---|---|
| (S)-3 | C | B |
| (S)-4 | C | C |
| (R)-6 | C | B |
| (R)-7 | C | B |
| (R)-8 | C | B |
| (S)-14 | B | C |

TABLE 3-continued $T_{1/2}$ in Liver Microsomes for selected compounds

| Compound No. | $T_{1/2}$ in HLM (min) | $T_{1/2}$ in MLM (min) |
|---|---|---|
| (S)-15 | B | C |
| (S)-18 | B | B |
| (S)-20 | A | A |
| (S)-25 | C | C |
| (S)-27 | C | C |
| (S)-28 | C | C |
| (S)-29 | C | C |
| (S)-30 | C | C |
| (S)-34 | C | B |
| (S)-35 | C | C |
| (S)-36 | C | B |
| (S)-37 | C | C |
| (S)-39 | A | A |
| 45 | A | A |
| (S)-46 | A | B |
| (S)-47 | A | B |
| (S)-51 | A | A |
| (S)-56 | A | A |
| (S)-58 | A | A |
| 65 | C | B |
| Tipifarnib | C | C |

Note:
For $T_{1/2}$ in HLM (min), A ($T_{1/2}$ > 100 min), B ($T_{1/2}$ 30-100 min)), C ($T_{1/2}$ < 30 min); for $T_{1/2}$ in MLM (min), A ($T_{1/2}$ > 15 min), B ($T_{1/2}$ 5-15 min)), C ($T_{1/2}$ < 5 min).

6.3 Exemplary Embodiments

One or more than one (including for instance all) of the following exemplary Embodiments may comprise each of the other embodiments or parts thereof.

A1. In an Embodiment, a compound of Formula (I):

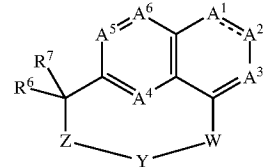

Formula (I)

or a pharmaceutically acceptable form thereof, wherein:
the dashed line indicates a single bond or double bond between $A^1$ and $A^2$;
$A^1$ is independently N, $NR^{1a}$, $CR^{1b}$, or —C(=O)—;
$A^2$ is independently N, $NR^{2a}$, $CR^{2b}$, or —C(=O)—;
$A^3$ is independently $CR^3$ or N;
$A^4$ is $CR^8$ or N;
$A^5$ and $A^6$ are each independently $CR^8$ or N, or $A^5$ and $A^6$ taken together are O, $NR^9$, or S;
W is a $C_{6-12}$ aryl or a 5-12 membered heteroaryl, each of which is optionally substituted with 1-4 $R^4$ substituents;
Y is a bond or a linker having a length of up to 6 atoms;
Z is a $C_{6-12}$ aryl or a 5-12 membered heteroaryl, each of which is optionally substituted with 1-4 $R^5$ substituents;
$R^{1a}$ and $R^{2a}$ are each independently $R^9$, —$OR^9$, —C(O)$R^9$, —C(O)$OR^9$, —C(O)$NR^{10}R^{11}$, —S(O)$_p R^9$, or —S(O)$_2 NR^{10}R^{11}$;
$R^{1b}$, $R^{2b}$, $R^3$, $R^5$ and $R^8$, at each occurrence, are each independently $R^9$, —$OR^9$, halo, CN, $NO_2$, —C(O)$R^9$, —C(O)$OR^9$, —OC(O)$R^9$, —OC(O)$OR^9$, —C(O)$NR^{10}R^{11}$, —$NR^{10}R^{11}$, —$NR^{10}C(O)R^9$, —$NR^{10}C(O)$ OR$^9$, —NR$^{10}$C(O)NR$^{10}$R$^{11}$, —NR$^{10}$S(O)$_2$R$^9$, —S(O)$_p$R$^9$, —S(O)$_2$NR$^{10}$R$^{11}$ or —NR$^{10}$S(O)$_2$NR$^{10}$R$^{11}$;

R$^4$, at each occurrence, is independently hydrogen, halo, C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, C$_{1-6}$ hydroxyalkoxy, C$_{1-6}$ heteroalkoxy, C$_{3-6}$ cycloalkoxy, 3-6 membered heterocycloalkoxy, —NR$^{14}$R$^{15}$, C$_{6-12}$ aryl, or 5-12 membered heteroaryl, wherein each C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, C$_{1-6}$ hydroxyalkoxy, C$_{1-6}$ heteroalkoxy, C$_{3-6}$ cycloalkoxy, 3-6 membered heterocycloalkoxy, C$_{6-12}$ aryl, or 5-12 membered heteroaryl of the R$^4$ is optionally independently substituted with one, two, three, four, five, or six substituents selected from halo, hydroxy, C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, and (O);

R$^6$ is CN, R$^9$, —OR$^9$, —C(O)R$^9$, —C(O)OR$^9$, —OC(O)R$^9$, —OC(O)OR$^9$, —C(O)NR$^{10}$R$^{11}$, —NR$^{10}$R$^{11}$, —NR$^{10}$R$^9$, —NR$^{10}$C(O)R$^9$, —NR$^{10}$C(O)OR$^9$, —NR$^{10}$C(O)NR$^{10}$R$^{11}$, —NR$^{10}$S(O)$_2$R$^9$, —NR$^{10}$C(NR$^{10}$)NROR$^{11}$, —S(O)$_p$R$^9$, —S(O)$_2$NR$^{10}$R$^{11}$ or —NR$^{10}$S(O)$_2$NR$^{10}$R$^{11}$;

R$^7$ is a 5-12 membered heteroaryl, optionally substituted with 1-4 substituents independently selected from halo, CN, NO$_2$, R$^9$, —OR$^9$, —C(O)R$^9$, —C(O)OR$^9$, —OC(O)R$^9$, —OC(O)OR$^9$, —C(O)NROR$^{11}$, —NR$^{10}$R$^{11}$, —NR$^{10}$C(O)R$^9$, —NR$^{10}$C(O)OR$^9$, —NR$^{10}$C(O)NR$^{10}$R$^{11}$, —NR$^{10}$S(O)$_2$R$^9$, —S(O)$_p$R$^9$, —S(O)$_2$NR$^{10}$R$^{11}$ and —NR$^{10}$S(O)$_2$NR$^{10}$R$^{11}$;

R$^9$, at each occurrence, is independently hydrogen, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{6-12}$ aryl, or 5-12 membered heteroaryl, wherein each C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{6-12}$ aryl, or 5-12 membered heteroaryl of the R$^9$ is optionally independently substituted with one, two, three, four, five, or six substituents selected from halo, hydroxy, CN, NO$_2$, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_3$-6 cycloalkyl, 3-6 membered heterocycloalkyl, C$_{1-6}$ alkoxy, C$_{1-6}$ haloalkoxy, (O), —C(O)R$^{12}$, —C(O)OR$^{12}$, —OC(O)R$^{12}$, —OC(O)OR$^{12}$, —C(O)NROR$^{11}$, —NROR$^{11}$, —NR$^{10}$C(O)R$^{12}$, —NR$^{10}$C(O)OR$^{12}$, —NR$^{10}$C(O)NR$^{10}$R$^{11}$, —NR$^{10}$S(O)$_2$R$^{12}$, —S(O)$_p$R$^{12}$, —S(O)$_2$NR'OR$^{11}$ and —NR$^{10}$S(O)$_2$NR$^{10}$R$^{11}$;

R$^{10}$ and R$^{11}$, at each occurrence, are each independently hydrogen, hydroxy, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{6-12}$ aryl, or 5-12 membered heteroaryl, or together with the N to which each is attached are combined to form a 3-6 membered heterocycloalkyl, wherein each C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{6-12}$ aryl, or 5-12 membered heteroaryl of the R$^{10}$ and the R$^{11}$ is optionally independently substituted with one, two, three, four, five, or six substituents selected from halo, hydroxy, CN, NO$_2$, C$_{1-6}$ alkyl, C$_{2-6}$ alkenyl, C$_{2-6}$ alkynyl, C$_{1-6}$ haloalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, (O), —C(O)R$^{13}$, —C(O)OR$^{13}$, —OC(O)R$^{13}$, —OC(O)OR$^{13}$, —C(O)NR$^{14}$R$^{15}$, —NR$^{14}$R$^{15}$, —NR$^{14}$C(O)R$^{13}$, —NR$^{14}$C(O)OR$^{13}$, —NR$^{14}$C(O)NR$^{14}$R$^{15}$, —NR$^{14}$S(O)$_2$R$^{13}$, —S(O)$_p$R$^{13}$, —S(O)$_2$NR$^{14}$R$^{15}$ and —NR$^{14}$S(O)$_2$NR$^{14}$R$^{15}$;

R$^{12}$, at each occurrence, is independently hydrogen, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{6-12}$ aryl, or 5-12 membered heteroaryl, wherein each C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{6-12}$ aryl, or 5-12 membered heteroaryl of the R$^{12}$ is optionally independently substituted with one, two, three, four, five, or six substituents selected from halo, hydroxy, CN, NO$_2$, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_3$-6 cycloalkyl, 3-6 membered heterocycloalkyl, C$_{1-6}$ alkoxy, C$_{1-6}$ haloalkoxy, (O), —C(O)R$^{13}$, —C(O)OR$^{13}$, —OC(O)R$^{13}$, —OC(O)OR$^{13}$, —C(O)NR$^{10}$R$^{11}$, —NR$^{10}$R$^{11}$, —NR$^{10}$C(O)R$^{13}$, —NR$^{10}$C(O)OR$^{13}$, —NR$^{10}$C(O)NR$^{10}$R$^{11}$, —NR$^{10}$S(O)$_2$R$^{13}$, —S(O)$_p$R$^{13}$, —S(O)$_2$NR$^{10}$R$^{11}$; and —NR$^{10}$S(O)$_2$NR$^{10}$R$^{11}$;

R$^{13}$, at each occurrence, is independently hydrogen, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ heteroalkyl, C$_{3-6}$ cycloalkyl, or 3-6 membered heterocycloalkyl;

R$^{14}$ and R$^{15}$, at each occurrence, are each independently hydrogen, hydroxy, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ heteroalkyl, C$_{3-6}$ cycloalkyl, 3-6 membered heterocycloalkyl, or C$_{1-6}$ alkoxy, or together with the N to which each is attached are combined to form a 3-6 membered heterocycloalkyl; and each p is independently an integer of 0, 1 or 2.

A2. The compound of Embodiment A1, wherein the compound is a compound of Formula (Ia):

Formula (Ia)

or a pharmaceutically acceptable form thereof.

A3. The compound of Embodiment A1, wherein the compound is a compound of Formula (Ib):

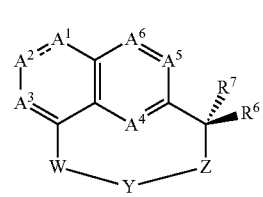

Formula (Ib)

or a pharmaceutically acceptable form thereof.

A4. The compound of any one of Embodiments A1-A3, wherein $A^1$ is N or $NR^{1a}$ A5. The compound of any one of Embodiments A1-A4, wherein $A^2$ is $CR^{2b}$ or —C(=O)—.

A6. The compound of any one of Embodiments A1-A5, wherein:
the bond between $A^1$ and $A^2$ is a single bond;
$A^1$ is $NR^{1a}$; and
$A^2$ is —C(=O)—.

A7. The compound of any one of Embodiments A1-A5, wherein: the bond between $A^1$ and $A^2$ is a double bond;
$A^1$ is N; and
$A^2$ is $CR^{2b}$.

A8. The compound of any one of Embodiments A1-A3, wherein $A^1$ is $CR^{1b}$ or —C(=O)—.

A9. The compound of any one of Embodiments A1-A3 or Embodiment A8, wherein $A^2$ is N or $NR^2a$ A10. The compound of any one of Embodiments A1-A3, A8 or A9, wherein:
the bond between $A^1$ and $A^2$ is a double bond;
$A^1$ is $CR^{1b}$; and
$A^2$ is N.

A11. The compound of any one of Embodiments A1-A3, A8 or A9, wherein:
the bond between $A^1$ and $A^2$ is a single bond;
$A^1$ is —C(=O)—; and
$A^2$ is $NR^2a$ A12. The compound of any one of Embodiments A1-A11, wherein:

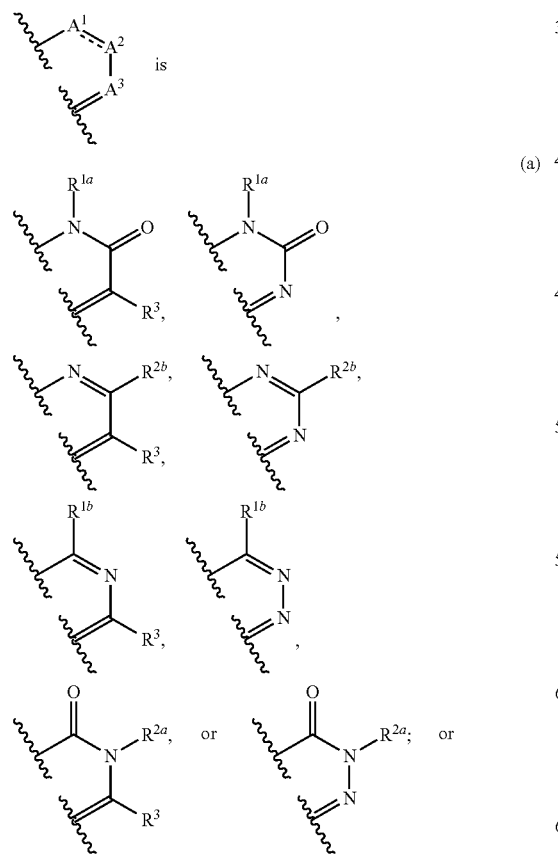

A13. The compound of Embodiment A12, wherein:

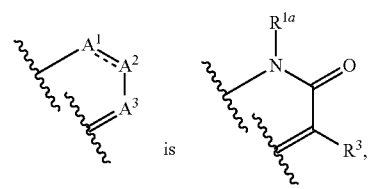

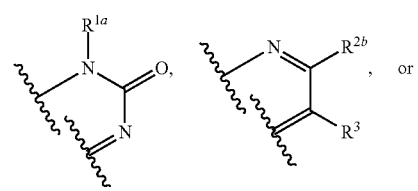

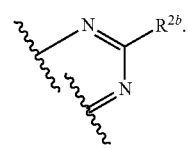

A14. The compound of Embodiment A12 or Embodiment A13, wherein:

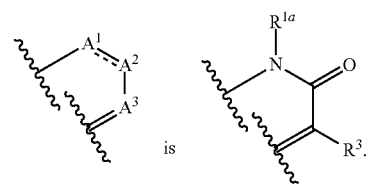

A15. The compound of Embodiment A12 or Embodiment A13, wherein:

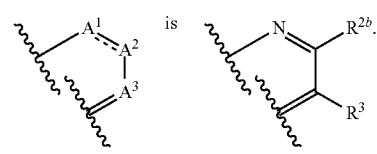

A16. The compound of Embodiment A12, wherein:

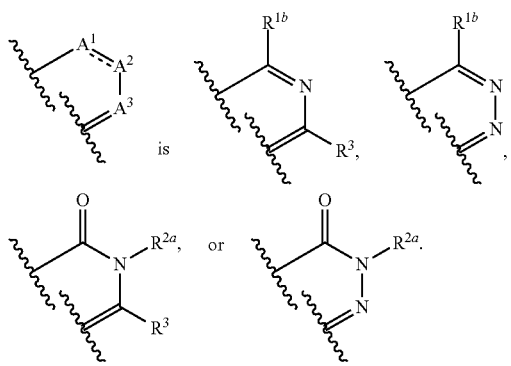

is

A17. The compound of Embodiment A12 or Embodiment A16, wherein:

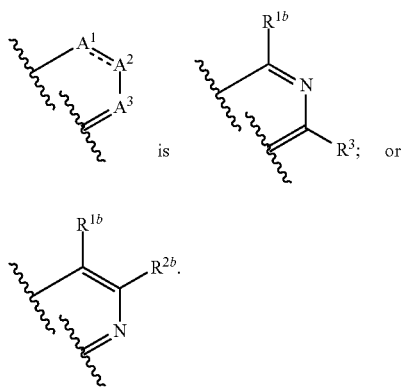

A18. The compound of any one of Embodiments A1-A17, wherein Y and the fused-ring system containing $A^1$, $A^2$, and $A^3$ are attached to W in a 1,2-relationship.
A19. The compound of any one of Embodiments A1-A17, wherein Y and the fused-ring system containing $A^1$, $A^2$, and $A^3$ are attached to W in a 1,3-relationship.
A20. The compound of any one of Embodiments A1-A19, wherein W is $C_{6-12}$ aryl.
A21. The compound of Embodiment A20, wherein W is phenyl.
A22. The compound of any one of Embodiments A1-A19, wherein W is 5-12 membered heteroaryl.
A23. The compound of Embodiment A22, wherein W is pyridyl.
A24. The compound of any one of Embodiments A1-A23, wherein W is substituted with one, two, three or four $R^4$ substituents.
A25. The compound of any one of Embodiments A1-A23, wherein W is substituted with one $R^4$ substituent.
A26. The compound of any one of Embodiments A1-A25, wherein the —(C($R^6$)($R^7$)(fused-ring system containing $A^4$, $A^5$, and $A^6$)) group, and Y are attached to Z in a 1,2-relationship.
A27. The compound of any one of Embodiments A1-A25, wherein the —(C($R^6$)($R^7$)(fused-ring system containing $A^4$, $A^5$, and $A^6$)) group, and Y are attached to Z in a 1,3-relationship.
A28. The compound of any one of Embodiments A1-A27, wherein Z is $C_{6-12}$ aryl.

A29. The compound of Embodiment A28, wherein Z is phenyl.
A30. The compound of any one of Embodiments A1-A27, wherein Z is 5-12 membered heteroaryl.
A31. The compound of Embodiment A30, wherein Z is pyridyl.
A32. The compound of any one of Embodiments A1-A31, wherein Z is substituted with one, two, three or four $R^5$ substituents.
A33. The compound of any one of Embodiments A1-A32, wherein Z is substituted with one $R^5$ substituent.
A34. The compound of any one of Embodiments A1-A33, wherein the compound is a compound of Formula (II):

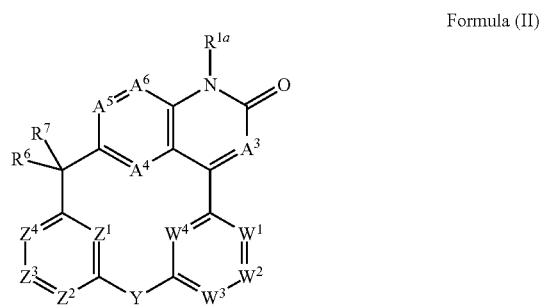

Formula (II)

wherein:
$W^1$, $W^2$, $W^3$, and $W^4$ are each independently N or $CR^4$, or $W^1$ and $W^2$ taken together is O, $NR^{4A}$ or S, or $W^2$ and $W^3$ taken together is O, $NR^{4A}$, or S;
$Z^1$, $Z^2$, $Z^3$, and $Z^4$ are each independently N or $CR^5$, or $Z^2$ and $Z^3$ taken together is O, $NR^{5A}$ or S, or $Z^3$ and $Z^4$ taken together is O, $NR^{5A}$, or S; and
$R^{4A}$ and $R^{5A}$ are independently hydrogen, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{4A}$ and the $R^{5A}$ is optionally independently substituted with one, two, three, four, five, or six substituents selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);
or a pharmaceutically acceptable form thereof.
A35. The compound of Embodiment A34, wherein the compound is a compound of Formula (IIa):

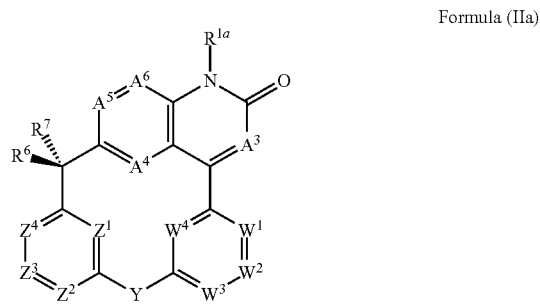

Formula (IIa)

or a pharmaceutically acceptable form thereof.

A36. The compound of Embodiment A34, wherein the compound is a compound of Formula (IIb):

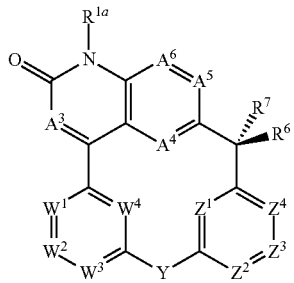

Formula (IIb)

or a pharmaceutically acceptable form thereof.

A37. The compound of Embodiment A34, wherein the compound is a compound of Formula (II-1):

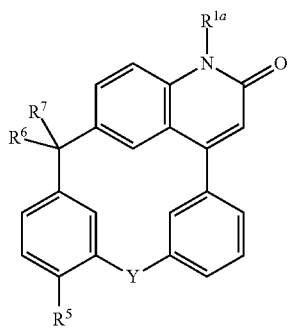

Formula (II-1)

or a pharmaceutically acceptable form thereof.

A38. The compound of Embodiment A37, wherein the compound is a compound of Formula (IIa-1) or Formula (IIb-1):

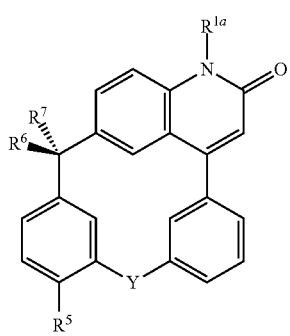

Formula (IIa-1)

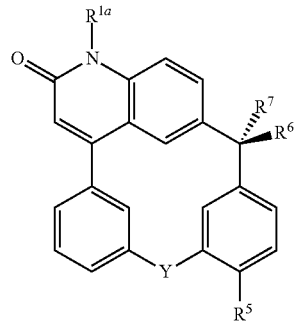

Formula (IIb-1)

or a pharmaceutically acceptable form thereof.

A39. The compound of Embodiment A34, wherein the compound is a compound of Formula (II-2):

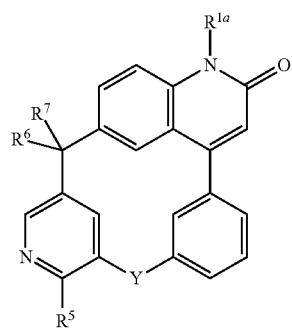

Formula (II-2)

or a pharmaceutically acceptable form thereof.

A40. The compound of Embodiment A39, wherein the compound is a compound of Formula (IIa-2) or Formula (IIb-2):

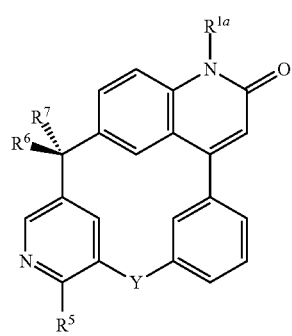

Formula (IIa-2)

Formula (IIb-2)

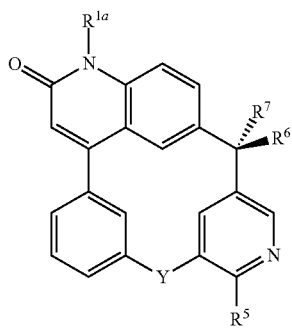

or a pharmaceutically acceptable form thereof.

A41. The compound of any one of Embodiments A1-A33, wherein the compound is a compound of Formula (III):

Formula (III)

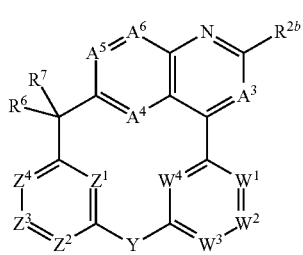

wherein:
- $W^1$, $W^2$, $W^3$, and $W^4$ are each independently N or $CR^4$, or $W^1$ and $W^2$ taken together is O, $NR^{4A}$ or S, or $W^2$ and $W^3$ taken together is O, $NR^{4A}$, or S;
- $Z^1$, $Z^2$, $Z^3$, and $Z^4$ are each independently N or $CR^5$, or $Z^2$ and $Z^3$ taken together is O, $NR^{5A}$ or S, or $Z^3$ and $Z^4$ taken together is O, $NR^{5A}$, or S; and
- $R^{4A}$ and $R^{5A}$ are independently hydrogen, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{4A}$ and the $R^{5A}$ is optionally independently substituted with one, two, three, four, five, or six substituents selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);

or a pharmaceutically acceptable form thereof.

A42. The compound of Embodiment A41, wherein the compound is a compound of Formula (IIIa):

Formula (IIIa)

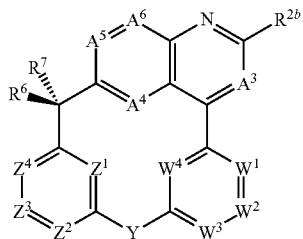

or a pharmaceutically acceptable form thereof.

A43. The compound of Embodiment A41, wherein the compound is a compound of

Formula (IIIb)

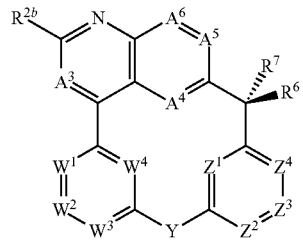

or a pharmaceutically acceptable form thereof.

A44. The compound of Embodiment A41, wherein the compound is a compound of Formula (III-1):

Formula (III-1)

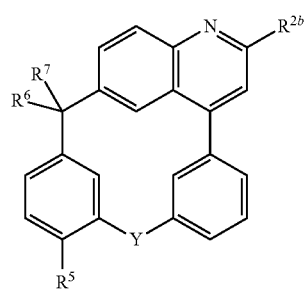

or a pharmaceutically acceptable form thereof.

A45. The compound of Embodiment A44, wherein the compound is a compound of Formula (IIIa-1) or Formula (IIIb-1):

Formula (IIIa-1)

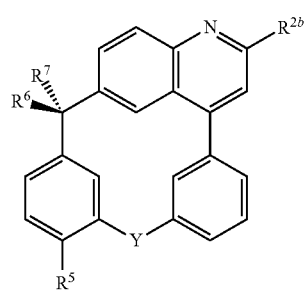

Formula (IIIb-1)

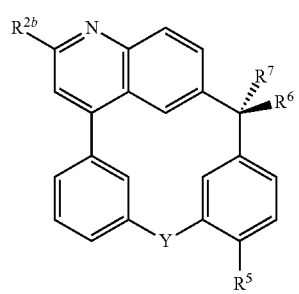

or a pharmaceutically acceptable form thereof

A46. The compound of Embodiment A41, wherein the compound is a compound of Formula (III-2):

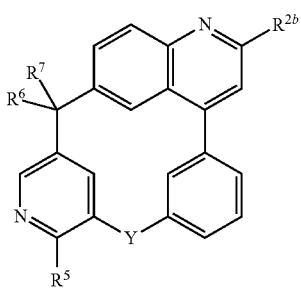

Formula (III-2)

or a pharmaceutically acceptable form thereof.

A47. The compound of Embodiment A46, wherein the compound is a compound of Formula (IIIa-2) or Formula (IIIb-2):

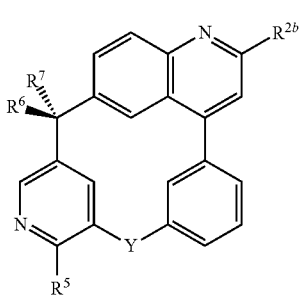

Formula (IIIa-2)

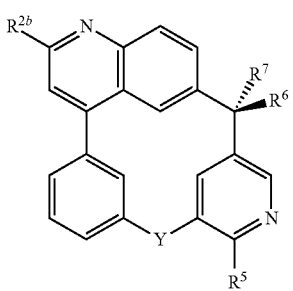

Formula (IIIb-2)

or a pharmaceutically acceptable form thereof.

A47-1. The compound of Embodiment A41, wherein the compound is a compound of Formula (III-3):

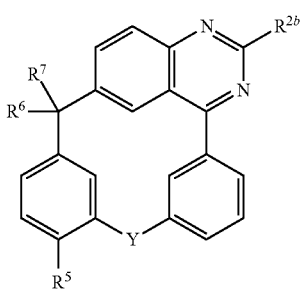

Formula (III-2)

or a pharmaceutically acceptable form thereof.

A47-2. The compound of Embodiment A47-1, wherein the compound is a compound of Formula (IIIa-3) or Formula (IIIb-3):

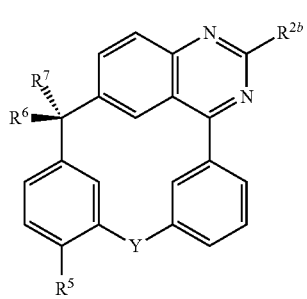

Formula (IIIa-3)

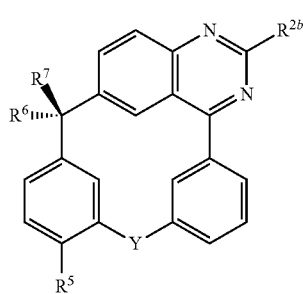

Formula (IIIa-3)

or a pharmaceutically acceptable form thereof.

A48. The compound of any one of Embodiments A1-A33, wherein the compound is a compound of Formula (IV):

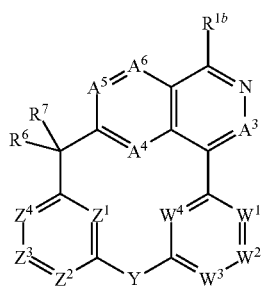

Formula (IV)

wherein:
 $W^1$, $W^2$, $W^3$, and $W^4$ are each independently N or $CR^4$, or $W^1$ and $W^2$ taken together is O, $NR^{4A}$ or S, or $W^2$ and $W^3$ taken together is O, $NR^{4A}$, or S;
 $Z^1$, $Z^2$, $Z^3$, and $Z^4$ are each independently N or $CR^5$, or $Z^2$ and $Z^3$ taken together is O, $NR^{5A}$ or S, or $Z^3$ and $Z^4$ taken together is O, $NR^{5A}$, or S; and
 $R^{4A}$ and $R^{5A}$ are independently hydrogen, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{4A}$ and the $R^{5A}$ is optionally independently substituted with one, two, three, four, five, or six substituents selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);

or a pharmaceutically acceptable form thereof.

A49. The compound of Embodiment A48, wherein the compound is a compound of Formula (IVa):

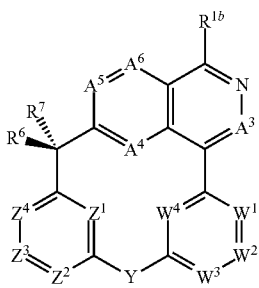

Formula (IVa)

or a pharmaceutically acceptable form thereof.

A50. The compound of Embodiment A48, wherein the compound is a compound of Formula (IVb):

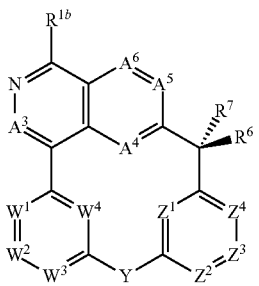

Formula (IVb)

or a pharmaceutically acceptable form thereof.

A51. The compound of Embodiment A48, wherein the compound is a compound of Formula (IV-1):

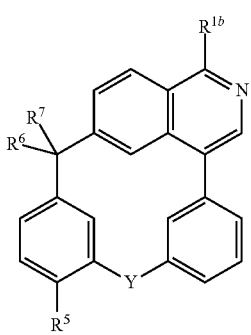

Formula (IV-1)

or a pharmaceutically acceptable form thereof.

A52. The compound of Embodiment A51, wherein the compound is a compound of Formula (IVa-1) or Formula (IVb-1):

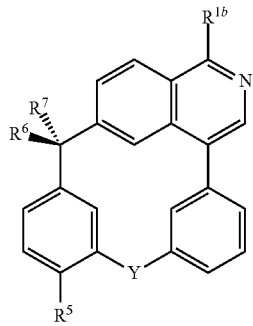

Formula (IVa-1)

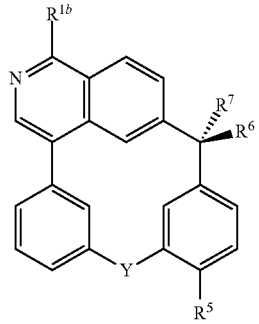

Formula (IVb-1)

or a pharmaceutically acceptable form thereof.

A53. The compound of Embodiment A48, wherein the compound is a compound of Formula (IV-2):

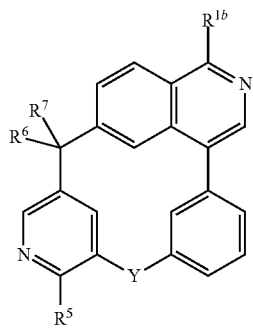

Formula (IV-2)

or a pharmaceutically acceptable form thereof.

A54. The compound of Embodiment A53, wherein the compound is a compound of Formula (IVa-2) or Formula (IVb-2):

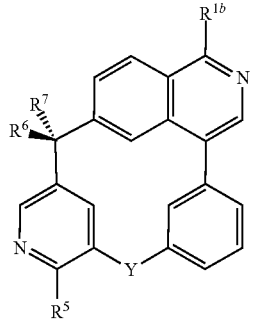

Formula (IVa-2)

-continued

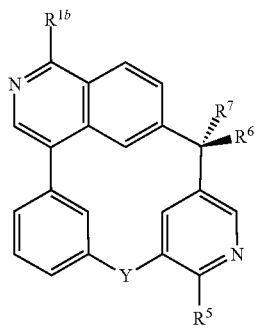

Formula (IVb-2)

or a pharmaceutically acceptable form thereof.

A54-1. The compound of any one of Embodiments A1-A33, wherein the compound is a compound of Formula (V):

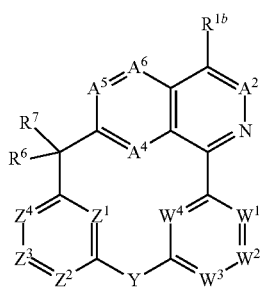

Formula (V)

wherein:
- $W^1$, $W^2$, $W^3$, and $W^4$ are each independently N or $CR^4$, or $W^1$ and $W^2$ taken together are O, $NR^{4A}$, or S, or $W^2$ and $W^3$ taken together are O, $NR^{4A}$, or S;
- $Z^1$, $Z^2$, $Z^3$, and $Z^4$ are each independently N or $CR^5$, or $Z^2$ and $Z^3$ taken together are O, $NR^{5A}$ or S, or $Z^3$ and $Z^4$ taken together are O, $NR^{5A}$, or S; and
- $R^{4A}$ and $R^{5A}$ are independently hydrogen, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{4A}$ and the $R^{5A}$ is optionally independently substituted with 1-6 substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);

or a pharmaceutically acceptable form thereof.

A54-2. The compound of Embodiment A54-1, wherein the compound of Formula (V) is a compound of Formula (Va):

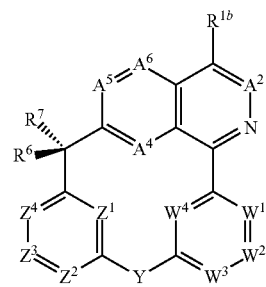

Formula (Va)

or a pharmaceutically acceptable form thereof.

A54-3. The compound of Embodiment A54-1, wherein the compound of Formula (V) is a compound of Formula (Vb):

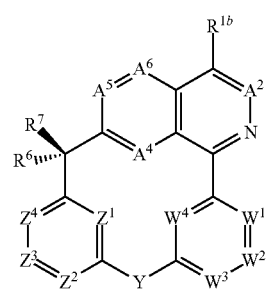

Formula (Vb)

or a pharmaceutically acceptable form thereof.

A54-4. The compound of Embodiment A54-1, wherein the compound of Formula (V) is a compound of Formula (V-1):

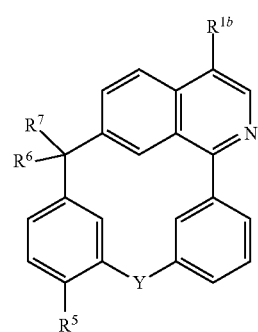

Formula (V-1)

or a pharmaceutically acceptable form thereof.

A54-5. The compound of Embodiment A54-4, wherein the compound of Formula (V-1) is a compound of Formula (Va-1) or Formula (Vb-1):

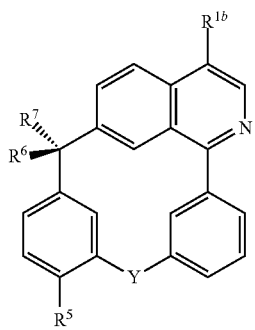

Formula (Va-1)

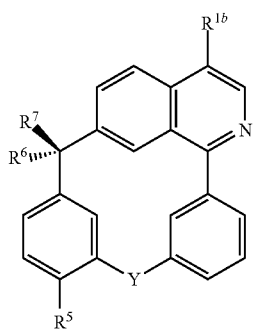

Formula (Vb-1)

or a pharmaceutically acceptable form thereof.

A54-6. The compound of any one of Embodiments A1-A33, wherein the compound is a compound of Formula (VI):

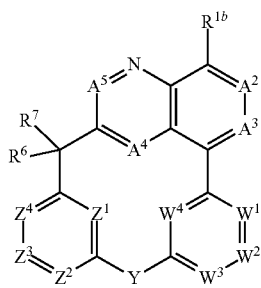

Formula (VI)

wherein:
  $W^1$, $W^2$, $W^3$, and $W^4$ are each independently N or $CR^4$, or $W^1$ and $W^2$ taken together are O, $NR^{4A}$, or S, or $W^2$ and $W^3$ taken together are O, $NR^{4A}$, or S;
  $Z^1$, $Z^2$, $Z^3$, and $Z^4$ are each independently N or $CR^5$, or $Z^2$ and $Z^3$ taken together are O, $NR^{5A}$ or S, or $Z^3$ and $Z^4$ taken together are O, $NR^{5A}$, or S; and
  $R^{4A}$ and $R^{5A}$ are independently hydrogen, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{4A}$ and the $R^{5A}$ is optionally independently substituted with 1-6 substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);

or a pharmaceutically acceptable form thereof.

A54-7. The compound of Embodiment A54-6, wherein the compound of Formula (VI) is a compound of Formula (VIa):

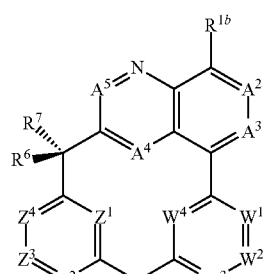

Formula (VIa)

or a pharmaceutically acceptable form thereof.

A54-8. The compound of Embodiment A54-6, wherein the compound of Formula (VI) is a compound of Formula (VIb):

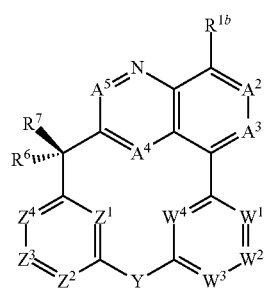

Formula (VIb)

or a pharmaceutically acceptable form thereof.

A54-9. The compound of Embodiment A54-6, wherein the compound of Formula (VI) is a compound of Formula (VI-1):

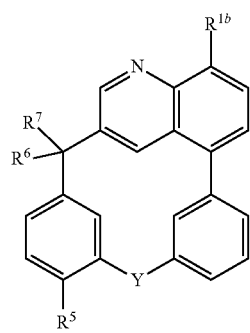

Formula (VI-1)

or a pharmaceutically acceptable form thereof.

A54-10. The compound of Embodiment A54-9, wherein the compound of Formula (VI-1) is a compound of Formula (VIa-1) or Formula (VIb-1):

Formula (VIa-1)

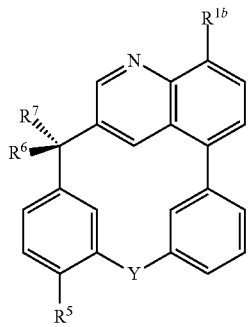

Formula (VIb-1)

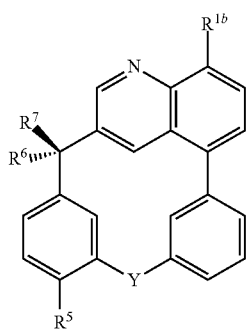

or a pharmaceutically acceptable form thereof.

A55. The compound of any one of Embodiments A1-A54-10, wherein $R^{1a}$ is independently $R^9$.

A56. The compound of any one of Embodiments A1-A55, wherein:

$R^{1a}$ is hydrogen, $C_{1-6}$ alkyl, or $C_{3-6}$ cycloalkyl, wherein the $C_{1-6}$ alkyl, or $C_{3-6}$ cycloalkyl are optionally independently substituted with one, two, three, four, five, or six substituents selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), —C(O)$R^{12}$, —C(O)O$R^{12}$, —OC(O)$R^{12}$, —OC(O)O$R^{12}$, —C(O)NRO$R^{11}$, —NR$^{10}$R$^{11}$, —NR$^{10}$C(O)R$^{12}$, —NR$^{10}$C(O)OR$^{12}$, —NR$^{10}$C(O)NR$^{10}$R$^{11}$, —NR$^{10}$S(O)$_2$R$^{12}$, —S(O)$_p$R$^{12}$, and —S(O)$_2$NR$^{10}$R$^{11}$.

A57. The compound of any one of Embodiments A1-A56, wherein $R^{1a}$ is hydrogen, $C_{1-3}$ alkyl, or $C_{3-4}$ cycloalkyl, wherein the $C_{1-3}$ alkyl, or $C_{3-4}$ cycloalkyl are optionally independently substituted with one, two, or three substituents selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_3$-6 cycloalkyl, 3-6 membered heterocycloalkyl, $C_{1-6}$ alkoxy, $C_{1-6}$ haloalkoxy, (O), —C(O)$R^{12}$, —C(O)O$R^{12}$, —OC(O)R$^{12}$, —OC(O)OR$^{12}$, —C(O)NROR$^{11}$, —NROR$^{11}$, —NR$^{10}$C(O)R$^{12}$, —NR$^{10}$C(O)OR$^{12}$, —NR$^{10}$C(O)NR$^{10}$R$^{11}$, —NR$^{10}$S(O)$_2$R$^{12}$, —S(O)$_p$R$^{12}$, and —S(O)$_2$NR$^{10}$R$^{11}$.

A58. The compound of any one of Embodiments A1-A57, wherein $R^{1a}$ is hydrogen, —CH$_3$, —CD$_3$, —CH$_2$CH$_3$, —CD$_2$CD$_3$, isopropyl, 2,3-dihydroxypropyl or cyclopropyl.

A59. The compound of any one of Embodiments A1-A58, wherein $R^{1a}$ is —CH$_3$, —CD$_3$, or cyclopropyl.

A60. The compound of any one of Embodiments A1-A59, wherein $R^{1a}$ is —CH$_3$ or —CD$_3$.

A61. The compound of any one of Embodiments A1-A59, wherein $R^{1a}$ is cyclopropyl.

A62. The compound of any one of Embodiments A1-A61, wherein $R^{2b}$ is $R^9$, —OR$^9$, halo, CN, NO$_2$, —C(O)R$^9$, —C(O)OR$^9$, —C(O)NR$^{10}$R$^{11}$, —NR$^{10}$R$^{11}$, —NR$^{10}$C(O)R$^9$, —S(O)$_p$R$^9$, or —S(O)$_2$NR$^{10}$R$^{11}$.

A63. The compound of any one of Embodiments A1-A62, wherein $R^{2b}$ is $R^9$, —OR$^9$, halo, CN, —C(O)NR$^{10}$R$^{11}$, or —NR$^{10}$R$^{11}$.

A64. The compound of any one of Embodiments A1-A63, wherein:

$R^{2b}$ is hydrogen, $C_{1-6}$ alkyl, $C_{3-6}$ cycloalkyl, hydroxy, $C_{1-6}$ alkoxy, $C_{3-6}$ cycloalkoxy, $C_{3-6}$ heterocycloalkoxy, halo, CN, —C(O)NR$^{10}$R$^{11}$, or —NR$^{10}$R$^{11}$; wherein $R^{10}$ and $R^{11}$, at each occurrence, are each independently hydrogen, $C_{1-6}$ alkyl, 3-6 membered heterocycloalkyl, or together with the N to which each is attached are combined to form a 3-6 membered heterocycloalkyl; or optionally wherein $R^{10}$ is H and $R^{11}$ is $C_{1-3}$haloalkyl, such as chloroethyl or fluoroethyl.

A65. The compound of any one of Embodiments A1-A64, wherein $R^{2b}$ is (a) hydrogen, $C_{1-3}$ alkyl, $C_{3-4}$ cycloalkyl, $C_{1-3}$ alkoxy, $C_{3-4}$ cycloalkoxy, $C_{3-4}$ heterocycloalkoxy, halo, CN, —C(O)NR$^{10}$R$^{11}$, or —NR$^{10}$R$^{11}$; wherein $R^{10}$ and $R^{11}$, at each occurrence, are each independently hydrogen, $C_{1-3}$ alkyl, 3-4 membered heterocycloalkyl, or together with the N to which each is attached are combined to form a 4-6 membered heterocycloalkyl; or optionally wherein $R^{10}$ is H and $R^{11}$ is $C_{1-3}$haloalkyl, such as chloroethyl or fluoroethyl.

A66. The compound of any one of Embodiments A1-A65, wherein $R^{2b}$ is (a) hydrogen, —CH$_3$, —CD$_3$, —CH$_2$CH$_3$, —CD$_2$CD$_3$, isopropyl, cyclopropyl, —OCH$_3$, —OCD$_3$, —OCH$_2$CH$_3$, —OCD$_2$CD$_3$, isopropoxy, cyclopropoxy, 3-oxetanylalkoxy, chloro, CN, morpholino, piperazinyl, 3-oxetanylamino, or —C(O)NH$_2$; or $R^{2b}$ is (b) —NH$_2$.

A67. The compound of any one of Embodiments A1-A61, wherein $R^{2b}$ is an electron-withdrawing group.

A68. The compound of Embodiment A67, wherein $R^{2b}$ is halo, CN, NO$_2$, —C(O)R$^9$, —C(O)OR$^9$, —C(O)NR$^{10}$R$^{11}$, —S(O)$_p$R$^9$, or —S(O)$_2$NR$^{10}$R$^{11}$.

A69. The compound of Embodiment A67 or Embodiment A68, wherein $R^{2b}$ is chloro, CN, —C(O)H, —C(O)CH$_3$, —C(O)OH, —C(O)OCH$_3$, —C(O)NH$_2$, —C(O)N(H)CH$_3$, —C(O)N(CH$_3$)$_2$, —S(O)CH$_3$, —S(O)$_2$CH$_3$, —S(O)$_2$NH$_2$, —S(O)$_2$N(H)CH$_3$, or —S(O)$_2$N(CH$_3$)$_2$.

A70. The compound of any one of Embodiments A1-A69, wherein $A^3$ is CR$^3$.

A71. The compound of any one of Embodiments A1-A70, wherein $R^3$ is independently $R^9$, —OR$^9$, halo, or CN.

A72. The compound of Embodiment A71, wherein $R^3$ is hydrogen.

A72-1. The compound of any one of Embodiments A1-A69, wherein $A^3$ is N.

A73. The compound of any one of Embodiments A1-A72-1, wherein $A^4$ is CR$^8$.

A74. The compound of any one of Embodiments A1-A72-1, wherein $A^4$ is N.

A75. The compound of any one of Embodiments A1-A74, wherein $A^5$ is CR$^8$.

A76. The compound of any one of Embodiments A1-A74, wherein $A^5$ is N.

A77. The compound of any one of Embodiments A1-A76, wherein $A^6$ is $CR^8$.
A78. The compound of any one of Embodiments A1-A76, wherein $A^6$ is N.
A79. The compound of any one of Embodiments A1-A72-1, wherein $A^4$ is N, and no more than one of $A^5$ and $A^6$ is N.
A80. The compound of any one of Embodiments A1-A72-1, wherein $A^5$ is N, and no more than one of $A^4$ and $A^6$ is N.
A81. The compound of any one of Embodiments A1-A72-1, wherein $A^6$ is N, and no more than one of $A^4$ and $A^5$ is N.
A82. The compound of any one of Embodiments A1-A72-1, wherein $A^4$, $A^5$ and $A^6$ are each independently $CR^8$.
A83. The compound of any one of Embodiments A1-A82, wherein $R^8$ is independently $R^9$, $-OR^9$, halo, or CN.
A84. The compound of Embodiment A83, wherein $R^8$ is hydrogen.
A85. The compound of any one of Embodiments A1-A84, wherein Y is a bond.
A86. The compound of any one of Embodiments A1-A84, wherein Y is a linker having a length of up to 5 atoms, up to 4 atoms, up to 3 atoms, or up to 2 atoms.
A87. The compound of any one of Embodiments A1-A84 or 86, wherein Y is in the direction of Z-Y-W.
A88. The compound of any one of Embodiments A1-A84, 86 or 87, wherein Y is a $C_{1-6}$ alkylene, wherein one or more $-CH_2-$ is optionally independently replaced by $-O-$, $-C(O)-$, $-N(R^{10})-$, $-N(R^{10})C(O)-$, $-C(O)N(R^{10})-$, $-N(R^{10})C(O)N(R^{11})-$, $-S(O)_p-$, $-N(R^{10})S(O)_2-$, $-S(O)_2N(R^{10})-$, or $-N(R^{10})S(O)_2N(R^{11})-$.
A89. The compound of any one of Embodiments A1-A84 or A86-A88, wherein:
Y is $-(CR^{16}R^{17})_q-$, $(CR^{16}R^{17})_mO(CR^{16}R^{17})_n-$, $(CR^{16}R^{17})_mC(O)(CR^{16}R^{17})_n-$, $-(CR^{16}R^{17})_mN(R^{10})(CR^{16}R^{17})_n-$, $-(CR^{16}R^{17})_mN(R^{10})C(O)(CR^{16}R^{17})_n$, $-(CR^{16}R^{17})_mC(O)N(R^{10})(CR^{16}R^{17})_n-$, $-(CR^{16}R^{17})_mN(R^{10})C(O)N(R^{11})(CR^{16}R^{17})_n-$, $-(CR^{16}R^{17})_mS(O)_p(CR^{16}R^{17})_n-$, $-(CR^{16}R^{17})_mN(R^{10})S(O)_2(CR^{16}R^{17})_n$, $-(CR^{16}R^{17})_mS(O)_2N(R^{10})(CR^{16}R^{17})_n-$, or $-(CR^{16}R^{17})_mN(R^{10})S(O)_2N(R^1)(CR^{16}R^{17})_n-$; and wherein:
$R^{16}$ and $R^{17}$, at each occurrence, are each independently hydrogen, halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, or 3-6 membered heterocycloalkoxy, or together with the C to which each is attached are combined to form a C(O), $C_{3-6}$ cycloalkyl, or 3-6 membered heterocycloalkyl;
each m is independently an integer of 0, 1, 2 or 3;
each n is independently an integer of 0, 1, 2 or 3;
wherein the sum of m and n is 0, 1, 2, 3, 4, 5, or 6;
each p is independently an integer of 0, 1 or 2; and
each q is independently an integer of 0, 1, 2, 3, 4, 5, or 6.
A90. The compound of Embodiment A89, wherein m is 0, 1, or 2.
A91. The compound of Embodiment A89 or Embodiment A90, wherein n is 0, 1, or 2.
A92. The compound of any one of Embodiments A89-A91, wherein:
Y is $-(CR^{16}R^{17})_q-$, $(CR^{16}R^{17})_mO(CR^{16}R^{17})_n-$, $(CR^{16}R^{17})_mC(O)(CR^{16}R^{17})_n-$, $-(CR^{16}R^{17})_mN(R^{10})(CR^{16}R^{17})_n-$, $(CR^{16}R^{17})_mN(R^{10})C(O)(CR^{16}R^{17})_n-$, $-(CR^{16}R^{17})_mC(O)N(R^{10})(CR^{16}R^{17})_n-$, $(CR^{16}R^{17})_mN(R^{10})S(O)_2(CR^{16}R^{17})_n-$, or $-(CR^{16}R^{17})_mS(O)_2N(R^{10})(CR^{16}R^{17})_n-$.
A93. The compound of any one of Embodiments A89-A92, wherein:
Y is $-(CR^{16}R^{17})_q-$, $(CR^{16}R^{17})_mO(CR^{16}R^{17})_n-$, $(CR^{16}R^{17})_mN(R^{10})C(O)(CR^{16}R^{17})_n-$, or $-(CR^{16}R^{17})_mC(O)N(R^{10})(CR^{16}R^{17})_n-$.
A94. The compound of any one of Embodiments A89-A93, wherein:
Y is $-(CR^{16}R^{17})_q-$.
A95. The compound of any one of Embodiments A89-A93, wherein:
Y is $-(CR^{16}R^{17})_mO(CR^{16}R^{17})_n-$.
A96. The compound of any one of Embodiments A89-A93, wherein:
Y is $-(CR^{16}R^{17})_mN(R^{10})C(O)(CR^{16}R^{17})_n-$.
A97. The compound of any one of Embodiments A89-A93, wherein:
Y is or $-(CR^{16}R^{17})_mC(O)N(R^{10})(CR^{16}R^{17})_n-$.
A98. The compound of any one of Embodiments A89-A97, wherein:
$R^{16}$ and $R^{17}$, at each occurrence, are each independently hydrogen, halo, hydroxy, CN, $NO_2$, $C_{1-3}$ alkyl, $C_{2-3}$ alkenyl, $C_{2-3}$ alkynyl, $C_{1-3}$ haloalkyl, $C_{1-3}$ hydroxyalkyl, $C_{1-3}$ heteroalkyl, $C_{3-5}$ cycloalkyl, 3-5 membered heterocycloalkyl, $C_{1-3}$ alkoxy, $C_{1-3}$ haloalkoxy, $C_{1-3}$ hydroxyalkoxy, $C_{1-3}$ heteroalkoxy, or 3-5 membered heterocycloalkoxy, or together with the C to which each is attached are combined to form a C(O), $C_{3-5}$ cycloalkyl, or 3-5 membered heterocycloalkyl.
A99. The compound of any one of Embodiments A89-A98, wherein:
$R^{16}$ and $R^{17}$, at each occurrence, are each independently hydrogen, chloro, hydroxy, CN, $NO_2$, methyl, ethyl, isopropyl, $-CF_3$, $-CH_2CF_3$, $-CH_2OH$, $-(CH_2)_2OH$, $-(CH_2)_2OCH_3$, cyclopropyl, 3-oxetanyl, methoxy, ethoxy, isopropoxy, cyclopropoxy, $-OCF_3$, $-OCH_2CF_3$, $-O(CH_2)_2OH$, $-O(CH_2)_2OCH_3$, or 3-oxetanylalkoxy, or together with the C to which each is attached are combined to form a C(O), cyclopropyl, or 3-5 membered heterocycloalkyl.
A100. The compound of any one of Embodiments A89-A99, wherein $R^{16}$ and $R^{17}$ are each hydrogen.
A101. The compound of any one of Embodiments A89-A93, A95 or A98-A100, wherein Y is $-(CH_2)O-$.
A102. The compound of any one of Embodiments A89-A93, A95 or A98-A100, wherein Y is $-O(CH_2)-$.
A103. The compound of any one of Embodiments A89-A93, A95 or A98-A100, wherein Y is $-(CH_2)_2O-$.
A104. The compound of any one of Embodiments A89-A93, A95 or A98-A100, wherein Y is $-O(CH_2)_2-$.
A105. The compound of any one of Embodiments A89-A94 or A98-A100, wherein Y is $-(CH_2)_2-$.
A106. The compound of any one of Embodiments A34-A105, wherein at least one of
$W^1$, $W^2$, $W^3$, and $W^4$ is N.
A107. The compound of any one of Embodiments A34-A105, wherein:
$W^1$, $W^2$, and $W^3$ are each independently $CR^4$, and $W^4$ is N;
$W^1$, $W^2$, and $W^4$ are each independently $CR^4$, and $W^3$ is N;
$W^1$, $W^3$, and $W^4$ are each independently $CR^4$, and $W^2$ is N; or
$W^2$, $W^3$, and $W^4$ are each independently $CR^4$, and $W^1$ is N.

A108. The compound of any one of Embodiments A34-A105, wherein $W^1$, $W^2$, $W^3$, and $W^4$ are each independently $CR^4$.

A109. The compound of any one of Embodiments A1-A108, wherein $R^4$ is independently hydrogen, halo, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, or —$NR^{14}R^{15}$, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, or 3-6 membered heterocycloalkoxy, of the $R^4$ are optionally independently substituted with one, two, three, four, five, or six substituents selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O).

A110. The compound of any one of Embodiments A1-A109, wherein $R^4$ is independently hydrogen, halo, $C_{1-6}$ alkyl, $C_{1-6}$ haloalkyl, $C_{3-6}$ cycloalkyl, $C_{1-6}$ alkoxy, or $C_{1-6}$ haloalkoxy, wherein each $C_{1-6}$ alkyl, $C_{1-6}$ haloalkyl, $C_{3-6}$ cycloalkyl, $C_{1-6}$ alkoxy, or $C_{1-6}$ haloalkoxy of the $R^4$ are optionally independently substituted with one, two, three, four, five, or six substituents selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O).

A111. The compound of any one of Embodiments A1-A110, wherein $R^4$ is independently hydrogen, halo, $C_{1-3}$ alkyl, $C_{1-3}$ haloalkyl, $C_{3-5}$ cycloalkyl, $C_{1-3}$ alkoxy, or $C_{1-3}$ haloalkoxy.

A112. The compound of any one of Embodiments A1-A111, wherein $R^4$ is independently hydrogen.

A113. The compound of any one of Embodiments A34-A112, wherein at least one of $Z^1$, $Z^2$, $Z^3$, and $Z^4$ is N.

A114. The compound of any one of Embodiments A34-A113, wherein: $Z^1$, $Z^2$, and $Z^3$ are each independently $CR^5$, and $Z^4$ is N;
$Z^1$, $Z^2$, and $Z^4$ are each independently $CR^5$, and $Z^3$ is N;
$Z^1$, $Z^3$, and $Z^4$ are each independently $CR^5$, and $Z^2$ is N; or
$Z^2$, $Z^3$, and $Z^4$ are each independently $CR^5$, and $Z^1$ is N.

A115. The compound of any one of Embodiments A34-A114, wherein $Z^1$, $Z^2$, and $Z^4$ are each independently $CR^5$, and $Z^3$ is N.

A116. The compound of any one of Embodiments A34-A112, wherein $Z^1$, $Z^2$, $Z^3$, and $Z^4$ are each independently $CR^5$.

A117. The compound of any one of Embodiments A1-A116, wherein $R^5$, at each occurrence, is independently $R^9$, —$OR^9$, halo, CN, $NO_2$, —$C(O)R^9$, —$C(O)OR^9$, —$C(O)NR^{10}R^{11}$, —$S(O)_pR^9$, or —$S(O)_2NR^{10}R^{11}$.

A118. The compound of any one of Embodiments A1-A117, wherein $R^5$, at each occurrence, is independently hydrogen, halo, CN, $NO_2$, —$C(O)CH_3$, —$C(O)OH$, —$C(O)OCH_3$, —$C(O)N(CH_3)_2$, —$S(O)_2CH_3$, or —$S(O)_2N(CH_3)_2$.

A119. The compound of any one of Embodiments A1-A118, wherein $R^5$ independently is hydrogen, halo or CN.

A120. The compound of any one of Embodiments A1-A119, wherein $R^5$ independently is hydrogen.

A121. The compound of any one of Embodiments A1-A118, wherein $R^5$ is independently an electron-withdrawing group.

A122. The compound of Embodiment A121, wherein $R^5$ independently is chloro.

A123. The compound of Embodiment A121, wherein $R^5$ independently is CN.

A124. The compound of any one of Embodiments A1-A123, wherein $R^7$ is an imidazolyl, a triazolyl, a tetrazolyl, an oxazolyl, a thiazolyl, an oxadiazolyl, a thiadiazolyl, a pyridyl, or a pyrimidinyl, optionally substituted with 1-4 substituents independently selected from halo, CN, $NO_2$, $R^9$, —$OR^9$, —$C(O)R^9$, —$C(O)OR^9$, —$OC(O)R^9$, —$OC(O)OR^9$, —$C(O)NR^{10}R^{11}$, —$NR^{10}R^{11}$, —$NR^{10}C(O)R^9$, —$NR^{10}C(O)OR^9$, —$NR^{10}C(O)NR^{10}R^{11}$, —$NR^{10}S(O)_2R^9$, —$S(O)_pR^9$, —$S(O)_2NR^{10}R^{11}$, or —$NR^{10}S(O)_2NR^{10}R^{11}$.

A125. The compound of any one of Embodiments A1-A124, wherein $R^7$ is imidazolyl or triazolyl, optionally substituted with 1-4 substituents independently selected from halo, CN, $NO_2$, $R^9$, —$OR^9$, —$C(O)R^9$, —$C(O)OR^9$, —$C(O)NR^{10}R^{11}$, —$NR^{10}R^{11}$, —$NR^{10}C(O)R^9$, —$S(O)_pR^9$, or —$S(O)_2NR^{10}R^{11}$.

A126. The compound of any one of Embodiments A1-A125, wherein $R^7$ is a C-linked imidazolyl or a C-linked triazolyl, optionally substituted with 1-4 substituents independently selected from halo, CN, $NO_2$, $R^9$, —$OR^9$, —$C(O)R^9$, —$C(O)OR^9$, —$C(O)NR^{10}R^{11}$, —$NR^{10}R^{11}$, —$NR^{10}C(O)R^9$, —$S(O)_pR^9$, or —$S(O)_2NR^{10}R^{11}$.

A127. The compound of any one of Embodiments A1-A125, wherein $R^7$ is an N-linked imidazolyl or an N-linked triazolyl, optionally substituted with 1-4 substituents independently selected from halo, CN, $NO_2$, $R^9$, —$OR^9$, —$C(O)R^9$, —$C(O)OR^9$, —$C(O)NR^{10}R^{11}$, —$NR^{10}R^{11}$, —$NR^{10}C(O)R^9$, —$S(O)_pR^9$, or —$S(O)_2NR^{10}R^{11}$.

A128. The compound of any one of Embodiments A1-A126, wherein $R^7$ is a methyl-substituted imidazolyl or a methyl-substituted triazolyl.

A129. The compound of any one of Embodiments A1-A127, wherein $R^7$ is a C-methyl-substituted imidazolyl or a C-methyl-substituted triazolyl.

A130. The compound of any one of Embodiments A1-A128, wherein $R^7$ is an N-methyl-substituted imidazolyl or an N-methyl-substituted triazolyl.

A131. The compound of any one of Embodiments A1-A126 or 128-130, wherein $R^7$ is:

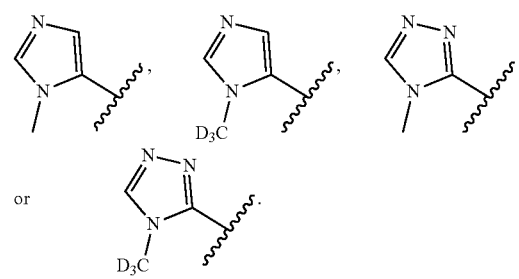

A132. The compound of any one of Embodiments A1-A126 or A128-A129, wherein $R^7$ is:

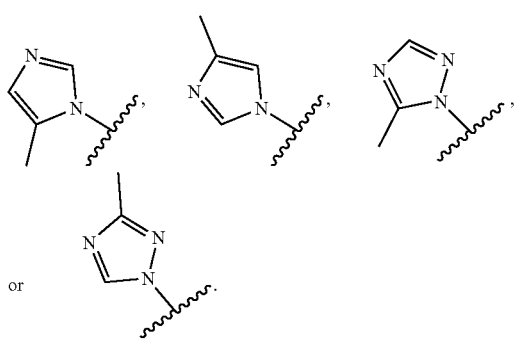

A133. The compound of any one of Embodiments A1-A132, wherein $R^6$ is CN, $R^9$, —$OR^9$, —$OC(O)R^9$, —$OC(O)OR^9$, —$NROR^{11}$, —$NR^{10}OR^9$, —$NR^{10}C(O)R^9$, or —$NR^1OC(NR^{10})NR^{10}R^{11}$.

A134. The compound of any one of Embodiments A1-A133, wherein $R^6$ is CN, $R^9$, —$OR^9$, —$NR^{10}R^{11}$, or —$NR^{10}OR^9$.

A135. The compound of any one of Embodiments A1-A134, wherein $R^6$ is CN, $R^9$, —$OR^9$, or —$NR^{10}R^{11}$.

A136. The compound of any one of Embodiments A133-A135, wherein:
$R^9$ is independently hydrogen or $C_{1-3}$ alkyl, wherein the $C_{1-3}$ alkyl is optionally substituted with CN.

A137. The compound of any one of Embodiments A133-A136, wherein:
$R^{10}$ and $R^{11}$ are each independently hydrogen, $C_{1-6}$ alkyl or $C_{1-6}$ alkoxy; or optionally wherein $R^{10}$ is H and $R^{11}$ is $C_{1-3}$haloalkyl, such as chloroethyl or fluoroethyl.

A138. The compound of any one of Embodiments A1-A137, wherein $R^6$ is hydrogen, —$CH_3$, hydroxy, —$OCH_3$, —$OCD_3$, —$NH_2$, —$NHCH_3$, or —$NH(OCH_3)$; or wherein $R^6$ is —$NH(CH_2CH_2)Cl$, —$NH(CH_2CH_2)F$, or N-linked morpholino.

A139. The compound of Embodiment A138, wherein $R^6$ is hydroxy.

A140. The compound of Embodiment A138, wherein $R^6$ is hydrogen.

A141. The compound of Embodiment A138, wherein $R^6$ is $NH_2$.

A142. The compound of any one of Embodiments A1-A141, wherein the compound has a MW of no more than 1,000 g/mol.

A143. The compound of Embodiment A142, wherein the compound has a MW of no more than 900 g/mol, no more than 800 g/mol, no more than 700 g/mol, no more than 600 g/mol, or no more than 500 g/mol.

A144. The compound of Embodiment A142, wherein the compound has a MW of no more than 600 g/mol.

A145. The compound of Embodiment A142, wherein the compound has a MW of no more than 500 g/mol.

A146. The compound of any one of Embodiments A1-A145, wherein the compound is selected from Compounds 1, 2, 3, 4, 5, 6, 7, 8, 9, 10, 11, 12, 13, 14, 15, 16, 17, 18, 19, 20, 21, 22, 23,24,25,26,27,28,29, 30,31,32,33,34,35,36,37,38,39,40,41, 42,43,44,45,46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, and 135, or a pharmaceutically acceptable form thereof.

A147. The compound of any one of Embodiments A1-A146, wherein the compound is selected from Compounds 1, 2, 3, 4, 6, 7, 8, 11, 13, 14, 15, 17, 18, 19, 20, 22, 23, 25, 26, 27, 28, 29, 30, 31, 32, 33, 34, 35, 36, 37, 38, 39, 41, 42, 43, 44, 45, 46, 47, 50, 51, 54, 55, 56, 57, 61, 62, 63, 65, 69, 76, 77, 79, 80, 92, 93, 94, 95, 96, 97, 98, 99, 100, 101, 102, 103, 104, 105, 106, 107, 108, 109, and 110, or a pharmaceutically acceptable form thereof.

A148. The compound of any one of Embodiments A1-A146, wherein the compound is selected from Compounds 5, 9, 10, 12, 16, 21, 24, 40, 43, 48, 49, 52, 53, 58, 59, 60, 64, 66, 67, 68, 70, 71, 72, 73, 74, 75, 78, 89, 90, and 91, or a pharmaceutically acceptable form thereof.

A149. The compound of any one of Embodiments A1-A146, wherein the compound is selected from Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 36, 37, 40, 41, 42, 43, 44, 45, 46, 47, 48, 52, 53, 54, 55, 56, 57, 58, 59, 60, 61, 62, 63, 64, 65, 66, 67, 68, 69, 70, 71, 72, 73, 74, 75, 81, 82, 83, 84, 85, 86, 87, 88, 89, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, and 135, or a pharmaceutically acceptable form thereof.

A150. The compound of any one of Embodiments A1-A146, wherein the compound is selected from Compounds 31, 32, 33, 34, 35, 38, 39, 49, 50, and 51, or a pharmaceutically acceptable form thereof.

A151. The compound of any one of Embodiments A1-A146, wherein the compound is selected from Compounds 1, 2, 3, 5, 6, 10, 11, 12, 13, 14, 16, 17, 18, 22, 23, 24, 25, 26, 28, 29, 31, 32, 36, 38, 40, 41, 42, 43, 44, 45, 49, 52, 53, 54, 55, 59, 60, 61, 63, 64, 65, 71, 72, 73, 78, 81, 83, 84, 85, 87, 88, 93, 94, 95, 112, 113, 114, 115, 117, 118, 119, and 120, or a pharmaceutically acceptable form thereof.

A152. The compound of any one of Embodiments A1-A146, wherein the compound is selected from Compounds 4, 7, 8, 9, 16, 19, 20, 21, 27, 30, 34, 35, 37, 39, 46, 47, 48, 51, 56, 57, 58, 62, 66, 67, 68, 69, 70, 74, 75, 82, 86, 89, and 92, or a pharmaceutically acceptable form thereof.

A153. The compound of any one of Embodiments A1-A146, wherein the compound is selected from Compounds 3, 4, 12, 13, 14, 15, 24, 25, 26, 27, 28, 29, 30, 31, 32, 33, 34, 35, 43, 44, 45, 46, 47, 48, 49, 50, 51, 59, 64, 65, 76, 77, 80, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, and 135, or a pharmaceutically acceptable form thereof.

A154. The compound of any one of Embodiments A1-A146, wherein the compound is selected from Compounds 5, 6, 7, 8, 9, 16, 17, 18, 19, 20, 21, 36, 37, 38, 39, 53, 54, 55, 56, 57, 58, 60, 61, 62, 66, 67, 68, 69, 70, 72, 73, 78, 85, 86, 88, 89, 90, and 91, or a pharmaceutically acceptable form thereof.

A155. The compound of any one of Embodiments A1-A146, wherein the compound is selected from Compounds 1, 2, 3, 4, 5, 6, 7, 8, 9, 93, 98, 103, 108, 113, 118, 123, 128, and 133, or a pharmaceutically acceptable form thereof.

A156. The compound of any one of Embodiments A1-A146, wherein the compound is selected from Compounds 10, 11, 12, 13, 14, 15, 16, 17, 18, 19, 20, 21, 92, 96, 101, 106, 111, 116, 121, 126, and 131, or a pharmaceutically acceptable form thereof.

A157. The compound of any one of Embodiments A1-A146, wherein the compound is selected from Compounds 22, 23, 24, 25, 26, 27, 28, 29, 30, 31, 32, 33, 34, 35, 36, 37, 38, 39, 97, 102, 107, 112, 117, 122, 127, and 132, or a pharmaceutically acceptable form thereof.

A158. The compound of any one of Embodiments A1-A146, wherein the compound is selected from Compounds 40, 41, 42, 43, 44, 45, 46, 47, 48, 49, 50, 51, 52, 53, 54, 55, 56, 57, 58, 59, 60, 61, 62, 66, 67, 68, 69, 70, 71, 72, 73, 74, 75, 76, 77, 78, 79, 80, 81, 82, 83, 84, 85, 86, 87, 88, 89, 90, 91, 95, 100, 105, 110, 115, 120, 125, 130, and 135, or a pharmaceutically acceptable form thereof.

A159. The compound of any one of Embodiments A1-A146, wherein the compound is selected from Compounds 63, 64, 65, 94, 99, 104, 109, 114, 119, 124, 129, and 134, or a pharmaceutically acceptable form thereof.

A160. The compound of any one of Embodiments A1-A146, wherein the compound is selected from Compounds 3, 4, 5, 6, 7, 8, 9, 11, 14, 15, 17, 18, 19, 20, 21, 23, 25, 27, 28, 29, 30, 34, 35, 36, 37, 38, 39, 42, 44, 45, 46, 47, 48, 50, 51, 53, 54, 55, 56, 57, 58, 61, 62, 65, 69, 70, 72, 78, 82, 83, 86, 88, 89, and 91, or a pharmaceutically acceptable form thereof.

A161. The compound of any one of Embodiments A1-A146, wherein the compound is selected from Compounds 4, 6, 7, 8, 9, 18, 19, 20, 21, 23, 26, 27, 28, 36, 37, 39, 46, 55, 56, 57, and 58, or a pharmaceutically acceptable form thereof.

A162. The compound of any one of Embodiments A1-A146, wherein the compound is selected from Compounds 4, 6, 7, 8, 18, 27, 34, 37, 46, 47, 48, 55, 57, and 58, or a pharmaceutically acceptable form thereof.

A163. The compound of any one of Embodiments A1-A146, wherein the compound is selected from Compounds 4, 6, 7, 8, 18, 27, 37, 46, 55, 57, and 58, or a pharmaceutically acceptable form thereof.

A164. The compound of any one of Embodiments A1-A163, wherein the pharmaceutically acceptable form of the compound is exclusive of a salt form.

A165. The compound of any one of Embodiments A1-A164, wherein the compound is a racemate or a mixture of diasteromers, or a mixture of stereoisomers.

A166. The compound of any one of Embodiments A1-A164, wherein the compound is a single enantiomer or a single diasteromer.

A167. The compound of any one of Embodiments A1-A164 or A166, wherein the compound is an (R)-enantiomer.

A168. The compound of any one of Embodiments A1-A167, wherein the compound has an enantiomeric excess of greater than 10% f the (R)-enantiomer.

A169. The compound of any one of Embodiments A1-A167, wherein the compound has an enantiomeric excess of 15% or more, 20% or more, 25% or more, 30% or more, 35% r more, 40% or more, 45% or more, 50% or more, 55% or more, 60% or more, 65% or more, 70% or more, 75% or more, 80% or more, 85% or more, 90% or more, 95% or more, 98% or more, 99% or more, of the (R)-enantiomer.

A170. The compound of any one of Embodiments A1-A167, wherein the compound has an enantiomeric excess of about 90%, about 91%, about 92%, about 93%, about 94%, about 95%, about 96%, about 97%, about 98%, or about 99%, of the (R)-enantiomer.

A171. The compound of any one of Embodiments A1-A164 or A166, wherein the compound is an (S)-enantiomer.

A172. The compound of any one of Embodiments A1-A166 or A171, wherein the compound has an enantiomeric excess of greater than 10% f the (S)-enantiomer.

A173. The compound of any one of Embodiments A1-A166 or A171, wherein the compound has an enantiomeric excess of 15% or more, 20% or more, 25% or more, 30% r more, 35% or more, 40% or more, 45% or more, 50% or more, 55% or more, 60% or more, 65% or more, 70% or more, 75% or more, 80% or more, 85% or more, 90% or more, 95% or more, 98% or more, 99% or more, of the (S)-enantiomer.

A174. The compound of any one of Embodiments A1-A166 or A171, wherein the compound has an enantiomeric excess of about 90%, about 91%, about 92%, about 93%, about 94%, about 95%, about 96%, about 97%, about 98%, or about 99%, of the (S)-enantiomer.

A175. A pharmaceutical composition comprising the compound or pharmaceutically acceptable form thereof, of any one of Embodiments A1-A174, and a pharmaceutically acceptable carrier, excipient or diluent.

A176. A method of inhibiting a farnesyltransferase, comprising contacting the farnesyltransferase with an effective amount of the compound or pharmaceutically acceptable form thereof, of any one of Embodiments A1-A174.

A177. A method of inhibiting a farnesyltransferase, comprising contacting the farnesyltransferase with an effective amount of the pharmaceutical composition of Embodiment A175.

A178. The method of Embodiment A176 or Embodiment A177, wherein the farnesyltransferase is present in a cell.

A179. The method of any one of Embodiments A176-A178, wherein the method inhibits farnesylation of H-Ras protein.

A180. The method of Embodiment A179, wherein the H-Ras protein has a mutation.

A181. The method of Embodiment A180, wherein the H-Ras protein mutation is or comprises a modification in a codon that encodes an amino acid substitution at a specific position selected from G12, G13, Q61, Q22, K117, A146, and any combination thereof, in the corresponding mutant H-Ras protein.

A182. The method of any one of Embodiments A176-A178, wherein the method inhibits farnesylation of N-Ras protein.

A183. The method of Embodiment A182, wherein the N-Ras protein has a mutation.

A184. The method of Embodiment A183, wherein the N-Ras protein mutation is or comprises a modification in a codon that encodes an amino acid substitution at a specific position selected from G12, G13, Q61, Q22, K117, A146, and any combination thereof, in the corresponding mutant N-Ras protein.

A185. The method of any one of Embodiments A176-A184, wherein the contacting of the farnesyltransferase takes place in a cell.

A186. The method of any one of Embodiments A178-A185, wherein the cell is in a subject.

A187. The method of any one of Embodiments A178-A186, wherein the cell is a mammalian cell.

A188. The method of any one of Embodiments A178-A187, wherein cell a human cell.

A189. The method of any one of Embodiments A186-A188, wherein the subject suffers from a cancer dependent on a farnesylated protein.

A190. The method of any one of Embodiments A176-A189, wherein the inhibition takes place in a subject suffering from cancer dependent on a farnesylated protein.

A191. The method of Embodiment A189 or Embodiment A190, wherein the cancer dependent on a farnesylated protein is a solid tumor.

A192. The method of Embodiment A191, wherein the cancer dependent on a farnesylated protein is a cancer dependent on farnesylated H-Ras protein.

A193. The method of any one of Embodiments A185-A192, wherein the cancer dependent on a farnesylated protein has an H-Ras protein mutation.

A194. The method of Embodiment A193, wherein the H-Ras protein mutation is or comprises a modification in a codon that encodes an amino acid substitution at a specific position selected from G12, G13, Q61, Q22, K117, A146, and any combination thereof, in the corresponding mutant H-Ras protein.

A195. The method of any one of Embodiments A185-A194, wherein the cancer dependent on a farnesylated protein is head and neck cancer.

A196. The method of any one of Embodiments A185-A195, wherein the cancer dependent on a farnesylated protein is Squamous Cell Carcinoma (SCC).

A197. The method of Embodiment A196, wherein the SCC is head and neck SCC (HNSCC), lung SCC (LSCC), thyroid SCC (TSCC), esophagus SCC (ESCC), bladder SCC (BSCC) or urothelial carcinoma (UC).

A198. The method of Embodiment A197, wherein the SCC is HNSCC.

A199. The method of Embodiment A198, wherein the HNSCC is HNSCC of the trachea, HNSCC of the maxilla, HNSCC of the oral cavity.

A200. The method of Embodiment A195, wherein the head and neck cancer is head and neck squamous cell carcinoma (HNSCC).

A201. The method of any one of Embodiments A185-A194, wherein the cancer dependent on a farnesylated protein is carcinoma, melanoma, sarcoma, or chronic granulomatous disease.

A202. The method of any one of Embodiments A185-A194, wherein the cancer dependent on a farnesylated protein is thyroid cancer, head and neck cancers, urothelial cancers, salivary cancers, cancers of the upper digestive tract, bladder cancer, breast cancer, ovarian cancer, brain cancer, gastric cancer, prostate cancer, lung cancer, colon cancer, skin cancer, liver cancer, or pancreatic cancer.

A203. The method of any one of Embodiments A185-A202, wherein the cancer dependent on a farnesylated protein is a cancer dependent on farnesylated N-Ras protein.

A204. The method of any one of Embodiments A185-A203, wherein the cancer dependent on a farnesylated protein has an N-Ras protein mutation.

A205. The method of Embodiment A204, wherein the N-Ras protein mutation is or comprises a modification in a codon that encodes an amino acid substitution at a specific position selected from G12, G13, Q61, Q22, K117, A146, and any combination thereof, in the corresponding mutant N-Ras protein.

A206. The method of any one of Embodiments A185-A205, wherein the cancer dependent on a farnesylated protein is melanoma, acute myeloid leukemia (AML), thyroid carcinoma, lung adenocarcinoma, rectal carcinoma, endometrial carcinoma, or colorectal carcinoma.

A207. The method of any one of Embodiments A185-A206, wherein the subject is a human.

A208. A method of treating cancer dependent on a farnesylated protein in a subject, comprising administering a therapeutically effective amount of the compound or pharmaceutically acceptable form thereof, of any one of Embodiments A1-A174 to the subject having cancer dependent on a farnesylated protein.

A209. A method of treating cancer dependent on a farnesylated protein in a subject, comprising administering a therapeutically effective amount of the pharmaceutical composition of Embodiment A175 to the subject having cancer dependent on a farnesylated protein.

A210. The method of Embodiment A208 or Embodiment A209, wherein the cancer dependent on a farnesylated protein is a solid tumor.

A211. The method of any one of Embodiments A208-A210, wherein the cancer dependent on a farnesylated protein is a cancer dependent on farnesylated H-Ras protein.

A212. The method of any one of Embodiments A208-A211, wherein the cancer dependent on a farnesylated protein has an H-Ras protein mutation.

A213. The method of Embodiment A212, wherein the H-Ras protein mutation is or comprises a modification in a codon that encodes an amino acid substitution at a specific position selected from G12, G13, Q61, Q22, K117, A146, and any combination thereof, in the corresponding mutant H-Ras protein.

A214. The method of Embodiment A212 or Embodiment A213, wherein determining the presence or absence of the H-Ras mutation comprises analyzing nucleic acids obtained from a sample from the subject.

A215. The method of Embodiment A214, wherein said sample is a tissue biopsy.

A216. The method of Embodiment A214, wherein said sample is a tumor biopsy.

A217. The method of any one of Embodiments A214-A216, wherein the H-Ras mutation is determined by sequencing, Polymerase Chain Reaction (PCR), DNA microarray, Mass Spectrometry (MS), Single Nucleotide Polymorphism (SNP) assay, denaturing high-performance liquid chromatography (DHPLC), or Restriction Fragment Length Polymorphism (RFLP) assay.

A218. The method of any one of Embodiments A208-A217, wherein the cancer dependent on a farnesylated protein is head and neck cancer.

A219. The method of any one of Embodiments A208-A218, wherein the cancer dependent on a farnesylated protein is Squamous Cell Carcinoma (SCC).

A220. The method of Embodiment A219, wherein the SCC is head and neck SCC (HNSCC), lung SCC (LSCC), thyroid SCC (TSCC), esophagus SCC (ESCC), bladder SCC (BSCC) or urothelial carcinoma (UC).

A221. The method of Embodiment A219 of Embodiment A220, wherein the SCC is HNSCC.

A222. The method of Embodiment A221, wherein the HNSCC is HNSCC of the trachea, HNSCC of the maxilla, HNSCC of the oral cavity.

A223. The method of Embodiment A218, wherein the head and neck cancer is head and neck squamous cell carcinoma (HNSCC).

A224. The method of any one of Embodiments A208-A223, wherein the cancer dependent on a farnesylated protein is a cancer dependent on farnesylated N-Ras protein.

A225. The method of any one of Embodiments A208-A224, wherein the cancer dependent on a farnesylated protein has an N-Ras protein mutation.

A226. The method of Embodiment A225, wherein the N-Ras mutation is or comprises a modification in a codon that encodes an amino acid substitution at a specific position selected from G12, G13, Q61, Q22, K117, A146, and any combination thereof, in the corresponding mutant N-Ras protein.

A227. The method of Embodiment A225 or Embodiment A226, wherein determining the presence or absence of the N-Ras mutation comprises analyzing nucleic acids obtained from a sample from the subject.

A228. The method of Embodiment A227, wherein said sample is a tissue biopsy.

A229. The method of Embodiment A238, wherein said sample is a tumor biopsy.

A230. The method of any one of Embodiments A227-A229, wherein the N-Ras mutation is determined by sequencing, Polymerase Chain Reaction (PCR), DNA microarray, Mass Spectrometry (MS), Single Nucleotide Polymorphism (SNP) assay, denaturing high-performance liquid chromatography (DHPLC), or Restriction Fragment Length Polymorphism (RFLP) assay.

A231. The method of any one of Embodiments A208-A230, wherein the cancer dependent on a farnesylated protein is melanoma, acute myeloid leukemia (AML), thyroid carcinoma, lung adenocarcinoma, rectal carcinoma, endometrial carcinoma, or colorectal carcinoma.

A232. The method of any one of Embodiments A185-A230, wherein the cancer dependent on a farnesylated protein is carcinoma, melanoma, sarcoma, or chronic granulomatous disease.

A233. The method of any one of Embodiments A185-A230, wherein the cancer dependent on a farnesylated protein is thyroid cancer, head and neck cancers, urothelial cancers, salivary cancers, cancers of the upper digestive tract, bladder cancer, breast cancer, ovarian cancer, brain cancer, gastric cancer, prostate cancer, lung cancer, colon cancer, skin cancer, liver cancer, or pancreatic cancer.

A234. The method of any one of Embodiments A208-A233, wherein the subject is a human.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference in its entirety. In case of conflict, the present application, including any definitions herein, will control.

We claim:
1. A compound of Formula (II):

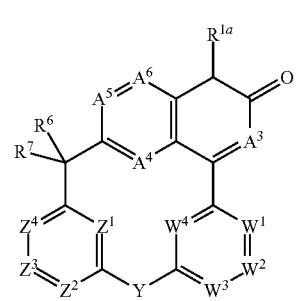

Formula (II)

wherein:
$A^3$ is $CR^3$ or N;
$A^4$ is $CR^8$ or N;
$A^5$ and $A^6$ are each independently $CR^8$ or N, or $A^5$ and $A^6$ taken together are O, $NR^9$, or S;
$W^1$, $W^2$, $W^3$, and $W^4$ are each independently N or $CR^4$, or $W^1$ and $W^2$ taken together are O, $NR^4$, or S, or $W^2$ and $W^3$ taken together are O, $NR^{4A}$, or S;
Y is a bond or a linker having a length of up to 6 atoms;
$Z^1$, $Z^2$, $Z^3$, and $Z^4$ are each independently N or $CR^5$, or $Z^2$ and $Z^3$ taken together are O, $NR^{5A}$, or S, or $Z^3$ and $Z^4$ taken together are O, $NR^{5A}$, or S;
$R^{1a}$ is $R^9$, $-OR^9$, $-C(O)R^9$, $-C(O)OR^9$, $-C(O)NR^{10}R^{11}$, $-S(O)_pR^9$, or $-S(O)_2NR^{10}R^{11}$;
$R^3$, $R^5$, and $R^8$, at each occurrence, are each independently $R^9$, $-OR^9$, halo, CN, $NO_2$, $-C(O)R^9$, $-C(O)OR^9$, $-OC(O)R^9$, $-OC(O)OR^9$, $-C(O)NR^{10}R^{11}$, $-NR^{10}R^{11}$, $-NR^{10}C(O)R^9$, $-NR^{10}C(O)OR^9$, $-NR^{10}C(O)NR^{10}R^{11}$, $-NR^{10}S(O)_2R^9$, $-S(O)_pR^9$, $-S(O)_2NR^{10}R^{11}$, or $-NR^{10}S(O)_2NR^{10}R^{11}$;
$R^4$, at each occurrence, is independently hydrogen, halo, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, $-NR^{14}R^{15}$, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, $C_{6-12}$ aryl, or 5-12 membered heteroaryl of the $R^4$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);
$R^{4A}$ and $R^{5A}$ are each independently hydrogen, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{4A}$ and the $R^4$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);

$R^6$ is CN, $R^9$, —$OR^9$, —$C(O)R^9$, —$C(O)OR^9$, —$OC(O)R^9$, —$OC(O)OR^9$, —$C(O)NR^{10}R^{11}$, —$NR^{10}R^{11}$, —$NR^{10}OR^9$, —$NR^{10}C(O)R^9$, —$NR^{10}C(O)OR^9$, —$NR^{10}C(O)NR^{10}R^{11}$, —$NR^{10}S(O)_2R^9$, —$NR^{10}C(NR^{10})NR^{10}R^{11}$, —$S(O)_pR^9$, —$S(O)_2NR^{10}R^{11}$, or —$NR^{10}S(O)_2NR^{10}R^{11}$;

$R^7$ is a 5-12 membered heteroaryl, optionally substituted with one, two, three, or four substituents independently selected from halo, CN, $NO_2$, $R^9$, —$OR^9$, —$C(O)R^9$, —$C(O)OR^9$, —$OC(O)R^9$, —$OC(O)OR^9$, —$C(O)NR^{10}R^{11}$, —$NROR^{11}$, —$NR^{10}C(O)R^9$, —$NR^{10}C(O)OR^9$, —$NR^{10}C(O)NR^{10}R^{11}$, —$NR^{10}S(O)_2R^9$, —$S(O)_pR^9$, —$S(O)_2NR^{10}R^{11}$, and —$NR^{10}S(O)_2NR^{10}R^{11}$;

$R^9$, at each occurrence, is independently hydrogen, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^9$ is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), —$C(O)R^{12}$, —$C(O)OR^{12}$, —$OC(O)R^{12}$, —$OC(O)OR^{12}$, —$C(O)NR^{10}R^{11}$, —$NR^{10}R^{11}$, —$NR^{10}C(O)R^{12}$, —$NR^{10}C(O)OR^{12}$, —$NR^{10}C(O)NR^{10}R^{11}$, —$NR^{10}S(O)_2R^{12}$, —$S(O)_pR^{12}$, —$S(O)_2NR^{10}R^{11}$, and —$NR^{10}S(O)_2NR^{10}R^{11}$;

$R^{10}$ and $R^{11}$, at each occurrence, are each independently hydrogen, hydroxy, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{6-12}$ aryl, or 5-12 membered heteroaryl, or together with the N to which each is attached are combined to form a 3-6 membered heterocycloalkyl, wherein each $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{6-12}$ aryl, or 5-12 membered heteroaryl of the $R^{10}$ and the $R^{11}$ is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), —$C(O)R^{13}$, —$C(O)OR^{13}$, —$OC(O)R^{13}$, —$OC(O)OR^{13}$, —$C(O)NR^{14}R^{15}$, —$NR^{14}R^{15}$, —$NR^{14}C(O)R^{13}$, —$NR^{14}C(O)OR^{13}$, —$NR^{14}C(O)NR^{14}R^{15}$, —$NR^{14}S(O)_2R^{13}$, —$S(O)_pR^{13}$—$S(O)_2NR^{14}R^{15}$, and —$NR^{14}S(O)_2NR^{14}R^{15}$;

$R^{12}$, at each occurrence, is independently hydrogen, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{12}$ is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), —$C(O)R^{13}$, —$C(O)R^{13}$, —$OC(O)R^{13}$, —$OC(O)OR^{13}$, —$C(O)NR^{10}R^{11}$, —$NR^{10}R^{11}$, —$NR^{10}C(O)R^{13}$, —$NR^{10}C(O)OR^{13}$, —$NR^{10}C(O)NR^{10}R^{11}$, —$NR^{10}S(O)_2R^{13}$, —$S(O)_pR^{13}$, —$S(O)_2NR^{10}R^{11}$, and —$NR^{10}S(O)_2NR^{10}R^{11}$;

$R^{13}$, at each occurrence, is independently hydrogen, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-6}$ cycloalkyl, or 3-6 membered heterocycloalkyl;

$R^{14}$ and $R^{15}$, at each occurrence, are each independently hydrogen, hydroxy, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-6}$ cycloalkyl, 3-6 membered heterocycloalkyl, or $C_{1-6}$ alkoxy, or together with the N to which each is attached are combined to form a 3-6 membered heterocycloalkyl; and each p is independently an integer of 0, 1, or 2;

or a pharmaceutically acceptable form thereof.

2. The compound of claim 1, wherein the compound is a compound of Formula (IIa) or is a compound of Formula (IIb):

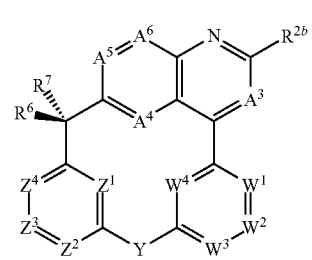

Formula (IIIa)

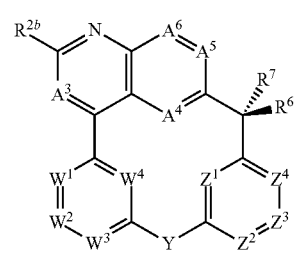

Formula (IIIb)

or a pharmaceutically acceptable form thereof.

3. The compound of claim 1, wherein $A^3$ is $CR^3$, optionally wherein $R^3$ is (a) $R^9$, —$OR^9$, halo, or CN; or (b) hydrogen.

4. The compound of claim 1, wherein $A^4$ is $CR^8$.

5. The compound of claim 1, wherein $A^5$ is $CR^8$.

6. The compound of claim 1, wherein $A^6$ is $CR^8$.

7. The compound of claim 1, wherein:
(a) $A^4$ is N, and no more than one of $A^5$ and $A^6$ is N; or
(b) $A^5$ is N, and no more than one of $A^4$ and $A^6$ is N; or
(c) $A^6$ is N, and no more than one of $A^4$ and $A^5$ is N; or
(d) $A^4$, $A^5$, and $A^6$ are each independently $CR^8$.

8. The compound of claim 1, wherein each $R^8$ is independently $R^9$, —$OR^9$, halo, or CN, optionally wherein each $R^8$ is hydrogen.

9. The compound of claim 1, wherein at least one of $W^1$, $W^2$, $W^3$, and $W^4$ is N, optionally, wherein:

$W^1$, $W^2$, and $W^3$ are each independently $CR^4$, and $W^4$ is N;

$W^1$, $W^2$, and $W^4$ are each independently $CR^4$, and $W^3$ is N;

$W^1$, $W^3$, and $W^4$ are each independently $CR^4$, and $W^2$ is N; or $W^2$, $W^3$, and $W^4$ are each independently $CR^4$, and $W^1$ is N.

10. The compound of claim 1, wherein $W^1$, $W^2$, $W^3$, and $W^4$ are each independently $CR^4$.

11. The compound of claim 1, wherein:

(a) each $R^4$ is independently hydrogen, halo, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, or $-NR^{14}R^{15}$, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, or 3-6 membered heterocycloalkoxy of the $R^4$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O); or (b) each $R^4$ is independently hydrogen, halo, $C_{1-6}$ alkyl, $C_{1-6}$ haloalkyl, $C_{3-6}$ cycloalkyl, $C_{1-6}$ alkoxy, or $C_{1-6}$ haloalkoxy, wherein each $C_{1-6}$ alkyl, $C_{1-6}$ haloalkyl, $C_{3-6}$ cycloalkyl, $C_{1-6}$ alkoxy, or $C_{1-6}$ haloalkoxy of the $R^4$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O); or (c) each $R^4$ is independently hydrogen, halo, $C_{1-3}$ alkyl, $C_{1-3}$ haloalkyl, $C_{3-5}$ cycloalkyl, $C_{1-3}$ alkoxy, or $C_{1-3}$ haloalkoxy; or (d) each $R^4$ is hydrogen.

12. The compound of claim 1, wherein at least one of $Z^1$, $Z^2$, $Z^3$, and $Z^4$ is N, optionally wherein:

$Z^1$, $Z^2$, and $Z^3$ are each independently $CR^5$, and $Z^4$ is N;

$Z^1$, $Z^2$, and $Z^4$ are each independently $CR^5$, and $Z^3$ is N;

$Z^1$, $Z^3$, and $Z^4$ are each independently $CR^5$, and $Z^2$ is N; or $Z^2$, $Z^3$, and $Z^4$ are each independently $CR^5$, and $Z^1$ is N.

13. The compound of claim 1, wherein $Z^1$, $Z^2$, $Z^3$, and $Z^4$ are each independently $CR^5$.

14. The compound of claim 1, wherein:

$R^5$, at each occurrence, is independently $R^9$, $-OR^9$, halo, CN, $NO_2$, $-C(O)R^9$, $-C(O)OR^9$, $-C(O)NR^{10}R^{11}$, $-S(O)_pR^9$, or $-S(O)_2NR^{10}R^{11}$; or $R^5$, at each occurrence, is independently hydrogen, halo, CN, $NO_2$, $-C(O)CH_3$, $-C(O)OH$, $-C(O)OCH_3$, $-C(O)N(CH_3)_2$, $-S(O)_2CH_3$, or $-S(O)_2N(CH_3)_2$; or each $R^5$ independently is hydrogen, halo, or CN; or each $R^5$ is hydrogen.

15. The compound of claim 1, wherein the compound is a compound of Formula (II-1), (IIa-1), (IIb-1), (11-2), (IIa-2), or (IIb-2):

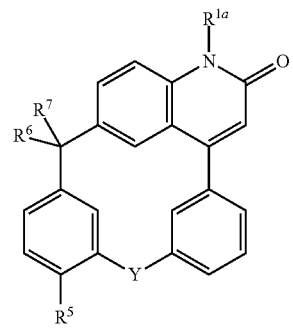

Formula (II-1)

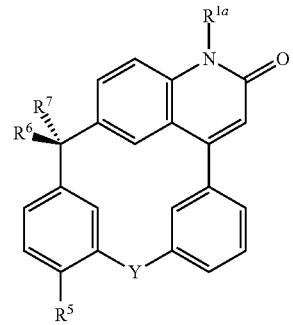

Formula (IIa-1)

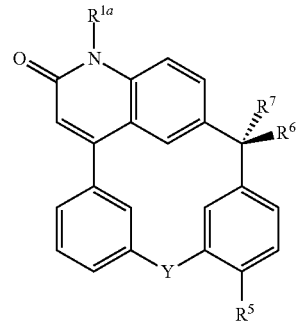

Formula (IIb-1)

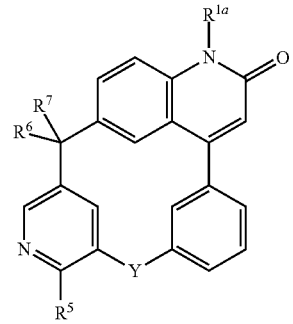

Formula (II-2)

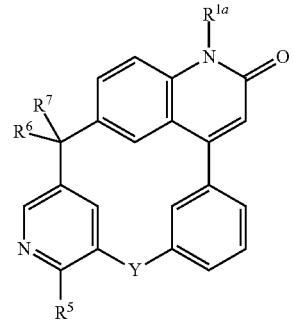

Formula (IIa-2)

-continued

Formula (IIb-2)

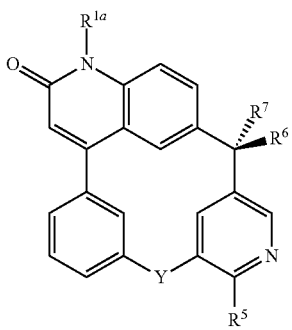

or a pharmaceutically acceptable form thereof.

16. The compound of claim 15, wherein $R^{1a}$ is $R^9$.

17. The compound of claim 15, wherein $R^{1a}$ is hydrogen, $C_{1-6}$ alkyl, or $C_{3-6}$ cycloalkyl, wherein each $C_{1-6}$ alkyl or $C_{3-6}$ cycloalkyl is optionally substituted with one, two, three, four, five, or six substituents independently selected from halo, hydroxy, CN, NO$_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), —C(O)R$^{12}$, —C(O)OR$^{12}$, —OC(O)R$^{12}$, —OC(O)OR$^{12}$, —C(O)NR$^{10}$R$^{11}$, —NR$^{10}$R$^{11}$, —NR$^{10}$C(O)R$^{12}$, —NR$^{10}$C(O)OR$^{12}$, —NR$^{10}$C(O)NR$^{10}$R$^{11}$, —NR$^{10}$S(O)$_2$R$^{12}$, —S(O)$_p$R$^{12}$, and —S(O)$_2$NR$^{10}$R$^{11}$.

18. The compound of claim 15, wherein $R^{1a}$ is hydrogen, $C_{1-3}$ alkyl, or $C_{3-4}$ cycloalkyl, wherein each $C_{1-3}$ alkyl or $C_{3-4}$ cycloalkyl is optionally substituted with one, two, or three substituents independently selected from halo, hydroxy, CN, NO$_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), —C(O)R$^{12}$, —C(O)OR$^{12}$, —OC(O)R$^{12}$, —OC(O)OR$^{12}$, —C(O)NR$^{10}$R$^{11}$, —NR$^{10}$R$^{11}$, —NR$^{10}$C(O)R$^{12}$, —NR$^{10}$C(O)OR$^{12}$, —NR$^{10}$C(O)NR$^{10}$R$^{11}$, —NR$^{10}$S(O)$_2$R$^{12}$, —S(O)$_p$R$^{12}$, and —S(O)$_2$NR$^{10}$R$^{11}$.

19. The compound of claim 15, wherein $R^{1a}$ is hydrogen, —CH$_3$, —CD$_3$, —CH$_2$CH$_3$, —CD$_2$CD$_3$, isopropyl, 2,3-dihydroxypropyl, or cyclopropyl.

20. The compound of claim 15, wherein Y is in the direction of Z-Y-W, and wherein Y is a $C_{1-6}$ alkylene, wherein one or more —CH$_2$— are optionally independently replaced by —O—, —C(O)—, —N(R$^{10}$)—, —N(R$^{10}$)C(O)—, —C(O)N(R$^{10}$)—, —N(R$^{10}$)C(O)N(R$^{11}$)—, —S(O)$_p$—, —N(R$^{11}$)S(O)$_2$—, —S(O)$_2$N(R$^{10}$)—, or —N(R$^{10}$)S(O)$_2$N(R$^{11}$)—, and wherein Y is no more than six atoms in length.

21. The compound of claim 20, wherein:
Y is —(CR$^{16}$R$^{17}$)$_q$—, —(CR$^{16}$R$^{17}$)$_m$O(CR$^{16}$R$^{17}$)$_n$—, —(CR$^{16}$R$^{17}$)$_m$C(O)(CR$^{16}$R$^{17}$)$_n$—, —(CR$^{16}$R$^{17}$)$_m$N(R$^{10}$)(CR$^{16}$R$^{17}$)$_n$—, —(CR$^{16}$R$^{17}$)$_m$N(R$^{10}$)C(O)(CR$^{16}$R$^{17}$)$_n$—, —(CR$^{16}$R$^{17}$)$_m$C(O)N(R$^{10}$)(CR$^{16}$R$^{17}$)$_n$—, —(CR$^{16}$R$^{17}$)$_m$N(R$^{10}$)C(O)N(R$^{11}$)(CR$^{16}$R$^{17}$)$_n$—, —(CR$^{16}$R$^{17}$)$_m$S(O)$_p$(CR$^{16}$R$^{17}$)$_n$—, —(CR$^{16}$R$^{17}$)$_m$N(R$^{10}$)S(O)$_2$(CR$^{16}$R$^{17}$)$_n$—, —(CR$^{16}$R$^{17}$)$_m$S(O)$_2$N(R$^{10}$)(CR$^{16}$R$^{17}$)$_n$—, or —(CR$^{16}$R$^{17}$)$_m$N(R$^{10}$)S(O)$_2$N(R$^{11}$)(CR$^{16}$R$^{17}$)$_n$—, and wherein Y is no more than six atoms in length; and
wherein:
$R^{16}$ and $R^{17}$, at each occurrence, are each independently hydrogen, halo, hydroxy, CN, NO$_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, or 3-6 membered heterocycloalkoxy, or together with the C to which each is attached are combined to form a C(O), $C_{3-6}$ cycloalkyl, or 3-6 membered heterocycloalkyl;

each m is independently an integer of 0, 1, 2, or 3;
each n is independently an integer of 0, 1, 2, or 3;
wherein the sum of m and n is 0, 1, 2, 3, 4, or 5; and
q is an integer of 0, 1, 2, 3, 4, 5, or 6;
optionally wherein each m is independently 0, 1, or 2; and
optionally wherein each n is independently 0, 1, or 2.

22. The compound of claim 20, wherein Y is —(CH$_2$)O—, or Y is —O(CH$_2$)—, or Y is —(CH$_2$)$_2$O—, or Y is —O(CH$_2$)$_2$—, or Y is —(CH$_2$)$_2$—.

23. The compound of claim 15, wherein $R^7$ is an imidazolyl, a triazolyl, a tetrazolyl, an oxazolyl, a thiazolyl, an oxadiazolyl, a thiadiazolyl, a pyridyl, or a pyrimidinyl, each optionally substituted with one, two, three, or four substituents independently selected from halo, CN, NO$_2$, R$^9$, —OR$^9$, —C(O)R$^9$, —C(O)OR$^9$, —OC(O)R$^9$, —OC(O)OR$^9$, —C(O)NR$^{10}$R$^{11}$, —NR$^{10}$R$^{11}$, —NR$^{10}$C(O)R$^9$, —NR$^{10}$C(O)OR$^9$, —NR$^{10}$C(O)NR$^{10}$R$^{11}$, —NR$^{10}$S(O)$_2$R$^9$, —S(O)$_p$R$^9$, —S(O)$_2$NR$^{10}$R$^{11}$, and —NR$^{10}$S(O)$_2$NR$^{10}$R$^{11}$;

optionally wherein $R^7$ is imidazolyl or triazolyl, each optionally substituted with one, two, three, or four substituents independently selected from halo, CN, NO$_2$, R$^9$, —OR$^9$, —C(O)R$^9$, —C(O)OR$^9$, —C(O)NR$^{10}$R$^{11}$, —NR$^{10}$R$^{11}$, —NR$^{10}$C(O)R$^9$, —S(O)$_p$R$^9$, and —S(O)$_2$NR$^{10}$R$^{11}$;

optionally wherein $R^7$ is a C-linked imidazolyl or a C-linked triazolyl, each optionally substituted with one, two, three, or four substituents independently selected from halo, CN, NO$_2$, R$^9$, —OR$^9$, —C(O)R$^9$, —C(O)OR$^9$, —C(O)NR$^{10}$R$^{11}$, —NR$^{10}$R$^{11}$, —NR$^{10}$C(O)R$^9$, —S(O)$_p$R$^9$, and —S(O)$_2$NR$^{10}$R$^{11}$.

24. The compound of claim 15, wherein $R^7$ is an N-linked imidazolyl or an N-linked triazolyl, each optionally substituted with one, two, three, or four substituents independently selected from halo, CN, NO$_2$, R$^9$, —OR$^9$, —C(O)R$^9$, —C(O)OR$^9$, —C(O)NR$^{10}$R$^{11}$, —NR$^{10}$R$^{11}$, —NR$^{10}$C(O)R$^9$, —S(O)$_p$R$^9$, or —S(O)$_2$NR$^{10}$R$^{11}$; optionally wherein $R^7$ is a methyl-substituted imidazolyl or a methyl-substituted triazolyl, or $R^7$ is a C-methyl-substituted imidazolyl or a C-methyl-substituted triazolyl, optionally wherein $R^7$ is:

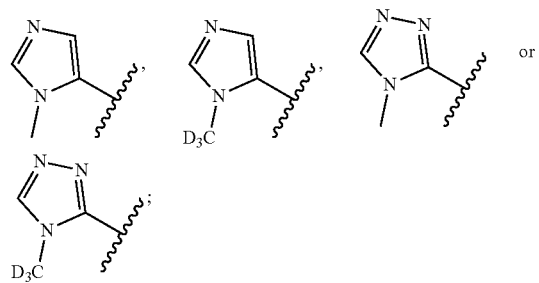

or $R^7$ is an N-methyl-substituted imidazolyl or an N-methyl-substituted triazolyl, optionally wherein $R^7$ is:

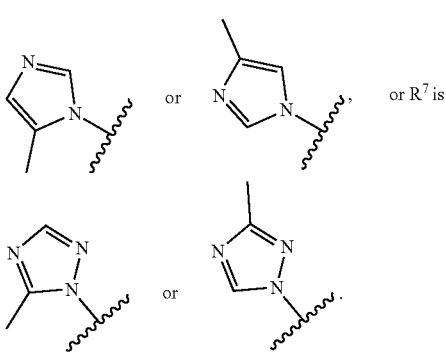

or $R^7$ is

25. The compound of claim 15, wherein $R^6$ is CN, $R^9$, —$OR^9$, —$OC(O)R^9$, —$OC(O)OR^9$, —$NR^{10}R^{11}$, —$NR^{10}OR^9$, —$NR^{10}C(O)R^9$, or —$NR^{10}C(NR^{10})NROR^{11}$, or wherein $R^6$ is CN, $R^9$, —$OR^9$, —$NR^{10}R^{11}$, or —$NR^{10}OR^9$, or wherein $R^6$ is CN, $R^9$, —$OR^9$, or —$NR^{10}R^{11}$, optionally wherein each $R^9$ is independently hydrogen or $C_{1-3}$ alkyl, wherein the $C_{1-3}$ alkyl is optionally substituted with CN, and optionally wherein $R^{10}$ and $R^{11}$ are each independently hydrogen, $C_{1-6}$ alkyl, or $C_{1-6}$ alkoxy.

26. The compound of claim 15, wherein $R^6$ is hydrogen, —$CH_3$, hydroxy, —$OCH_3$, —$OCD_3$, —$NH_2$, —$NHCH_3$, or —$NH(OCH_3)$, or $R^6$ is hydroxy, or $R^6$ is hydrogen, or $R^6$ is $NH_2$, or $R^6$ is —$NH(CH_2CH_2)Cl$, —$NH(CH_2CH_2)F$, or N-linked morpholino.

27. The compound of claim 15, wherein:
Y is —$(CH_2)_q$— or —$(CH_2)_mO(CH_2)_n$—;
$R^{1a}$ is $R^9$;
$R^5$ is $R^9$, —$OR^9$, halo, CN, $NO_2$, —$C(O)R^9$, —$C(O)OR^9$, —$C(O)NR^{10}R^{11}$, —$S(O)_pR^9$, or —$S(O)_2NR^{10}R^{11}$;
$R^6$ is CN, $R^9$, —$OR^9$, —$NR^{10}R^{11}$, or —$NR^{10}R^9$;
$R^7$ is a 5-12 membered heteroaryl, optionally substituted with one, two, three, or four substituents independently selected from halo, CN, $NO_2$, $R^9$, —$OR^9$, —$C(O)R^9$, —$C(O)OR^9$, —$C(O)NR^{10}R^{11}$, —$NR^{10}R^{11}$, —$NR^{10}C(O)R^9$, —$NR^{10}C(O)OR^9$, —$NR^{10}C(O)NR^{10}R^{11}$, —$NR^{10}S(O)_2R^9$, —$S(O)_pR^9$, —$S(O)_2NR^{10}R^{11}$ or —$NR^{10}S(O)_2NR^{10}R^{11}$;
$R^9$, at each occurrence, is independently hydrogen, $C_{1-4}$ alkyl, $C_{1-4}$ hydroxyalkyl, $C_{1-4}$ heteroalkyl, $C_{3-5}$ cycloalkyl, or 3-6 membered heterocycloalkyl, wherein each $C_{1-4}$ alkyl, $C_{1-4}$ hydroxyalkyl, $C_{1-4}$ heteroalkyl, $C_{3-5}$ cycloalkyl, or 3-6 membered heterocycloalkyl is optionally substituted with one, two, three, four, or five substituents independently selected from halo, hydroxy, CN, $C_{1-3}$ alkyl, $C_{1-3}$ haloalkyl, $C_{1-3}$ hydroxyalkyl, $C_{1-3}$ heteroalkyl, $C_{3-5}$ cycloalkyl, 3-6 membered heterocycloalkyl, $C_{1-3}$ alkoxy, $C_{1-3}$ haloalkoxy, (O), and —$NR^{10}R^{11}$;
$R^{10}$ and $R^{11}$, at each occurrence, are each independently hydrogen, $C_{1-3}$ alkyl, $C_{1-3}$ haloalkyl, $C_{1-3}$ hydroxyalkyl, $C_{1-3}$ heteroalkyl, $C_{3-5}$ cycloalkyl, 3-6 membered heterocycloalkyl, or $C_{1-3}$ alkoxy, or together with the N to which each is attached are combined to form a 3-6 membered heterocycloalkyl, wherein each $C_{1-3}$ alkyl, $C_{1-3}$ haloalkyl, $C_{1-3}$ hydroxyalkyl, $C_{1-3}$ heteroalkyl, $C_{3-5}$ cycloalkyl, 3-6 membered heterocycloalkyl, or $C_{1-3}$ alkoxy of the $R^{10}$ and $R^{11}$ is each optionally substituted with one, two, three, four or five substituents independently selected from halo, hydroxy, CN, $C_{1-3}$ alkyl, $C_{1-3}$ haloalkyl, $C_{1-3}$ heteroalkyl, $C_{3-5}$ cycloalkyl, 3-6 membered heterocycloalkyl, $C_{1-3}$ alkoxy, $C_{1-3}$ haloalkoxy, (O), and —$NR^{14}R^{15}$;
$R^{14}$ and $R^{15}$, at each occurrence, are each independently hydrogen, hydroxy, $C_{1-3}$ alkyl, $C_{1-3}$ hydroxyalkyl, $C_{1-3}$ heteroalkyl, $C_{3-5}$ cycloalkyl, or 3-6 membered heterocycloalkyl, or $C_{1-3}$ alkoxy, or together with the N to which each is attached are combined to form a 3-6 membered heterocycloalkyl;
each m is independently an integer of 0, 1, 2, or 3;
each n is independently an integer of 0, 1, 2, or 3;
wherein the sum of m and n is 0, 1, 2, 3, 4, or 5; and
q is an integer of 0, 1, 2, 3, 4, or 5.

28. The compound of claim 15, wherein:
Y is —$(CH_2)_q$— or —$(CH_2)_mO(CH_2)_n$—;
$R^{1a}$ is hydrogen, —$CH_3$, —$CD_3$, —$CH_2CH_3$, —$CD_2CD_3$, isopropyl, 2,3-dihydroxypropyl, or cyclopropyl;
$R^5$ is hydrogen, halo, CN, $NO_2$, —$C(O)CH_3$, —$S(O)CH_3$, —$S(O)_2CH_3$, —$S(O)_2NH_2$, —$S(O)_2NHCH_3$, or —$S(O)_2N(CH_3)_2$;
$R^6$ is hydrogen, —$CH_3$, hydroxy, —$OCH_3$, —$OCD_3$, —$NH_2$, —$NHCH_3$, or —$NH(OCH_3)$; or $R^6$ is —$NH(CH_2CH_2)Cl$, —$NH(CH_2CH_2)F$, or N-linked morpholino;
$R^7$ is an imidazolyl, a triazolyl, a tetrazolyl, an oxazolyl, a thiazolyl, an oxadiazolyl, a thiadiazolyl, a pyridyl, or a pyrimidinyl, each optionally substituted with one, two, three, or four substituents independently selected from —$CH_3$, —$CD_3$, —$CH_2CH_3$, —$CD_2CD_3$, isopropyl, cyclopropyl, —$OCH_3$, —$OCD_3$, —$OCH_2CH_3$, —$OCD_2CD_3$, isopropoxy, cyclopropoxy, chloro, and CN;
each m is independently an integer of 0, 1, or 2;
each n is independently an integer of 0, 1, or 2;
wherein the sum of m and n is 0, 1, 2, 3, or 4; and
q is an integer of 0, 1, 2, 3, 4, or 5.

29. The compound of claim 15, wherein:
Y is —$(CH_2)_2$—, —$O(CH_2)$—, —$O(CH_2)_2$—, —$(CH_2)O$—, or —$(CH_2)_2O$—;
$R^{1a}$ is hydrogen, —$CH_3$, —$CD_3$, 2,3-dihydroxypropyl, or cyclopropyl;
$R^5$ is hydrogen, chloro, bromo, or CN;
$R^6$ is hydrogen, hydroxy, —$OCH_3$, —$OCD_3$, —$NH_2$, or —$NHCH_3$; and
$R^7$ is an imidazolyl, a triazolyl, a tetrazolyl, an oxazolyl, a thiazolyl, an oxadiazolyl, a thiadiazolyl, a pyridyl, or a pyrimidinyl, each optionally substituted with one, two, three, or four substituents independently selected from —$CH_3$, —$CD_3$, —$CH_2CH_3$, —$CD_2CD_3$, isopropyl, cyclopropyl, —$OCH_3$, —$OCD_3$, —$OCH_2CH_3$, —$OCD_2CD_3$, isopropoxy, cyclopropoxy, chloro, and CN.

30. The compound of claim 15, wherein:
Y is —$(CH_2)_2$—, —$O(CH_2)$—, —$O(CH_2)_2$—, —$(CH_2)O$—, or —$(CH_2)_2O$—;
$R^{1a}$ is hydrogen, —$CH_3$, —$CD_3$, 2,3-dihydroxypropyl, or cyclopropyl;
$R^5$ is hydrogen, chloro, bromo, or CN;
$R^6$ is hydrogen, hydroxy, —$OCH_3$, —$OCD_3$, —$NH_2$, or —$NHCH_3$; and
$R^7$ is a methyl-substituted imidazolyl or a methyl-substituted triazolyl.

31. The compound of claim 15, wherein:
Y is —$(CH_2)_2$—, —$O(CH_2)$—, —$O(CH_2)_2$—, —$(CH_2)O$—, or —$(CH_2)_2O$—;
$R^{1a}$ is hydrogen, —$CH_3$, —$CD_3$, 2,3-dihydroxypropyl, or cyclopropyl;
$R^5$ is hydrogen, chloro, bromo, or CN;

R⁶ is hydrogen, hydroxy, —OCH₃, —OCD₃, —NH₂, or —NHCH₃; and
R⁷ is

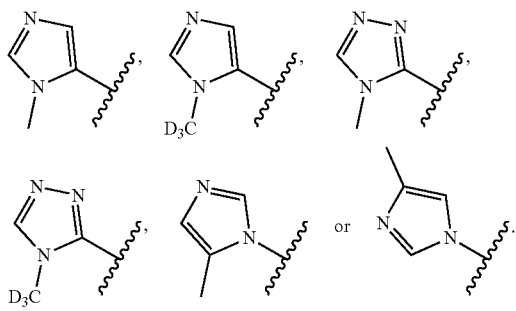

32. The compound of claim 15, wherein:
Y is —(CH₂)₂—, —O(CH₂)—, —O(CH₂)₂—, —(CH₂)O—, or —(CH₂)₂O—;
R¹ᵃ is hydrogen, —CH₃, —CD₃, 2,3-dihydroxypropyl, or cyclopropyl;
R⁵ is hydrogen, chloro, bromo, or CN;
R⁶ is hydrogen, hydroxy, —OCH₃, —OCD₃, —NH₂, or —NHCH₃; and
R⁷ is

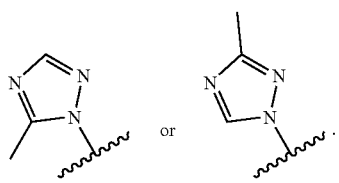

33. The compound of claim 1, wherein:
the compound has a molecular weight (MW) of no more than 1,000 g/mol; or
the compound has a MW of no more than 900 g/mol, no more than 800 g/mol, no more than 700 g/mol, no more than 600 g/mol, or no more than 500 g/mol.

34. The compound of claim 15, wherein the compound is a compound of Formula (II-1), (IIa-1), or (IIb-1), or a pharmaceutically acceptable form thereof.

35. The compound of claim 15, wherein the compound is a compound of Formula (II-2), (IIa-2), or (IIb-2), or a pharmaceutically acceptable form thereof.

36. The compound of claim 1, wherein the pharmaceutically acceptable form of the compound is exclusive of a salt form.

37. The compound of claim 1, wherein the compound is a racemate, a mixture of diastereomers, or a mixture of stereoisomers, or a pharmaceutically acceptable form thereof.

38. The compound of claim 1, wherein the compound is a single enantiomer or a single diastereomer, or a pharmaceutically acceptable form thereof.

39. The compound of claim 1, wherein the compound is a single enantiomer with an (R) configuration at the R⁶/R⁷-substituted carbon, or a pharmaceutically acceptable form thereof.

40. The compound of claim 1, wherein the compound is a single enantiomer with an (S) configuration at the R⁶/R⁷-substituted carbon, or a pharmaceutically acceptable form thereof.

41. A pharmaceutical composition comprising the compound or pharmaceutically acceptable form thereof of claim 1 and a pharmaceutically acceptable carrier, excipient, or diluent.

42. The compound of claim 1, wherein the compound is:

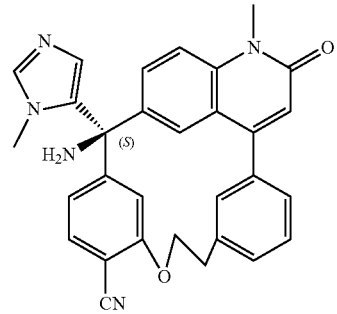

or a pharmaceutically acceptable form thereof.

43. A pharmaceutical composition comprising the compound or pharmaceutically acceptable form thereof of claim 42 and a pharmaceutically acceptable carrier, excipient, or diluent.

44. The compound of claim 1 wherein the compound is:

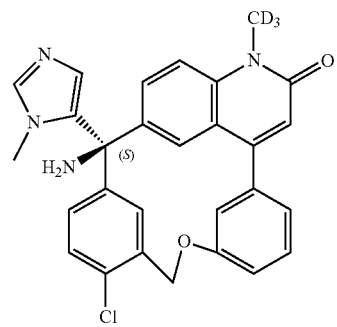

or a pharmaceutically acceptable form thereof.

45. A pharmaceutical composition comprising the compound or pharmaceutically acceptable form thereof of claim 44 and a pharmaceutically acceptable carrier, excipient, or diluent.

46. The compound of claim 1, wherein the compound is:

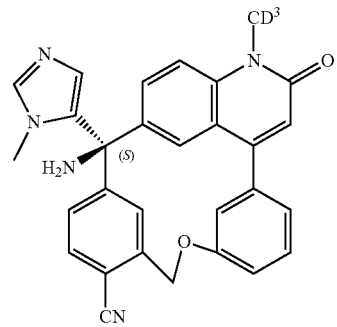

or a pharmaceutically acceptable form thereof.

47. A pharmaceutical composition comprising the compound or pharmaceutically acceptable form thereof of claim 46 and a pharmaceutically acceptable carrier, excipient, or diluent.

48. A compound of Formula (III):

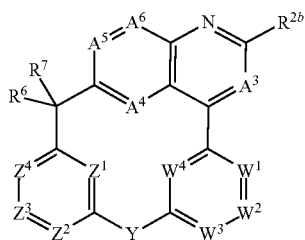

Formula (III)

wherein:
- $A^3$ is $CR^3$ or N;
- $A^4$ is $CR^8$ or N;
- $A^5$ and $A^6$ are each independently $CR^8$ or N, or $A^5$ and $A^6$ taken together are O, $NR^9$, or S;
- $W^1$, $W^2$, $W^3$, and $W^4$ are each independently N or $CR^4$, or $W^1$ and $W^2$ taken together are O, $NR^4$, or S, or $W^2$ and $W^3$ taken together are O, $NR^{4A}$, or S;
- Y is a bond or a linker having a length of up to 6 atoms;
- $Z^1$, $Z^2$, $Z^3$, and $Z^4$ are each independently N or $CR^5$, or $Z^2$ and $Z^3$ taken together are O, $NR^{5A}$, or S, or $Z^3$ and $Z^4$ taken together are O, $NR^{5A}$, or S;
- $R^{2b}$, $R^3$, $R^5$, and $R^8$, at each occurrence, are each independently $R^9$, $-OR^9$, halo, CN, $NO_2$, $-C(O)R^9$, $-C(O)OR^9$, $-OC(O)R^9$, $-OC(O)OR^9$, $-C(O)NR^{10}R^{11}$, $-NR^{10}R^{11}$, $-NR^{10}C(O)R^9$, $-NR^{10}C(O)OR^9$, $-NR^{10}C(O)NR^{10}R^{11}$, $-NR^{10}S(O)_2R^9$, $-S(O)_pR^9$, $-S(O)_2NR^{10}R^{11}$, or $-NR^{10}S(O)_2NR^{10}R^{11}$;
- $R^4$, at each occurrence, is independently hydrogen, halo, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, $-NR^{14}R^{15}$, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, $C_{6-12}$ aryl, or 5-12 membered heteroaryl of the $R^4$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);
- $R^{4A}$ and $R^{5A}$ are each independently hydrogen, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{4A}$ and the $R^A$ is optionally substituted with one, two, three, four, five or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);
- $R^6$ is CN, $R^9$, $-OR^9$, $-C(O)R^9$, $-C(O)OR^9$, $-OC(O)R^9$, $-OC(O)OR^9$, $-C(O)NR^{10}R^{11}$, $-NR^{10}R^{11}$, $-NR^{10}R^9$, $-NR^{10}C(O)R^9$, $-NR^{10}C(O)OR^9$, $-NR^{10}C(O)NR^{10}R^{11}$, $-NR^{10}S(O)_2R^9$, $-NR^{10}C(NR^{10})NR^{10}R^{11}$, $-S(O)_pR^9$, $-S(O)_2NR^{10}R^{11}$, or $-NR^{10}S(O)_2NR^{10}R^{11}$;
- $R^7$ is a 5-12 membered heteroaryl, optionally substituted with one, two, three, or four substituents independently selected from halo, CN, $NO_2$, $R^9$, $-OR^9$, $-C(O)R^9$, $-C(O)OR^9$, $-OC(O)R^9$, $-OC(O)OR^9$, $-C(O)NR^{10}R^{11}$, $-NR^{10}R^{11}$, $-NR^{10}C(O)R^9$, $-NR^{10}C(O)OR^9$, $-NR^{10}C(O)NROR^{11}$, $-NR^{10}S(O)_2R^9$, $-S(O)_pR^9$, $-S(O)_2NR^{10}R^{11}$, and $-NR^{10}S(O)_2NR^{10}R^{11}$;
- $R^9$, at each occurrence, is independently hydrogen, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^9$ is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), $-C(O)R^{12}$, $-C(O)OR^{12}$, $-OC(O)R^{12}$, $-OC(O)OR^{12}$, $-C(O)NR^{10}R^{11}$, $-NR^{10}R^{11}$, $-NR^{10}C(O)R^{12}$, $-NR^{10}C(O)OR^{12}$, $-NR^{10}C(O)NR^{10}R^{11}$, $-NR^{10}S(O)_2R^{12}$, $-S(O)_pR^{12}$, $-S(O)_2NR^{10}R^{11}$, and $-NR^{10}S(O)_2NR^{10}R^{11}$;
- $R^{10}$ and $R^{11}$, at each occurrence, are each independently hydrogen, hydroxy, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{6-12}$ aryl, or 5-12 membered heteroaryl, or together with the N to which each is attached are combined to form a 3-6 membered heterocycloalkyl, wherein each $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{6-12}$ aryl, or 5-12 membered heteroaryl of the $R^{10}$ and the $R^{11}$ is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), $-C(O)R^{13}$, $-C(O)OR^{13}$, $-OC(O)R^{13}$, $-OC(O)OR^{13}$, $-C(O)NR^{14}R^{15}$, $-NR^{14}R^{15}$, $-NR^{14}C(O)R^{13}$, $-NR^{14}C(O)OR^{13}$, $-NR^{14}C(O)NR^{14}R^{15}$, $-NR^{14}S(O)_2R^{13}$, $-S(O)_pR^{13}$, $-S(O)_2NR^{14}R^{15}$, and $-NR^{14}S(O)_2NR^{14}R^{15}$;
- $R^{12}$, at each occurrence, is independently hydrogen, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{12}$ is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), $-C(O)R^{13}$, —C(O)R$^{13}$, —OC(O)R$^{13}$, —OC(O)OR$^{13}$, —C(O)NR$^{10}$R$^{11}$, —NR$^{10}$R$^{11}$, —NR$^{10}$C(O)R$^{13}$, —NR$^{10}$C(O)OR$^{13}$, —NR$^{10}$C(O)NR$^{10}$R$^{11}$, —NR$^{10}$S(O)$_2$R$^{13}$, —S(O)$_p$R$^{13}$, —S(O)$_2$NR$^{10}$R$^{11}$, and —NR$^{10}$S(O)$_2$NR$^{10}$R$^{11}$;

R$^{13}$, at each occurrence, is independently hydrogen, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ heteroalkyl, C$_{3-6}$ cycloalkyl, or 3-6 membered heterocycloalkyl;

R$^{14}$ and R$^{15}$, at each occurrence, are each independently hydrogen, hydroxy, C$_{1-4}$ alkyl, C$_{2-4}$ alkenyl, C$_{2-4}$ alkynyl, C$_{1-4}$ haloalkyl, C$_{1-4}$ hydroxyalkyl, C$_{1-4}$ heteroalkyl, C$_{3-6}$ cycloalkyl, 3-6 membered heterocycloalkyl, or C$_{1-6}$ alkoxy, or together with the N to which each is attached are combined to form a 3-6 membered heterocycloalkyl; and each p is independently an integer of 0, 1, or 2;

or a pharmaceutically acceptable form thereof.

49. The compound of claim 48, wherein the compound is a compound of Formula (IIIa) or is a compound of Formula (IIIb):

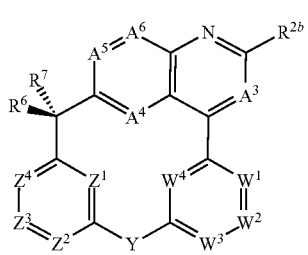

Formula (IIIa)

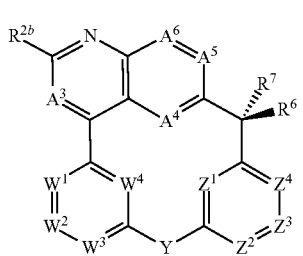

Formula (IIIb)

or a pharmaceutically acceptable form thereof.

50. The compound of claim 48, wherein A$^3$ is CR$^3$, optionally wherein R$^3$ is (a) R$^9$, —OR$^9$, halo, or CN; or (b) hydrogen.

51. The compound of claim 48, wherein A$^4$ is CR$^8$.
52. The compound of claim 48, wherein A$^5$ is CR$^8$.
53. The compound of claim 48, wherein A$^6$ is CR$^8$.
54. The compound of claim 48, wherein:
   (a) A$^4$ is N, and no more than one of A$^5$ and A$^6$ is N; or
   (b) A$^5$ is N, and no more than one of A$^4$ and A$^6$ is N; or
   (c) A$^6$ is N, and no more than one of A$^4$ and A$^5$ is N; or
   (d) A$^4$, A$^5$, and A$^6$ are each independently CR$^8$.
55. The compound of claim 48, wherein each R$^8$ is independently R$^9$, —OR$^9$, halo, or CN, optionally wherein each R$^8$ is hydrogen.
56. The compound of claim 48, wherein at least one of W$^1$, W$^2$, W$^3$, and W$^4$ is N, optionally, wherein:
   W$^1$, W$^2$, and W$^3$ are each independently CR$^4$, and W$^4$ is N;
   W$^1$, W$^2$, and W$^4$ are each independently CR$^4$, and W$^3$ is N;
   W$^1$, W$^3$, and W$^4$ are each independently CR$^4$, and W$^2$ is N; or
   W$^2$, W$^3$, and W$^4$ are each independently CR$^4$, and W$^1$ is N.

57. The compound of claim 48, wherein W$^1$, W$^2$, W$^3$, and W$^4$ are each independently CR$^4$.

58. The compound of claim 48, wherein:
   (a) each R$^4$ is independently hydrogen, halo, C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, C$_{1-6}$ hydroxyalkoxy, C$_{1-6}$ heteroalkoxy, C$_{3-6}$ cycloalkoxy, 3-6 membered heterocycloalkoxy, or —NR$^{14}$R$^{15}$, wherein each C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, C$_{1-6}$ hydroxyalkoxy, C$_{1-6}$ heteroalkoxy, C$_{3-6}$ cycloalkoxy, or 3-6 membered heterocycloalkoxy of the R$^4$ is optionally substituted with one, two, three, four, five, or six substituents independently selected from halo, hydroxy, C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, and (O); or
   (b) each R$^4$ is independently hydrogen, halo, C$_{1-6}$ alkyl, C$_{1-6}$ haloalkyl, C$_{3-6}$ cycloalkyl, C$_{1-6}$ alkoxy, or C$_{1-6}$ haloalkoxy, wherein each C$_{1-6}$ alkyl, C$_{1-6}$ haloalkyl, C$_{3-6}$ cycloalkyl, C$_{1-6}$ alkoxy, or C$_{1-6}$ haloalkoxy of the R$^4$ is optionally substituted with one, two, three, four, five, or six substituents independently selected from halo, hydroxy, C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, and (O); or
   (c) each R$^4$ is independently hydrogen, halo, C$_{1-3}$ alkyl, C$_{1-3}$ haloalkyl, C$_{3-5}$ cycloalkyl, C$_{1-3}$ alkoxy, or C$_{1-3}$ haloalkoxy; or
   (d) each R$^4$ is hydrogen.

59. The compound of claim 48, wherein at least one of Z$^1$, Z$^2$, Z$^3$, and Z$^4$ is N, optionally wherein:
   Z$^1$, Z$^2$, and Z$^3$ are each independently CR$^5$, and Z$^4$ is N;
   Z$^1$, Z$^2$, and Z$^4$ are each independently CR$^5$, and Z$^3$ is N;
   Z$^1$, Z$^3$, and Z$^4$ are each independently CR$^5$, and Z$^2$ is N; or
   Z$^2$, Z$^3$, and Z$^4$ are each independently CR$^5$, and Z$^1$ is N.

60. The compound of claim 48, wherein Z$^1$, Z$^2$, Z$^3$, and Z$^4$ are each independently CR$^5$.

61. The compound of claim 48, wherein:
   R$^5$, at each occurrence, is independently R$^9$, —OR$^9$, halo, CN, NO$_2$, —C(O)R$^9$, —C(O)OR$^9$, —C(O)NR$^{10}$R$^{11}$, —S(O)$_p$R$^9$, or —S(O)$_2$NR$^{10}$R$^{11}$; or
   R$^5$, at each occurrence, is independently hydrogen, halo, CN, NO$_2$, —C(O)CH$_3$, —C(O)OH, —C(O)OCH$_3$, —C(O)N(CH$_3$)$_2$, —S(O)$_2$CH$_3$, or —S(O)$_2$N(CH$_3$)$_2$; or
   each R$^5$ independently is hydrogen, halo, or CN; or
   each R$^5$ is hydrogen.

62. The compound of claim 48, wherein the compound is a compound of Formula (III-1), (IIIa-1), (IIIb-1), (III-2), (IIIa-2), (IIIb-2) (III-3), (IIIa-3) or (IIIb-3):

Formula (III-1)

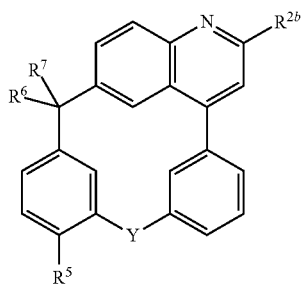

Formula (IIIa-1)

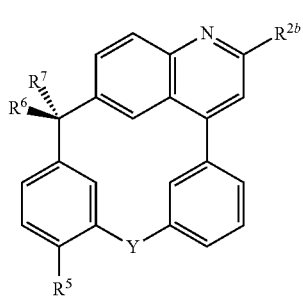

Formula (IIIb-1)

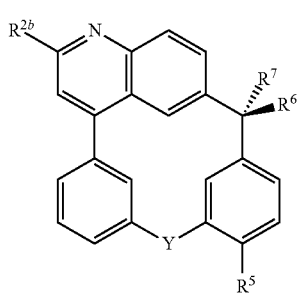

Formula (III-2)

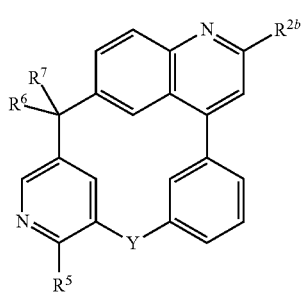

Formula (IIIa-2)

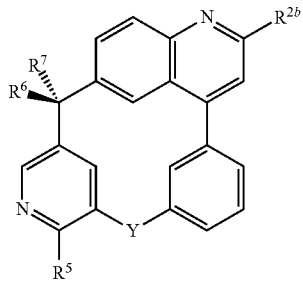

Formula (IIIb-2)

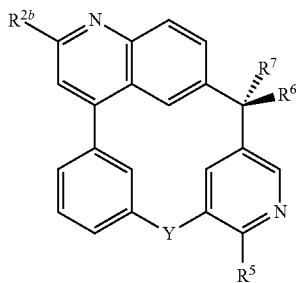

Formula (III-3)

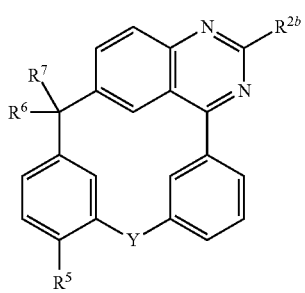

Formula (IIIa-3)

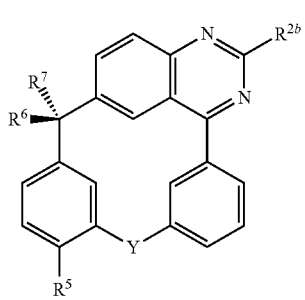

Formula (IIIb-3)

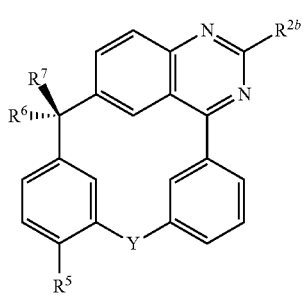

or a pharmaceutically acceptable form thereof.

63. The compound of claim 62, wherein $R^{2b}$ is $R^9$, —$OR^9$, halo, CN, $NO_2$, —$C(O)R^9$, —$C(O)OR^9$, —$C(O)NR^{10}R^{11}$, —$NR^{10}R^{11}$, —$NR^{10}C(O)R^9$, —$S(O)_pR^9$, or —$S(O)_2NR^{10}R^{11}$.

64. The compound of claim 62, wherein $R^{2b}$ is:
  (a) $R^9$, —$OR^9$, halo, CN, —$C(O)NR^{10}R^{11}$, or —$NR^{10}R^{11}$; or
  (b) hydrogen, $C_{1-6}$ alkyl, $C_{3-6}$ cycloalkyl, hydroxy, $C_{1-6}$ alkoxy, $C_{3-6}$ cycloalkoxy, $C_{3-6}$ heterocycloalkoxy, halo, CN, —$C(O)NR^{10}R^{11}$, or —$NR^{10}R^{11}$; wherein $R^{10}$ and $R^{11}$, at each occurrence, are each independently hydrogen, $C_{1-6}$ alkyl, 3-6 membered heterocycloalkyl, or together with the N to which each is attached are combined to form a 3-6 membered heterocycloalkyl; or
  (c) hydrogen, $C_{1-3}$ alkyl, $C_{3-4}$ cycloalkyl, $C_{1-3}$ alkoxy, $C_{3-4}$ cycloalkoxy, $C_{3-4}$ heterocycloalkoxy, halo, CN, —$C(O)NR^{10}R^{11}$, or —$NR^{10}R^{11}$; wherein $R^{10}$ and $R^{11}$, at each occurrence, are each independently hydrogen, $C_{1-3}$ alkyl, 3-4 membered heterocycloalkyl, or together with the N to which each is attached are combined to form a 4-6 membered heterocycloalkyl; or
(d) hydrogen, —CH$_3$, —CD$_3$, —CH$_2$CH$_3$, —CD$_2$CD$_3$, isopropyl, cyclopropyl, —OCH$_3$, —OCD$_3$, —OCH$_2$CH$_3$, —OCD$_2$CD$_3$, isopropoxy, cyclopropoxy, 3-oxetanylalkoxy, chloro, CN, morpholino, piperazinyl, 3-oxetanylamino, or —C(O)NH$_2$; or
(e) —NH$_2$.

65. The compound of claim 62, wherein R$^{2b}$ is an electron-withdrawing group, optionally wherein R$^{2b}$ is:
(a) halo, CN, NO$_2$, —C(O)R$^9$, —C(O)OR$^9$, —C(O)NR$^{10}$R$^{11}$, —S(O)$_p$R$^9$, or —S(O)$_2$NR$^{10}$R$^{11}$; or
(b) chloro, CN, —C(O)H, —C(O)CH$_3$, —C(O)OH, —C(O)OCH$_3$, —C(O)NH$_2$, —C(O)N(H)CH$_3$, —C(O)N(CH$_3$)$_2$, —S(O)CH$_3$, —S(O)$_2$CH$_3$, —S(O)$_2$NH$_2$, —S(O)$_2$N(H)CH$_3$, or —S(O)$_2$N(CH$_3$)$_2$.

66. The compound of claim 62, wherein Y is in the direction of Z-Y-W, and wherein Y is a C$_{1-6}$ alkylene, wherein one or more —CH$_2$— are optionally independently replaced by —O—, —C(O)—, —N(R$^{10}$)—, —N(R$^{10}$)C(O)—, —C(O)N(R$^{10}$)—, —N(R$^{10}$)C(O)N(R$^{11}$)—, —S(O)$_p$—, —N(R$^{11}$)S(O)$_2$—, —S(O)$_2$N(R$^{10}$)—, or —N(R$^{10}$)S(O)$_2$N(R$^{11}$)—, and wherein Y is no more than six atoms in length.

67. The compound of claim 66, wherein:
Y is —(CR$^{16}$R$^{17}$)$_q$, —(CR$^{16}$R$^{17}$)$_m$O(CR$^{16}$R$^{17}$)$_n$—, —(CR$^{16}$R$^{17}$)$_m$C(O)(CR$^{16}$R$^{17}$)$_n$—, —(CR$^{16}$R$^{17}$)$_m$N(R$^{10}$)(CR$^{16}$R$^{17}$)$_n$—, —(CR$^{16}$R$^{17}$)$_m$N(R$^{10}$)C(O)(CR$^{16}$R$^{17}$)$_n$—, —(CR$^{16}$R$^{17}$)$_m$C(O)N(R$^{10}$)(CR$^{16}$R$^{17}$)$_n$—, —(CR$^{16}$R$^{17}$)$_m$N(R$^{10}$)C(O)N(R$^{11}$)(CR$^{16}$R$^{17}$)$_n$—, —(CR$^{16}$R$^{17}$)$_m$S(O)$_p$(CR$^{16}$R$^{17}$)$_n$—(CR$^{16}$R$^{17}$)$_m$N(R$^{10}$)S(O)$_2$(CR$^{16}$R$^{17}$)$_n$, —(CR$^{16}$R$^{17}$)$_m$S(O)$_2$N(R$^{10}$)(CR$^{16}$R$^{17}$)$_n$—, or —(CR$^{16}$R$^{17}$)$_m$N(R$^{10}$)S(O)$_2$N(R$^{11}$)(CR$^{16}$R$^{17}$)$_n$, and wherein Y is no more than six atoms in length; and
wherein:
R$^{16}$ and R$^{17}$, at each occurrence, are each independently hydrogen, halo, hydroxy, CN, NO$_2$, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, C$_{1-6}$ hydroxyalkoxy, C$_{1-6}$ heteroalkoxy, or 3-6 membered heterocycloalkoxy, or together with the C to which each is attached are combined to form a C(O), C$_{3-6}$ cycloalkyl, or 3-6 membered heterocycloalkyl;
each m is independently an integer of 0, 1, 2, or 3;
each n is independently an integer of 0, 1, 2, or 3;
wherein the sum of m and n is 0, 1, 2, 3, 4, or 5; and
q is an integer of 0, 1, 2, 3, 4, 5, or 6;
optionally wherein each m is independently 0, 1, or 2; and optionally wherein each n is independently 0, 1, or 2.

68. The compound of claim 66, wherein Y is —(CH$_2$)O—, or Y is —O(CH$_2$)—, or Y is —(CH$_2$)$_2$O—, or Y is —O(CH$_2$)$_2$—, or Y is —(CH$_2$)$_2$—.

69. The compound of claim 62, wherein R$^7$ is an imidazolyl, a triazolyl, a tetrazolyl, an oxazolyl, a thiazolyl, an oxadiazolyl, a thiadiazolyl, a pyridyl, or a pyrimidinyl, each optionally substituted with one, two, three, or four substituents independently selected from halo, CN, NO$_2$, R$^9$, —OR$^9$, —C(O)R$^9$, —C(O)OR$^9$, —OC(O)R$^9$, —OC(O)OR$^9$, —C(O)NR$^{10}$R$^{11}$, —NR$^{10}$R$^{11}$, —NR$^{10}$C(O)R$^9$, —NR$^{10}$C(O)OR$^9$, —NR$^{10}$C(O)NR$^{10}$R$^{11}$, —NR$^{10}$S(O)$_2$R$^9$, —S(O)$_p$R$^9$, —S(O)$_2$NR$^{10}$R$^{11}$, and —NR$^{10}$S(O)$_2$NR$^{10}$R$^{11}$;
optionally wherein R$^7$ is imidazolyl or triazolyl, each optionally substituted with one, two, three, or four substituents independently selected from halo, CN, NO$_2$, R$^9$, —OR$^9$, —C(O)R$^9$, —C(O)OR$^9$, —C(O)NR$^{10}$R$^{11}$, —NR$^{10}$R$^{11}$, —NR$^{10}$C(O)R$^9$, —S(O)$_p$R$^9$, and —S(O)$_2$NR$^{10}$R$^{11}$;
optionally wherein R$^7$ is a C-linked imidazolyl or a C-linked triazolyl, each optionally substituted with one, two, three, or four substituents independently selected from halo, CN, NO$_2$, R$^9$, —OR$^9$, —C(O)R$^9$, —C(O)OR$^9$, —C(O)NR$^{10}$R$^{11}$, —NR$^{10}$R$^{11}$, —NR$^{10}$C(O)R$^9$, —S(O)$_p$R$^9$, and —S(O)$_2$NR$^{10}$R$^{11}$.

70. The compound of claim 62, wherein R$^7$ is an N-linked imidazolyl or an N-linked triazolyl, optionally substituted with one, two, three, or four substituents independently selected from halo, CN, NO$_2$, R$^9$, —OR$^9$, —C(O)R$^9$, —C(O)OR$^9$, —C(O)NR$^{10}$R$^{11}$, —NR$^{10}$R$^{11}$, —NR$^{10}$C(O)R$^9$, —S(O)$_p$R$^9$, or —S(O)$_2$NR$^{10}$R$^{11}$; optionally wherein R$^7$ is a methyl-substituted imidazolyl or a methyl-substituted triazolyl, or
R$^7$ is a C-methyl-substituted imidazolyl or a C-methyl-substituted triazolyl, optionally wherein R$^7$ is:

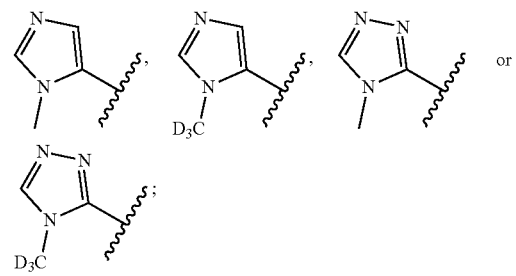

or R$^7$ is an N-methyl-substituted imidazolyl or an N-methyl-substituted triazolyl, optionally wherein R$^7$ is:

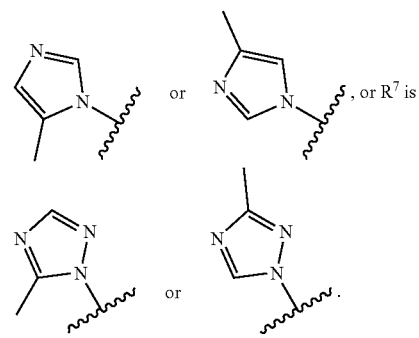

71. The compound of claim 62, wherein R$^6$ is CN, R$^9$, —OR$^9$, —OC(O)R$^9$, —OC(O)OR$^9$, —NR$^{10}$R$^{11}$, —NR$^{10}$R$^9$, —NR$^{10}$C(O)R$^9$, or —NR$^{10}$C(NR$^{10}$)NR$^{10}$R$^{11}$, or wherein R$^6$ is CN, R$^9$, —OR$^9$, —NR$^{10}$R$^{11}$, or —NR$^{10}$R$^9$, or wherein R$^6$ is CN, R$^9$, —OR$^9$, or —NR$^{10}$R$^{11}$, optionally wherein each R$^9$ is independently hydrogen or C$_{1-3}$ alkyl, wherein the C$_{1-3}$ alkyl is optionally substituted with CN, and optionally wherein R$^{10}$ and R$^{11}$ are each independently hydrogen, C$_{1-6}$ alkyl, or C$_{1-6}$ alkoxy.

72. The compound of claim 62, wherein R$^6$ is hydrogen, —CH$_3$, hydroxy, —OCH$_3$, —OCD$_3$, —NH$_2$, —NHCH$_3$, or —NH(OCH$_3$), or R$^6$ is hydroxy, or R$^6$ is hydrogen, or R$^6$ is NH$_2$, or R$^6$ is —NH(CH$_2$CH$_2$)Cl, —NH(CH$_2$CH$_2$)F, or N-linked morpholino.

73. The compound of claim 62, wherein:
Y is —(CH$_2$)$_q$ or —(CH$_2$)$_m$O(CH$_2$)$_n$—;
R$^{2b}$ is R$^9$, —OR$^9$, halo, CN, —C(O)NR$^{10}$R$^{11}$ or —NR$^{10}$R$^{11}$;
R$^5$ is R$^9$, —OR$^9$, halo, CN, NO$_2$, —C(O)R$^9$, —C(O)OR$^9$, —C(O)NR$^{10}$R$^{11}$, —S(O)$_p$R$^9$, or —S(O)$_2$NR$^{10}$R$^{11}$;
R$^6$ is CN, R$^9$, —OR$^9$, —NR$^{10}$R$^{11}$, or —NR$^{10}$OR$^9$;
R$^7$ is a 5-12 membered heteroaryl, optionally substituted with one, two, three, or four substituents independently selected from halo, CN, NO$_2$, R$^9$, —OR$^9$, —C(O)R$^9$, —C(O)OR$^9$, —C(O)NR$^{10}$R$^{11}$, —NR$^{10}$R$^{11}$, —NR$^{10}$C(O)R$^9$, —NR$^{10}$C(O)OR$^9$, —NR$^{10}$C(O)NR$^{10}$R$^{11}$, —NR$^{10}$S(O)$_2$R$^9$, —S(O)$_p$R$^9$, —S(O)$_2$NR$^{10}$R$^{11}$ or —NR$^{10}$S(O)$_2$NR$^{10}$R$^{11}$;
R$^9$, at each occurrence, is independently hydrogen, C$_{1-4}$ alkyl, C$_{1-4}$ hydroxyalkyl, C$_{1-4}$ heteroalkyl, C$_{3-5}$ cycloalkyl, or 3-6 membered heterocycloalkyl, wherein each C$_{1-4}$ alkyl, C$_{1-4}$ hydroxyalkyl, C$_{1-4}$ heteroalkyl, C$_{3-5}$ cycloalkyl, or 3-6 membered heterocycloalkyl, is optionally substituted with one, two, three, four, or five substituents independently selected from halo, hydroxy, CN, C$_{1-3}$ alkyl, C$_{1-3}$ haloalkyl, C$_{1-3}$ hydroxyalkyl, C$_{1-3}$ heteroalkyl, C$_{3-5}$ cycloalkyl, 3-6 membered heterocycloalkyl, C$_{1-3}$ alkoxy, C$_{1-3}$ haloalkoxy, (O), and —NR$^{10}$R$^{11}$;
R$^{10}$ and R$^{11}$, at each occurrence, are each independently hydrogen, C$_{1-3}$ alkyl, C$_{1-3}$ haloalkyl, C$_{1-3}$ hydroxyalkyl, C$_{1-3}$ heteroalkyl, C$_{3-5}$ cycloalkyl, 3-6 membered heterocycloalkyl, or C$_{1-3}$ alkoxy, or together with the N to which each is attached are combined to form a 3-6 membered heterocycloalkyl, wherein each C$_{1-3}$ alkyl, C$_{1-3}$ haloalkyl, C$_{1-3}$ hydroxyalkyl, C$_{1-3}$ heteroalkyl, C$_{3-5}$ cycloalkyl, 3-6 membered heterocycloalkyl, or C$_{1-3}$ alkoxy of the R$^{10}$ and R$^{11}$ is each optionally substituted with one, two, three, four, or five substituents independently selected from halo, hydroxy, CN, C$_{1-3}$ alkyl, C$_{1-3}$ haloalkyl, C$_{1-3}$ heteroalkyl, C$_{3-5}$ cycloalkyl, 3-6 membered heterocycloalkyl, C$_{1-3}$ alkoxy, C$_{1-3}$ haloalkoxy, (O), and —NR$^{14}$R$^{15}$;
R$^{14}$ and R$^{15}$, at each occurrence, are each independently hydrogen, hydroxy, C$_{1-3}$ alkyl, C$_{1-3}$ hydroxyalkyl, C$_{1-3}$ heteroalkyl, C$_{3-5}$ cycloalkyl, 3-6 membered heterocycloalkyl, or C$_{1-3}$ alkoxy, or together with the N to which each is attached are combined to form a 3-6 membered heterocycloalkyl;
each m is independently an integer of 0, 1, or 2;
each n is independently an integer of 0, 1, 2, or 3;
wherein the sum of m and n is 0, 1, 2, 3, 4, or 5; and
q is an integer of 0, 1, 2, 3, 4, or 5.

74. The compound of claim 62, wherein:
Y is —(CH$_2$)$_q$ or —(CH$_2$)$_m$O(CH$_2$)$_n$—;
R$^{2b}$ is (a) hydrogen, —CH$_3$, —CD$_3$, —CH$_2$CH$_3$, —CD$_2$CD$_3$, isopropyl, cyclopropyl, —OCH$_3$, —OCD$_3$, —OCH$_2$CH$_3$, —OCD$_2$CD$_3$, isopropoxy, cyclopropoxy, 3-oxetanylalkoxy, chloro, CN, morpholino, piperazinyl, 3-oxetanylamino, or —C(O)NH$_2$; or R$^{2b}$ is (b) —NH$_2$;
R$^5$ is hydrogen, halo, CN, NO$_2$, —C(O)CH$_3$, —S(O)CH$_3$, —S(O)$_2$CH$_3$, —S(O)$_2$NH$_2$, —S(O)$_2$NHCH$_3$, or —S(O)$_2$N(CH$_3$)$_2$;
R$^6$ is hydrogen, —CH$_3$, hydroxy, —OCH$_3$, —OCD$_3$, —NH$_2$, —NHCH$_3$, or —NH(OCH$_3$); or R$^6$ is —NH(CH$_2$CH$_2$)Cl, —NH(CH$_2$CH$_2$)F, or N-linked morpholino;
R$^7$ is an imidazolyl, a triazolyl, a tetrazolyl, an oxazolyl, a thiazolyl, an oxadiazolyl, a thiadiazolyl, a pyridyl, or a pyrimidinyl, each optionally substituted with one, two, three, or four substituents independently selected from —CH$_3$, —CD$_3$, —CH$_2$CH$_3$, —CD$_2$CD$_3$, isopropyl, cyclopropyl, —OCH$_3$, —OCD$_3$, —OCH$_2$CH$_3$, —OCD$_2$CD$_3$, isopropoxy, cyclopropoxy, chloro, and CN;
each m is independently an integer of 0, 1, or 2;
each n is independently an integer of 0, 1, or 2;
wherein the sum of m and n is 0, 1, 2, 3, or 4; and
q is an integer of 0, 1, 2, 3, 4, or 5.

75. The compound of claim 62, wherein:
Y is —(CH$_2$)$_2$—, —O(CH$_2$)—, —O(CH$_2$)$_2$—, —(CH$_2$)O—, or —(CH$_2$)$_2$O—;
R$^{2b}$ is (a) —OCH$_3$, —OCD$_3$, 3-oxetanylalkoxy, chloro, CN, morpholino, piperazinyl, 3-oxetanylamino, or —C(O)NH$_2$; or R$^{2b}$ is (b) —NH$_2$;
R$^5$ is hydrogen, chloro, bromo, or CN;
R$^6$ is hydrogen, hydroxy, —OCH$_3$, —OCD$_3$, —NH$_2$, or —NHCH$_3$; and
R$^7$ is an imidazolyl, a triazolyl, a tetrazolyl, an oxazolyl, a thiazolyl, an oxadiazolyl, a thiadiazolyl, a pyridyl, or a pyrimidinyl, each optionally substituted with one, two, three, or four substituents independently selected from —CH$_3$, —CD$_3$, —CH$_2$CH$_3$, —CD$_2$CD$_3$, isopropyl, cyclopropyl, —OCH$_3$, —OCD$_3$, —OCH$_2$CH$_3$, —OCD$_2$CD$_3$, isopropoxy, cyclopropoxy, chloro, and CN.

76. The compound of claim 62, wherein:
Y is —(CH$_2$)$_2$—, —O(CH$_2$)—, —O(CH$_2$)$_2$—, —(CH$_2$)O—, or —(CH$_2$)$_2$O—;
R$^{2b}$ is (a) —OCH$_3$, —OCD$_3$, 3-oxetanylalkoxy, chloro, CN, morpholino, piperazinyl, 3-oxetanylamino, or —C(O)NH$_2$; or R$^{2b}$ is (b) —NH$_2$;
R$^5$ is hydrogen, chloro, bromo, or CN;
R$^6$ is hydrogen, hydroxy, —OCH$_3$, —OCD$_3$, —NH$_2$, or —NHCH$_3$; and
R$^7$ is a methyl-substituted imidazolyl or a methyl-substituted triazolyl.

77. The compound of claim 62, wherein:
Y is —(CH$_2$)$_2$—, —O(CH$_2$)—, —O(CH$_2$)$_2$—, —(CH$_2$)O—, or —(CH$_2$)$_2$O—;
R$^{2b}$ is (a) —OCH$_3$, —OCD$_3$, 3-oxetanylalkoxy, chloro, CN, morpholino, piperazinyl, 3-oxetanylamino, or —C(O)NH$_2$; or R$^{2b}$ is (b) —NH$_2$;
R$^5$ is hydrogen, chloro, bromo, or CN;
R$^6$ is hydrogen, hydroxy, —OCH$_3$, —OCD$_3$, —NH$_2$, or —NHCH$_3$; and
R$^7$ is

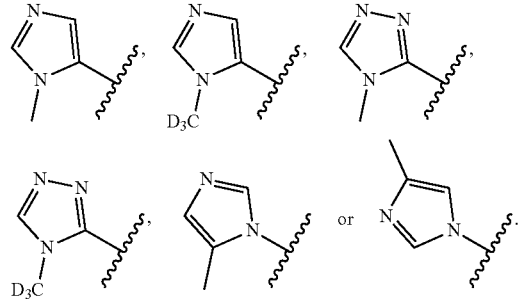

78. The compound of claim 62, wherein:
Y is —(CH$_2$)$_2$—, —O(CH$_2$)—, —O(CH$_2$)$_2$—, —(CH$_2$)O—, or —(CH$_2$)$_2$O—;

$R^{2b}$ is (a) —OCH$_3$, —OCD$_3$, 3-oxetanylalkoxy, chloro, CN, morpholino, piperazinyl, 3-oxetanylamino, or —C(O)NH$_2$; or $R^{2b}$ is (b) —NH$_2$;
$R^5$ is hydrogen, chloro, bromo, or CN;
$R^6$ is hydrogen, hydroxy, —OCH$_3$, —OCD$_3$, —NH$_2$, or —NHCH$_3$; and
$R^7$ is

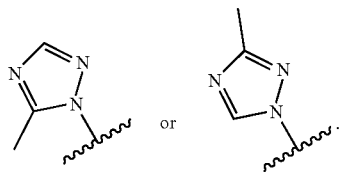

79. The compound of claim 48, wherein:
the compound has a molecular weight (MW) of no more than 1,000 g/mol; or
the compound has a MW of no more than 900 g/mol, no more than 800 g/mol, no more than 700 g/mol, no more than 600 g/mol, or no more than 500 g/mol.
80. The compound of claim 62, wherein the compound is a compound of Formula (III-1), (IIIa-1), or (IIIb-1), or a pharmaceutically acceptable form thereof.
81. The compound of claim 62, wherein the compound is a compound of Formula (III-2), (IIIa-2), or (IIIb-2), or a pharmaceutically acceptable form thereof.
82. The compound of claim 62, wherein the compound is a compound of Formula (III-3), (IIIa-3), or (IIIb-3), or a pharmaceutically acceptable form thereof.
83. The compound of claim 48, wherein the pharmaceutically acceptable form of the compound is exclusive of a salt form.
84. The compound of claim 48, wherein the compound is a racemate, a mixture of diastereomers, or a mixture of stereoisomers, or a pharmaceutically acceptable form thereof.
85. The compound of claim 48, wherein the compound is a single enantiomer or a single diastereomer, or a pharmaceutically acceptable form thereof.
86. The compound of claim 48, wherein the compound is a single enantiomer with an (R) configuration at the $R^6/R^7$-substituted carbon, or a pharmaceutically acceptable form thereof.
87. The compound of claim 48, wherein the compound is a single enantiomer with an (S) configuration at the $R^6/R^7$-substituted carbon, or a pharmaceutically acceptable form thereof.
88. A pharmaceutical composition comprising the compound or pharmaceutically acceptable form thereof of claim 48 and a pharmaceutically acceptable carrier, excipient, or diluent.
89. The compound of claim 48, wherein the compound is:

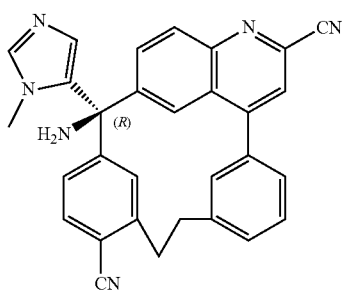

or a pharmaceutically acceptable form thereof.

90. A pharmaceutical composition comprising the compound or pharmaceutically acceptable form thereof of claim 89 and a pharmaceutically acceptable carrier, excipient, or diluent.
91. The compound of claim 48, wherein the compound is:

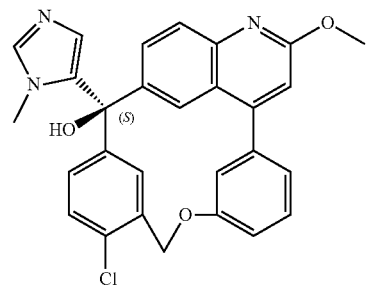

or a pharmaceutically acceptable form thereof.
92. A pharmaceutical composition comprising the compound or pharmaceutically acceptable form thereof of claim 91 and a pharmaceutically acceptable carrier, excipient, or diluent.
93. The compound of claim 48, wherein the compound is:

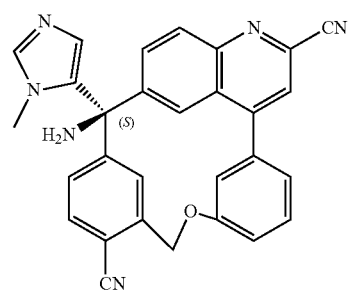

or a pharmaceutically acceptable form thereof.
94. A pharmaceutical composition comprising the compound or pharmaceutically acceptable form thereof of claim 93 and a pharmaceutically acceptable carrier, excipient, or diluent.
95. A compound of Formula (IV):

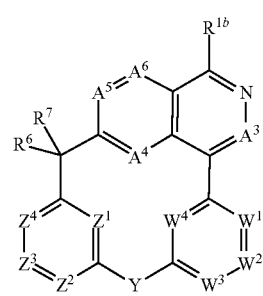

Formula (IV)

wherein:
$A^3$ is $CR^3$ or N;
$A^4$ is $CR^8$ or N;
$A^5$ and $A^6$ are each independently $CR^8$ or N, or $A^5$ and $A^6$ taken together are O, $NR^9$, or S;

$W^1$, $W^2$, $W^3$, and $W^4$ are each independently N or $CR^4$, or $W^1$ and $W^2$ taken together are O, $NR^4$, or S, or $W^2$ and $W^3$ taken together are O, $NR^{4A}$, or S;

Y is a bond or a linker having a length of up to 6 atoms;

$Z^1$, $Z^2$, $Z^3$, and $Z^4$ are each independently N or $CR^5$, or $Z^2$ and $Z^3$ taken together are O, $NR^A$, or S, or $Z^3$ and $Z^4$ taken together are O, $NR^A$, or S;

$R^{1b}$, $R^3$, $R^5$, and $R^8$, at each occurrence, are each independently $R^9$, $-OR^9$, halo, CN, $NO_2$, $-C(O)R^9$, $-C(O)OR^9$, $-OC(O)R^9$, $-OC(O)OR^9$, $-C(O)NR^{10}R^{11}$, $-NROR^{11}$, $-NR^{10}C(O)R^9$, $-NR^{10}C(O)OR^9$, $-NR^{10}C(O)NR^{10}R^{11}$, $-NR^{10}S(O)_2R^9$, $-S(O)_pR^9$, $-S(O)_2NR^{10}R^{11}$, or $-NR^{10}S(O)_2NR^{10}R^{11}$;

$R^4$, at each occurrence, is independently hydrogen, halo, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, $-NR^{14}R^{15}$, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, $C_{6-12}$ aryl, or 5-12 membered heteroaryl of the $R^4$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);

$R^{4A}$ and $R^{5A}$ are each independently hydrogen, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{4A}$ and the $R^{5A}$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);

$R^6$ is CN, $R^9$, $-OR^9$, $-C(O)R^9$, $-C(O)OR^9$, $-OC(O)R^9$, $-OC(O)OR^9$, $-C(O)NR^{10}R^{11}$, $-NR^{10}R^{11}$, $-NR^{10}R^9$, $-NR^{10}C(O)R^9$, $-NR^{10}C(O)OR^9$, $-NR^{10}C(O)NR^{10}R^{11}$, $-NR^{10}S(O)_2R^9$, $-NR^{10}C(NR^{10})NR^{10}R^{11}$, $-S(O)_pR^9$, $-S(O)_2NR^{10}R^{11}$, or $-NR^{10}S(O)_2NR^{10}R^{11}$;

$R^7$ is a 5-12 membered heteroaryl, optionally substituted with one, two, three, or four substituents independently selected from halo, CN, $NO_2$, $R^9$, $-OR^9$, $-C(O)R^9$, $-C(O)OR^9$, $-OC(O)R^9$, $-OC(O)OR^9$, $-C(O)NR^{10}R^{11}$, $-NROR^{11}$, $-NR^{10}C(O)R^9$, $-NR^{10}C(O)OR^9$, $-NR^{10}C(O)NR^{10}R^{11}$, $-NR^{10}S(O)_2R^9$, $-S(O)_pR^9$, $-S(O)_2NR^{10}R^{11}$, and $-NR^{10}S(O)_2NR^{10}R^{11}$;

$R^9$, at each occurrence, is independently hydrogen, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^9$ is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), $-C(O)R^{12}$, $-C(O)OR^{12}$, $-OC(O)R^{12}$, $-OC(O)OR^{12}$, $-C(O)NR^{10}R^{11}$, $-NR^{10}R^{11}$, $-NR^{10}C(O)R^{12}$, $-NR^{10}C(O)OR^{12}$, $-NR^{10}C(O)NR^{10}R^{11}$, $-NR^{10}S(O)_2R^{12}$, $-S(O)_pR^{12}$, $-S(O)_2NR^{10}R^{11}$, and $-NR^{10}S(O)_2NR^{10}R^{11}$;

$R^{10}$ and $R^{11}$, at each occurrence, are each independently hydrogen, hydroxy, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{6-12}$ aryl, or 5-12 membered heteroaryl, or together with the N to which each is attached are combined to form a 3-6 membered heterocycloalkyl, wherein each $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{6-12}$ aryl, or 5-12 membered heteroaryl of the $R^{10}$ and the $R^{11}$ is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), $-C(O)R^{13}$, $-C(O)OR^{13}$, $-OC(O)R^{13}$, $-OC(O)OR^{13}$, $-C(O)NR^{14}R^{15}$, $-NR^{14}R^{15}$, $-NR^{14}C(O)R^{13}$, $-NR^{14}C(O)OR^{13}$, $-NR^{14}C(O)NR^{14}R^{15}$, $-NR^{14}S(O)_2R^{13}$, $-S(O)_pR^{13}$, $-S(O)_2NR^{14}R^{15}$, and $-NR^{14}S(O)_2NR^{14}R^{15}$;

$R^{12}$, at each occurrence, is independently hydrogen, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{12}$ is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), $-C(O)R^{13}$, $-C(O)R^{13}$, $-OC(O)R^{13}$, $-OC(O)OR^{13}$, $-C(O)NR^{10}R^{11}$, $-NR^{10}R^{11}$, $-NR^{10}C(O)R^{13}$, $-NR^{10}C(O)OR^{13}$, $-NR^{10}C(O)NR^{10}R^{11}$, $-NR^{10}S(O)_2R^{13}$, $-S(O)_pR^{13}$, $-S(O)_2NR^{10}R^{11}$, and $-NR^{10}S(O)_2NR^{10}R^{11}$;

$R^{13}$, at each occurrence, is independently hydrogen, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-6}$ cycloalkyl, or 3-6 membered heterocycloalkyl;

$R^{14}$ and $R^{15}$, at each occurrence, are each independently hydrogen, hydroxy, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-6}$ cycloalkyl, 3-6 membered heterocycloalkyl, or $C_{1-6}$ alkoxy, or together with the N to which each is attached are combined to form a 3-6 membered heterocycloalkyl; and each p is independently an integer of 0, 1, or 2;

or a pharmaceutically acceptable form thereof.

96. The compound of claim 95, wherein the compound is a compound of Formula (IVa) or is a compound of Formula (IVb):

Formula (IVa)

Formula (IVb)

or a pharmaceutically acceptable form thereof.

97. The compound of claim 95, wherein $A^3$ is $CR^3$, optionally wherein $R^3$ is (a) $R^9$, —$OR^9$, halo, or CN; or (b) hydrogen.

98. The compound of claim 95, wherein $A^4$ is $CR^8$.

99. The compound of claim 95, wherein $A^5$ is $CR^8$.

100. The compound of claim 95, wherein $A^6$ is $CR^8$.

101. The compound of claim 95, wherein:
(a) $A^4$ is N, and no more than one of $A^5$ and $A^6$ is N; or
(b) $A^5$ is N, and no more than one of $A^4$ and $A^6$ is N; or
(c) $A^6$ is N, and no more than one of $A^4$ and $A^5$ is N; or
(d) $A^4$, $A^5$ and $A^6$ are each independently $CR^8$.

102. The compound of claim 95, wherein each $R^8$ is independently $R^9$, —$OR^9$, halo, or CN, optionally wherein each $R^8$ is hydrogen.

103. The compound of claim 95, wherein at least one of $W^1$, $W^2$, $W^3$, and $W^4$ is N, optionally, wherein:
$W^1$, $W^2$, and $W^3$ are each independently $CR^4$, and $W^4$ is N;
$W^1$, $W^2$, and $W^4$ are each independently $CR^4$, and $W^3$ is N;
$W^1$, $W^3$, and $W^4$ are each independently $CR^4$, and $W^2$ is N; or
$W^2$, $W^3$, and $W^4$ are each independently $CR^4$, and $W^1$ is N.

104. The compound of claim 95, wherein $W^1$, $W^2$, $W^3$, and $W^4$ are each independently $CR^4$.

105. The compound of claim 95, wherein:
(a) each $R^4$ is independently hydrogen, halo, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, or —$NR^{14}R^{15}$, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, or 3-6 membered heterocycloalkoxy of the $R^4$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O); or
(b) each $R^4$ is independently hydrogen, halo, $C_{1-6}$ alkyl, $C_{1-6}$ haloalkyl, $C_{3-6}$ cycloalkyl, $C_{1-6}$ alkoxy, or $C_{1-6}$ haloalkoxy, wherein each $C_{1-6}$ alkyl, $C_{1-6}$ haloalkyl, $C_{3-6}$ cycloalkyl, $C_{1-6}$ alkoxy, or $C_{1-6}$ haloalkoxy of the $R^4$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O); or
(c) each $R^4$ is independently hydrogen, halo, $C_{1-3}$ alkyl, $C_{1-3}$ haloalkyl, $C_{3-5}$ cycloalkyl, $C_{1-3}$ alkoxy, or $C_{1-3}$ haloalkoxy; or
(d) each $R^4$ is hydrogen.

106. The compound of claim 95, wherein at least one of $Z^1$, $Z^2$, $Z^3$, and $Z^4$ is N, optionally wherein:
$Z^1$, $Z^2$, and $Z^3$ are each independently $CR^5$, and $Z^4$ is N;
$Z^1$, $Z^2$, and $Z^4$ are each independently $CR^5$, and $Z^3$ is N;
$Z^1$, $Z^3$, and $Z^4$ are each independently $CR^5$, and $Z^2$ is N; or
$Z^2$, $Z^3$, and $Z^4$ are each independently $CR^5$, and $Z^1$ is N.

107. The compound of claim 95, wherein $Z^1$, $Z^2$, $Z^3$, and $Z^4$ are each independently $CR^5$.

108. The compound of claim 95, wherein:
$R^5$, at each occurrence, is independently $R^9$, —$OR^9$, halo, CN, $NO_2$, —$C(O)R^9$, —$C(O)OR^9$, —$C(O)NR^{10}R^{11}$, —$S(O)_pR^9$, or —$S(O)_2NR^{10}R^{11}$; or
$R^5$, at each occurrence, is independently hydrogen, halo, CN, $NO_2$, —$C(O)CH_3$, —$C(O)OH$, —$C(O)OCH_3$, —$C(O)N(CH_3)_2$, —$S(O)_2CH_3$, or —$S(O)_2N(CH_3)_2$; or
each $R^5$ independently is hydrogen, halo or CN; or
each $R^5$ is hydrogen.

109. The compound of claim 95, wherein the compound is a compound of Formula (IV-1), (IVa-1), (IVb-1), (IV-2), (IVa-2), or (IVb-2):

Formula (IV-1)

Formula (IVa-1)

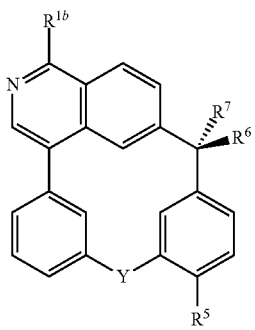

Formula (IVb-1)

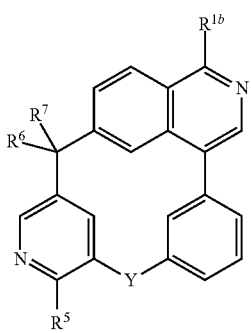

Formula (IV-2)

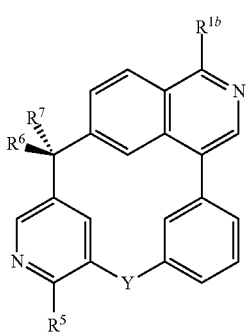

Formula (IVa-2)

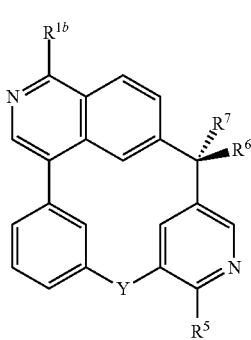

Formula (IVb-2)

or a pharmaceutically acceptable form thereof.

110. The compound of claim 109, wherein $R^{1b}$ is $R^9$, —$OR^9$, halo, CN, $NO_2$, —$C(O)R^9$, —$C(O)OR^9$, —$C(O)NR^{10}R^{11}$, —$NROR^{11}$, —$NR^{10}C(O)R^9$, —$S(O)_pR^9$, or —$S(O)_2NR^{10}R^{11}$.

111. The compound of claim 109, wherein $R^{1b}$ is hydrogen, $C_{1-6}$ alkyl, $C_{3-6}$ cycloalkyl, $C_{1-6}$ alkoxy, $C_{3-6}$ cycloalkoxy, halo or CN, wherein each $C_{1-6}$ alkyl, $C_{3-6}$ cycloalkyl, $C_{1-6}$ alkoxy, or $C_{3-6}$ cycloalkoxy is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), —$C(O)R^{12}$, —$C(O)OR^{12}$, —$OC(O)R^{12}$, —$OC(O)OR^{12}$, —$C(O)NR^{10}R^{11}$, —$NR^{10}R^{11}$, —$NR^{10}C(O)R^{12}$, —$NR^{10}C(O)OR^{12}$, —$NR^{10}C(O)NR^{10}R^{11}$, —$NR^{10}S(O)_2R^{12}$, —$S(O)_pR^{12}$, and —$S(O)_2NR^{10}R^{11}$.

112. The compound of claim 109, wherein $R^{1b}$ is hydrogen, —$CH_3$, —$CD_3$, —$CF_3$, —$CH_2CH_3$, —$CD_2CD_3$, isopropyl, 2,3-dihydroxypropyl, cyclopropyl, —$OCH_3$, —$OCD_3$, —$OCF_3$, —$OCH_2CH_3$, —$OCD_2CD_3$, isopropoxy, 2,3-dihydroxypropoxy, or cyclopropoxy.

113. The compound of claim 109, wherein Y is in the direction of Z-Y-W, and wherein Y is a $C_{1-6}$ alkylene, wherein one or more —$CH_2$— are optionally independently replaced by —O—, —C(O)—, —$N(R^{10})$—, —$N(R^{10})C(O)$—, —$C(O)N(R^{10})$—, —$N(R^{10})C(O)N(R^{11})$—, —$S(O)_p$—, —$N(R^{10})S(O)_2$—, —$S(O)_2N(R^{10})$—, or —$N(R^{10})S(O)_2N(R^{11})$—, and wherein Y is no more than six atoms in length.

114. The compound of claim 113, wherein:
Y is —$(CR^{16}R^{17})_q$—, —$(CR^{16}R^{17})_mO(CR^{16}R^{17})_n$—, —$(CR^{16}R^{17})_mC(O)(CR^{16}R^{17})_n$—, —$(CR^{16}R^{17})_mN(R^{10})(CR^{16}R^{17})_n$—, —$(CR^{16}R^{17})_mN(R^{10})C(O)(CR^{16}R^{17})_n$—, —$(CR^{16}R^{17})_mC(O)N(R^{10})(CR^{16}R^{17})_n$—, —$(CR^{16}R^{17})_mN(R^{10})C(O)N(R^{11})(CR^{16}R^{17})_n$—, —$(CR^{16}R^{17})_mS(O)_p(CR^{16}R^{17})_n$—, —$(CR^{16}R^{17})_mN(R^{10})S(O)_2(CR^{16}R^{17})_n$—, —$(CR^{16}R^{17})_mS(O)_2N(R^{10})(CR^{16}R^{17})_n$—, or —$(CR^{16}R^{17})_mN(R^{10})S(O)_2N(R^1)(CR^{16}R^{17})_n$, and wherein Y is no more than six atoms in length; and wherein:
$R^{16}$ and $R^{17}$, at each occurrence, are each independently hydrogen, halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, or 3-6 membered heterocycloalkoxy, or together with the C to which each is attached are combined to form a C(O), $C_{3-6}$ cycloalkyl, or 3-6 membered heterocycloalkyl;
each m is independently an integer of 0, 1, 2, or 3;
each n is independently an integer of 0, 1, 2, or 3;
wherein the sum of m and n is 0, 1, 2, 3, 4, or 5; and
q is an integer of 0, 1, 2, 3, 4, 5, or 6;
optionally wherein each m is independently 0, 1, or 2; and
optionally wherein each n is independently 0, 1, or 2.

115. The compound of claim 113, wherein Y is —$(CH_2)O$—, or Y is —$O(CH_2)$—, or Y is —$(CH_2)_2O$—, or Y is —$O(CH_2)_2$—, or Y is —$(CH_2)_2$—.

116. The compound of claim 109, wherein $R^7$ is an imidazolyl, a triazolyl, a tetrazolyl, an oxazolyl, a thiazolyl, an oxadiazolyl, a thiadiazolyl, a pyridyl, or a pyrimidinyl, each optionally substituted with one, two, three, or four substituents independently selected from halo, CN, $NO_2$, $R^9$, —$OR^9$, —$C(O)R^9$, —$C(O)OR^9$, —$OC(O)R^9$, —$OC(O)OR^9$, —$C(O)NR^{10}R^{11}$, —$NR^{10}R^{11}$, —$NR^{10}C(O)R^9$, —$NR^{10}C(O)OR^9$, —$NR^{10}C(O)NR^{10}R^{11}$, —$NR^{10}S(O)_2R^9$, —$S(O)_pR^9$, —$S(O)_2NR^{10}R^{11}$, and —$NR^{10}S(O)_2NR^{10}R^{11}$;
optionally wherein $R^8$ is imidazolyl or triazolyl, each optionally substituted with one, two, three, or four substituents independently selected from halo, CN, $NO_2$, $R^9$, —$OR^9$, —$C(O)R^9$, —$C(O)OR^9$, —$C(O)NR^{10}R^{11}$, —$NR^{10}R^{11}$, —$NR^{10}C(O)R^9$, —$S(O)_pR^9$, and —$S(O)_2NR^{10}R^{11}$;
optionally wherein $R^8$ is a C-linked imidazolyl or a C-linked triazolyl, each optionally substituted with one, two, three, or four substituents independently selected from halo, CN, $NO_2$, $R^9$, —$OR^9$, —$C(O)R^9$, —$C(O)$ OR$^9$, —C(O)NR$^{10}$R$^{11}$, —NR$^{10}$R$^{11}$, —NR$^{10}$C(O)R$^9$, —S(O)$_p$R$^9$, and —S(O)$_2$NR$^{10}$R$^{11}$.

117. The compound of claim 109, wherein R$^7$ is an N-linked imidazolyl or an N-linked triazolyl, each optionally substituted with one, two, three, or four substituents independently selected from halo, CN, NO$_2$, R$^9$, —OR$^9$, —C(O)R$^9$, —C(O)OR$^9$, —C(O)NR$^{10}$R$^{11}$, —NR$^{10}$R$^{11}$, —NR$^{10}$C(O)R$^9$, —S(O)$_p$R$^9$, or —S(O)$_2$NR$^{10}$R$^{11}$; optionally wherein R$^8$ is a methyl-substituted imidazolyl or a methyl-substituted triazolyl, or R$^7$ is a C-methyl-substituted imidazolyl or a C-methyl-substituted triazolyl, optionally wherein R$^7$ is:

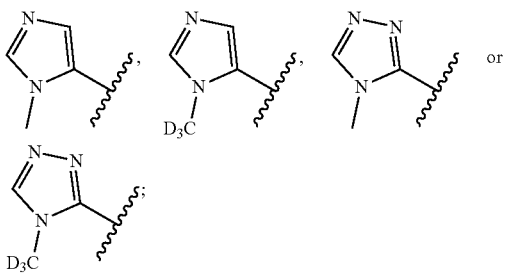

or R$^7$ is an N-methyl-substituted imidazolyl or an N-methyl-substituted triazolyl, optionally wherein R$^7$ is:

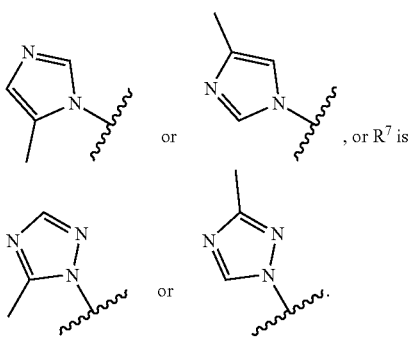

118. The compound of claim 109, wherein R$^6$ is CN, R$^9$, —OR$^9$, —OC(O)R$^9$, —OC(O)OR$^9$, —NR$^{10}$R$^{11}$, —NR$^{10}$R$^9$, —NR$^{10}$C(O)R$^9$, or —NR$^{10}$C(NR$^{10}$)NR$^{10}$R$^{11}$, or wherein R$^6$ is CN, R$^9$, —OR$^9$, —NR$^{10}$R$^{11}$, or —NR$^{10}$OR$^9$, or wherein R$^6$ is CN, R$^9$, —OR$^9$, or —NR$^{10}$R$^{11}$, optionally wherein each R$^9$ is independently hydrogen or C$_{1-3}$ alkyl, wherein the C$_{1-3}$ alkyl is optionally substituted with CN, and optionally wherein R$^{10}$ and R$^{11}$ are each independently hydrogen, C$_{1-6}$ alkyl, or C$_{1-6}$ alkoxy.

119. The compound of claim 109, wherein R$^6$ is hydrogen, —CH$_3$, hydroxy, —OCH$_3$, —OCD$_3$, —NH$_2$, —NHCH$_3$, or —NH(OCH$_3$), or R$^6$ is hydroxy, or R$^6$ is hydrogen, or R$^6$ is NH$_2$, or R$^6$ is —NH(CH$_2$CH$_2$)Cl, —NH(CH$_2$CH$_2$)F, or N-linked morpholino.

120. The compound of claim 95, wherein:
the compound has a molecular weight (MW) of no more than 1,000 g/mol; or
the compound has a MW of no more than 900 g/mol, no more than 800 g/mol, no more than 700 g/mol, no more than 600 g/mol, or no more than 500 g/mol.

121. The compound of claim 109, wherein the compound is a compound of Formula (IV-1), (IVa-1), or (IVb-1), or a pharmaceutically acceptable form thereof.

122. The compound of claim 109, wherein the compound is a compound of Formula (IV-2), (IVa-2), or (IVb-2), or a pharmaceutically acceptable form thereof.

123. The compound of claim 95, wherein the pharmaceutically acceptable form of the compound is exclusive of a salt form.

124. The compound of claim 95, wherein the compound is a racemate, a mixture of diastereomers, or a mixture of stereoisomers, or a pharmaceutically acceptable form thereof.

125. The compound of claim 95, wherein the compound is a single enantiomer or a single diastereomer, or a pharmaceutically acceptable form thereof.

126. The compound of claim 95, wherein the compound is a single enantiomer with an (R) configuration at the R$^6$/R$^7$-substituted carbon, or a pharmaceutically acceptable form thereof.

127. The compound of claim 95, wherein the compound is a single enantiomer with an (S) configuration at the R$^6$/R$^7$-substituted carbon, or a pharmaceutically acceptable form thereof.

128. A pharmaceutical composition comprising the compound or pharmaceutically acceptable form thereof of claim 95 and a pharmaceutically acceptable carrier, excipient, or diluent.

129. A compound of Formula (V):

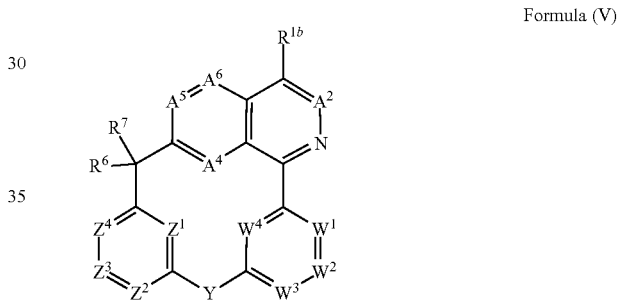

Formula (V)

wherein:
A$^2$ is N, NR$^{2a}$, CR$^{2b}$, or —C(=O)—;
A$^4$ is CR$^8$ or N;
A$^5$ and A$^6$ are each independently CR$^8$ or N, or A$^5$ and A$^6$ taken together are O, NR$^9$, or S;
W$^1$, W$^2$, W$^3$, and W$^4$ are each independently N or CR$^4$, or W$^1$ and W$^2$ taken together is O, NR$^4$, or S, or W$^2$ and W$^3$ taken together is O, NR$^{4A}$, or S;
Y is a bond or a linker having a length of up to 6 atoms;
Z$^1$, Z$^2$, Z$^3$, and Z$^4$ are each independently N or CR$^5$, or Z$^2$ and Z$^3$ taken together is O, NR$^{5A}$, or S, or Z$^3$ and Z$^4$ taken together is O, NR$^{5A}$, or S;
R$^{2a}$ is R$^9$, —OR$^9$, —C(O)R$^9$, —C(O)OR$^9$, —C(O)NR$^{10}$R$^{11}$, —S(O)$_p$R$^9$, or —S(O)$_2$NR$^{10}$R$^{11}$;
R$^{1b}$, R$^{2b}$, R$^5$, and R$^8$, at each occurrence, are each independently R$^9$, —OR$^9$, halo, CN, NO$_2$, —C(O)R$^9$, —C(O)OR$^9$, —OC(O)R$^9$, —OC(O)OR$^9$, —C(O) NR$^{10}$R$^{11}$, —NR$^{10}$R$^{11}$, —NR$^{10}$C(O)R$^9$, —NR$^{10}$C(O) OR$^9$, —NR$^{10}$C(O)NR$^{10}$R$^{11}$, —NR$^{10}$S(O)$_2$R$^9$, —S(O)$_p$R$^9$, —S(O)$_2$NR$^{10}$R$^{11}$, or —NR$^{10}$S(O)$_2$NR$^{10}$R$^{11}$;
R$^4$, at each occurrence, is independently hydrogen, halo, C$_{1-6}$ alkyl, C$_{1-6}$ haloalkyl, C$_{1-6}$ hydroxyalkyl, C$_{1-6}$ heteroalkyl, C$_{3-6}$ cycloalkyl, 3-6 membered heterocycloalkyl, C$_{1-6}$ alkoxy, C$_{1-6}$ haloalkoxy, C$_{1-6}$ hydroxyalkoxy, C$_{1-6}$ heteroalkoxy, C$_{3-6}$ cycloalkoxy, 3-6 membered heterocycloalkoxy, —NR$^{14}$R$^{15}$, C$_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, $C_{6-12}$ aryl, or 5-12 membered heteroaryl of the $R^4$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);

$R^{4,4}$ and $R^A$ are each independently hydrogen, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{4,4}$ and the $R^A$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);

$R^6$ is CN, $R^9$, —$OR^9$, —$C(O)R^9$, —$C(O)OR^9$, —$OC(O)R^9$, —$OC(O)OR^9$, —$C(O)NR^{10}R^{11}$, —$NR^{10}R^{11}$, —$NR^{10}R^9$, —$NR^{10}C(O)R^9$, —$NR^{10}C(O)OR^9$, —$NR^{10}C(O)NR^{10}R^{11}$, —$NR^{10}S(O)_2R^9$, —$NR^{10}C(NR^{10})NR^{10}R^{11}$, —$S(O)_pR^9$, —$S(O)_2NR^{10}R^{11}$, or —$NR^{10}S(O)_2NR^{10}R^{11}$;

$R^7$ is a 5-12 membered heteroaryl, optionally substituted with one, two, three, or four substituents independently selected from halo, CN, $NO_2$, $R^9$, —$OR^9$, —$C(O)R^9$, —$C(O)OR^9$, —$OC(O)R^9$, —$OC(O)OR^9$, —$C(O)NR^{10}R^{11}$, —$NROR^{11}$, —$NR^{10}C(O)R^9$, —$NR^{10}C(O)OR^9$, —$NR^{10}C(O)NR^{10}R^{11}$, —$NR^{10}S(O)_2R^9$, —$S(O)_pR^9$, —$S(O)_2NR^{10}R^{11}$, and —$NR^{10}S(O)_2NR^{10}R^{11}$;

$R^9$, at each occurrence, is independently hydrogen, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^9$ is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), —$C(O)R^{12}$, —$C(O)OR^{12}$, —$OC(O)R^{12}$, —$OC(O)OR^{12}$, —$C(O)NR^{10}R^{11}$, —$NR^{10}R^{11}$, —$NR^{10}C(O)R^{12}$, —$NR^{10}C(O)OR^{12}$, —$NR^{10}C(O)NR^{10}R^{11}$, —$NR^{10}S(O)_2R^{12}$, —$S(O)_pR^{12}$, —$S(O)_2NR^{10}R^{11}$, and —$NR^{10}S(O)_2NR^{10}R^{11}$;

$R^{10}$ and $R^{11}$, at each occurrence, are each independently hydrogen, hydroxy, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{6-12}$ aryl, or 5-12 membered heteroaryl, or together with the N to which each is attached are combined to form a 3-6 membered heterocycloalkyl, wherein each $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{6-12}$ aryl, or 5-12 membered heteroaryl of the $R^{10}$ and the $R^{11}$ is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), —$C(O)R^{13}$, —$C(O)OR^{13}$, —$OC(O)R^{13}$, —$OC(O)OR^{13}$, —$C(O)NR^{14}R^{15}$, —$NR^{14}R^{15}$, —$NR^{14}C(O)R^{13}$, —$NR^{14}C(O)OR^{13}$, —$NR^{14}C(O)NR^{14}R^{15}$, —$NR^{14}S(O)_2R^{13}$, —$S(O)_pR^{13}$, —$S(O)_2NR^{14}R^{15}$, and —$NR^{14}S(O)_2NR^{14}R^{15}$;

$R^{12}$, at each occurrence, is independently hydrogen, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{12}$ is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), —$C(O)R^{13}$, —$C(O)OR^{13}$, —$OC(O)R^{13}$, —$OC(O)OR^{13}$, —$C(O)NR^{10}R^{11}$, —$NR^{10}R^{11}$, —$NR^{10}C(O)R^{13}$, —$NR^{10}C(O)OR^{13}$, —$NR^{10}C(O)NR^{10}R^{11}$, —$NR^{10}S(O)_2R^{13}$, —$S(O)_pR^{13}$, —$S(O)_2NR^{10}R^{11}$, and —$NR^{10}S(O)_2NR^{10}R^{11}$;

$R^{13}$, at each occurrence, is independently hydrogen, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-6}$ cycloalkyl, or 3-6 membered heterocycloalkyl;

$R^{14}$ and $R^{15}$, at each occurrence, are each independently hydrogen, hydroxy, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-6}$ cycloalkyl, 3-6 membered heterocycloalkyl, or $C_{1-6}$ alkoxy, or together with the N to which each is attached are combined to form a 3-6 membered heterocycloalkyl; and each p is independently an integer of 0, 1, or 2;

or a pharmaceutically acceptable form thereof.

130. The compound of claim 129, wherein the compound is a compound of Formula (Va) or is a compound of Formula (Vb):

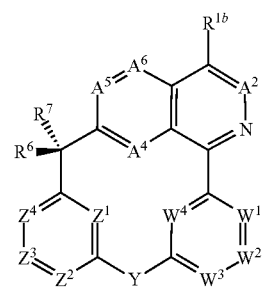

Formula (Va)

Formula (Vb)

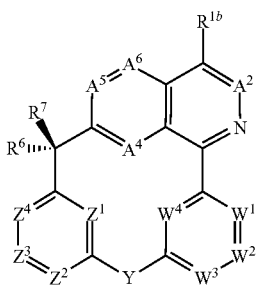

or a pharmaceutically acceptable form thereof.

131. The compound of claim 129, wherein $A^2$ is $CR^2$.
132. The compound of claim 129, wherein A4 is $CR^8$.
133. The compound of claim 129, wherein $A^2$ is $CR^8$.
134. The compound of claim 129, wherein $A^6$ is $CR^8$.
135. The compound of claim 129, wherein:
  (a) $A^4$ is N, and no more than one of $A^5$ and $A^6$ is N; or
  (b) $A^5$ is N, and no more than one of $A^4$ and $A^6$ is N; or
  (c) $A^6$ is N, and no more than one of $A^4$ and $A^5$ is N; or
  (d) $A^4$, $A^5$, and $A^6$ are each independently $CR^8$.
136. The compound of claim 129, wherein each $R^8$ is independently $R^9$, —$OR^9$, halo, or CN, optionally wherein each $R^8$ is hydrogen.
137. The compound of claim 129, wherein at least one of $W^1$, $W^2$, $W^3$, and $W^4$ is N, optionally, wherein:
  $W^1$, $W^2$, and $W^3$ are each independently $CR^4$, and $W^4$ is N;
  $W^1$, $W^2$, and $W^4$ are each independently $CR^4$, and $W^3$ is N;
  $W^1$, $W^3$, and $W^4$ are each independently $CR^4$, and $W^2$ is N; or
  $W^2$, $W^3$, and $W^4$ are each independently $CR^4$, and $W^1$ is N.
138. The compound of claim 129, wherein $W^1$, $W^2$, $W^3$, and $W^4$ are each independently $CR^4$.
139. The compound of claim 129, wherein:
  (a) each $R^4$ is independently hydrogen, halo, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, or —$NR^{14}R^{15}$, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, or 3-6 membered heterocycloalkoxy of the $R^4$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O); or
  (b) each $R^4$ is independently hydrogen, halo, $C_{1-6}$ alkyl, $C_{1-6}$ haloalkyl, $C_{3-6}$ cycloalkyl, $C_{1-6}$ alkoxy, or $C_{1-6}$ haloalkoxy, wherein each $C_{1-6}$ alkyl, $C_{1-6}$ haloalkyl, $C_{3-6}$ cycloalkyl, $C_{1-6}$ alkoxy, or $C_{1-6}$ haloalkoxy of the $R^4$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O); or
  (c) each $R^4$ is independently hydrogen, halo, $C_{1-3}$ alkyl, $C_{1-3}$ haloalkyl, $C_{3-5}$ cycloalkyl, $C_{1-3}$ alkoxy, or $C_{1-3}$ haloalkoxy; or
  (d) each $R^4$ is hydrogen.

140. The compound of claim 129, wherein at least one of $Z^1$, $Z^2$, $Z^3$, and $Z^4$ is N, optionally wherein:
  $Z^1$, $Z^2$, and $Z^3$ are each independently $CR^5$, and $Z^4$ is N;
  $Z^1$, $Z^2$, and $Z^4$ are each independently $CR^5$, and $Z^3$ is N;
  $Z^1$, $Z^3$, and $Z^4$ are each independently $CR^5$, and $Z^2$ is N; or
  $Z^2$, $Z^3$, and $Z^4$ are each independently $CR^5$, and $Z^1$ is N.

141. The compound of claim 129, wherein $Z^1$, $Z^2$, $Z^3$, and $Z^4$ are each independently $CR^5$.

142. The compound of claim 129, wherein:
  $R^5$, at each occurrence, is independently $R^9$, —$OR^9$, halo, CN, $NO_2$, —$C(O)R^9$, —$C(O)OR^9$, —$C(O)NR^{10}R^{11}$, —$S(O)_pR^9$, or —$S(O)_2NR^{10}R^{11}$; or
  $R^5$, at each occurrence, is independently hydrogen, halo, CN, $NO_2$, —$C(O)CH_3$, —$C(O)OH$, —$C(O)OCH_3$, —$C(O)N(CH_3)_2$, —$S(O)_2CH_3$, or —$S(O)_2N(CH_3)_2$; or
  each $R^5$ independently is hydrogen, halo or CN; or
  each $R^5$ is hydrogen.

143. The compound of claim 129, wherein the compound is a compound of Formula (V-1), (Va-1), or (Vb-1):

Formula (V-1)

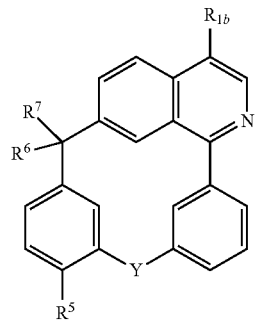

Formula (Va-1)

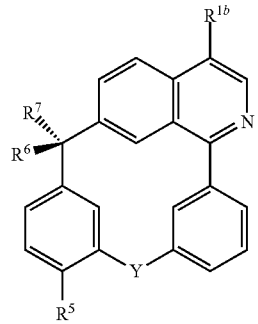

Formula (Vb-1)

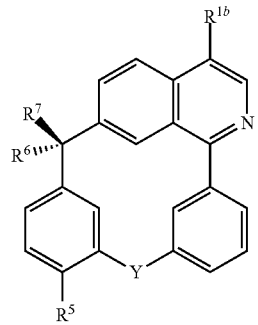

or a pharmaceutically acceptable form thereof.

144. The compound of claim 143, wherein $R^{1b}$ is $R^9$, —$OR^9$, halo, CN, $NO_2$, —$C(O)R^9$, —$C(O)OR^9$, —$C(O)NR^{10}R^{11}$, —$NR^{10}R^{11}$, —$NR^{10}C(O)R^9$, —$S(O)_pR^9$, or —$S(O)_2NR^{10}R^{11}$.

145. The compound of claim 143, wherein $R^{1b}$ is hydrogen, $C_{1-6}$ alkyl, $C_{3-6}$ cycloalkyl, $C_{1-6}$ alkoxy, $C_{3-6}$ cycloalkoxy, halo or CN, wherein each $C_{1-6}$ alkyl, $C_{3-6}$ cycloalkyl, $C_{1-6}$ alkoxy, or $C_{3-6}$ cycloalkoxy is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), —$C(O)R^{12}$, —$C(O)OR^{12}$, —$OC(O)R^{12}$, —$OC(O)OR^{12}$, —$C(O)NR^{10}R^{11}$, —$NR^{10}R^{11}$, —$NR^{10}C(O)R^{12}$, —$NR^{10}C(O)OR^{12}$, —$NR^{10}C(O)NR^{10}R^{11}$, —$NR^{10}S(O)_2R^{12}$, —$S(O)_pR^{12}$, and —$S(O)_2NR^{10}R^{11}$.

146. The compound of claim 143, wherein $R^{1b}$ is hydrogen, —$CH_3$, —$CD_3$, —$CF_3$, —$CH_2CH_3$, —$CD_2CD_3$, isopropyl, 2,3-dihydroxypropyl, cyclopropyl, —$OCH_3$, —$OCD_3$, —$OCF_3$, —$OCH_2CH_3$, —$OCD_2CD_3$, isopropoxy, 2,3-dihydroxypropoxy, or cyclopropoxy.

147. The compound of claim 143, wherein Y is in the direction of Z-Y-W, and wherein Y is a $C_{1-6}$ alkylene, wherein one or more —$CH_2$— are optionally independently replaced by —O—, —C(O)—, —$N(R^{10})$—, —$N(R^{10})C(O)$—, —$C(O)N(R^{10})$—, —$N(R^{10})C(O)N(R^{11})$—, —$S(O)_p$—, —$N(R^{10})S(O)_2$—, —$S(O)_2N(R^{10})$—, or —$N(R^{10})S(O)_2N(R^{11})$—, and wherein Y is no more than six atoms in length.

148. The compound of claim 147, wherein:
Y is —$(CR^{16}R^{17})_q$—, —$(CR^{16}R^{17})_mO(CR^{16}R^{17})_n$—, —$(CR^{16}R^{17})_mC(O)(CR^{16}R^{17})_n$—, —$(CR^{16}R^{17})_mN(R^{10})(CR^{16}R^{17})_n$—, —$(CR^{16}R^{17})_mN(R^{10})C(O)(CR^{16}R^{17})_n$—, —$(CR^{16}R^{17})_mC(O)N(R^{10})(CR^{16}R^{17})_n$—, —$(CR^{16}R^{17})_mN(R^{10})C(O)N(R^{11})(CR^{16}R^{17})_n$—, —$(CR^{16}R^{17})_mS(O)_p(CR^{16}R^{17})_n$—, —$(CR^{16}R^{17})_mN(R^{10})S(O)_2(CR^{16}R^{17})_n$—, —$(CR^{16}R^{17})_mS(O)_2N(R^{10})(CR^{16}R^{17})_n$—, or —$(CR^{16}R^{17})_mN(R^{10})S(O)_2N(R^{11})(CR^{16}R^{17})_n$—, and wherein Y is no more than six atoms in length; and
wherein:
$R^{16}$ and $R^{17}$, at each occurrence, are each independently hydrogen, halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, or 3-6 membered heterocycloalkoxy, or together with the C to which each is attached are combined to form a C(O), $C_{3-6}$ cycloalkyl, or 3-6 membered heterocycloalkyl;
each m is independently an integer of 0, 1, 2, or 3;
each n is independently an integer of 0, 1, 2, or 3;
wherein the sum of m and n is 0, 1, 2, 3, 4, or 5; and
q is an integer of 0, 1, 2, 3, 4, 5, or 6;
optionally wherein each m is independently 0, 1, or 2; and
optionally wherein each n is independently 0, 1, or 2.

149. The compound of claim 147, wherein Y is —$(CH_2)O$—, or Y is —$O(CH_2)$—, or Y is —$(CH_2)_2O$—, or Y is —$O(CH_2)_2$—, or Y is —$(CH_2)_2$—.

150. The compound of claim 143, wherein $R^7$ is an imidazolyl, a triazolyl, a tetrazolyl, an oxazolyl, a thiazolyl, an oxadiazolyl, a thiadiazolyl, a pyridyl, or a pyrimidinyl, each optionally substituted with one, two, three, or four substituents independently selected from halo, CN, $NO_2$, $R^9$, —$OR^9$, —$C(O)R^9$, —$C(O)OR^9$, —$OC(O)R^9$, —$OC(O)OR^9$, —$C(O)NR^{10}R^{11}$, —$NR^{10}R^{11}$, —$NR^{10}C(O)R^9$, —$NR^{10}C(O)OR^9$, —$NR^{10}C(O)NR^{10}R^{11}$, —$NR^{10}S(O)_2R^9$, —$S(O)_pR^9$, —$S(O)_2NR^{10}R^{11}$, and —$NR^{10}S(O)_2NR^{10}R^{11}$;
optionally wherein $R^7$ is imidazolyl or triazolyl, each optionally substituted with one, two, three, or four substituents independently selected from halo, CN, $NO_2$, $R^9$, —$OR^9$, —$C(O)R^9$, —$C(O)OR^9$, —$C(O)NR^{10}R^{11}$, —$NR^{10}R^{11}$, —$NR^{10}C(O)R^9$, —$S(O)_pR^9$, and —$S(O)_2NR^{10}R^{11}$;
optionally wherein $R^8$ is a C-linked imidazolyl or a C-linked triazolyl, each optionally substituted with one, two, three, or four substituents independently selected from halo, CN, $NO_2$, $R^9$, —$OR^9$, —$C(O)R^9$, —$C(O)OR^9$, —$C(O)NR^{10}R^{11}$, —$NR^{10}R^{11}$, —$NR^{10}C(O)R^9$, —$S(O)_pR^9$, and —$S(O)_2NR^{10}R^{11}$.

151. The compound of claim 143, wherein $R^7$ is an N-linked imidazolyl or an N-linked triazolyl, each optionally substituted with one, two, three, or four substituents independently selected from halo, CN, $NO_2$, $R^9$, —$OR^9$, —$C(O)R^9$, —$C(O)OR^9$, —$C(O)NR^{10}R^{11}$, —$NR^{10}R^{11}$, —$NR^{10}C(O)R^9$, —$S(O)_pR^9$, or —$S(O)_2NR^{10}R^{11}$; optionally wherein $R^8$ is a methyl-substituted imidazolyl or a methyl-substituted triazolyl, or
$R^7$ is a C-methyl-substituted imidazolyl or a C-methyl-substituted triazolyl, optionally wherein $R^7$ is:

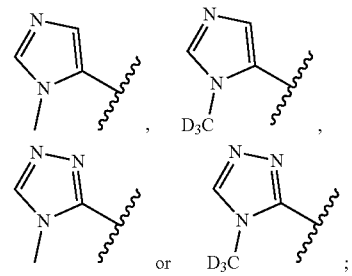

or $R^7$ is an N-methyl-substituted imidazolyl or an N-methyl-substituted triazolyl, optionally wherein $R^7$ is:

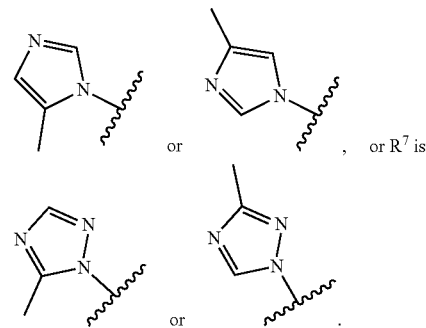

152. The compound of claim 143, wherein $R^6$ is CN, $R^9$, —$OR^9$, —$OC(O)R^9$, —$OC(O)OR^9$, —$NR^{10}R^{11}$, —$NR^{10}R^9$, —$NR^{10}C(O)R^9$, or —$NR^{10}C(NR^{10})NR^{10}R^{11}$, or wherein $R^6$ is CN, $R^9$, —$OR^9$, —$NR^{10}R^{11}$, or —$NR^{10}OR^9$, or wherein $R^6$ is CN, $R^9$, —$OR^9$, or —$NR^{10}R^{11}$, optionally wherein each $R^9$ is independently hydrogen or $C_{1-3}$ alkyl, wherein the $C_{1-3}$ alkyl is optionally substituted with CN, and optionally wherein $R^{10}$ and $R^{11}$ are each independently hydrogen, $C_{1-6}$ alkyl, or $C_{1-6}$ alkoxy.

153. The compound of claim 143, wherein $R^6$ is hydrogen, —$CH_3$, hydroxy, —$OCH_3$, —$OCD_3$, —$NH_2$, —$NHCH_3$, or —$NH(OCH_3)$, or $R^6$ is hydroxy, or $R^6$ is hydrogen, or $R^6$ is $NH_2$, or $R^6$ is —$NH(CH_2CH_2)Cl$, —$NH(CH_2CH_2)F$, or N-linked morpholino.

154. The compound of claim 129, wherein:
the compound has a molecular weight (MW) of no more than 1,000 g/mol; or
the compound has a MW of no more than 900 g/mol, no more than 800 g/mol, no more than 700 g/mol, no more than 600 g/mol, or no more than 500 g/mol.

155. The compound of claim 129, wherein the pharmaceutically acceptable form of the compound is exclusive of a salt form.

156. The compound of claim 129, wherein the compound is a racemate, a mixture of diastereomers, or a mixture of stereoisomers, or a pharmaceutically acceptable form thereof.

157. The compound of claim 129, wherein the compound is a single enantiomer or a single diastereomer, or a pharmaceutically acceptable form thereof.

158. The compound of claim 129, wherein the compound is a single enantiomer with an (R) configuration at the $R^6/R^7$-substituted carbon, or a pharmaceutically acceptable form thereof.

159. The compound of claim 129, wherein the compound is a single enantiomer with an (S) configuration at the $R^6/R^7$-substituted carbon, or a pharmaceutically acceptable form thereof.

160. A pharmaceutical composition comprising the compound or pharmaceutically acceptable form thereof of claim 129 and a pharmaceutically acceptable carrier, excipient, or diluent.

161. A compound of Formula (VI):

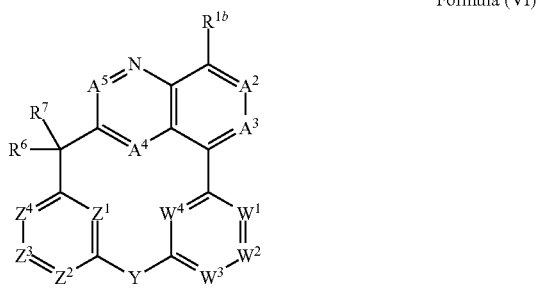

Formula (VI)

wherein:
$A^2$ is N, $NR^{2a}$, $CR^{2b}$, or —C(=O)—;
$A^3$ is $CR^3$ or N;
$A^4$ is $CR^8$ or N;
$A^5$ is $CR^8$ or N;
$W^1$, $W^2$, $W^3$, and $W^4$ are each independently N or $CR^4$, or $W^1$ and $W^2$ taken together are O, $NR^4$, or S, or $W^2$ and $W^3$ taken together are O, $NR^4$, or S;
Y is a bond or a linker having a length of up to 6 atoms;
$Z^1$, $Z^2$, $Z^3$, and $Z^4$ are each independently N or $CR^5$, or $Z^2$ and $Z^3$ taken together are O, $NR^{5A}$, or S, or $Z^3$ and $Z^4$ taken together are O, $NR^{5A}$, or S;
$R^{2a}$ is $R^9$, —$OR^9$, —$C(O)R^9$, —$C(O)OR^9$, —$C(O)NR^{10}R^{11}$, —$S(O)_pR^9$, or —$S(O)_2NR^{10}R^{11}$;
$R^{1b}$, $R^{2b}$, $R^3$, $R^5$, and $R^8$, at each occurrence, are each independently $R^9$, —$OR^9$, halo, CN, $NO_2$, —$C(O)R^9$, —$C(O)OR^9$, —$OC(O)R^9$, —$OC(O)OR^9$, —$C(O)NR^{10}R^{11}$, —$NR^{10}R^{11}$, —$NR^{10}C(O)R^9$, —$NR^{10}C(O)OR^9$, —$NR^{10}C(O)NR^{10}R^{11}$, —$NR^{10}S(O)_2R^9$, —$S(O)_pR^9$, —$S(O)_2NR^{10}R^{11}$, or —$NR^{10}S(O)_2NR^{10}R^{11}$;

$R^4$, at each occurrence, is independently hydrogen, halo, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, —$NR^{14}R^{15}$, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, $C_{6-12}$ aryl, or 5-12 membered heteroaryl of the $R^4$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);

$R^{4A}$ and $R^{5A}$ are each independently hydrogen, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{4A}$ and the $R^4$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O);

$R^6$ is CN, $R^9$, —$OR^9$, —$C(O)R^9$, —$C(O)OR^9$, —$OC(O)R^9$, —$OC(O)OR^9$, —$C(O)NR^{10}R^{11}$, —$NR^1R^1$, —$NR^{10}R^9$, —$NR^{10}C(O)R^9$, —$NR^{10}C(O)OR^9$, —$NR^{10}C(O)NR^{10}R^{11}$, —$NR^{10}S(O)_2R^9$, —$NR^{10}C(NR^{10})NR^{10}R^{11}$, —$S(O)_pR^9$, —$S(O)_2NR^{10}R^{11}$, or —$NR^{10}S(O)_2NR^{10}R^{11}$;

$R^7$ is a 5-12 membered heteroaryl, optionally substituted with one, two, three, or four substituents independently selected from halo, CN, $NO_2$, $R^9$, —$OR^9$, —$C(O)R^9$, —$C(O)OR^9$, —$OC(O)R^9$, —$OC(O)OR^9$, —$C(O)NR^{10}R^{11}$, —$NR^{10}R^{11}$, —$NR^{10}C(O)R^9$, —$NR^{10}C(O)OR^9$, —$NR^{10}C(O)NROR^{11}$, —$NR^{10}S(O)_2R^9$, —$S(O)_pR^9$, —$S(O)_2NR^{10}R^{11}$, and —$NR^{10}S(O)_2NR^{10}R^{11}$;

$R^9$, at each occurrence, is independently hydrogen, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^9$ is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), —$C(O)R^{12}$, —$C(O)OR^{12}$, —$OC(O)R^{12}$, —$OC(O)OR^{12}$, —$C(O)NR^{10}R^{11}$, —$NR^{10}R^{11}$, —$NR^{10}C(O)R^{12}$, —$NR^{10}C(O)OR^{12}$, —$NR^{10}C(O)NR^{10}R^{11}$, —$NR^{10}S(O)_2R^{12}$, —$S(O)_pR^{12}$, —$S(O)_2NR^{10}R^{11}$, and —$NR^{10}S(O)_2NR^{10}R^{11}$;

$R^{10}$ and $R^{11}$, at each occurrence, are each independently hydrogen, hydroxy, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{6-12}$ aryl, or 5-12 membered heteroaryl, or together with the N to which each is attached are combined to form a 3-6 membered heterocycloalkyl, wherein each $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{6-12}$ aryl, or 5-12 membered heteroaryl of the $R^{10}$ and the $R^{11}$ is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), $-C(O)R^{13}$, $-C(O)OR^{13}$, $-OC(O)R^{13}$, $-OC(O)OR^{13}$, $-C(O)NR^{14}R^{11}$, $-NR^{14}R^{15}$, $-NR^{14}C(O)R^{13}$, $-NR^{14}C(O)OR^{13}$, $-NR^{14}C(O)NR^{14}R^{15}$, $-NR^{14}S(O)_2R^{13}$, $-S(O)_pR^{13}$, $-S(O)_2NR^{14}R^{15}$, and $-NR^{14}S(O)_2NR^{14}R^{15}$;

$R^{12}$, at each occurrence, is independently hydrogen, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl, wherein each $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{6-12}$ aryl, or 5-12 membered heteroaryl of the $R^{12}$ is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), $-C(O)R^{13}$, $-C(O)OR^{13}$, $-OC(O)R^{13}$, $-OC(O)OR^{13}$, $-C(O)NR^{10}R^{11}$, $-NR^{10}R^{11}$, $-NR^{10}C(O)R^{13}$, $-NR^{10}C(O)OR^{13}$, $-NR^{10}C(O)NR^{10}R^{11}$, $-NR^{10}S(O)_2R^{13}$, $-S(O)_pR^{13}$, $-S(O)_2NR^{10}R^{11}$, and $-NR^{10}S(O)_2NR^{10}R^{11}$;

$R^{13}$, at each occurrence, is independently hydrogen, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-6}$ cycloalkyl, or 3-6 membered heterocycloalkyl;

$R^{14}$ and $R^{15}$, at each occurrence, are each independently hydrogen, hydroxy, $C_{1-4}$ alkyl, $C_{2-4}$ alkenyl, $C_{2-4}$ alkynyl, $C_{1-4}$ haloalkyl, $C_{1-4}$ hydroxyalkyl, $C_{1-4}$ heteroalkyl, $C_{3-6}$ cycloalkyl, 3-6 membered heterocycloalkyl, or $C_{1-6}$ alkoxy, or together with the N to which each is attached are combined to form a 3-6 membered heterocycloalkyl; and each p is independently an integer of 0, 1, or 2;

or a pharmaceutically acceptable form thereof.

162. The compound of claim 161, wherein the compound is a compound of Formula (VIa) or is a compound of Formula (VIb):

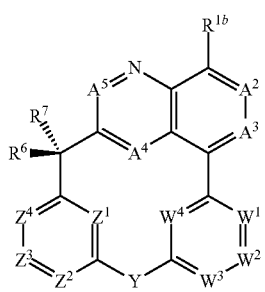

Formula (VIa)

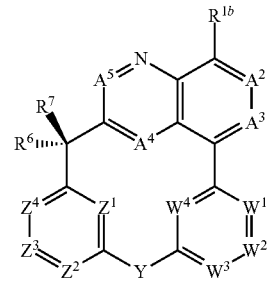

Formula (VIb)

or a pharmaceutically acceptable form thereof.

163. The compound of claim 161, wherein $A^2$ is $CR^{2b}$.

164. The compound of claim 161, wherein $A^3$ is $CR^3$, optionally wherein $R^3$ is (a) $R^9$, $-OR^9$, halo, or CN; or (b) hydrogen.

165. The compound of claim 161, wherein $A^4$ is $CR^8$.

166. The compound of claim 161, wherein $A^5$ is $CR^8$.

167. The compound of claim 161, wherein:
  (a) $A^4$ or $A^5$ is N; or
  (b) $A^4$ and $A^5$ are each independently $CR^8$.

168. The compound of claim 161, wherein each $R^8$ is independently $R^9$, $-OR^9$, halo, or CN, optionally wherein each $R^8$ is hydrogen.

169. The compound of claim 161, wherein at least one of $W^1$, $W^2$, $W^3$, and $W^4$ is N, optionally, wherein:
  $W^1$, $W^2$, and $W^3$ are each independently $CR^4$, and $W^4$ is N;
  $W^1$, $W^2$, and $W^4$ are each independently $CR^4$, and $W^3$ is N;
  $W^1$, $W^3$, and $W^4$ are each independently $CR^4$, and $W^2$ is N; or
  $W^2$, $W^3$, and $W^4$ are each independently $CR^4$, and $W^1$ is N.

170. The compound of claim 161, wherein $W^1$, $W^2$, $W^3$, and $W^4$ are each independently $CR^4$.

171. The compound of claim 161, wherein:
  (a) each $R^4$ is independently hydrogen, halo, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, 3-6 membered heterocycloalkoxy, or $-NR^{14}R^{15}$, wherein each $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, $C_{3-6}$ cycloalkoxy, or 3-6 membered heterocycloalkoxy of the $R^4$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O); or
  (b) each $R^4$ is independently hydrogen, halo, $C_{1-6}$ alkyl, $C_{1-6}$ haloalkyl, $C_{3-6}$ cycloalkyl, $C_{1-6}$ alkoxy, or $C_{1-6}$ haloalkoxy, wherein each $C_{1-6}$ alkyl, $C_{1-6}$ haloalkyl, $C_{3-6}$ cycloalkyl, $C_{1-6}$ alkoxy, or $C_{1-6}$ haloalkoxy of the $R^4$ is optionally substituted with one, two, three, four, five, or six substituents independently selected from halo, hydroxy, $C_{1-6}$ alkyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, and (O); or (c) each $R^4$ is independently hydrogen, halo, $C_{1-3}$ alkyl, $C_{1-3}$ haloalkyl, $C_{3-5}$ cycloalkyl, $C_{1-3}$ alkoxy, or $C_{1-3}$ haloalkoxy; or (d) each $R^4$ is hydrogen.

172. The compound of claim 161, wherein at least one of $Z^1$, $Z^2$, $Z^3$, and $Z^4$ is N, optionally wherein:

$Z^1$, $Z^2$, and $Z^3$ are each independently $CR^5$, and $Z^4$ is N;
$Z^1$, $Z^2$, and $Z^4$ are each independently $CR^5$, and $Z^3$ is N;
$Z^1$, $Z^3$, and $Z^4$ are each independently $CR^5$, and $Z^2$ is N; or
$Z^2$, $Z^3$, and $Z^4$ are each independently $CR^5$, and $Z^1$ is N.

173. The compound of claim 161, wherein $Z^1$, $Z^2$, $Z^3$, and $Z^4$ are each independently $CR^5$.

174. The compound of claim 161, wherein:

$R^5$, at each occurrence, is independently $R^9$, —$OR^9$, halo, CN, $NO_2$, —$C(O)R^9$, —$C(O)OR^9$, —$C(O)NR^{10}R^{11}$, —$S(O)_pR^9$, or —$S(O)_2NR^{10}R^{11}$; or $R^5$, at each occurrence, is independently hydrogen, halo, CN, $NO_2$, —$C(O)CH_3$, —$C(O)OH$, —$C(O)OCH_3$, —$C(O)N(CH_3)_2$, —$S(O)_2CH_3$, or —$S(O)_2N(CH_3)_2$; or each $R^5$ independently is hydrogen, halo or CN; or each $R^5$ is hydrogen.

175. The compound of claim 161, wherein the compound is a compound of Formula (VI-1), (VIa-1), or (VIb-1):

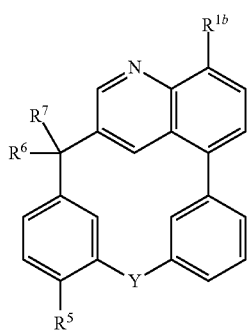

Formula (VI-1)

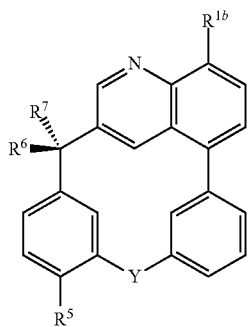

Formula (VIa-1)

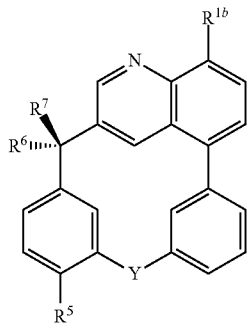

Formula (VIb-1)

or a pharmaceutically acceptable form thereof.

176. The compound of claim 175, wherein $R^{1b}$ is $R^9$, —$OR^9$, halo, CN, $NO_2$, —$C(O)R^9$, —$C(O)OR^9$, —$C(O)NR^{10}R^{11}$, —$NR^{10}R^{11}$, —$NR^{10}C(O)R^9$, —$S(O)_pR^9$, or —$S(O)_2NR^{10}R^{11}$.

177. The compound of claim 175, wherein $R^{1b}$ is hydrogen, $C_{1-6}$ alkyl, $C_{3-6}$ cycloalkyl, $C_{1-6}$ alkoxy, $C_{3-6}$ cycloalkoxy, halo or CN, wherein each $C_{1-6}$ alkyl, $C_{3-6}$ cycloalkyl, $C_{1-6}$ alkoxy, or $C_{3-6}$ cycloalkoxy is optionally substituted with one, two, three, four, five, or six substituents independently selected from halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, (O), —$C(O)R^{12}$, —$C(O)OR^{12}$, —$OC(O)R^{12}$, —$OC(O)OR^{12}$, —$C(O)NR^{10}R^{11}$, —$NR^{10}R^{11}$, —$NR^{10}C(O)R^{12}$, —$NR^{10}C(O)OR^{12}$, —$NR^{10}C(O)NR^{10}R^{11}$, —$NR^{10}S(O)_2R^{12}$, —$S(O)_pR^{12}$, and —$S(O)_2NR^{10}R^{11}$.

178. The compound of claim 175, wherein $R^{1b}$ is hydrogen, —$CH_3$, —$CD_3$, —$CF_3$, —$CH_2CH_3$, —$CD_2CD_3$, isopropyl, 2,3-dihydroxypropyl, cyclopropyl, —$OCH_3$, —$OCD_3$, —$OCF_3$, —$OCH_2CH_3$, —$OCD_2CD_3$, isopropoxy, 2,3-dihydroxypropoxy, or cyclopropoxy.

179. The compound of claim 175, wherein Y is in the direction of Z-Y-W, and wherein Y is a $C_{1-6}$ alkylene, wherein one or more —$CH_2$— are optionally independently replaced by —O—, —$C(O)$—, —$N(R^{10})$—, —$N(R^{10})C(O)$—, —$C(O)N(R^{10})$—, —$N(R^{10})C(O)N(R^{11})$—, —$S(O)_p$—, —$N(R^{11})S(O)_2$—, —$S(O)_2N(R^{10})$—, or —$N(R^{10})S(O)_2N(R^{11})$—, and wherein Y is no more than six atoms in length.

180. The compound of claim 179, wherein:

Y is —$(CR^{16}R^{17})_q$, —$(CR^{16}R^{17})_mO(CR^{16}R^{17})_n$, —$(CR^{16}R^{17})_mC(O)(CR^{16}R^{17})_n$—, —$(CR^{16}R^{17})_mN(R^{10})(CR^{16}R^{17})_n$, —$(CR^{16}R^{17})_mN(R^{10})C(O)(CR^{16}R^{17})_n$, —$(CR^{16}R^{17})_mC(O)N(R^{10})(CR^{16}R^{17})_n$—, —$(CR^{16}R^{17})_mN(R^{10})C(O)N(R^{11})(CR^{16}R^7)_n$, —$(CR^{16}R^{17})_mS(O)_p(CR^{16}R^{17})_n$—, —$(CR^{16}R^{17})_mN(R^{10})S(O)_2(CR^{16}R^{17})_n$, —$(CR^{16}R^{17})_mS(O)_2N(R^{10})(CR^{16}R^{17})_n$—, or —$(CR^{16}R^{17})_mN(R^{10})S(O)_2N(R^{11})(CR^{16}R^{17})_n$, and wherein Y is no more than six atoms in length; and wherein:

$R^{16}$ and $R^{17}$, at each occurrence, are each independently hydrogen, halo, hydroxy, CN, $NO_2$, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ heteroalkyl, $C_{3-6}$ cycloalkyl, 3-6 membered heterocycloalkyl, $C_{1-6}$ alkoxy, $C_{1-6}$ haloalkoxy, $C_{1-6}$ hydroxyalkoxy, $C_{1-6}$ heteroalkoxy, or 3-6 membered heterocycloalkoxy, or together with the C to which each is attached are combined to form a C(O), $C_{3-6}$ cycloalkyl, or 3-6 membered heterocycloalkyl;

each m is independently an integer of 0, 1, 2, or 3;
each n is independently an integer of 0, 1, 2, or 3;
wherein the sum of m and n is 0, 1, 2, 3, 4, or 5; and
q is an integer of 0, 1, 2, 3, 4, 5, or 6;
optionally wherein each m is independently 0, 1, or 2; and
optionally wherein each n is independently 0, 1, or 2.

181. The compound of claim 179, wherein Y is —$(CH_2)O$—, or Y is —$O(CH_2)$—, or Y is —$(CH_2)_2O$—, or Y is —$O(CH_2)_2$—, or Y is —$(CH_2)_2$—.

182. The compound of claim 175, wherein $R^7$ is an imidazolyl, a triazolyl, a tetrazolyl, an oxazolyl, a thiazolyl, an oxadiazolyl, a thiadiazolyl, a pyridyl, or a pyrimidinyl, each optionally substituted with one, two, three, or four substituents independently selected from halo, CN, $NO_2$, $R^9$, —$OR^9$, —$C(O)R^9$, —$C(O)OR^9$, —$OC(O)R^9$, —$OC(O)$ OR$^9$, —C(O)NR$^{10}$R$^{11}$, —NR$^{10}$R$^{11}$, —NR$^{10}$C(O)R$^9$, —NR$^{10}$C(O)OR$^9$, —NR$^{10}$C(O)NR$^{10}$R$^{11}$, —NR$^{10}$S(O)$_2$R$^9$, —S(O)$_p$R$^9$, —S(O)$_2$NR$^{10}$R$^{11}$, and —NR$^{10}$S(O)$_2$NR$^{10}$R$^{11}$;
optionally wherein R$^7$ is imidazolyl or triazolyl, each optionally substituted with one, two, three, or four substituents independently selected from halo, CN, NO$_2$, R$^9$, —OR$^9$, —C(O)R$^9$, —C(O)OR$^9$, —C(O)NR$^{10}$R$^{11}$, —NR$^{10}$R$^{11}$, —NR$^{10}$C(O)R$^9$, —S(O)$_p$R$^9$, and —S(O)$_2$NR$^{10}$R$^{11}$;
optionally wherein R$^7$ is a C-linked imidazolyl or a C-linked triazolyl, each optionally substituted with one, two, three, or four substituents independently selected from halo, CN, NO$_2$, R$^9$, —OR$^9$, —C(O)R$^9$, —C(O)OR$^9$, —C(O)NR$^{10}$R$^{11}$, —NROR$^{11}$, —NR$^{10}$C(O)R$^9$, —S(O)$_p$R$^9$, and —S(O)$_2$NR$^{10}$R$^{11}$.

183. The compound of claim 175, wherein R$^7$ is an N-linked imidazolyl or an N-linked triazolyl, each optionally substituted with one, two, three, or four substituents independently selected from halo, CN, NO$_2$, R$^9$, —OR$^9$, —C(O)R$^9$, —C(O)OR$^9$, —C(O)NR$^{10}$R$^{11}$, —NR$^{10}$R$^{11}$, —NR$^{10}$C(O)R$^9$, —S(O)$_p$R$^9$, or —S(O)$_2$NR$^{10}$R$^{11}$; optionally wherein R$^7$ is a methyl-substituted imidazolyl or a methyl-substituted triazolyl, or R$^7$ is a C-methyl-substituted imidazolyl or a C-methyl-substituted triazolyl, optionally wherein R$^7$ is:

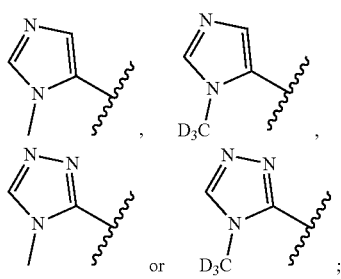

or R$^7$ is an N-methyl-substituted imidazolyl or an N-methyl-substituted triazolyl, optionally wherein R$^7$ is:

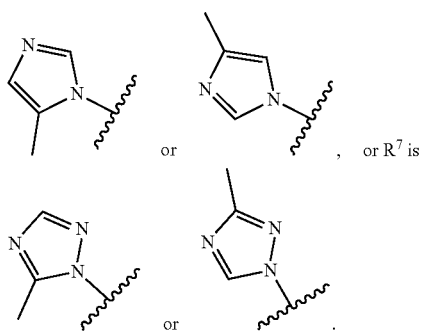

184. The compound of claim 175, wherein R$^6$ is CN, R$^9$, —OR$^9$, —OC(O)R$^9$, —OC(O)OR$^9$, —NR$^{10}$R$^{11}$, —NR$^{10}$OR$^9$, —NR$^{10}$C(O)R$^9$, or —NR$^{10}$C(NR$^{10}$)NR$^{10}$R$^{11}$, or wherein R$^6$ is CN, R$^9$, —OR$^9$, —NR$^{10}$R$^{11}$, or —NR$^{10}$OR$^9$, or wherein R$^6$ is CN, R$^9$, —OR$^9$, or —NR$^{10}$R$^{11}$, optionally wherein each R$^9$ is independently hydrogen or C$_{1-3}$ alkyl, wherein the C$_{1-3}$ alkyl is optionally substituted with CN, and optionally wherein R$^{10}$ and R$^{11}$ are each independently hydrogen, C$_{1-6}$ alkyl, or C$_{1-6}$ alkoxy.

185. The compound of claim 175, wherein R$^6$ is hydrogen, —CH$_3$, hydroxy, —OCH$_3$, —OCD$_3$, —NH$_2$, —NHCH$_3$, or —NH(OCH$_3$), or R$^6$ is hydroxy, or R$^6$ is hydrogen, or R$^6$ is NH$_2$, or R$^6$ is —NH(CH$_2$CH$_2$)Cl, —NH(CH$_2$CH$_2$)F, or N-linked morpholino.

186. The compound of claim 161, wherein:
the compound has a molecular weight (MW) of no more than 1,000 g/mol; or
the compound has a MW of no more than 900 g/mol, no more than 800 g/mol, no more than 700 g/mol, no more than 600 g/mol, or no more than 500 g/mol.

187. The compound of claim 161, wherein the pharmaceutically acceptable form of the compound is exclusive of a salt form.

188. The compound of claim 161, wherein the compound is a racemate, a mixture of diastereomers, or a mixture of stereoisomers, or a pharmaceutically acceptable form thereof.

189. The compound of claim 161, wherein the compound is a single enantiomer or a single diastereomer, or a pharmaceutically acceptable form thereof.

190. The compound of claim 161, wherein the compound is a single enantiomer with an (R) configuration at the R$^6$/R$^7$-substituted carbon, or a pharmaceutically acceptable form thereof.

191. The compound of claim 161, wherein the compound is a single enantiomer with an (S) configuration at the R$^6$/R$^7$-substituted carbon, or a pharmaceutically acceptable form thereof.

192. A pharmaceutical composition comprising the compound or pharmaceutically acceptable form thereof of claim 161 and a pharmaceutically acceptable carrier, excipient, or diluent.

193. A compound selected from the group consisting of:
3-hydroxy-3-(1-methyl-1H-imidazol-5-yl)-2$^1$,2$^2$-dihydro-2(4,6)-quinolina-1,4(1,3)-dibenzenacyclohexaphan-2$^2$-one;
3-hydroxy-2$^1$-methyl-3-(1-methyl-1H-imidazol-5-yl)-2$^1$,2$^2$-dihydro-2(4,6)-quinolina-1,4(1,3)-dibenzenacyclohexaphan-2$^2$-one;
4$^4$-chloro-3-hydroxy-2$^1$-methyl-3-(1-methyl-1H-imidazol-5-yl)-2$^1$,2$^2$-dihydro-2(4,6)-quinolina-1,4(1,3)-dibenzenacyclohexaphan-2$^2$-one;
3-amino-4$^4$-chloro-2$^1$-methyl-3-(1-methyl-1H-imidazol-5-yl)-2$^1$,2$^2$-dihydro-2(4,6)-quinolina-1,4(1,3)-dibenzenacyclohexaphan-2$^2$-one;
3-hydroxy-2$^2$-methoxy-3-(1-methyl-1H-imidazol-5-yl)-2(4,6)-quinolina-1,4(1,3)-dibenzenacyclohexaphane-4$^4$-carbonitrile;
3-hydroxy-2$^1$-methyl-3-(1-methyl-1H-imidazol-5-yl)-2$^2$-oxo-2$^1$,2$^2$-dihydro-2(4,6)-quinolina-1,4(1,3)-dibenzenacyclohexaphane-4$^4$-carbonitrile;
3-amino-2$^1$-methyl-3-(1-methyl-1H-imidazol-5-yl)-2$^2$-oxo-2$^1$,2$^2$-dihydro-2(4,6)-quinolina-1,4(1,3)-dibenzenacyclohexaphane-4$^4$-carbonitrile;
3-amino-2$^1$-(methyl-d$_3$)-3-(1-methyl-1H-imidazol-5-yl)-2$^2$-oxo-2$^1$,2$^2$-dihydro-2(4,6)-quinolina-1,4(1,3)-dibenzenacyclohexaphane-4$^4$-carbonitrile;
3-amino-3-(1-methyl-1H-imidazol-5-yl)-2(4,6)-quinolina-1,4(1,3)-dibenzenacyclohexaphane-2$^2$,4$^4$-dicarbonitrile;
2$^2$-methoxy-3-(1-methyl-1H-imidazol-5-yl)-5-oxa-2(4,6)-quinolina-1,4(1,3)-dibenzenacyclohexaphan-3-ol;
3-hydroxy-2$^1$-methyl-3-(1-methyl-1H-imidazol-5-yl)-2$^1$,2$^2$-dihydro-5-oxa-2(4,6)-quinolina-1,4(1,3)-dibenzenacyclohexaphan-2$^2$-one;

4⁴-chloro-2²-methoxy-3-(1-methyl-1H-imidazol-5-yl)-5-oxa-2(4,6)-quinolina-1,4(1,3)-dibenzenacyclohexaphan-3-ol;

4⁴-chloro-3-hydroxy-3-(1-methyl-1H-imidazol-5-yl)-2¹,2²-dihydro-5-oxa-2(4,6)-quinolina-1,4(1,3)-dibenzenacyclohexaphan-2²-one;

4⁴-chloro-3-hydroxy-2¹-methyl-3-(1-methyl-1H-imidazol-5-yl)-2¹,2²-dihydro-5-oxa-2(4,6)-quinolina-1,4(1,3)-dibenzenacyclohexaphan-2²-one;

3-amino-4⁴-chloro-2¹-methyl-3-(1-methyl-1H-imidazol-5-yl)-2¹,2²-dihydro-5-oxa-2(4,6)-quinolina-1,4(1,3)-dibenzenacyclohexaphan-2²-one;

3-hydroxy-2²-methoxy-3-(1-methyl-1H-imidazol-5-yl)-5-oxa-2(4,6)-quinolina-1,4(1,3)-dibenzenacyclohexaphane-4⁴-carbonitrile;

3-hydroxy-3-(1-methyl-1H-imidazol-5-yl)-2²-oxo-2¹,2²-dihydro-5-oxa-2(4,6)-quinolina-1,4(1,3)-dibenzenacyclohexaphane-4⁴-carbonitrile;

3-hydroxy-2¹-methyl-3-(1-methyl-1H-imidazol-5-yl)-2²-oxo-2¹,2²-dihydro-5-oxa-2(4,6)-quinolina-1,4(1,3)-dibenzenacyclohexaphane-4⁴-carbonitrile;

3-amino-2¹-methyl-3-(1-methyl-1H-imidazol-5-yl)-2²-oxo-2¹,2²-dihydro-5-oxa-2(4,6)-quinolina-1,4(1,3)-dibenzenacyclohexaphane-4⁴-carbonitrile;

3-amino-2¹-(methyl-d₃)-3-(1-methyl-1H-imidazol-5-yl)-2²-oxo-2¹,2²-dihydro-5-oxa-2(4,6)-quinolina-1,4(1,3)-dibenzenacyclohexaphane-4⁴-carbonitrile;

3-amino-3-(1-methyl-1H-imidazol-5-yl)-5-oxa-2(4,6)-quinolina-1,4(1,3)-dibenzenacyclohexaphane-2²,4⁴-dicarbonitrile;

3-hydroxy-3-(1-methyl-1H-imidazol-5-yl)-2¹,2²-dihydro-5-oxa-2(4,6)-quinolina-1,4(1,3)-dibenzenacycloheptaphan-22-one;

3-hydroxy-2¹-methyl-3-(1-methyl-1H-imidazol-5-yl)-2¹,2²-dihydro-5-oxa-2(4,6)-quinolina-1,4(1,3)-dibenzenacycloheptaphan-2²-one;

4⁴-chloro-2²-methoxy-3-(1-methyl-1H-imidazol-5-yl)-5-oxa-2(4,6)-quinolina-1,4(1,3)-dibenzenacycloheptaphan-3-ol;

4⁴-chloro-3-hydroxy-3-(1-methyl-1H-imidazol-5-yl)-2¹,2²-dihydro-5-oxa-2(4,6)-quinolina-1,4(1,3)-dibenzenacycloheptaphan-2²-one;

4⁴-chloro-3-hydroxy-2¹-methyl-3-(1-methyl-1H-imidazol-5-yl)-2¹,2²-dihydro-5-oxa-2(4,6)-quinolina-1,4(1,3)-dibenzenacycloheptaphan-2²-one;

3-amino-4⁴-chloro-2¹-methyl-3-(1-methyl-1H-imidazol-5-yl)-2¹,2²-dihydro-5-oxa-2(4,6)-quinolina-1,4(1,3)-dibenzenacycloheptaphan-2²-one;

4⁴-chloro-3-hydroxy-2¹-(methyl-d₃)-3-(1-methyl-1H-imidazol-5-yl)-2¹,2²-dihydro-5-oxa-2(4,6)-quinolina-1,4(1,3)-dibenzenacycloheptaphan-2²-one;

4⁴-chloro-2¹-cyclopropyl-3-hydroxy-3-(1-methyl-1H-imidazol-5-yl)-2¹,2²-dihydro-5-oxa-2(4,6)-quinolina-1,4(1,3)-dibenzenacycloheptaphan-2²-one;

3-amino-4⁴-chloro-2¹-cyclopropyl-3-(1-methyl-1H-imidazol-5-yl)-2¹,2²-dihydro-5-oxa-2(4,6)-quinolina-1,4(1,3)-dibenzenacycloheptaphan-2²-one;

4⁴-chloro-3-hydroxy-3-(4-methyl-4H-1,2,4-triazol-3-yl)-2¹,2²-dihydro-5-oxa-2(4,6)-quinolina-1,4(1,3)-dibenzenacycloheptaphan-2²-one;

4⁴-chloro-3-hydroxy-2¹-(methyl-d₃)-3-(4-methyl-4H-1,2,4-triazol-3-yl)-2¹,2²-dihydro-5-oxa-2(4,6)-quinolina-1,4(1,3)-dibenzenacycloheptaphan-2²-one;

4⁴-chloro-3-(methoxy-d₃)-2¹-(methyl-d₃)-3-(4-methyl-4H-1,2,4-triazol-3-yl)-2¹,2²-dihydro-5-oxa-2(4,6)-quinolina-1,4(1,3)-dibenzenacycloheptaphan-2²-one;

3-amino-4⁴-chloro-2¹-(methyl-d₃)-3-(4-methyl-4H-1,2,4-triazol-3-yl)-2¹,2²-dihydro-5-oxa-2(4,6)-quinolina-1,4(1,3)-dibenzenacycloheptaphan-2²-one;

3-amino-4⁴-chloro-2¹-cyclopropyl-3-(4-methyl-4H-1,2,4-triazol-3-yl)-2¹,2²-dihydro-5-oxa-2(4,6)-quinolina-1,4(1,3)-dibenzenacycloheptaphan-2²-one;

3-hydroxy-2¹-methyl-3-(1-methyl-1H-imidazol-5-yl)-2²-oxo-2¹,2²-dihydro-5-oxa-2(4,6)-quinolina-1,4(1,3)-dibenzenacycloheptaphane-4⁴-carbonitrile;

3-amino-2¹-methyl-3-(1-methyl-1H-imidazol-5-yl)-2²-oxo-2¹,2²-dihydro-5-oxa-2(4,6)-quinolina-1,4(1,3)-dibenzenacycloheptaphane-4⁴-carbonitrile;

3-hydroxy-2¹-methyl-3-(4-methyl-4H-1,2,4-triazol-3-yl)-2²-oxo-2¹,2²-dihydro-5-oxa-2(4,6)-quinolina-1,4(1,3)-dibenzenacycloheptaphane-4⁴-carbonitrile;

3-amino-2¹-methyl-3-(4-methyl-4H-1,2,4-triazol-3-yl)-2²-oxo-2¹,2²-dihydro-5-oxa-2(4,6)-quinolina-1,4(1,3)-dibenzenacycloheptaphane-4⁴-carbonitrile;

2²-methoxy-3-(1-methyl-1H-imidazol-5-yl)-6-oxa-2(4,6)-quinolina-1,4(1,3)-dibenzenacyclohexaphan-3-ol;

3-hydroxy-3-(1-methyl-1H-imidazol-5-yl)-2¹,2²-dihydro-6-oxa-2(4,6)-quinolina-1,4(1,3)-dibenzenacyclohexaphan-22-one;

3-hydroxy-2¹-methyl-3-(1-methyl-1H-imidazol-5-yl)-2¹,2²-dihydro-6-oxa-2(4,6)-quinolina-1,4(1,3)-dibenzenacyclohexaphan-2²-one;

4⁴-chloro-2²-methoxy-3-(1-methyl-1H-imidazol-5-yl)-6-oxa-2(4,6)-quinolina-1,4(1,3)-dibenzenacyclohexaphan-3-ol;

4⁴-chloro-3-hydroxy-3-(1-methyl-1H-imidazol-5-yl)-2¹,2²-dihydro-6-oxa-2(4,6)-quinolina-1,4(1,3)-dibenzenacyclohexaphan-2²-one;

4⁴-chloro-3-hydroxy-2¹-methyl-3-(1-methyl-1H-imidazol-5-yl)-2¹,2²-dihydro-6-oxa-2(4,6)-quinolina-1,4(1,3)-dibenzenacyclohexaphan-2²-one;

3-amino-4⁴-chloro-2¹-methyl-3-(1-methyl-1H-imidazol-5-yl)-2¹,2²-dihydro-6-oxa-2(4,6)-quinolina-1,4(1,3)-dibenzenacyclohexaphan-2²-one;

3-amino-4⁴-chloro-2¹-(methyl-d₃)-3-(1-methyl-1H-imidazol-5-yl)-2¹,2²-dihydro-6-oxa-2(4,6)-quinolina-1,4(1,3)-dibenzenacyclohexaphan-2²-one;

3-amino-4⁴-chloro-3-(1-methyl-1H-imidazol-5-yl)-6-oxa-2(4,6)-quinolina-1,4(1,3)-dibenzenacyclohexaphane-2²-carbonitrile;

4⁴-chloro-2²-methoxy-3-(4-methyl-4H-1,2,4-triazol-3-yl)-6-oxa-2(4,6)-quinolina-1,4(1,3)-dibenzenacyclohexaphan-3-ol;

4⁴-chloro-2¹-methyl-3-(4-methyl-4H-1,2,4-triazol-3-yl)-3-(methylamino)-2¹,2²-dihydro-6-oxa-2(4,6)-quinolina-1,4(1,3)-dibenzenacyclohexaphan-2²-one;

3-amino-4⁴-chloro-2¹-methyl-3-(4-methyl-4H-1,2,4-triazol-3-yl)-2¹,2²-dihydro-6-oxa-2(4,6)-quinolina-1,4(1,3)-dibenzenacyclohexaphan-2²-one;

4⁴-bromo-2²-methoxy-3-(1-methyl-1H-imidazol-5-yl)-6-oxa-2(4,6)-quinolina-1,4(1,3)-dibenzenacyclohexaphan-3-ol;

3-hydroxy-2²-methoxy-3-(1-methyl-1H-imidazol-5-yl)-6-oxa-2(4,6)-quinolina-1,4(1,3)-dibenzenacyclohexaphane-4⁴-carbonitrile;

3-hydroxy-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile;

3-hydroxy-2¹-(methyl-d₃)-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile;

3-amino-$2^1$-(methyl-$d_3$)-3-(1-methyl-1H-imidazol-5-yl)-$2^2$-oxo-$2^1,2^2$-dihydro-6-oxa-2(4,6)-quinolina-1,4(1,3)-dibenzenacyclohexaphane-$4^4$-carbonitrile;

3-amino-$2^1$-cyclopropyl-3-(1-methyl-1H-imidazol-5-yl)-$2^2$-oxo-$2^1,2^2$-dihydro-6-oxa-2(4,6)-quinolina-1,4(1,3)-dibenzenacyclohexaphane-$4^4$-carbonitrile;

3-amino-3-(1-methyl-1H-imidazol-5-yl)-6-oxa-2(4,6)-quinolina-1,4(1,3)-dibenzenacyclohexaphane-$2^2,4^4$-dicarbonitrile;

$4^6$-chloro-$2^2$-methoxy-3-(1-methyl-1H-imidazol-5-yl)-6-oxa-2(4,6)-quinolina-4(3,5)-pyridina-1(1,3)-benzenacyclohexaphan-3-ol;

3-hydroxy-$2^2$-methoxy-3-(1-methyl-1H-imidazol-5-yl)-6-oxa-2(4,6)-quinolina-4(3,5)-pyridina-1(1,3)-benzenacyclohexaphane-$4^6$-carbonitrile;

3-hydroxy-$2^1$-(methyl-$d_3$)-3-(1-methyl-1H-imidazol-5-yl)-$2^2$-oxo-$2^1,2^2$-dihydro-6-oxa-2(4,6)-quinolina-4(3,5)-pyridina-1(1,3)-benzenacyclohexaphane-$4^6$-carbonitrile;

3-amino-$2^1$-(methyl-$d_3$)-3-(1-methyl-1H-imidazol-5-yl)-$2^2$-oxo-$2^1,2^2$-dihydro-6-oxa-2(4,6)-quinolina-4(3,5)-pyridina-1(1,3)-benzenacyclohexaphane-$4^6$-carbonitrile;

3-hydroxy-$2^1$-methyl-3-(1-methyl-1H-imidazol-5-yl)-$2^1,2^2$-dihydro-7-oxa-2(4,6)-quinolina-1,4(1,3)-dibenzenacycloheptaphan-$2^2$-one;

$4^4$-chloro-$2^2$-methoxy-3-(1-methyl-1H-imidazol-5-yl)-7-oxa-2(4,6)-quinolina-1,4(1,3)-dibenzenacycloheptaphan-3-ol;

$4^4$-chloro-3-hydroxy-$2^1$-methyl-3-(1-methyl-1H-imidazol-5-yl)-$2^1,2^2$-dihydro-7-oxa-2(4,6)-quinolina-1,4(1,3)-dibenzenacycloheptaphan-$2^2$-one;

3-amino-3-(1-methyl-1H-imidazol-5-yl)-$2^2$-morpholino-6-oxa-2(4,6)-quinolina-1,4(1,3)-dibenzenacyclohexaphane-$4^4$-carbonitrile;

3-amino-3-(1-methyl-1H-imidazol-5-yl)-$2^2$-(piperazin-1-yl)-6-oxa-2(4,6)-quinolina-1,4(1,3)-dibenzenacyclohexaphane-$4^4$-carbonitrile;

3-amino-3-(1-methyl-1H-imidazol-5-yl)-$2^2$-(oxetan-3-ylamino)-6-oxa-2(4,6)-quinolina-1,4(1,3)-dibenzenacyclohexaphane-$4^4$-carbonitrile;

3-amino-$2^1$-(2,3-dihydroxypropyl)-3-(1-methyl-1H-imidazol-5-yl)-$2^2$-oxo-$2^1,2^2$-dihydro-6-oxa-2(4,6)-quinolina-1,4(1,3)-dibenzenacyclohexaphane-$4^4$-carbonitrile;

3-amino-3-(1-(methyl-$d_3$)-1H-imidazol-5-yl)-6-oxa-2(4,6)-quinolina-1,4(1,3)-dibenzenacyclohexaphane-$2^2,4^4$-dicarbonitrile;

$4^4$-bromo-$2^2$-chloro-3-(1-methyl-1H-imidazol-5-yl)-6-oxa-2(4,6)-quinolina-1,4(1,3)-dibenzenacyclohexaphan-3-ol;

3-hydroxy-3-(1-methyl-1H-imidazol-5-yl)-6-oxa-2(4,6)-quinolina-1,4(1,3)-dibenzenacyclohexaphane-$2^2,4^4$-dicarbonitrile;

$4^4$-cyano-3-hydroxy-3-(1-methyl-1H-imidazol-5-yl)-6-oxa-2(4,6)-quinolina-1,4(1,3)-dibenzenacyclohexaphane-$2^2$-carboxamide;

$4^4$-bromo-$2^2$-chloro-3-(1-methyl-1H-imidazol-5-yl)-6-oxa-2(4,6)-quinolina-1,4(1,3)-dibenzenacyclohexaphan-3-amine;

$4^4$-bromo-3-(1-methyl-1H-imidazol-5-yl)-$2^2$-(oxetan-3-yloxy)-6-oxa-2(4,6)-quinolina-1,4(1,3)-dibenzenacyclohexaphan-3-amine;

$4^4$-chloro-$2^1$-(methyl-$d_3$)-3-(5-methyl-1H-imidazol-1-yl)-$2^1,2^2$-dihydro-6-oxa-2(4,6)-quinolina-1,4(1,3)-dibenzenacyclohexaphan-$2^2$-one;

$4^4$-chloro-$2^1$-(methyl-$d_3$)-3-(4-methyl-1H-imidazol-1-yl)-$2^1,2^2$-dihydro-6-oxa-2(4,6)-quinolina-1,4(1,3)-dibenzenacyclohexaphan-$2^2$-one;

3-hydroxy-3-(1-(methyl-$d_3$)-1H-imidazol-5-yl)-6-oxa-2(4,6)-quinolina-1,4(1,3)-dibenzenacyclohexaphane-$2^2,4^4$-dicarbonitrile;

$4^4$-chloro-$2^1$-(methyl-$d_3$)-3-(5-methyl-1H-1,2,4-triazol-1-yl)-$2^1,2^2$-dihydro-6-oxa-2(4,6)-quinolina-1,4(1,3)-dibenzenacyclohexaphan-$2^2$-one;

$4^4$-chloro-$2^1$-(methyl-$d_3$)-3-(3-methyl-1H-1,2,4-triazol-1-yl)-$2^1,2^2$-dihydro-6-oxa-2(4,6)-quinolina-1,4(1,3)-dibenzenacyclohexaphan-$2^2$-one;

$4^4$-bromo-$2^2$-chloro-3-(1-methyl-1H-imidazol-5-yl)-6-oxa-2(4,6)-quinazolina-1,4(1,3)-dibenzenacyclohexaphan-3-ol;

$4^4$-bromo-3-(1-methyl-1H-imidazol-5-yl)-6-oxa-2(4,6)-quinazolina-1,4(1,3)-dibenzenacyclohexaphane-$2^2$,3-diamine;

$4^4$-bromo-3-(1-methyl-1H-imidazol-5-yl)-6-oxa-2(4,6)-isoquinolina-1,4(1,3)-dibenzenacyclohexaphan-3-ol;

$4^4$-bromo-3-(1-methyl-1H-imidazol-5-yl)-6-oxa-2(1,7)-isoquinolina-1,4(1,3)-dibenzenacyclohexaphan-3-ol;

3-hydroxy-3-(1-methyl-1H-imidazol-5-yl)-6-oxa-2(1,7)-isoquinolina-1,4(1,3)-dibenzenacyclohexaphane-$4^4$-carbonitrile;

3-amino-3-(1-methyl-1H-imidazol-5-yl)-6-oxa-2(1,7)-isoquinolina-1,4(1,3)-dibenzenacyclohexaphane-$4^4$-carbonitrile;

$4^4$-bromo-$2^7$-methoxy-3-(1-methyl-1H-imidazol-5-yl)-6-oxa-2(5,3)-quinolina-1,4(1,3)-dibenzenacyclohexaphan-3-ol;

3-hydroxy-$2^7$-methoxy-3-(1-methyl-1H-imidazol-5-yl)-6-oxa-2(5,3)-quinolina-1,4(1,3)-dibenzenacyclohexaphane-$4^4$-carbonitrile;

3-amino-3-(1-methyl-1H-imidazol-5-yl)-$2^2$-(oxetan-3-yloxy)-6-oxa-2(4,6)-quinolina-1,4(1,3)-dibenzenacyclohexaphane-$4^4$-carbonitrile;

3-(4-methyl-1H-imidazol-1-yl)-6-oxa-2(4,6)-quinolina-1,4(1,3)-dibenzenacyclohexaphane-$2^2,4^4$-dicarbonitrile;

3-(5-methyl-1H-imidazol-1-yl)-6-oxa-2(4,6)-quinolina-1,4(1,3)-dibenzenacyclohexaphane-$2^2,4^4$-dicarbonitrile;

3-amino-$4^4$-chloro-$2^1$-cyclopropyl-3-(1-methyl-1H-imidazol-5-yl)-$2^1,2^2$-dihydro-5-oxa-2(4,6)-quinolina-1,4(1,3)-dibenzenacyclohexaphan-$2^2$-one;

$4^4$-chloro-$2^1$-cyclopropyl-3-hydroxy-3-(1-methyl-1H-imidazol-5-yl)-$2^1,2^2$-dihydro-2(4,6)-quinolina-1,4(1,3)-dibenzenacyclohexaphan-$2^2$-one;

$4^4$-chloro-$2^1$-cyclopropyl-3-hydroxy-3-(1-methyl-1H-imidazol-5-yl)-$2^1,2^2$-dihydro-7-oxa-2(4,6)-quinolina-1,4(1,3)-dibenzenacycloheptaphan-$2^2$-one;

$4^4$-chloro-$2^1$-cyclopropyl-3-hydroxy-3-(1-methyl-1H-imidazol-5-yl)-$2^1,2^2$-dihydro-6-oxa-2(4,6)-quinolina-1,4(1,3)-dibenzenacyclohexaphan-$2^2$-one;

$4^4$-chloro-$2^1$-cyclopropyl-3-((2-fluoroethyl)amino)-3-(1-methyl-1H-imidazol-5-yl)-$2^1,2^2$-dihydro-5-oxa-2(4,6)-quinolina-1,4(1,3)-dibenzenacyclohexaphan-$2^2$-one;

$4^4$-chloro-$2^1$-cyclopropyl-3-((2-fluoroethyl)amino)-3-(1-methyl-1H-imidazol-5-yl)-$2^1,2^2$-dihydro-5-oxa-2(4,6)-quinolina-1,4(1,3)-dibenzenacycloheptaphan-$2^2$-one;

$4^4$-chloro-$2^1$-cyclopropyl-3-((2-fluoroethyl)amino)-3-(1-methyl-1H-imidazol-5-yl)-$2^1,2^2$-dihydro-2(4,6)-quinolina-1,4(1,3)-dibenzenacyclohexaphan-$2^2$-one;

$4^4$-chloro-$2^1$-cyclopropyl-3-((2-fluoroethyl)amino)-3-(1-methyl-1H-imidazol-5-yl)-$2^1,2^2$-dihydro-7-oxa-2(4,6)-quinolina-1,4(1,3)-dibenzenacycloheptaphan-$2^2$-one;

$4^4$-chloro-$2^1$-cyclopropyl-3-((2-fluoroethyl)amino)-3-(1-methyl-1H-imidazol-5-yl)-$2^1$,$2^2$-dihydro-6-oxa-2(4,6)-quinolina-1,4(1,3)-dibenzenacyclohexaphan-$2^2$-one;

$4^4$-chloro-3-((2-chloroethyl)amino)-$2^1$-cyclopropyl-3-(1-methyl-1H-imidazol-5-yl)-$2^1$,$2^2$-dihydro-5-oxa-2(4,6)-quinolina-1,4(1,3)-dibenzenacyclohexaphan-$2^2$-one;

$4^4$-chloro-3-((2-chloroethyl)amino)-$2^1$-cyclopropyl-3-(1-methyl-1H-imidazol-5-yl)-$2^1$,$2^2$-dihydro-5-oxa-2(4,6)-quinolina-1,4(1,3)-dibenzenacycloheptaphan-$2^2$-one;

$4^4$-chloro-3-((2-chloroethyl)amino)-$2^1$-cyclopropyl-3-(1-methyl-1H-imidazol-5-yl)-$2^1$,$2^2$-dihydro-2(4,6)-quinolina-1,4(1,3)-dibenzenacyclohexaphan-$2^2$-one;

$4^4$-chloro-3-((2-chloroethyl)amino)-$2^1$-cyclopropyl-3-(1-methyl-1H-imidazol-5-yl)-$2^1$,$2^2$-dihydro-7-oxa-2(4,6)-quinolina-1,4(1,3)-dibenzenacycloheptaphan-$2^2$-one;

$4^4$-chloro-3-((2-chloroethyl)amino)-$2^1$-cyclopropyl-3-(1-methyl-1H-imidazol-5-yl)-$2^1$,$2^2$-dihydro-6-oxa-2(4,6)-quinolina-1,4(1,3)-dibenzenacyclohexaphan-$2^2$-one;

$4^4$-chloro-$2^1$-cyclopropyl-3-(1-methyl-1H-imidazol-5-yl)-3-morpholino-$2^1$,$2^2$-dihydro-5-oxa-2(4,6)-quinolina-1,4(1,3)-dibenzenacyclohexaphan-$2^2$-one;

$4^4$-chloro-$2^1$-cyclopropyl-3-(1-methyl-1H-imidazol-5-yl)-3-morpholino-$2^1$,$2^2$-dihydro-5-oxa-2(4,6)-quinolina-1,4(1,3)-dibenzenacycloheptaphan-$2^2$-one;

$4^4$-chloro-$2^1$-cyclopropyl-3-(1-methyl-1H-imidazol-5-yl)-3-morpholino-$2^1$,$2^2$-dihydro-2(4,6)-quinolina-1,4(1,3)-dibenzenacyclohexaphan-$2^2$-one;

$4^4$-chloro-$2^1$-cyclopropyl-3-(1-methyl-1H-imidazol-5-yl)-3-morpholino-$2^1$,$2^2$-dihydro-7-oxa-2(4,6)-quinolina-1,4(1,3)-dibenzenacycloheptaphan-$2^2$-one;

$4^4$-chloro-$2^1$-cyclopropyl-3-(1-methyl-1H-imidazol-5-yl)-3-morpholino-$2^1$,$2^2$-dihydro-6-oxa-2(4,6)-quinolina-1,4(1,3)-dibenzenacyclohexaphane;

$4^4$-chloro-3-(1-methyl-1H-imidazol-5-yl)-5-oxa-2(4,6)-quinolina-1,4(1,3)-dibenzenacyclohexaphan-3-amine;

$4^4$-chloro-3-(1-methyl-1H-imidazol-5-yl)-5-oxa-2(4,6)-quinolina-1,4(1,3)-dibenzenacycloheptaphan-3-ol;

$4^4$-chloro-3-(1-methyl-1H-imidazol-5-yl)-2(4,6)-quinolina-1,4(1,3)-dibenzenacyclohexaphan-3-ol;

$4^4$-chloro-3-(1-methyl-1H-imidazol-5-yl)-7-oxa-2(4,6)-quinolina-1,4(1,3)-dibenzenacycloheptaphan-3-ol;

$4^4$-chloro-3-(1-methyl-1H-imidazol-5-yl)-6-oxa-2(4,6)-quinolina-1,4(1,3)-dibenzenacyclohexaphan-3-ol;

$4^4$-chloro-3-(1-methyl-1H-imidazol-5-yl)-5-oxa-2(1,7)-isoquinolina-1,4(1,3)-dibenzenacyclohexaphan-3-amine;

$4^4$-chloro-3-(1-methyl-1H-imidazol-5-yl)-5-oxa-2(1,7)-isoquinolina-1,4(1,3)-dibenzenacycloheptaphan-3-ol;

$4^4$-chloro-3-(1-methyl-1H-imidazol-5-yl)-2(1,7)-isoquinolina-1,4(1,3)-dibenzenacyclohexaphan-3-ol;

$4^4$-chloro-3-(1-methyl-1H-imidazol-5-yl)-7-oxa-2(1,7)-isoquinolina-1,4(1,3)-dibenzenacycloheptaphan-3-ol;

$4^4$-chloro-3-(1-methyl-1H-imidazol-5-yl)-6-oxa-2(1,7)-isoquinolina-1,4(1,3)-dibenzenacyclohexaphan-3-ol;

$4^4$-chloro-N-(2-fluoroethyl)-3-(1-methyl-1H-imidazol-5-yl)-5-oxa-2(1,7)-isoquinolina-1,4(1,3)-dibenzenacyclohexaphan-3-amine;

$4^4$-chloro-N-(2-fluoroethyl)-3-(1-methyl-1H-imidazol-5-yl)-5-oxa-2(1,7)-isoquinolina-1,4(1,3)-dibenzenacycloheptaphan-3-amine;

$4^4$-chloro-N-(2-fluoroethyl)-3-(1-methyl-1H-imidazol-5-yl)-2(1,7)-isoquinolina-1,4(1,3)-dibenzenacyclohexaphan-3-amine;

$4^4$-chloro-N-(2-fluoroethyl)-3-(1-methyl-1H-imidazol-5-yl)-7-oxa-2(1,7)-isoquinolina-1,4(1,3)-dibenzenacycloheptaphan-3-amine;

$4^4$-chloro-N-(2-fluoroethyl)-3-(1-methyl-1H-imidazol-5-yl)-6-oxa-2(1,7)-isoquinolina-1,4(1,3)-dibenzenacyclohexaphan-3-amine;

$4^4$-chloro-N-(2-chloroethyl)-3-(1-methyl-1H-imidazol-5-yl)-5-oxa-2(1,7)-isoquinolina-1,4(1,3)-dibenzenacyclohexaphan-3-amine;

$4^4$-chloro-N-(2-chloroethyl)-3-(1-methyl-1H-imidazol-5-yl)-5-oxa-2(1,7)-isoquinolina-1,4(1,3)-dibenzenacycloheptaphan-3-amine;

$4^4$-chloro-N-(2-chloroethyl)-3-(1-methyl-1H-imidazol-5-yl)-2(1,7)-isoquinolina-1,4(1,3)-dibenzenacyclohexaphan-3-amine;

$4^4$-chloro-N-(2-chloroethyl)-3-(1-methyl-1H-imidazol-5-yl)-7-oxa-2(1,7)-isoquinolina-1,4(1,3)-dibenzenacycloheptaphan-3-amine;

$4^4$-chloro-N-(2-chloroethyl)-3-(1-methyl-1H-imidazol-5-yl)-6-oxa-2(1,7)-isoquinolina-1,4(1,3)-dibenzenacyclohexaphan-3-amine;

$4^4$-chloro-3-(1-methyl-1H-imidazol-5-yl)-3-morpholino-5-oxa-2(1,7)-isoquinolina-1,4(1,3)-dibenzenacyclohexaphane;

$4^4$-chloro-3-(1-methyl-1H-imidazol-5-yl)-3-morpholino-5-oxa-2(1,7)-isoquinolina-1,4(1,3)-dibenzenacycloheptaphane;

4-($4^4$-chloro-3-(1-methyl-1H-imidazol-5-yl)-2(1,7)-isoquinolina-1,4(1,3)-dibenzenacyclohexaphane-3-yl)morpholine;

$4^4$-chloro-3-(1-methyl-1H-imidazol-5-yl)-3-morpholino-7-oxa-2(1,7)-isoquinolina-1,4(1,3)-dibenzenacycloheptaphane; and $4^4$-chloro-3-(1-methyl-1H-imidazol-5-yl)-3-morpholino-6-oxa-2(1,7)-isoquinolina-1,4(1,3)-dibenzenacyclohexaphane;

including an (R)- or (S)-enantiomer or racemate thereof, or a pharmaceutically acceptable form thereof.

194. The compound of claim 193, wherein the compound is an (R)-enantiomer, or a pharmaceutically acceptable form thereof.

195. The compound of claim 193, wherein the compound is an (S)-enantiomer, or a pharmaceutically acceptable form thereof.

196. A pharmaceutical composition comprising the compound or pharmaceutically acceptable form thereof of claim 193 and a pharmaceutically acceptable carrier, excipient, or diluent.

197. The compound of claim 193, wherein the compound is selected from:

3-hydroxy-3-(1-methyl-1H-imidazol-5-yl)-$2^1$,$2^2$-dihydro-2(4,6)-quinolina-1,4(1,3)-dibenzenacyclohexaphan-$2^2$-one;

3-hydroxy-$2^1$-methyl-3-(1-methyl-1H-imidazol-5-yl)-$2^1$,$2^2$-dihydro-2(4,6)-quinolina-1,4(1,3)-dibenzenacyclohexaphan-22-one;

$4^4$-chloro-3-hydroxy-$2^1$-methyl-3-(1-methyl-1H-imidazol-5-yl)-$2^1$,$2^2$-dihydro-2(4,6)-quinolina-1,4(1,3)-dibenzenacyclohexaphan-$2^2$-one;

3-amino-$4^4$-chloro-$2^1$-methyl-3-(1-methyl-1H-imidazol-5-yl)-$2^1$,$2^2$-dihydro-2(4,6)-quinolina-1,4(1,3)-dibenzenacyclohexaphan-$2^2$-one;

3-hydroxy-$2^1$-methyl-3-(1-methyl-1H-imidazol-5-yl)-$2^2$-oxo-$2^1$,$2^2$-dihydro-2(4,6)-quinolina-1,4(1,3)-dibenzenacyclohexaphane-$4^4$-carbonitrile;

3-amino-$2^1$-methyl-3-(1-methyl-1H-imidazol-5-yl)-$2^2$-oxo-$2^1$,$2^2$-dihydro-2(4,6)-quinolina-1,4(1,3)-dibenzenacyclohexaphane-$4^4$-carbonitrile;

3-amino-2¹-(methyl-d₃)-3-(1-methyl-1H-imidazol-5-yl)-2²-oxo-2¹,2²-dihydro-2(4,6)-quinolina-1,4(1,3)-dibenzenacyclohexaphane-4⁴-carbonitrile;

3-hydroxy-2¹-methyl-3-(1-methyl-1H-imidazol-5-yl)-2¹,2²-dihydro-5-oxa-2(4,6)-quinolina-1,4(1,3)-dibenzenacyclohexaphan-2²-one;

4⁴-chloro-3-hydroxy-3-(1-methyl-1H-imidazol-5-yl)-2¹,2²-dihydro-5-oxa-2(4,6)-quinolina-1,4(1,3)-dibenzenacyclohexaphan-2²-one;

4⁴-chloro-3-hydroxy-2¹-methyl-3-(1-methyl-1H-imidazol-5-yl)-2¹,2²-dihydro-5-oxa-2(4,6)-quinolina-1,4(1,3)-dibenzenacyclohexaphan-2²-one;

3-amino-4⁴-chloro-2¹-methyl-3-(1-methyl-1H-imidazol-5-yl)-2¹,2²-dihydro-5-oxa-2(4,6)-quinolina-1,4(1,3)-dibenzenacyclohexaphan-2²-one;

3-hydroxy-3-(1-methyl-1H-imidazol-5-yl)-2²-oxo-2¹,2²-dihydro-5-oxa-2(4,6)-quinolina-1,4(1,3)-dibenzenacyclohexaphane-4⁴-carbonitrile;

3-hydroxy-2¹-methyl-3-(1-methyl-1H-imidazol-5-yl)-2²-oxo-2¹,2²-dihydro-5-oxa-2(4,6)-quinolina-1,4(1,3)-dibenzenacyclohexaphane-4⁴-carbonitrile;

3-amino-2¹-methyl-3-(1-methyl-1H-imidazol-5-yl)-2²-oxo-2¹,2²-dihydro-5-oxa-2(4,6)-quinolina-1,4(1,3)-dibenzenacyclohexaphane-4⁴-carbonitrile;

3-amino-2¹-(methyl-d₃)-3-(1-methyl-1H-imidazol-5-yl)-2²-oxo-2¹,2²-dihydro-5-oxa-2(4,6)-quinolina-1,4(1,3)-dibenzenacyclohexaphane-4⁴-carbonitrile;

3-hydroxy-3-(1-methyl-1H-imidazol-5-yl)-2¹,2²-dihydro-5-oxa-2(4,6)-quinolina-1,4(1,3)-dibenzenacycloheptaphan-2²-one;

3-hydroxy-2¹-methyl-3-(1-methyl-1H-imidazol-5-yl)-2¹,2²-dihydro-5-oxa-2(4,6)-quinolina-1,4(1,3)-dibenzenacycloheptaphan-2²-one;

4⁴-chloro-3-hydroxy-3-(1-methyl-1H-imidazol-5-yl)-2¹,2²-dihydro-5-oxa-2(4,6)-quinolina-1,4(1,3)-dibenzenacycloheptaphan-2²-one;

4⁴-chloro-3-hydroxy-2¹-methyl-3-(1-methyl-1H-imidazol-5-yl)-2¹,2²-dihydro-5-oxa-2(4,6)-quinolina-1,4(1,3)-dibenzenacycloheptaphan-2²-one;

3-amino-4⁴-chloro-2¹-methyl-3-(1-methyl-1H-imidazol-5-yl)-2¹,2²-dihydro-5-oxa-2(4,6)-quinolina-1,4(1,3)-dibenzenacycloheptaphan-2²-one;

4⁴-chloro-3-hydroxy-2¹-(methyl-d₃)-3-(1-methyl-1H-imidazol-5-yl)-2¹,2²-dihydro-5-oxa-2(4,6)-quinolina-1,4(1,3)-dibenzenacycloheptaphan-2²-one;

4⁴-chloro-2¹-cyclopropyl-3-hydroxy-3-(1-methyl-1H-imidazol-5-yl)-2¹,2²-dihydro-5-oxa-2(4,6)-quinolina-1,4(1,3)-dibenzenacycloheptaphan-2²-one;

3-amino-4⁴-chloro-2¹-cyclopropyl-3-(1-methyl-1H-imidazol-5-yl)-2¹,2²-dihydro-5-oxa-2(4,6)-quinolina-1,4(1,3)-dibenzenacycloheptaphan-2²-one;

4⁴-chloro-3-hydroxy-3-(4-methyl-4H-1,2,4-triazol-3-yl)-2¹,2²-dihydro-5-oxa-2(4,6)-quinolina-1,4(1,3)-dibenzenacycloheptaphan-2²-one;

4⁴-chloro-3-hydroxy-2¹-(methyl-d₃)-3-(4-methyl-4H-1,2,4-triazol-3-yl)-2¹,2²-dihydro-5-oxa-2(4,6)-quinolina-1,4(1,3)-dibenzenacycloheptaphan-2²-one;

4⁴-chloro-3-(methoxy-d₃)-2¹-(methyl-d₃)-3-(4-methyl-4H-1,2,4-triazol-3-yl)-2¹,2²-dihydro-5-oxa-2(4,6)-quinolina-1,4(1,3)-dibenzenacycloheptaphan-2²-one;

3-amino-4⁴-chloro-2¹-(methyl-d₃)-3-(4-methyl-4H-1,2,4-triazol-3-yl)-2¹,2²-dihydro-5-oxa-2(4,6)-quinolina-1,4(1,3)-dibenzenacycloheptaphan-2²-one;

3-amino-4⁴-chloro-2¹-cyclopropyl-3-(4-methyl-4H-1,2,4-triazol-3-yl)-2¹,2²-dihydro-5-oxa-2(4,6)-quinolina-1,4(1,3)-dibenzenacycloheptaphan-2²-one;

3-hydroxy-2¹-methyl-3-(1-methyl-1H-imidazol-5-yl)-2²-oxo-2¹,2²-dihydro-5-oxa-2(4,6)-quinolina-1,4(1,3)-dibenzenacycloheptaphane-4⁴-carbonitrile;

3-amino-2¹-methyl-3-(1-methyl-1H-imidazol-5-yl)-2²-oxo-2¹,2²-dihydro-5-oxa-2(4,6)-quinolina-1,4(1,3)-dibenzenacycloheptaphane-4⁴-carbonitrile;

3-hydroxy-2¹-methyl-3-(4-methyl-4H-1,2,4-triazol-3-yl)-2²-oxo-2¹,2²-dihydro-5-oxa-2(4,6)-quinolina-1,4(1,3)-dibenzenacycloheptaphane-4⁴-carbonitrile;

3-amino-2¹-methyl-3-(4-methyl-4H-1,2,4-triazol-3-yl)-2²-oxo-2¹,2²-dihydro-5-oxa-2(4,6)-quinolina-1,4(1,3)-dibenzenacycloheptaphane-4⁴-carbonitrile;

3-hydroxy-3-(1-methyl-1H-imidazol-5-yl)-2¹,2²-dihydro-6-oxa-2(4,6)-quinolina-1,4(1,3)-dibenzenacyclohexaphan-2²-one;

3-hydroxy-2¹-methyl-3-(1-methyl-1H-imidazol-5-yl)-2¹,2²-dihydro-6-oxa-2(4,6)-quinolina-1,4(1,3)-dibenzenacyclohexaphan-2²-one;

4⁴-chloro-3-hydroxy-3-(1-methyl-1H-imidazol-5-yl)-2¹,2²-dihydro-6-oxa-2(4,6)-quinolina-1,4(1,3)-dibenzenacyclohexaphan-2²-one;

4⁴-chloro-3-hydroxy-2¹-methyl-3-(1-methyl-1H-imidazol-5-yl)-2¹,2²-dihydro-6-oxa-2(4,6)-quinolina-1,4(1,3)-dibenzenacyclohexaphan-2²-one;

3-amino-4⁴-chloro-2¹-methyl-3-(1-methyl-1H-imidazol-5-yl)-2¹,2²-dihydro-6-oxa-2(4,6)-quinolina-1,4(1,3)-dibenzenacyclohexaphan-2²-one;

3-amino-4⁴-chloro-2¹-(methyl-d₃)-3-(1-methyl-1H-imidazol-5-yl)-2¹,2²-dihydro-6-oxa-2(4,6)-quinolina-1,4(1,3)-dibenzenacyclohexaphan-2²-one;

4⁴-chloro-2¹-methyl-3-(4-methyl-4H-1,2,4-triazol-3-yl)-3-(methylamino)-2¹,2²-dihydro-6-oxa-2(4,6)-quinolina-1,4(1,3)-dibenzenacyclohexaphan-2²-one;

3-amino-4⁴-chloro-2¹-methyl-3-(4-methyl-4H-1,2,4-triazol-3-yl)-2¹,2²-dihydro-6-oxa-2(4,6)-quinolina-1,4(1,3)-dibenzenacyclohexaphan-2²-one;

3-hydroxy-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile;

3-hydroxy-2¹-(methyl-d₃)-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile;

3-amino-2¹-(methyl-d₃)-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile;

3-amino-2¹-cyclopropyl-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile;

3-hydroxy-2¹-(methyl-d₃)-3-(1-methyl-1H-imidazol-5-yl)-2²-oxo-2¹,2²-dihydro-6-oxa-2(4,6)-quinolina-4(3,5)-pyridina-1(1,3)-benzenacyclohexaphane-4⁶-carbonitrile;

3-amino-2¹-(methyl-d₃)-3-(1-methyl-1H-imidazol-5-yl)-2²-oxo-2¹,2²-dihydro-6-oxa-2(4,6)-quinolina-4(3,5)-pyridina-1(1,3)-benzenacyclohexaphane-4⁶-carbonitrile;

3-hydroxy-2¹-methyl-3-(1-methyl-1H-imidazol-5-yl)-2¹,2²-dihydro-7-oxa-2(4,6)-quinolina-1,4(1,3)-dibenzenacycloheptaphan-2²-one;

4⁴-chloro-3-hydroxy-2¹-methyl-3-(1-methyl-1H-imidazol-5-yl)-2¹,2²-dihydro-7-oxa-2(4,6)-quinolina-1,4(1,3)-dibenzenacycloheptaphan-2²-one;

3-amino-2¹-(2,3-dihydroxypropyl)-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile;

$4^4$-chloro-$2^1$-(methyl-d$_3$)-3-(5-methyl-1H-imidazol-1-yl)-$2^1$,$2^2$-dihydro-6-oxa-2(4,6)-quinolina-1,4(1,3)-dibenzenacyclohexaphan-$2^2$-one;

$4^4$-chloro-$2^1$-(methyl-d$_3$)-3-(4-methyl-1H-imidazol-1-yl)-$2^1$,$2^2$-dihydro-6-oxa-2(4,6)-quinolina-1,4(1,3)-dibenzenacyclohexaphan-$2^2$-one;

$4^4$-chloro-$2^1$-(methyl-d$_3$)-3-(5-methyl-1H-1,2,4-triazol-1-yl)-$2^1$,$2^2$-dihydro-6-oxa-2(4,6)-quinolina-1,4(1,3)-dibenzenacyclohexaphan-$2^2$-one;

$4^4$-chloro-$2^1$-(methyl-d$_3$)-3-(3-methyl-1H-1,2,4-triazol-1-yl)-$2^1$,$2^2$-dihydro-6-oxa-2(4,6)-quinolina-1,4(1,3)-dibenzenacyclohexaphan-$2^2$-one;

3-amino-$4^4$-chloro-$2^1$-cyclopropyl-3-(1-methyl-1H-imidazol-5-yl)-$2^1$,$2^2$-dihydro-5-oxa-2(4,6)-quinolina-1,4(1,3)-dibenzenacyclohexaphan-$2^2$-one;

$4^4$-chloro-$2^1$-cyclopropyl-3-hydroxy-3-(1-methyl-1H-imidazol-5-yl)-$2^1$,$2^2$-dihydro-2(4,6)-quinolina-1,4(1,3)-dibenzenacyclohexaphan-$2^2$-one;

$4^4$-chloro-$2^1$-cyclopropyl-3-hydroxy-3-(1-methyl-1H-imidazol-5-yl)-$2^1$,$2^2$-dihydro-7-oxa-2(4,6)-quinolina-1,4(1,3)-dibenzenacycloheptaphan-$2^2$-one;

$4^4$-chloro-$2^1$-cyclopropyl-3-hydroxy-3-(1-methyl-1H-imidazol-5-yl)-$2^1$,$2^2$-dihydro-6-oxa-2(4,6)-quinolina-1,4(1,3)-dibenzenacyclohexaphan-$2^2$-one;

$4^4$-chloro-$2^1$-cyclopropyl-3-((2-fluoroethyl)amino)-3-(1-methyl-1H-imidazol-5-yl)-$2^1$,$2^2$-dihydro-5-oxa-2(4,6)-quinolina-1,4(1,3)-dibenzenacyclohexaphan-$2^2$-one;

$4^4$-chloro-$2^1$-cyclopropyl-3-((2-fluoroethyl)amino)-3-(1-methyl-1H-imidazol-5-yl)-$2^1$,$2^2$-dihydro-5-oxa-2(4,6)-quinolina-1,4(1,3)-dibenzenacycloheptaphan-$2^2$-one;

$4^4$-chloro-$2^1$-cyclopropyl-3-((2-fluoroethyl)amino)-3-(1-methyl-1H-imidazol-5-yl)-$2^1$,$2^2$-dihydro-2(4,6)-quinolina-1,4(1,3)-dibenzenacyclohexaphan-$2^2$-one;

$4^4$-chloro-$2^1$-cyclopropyl-3-((2-fluoroethyl)amino)-3-(1-methyl-1H-imidazol-5-yl)-$2^1$,$2^2$-dihydro-7-oxa-2(4,6)-quinolina-1,4(1,3)-dibenzenacycloheptaphan-$2^2$-one;

$4^4$-chloro-$2^1$-cyclopropyl-3-((2-fluoroethyl)amino)-3-(1-methyl-1H-imidazol-5-yl)-$2^1$,$2^2$-dihydro-6-oxa-2(4,6)-quinolina-1,4(1,3)-dibenzenacyclohexaphan-$2^2$-one;

$4^4$-chloro-3-((2-chloroethyl)amino)-$2^1$-cyclopropyl-3-(1-methyl-1H-imidazol-5-yl)-$2^1$,$2^2$-dihydro-5-oxa-2(4,6)-quinolina-1,4(1,3)-dibenzenacyclohexaphan-$2^2$-one;

$4^4$-chloro-3-((2-chloroethyl)amino)-$2^1$-cyclopropyl-3-(1-methyl-1H-imidazol-5-yl)-$2^1$,$2^2$-dihydro-5-oxa-2(4,6)-quinolina-1,4(1,3)-dibenzenacycloheptaphan-$2^2$-one;

$4^4$-chloro-3-((2-chloroethyl)amino)-$2^1$-cyclopropyl-3-(1-methyl-1H-imidazol-5-yl)-$2^1$,$2^2$-dihydro-2(4,6)-quinolina-1,4(1,3)-dibenzenacyclohexaphan-$2^2$-one;

$4^4$-chloro-3-((2-chloroethyl)amino)-$2^1$-cyclopropyl-3-(1-methyl-1H-imidazol-5-yl)-$2^1$,$2^2$-dihydro-7-oxa-2(4,6)-quinolina-1,4(1,3)-dibenzenacycloheptaphan-$2^2$-one;

$4^4$-chloro-3-((2-chloroethyl)amino)-$2^1$-cyclopropyl-3-(1-methyl-1H-imidazol-5-yl)-$2^1$,$2^2$-dihydro-6-oxa-2(4,6)-quinolina-1,4(1,3)-dibenzenacyclohexaphan-$2^2$-one;

$4^4$-chloro-$2^1$-cyclopropyl-3-(1-methyl-1H-imidazol-5-yl)-3-morpholino-$2^1$,$2^2$-dihydro-5-oxa-2(4,6)-quinolina-1,4(1,3)-dibenzenacyclohexaphan-$2^2$-one;

$4^4$-chloro-$2^1$-cyclopropyl-3-(1-methyl-1H-imidazol-5-yl)-3-morpholino-$2^1$,$2^2$-dihydro-5-oxa-2(4,6)-quinolina-1,4(1,3)-dibenzenacycloheptaphan-$2^2$-one;

$4^4$-chloro-$2^1$-cyclopropyl-3-(1-methyl-1H-imidazol-5-yl)-3-morpholino-$2^1$,$2^2$-dihydro-2(4,6)-quinolina-1,4(1,3)-dibenzenacyclohexaphan-$2^2$-one; and $4^4$-chloro-$2^1$-cyclopropyl-3-(1-methyl-1H-imidazol-5-yl)-3-morpholino-$2^1$,$2^2$-dihydro-7-oxa-2(4,6)-quinolina-1,4(1,3)-dibenzenacycloheptaphan-$2^2$-one;

including an (R)- or (S)-enantiomer or racemate thereof, or a pharmaceutically acceptable form thereof.

198. A pharmaceutical composition comprising the compound or pharmaceutically acceptable form thereof of claim 197 and a pharmaceutically acceptable carrier, excipient, or diluent.

199. The compound of claim 193, wherein the compound is selected from:

3-hydroxy-$2^2$-methoxy-3-(1-methyl-1H-imidazol-5-yl)-2(4,6)-quinolina-1,4(1,3)-dibenzenacyclohexaphane-$4^4$-carbonitrile;

3-amino-3-(1-methyl-1H-imidazol-5-yl)-2(4,6)-quinolina-1,4(1,3)-dibenzenacyclohexaphane-$2^2$,$4^4$-dicarbonitrile;

$2^2$-methoxy-3-(1-methyl-1H-imidazol-5-yl)-5-oxa-2(4,6)-quinolina-1,4(1,3)-dibenzenacyclohexaphan-3-ol;

$4^4$-chloro-$2^2$-methoxy-3-(1-methyl-1H-imidazol-5-yl)-5-oxa-2(4,6)-quinolina-1,4(1,3)-dibenzenacyclohexaphan-3-ol;

3-hydroxy-$2^2$-methoxy-3-(1-methyl-1H-imidazol-5-yl)-5-oxa-2(4,6)-quinolina-1,4(1,3)-dibenzenacyclohexaphane-$4^4$-carbonitrile;

3-amino-3-(1-methyl-1H-imidazol-5-yl)-5-oxa-2(4,6)-quinolina-1,4(1,3)-dibenzenacyclohexaphane-$2^2$,$4^4$-dicarbonitrile;

$4^4$-chloro-$2^2$-methoxy-3-(1-methyl-1H-imidazol-5-yl)-5-oxa-2(4,6)-quinolina-1,4(1,3)-dibenzenacycloheptaphan-3-ol;

$2^2$-methoxy-3-(1-methyl-1H-imidazol-5-yl)-6-oxa-2(4,6)-quinolina-1,4(1,3)-dibenzenacyclohexaphan-3-ol;

$4^4$-chloro-$2^2$-methoxy-3-(1-methyl-1H-imidazol-5-yl)-6-oxa-2(4,6)-quinolina-1,4(1,3)-dibenzenacyclohexaphan-3-ol;

3-amino-$4^4$-chloro-3-(1-methyl-1H-imidazol-5-yl)-6-oxa-2(4,6)-quinolina-1,4(1,3)-dibenzenacyclohexaphane-$2^2$-carbonitrile;

$4^4$-chloro-$2^2$-methoxy-3-(4-methyl-4H-1,2,4-triazol-3-yl)-6-oxa-2(4,6)-quinolina-1,4(1,3)-dibenzenacyclohexaphan-3-ol;

$4^4$-bromo-$2^2$-methoxy-3-(1-methyl-1H-imidazol-5-yl)-6-oxa-2(4,6)-quinolina-1,4(1,3)-dibenzenacyclohexaphan-3-ol;

3-hydroxy-$2^2$-methoxy-3-(1-methyl-1H-imidazol-5-yl)-6-oxa-2(4,6)-quinolina-1,4(1,3)-dibenzenacyclohexaphane-$4^4$-carbonitrile;

3-amino-3-(1-methyl-1H-imidazol-5-yl)-6-oxa-2(4,6)-quinolina-1,4(1,3)-dibenzenacyclohexaphane-$2^2$,$4^4$-dicarbonitrile;

$4^6$-chloro-$2^2$-methoxy-3-(1-methyl-1H-imidazol-5-yl)-6-oxa-2(4,6)-quinolina-4(3,5)-pyridina-1(1,3)-benzenacyclohexaphan-3-ol;

3-hydroxy-$2^2$-methoxy-3-(1-methyl-1H-imidazol-5-yl)-6-oxa-2(4,6)-quinolina-4(3,5)-pyridina-1(1,3)-benzenacyclohexaphane-$4^6$-carbonitrile;

$4^4$-chloro-$2^2$-methoxy-3-(1-methyl-1H-imidazol-5-yl)-7-oxa-2(4,6)-quinolina-1,4(1,3)-dibenzenacycloheptaphan-3-ol;

3-amino-3-(1-methyl-1H-imidazol-5-yl)-$2^2$-morpholino-6-oxa-2(4,6)-quinolina-1,4(1,3)-dibenzenacyclohexaphane-$4^4$-carbonitrile;

3-amino-3-(1-methyl-1H-imidazol-5-yl)-$2^2$-(piperazin-1-yl)-6-oxa-2(4,6)-quinolina-1,4(1,3)-dibenzenacyclohexaphane-$4^4$-carbonitrile;

3-amino-3-(1-methyl-1H-imidazol-5-yl)-$2^2$-(oxetan-3-ylamino)-6-oxa-2(4,6)-quinolina-1,4(1,3)-dibenzenacyclohexaphane-$4^4$-carbonitrile;

3-amino-3-(1-(methyl-d₃)-1H-imidazol-5-yl)-6-oxa-2(4,6)-quinolina-1,4(1,3)-dibenzenacyclohexaphane-2²,4⁴-dicarbonitrile;

4⁴-bromo-2²-chloro-3-(1-methyl-1H-imidazol-5-yl)-6-oxa-2(4,6)-quinolina-1,4(1,3)-dibenzenacyclohexaphan-3-ol;

3-hydroxy-3-(1-methyl-1H-imidazol-5-yl)-6-oxa-2(4,6)-quinolina-1,4(1,3)-dibenzenacyclohexaphane-2²,4⁴-dicarbonitrile;

4⁴-cyano-3-hydroxy-3-(1-methyl-1H-imidazol-5-yl)-6-oxa-2(4,6)-quinolina-1,4(1,3)-dibenzenacyclohexaphane-2²-carboxamide;

4⁴-bromo-2²-chloro-3-(1-methyl-1H-imidazol-5-yl)-6-oxa-2(4,6)-quinolina-1,4(1,3)-dibenzenacyclohexaphan-3-amine;

4⁴-bromo-3-(1-methyl-1H-imidazol-5-yl)-2²-(oxetan-3-yloxy)-6-oxa-2(4,6)-quinolina-1,4(1,3)-dibenzenacyclohexaphan-3-amine;

3-hydroxy-3-(1-(methyl-d₃)-1H-imidazol-5-yl)-6-oxa-2(4,6)-quinolina-1,4(1,3)-dibenzenacyclohexaphane-2²,4⁴-dicarbonitrile;

4⁴-bromo-2²-chloro-3-(1-methyl-1H-imidazol-5-yl)-6-oxa-2(4,6)-quinazolina-1,4(1,3)-dibenzenacyclohexaphan-3-ol;

4⁴-bromo-3-(1-methyl-1H-imidazol-5-yl)-6-oxa-2(4,6)-quinazolina-1,4(1,3)-dibenzenacyclohexaphane-2²,3-diamine;

3-amino-3-(1-methyl-1H-imidazol-5-yl)-2²-(oxetan-3-yloxy)-6-oxa-2(4,6)-quinolina-1,4(1,3)-dibenzenacyclohexaphane-4⁴-carbonitrile;

3-(4-methyl-1H-imidazol-1-yl)-6-oxa-2(4,6)-quinolina-1,4(1,3)-dibenzenacyclohexaphane-2²,4⁴-dicarbonitrile;

3-(5-methyl-1H-imidazol-1-yl)-6-oxa-2(4,6)-quinolina-1,4(1,3)-dibenzenacyclohexaphane-2²,4⁴-dicarbonitrile;

4⁴-chloro-3-(1-methyl-1H-imidazol-5-yl)-5-oxa-2(4,6)-quinolina-1,4(1,3)-dibenzenacyclohexaphan-3-amine;

4⁴-chloro-3-(1-methyl-1H-imidazol-5-yl)-5-oxa-2(4,6)-quinolina-1,4(1,3)-dibenzenacycloheptaphan-3-ol;

4⁴-chloro-3-(1-methyl-1H-imidazol-5-yl)-2(4,6)-quinolina-1,4(1,3)-dibenzenacyclohexaphan-3-ol;

4⁴-chloro-3-(1-methyl-1H-imidazol-5-yl)-7-oxa-2(4,6)-quinolina-1,4(1,3)-dibenzenacycloheptaphan-3-ol; and 4⁴-chloro-3-(1-methyl-1H-imidazol-5-yl)-6-oxa-2(4,6)-quinolina-1,4(1,3)-dibenzenacyclohexaphan-3-ol;

including an (R)- or (S)-enantiomer or racemate thereof, or a pharmaceutically acceptable form thereof.

200. A pharmaceutical composition comprising the compound or pharmaceutically acceptable form thereof of claim 199 and a pharmaceutically acceptable carrier, excipient, or diluent.

201. The compound of claim 193, wherein the compound is:
4⁴-bromo-3-(1-methyl-1H-imidazol-5-yl)-6-oxa-2(4,6)-isoquinolina-1,4(1,3)-dibenzenacyclohexaphan-3-ol;
including an (R)- or (S)-enantiomer or racemate thereof, or a pharmaceutically acceptable form thereof.

202. A pharmaceutical composition comprising the compound or pharmaceutically acceptable form thereof of claim 201 and a pharmaceutically acceptable carrier, excipient, or diluent.

203. The compound of claim 193, wherein the compound is selected from:
4⁴-bromo-3-(1-methyl-1H-imidazol-5-yl)-6-oxa-2(1,7)-isoquinolina-1,4(1,3)-dibenzenacyclohexaphan-3-ol;
3-hydroxy-3-(1-methyl-1H-imidazol-5-yl)-6-oxa-2(1,7)-isoquinolina-1,4(1,3)-dibenzenacyclohexaphane-4⁴-carbonitrile;

3-amino-3-(1-methyl-1H-imidazol-5-yl)-6-oxa-2(1,7)-isoquinolina-1,4(1,3)-dibenzenacyclohexaphane-4⁴-carbonitrile;

4⁴-chloro-3-(1-methyl-1H-imidazol-5-yl)-5-oxa-2(1,7)-isoquinolina-1,4(1,3)-dibenzenacyclohexaphan-3-amine;

4⁴-chloro-3-(1-methyl-1H-imidazol-5-yl)-5-oxa-2(1,7)-isoquinolina-1,4(1,3)-dibenzenacycloheptaphan-3-ol;

4⁴-chloro-3-(1-methyl-1H-imidazol-5-yl)-2(1,7)-isoquinolina-1,4(1,3)-dibenzenacyclohexaphan-3-ol;

4⁴-chloro-3-(1-methyl-1H-imidazol-5-yl)-7-oxa-2(1,7)-isoquinolina-1,4(1,3)-dibenzenacycloheptaphan-3-ol;

4⁴-chloro-3-(1-methyl-1H-imidazol-5-yl)-6-oxa-2(1,7)-isoquinolina-1,4(1,3)-dibenzenacyclohexaphan-3-ol;

4⁴-chloro-N-(2-fluoroethyl)-3-(1-methyl-1H-imidazol-5-yl)-5-oxa-2(1,7)-isoquinolina-1,4(1,3)-dibenzenacyclohexaphan-3-amine;

4⁴-chloro-N-(2-fluoroethyl)-3-(1-methyl-1H-imidazol-5-yl)-5-oxa-2(1,7)-isoquinolina-1,4(1,3)-dibenzenacycloheptaphan-3-amine;

4⁴-chloro-N-(2-fluoroethyl)-3-(1-methyl-1H-imidazol-5-yl)-2(1,7)-isoquinolina-1,4(1,3)-dibenzenacyclohexaphan-3-amine;

4⁴-chloro-N-(2-fluoroethyl)-3-(1-methyl-1H-imidazol-5-yl)-7-oxa-2(1,7)-isoquinolina-1,4(1,3)-dibenzenacycloheptaphan-3-amine;

4⁴-chloro-N-(2-fluoroethyl)-3-(1-methyl-1H-imidazol-5-yl)-6-oxa-2(1,7)-isoquinolina-1,4(1,3)-dibenzenacyclohexaphan-3-amine;

4⁴-chloro-N-(2-chloroethyl)-3-(1-methyl-1H-imidazol-5-yl)-5-oxa-2(1,7)-isoquinolina-1,4(1,3)-dibenzenacyclohexaphan-3-amine;

4⁴-chloro-N-(2-chloroethyl)-3-(1-methyl-1H-imidazol-5-yl)-5-oxa-2(1,7)-isoquinolina-1,4(1,3)-dibenzenacycloheptaphan-3-amine;

4⁴-chloro-N-(2-chloroethyl)-3-(1-methyl-1H-imidazol-5-yl)-2(1,7)-isoquinolina-1,4(1,3)-dibenzenacyclohexaphan-3-amine;

4⁴-chloro-N-(2-chloroethyl)-3-(1-methyl-1H-imidazol-5-yl)-7-oxa-2(1,7)-isoquinolina-1,4(1,3)-dibenzenacycloheptaphan-3-amine;

4⁴-chloro-N-(2-chloroethyl)-3-(1-methyl-1H-imidazol-5-yl)-6-oxa-2(1,7)-isoquinolina-1,4(1,3)-dibenzenacyclohexaphan-3-amine;

4⁴-chloro-3-(1-methyl-1H-imidazol-5-yl)-3-morpholino-5-oxa-2(1,7)-isoquinolina-1,4(1,3)-dibenzenacyclohexaphane;

4⁴-chloro-3-(1-methyl-1H-imidazol-5-yl)-3-morpholino-5-oxa-2(1,7)-isoquinolina-1,4(1,3)-dibenzenacycloheptaphane;

4-(4⁴-chloro-3-(1-methyl-1H-imidazol-5-yl)-2(1,7)-isoquinolina-1,4(1,3)-dibenzenacyclohexaphane-3-yl)morpholine;

4⁴-chloro-3-(1-methyl-1H-imidazol-5-yl)-3-morpholino-7-oxa-2(1,7)-isoquinolina-1,4(1,3)-dibenzenacycloheptaphane; and 4⁴-chloro-3-(1-methyl-1H-imidazol-5-yl)-3-morpholino-6-oxa-2(1,7)-isoquinolina-1,4(1,3)-dibenzenacyclohexaphane;

including an (R)- or (S)-enantiomer or racemate thereof, or a pharmaceutically acceptable form thereof.

204. A pharmaceutical composition comprising the compound or pharmaceutically acceptable form thereof of claim 203 and a pharmaceutically acceptable carrier, excipient, or diluent.

205. The compound of claim 193, wherein the compound is selected from:

4⁴-bromo-2⁷-methoxy-3-(1-methyl-1H-imidazol-5-yl)-6-oxa-2(5,3)-quinolina-1,4(1,3)-dibenzenacyclohexaphan-3-ol; and 3-hydroxy-2⁷-methoxy-3-(1-methyl-1H-imidazol-5-yl)-6-oxa-2(5,3)-quinolina-1,4(1,3)-dibenzenacyclohexaphane-4⁴-carbonitrile;

including an (R)- or (S)-enantiomer or racemate thereof, or a pharmaceutically acceptable form thereof.

206. A pharmaceutical composition comprising the compound or pharmaceutically acceptable form thereof of claim 205 and a pharmaceutically acceptable carrier, excipient, or diluent.

207. The compound of claim 193, wherein the compound is:

3-amino-2¹-methyl-3-(1-methyl-1H-imidazol-5-yl)-2²-oxo-2¹,2²-dihydro-5-oxa-2(4,6)-quinolina-1,4(1,3)-dibenzenacycloheptaphane-4⁴-carbonitrile;

or an (R)- or (S)-enantiomer thereof, or a pharmaceutically acceptable form thereof.

208. A pharmaceutical composition comprising the compound or pharmaceutically acceptable form thereof of claim 207 and a pharmaceutically acceptable carrier, excipient, or diluent.

209. The compound of claim 193, wherein the compound is:

3-amino-4⁴-chloro-2¹-(methyl-d₃)-3-(1-methyl-1H-imidazol-5-yl)-2¹,2²-dihydro-6-oxa-2(4,6)-quinolina-1,4(1,3)-dibenzenacyclohexaphan-2²-one;

or an (R)- or (S)-enantiomer thereof, or a pharmaceutically acceptable form thereof.

210. A pharmaceutical composition comprising the compound or pharmaceutically acceptable form thereof of claim 209 and a pharmaceutically acceptable carrier, excipient, or diluent.

211. The compound of claim 193, wherein the compound is:

3-amino-2¹-(methyl-d₃)-3-(1-methyl-1H-imidazol-5-yl)-2²-oxo-2¹,2²-dihydro-6-oxa-2(4,6)-quinolina-1,4(1,3)-dibenzenacyclohexaphane-4⁴-carbonitrile;

or an (R)- or (S)-enantiomer thereof, or a pharmaceutically acceptable form thereof.

212. A pharmaceutical composition comprising the compound or pharmaceutically acceptable form thereof of claim 211 and a pharmaceutically acceptable carrier, excipient, or diluent.

213. The compound of claim 193, wherein the compound is:

3-amino-3-(1-methyl-1H-imidazol-5-yl)-2(4,6)-quinolina-1,4(1,3)-dibenzenacyclohexaphane-2² 4⁴-dicarbonitrile;

or an (R)- or (S)-enantiomer thereof, or a pharmaceutically acceptable form thereof.

214. A pharmaceutical composition comprising the compound or pharmaceutically acceptable form thereof of claim 213 and a pharmaceutically acceptable carrier, excipient, or diluent.

215. The compound of claim 193, wherein the compound is:

4⁴-chloro-2²-methoxy-3-(1-methyl-1H-imidazol-5-yl)-6-oxa-2(4,6)-quinolina-1,4(1,3)-dibenzenacyclohexaphan-3-ol;

or an (R)- or (S)-enantiomer thereof, or a pharmaceutically acceptable form thereof.

216. A pharmaceutical composition comprising the compound or pharmaceutically acceptable form thereof of claim 215 and a pharmaceutically acceptable carrier, excipient, or diluent.

217. The compound of claim 193, wherein the compound is:

3-amino-3-(1-methyl-1H-imidazol-5-yl)-6-oxa-2(4,6)-quinolina-1,4(1,3)-dibenzenacyclohexaphane-22,44-dicarbonitrile;

or an (R)- or (S)-enantiomer thereof, or a pharmaceutically acceptable form thereof.

218. A pharmaceutical composition comprising the compound or pharmaceutically acceptable form thereof of claim 217 and a pharmaceutically acceptable carrier, excipient, or diluent.

219. The compound of claim 193, wherein the compound is:

3-amino-3-(1-methyl-1H-imidazol-5-yl)-6-oxa-2(1,7)-isoquinolina-1,4(1,3)-dibenzenacyclohexaphane-4⁴-carbonitrile;

or an (R)- or (S)-enantiomer thereof, or a pharmaceutically acceptable form thereof.

220. A pharmaceutical composition comprising the compound or pharmaceutically acceptable form thereof of claim 219 and a pharmaceutically acceptable carrier, excipient, or diluent.

221. The compound of claim 129, wherein the compound is:

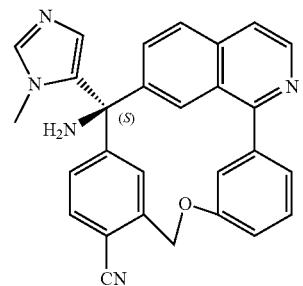

or a pharmaceutically acceptable form thereof.

222. A pharmaceutical composition comprising the compound or pharmaceutically acceptable form thereof of claim 221 and a pharmaceutically acceptable carrier, excipient, or diluent.

* * * * *